US009949966B2

(12) United States Patent
Han et al.

(10) Patent No.: US 9,949,966 B2
(45) Date of Patent: *Apr. 24, 2018

(54) DIHYDROQUINOLIZINONES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Xingchun Han, Shanghai (CN); Hassan Javanbakht, Basel (CH); Min Jiang, Shanghai (CN); Chungen Liang, Shanghai (CN); Jianping Wang, Shanghai (CN); Yongguang Wang, Shanghai (CN); Zhanguo Wang, Shanghai (CN); Robert James Weikert, Basel (CH); Song Yang, Shanghai (CN); Chengang Zhou, Shanghai (CN)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,815

(22) Filed: Jun. 21, 2016

(65) Prior Publication Data
US 2016/0296515 A1    Oct. 13, 2016

Related U.S. Application Data

(60) Division of application No. 14/610,454, filed on Jan. 30, 2015, now Pat. No. 9,458,153, which is a continuation of application No. PCT/CN2014/094206, filed on Dec. 18, 2014, and a continuation of application No. PCT/CN2014/071854, filed on Jan. 30, 2014.

(51) Int. Cl.
| | |
|---|---|
| A61K 31/4375 | (2006.01) |
| C07D 455/06 | (2006.01) |
| A61K 31/4745 | (2006.01) |
| C07D 471/04 | (2006.01) |
| A61K 31/496 | (2006.01) |
| A61K 31/5377 | (2006.01) |

(52) U.S. Cl.
CPC ........ *A61K 31/4745* (2013.01); *A61K 31/496* (2013.01); *A61K 31/5377* (2013.01); *C07D 455/06* (2013.01); *C07D 471/04* (2013.01)

(58) Field of Classification Search
CPC  C07D 455/06; C07D 471/04; A61K 31/4745; A61K 31/496; A61K 31/5377
USPC ........................................... 546/95; 514/290
See application file for complete search history.

(56) References Cited

U.S. PATENT DOCUMENTS 9,458,153 B2 * 10/2016 Han ............... C07D 455/06
9,637,485 B2 *  5/2017 Han ............... C07D 471/04

FOREIGN PATENT DOCUMENTS

JP    60-197684    * 10/1985
JP    60-197684 A    10/1985

OTHER PUBLICATIONS

Acs et al., Proc Natl Acad Sci USA 84:4641-4644 ( 1987).
Ansel et al. Pharmaceutical Dosage Forms and Drug Delivery Systems, ( 2004).
Ansel et al. Pharmaceutical Dosage Forms and Drug Delivery Systems 6th edition,:196 1456-1457 ( 1995).
Bastin et al., "Salt selection and optimisation procedures for pharmaceutical new chemical entities" Organic Process Res & Dev 4:427-435 ( 2000).
Belloni et al., "IFN-α inhibits HBV transcription and replication in cell culture and in humanized mice by targeting the epigenetic regulation of the nuclear cccDNa minichromosome" J Clin Invest 122(2):529-537 (Feb. 2012).
Buster et al "Peginterferon alpha-2b is safe and effective in HBeAg-Positive chronic hepatitis B patients with advanced fibrosis" Hepatology 46:388-394 ( 2007).
CAS Registry Database, XP002736278, Jun. 9, 2008.
Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48:1229-1236 ( 2005).
Fisicaro et al., "Antiviral intrahepatic T-cell responses can be restored by blocking programmed death-1 pathway in chronic hepatits B" Gastroenterology 138:682-693 ( 2010).
Gennaro et al. Remington: The Science and Practice of Pharmacy (Press), Philadelphia:Lippincott, Williams & Wilkins, ( 2000).
Janssen et al., "Pegylated interferon alfa-2b alone or in combination with lamivudine for HBeAg-positive chronic hepatitis B: a randomised trial" Lancet 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring muti-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).

(Continued)

*Primary Examiner* — Rita J Desai
(74) *Attorney, Agent, or Firm* — Brian L. Buckwalter

(57) ABSTRACT

The invention provides novel compounds having the general formula:

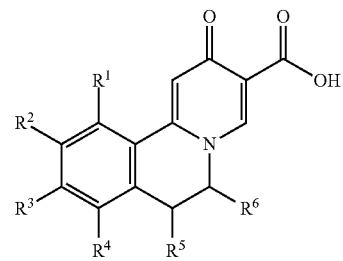

wherein $R^1$, $R^2$, $R^3$, $R^4$, $R^5$ and $R^6$ are as described herein, compositions including the compounds and methods of using the compounds.

21 Claims, 1 Drawing Sheet

(56) References Cited

OTHER PUBLICATIONS

Mao et al., "Indoleamine 2,3-dioxygenase mediates the antiviral effect of gagamma interferon against hepatitis B virus in human hepatocyte-derived cells" J Virol 85(2):1048-1057 (Jan. 2011).

Mao et al., "Inhibition of hepatitis B virus replication by the host zinc finger antiviral protein" PLoS Pathogens 9(7 Suppl 1-18):e1003494 (Jul. 2013).

Marcellin et al., "Peginterferon alfa-2a alone, lamivudine alone, and the two in combination in patients with HBeAg-negative chronic hepatitis B" New E J Med 351(12):1206-1217 (Sep. 16, 2004).

Nayersina et al., "HLA A2 restricted cytotoxic T lymphocyte responses to multiple hepatitis B surface antigen epitopes during hepatitis B virus infection" J Immunol 150:4659-4671 (May 15, 1993).

Op den Brouw et al., "Hepatitis B virus surface antigen impairs myeloid dendritic cell function: a possible immune escape mechanism of hepatitis B virus" Immunol 126:280-290 (2008).

Quasdorff et al., "Control of hepatitis B virus at the level of transcription" J Viral Hepatitis 17:527-536 (2010).

Rowe, R. Handbook of Pharmaceutical Excipients Chicago: Pharmaceutical Press, (2005).

Schulze et al., "Hepatitis B virus infection initiates with a large surface protein-dependent binding to heparan sulfate proteoglycans" Hepatology 46:1759-1768 (2007).

Shi et al., "Hepatitis B virus suppresses the functional interaction between natural killer cells and plasmacytoid dendritic cells" J Viral Hepatitis 19:e26-e33 (2012).

Wieland et al., "Stealth and cunning. hepatitis B and hepatitis C viruses" J Virol 79(15):9369-9380 (Aug. 2005).

Woltman et al., "Hepatitis B virus lacks immune activating capacity, but actively inhibits plasmacytoid dendritic cell function" PLoS ONE 6(1 Suppl 1-14):e15324 (Jan. 2011).

Yan et al "Molecular determinants of hepatitis B and D virus entry restriction in mouse sodium taurocholate cotransporting polypeptide" J Virol 87(14):7977-7991 (Jul. 2013).

* cited by examiner

DIHYDROQUINOLIZINONES FOR THE TREATMENT AND PROPHYLAXIS OF HEPATITIS B VIRUS INFECTION

This application is a divisional of U.S. application Ser. No. 14/610,454, file Jan. 30, 2015 which claims the benefit of priority to International Application No. PCT/CN2014/071854, filed Jan. 30, 2014, and International Application No. PCT/CN2014/094206, filed Dec. 18, 2014, each of which is incorporated herein by reference in its entirety.

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel dihydroquinolizinones having pharmaceutical activity, their manufacture, pharmaceutical compositions containing them and their potential use as medicaments.

The present invention relates to compounds of formula I

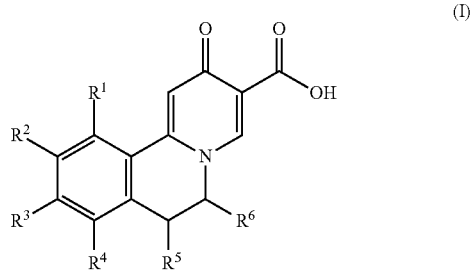

wherein $R^1$ to $R^6$ are as described below, or to pharmaceutically acceptable salts, or to enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433;

Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to novel compounds of formula I

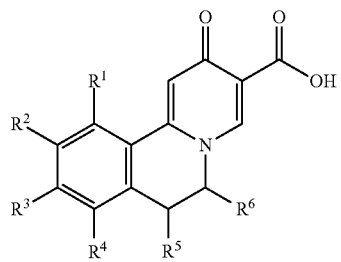

(I)

wherein
$R^1$ is hydrogen, halogen, $C_{1-6}$alkyl, $C_{1-6}$alkylamino or $C_{1-6}$alkoxy;
$R^2$ is hydrogen; halogen; $C_{1-6}$alkyl, which is unsubstituted or once, twice or three times substituted by fluoro; $C_{1-6}$alkoxy, which is unsubstituted or once, twice or three times substituted by fluoro; cyano; $C_{3-7}$cycloalkyl; hydroxy or phenyl-$C_xH_{2x}$—O—;
$R^3$ is hydrogen;
halogen;
$C_{1-6}$alkyl, which is unsubstituted or once, twice or three times substituted by fluoro;
cyano;
pyrrolidinyl;
amino;
phenyl-$C_xH_{2x}$—N($C_{1-6}$alkyl)-;
$C_{1-6}$alkoxycarbonylpiperazinyl;
or $R^7$—O—, wherein $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-6}$alkyl; $C_{1-6}$alkylcarbonylamino$C_{1-6}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; cyano$C_{1-6}$alkyl; $C_{3-7}$cycloalkyl$C_{1-6}$alkyl; cyano$C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; di$C_{1-6}$alkylamino$C_{1-6}$alkoxy$C_{1-6}$alkyl; carboxy$C_{1-6}$alkyl; or $C_{1-6}$alkoxycarbonylamino$C_{1-8}$alkyl; heteroaryl$C_{1-6}$alkyl, wherein heteroaryl is N-containing monocyclic heteroaryl; or heterocycloalkyl$C_{1-6}$alkyl, wherein heterocycloalkyl is monocyclic heterocycloalkyl;
$R^4$ is hydrogen, halogen, $C_{1-6}$alkyl, cyano or $C_{1-6}$alkoxy;
provided that $R^1$, $R^2$, $R^3$ and $R^4$ are not hydrogen simultaneously;
$R^5$ is hydrogen or $C_{1-6}$alkyl;
$R^6$ is hydrogen; $C_{1-6}$alkyl, which is unsubstituted or once, twice or three times substituted by fluoro; $C_{3-7}$cycloalkyl, which is unsubstituted or once, twice or three times substituted by fluoro or $C_{1-6}$alkyl; or phenyl-$C_xH_{2x}$—;
x is 1-6;
with the proviso that 6-methyl-2-oxo-9-pyrrolidin-1-yl-6,7-dihydrobenzo[a]quinolizine-3-carboxylic acid; 9-fluoro-6-methyl-2-oxo-6,7-dihydrobenzo[a]quinolizine-3-carboxylic acid; and 9,10-difluoro-6-methyl-2-oxo-6,7-dihydrobenzo[a]quinolizine-3-carboxylic acid are excluded; or pharmaceutically acceptable salts, or enantiomers thereof.

The invention is also relates to their manufacture, medicaments based on a compound in accordance with the invention and their production as well as the use of compounds of formula I as HBsAg inhibitors and HBV DNA production inhibitors. Accordingly, the compounds of formula I are useful for the treatment or prophylaxis of HBV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{2-6}$alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl and vinyl.

The term "$C_{2-6}$alkynyl" denotes an unsaturated, linear or branched chain alkynyl group containing 2 to 6, particularly 2 to 4 carbon atoms, for example ethynyl, 1-propynyl, propargyl, butynyl and the like. Particular "$C_{2-6}$alkynyl" groups are ethynyl and 1-propynyl.

The term "$C_xH_{2x}$" alone or in combination signifies a saturated, linear- or branched chain alkyl group containing 1 to 6, particularly 1 to 4 carbon atoms.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "monocyclic heteroaryl" denotes a monovalent aromatic heterocyclic mono-ring system of 5 to 8 ring atoms, comprising 1, 2, 3 or 4 heteroatoms selected from N, O and S, the remaining ring atoms being carbon. Examples of monocyclic heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, isothiazolyl and the like.

The term "N-containing monocyclic heteroaryl" refers to a monocyclic heteroaryl wherein at least one of the heteroatoms is N. Examples for N-containing monocyclic heteroaryl are pyrrolyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, isothiazolyl and the like. Particular "N-containing monocyclic heteroaryl" groups are imidazolyl, pyrazolyl and triazolyl, and more particularly imidazol-1-yl, pyrazol-1-yl and 1,2,4-triazol-1-yl.

The term "monocyclic heterocycloalkyl" is a monovalent saturated or partly unsaturated monocyclic ring system of 3 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular "monocyclic heterocycloalkyl" groups are morpholinyl, 2-oxo-pyrrolidinyl, pyrrolidinyl, tetrahydropyranyl, and more particularly pyrrolidin-1-yl, 2-oxo-pyrrolidin-1-yl, tetrahydropyran-4-yl and morpholin-1-yl.

The term "amino", alone or in combination, refers to primary (—$NH_2$), secondary (—NH—) or tertiary amino

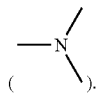

The term "carbonyl" alone or in combination refers to the group —C(O)—.

The term "cyano" alone or in combination refers to the group —CN.

The term "halogen" means fluorine, chlorine, bromine or iodine. Halogen is particularly fluorine, chlorine or bromine.

The term "hydroxy" alone or in combination refers to the group —OH.

The term "2-oxo-pyrrolidinyl" alone or in combination refers to the group

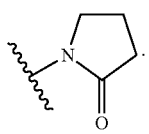

The term "sulfonyl" alone or in combination refers to the group —$S(O)_2$—.

The term "$C_{1-6}$alkylamino" refers to amino group as defined above wherein at least one of the hydrogen atoms of the amino group is replaced by a $C_{1-6}$alkyl group.

The term "$C_{1-6}$alkylsulfonyl" refers to a group $C_{1-6}$alkyl-$S(O)_2$—, wherein the "$C_{1-6}$alkyl" is as defined above.

The term "aminocarbonyl" refers to a group amino-C(O)—, wherein the "amino" is as defined above.

The term "cyano$C_{3-7}$cycloalkyl" refers to $C_{3-7}$cycloalkyl group as defined above wherein at least one of the hydrogen atoms of the $C_{3-7}$cycloalkyl group is replaced by a cyano group.

The term "pyrrolidinylcarbonyl" refers to a group pyrrolidinyl-C(O)—.

The term "enantiomer" denotes two stereoisomers of a compound which are non-superimposable mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such asp-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention provides (i) compounds of formula I:

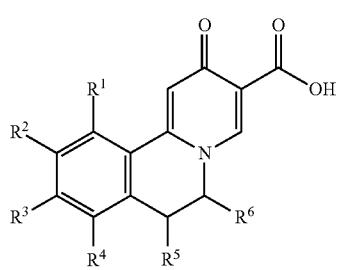

wherein $R^1$ is hydrogen, halogen, $C_{1-6}$alkyl, $C_{1-6}$alkylamino or $C_{1-6}$alkoxy;

$R^2$ is hydrogen; halogen; $C_{1-6}$alkyl, which is unsubstituted or once, twice or three times substituted by fluoro; $C_{1-6}$alkoxy, which is unsubstituted or once, twice or three times substituted by fluoro; cyano; $C_{3-7}$cycloalkyl; hydroxy or phenyl-$C_xH_{2x}$—O—;

$R^3$ is hydrogen;
halogen;
$C_{1-6}$alkyl, which is unsubstituted or once, twice or three times substituted by fluoro;
cyano;
pyrrolidinyl;
amino;
phenyl-$C_xH_{2x}$—N($C_{1-6}$alkyl)-;
$C_{1-6}$alkoxycarbonylpiperazinyl;
or $R^7$—O—, wherein $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; cyano$C_{1-6}$alkyl; $C_{3-7}$cycloalkyl$C_{1-6}$alkyl; cyano$C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; di$C_{1-6}$alkylamino$C_{1-6}$alkoxy$C_{1-6}$alkyl; carboxy$C_{1-6}$alkyl; or $C_{1-6}$alkoxycarbonylamino$C_{1-8}$alkyl; heteroaryl$C_{1-6}$alkyl, wherein heteroaryl is N-containing monocyclic heteroaryl; or heterocycloalkyl$C_{1-6}$alkyl, wherein heterocycloalkyl is monocyclic heterocycloalkyl;

$R^4$ is hydrogen, halogen, $C_{1-6}$alkyl, cyano or $C_{1-6}$alkoxy;
provided that $R^1$, $R^2$, $R^3$ and $R^4$ are not hydrogen simultaneously;

$R^5$ is hydrogen or $C_{1-6}$alkyl;

$R^6$ is hydrogen; $C_{1-6}$alkyl, which is unsubstituted or once, twice or three times substituted by fluoro; $C_{3-7}$cycloalkyl, which is unsubstituted or once, twice or three times substituted by fluoro or $C_{1-6}$alkyl; or phenyl-$C_xH_{2x}$—;

x is 1-6;

with the proviso that 6-methyl-2-oxo-9-pyrrolidin-1-yl-6,7-dihydrobenzo[a]quinolizine-3-carboxylic acid, 9-fluoro-6-methyl-2-oxo-6,7-dihydrobenzo[a]quinolizine-3-carboxylic acid, and 9,10-difluoro-6-methyl-2-oxo-6,7-dihydrobenzo[a]quinolizine-3-carboxylic acid are excluded; or pharmaceutically acceptable salts, or enantiomers thereof.

A further embodiment of present invention is (ii) a compound of formula I, wherein $R^1$ is hydrogen, fluoro, chloro, bromo, methyl, methylamino, methoxy or ethoxy;

$R^2$ is hydrogen, fluoro, chloro, bromo, methyl, ethyl, trifluoromethyl, methoxy, ethoxy, propoxy, trifluoromethoxy, cyano, cyclopropyl, hydroxy or phenylmethyl-O—;

$R^3$ is hydrogen, bromo, methyl, propyl, trifluoromethyl, cyano, phenylmethyl-N(methyl)-, tert-butoxycarbonylpiperazinyl, hydroxy, methoxy, ethoxy, propoxy, isopropoxy, butoxy, isobutoxy, difluoromethylmethyl-O—, difluoromethylethyl-O—, trifluoromethoxy, trifluoromethylmethyl-O—, trifluoromethyl ethyl-O—, ethyldifluoromethyl-O—, vinyldifluoromethyl-O—, propargyl-O—, hydroxymethylpropargyl-O—, methoxyethyl-O—, methoxypropyl-O—, methoxybutyl-O—, ethoxyethyl-O—, methoxyethyl-O-ethyl-O—, aminoethyl-O—, aminopentyl-O—, aminohexyl-O—, aminooctyl-O—, tert-butoxycarbonylaminopentyl-O—, tert-butoxycarbonylaminohexyl-O—, tert-butoxycarbonylaminooctyl-O—, methylcarbonylaminoethyl-O—, methylcarbonylaminopentyl-O—, methylsulfonylaminoethyl-O—, methylsulfonylaminopentyl-O—, methylsulfonylethyl-O—, methylsulfonylpropyl-O—, methylsulfanylpropyl-O—, cyanopropyl-O—, cyanocyclopropylmethyl-O—, cyclopropylmethyl-O—, cyclohexylethyl-O—, hydroxyethyl-O—, hydroxypropyl-O—, hydroxy-dimethylpropyl-O—, hydroxy-difluoropropyl-O—, hydroxybutyl-O—, hydroxypentyl-O—, hydroxyhexyl-O—, aminoethyl-O-propyl-O—, ethylamino-ethyl-O-propyl-O—, imidazolylethyl-O—, pyrazolylpropyl-O—, triazolylpropyl-O—, morpholinyl ethyl-O—, morpholinylpropyl-O—, (2-oxo-pyrrolidinyl)ethyl-O—, (2-oxo-pyrrolidinyl)propyl-O—, phenylmethyl-O—, phenylethyl-O—, pyrrolidinylethyl-O—, pyrrolidinylpropyl-O—, pyrrolidinylcarbonylmethyl-O—, tetrahydropyranylmethyl-O— or carboxypropyl-O—;

$R^4$ is hydrogen, fluoro, chloro, bromo, methyl or cyano;

provided that $R^1$, $R^2$, $R^3$ and $R^4$ are not hydrogen simultaneously;

$R^5$ is hydrogen or methyl;

$R^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;

or pharmaceutically acceptable salts, or enantiomers thereof.

Another embodiment of present invention is (iii) a compound of formula I, wherein $R^1$ is hydrogen, halogen, $C_{1-6}$alkylamino or $C_{1-6}$alkoxy;

$R^2$ is hydrogen, halogen, $C_{1-6}$alkyl, $C_{1-6}$alkoxy, $C_{3-7}$cycloalkyl, hydroxy or phenyl-$C_xH_{2x}$—O—;

$R^3$ is hydrogen;
halogen;
$C_{1-6}$alkyl;
cyano;
phenyl-$C_xH_{2x}$—N($C_{1-6}$alkyl)-;
$C_{1-6}$alkoxycarbonylpiperazinyl;
or $R^7$—O—, wherein $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; $C_{3-7}$cycloalkyl$C_{1-6}$alkyl; cyano$C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; carboxy$C_{1-6}$alkyl; $C_{1-6}$alkoxycarbonylamino$C_{1-8}$alkyl; heteroaryl$C_{1-6}$alkyl, wherein heteroaryl is N-containing monocyclic heteroaryl; or heterocycloalkyl$C_{1-6}$alkyl, wherein heterocycloalkyl is monocyclic heterocycloalkyl;

$R^4$ is hydrogen, halogen, $C_{1-6}$alkyl or cyano;

provided that $R^1$, $R^2$, $R^3$ and $R^4$ are not hydrogen simultaneously;

R$^5$ is hydrogen or C$_{1-6}$alkyl;
R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;
x is 1-6;
with the proviso that 9-fluoro-6-methyl-2-oxo-6,7-dihydrobenzo[a]quinolizine-3-carboxylic acid and 9,10-difluoro-6-methyl-2-oxo-6,7-dihydrobenzo[a]quinolizine-3-carboxylic acid are excluded;
or pharmaceutically acceptable salts, or enantiomers thereof.

A further embodiment of present invention is (iv) a compound of formula I, wherein
R$^1$ is hydrogen, fluoro, chloro, bromo, methylamino, methoxy or ethoxy;
R$^2$ is hydrogen, fluoro, chloro, methyl, ethyl, methoxy, ethoxy, propoxy, cyclopropyl, hydroxy or phenylmethyl-O—;
R$^3$ is hydrogen, bromo, methyl, propyl, cyano, phenylmethyl-N(methyl)-, tert-butoxycarbonylpiperazinyl, hydroxy, methoxy, ethoxy, propoxy, isopropoxy, butoxy, isobutoxy, difluoromethylmethyl-O—, difluoromethylethyl-O—, trifluoromethylmethyl-O—, ethyldifluoromethyl-O—, vinyldifluoromethyl-O—, propargyl-O—, hydroxymethylpropargyl-O—, methoxyethyl-O—, methoxypropyl-O—, methoxybutyl-O—, ethoxyethyl-O—, methoxyethyl-O-ethyl-O—, aminoethyl-O—, aminopentyl-O—, aminohexyl-O—, aminooctyl-O—, tert-butoxycarbonylaminopentyl-O—, tert-butoxycarbonylaminohexyl-O—, tert-butoxycarbonylaminooctyl-O—, methylcarbonylaminoethyl-O—, methylcarbonylaminopentyl-O—, methylsulfonylaminoethyl-O—, methylsulfonylaminopentyl-O—, methylsulfonylethyl-O—, methylsulfonylpropyl-O—, methylsulfanylpropyl-O—, cyanopropyl-O—, cyanocyclopropylmethyl-O—, cyclopropylmethyl-O—, cyclohexylethyl-O—, hydroxyethyl-O—, hydroxypropyl-O—, hydroxy-dimethylpropyl-O—, hydroxy-difluoropropyl-O—, hydroxybutyl-O—, hydroxypentyl-O—, hydroxyhexyl-O—, aminoethyl-O-propyl-O—, ethylamino-ethyl-O-propyl-O—, imidazolylethyl-O—, pyrazolylpropyl-O—, triazolylpropyl-O—, morpholinyl ethyl-O—, morpholinylpropyl-O—, (2-oxo-pyrrolidinyl)ethyl-O—, (2-oxo-pyrrolidinyl)propyl-O—, phenylmethyl-O—, phenylethyl-O—, pyrrolidinylethyl-O—, pyrrolidinylpropyl-O—, pyrrolidinylcarbonylmethyl-O—, tetrahydropyranylmethyl-O— or carboxypropyl-O—;
R$^4$ is hydrogen, chloro, bromo, methyl or cyano;
provided that R$^1$, R$^2$, R$^3$ and R$^4$ are not hydrogen simultaneously;
R$^5$ is hydrogen or methyl;
R$^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;
or pharmaceutically acceptable salts, or enantiomers thereof.

Another embodiment of present invention is (v) a compound of formula IA

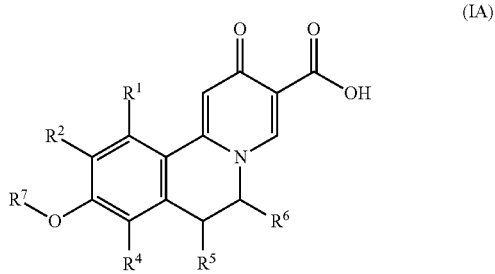

(IA)

wherein
R$^1$ is hydrogen, halogen or C$_{1-6}$alkoxy;
R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;
R$^4$ is hydrogen or halogen;
R$^5$ is hydrogen or C$_{1-6}$alkyl;
R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;
R$^7$ is hydrogen; C$_{1-6}$alkyl, which is unsubstituted or substituted with one to three substituents independently selected from fluoro, hydroxy and ethenyl; C$_{1-6}$alkoxyC$_{1-6}$alkyl; C$_{1-6}$alkoxyC$_{1-6}$alkoxyC$_{1-6}$alkyl; aminoC$_{1-6}$alkyl; C$_{1-6}$alkylcarbonylaminoC$_{1-6}$alkyl; C$_{1-6}$alkylsulfonylaminoC$_{1-8}$alkyl; C$_{1-6}$alkylsulfanylC$_{1-6}$alkyl; C$_{1-6}$alkylsulfonylC$_{1-6}$alkyl; cyanoC$_{1-6}$alkyl; C$_{3-7}$cycloalkylC$_{1-6}$alkyl; cyanoC$_{3-7}$cycloalkylC$_{1-6}$alkyl; phenylC$_{1-6}$alkyl; pyrrolidinylcarbonylC$_{1-6}$alkyl; C$_{2-6}$alkynyl; hydroxyC$_{1-6}$alkylC$_{2-6}$alkynyl; aminoC$_{1-6}$alkoxyC$_{1-6}$alkyl; C$_{1-6}$alkylaminoC$_{1-6}$alkoxyC$_{1-6}$alkyl; carboxyC$_{1-6}$alkyl; C$_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl;
x is 1-6;
or pharmaceutically acceptable salts, or enantiomers thereof.

A further embodiment of present invention is (vi) a compound of formula IA, wherein
R$^1$ is hydrogen, fluoro, chloro or methoxy;
R$^2$ is hydrogen, fluoro, chloro, methyl, ethyl, methoxy, ethoxy, propoxy, cyclopropyl, hydroxy or phenylmethyl-O—;
R$^4$ is hydrogen or chloro;
R$^5$ is hydrogen or methyl;
R$^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;
R$^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminopentyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylamino-ethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl;
or pharmaceutically acceptable salts, or enantiomers thereof.

Another embodiment of present invention is (vii) a compound of formula IA, wherein
R$^1$ is hydrogen or halogen;
R$^2$ is C$_{1-6}$alkyl, halogen or C$_{3-7}$cycloalkyl;

$R^4$ is hydrogen;
$R^5$ is hydrogen or $C_{1-6}$alkyl;
$R^6$ is $C_{1-6}$alkyl or $C_{1-6}$alkyl$C_{3-7}$cycloalkyl;
$R^7$ is $C_{1-6}$alkyl, $C_{1-6}$alkoxy$C_{1-6}$alkyl or phenyl$C_{1-6}$alkyl;
or pharmaceutically acceptable salts, or enantiomers thereof.

A further embodiment of present invention is (viii) a compound of formula IA, wherein
$R^1$ is hydrogen, fluoro or chloro;
$R^2$ is methyl, ethyl, fluoro, chloro or cyclopropyl;
$R^4$ is hydrogen;
$R^5$ is hydrogen or methyl;
$R^6$ is methyl, ethyl, isopropyl, isobutyl, tert-butyl or methylcyclopropyl;
$R^7$ is methyl, ethyl, methoxyethyl, methoxypropyl or phenylmethyl;
or pharmaceutically acceptable salts, or enantiomers thereof.

Another embodiment of present invention is (ix) a compound of formula IA, wherein
$R^1$ is hydrogen;
$R^2$ is $C_{1-6}$alkoxy;
$R^4$ is hydrogen or halogen;
$R^5$ is hydrogen or $C_{1-6}$alkyl;
$R^6$ is hydrogen; $C_{1-6}$alkyl, which is unsubstituted or once, twice or three times substituted by fluoro; $C_{3-7}$cycloalkyl; $C_{1-6}$alkyl$C_{3-7}$cycloalkyl; or phenyl-$C_xH_{2x}$—;
$R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkylsulfanyl$C_{1-6}$alkyl; $C_{1-6}$alkylsulfonyl$C_{1-6}$alkyl; cyano$C_{1-6}$alkyl; cyano$C_{3-7}$cycloalkyl$C_{1-6}$alkyl; $C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; carboxy$C_{1-6}$alkyl; $C_{1-6}$alkoxycarbonylamino$C_{1-8}$alkyl; imidazolyl$C_{1-6}$alkyl; pyrazolyl$C_{1-6}$alkyl; triazolyl$C_{1-6}$alkyl; morpholinyl$C_{1-6}$alkyl; (2-oxo-pyrrolidinyl)$C_{1-6}$alkyl; pyrrolidinyl$C_{1-6}$alkyl; or tetrahydropyranyl$C_{1-6}$alkyl;
x is 1-6;
or pharmaceutically acceptable salts, or enantiomers thereof.

A further embodiment of present invention is (x) a compound of formula IA, wherein
$R^1$ is hydrogen;
$R^2$ is methoxy, ethoxy or propoxy;
$R^4$ is hydrogen or chloro;
$R^5$ is hydrogen or methyl;
$R^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;
$R^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminopentyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylaminoethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl;
or pharmaceutically acceptable salts, or enantiomers thereof.

Another embodiment of present invention is (xi) a compound of formula IA, wherein
$R^1$ is hydrogen or halogen;
$R^2$ is halogen, $C_{1-6}$alkyl, $C_{1-6}$alkoxy or $C_{3-7}$cycloalkyl;
$R^4$ is hydrogen;
$R^5$ is hydrogen or $C_{1-6}$alkyl;
$R^6$ is $C_{1-6}$alkyl, which is unsubstituted or once, twice or three times substituted by fluoro; $C_{3-7}$cycloalkyl or $C_{1-6}$alkyl$C_{3-7}$cycloalkyl;
$R^7$ is $C_{1-6}$alkyl, which is unsubstituted or substituted with one to three substituents independently selected from fluoro and hydroxy; $C_{1-6}$alkoxy$C_{1-6}$alkyl; amino$C_{1-6}$alkyl; $C_{1-6}$alkylcarbonylamino$C_{1-6}$alkyl; $C_{1-6}$alkylsulfonylamino$C_{1-6}$alkyl; $C_{1-6}$alkylsulfanyl$C_{1-6}$alkyl; $C_{1-6}$alkylsulfonyl$C_{1-6}$alkyl; $C_{3-7}$cycloalkyl$C_{1-6}$alkyl; phenyl$C_{1-6}$alkyl; $C_{1-6}$alkylamino$C_{1-6}$alkoxy$C_{1-6}$alkyl; $C_{1-6}$alkoxycarbonylamino$C_{1-6}$alkyl; morpholinyl$C_{1-6}$alkyl or tetrahydropyranyl$C_{1-6}$alkyl;
or pharmaceutically acceptable salts, or enantiomers thereof.

A further embodiment of present invention is (xii) a compound of formula IA, wherein
$R^1$ is hydrogen, fluoro, or chloro;
$R^2$ is fluoro, chloro, methyl, ethyl, methoxy, ethoxy or cyclopropyl;
$R^4$ is hydrogen;
$R^5$ is hydrogen or methyl;
$R^6$ is methyl, ethyl, isopropyl, isobutyl, tert-butyl, trifluoromethylmethyl, cyclobutyl or methylcyclopropyl;
$R^7$ is methyl, ethyl, propyl, butyl, isobutyl, cyclopropylmethyl, difluoromethylmethyl, difluoromethylethyl, trifluoromethylmethyl, ethyldifluoromethyl, methoxyethyl, methoxypropyl, ethoxyethyl, aminohexyl, aminooctyl, tert-butoxycarbonylaminopentyl, tert-butoxycarbonylaminooctyl, methylcarbonylaminopentyl, methylsulfonylaminopentyl, methylsulfonylpropyl, methylsulfanylpropyl, hydroxypropyl, hydroxy-dimethylpropyl, hydroxy-difluoropropyl, hydroxybutyl, hydroxypentyl, hydroxyhexyl, ethylamino-ethyl-O-propyl-, morpholinylethyl, morpholinylpropyl, phenylmethyl or tetrahydropyranylmethyl;
or pharmaceutically acceptable salts, or enantiomers thereof.

Another embodiment of present invention is (xiii) a compound of formula I or pharmaceutically acceptable salts, or enantiomers thereof, wherein $R^1$ is hydrogen.

Another embodiment of present invention is (xiv) a compound of formula I or pharmaceutically acceptable salts, or enantiomers thereof, wherein $R^2$ is halogen or $C_{1-6}$alkoxy.

A further embodiment of present invention is (xv) a compound of formula I or pharmaceutically acceptable salts, or enantiomers thereof, wherein $R^2$ is chloro or methoxy.

Another embodiment of present invention is (xvi) a compound of formula I or pharmaceutically acceptable salts, or enantiomers thereof, wherein $R^5$ is hydrogen.

Another embodiment of present invention is (xvii) a compound of formula I or pharmaceutically acceptable salts, or enantiomers thereof, wherein $R^6$ is $C_{1-6}$alkyl or $C_{1-6}$alkyl$C_{3-7}$cycloalkyl.

A further embodiment of present invention is (xv) a compound of formula I or pharmaceutically acceptable salts, or enantiomers thereof, wherein $R^6$ is ethyl, isopropyl, tert-butyl or methylcyclopropyl.

Another embodiment of present invention is (xix) a compound of formula IA or pharmaceutically acceptable salts, or enantiomers thereof, wherein $R^7$ is $C_{1-6}$alkoxy$C_{1-6}$alkyl, hydroxy$C_{1-6}$alkyl or amino$C_{1-6}$alkyl.

A further embodiment of present invention is (xx) a compound of formula IA or pharmaceutically acceptable salts, or enantiomers thereof, wherein $R^7$ is methoxyethyl, methoxypropyl, hydroxydimethylpropyl, hydroxybutyl, hydroxypentyl, hydroxyhexyl, aminobutyl, aminopentyl or aminohexyl.

Another embodiment of present invention is (xxi) a compound of formula I, wherein
$R^1$ is hydrogen, halogen, $C_{1-6}$alkylamino or $C_{1-6}$alkoxy;
$R^2$ is hydrogen, $C_{1-6}$alkyl or $C_{1-6}$alkoxy;
$R^3$ is hydrogen; halogen; $C_{1-6}$alkyl; cyano; $C_{1-6}$alkoxycarbonylpiperazinyl or phenyl-$C_xH_{2x}$—N($C_{1-6}$alkyl)-, wherein x is 1-8;
$R^4$ is hydrogen, halogen, $C_{1-6}$alkyl or cyano;
provided that $R^1$, $R^2$, $R^3$ and $R^4$ are not hydrogen simultaneously;
$R^5$ is hydrogen;
$R^6$ is $C_{1-6}$alkyl;
or pharmaceutically acceptable salts, or enantiomers thereof.

A further embodiment of present invention is (xxii) a compound of formula I, wherein
$R^1$ is hydrogen, bromo, methylamino or ethoxy;
$R^2$ is hydrogen, methyl or methoxy;
$R^3$ is hydrogen, bromo, methyl, propyl, cyano, tert-butoxycarbonylpiperazinyl or phenylmethyl-N(methyl)-;
$R^4$ is hydrogen, bromo, methyl or cyano;
provided that $R^1$, $R^2$, $R^3$ and $R^4$ are not hydrogen simultaneously;
$R^5$ is hydrogen;
$R^6$ is methyl or ethyl;
or pharmaceutically acceptable salts, or enantiomers thereof.

Another embodiment of present invention is (xxiii) a compound of formula I, wherein
$R^1$ is hydrogen, halogen, $C_{1-6}$alkyl, $C_{1-6}$alkylamino or $C_{1-6}$alkoxy;
$R^2$ is hydrogen; halogen; $C_{1-6}$alkyl, which is unsubstituted or once or more times substituted by fluoro; $C_{1-6}$alkoxy, which is unsubstituted or once or more times substituted by fluoro; cyano; $C_{3-7}$cycloalkyl; hydroxy or phenyl-$C_xH_{2x}$—O—;
$R^3$ is hydrogen; halogen; $C_{1-6}$alkyl, which is unsubstituted or once or more times substituted by fluoro; cyano; morpholinyl; pyrrolidinyl; phenyl-$C_xH_{2x}$—N($C_{1-6}$alkyl)-; $C_{1-6}$alkoxycarbonylpiperazinyl; or
$R^7$—O—;
  wherein $R^7$ is hydrogen; $C_{1-6}$alkyl, which is unsubstituted or once or more times substituted by fluoro; or $R^8$—$C_xH_{2x}$—;
  wherein $R^8$ is $C_{1-6}$alkoxy, $C_{1-6}$alkoxy-$C_xH_{2x}$—O—, $C_{1-6}$alkylcarbonylamino, $C_{1-6}$alkylsulfonylamino, $C_{1-6}$alkylsulfonyl, aminocarbonyl, cyano, cyano$C_{3-7}$cycloalkyl, $C_{3-7}$cycloalkyl, di$C_{1-6}$alkylamino, hydroxy, imidazolyl, morpholinyl, 2-oxo-pyrrolidinyl, phenyl, pyrrolidinyl, pyrrolidinylcarbonyl or tetrahydropyranyl;
$R^4$ is hydrogen, halogen, $C_{1-6}$alkyl or cyano;
provided that $R^1$, $R^2$, $R^3$ and $R^4$ are not hydrogen simultaneously;
$R^5$ is hydrogen or $C_{1-6}$alkyl;
$R^6$ is hydrogen; $C_{1-6}$alkyl, which is unsubstituted or once or more times substituted by fluoro; $C_{3-7}$cycloalkyl or $C_{3-7}$cycloalkyl-$C_xH_{2x}$—;
x is 1-6;
with the proviso that 6-methyl-2-oxo-9-pyrrolidin-1-yl-6,7-dihydrobenzo[a]quinolizine-3-carboxylic acid, 9-fluoro-6-methyl-2-oxo-6,7-dihydrobenzo[a]quinolizine-3-carboxylic acid, and 9,10-difluoro-6-methyl-2-oxo-6,7-dihydrobenzo[a]quinolizine-3-carboxylic acid are excluded; or pharmaceutically acceptable salts, or enantiomers thereof.

A further embodiment of present invention is (xxiv) a compound of formula I, wherein
$R^1$ is hydrogen, fluoro, chloro, bromo, methyl, methylamino, methoxy or ethoxy;
$R^2$ is hydrogen, fluoro, chloro, bromo, methyl, ethyl, trifluoromethyl, methoxy, ethoxy, propoxy, trifluoromethoxy, cyano, cyclopropyl, hydroxy or phenylmethyl-O—;
$R^3$ is hydrogen, bromo, methyl, propyl, trifluoromethyl, cyano, morpholinyl, pyrrolidinyl, phenylmethyl-N(methyl)-, tert-butoxycarbonylpiperazinyl, hydroxy, methoxy, ethoxy, propoxy, isopropoxy, isobutoxy, butoxy, difluoromethylmethyl-O—, difluoromethylethyl-O—, trifluoromethoxy, trifluoromethylmethyl-O—, trifluoromethylethyl-O—, methoxyethyl-O—, methoxypropyl-O—, ethoxyethyl-O—, methoxyethyl-O-ethyl-O—, methylcarbonylaminoethyl-O—, methylsulfonylaminoethyl-O—, methylsulfonylethyl-O—, aminocarbonylmethyl-O—, cyanomethyl-O—, cyanopropyl-O—, cyanocyclopropylmethyl-O—, cyclopropylmethyl-O—, cyclohexylethyl-O—, diethylaminoethyl-O—, hydroxyethyl-O—, hydroxypropyl-O—, hydroxy-2,2-dimethylpropyl-O—, imidazolylethyl-O—, morpholinylethyl-O—, 2-oxo-pyrrolidin-1-ylethyl-O—, phenylmethyl-O—, phenylethyl-O—, pyrrolidinylethyl-O—, pyrrolidinylcarbonylmethyl-O— or tetrahydropyran-4-ylmethyl-O—;
$R^4$ is hydrogen, fluoro, chloro, bromo, methyl or cyano;
provided that $R^1$, $R^2$, $R^3$ and $R^4$ are not hydrogen simultaneously;
$R^5$ is hydrogen or methyl;
$R^6$ is hydrogen, methyl, ethyl, propyl, isopropyl, isobutyl, trifluoromethyl, trifluoroethyl, cyclopropyl, cyclobutyl or cyclopropylmethyl;
with the proviso that 6-methyl-2-oxo-9-pyrrolidin-1-yl-6,7-dihydrobenzo[a]quinolizine-3-carboxylic acid is excluded;
or pharmaceutically acceptable salts, or enantiomers thereof.

Another embodiment of present invention is (xxv) a compound of formula I, wherein
$R^1$ is hydrogen, halogen, $C_{1-6}$alkylamino or $C_{1-6}$alkoxy;
$R^2$ is hydrogen, halogen, $C_{1-6}$alkyl, $C_{1-6}$alkoxy, $C_{3-7}$cycloalkyl, hydroxy or phenyl-$C_xH_{2x}$—O—;
$R^3$ is hydrogen; halogen; $C_{1-6}$alkyl; cyano; phenyl-$C_xH_{2x}$—N($C_{1-6}$alkyl)-; $C_{1-6}$alkoxycarbonylpiperazinyl; or
$R^7$—O—;
  wherein $R^7$ is hydrogen; $C_{1-6}$alkyl, which is unsubstituted or once or more times substituted by fluoro; or $R^8$—$C_xH_{2x}$—;
  wherein $R^8$ is $C_{1-6}$alkoxy, $C_{1-6}$alkoxy-$C_xH_{2x}$—O—, $C_{1-6}$alkylcarbonylamino, $C_{1-6}$alkylsulfonylamino, $C_{1-6}$alkylsulfonyl, cyano, cyano$C_{3-7}$cycloalkyl, $C_{3-7}$cycloalkyl, hydroxy, imidazolyl, morpholinyl, 2-oxo-pyrrolidin-1-yl, phenyl, pyrrolidinyl, pyrrolidinylcarbonyl or tetrahydropyran-4-yl;
$R^4$ is hydrogen, halogen, $C_{1-6}$alkyl or cyano;
provided that $R^1$, $R^2$, $R^3$ and $R^4$ are not hydrogen simultaneously;

R$^5$ is hydrogen or C$_{1-6}$alkyl;
R$^6$ is hydrogen; C$_{1-6}$alkyl, which is unsubstituted or once or more times substituted by fluoro; or C$_{3-7}$cycloalkyl;
x is 1-6;
with the proviso that 9-fluoro-6-methyl-2-oxo-6,7-dihydrobenzo[a]quinolizine-3-carboxylic acid and 9,10-difluoro-6-methyl-2-oxo-6,7-dihydrobenzo[a]quinolizine-3-carboxylic acid are excluded;
or pharmaceutically acceptable salts, or enantiomers thereof.

A further embodiment of present invention is (xxvi) a compound of formula I, wherein
R$^1$ is hydrogen, chloro, bromo, methylamino, methoxy or ethoxy;
R$^2$ is hydrogen, fluoro, chloro, methyl, ethyl, methoxy, ethoxy, propoxy, cyclopropyl, hydroxy or phenylmethyl-O—;
R$^3$ is hydrogen, bromo, methyl, propyl, cyano, phenylmethyl-N(methyl)-, tert-butoxycarbonylpiperazinyl, hydroxy, methoxy, ethoxy, propoxy, isopropoxy, isobutoxy, butoxy, difluoromethylmethyl-O—, trifluoromethylmethyl-O—, methoxyethyl-O—, methoxypropyl-O—, ethoxyethyl-O—, methoxyethyl-O-ethyl-O—, methylcarbonylaminoethyl-O—, methylsulfonylaminoethyl-O—, methylsulfonylethyl-O—, cyanomethyl-O—, cyanopropyl-O—, cyanocyclopropylmethyl-O—, cyclopropylmethyl-O—, cyclohexylethyl-O—, hydroxyethyl-O—, hydroxypropyl-O—, hydroxy-2,2-dimethylpropyl-O—, imidazolylethyl-O—, morpholinylethyl-O—, 2-oxo-pyrrolidin-1-ylethyl-O—, phenylmethyl-O—, phenylethyl-O—, pyrrolidinylethyl-O—, pyrrolidinyl carb onylmethyl-O— or tetrahydropyran-4-ylmethyl-O—;
R$^4$ is hydrogen, chloro, bromo, methyl or cyano;
provided that R$^1$, R$^2$, R$^3$ and R$^4$ are not hydrogen simultaneously;
R$^5$ is hydrogen or methyl;
R$^6$ is hydrogen, methyl, ethyl, propyl, isopropyl, isobutyl, trifluoromethyl or cyclopropyl; or pharmaceutically acceptable salts, or enantiomers thereof.

Another embodiment of present invention is (xxvii) a compound of formula IA

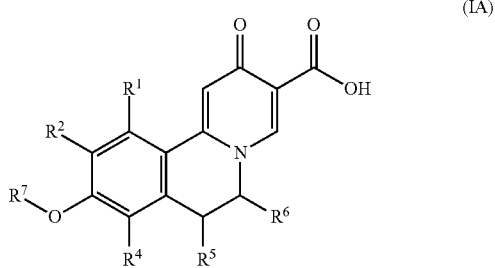

(IA)

wherein
R$^1$ is hydrogen, halogen or C$_{1-6}$alkoxy;
R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;
R$^4$ is hydrogen or halogen;
R$^5$ is hydrogen;
R$^6$ is C$_{1-6}$alkyl, which is unsubstituted or once or more times substituted by fluoro; or C$_{3-7}$cycloalkyl;
R$^7$ is hydrogen; C$_{1-6}$alkyl, which is unsubstituted or once or more times substituted by fluoro; or R$^8$—C$_x$H$_{2x}$—;
wherein R$^8$ is C$_{1-6}$alkoxy, C$_{1-6}$alkoxy-C$_x$H$_{2x}$—O—, C$_{1-6}$alkylcarbonylamino, C$_{1-6}$alkylsulfonylamino, C$_{1-6}$alkylsulfonyl, cyano, cyanoC$_{3-7}$cycloalkyl, C$_{3-7}$cycloalkyl, hydroxy, imidazolyl, morpholinyl, 2-oxo-pyrrolidin-1-yl, phenyl, pyrrolidinyl, pyrrolidinylcarbonyl or tetrahydropyran-4-yl;
x is 1-6;
or pharmaceutically acceptable salts, or enantiomers thereof.

A further embodiment of present invention is (xxviii) a compound of formula IA or pharmaceutically acceptable salts, or enantiomers thereof, wherein
R$^1$ is hydrogen, chloro or methoxy;
R$^2$ is hydrogen, fluoro, chloro, methyl, ethyl, methoxy, ethoxy, propoxy, cyclopropyl, hydroxy or phenylmethyl-O—;
R$^4$ is hydrogen or chloro;
R$^5$ is hydrogen;
R$^6$ is methyl, ethyl, propyl, isopropyl, isobutyl, trifluoromethyl or cyclopropyl;
R$^7$ is hydrogen, methyl, ethyl, propyl, isopropyl, isobutyl, butyl, difluoroethyl, trifluoroethyl, methoxyethyl, methoxypropyl, ethoxyethyl, methoxyethyl-O-ethyl, methylcarbonylaminoethyl, methylsulfonylaminoethyl, methylsulfonylethyl, cyanomethyl, cyanopropyl, cyanocyclopropylmethyl, cyclopropylmethyl, cyclohexylethyl, hydroxyethyl, hydroxypropyl, hydroxy-2,2-dimethylpropyl, imidazolylethyl, morpholinylethyl, 2-oxo-pyrrolidin-1-ylethyl, phenylmethyl, phenylethyl, pyrrolidinylethyl, pyrrolidinylcarbonylmethyl or tetrahydropyran-4-ylmethyl.

Another embodiment of present invention is (xxix) a compound of formula IA or pharmaceutically acceptable salts, or enantiomers thereof, wherein
R$^1$ is hydrogen;
R$^2$ is halogen;
R$^4$ is hydrogen;
R$^5$ is hydrogen;
R$^6$ is C$_{1-6}$alkyl;
R$^7$ is C$_{1-6}$alkyl or C$_{1-6}$alkoxy-C$_x$H$_{2x}$—;
x is 1-6.

Another embodiment of present invention is (xxx) a compound of formula IA or pharmaceutically acceptable salts, or enantiomers thereof, wherein
R$^1$ is hydrogen;
R$^2$ is C$_{1-6}$alkyl or C$_{3-7}$cycloalkyl;
R$^4$ is hydrogen;
R$^5$ is hydrogen;
R$^6$ is C$_{1-6}$alkyl;
R$^7$ is C$_{1-6}$alkyl or phenyl-C$_x$H$_{2x}$—;
x is 1-6.

Another embodiment of present invention is (xxxi) a compound of formula IA or pharmaceutically acceptable salts, or enantiomers thereof, wherein
R$^1$ is hydrogen;
R$^2$ is C$_{1-6}$alkoxy;
R$^4$ is hydrogen or halogen;
R$^5$ is hydrogen;
R$^6$ is C$_{1-6}$alkyl, which is unsubstituted or once or more times substituted by fluoro; or C$_{3-7}$cycloalkyl;
R$^7$ is hydrogen; C$_{1-6}$alkyl, which is unsubstituted or once or more times substituted by fluoro; or R$^8$—C$_x$H$_{2x}$—;
wherein R$^8$ is C$_{1-6}$alkoxy, C$_{1-6}$alkoxy-C$_x$H$_{2x}$—O—, C$_{1-6}$alkylcarbonylamino, C$_{1-6}$alkylsulfonylamino, C$_{1-6}$alkylsulfonyl, cyano, cyanoC$_{3-7}$cycloalkyl, C$_{3-7}$cycloalkyl, hydroxy, imidazolyl, morpholinyl, 2-oxo-pyrrolidin-1-yl, phenyl, pyrrolidinyl, pyrrolidinylcarbonyl or tetrahydropyran-4-yl;

x is 1-6.

A further embodiment of present invention is (xxxii) a compound of formula IA or pharmaceutically acceptable salts, or enantiomers thereof, wherein $R^1$ is hydrogen;
$R^2$ is methoxy, ethoxy or propoxy;
$R^4$ is hydrogen or chloro;
$R^5$ is hydrogen;
$R^6$ is methyl, ethyl, propyl, isopropyl, isobutyl, trifluoromethyl or cyclopropyl;
$R^7$ is hydrogen, methyl, ethyl, propyl, isopropyl, isobutyl, butyl, difluoroethyl, trifluoroethyl, methoxyethyl, methoxypropyl, ethoxyethyl, methoxyethyl-O-ethyl, methylcarbonylaminoethyl, methylsulfonylaminoethyl, methylsulfonylethyl, cyanomethyl, cyanopropyl, cyanocyclopropylmethyl, cyclopropylmethyl, cyclohexylethyl, hydroxyethyl, hydroxypropyl, hydroxy-2,2-dimethylpropyl, imidazolylethyl, morpholinylethyl, 2-oxo-pyrrolidin-1-ylethyl, phenylmethyl, phenylethyl, pyrrolidinylethyl, pyrrolidinylcarbonylmethyl or tetrahydropyran-4-ylmethyl.

Another embodiment of present invention is (xxxiii) a compound of formula I or pharmaceutically acceptable salts, or enantiomers thereof, wherein $R^1$ is hydrogen;
$R^2$ is $C_{1-6}$alkoxy;
$R^3$ is $C_{1-6}$alkoxy;
$R^4$ is hydrogen;
$R^5$ is hydrogen or $C_{1-6}$alkyl;
$R^6$ is hydrogen.

Another embodiment of present invention is (xxxiv) a compound of formula I or pharmaceutically acceptable salts, or enantiomers thereof, wherein $R^1$ is hydrogen, halogen, $C_{1-6}$alkylamino or $C_{1-6}$alkoxy;
$R^2$ is hydrogen, $C_{1-6}$alkyl or $C_{1-6}$alkoxy;
$R^3$ is hydrogen, bromo, $C_{1-6}$alkyl, $C_{1-6}$alkoxycarbonylpiperazinyl, cyano or phenyl-$C_xH_{2x}$—N($C_{1-6}$alkyl)-;
$R^4$ is hydrogen, halogen, $C_{1-6}$alkyl or cyano;
provided that $R^1$, $R^2$, $R^3$ and $R^4$ are not hydrogen simultaneously;
$R^5$ is hydrogen;
$R^6$ is $C_{1-6}$alkyl;
x is 1-6.

A further embodiment of present invention is (xxxv) a compound of formula I or pharmaceutically acceptable salts, or enantiomers thereof, wherein $R^1$ is hydrogen, bromo, methylamino or ethoxy;
$R^2$ is hydrogen, methyl or methoxy;
$R^3$ is hydrogen, bromo, methyl, propyl, tert-butoxycarbonylpiperazinyl, cyano or phenylmethyl-N(methyl)-;
$R^4$ is hydrogen, bromo, methyl or cyano;
provided that $R^1$, $R^2$, $R^3$ and $R^4$ are not hydrogen simultaneously;
$R^5$ is hydrogen;
$R^6$ is methyl or ethyl.

Particular compounds of formula I according to the invention are the following:

9-Benzyloxy-10-methoxy-6-methyl-2-oxo-6,7-dihydrobenzo[a]quinolizine-3-carboxylic acid;
9-Hydroxy-10-methoxy-6-methyl-2-oxo-6,7-dihydrobenzo[a]quinolizine-3-carboxylic acid;
9,11-Dimethoxy-6-methyl-2-oxo-6,7-dihydrobenzo[a]quinolizine-3-carboxylic acid;
9-Ethoxy-10-methoxy-6-methyl-2-oxo-6,7-dihydrobenzo[a]quinolizine-3-carboxylic acid;
9,10-Diethoxy-6-ethyl-2-oxo-6,7-dihydrobenzo[a]quinolizine-3-carboxylic acid;
(+)-9,10-Diethoxy-6-ethyl-2-oxo-6,7-dihydrobenzo[a]quinolizine-3-carboxylic acid;
(−)-9,10-Diethoxy-6-ethyl-2-oxo-6,7-dihydrobenzo[a]quinolizine-3-carboxylic acid;
9-Benzyloxy-6-ethyl-10-methoxy-2-oxo-6,7-dihydrobenzo[a]quinolizine-3-carboxylic acid;
(+)-9-Benzyloxy-6-ethyl-10-methoxy-2-oxo-6,7-dihydrobenzo[a]quinolizine-3-carboxylic acid;
(−)-9-Benzyloxy-6-ethyl-10-methoxy-2-oxo-6,7-dihydrobenzo[a]quinolizine-3-carboxylic acid;
(+)-6-Ethyl-10-methoxy-2-oxo-9-(2,2,2-trifluoroethoxy)-6,7-dihydrobenzo[a]quinolizine-3-carboxylic acid;
(−)-6-Ethyl-10-methoxy-2-oxo-9-(2,2,2-trifluoroethoxy)-6,7-dihydrobenzo[a]quinolizine-3-carboxylic acid;
6-Ethyl-9-isopropoxy-10-methoxy-2-oxo-6,7-dihydrobenzo[a]quinolizine-3-carboxylic acid;
6-Ethyl-10-methoxy-2-oxo-9-(2-phenylethoxy)-6,7-dihydrobenzo[a]quinolizine-3-carboxylic acid;
9-Butoxy-6-ethyl-10-methoxy-2-oxo-6,7-dihydrobenzo[a]quinolizine-3-carboxylic acid;
9-(2-Cyclohexylethoxy)-6-ethyl-10-methoxy-2-oxo-6,7-dihydrobenzo[a]quinolizine-3-carboxylic acid;
6-Ethyl-10-methoxy-2-oxo-9-prop-2-ynoxy-6,7-dihydrobenzo[a]quinolizine-3-carboxylic acid;
6-Ethyl-10-methoxy-2-oxo-9-(2-oxo-2-pyrrolidin-1-ylethoxy)-6,7-dihydrobenzo[a]quinolizine-3-carboxylic acid;
6-Ethyl-10-methoxy-9-[2-(2-methoxyethoxy)ethoxy]-2-oxo-6,7-dihydrobenzo[a]quinolizine-3-carboxylic acid;
6-Ethyl-10-methoxy-9-(2-morpholinoethoxy)-2-oxo-6,7-dihydrobenzo[a]quinolizine-3-carboxylic acid;
6-Ethyl-9-(2-hydroxyethoxy)-10-methoxy-2-oxo-6,7-dihydrobenzo[a]quinolizine-3-carboxylic acid;
6-Ethyl-9-(3-hydroxy-2,2-dimethyl-propoxy)-10-methoxy-2-oxo-6,7-dihydrobenzo[a]quinolizine-3-carboxylic acid;
(+)-6-Ethyl-9-(3-hydroxy-2,2-dimethyl-propoxy)-10-methoxy-2-oxo-6,7-dihydrobenzo[a]quinolizine-3-carboxylic acid;
(−)-6-Ethyl-9-(3-hydroxy-2,2-dimethyl-propoxy)-10-methoxy-2-oxo-6,7-dihydrobenzo[a]quinolizine-3-carboxylic acid;
6-Ethyl-9-(3-hydroxypropoxy)-10-methoxy-2-oxo-6,7-dihydrobenzo[a]quinolizine-3-carboxylic acid;
6-Ethyl-9-(2-imidazol-1-ylethoxy)-10-methoxy-2-oxo-6,7-dihydrobenzo[a]quinolizine-3-carboxylic acid;
6-Ethyl-10-methoxy-9-(2-methoxyethoxy)-2-oxo-6,7-dihydrobenzo[a]quinolizine-3-carboxylic acid;
(+)-6-Ethyl-10-methoxy-9-(2-methoxyethoxy)-2-oxo-6,7-dihydrobenzo[a]quinolizine-3-carboxylic acid;
(−)-6-Ethyl-10-methoxy-9-(2-methoxyethoxy)-2-oxo-6,7-dihydrobenzo[a]quinolizine-3-carboxylic acid;
9-(Cyclopropylmethoxy)-6-ethyl-10-methoxy-2-oxo-6,7-dihydrobenzo[a]quinolizine-3-carboxylic acid;
(+)-9-(Cyclopropylmethoxy)-6-ethyl-10-methoxy-2-oxo-6,7-dihydrobenzo[a]quinolizine-3-carboxylic acid;
(−)-9-(Cyclopropylmethoxy)-6-ethyl-10-methoxy-2-oxo-6,7-dihydrobenzo[a]quinolizine-3-carboxylic acid;
6-Ethyl-9-isobutoxy-10-methoxy-2-oxo-6,7-dihydrobenzo[a]quinolizine-3-carboxylic acid;
(+)-6-Ethyl-9-isobutoxy-10-methoxy-2-oxo-6,7-dihydrobenzo[a]quinolizine-3-carboxylic acid;
(−)-6-Ethyl-9-isobutoxy-10-methoxy-2-oxo-6,7-dihydrobenzo[a]quinolizine-3-carboxylic acid;

9-Ethoxy-6-ethyl-10-methoxy-2-oxo-6,7-dihydrobenzo[a]quinolizine-3-carboxylic acid;
(+)-9-Ethoxy-6-ethyl-10-methoxy-2-oxo-6,7-dihydrobenzo[a]quinolizine-3-carboxylic acid;
(−)-9-Ethoxy-6-ethyl-10-methoxy-2-oxo-6,7-dihydrobenzo[a]quinolizine-3-carboxylic acid;
6-Ethyl-10-methoxy-9-(3-methoxypropoxy)-2-oxo-6,7-dihydrobenzo[a]quinolizine-3-carboxylic acid;
(+)-6-Ethyl-10-methoxy-9-(3-methoxypropoxy)-2-oxo-6,7-dihydrobenzo[a]quinolizine-3-carboxylic acid;
(−)-6-Ethyl-10-methoxy-9-(3-methoxypropoxy)-2-oxo-6,7-dihydrobenzo[a]quinolizine-3-carboxylic acid;
9-(2-Ethoxyethoxy)-6-ethyl-10-methoxy-2-oxo-6,7-dihydrobenzo[a]quinolizine-3-carboxylic acid;
(+)-9-(2-Ethoxyethoxy)-6-ethyl-10-methoxy-2-oxo-6,7-dihydrobenzo[a]quinolizine-3-carboxylic acid;
(−)-9-(2-Ethoxyethoxy)-6-ethyl-10-methoxy-2-oxo-6,7-dihydrobenzo[a]quinolizine-3-carboxylic acid;
9-(2,2-Difluoroethoxy)-6-ethyl-10-methoxy-2-oxo-6,7-dihydrobenzo[a]quinolizine-3-carboxylic acid;
(+)-9-(2,2-Difluoroethoxy)-6-ethyl-10-methoxy-2-oxo-6,7-dihydrobenzo[a]quinolizine-3-carboxylic acid;
(−)-9-(2,2-Difluoroethoxy)-6-ethyl-10-methoxy-2-oxo-6,7-dihydrobenzo[a]quinolizine-3-carboxylic acid;
6-Ethyl-10-methoxy-2-oxo-9-(tetrahydropyran-4-ylmethoxy)-6,7-dihydrobenzo[a]quinolizine-3-carboxylic acid;
(+)-6-Ethyl-10-methoxy-2-oxo-9-(tetrahydropyran-4-ylmethoxy)-6,7-dihydrobenzo[a]quinolizine-3-carboxylic acid;
(−)-6-Ethyl-10-methoxy-2-oxo-9-(tetrahydropyran-4-ylmethoxy)-6,7-dihydrobenzo[a]quinolizine-3-carboxylic acid;
6-Ethyl-10-methoxy-2-oxo-9-(2-pyrrolidin-1-ylethoxy)-6,7-dihydrobenzo[a]quinolizine-3-carboxylic acid;
9-(3-Cyanopropoxy)-6-ethyl-10-methoxy-2-oxo-6,7-dihydrobenzo[a]quinolizine-3-carboxylic acid;
6-Ethyl-10-methoxy-9-(2-methylsulfonylethoxy)-2-oxo-6,7-dihydrobenzo[a]quinolizine-3-carboxylic acid;
6-Ethyl-10-methoxy-2-oxo-9-[2-(2-oxopyrrolidin-1-yl)ethoxy]-6,7-dihydrobenzo[a]quinolizine-3-carboxylic acid;
(+)-6-Ethyl-10-methoxy-2-oxo-9-[2-(2-oxopyrrolidin-1-yl)ethoxy]-6,7-dihydrobenzo[a]quinolizine-3-carboxylic acid;
6-Ethyl-9-[2-(methanesulfonamido)ethoxy]-10-methoxy-2-oxo-6,7-dihydrobenzo[a]quinolizine-3-carboxylic acid;
9-[(1-Cyanocyclopropyl)methoxy]-6-ethyl-10-methoxy-2-oxo-6,7-dihydrobenzo[a]quinolizine-3-carboxylic acid;
9-(2-Acetamidoethoxy)-6-ethyl-10-methoxy-2-oxo-6,7-dihydrobenzo[a]quinolizine-3-carboxylic acid;
10-Chloro-9-methoxy-6-methyl-2-oxo-6,7-dihydrobenzo[a]quinolizine-3-carboxylic acid;
9,10-Dimethoxy-6-methyl-2-oxo-6,7-dihydrobenzo[a]quinolizine-3-carboxylic acid;
(+)-9,10-Dimethoxy-6-methyl-2-oxo-6,7-dihydrobenzo[a]quinolizine-3-carboxylic acid;
(−)-9,10-Dimethoxy-6-methyl-2-oxo-6,7-dihydrobenzo[a]quinolizine-3-carboxylic acid;
9,10-Dimethoxy-7-methyl-2-oxo-6,7-dihydrobenzo[a]quinolizine-3-carboxylic acid;
6-Ethyl-9,10-dimethoxy-2-oxo-6,7-dihydrobenzo[a]quinolizine-3-carboxylic acid;
(6R)-(+)-6-Ethyl-9,10-dimethoxy-2-oxo-6,7-dihydrobenzo[a]quinolizine-3-carboxylic acid;
(6S)-(−)-6-Ethyl-9,10-dimethoxy-2-oxo-6,7-dihydrobenzo[a]quinolizine-3-carboxylic acid;
9-Methoxy-6,10-dimethyl-2-oxo-6,7-dihydrobenzo[a]quinolizine-3-carboxylic acid;
9,10-Diethoxy-6-methyl-2-oxo-6,7-dihydrobenzo[a]quinolizine-3-carboxylic acid;
9-Ethoxy-6-methyl-10-hydroxy-2-oxo-6,7-dihydrobenzo[a]quinolizine-3-carboxylic acid;
9,10-Diethoxy-2-oxo-6,7-dihydrobenzo[a]quinolizine-3-carboxylic acid;
2-Oxo-9,10-dipropoxy-6,7-dihydrobenzo[a]quinolizine-3-carboxylic acid;
6-Ethyl-10-methoxy-2-oxo-9-propoxy-6,7-dihydrobenzo[a]quinolizine-3-carboxylic acid;
(+)-6-Ethyl-10-methoxy-2-oxo-9-propoxyl-6,7-dihydrobenzo[a]quinolizine-3-carboxylic acid;
(−)-6-Ethyl-10-methoxy-2-oxo-9-propoxyl-6,7-dihydrobenzo[a]quinolizine-3-carboxylic acid;
8-Chloro-9-methoxy-6-methyl-2-oxo-6,7-dihydrobenzo[a]quinolizine-3-carboxylic acid;
8-Chloro-9,10-dimethoxy-6-methyl-2-oxo-6,7-dihydrobenzo[a]quinolizine-3-carboxylic acid;
10-Benzyloxy-9-methoxy-6-methyl-2-oxo-6,7-dihydrobenzo[a]quinolizine-3-carboxylic acid;
10-Ethoxy-9-methoxy-6-methyl-2-oxo-6,7-dihydrobenzo[a]quinolizine-3-carboxylic acid;
9-Methoxy-6-methyl-2-oxo-10-propoxy-6,7-dihydrobenzo[a]quinolizine-3-carboxylic acid;
6,10-Diethyl-9-methoxy-2-oxo-6,7-dihydrobenzo[a]quinolizine-3-carboxylic acid;
10-Cyclopropyl-6-ethyl-9-methoxy-2-oxo-6,7-dihydrobenzo[a]quinolizine-3-carboxylic acid;
(+)-10-Cyclopropyl-6-ethyl-9-methoxy-2-oxo-6,7-dihydrobenzo[a]quinolizine-3-carboxylic acid;
(−)-10-Cyclopropyl-6-ethyl-9-methoxy-2-oxo-6,7-dihydrobenzo[a]quinolizine-3-carboxylic acid;
9,10-Dimethoxy-2-oxo-6-propyl-6,7-dihydrobenzo[a]quinolizine-3-carboxylic acid;
6-Cyclopropyl-9,10-dimethoxy-2-oxo-6,7-dihydrobenzo[a]quinolizine-3-carboxylic acid;
6-Isopropyl-9,10-dimethoxy-2-oxo-6,7-dihydrobenzo[a]quinolizine-3-carboxylic acid;
(+)-6-Isopropyl-9,10-dimethoxy-2-oxo-6,7-dihydrobenzo[a]quinolizine-3-carboxylic acid;
(−)-6-Isopropyl-9,10-dimethoxy-2-oxo-6,7-dihydrobenzo[a]quinolizine-3-carboxylic acid;
6-Isobutyl-9,10-dimethoxy-2-oxo-6,7-dihydrobenzo[a]quinolizine-3-carboxylic acid;
(+)-6-Isobutyl-9,10-dimethoxy-2-oxo-6,7-dihydrobenzo[a]quinolizine-3-carboxylic acid;
(−)-6-Isobutyl-9,10-dimethoxy-2-oxo-6,7-dihydrobenzo[a]quinolizine-3-carboxylic acid;
10-Chloro-6-isobutyl-9-(2-methoxyethoxy)-2-oxo-6,7-dihydrobenzo[a]quinolizine-3-carboxylic acid;
(+)-10-Chloro-6-isobutyl-9-(2-methoxyethoxy)-2-oxo-6,7-dihydrobenzo[a]quinolizine-3-carboxylic acid;
(−)-10-Chloro-6-isobutyl-9-(2-methoxyethoxy)-2-oxo-6,7-dihydrobenzo[a]quinolizine-3-carboxylic acid;
10-Chloro-6-isopropyl-9-(2-methoxyethoxy)-2-oxo-6,7-dihydrobenzo[a]quinolizine-3-carboxylic acid;
(+)-10-Chloro-6-isopropyl-9-(2-methoxyethoxy)-2-oxo-6,7-dihydrobenzo[a]quinolizine-3-carboxylic acid;
(−)-10-Chloro-6-isopropyl-9-(2-methoxyethoxy)-2-oxo-6,7-dihydrobenzo[a]quinolizine-3-carboxylic acid;
10-Fluoro-6-isopropyl-9-(2-methoxyethoxy)-2-oxo-6,7-dihydrobenzo[a]quinolizine-3-carboxylic acid;
11-Chloro-6-isopropyl-9-(2-methoxyethoxy)-2-oxo-6,7-dihydrobenzo[a]quinolizine-3-carboxylic acid;

9,10-Dimethoxy-2-oxo-6-(trifluoromethyl)-6,7-dihydrobenzo[a]quinolizine-3-carboxylic acid;

9-Benzyloxy-6-ethyl-10-methyl-2-oxo-6,7-dihydrobenzo[a]quinolizine-3-carboxylic acid;

(+)-9-Benzyloxy-6-ethyl-10-methyl-2-oxo-6,7-dihydrobenzo[a]quinolizine-3-carboxylic acid;

(−)-9-Benzyloxy-6-ethyl-10-methyl-2-oxo-6,7-dihydrobenzo[a]quinolizine-3-carboxylic acid;

(+)-10-Chloro-9-ethoxy-6-ethyl-2-oxo-6,7-dihydrobenzo[a]quinolizine-3-carboxylic acid;

(−)-10-Chloro-9-ethoxy-6-ethyl-2-oxo-6,7-dihydrobenzo[a]quinolizine-3-carboxylic acid;

10-Chloro-6-isopropyl-9-(3-methoxypropoxy)-2-oxo-6,7-dihydrobenzo[a]quinolizine-3-carboxylic acid;

(+)-10-Chloro-6-isopropyl-9-(3-methoxypropoxy)-2-oxo-6,7-dihydrobenzo[a]quinolizine-3-carboxylic acid;

(−)-10-Chloro-6-isopropyl-9-(3-methoxypropoxy)-2-oxo-6,7-dihydrobenzo[a]quinolizine-3-carboxylic acid;

10-Methoxy-6-isopropyl-9-(3-methoxypropoxy)-2-oxo-6,7-dihydrobenzo[a]quinolizine-3-carboxylic acid;

(+)-10-Methoxy-6-isopropyl-9-(3-methoxypropoxy)-2-oxo-6,7-dihydrobenzo[a]quinolizine-3-carboxylic acid;

(−)-10-Methoxy-6-isopropyl-9-(3-methoxypropoxy)-2-oxo-6,7-dihydrobenzo[a]quinolizine-3-carboxylic acid;

6-Isopropyl-10-methoxy-2-oxo-9-(2,2,2-trifluoroethoxy)-6,7-dihydrobenzo[a]quinolizine-3-carboxylic acid;

(+)-6-Isopropyl-10-methoxy-2-oxo-9-(2,2,2-trifluoroethoxy)-6,7-dihydrobenzo[a]quinolizine-3-carboxylic acid;

(−)-6-Isopropyl-10-methoxy-2-oxo-9-(2,2,2-trifluoroethoxy)-6,7-dihydrobenzo[a]quinolizine-3-carboxylic acid;

(+)-6-Isopropyl-10-methoxy-9-(2-methoxyethoxy)-2-oxo-6,7-dihydrobenzo[a]quinolizine-3-carboxylic acid;

(−)-6-Isopropyl-10-methoxy-9-(2-methoxyethoxy)-2-oxo-6,7-dihydrobenzo[a]quinolizine-3-carboxylic acid;

6-tert-Butyl-10-methoxy-9-(3-methoxypropoxy)-2-oxo-6,7-dihydrobenzo[a]quinolizine-3-carboxylic acid;

(+)-6-tert-Butyl-10-methoxy-9-(3-methoxypropoxy)-2-oxo-6,7-dihydrobenzo[a]quinolizine-3-carboxylic acid;

(−)-6-tert-Butyl-10-methoxy-9-(3-methoxypropoxy)-2-oxo-6,7-dihydrobenzo[a]quinolizine-3-carboxylic acid;

10-Methoxy-9-(2-methoxyethoxy)-6-(1-methylcyclopropyl)-2-oxo-6,7-dihydrobenzo[a]quinolizine-3-carboxylic acid;

(+)-10-Methoxy-9-(2-methoxyethoxy)-6-(1-methylcyclopropyl)-2-oxo-6,7-dihydrobenzo[a]quinolizine-3-carboxylic acid;

(−)-10-Methoxy-9-(2-methoxyethoxy)-6-(1-methylcyclopropyl)-2-oxo-6,7-dihydrobenzo[a]quinolizine-3-carboxylic acid;

11-Chloro-10-fluoro-6-isopropyl-9-(3-methoxypropoxy)-2-oxo-6,7-dihydrobenzo[a]quinolizine-3-carboxylic acid;

(+)-11-Chloro-10-fluoro-6-isopropyl-9-(3-methoxypropoxy)-2-oxo-6,7-dihydrobenzo[a]quinolizine-3-carboxylic acid;

(−)-11-Chloro-10-fluoro-6-isopropyl-9-(3-methoxypropoxy)-2-oxo-6,7-dihydrobenzo[a]quinolizine-3-carboxylic acid;

10-Fluoro-6-isopropyl-9-(3-methoxypropoxy)-2-oxo-6,7-dihydrobenzo[a]quinolizine-3-carboxylic acid;

6-tert-Butyl-9-(2,2-difluoro-3-hydroxy-propoxy)-10-methoxy-2-oxo-6,7-dihydrobenzo[a]quinolizine-3-carboxylic acid;

(+)-9-(2,2-Difluoroethoxy)-6-isopropyl-10-methoxy-2-oxo-6,7-dihydrobenzo[a]quinolizine-3-carboxylic acid;

(−)-9-(2,2-Difluoroethoxy)-6-isopropyl-10-methoxy-2-oxo-6,7-dihydrobenzo[a]quinolizine-3-carboxylic acid;

9-(3-Hydroxy-2,2-dimethyl-propoxy)-6-isopropyl-10-methoxy-2-oxo-6,7-dihydrobenzo[a]quinolizine-3-carboxylic acid;

(+)-9-(3-Hydroxy-2,2-dimethyl-propoxy)-6-isopropyl-10-methoxy-2-oxo-6,7-dihydrobenzo[a]quinolizine-3-carboxylic acid;

(−)-9-(3-Hydroxy-2,2-dimethyl-propoxy)-6-isopropyl-10-methoxy-2-oxo-6,7-dihydrobenzo[a]quinolizine-3-carboxylic acid;

9-(3-Hydroxypropoxy)-6-isopropyl-10-methoxy-2-oxo-6,7-dihydrobenzo[a]quinolizine-3-carboxylic acid;

6-Isopropyl-10-methoxy-9-(4-methoxybutoxy)-2-oxo-6,7-dihydrobenzo[a]quinolizine-3-carboxylic acid;

6-tert-Butyl-9-(3-hydroxy-2,2-dimethyl-propoxy)-10-methoxy-2-oxo-6,7-dihydrobenzo[a]quinolizine-3-carboxylic acid;

(+)-6-tert-Butyl-9-(3-hydroxy-2,2-dimethyl-propoxy)-10-methoxy-2-oxo-6,7-dihydrobenzo[a]quinolizine-3-carboxylic acid;

(−)-6-tert-Butyl-9-(3-hydroxy-2,2-dimethyl-propoxy)-10-methoxy-2-oxo-6,7-dihydrobenzo[a]quinolizine-3-carboxylic acid;

6-tert-Butyl-9-(5-hydroxypentoxy)-10-methoxy-2-oxo-6,7-dihydrobenzo[a]quinolizine-3-carboxylic acid;

(+)-6-tert-Butyl-9-(5-hydroxypentoxy)-10-methoxy-2-oxo-6,7-dihydrobenzo[a]quinolizine-3-carboxylic acid;

(−)-6-tert-Butyl-9-(5-hydroxypentoxy)-10-methoxy-2-oxo-6,7-dihydrobenzo[a]quinolizine-3-carboxylic acid;

6-tert-Butyl-9-(6-hydroxyhexoxy)-10-methoxy-2-oxo-6,7-dihydrobenzo[a]quinolizine-3-carboxylic acid;

(+)-6-tert-Butyl-9-(6-hydroxyhexoxy)-10-methoxy-2-oxo-6,7-dihydrobenzo[a]quinolizine-3-carboxylic acid;

(−)-6-tert-Butyl-9-(6-hydroxyhexoxy)-10-methoxy-2-oxo-6,7-dihydrobenzo[a]quinolizine-3-carboxylic acid;

6-tert-Butyl-9-(4-hydroxybutoxy)-10-methoxy-2-oxo-6,7-dihydrobenzo[a]quinolizine-3-carboxylic acid;

6-tert-Butyl-9-(4-hydroxybut-2-ynoxy)-10-methoxy-2-oxo-6,7-dihydrobenzo[a]quinolizine-3-carboxylic acid;

9-(6-Aminohexoxy)-6-tert-butyl-10-methoxy-2-oxo-6,7-dihydrobenzo[a]quinolizine-3-carboxylic acid;

9-[6-(tert-Butoxycarbonylamino)hexoxy]-6-tert-butyl-10-methoxy-2-oxo-6,7-dihydrobenzo[a]quinolizine-3-carboxylic acid;

(+)-9-[6-(tert-Butoxycarbonylamino)hexoxy]-6-tert-butyl-10-methoxy-2-oxo-6,7-dihydrobenzo[a]quinolizine-3-carboxylic acid;

(−)-9-[6-(tert-Butoxycarbonylamino)hexoxy]-6-tert-butyl-10-methoxy-2-oxo-6,7-dihydrobenzo[a]quinolizine-3-carboxylic acid;

(+)-9-(6-Aminohexoxy)-6-tert-butyl-1-methoxy-2-oxo-6,7-dihydrobenzo[a]quinolizine-3-carboxylic acid hydrochloride;

(−)-9-(6-Aminohexoxy)-6-tert-butyl-10-methoxy-2-oxo-6,7-dihydrobenzo[a]quinolizine-3-carboxylic acid hydrochloride;

9-(8-Aminooctoxy)-6-tert-butyl-10-methoxy-2-oxo-6,7-dihydrobenzo[a]quinolizine-3-carboxylic acid;

9-[8-(tert-Butoxycarbonylamino)octoxy]-6-tert-butyl-10-methoxy-2-oxo-6,7-dihydrobenzo[a]quinolizine-3-carboxylic acid;

(+)-9-[8-(tert-Butoxycarbonylamino)octoxy]-6-tert-butyl-10-methoxy-2-oxo-6,7-dihydrobenzo[a]quinolizine-3-carboxylic acid;

(−)-9-[8-(tert-Butoxycarbonylamino)octoxy]-6-tert-butyl-10-methoxy-2-oxo-6,7-dihydrobenzo[a]quinolizine-3-carboxylic acid;

(+)-9-(8-Aminooctoxy)-6-tert-butyl-10-methoxy-2-oxo-6,7-dihydrobenzo[a]quinolizine-3-carboxylic acid hydrochloride;

(−)-9-(8-Aminooctoxy)-6-tert-butyl-10-methoxy-2-oxo-6,7-dihydrobenzo[a]quinolizine-3-carboxylic acid hydrochloride;

9-[5-(tert-Butoxycarbonylamino)pentoxy]-6-tert-butyl-10-methoxy-2-oxo-6,7-dihydrobenzo[a]quinolizine-3-carboxylic acid;

(+)-9-(5-Aminopentoxy)-6-tert-butyl-10-methoxy-2-oxo-6,7-dihydrobenzo[a]quinolizine-3-carboxylic acid hydrochloride;

(−)-9-(5-Aminopentoxy)-6-tert-butyl-10-methoxy-2-oxo-6,7-dihydrobenzo[a]quinolizine-3-carboxylic acid hydrochloride;

9-(5-Acetamidopentoxy)-6-tert-butyl-10-methoxy-2-oxo-6,7-dihydrobenzo[a]quinolizine-3-carboxylic acid;

6-tert-Butyl-9-[5-(methanesulfonamido)pentoxy]-10-methoxy-2-oxo-6,7-dihydrobenzo[a]quinolizine-3-carboxylic acid;

9-(2-Aminoethoxy)-6-tert-butyl-10-methoxy-2-oxo-6,7-dihydrobenzo[a]quinolizine-3-carboxylic acid;

9-[3-(2-Aminoethoxy)propoxy]-6-tert-butyl-10-methoxy-2-oxo-6,7-dihydrobenzo[a]quinolizine-3-carboxylic acid;

6-tert-Butyl-9-[3-[2-(ethylamino)ethoxy]propoxy]-10-methoxy-2-oxo-6,7-dihydrobenzo[a]quinolizine-3-carboxylic acid;

6-tert-Butyl-9-(3,3-difluoropropoxy)-10-methoxy-2-oxo-6,7-dihydrobenzo[a]quinolizine-3-carboxylic acid;

6-tert-Butyl-9-(1,1-difluoropropoxy)-10-methoxy-2-oxo-6,7-dihydrobenzo[a]quinolizine-3-carboxylic acid;

6-tert-Butyl-9-(1,1-difluoroallyloxy)-10-methoxy-2-oxo-6,7-dihydrobenzo[a]quinolizine-3-carboxylic acid;

6-tert-Butyl-10-methoxy-9-(3-methylsulfanylpropoxy)-2-oxo-6,7-dihydrobenzo[a]quinolizine-3-carboxylic acid;

(+)-6-tert-Butyl-10-methoxy-9-(3-methylsulfanylpropoxy)-2-oxo-6,7-dihydrobenzo[a]quinolizine-3-carboxylic acid;

(−)-6-tert-Butyl-10-methoxy-9-(3-methylsulfanylpropoxy)-2-oxo-6,7-dihydrobenzo[a]quinolizine-3-carboxylic acid;

6-tert-Butyl-10-methoxy-9-(3-methylsulfonylpropoxy)-2-oxo-6,7-dihydrobenzo[a]quinolizine-3-carboxylic acid;

(+)-6-tert-Butyl-10-methoxy-9-(3-methylsulfonylpropoxy)-2-oxo-6,7-dihydrobenzo[a]quinolizine-3-carboxylic acid;

(−)-6-tert-Butyl-10-methoxy-9-(3-methylsulfonylpropoxy)-2-oxo-6,7-dihydrobenzo[a]quinolizine-3-carboxylic acid;

6-tert-Butyl-10-methoxy-9-(2-morpholinoethoxy)-2-oxo-6,7-dihydrobenzo[a]quinolizine-3-carboxylic acid hydrochloride;

(+)-6-tert-Butyl-10-methoxy-9-(2-morpholinoethoxy)-2-oxo-6,7-dihydrobenzo[a]quinolizine-3-carboxylic acid;

(−)-6-tert-Butyl-10-methoxy-9-(2-morpholinoethoxy)-2-oxo-6,7-dihydrobenzo[a]quinolizine-3-carboxylic acid;

6-tert-Butyl-10-methoxy-9-(3-morpholinopropoxy)-2-oxo-6,7-dihydrobenzo[a]quinolizine-3-carboxylic acid hydrochloride;

(+)-6-tert-Butyl-10-methoxy-9-(3-morpholinopropoxy)-2-oxo-6,7-dihydrobenzo[a]quinolizine-3-carboxylic acid;

(−)-6-tert-Butyl-10-methoxy-9-(3-morpholinopropoxy)-2-oxo-6,7-dihydrobenzo[a]quinolizine-3-carboxylic acid;

6-tert-Butyl-10-methoxy-2-oxo-9-[3-(2-oxopyrrolidin-1-yl)propoxy]-6,7-dihydrobenzo[a]quinolizine-3-carboxylic acid;

6-tert-Butyl-10-methoxy-2-oxo-9-(3-pyrrolidin-1-ylpropoxy)-6,7-dihydrobenzo[a]quinolizine-3-carboxylic acid;

6-Cyclobutyl-10-methoxy-9-(3-methoxypropoxy)-2-oxo-6,7-dihydrobenzo[a]quinolizine-3-carboxylic acid;

9,10-Dimethoxy-2-oxo-6-(2,2,2-trifluoroethyl)-6,7-dihydrobenzo[a]quinolizine-3-carboxylic acid;

10-Methoxy-9-(3-methoxypropoxy)-2-oxo-6-(2,2,2-trifluoroethyl)-6,7-dihydrobenzo[a]quinolizine-3-carboxylic acid;

(+)-10-Methoxy-9-(3-methoxypropoxy)-2-oxo-6-(2,2,2-trifluoroethyl)-6,7-dihydrobenzo[a]quinolizine-3-carboxylic acid;

(−)-10-Methoxy-9-(3-methoxypropoxy)-2-oxo-6-(2,2,2-trifluoroethyl)-6,7-dihydrobenzo[a]quinolizine-3-carboxylic acid;

6-tert-Butyl-10-chloro-9-(3-methoxypropoxy)-2-oxo-6,7-dihydrobenzo[a]quinolizine-3-carboxylic acid;

(+)-6-tert-Butyl-10-chloro-9-(3-methoxypropoxy)-2-oxo-6,7-dihydrobenzo[a]quinolizine-3-carboxylic acid;

(−)-6-tert-Butyl-10-chloro-9-(3-methoxypropoxy)-2-oxo-6,7-dihydrobenzo[a]quinolizine-3-carboxylic acid;

10-Chloro-9-(3-methoxypropoxy)-6-(1-methylcyclopropyl)-2-oxo-6,7-dihydrobenzo[a]quinolizine-3-carboxylic acid;

(+)-10-Chloro-9-(3-methoxypropoxy)-6-(1-methylcyclopropyl)-2-oxo-6,7-dihydrobenzo[a]quinolizine-3-carboxylic acid;

(−)-10-Chloro-9-(3-methoxypropoxy)-6-(1-methylcyclopropyl)-2-oxo-6,7-dihydrobenzo[a]quinolizine-3-carboxylic acid;

10-Methoxy-9-(3-methoxypropoxy)-6-(1-methylcyclopropyl)-2-oxo-6,7-dihydrobenzo[a]quinolizine-3-carboxylic acid;

(+)-10-Methoxy-9-(3-methoxypropoxy)-6-(1-methylcyclopropyl)-2-oxo-6,7-dihydrobenzo[a]quinolizine-3-carboxylic acid;

(−)-10-Methoxy-9-(3-methoxypropoxy)-6-(1-methylcyclopropyl)-2-oxo-6,7-dihydrobenzo[a]quinolizine-3-carboxylic acid;

6-Benzyl-9,10-dimethoxy-2-oxo-6,7-dihydrobenzo[a]quinolizine-3-carboxylic acid;

10-Chloro-6-ethyl-9-(2-methoxyethoxy)-7-methyl-2-oxo-6,7-dihydrobenzo[a]quinolizine-3-carboxylic acid;

(6R*,7S*)-10-Chloro-6-ethyl-9-(2-methoxyethoxy)-7-methyl-2-oxo-6,7-dihydrobenzo[a]quinolizine-3-carboxylic acid;

(6R*,7R*)-10-Chloro-6-ethyl-9-(2-methoxyethoxy)-7-methyl-2-oxo-6,7-dihydrobenzo[a]quinolizine-3-carboxylic acid;

10,11-Difluoro-6-isopropyl-9-(3-methoxypropoxy)-2-oxo-6,7-dihydrobenzo[a]quinolizine-3-carboxylic acid;

(+)-10,11-Difluoro-6-isopropyl-9-(3-methoxypropoxy)-2-oxo-6,7-dihydrobenzo[a]quinolizine-3-carboxylic acid;

(−)-10,11-Difluoro-6-isopropyl-9-(3-methoxypropoxy)-2-oxo-6,7-dihydrobenzo[a]quinolizine-3-carboxylic acid;

6-tert-Butyl-10-methoxy-2-oxo-9-(3-pyrazol-1-ylpropoxy)-6,7-dihydrobenzo[a]quinolizine-3-carboxylic acid;

6-tert-Butyl-10-methoxy-2-oxo-9-[3-(1,2,4-triazol-1-yl)propoxy]-6,7-dihydrobenzo[a]quinolizine-3-carboxylic acid;

6-tert-Butyl-9-(3-carboxypropoxy)-10-methoxy-2-oxo-6,7-dihydrobenzo[a]quinolizine-3-carboxylic acid;

9-Bromo-6-methyl-2-oxo-6,7-dihydrobenzo[a]quinolizine-3-carboxylic acid;

11-Bromo-6-methyl-2-oxo-6,7-dihydrobenzo[a]quinolizine-3-carboxylic acid;

(+)-9-Bromo-6-methyl-2-oxo-6,7-dihydrobenzo[a]quinolizine-3-carboxylic acid;

9-(4-tert-Butoxycarbonylpiperazin-1-yl)-6-methyl-2-oxo-6,7-dihydrobenzo[a]quinolizine-3-carboxylic acid;

9-[Benzyl(methyl)amino]-6-methyl-2-oxo-6,7-dihydrobenzo[a]quinolizine-3-carboxylic acid;
6-Methyl-11-(methylamino)-2-oxo-6,7-dihydrobenzo[a]quinolizine-3-carboxylic acid;
6-Ethyl-10-methoxy-2-oxo-9-propyl-6,7-dihydrobenzo[a]quinolizine-3-carboxylic acid;
10-Methoxy-6-methyl-2-oxo-6,7-dihydrobenzo[a]quinolizine-3-carboxylic acid;
9-Bromo-6-ethyl-10-methoxy-2-oxo-6,7-dihydrobenzo[a]quinolizine-3-carboxylic acid;
9-Cyano-6-ethyl-10-methoxy-2-oxo-6,7-dihydrobenzo[a]quinolizine-3-carboxylic acid;
8-Bromo-11-ethoxy-6-ethyl-2-oxo-6,7-dihydrobenzo[a]quinolizine-3-carboxylic acid;
8-Cyano-11-ethoxy-6-ethyl-2-oxo-6,7-dihydrobenzo[a]quinolizine-3-carboxylic acid;
6-Ethyl-9,10-dimethyl-2-oxo-6,7-dihydrobenzo[a]quinolizine-3-carboxylic acid;
6-Ethyl-8,9-dimethyl-2-oxo-6,7-dihydrobenzo[a]quinolizine-3-carboxylic acid;
or pharmaceutically acceptable salt, enantiomer or diastereomer thereof.

More particularly, the invention relates to the following compounds of formula I:
9-Benzyloxy-10-methoxy-6-methyl-2-oxo-6,7-dihydrobenzo[a]quinolizine-3-carboxylic acid;
9,10-Diethoxy-6-ethyl-2-oxo-6,7-dihydrobenzo[a]quinolizine-3-carboxylic acid;
(+)-6-Ethyl-10-methoxy-2-oxo-9-(2,2,2-trifluoroethoxy)-6,7-dihydrobenzo[a]quinolizine-3-carboxylic acid;
9-Butoxy-6-ethyl-10-methoxy-2-oxo-6,7-dihydrobenzo[a]quinolizine-3-carboxylic acid;
6-Ethyl-9-(3-hydroxy-2,2-dimethyl-propoxy)-10-methoxy-2-oxo-6,7-dihydrobenzo[a]quinolizine-3-carboxylic acid;
6-Ethyl-10-methoxy-9-(2-methoxyethoxy)-2-oxo-6,7-dihydrobenzo[a]quinolizine-3-carboxylic acid;
9-(Cyclopropylmethoxy)-6-ethyl-10-methoxy-2-oxo-6,7-dihydrobenzo[a]quinolizine-3-carboxylic acid;
6-Ethyl-9-isobutoxy-10-methoxy-2-oxo-6,7-dihydrobenzo[a]quinolizine-3-carboxylic acid;
9-Ethoxy-6-ethyl-10-methoxy-2-oxo-6,7-dihydrobenzo[a]quinolizine-3-carboxylic acid;
6-Ethyl-10-methoxy-9-(3-methoxypropoxy)-2-oxo-6,7-dihydrobenzo[a]quinolizine-3-carboxylic acid;
9-(2-Ethoxyethoxy)-6-ethyl-10-methoxy-2-oxo-6,7-dihydrobenzo[a]quinolizine-3-carboxylic acid;
6-Ethyl-10-methoxy-2-oxo-9-(tetrahydropyran-4-ylmethoxy)-6,7-dihydrobenzo[a]quinolizine-3-carboxylic acid;
6-Ethyl-9,10-dimethoxy-2-oxo-6,7-dihydrobenzo[a]quinolizine-3-carboxylic acid;
(6R)-(+)-6-Ethyl-9,10-dimethoxy-2-oxo-6,7-dihydrobenzo[a]quinolizine-3-carboxylic acid;
6-Ethyl-10-methoxy-2-oxo-9-propoxy-6,7-dihydrobenzo[a]quinolizine-3-carboxylic acid;
6,10-Diethyl-9-methoxy-2-oxo-6,7-dihydrobenzo[a]quinolizine-3-carboxylic acid;
10-Cyclopropyl-6-ethyl-9-methoxy-2-oxo-6,7-dihydrobenzo[a]quinolizine-3-carboxylic acid;
6-Isopropyl-9,10-dimethoxy-2-oxo-6,7-dihydrobenzo[a]quinolizine-3-carboxylic acid;
6-Isobutyl-9,10-dimethoxy-2-oxo-6,7-dihydrobenzo[a]quinolizine-3-carboxylic acid;
10-Chloro-6-isobutyl-9-(2-methoxyethoxy)-2-oxo-6,7-dihydrobenzo[a]quinolizine-3-carboxylic acid;
10-Chloro-6-isopropyl-9-(2-methoxyethoxy)-2-oxo-6,7-dihydrobenzo[a]quinolizine-3-carboxylic acid;
10-Fluoro-6-isopropyl-9-(2-methoxyethoxy)-2-oxo-6,7-dihydrobenzo[a]quinolizine-3-carboxylic acid;
9-Benzyloxy-6-ethyl-10-methyl-2-oxo-6,7-dihydrobenzo[a]quinolizine-3-carboxylic acid;
10-Chloro-6-isopropyl-9-(3-methoxypropoxy)-2-oxo-6,7-dihydrobenzo[a]quinolizine-3-carboxylic acid;
10-Methoxy-6-isopropyl-9-(3-methoxypropoxy)-2-oxo-6,7-dihydrobenzo[a]quinolizine-3-carboxylic acid;
(+)-10-Methoxy-6-isopropyl-9-(3-methoxypropoxy)-2-oxo-6,7-dihydrobenzo[a]quinolizine-3-carboxylic acid;
6-Isopropyl-10-methoxy-2-oxo-9-(2,2,2-trifluoroethoxy)-6,7-dihydrobenzo[a]quinolizine-3-carboxylic acid;
(+)-6-Isopropyl-10-methoxy-9-(2-methoxyethoxy)-2-oxo-6,7-dihydrobenzo[a]quinolizine-3-carboxylic acid;
6-tert-Butyl-10-methoxy-9-(3-methoxypropoxy)-2-oxo-6,7-dihydrobenzo[a]quinolizine-3-carboxylic acid;
(+)-6-tert-Butyl-10-methoxy-9-(3-methoxypropoxy)-2-oxo-6,7-dihydrobenzo[a]quinolizine-3-carboxylic acid;
10-Methoxy-9-(2-methoxyethoxy)-6-(1-methylcyclopropyl)-2-oxo-6,7-dihydrobenzo[a]quinolizine-3-carboxylic acid;
(+)-10-Methoxy-9-(2-methoxyethoxy)-6-(1-methylcyclopropyl)-2-oxo-6,7-dihydrobenzo[a]quinolizine-3-carboxylic acid;
11-Chloro-10-fluoro-6-isopropyl-9-(3-methoxypropoxy)-2-oxo-6,7-dihydrobenzo[a]quinolizine-3-carboxylic acid;
10-Fluoro-6-isopropyl-9-(3-methoxypropoxy)-2-oxo-6,7-dihydrobenzo[a]quinolizine-3-carboxylic acid;
6-tert-Butyl-9-(2,2-difluoro-3-hydroxy-propoxy)-10-methoxy-2-oxo-6,7-dihydrobenzo[a]quinolizine-3-carboxylic acid;
(+)-9-(2,2-Difluoroethoxy)-6-isopropyl-10-methoxy-2-oxo-6,7-dihydrobenzo[a]quinolizine-3-carboxylic acid;
9-(3-Hydroxy-2,2-dimethyl-propoxy)-6-isopropyl-10-methoxy-2-oxo-6,7-dihydrobenzo[a]quinolizine-3-carboxylic acid;
9-(3-Hydroxypropoxy)-6-isopropyl-10-methoxy-2-oxo-6,7-dihydrobenzo[a]quinolizine-3-carboxylic acid;
6-Isopropyl-10-methoxy-9-(4-methoxybutoxy)-2-oxo-6,7-dihydrobenzo[a]quinolizine-3-carboxylic acid;
6-tert-Butyl-9-(3-hydroxy-2,2-dimethyl-propoxy)-10-methoxy-2-oxo-6,7-dihydrobenzo[a]quinolizine-3-carboxylic acid;
6-tert-Butyl-9-(5-hydroxypentoxy)-10-methoxy-2-oxo-6,7-dihydrobenzo[a]quinolizine-3-carboxylic acid;
6-tert-Butyl-9-(6-hydroxyhexoxy)-10-methoxy-2-oxo-6,7-dihydrobenzo[a]quinolizine-3-carboxylic acid;
6-tert-Butyl-9-(4-hydroxybutoxy)-10-methoxy-2-oxo-6,7-dihydrobenzo[a]quinolizine-3-carboxylic acid;
9-(6-Aminohexoxy)-6-tert-butyl-10-methoxy-2-oxo-6,7-dihydrobenzo[a]quinolizine-3-carboxylic acid;
9-[8-(tert-Butoxycarbonylamino)octoxy]-6-tert-butyl-10-methoxy-2-oxo-6,7-dihydrobenzo[a]quinolizine-3-carboxylic acid;
9-[5-(tert-Butoxycarbonylamino)pentoxy]-6-tert-butyl-10-methoxy-2-oxo-6,7-dihydrobenzo[a]quinolizine-3-carboxylic acid;
9-(5-Acetamidopentoxy)-6-tert-butyl-10-methoxy-2-oxo-6,7-dihydrobenzo[a]quinolizine-3-carboxylic acid;
6-tert-Butyl-9-[5-(methanesulfonamido)pentoxy]-10-methoxy-2-oxo-6,7-dihydrobenzo[a]quinolizine-3-carboxylic acid;
6-tert-Butyl-9-[3-[2-(ethylamino)ethoxy]prop oxy]-10-methoxy-2-oxo-6,7-dihydrobenzo[a]quinolizine-3-carboxylic acid;
6-tert-Butyl-9-(3, 3-difluoropropoxy)-10-methoxy-2-oxo-6,7-dihydrobenzo[a]quinolizine-3-carboxylic acid;

6-tert-Butyl-9-(1,1-difluoropropoxy)-10-methoxy-2-oxo-6,7-dihydrobenzo[a]quinolizine-3-carboxylic acid;
6-tert-Butyl-10-methoxy-9-(3-methylsulfanylpropoxy)-2-oxo-6,7-dihydrobenzo[a]quinolizine-3-carboxylic acid;
6-tert-Butyl-10-methoxy-9-(3-methylsulfonylpropoxy)-2-oxo-6,7-dihydrobenzo[a]quinolizine-3-carboxylic acid;
6-tert-Butyl-10-methoxy-9-(2-morpholinoethoxy)-2-oxo-6,7-dihydrobenzo[a]quinolizine-3-carboxylic acid hydrochloride;
6-tert-Butyl-10-methoxy-9-(3-morpholinopropoxy)-2-oxo-6,7-dihydrobenzo[a]quinolizine-3-carboxylic acid hydrochloride;
6-Cyclobutyl-10-methoxy-9-(3-methoxypropoxy)-2-oxo-6,7-dihydrobenzo[a]quinolizine-3-carboxylic acid;
10-Methoxy-9-(3-methoxypropoxy)-2-oxo-6-(2,2,2-trifluoroethyl)-6,7-dihydrobenzo[a]quinolizine-3-carboxylic acid;
6-tert-Butyl-10-chloro-9-(3-methoxypropoxy)-2-oxo-6,7-dihydrobenzo[a]quinolizine-3-carboxylic acid;
10-Chloro-9-(3-methoxypropoxy)-6-(1-methylcyclopropyl)-2-oxo-6,7-dihydrobenzo[a]quinolizine-3-carboxylic acid;
10-Methoxy-9-(3-methoxypropoxy)-6-(1-methylcyclopropyl)-2-oxo-6,7-dihydrobenzo[a]quinolizine-3-carboxylic acid;
(6R*,7S*)-10-Chloro-6-ethyl-9-(2-methoxyethoxy)-7-methyl-2-oxo-6,7-dihydrobenzo[a]quinolizine-3-carboxylic acid;
10,11-Difluoro-6-isopropyl-9-(3-methoxypropoxy)-2-oxo-6,7-dihydrobenzo[a]quinolizine-3-carboxylic acid;
or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^8$ and x are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Intermediates (Scheme 1)

Scheme 1

Method 1)

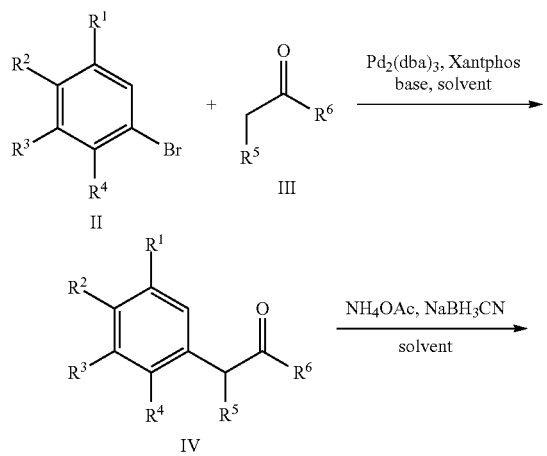

Method 2)

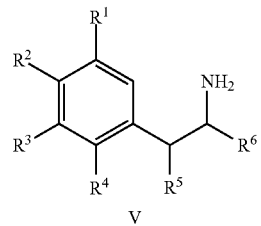

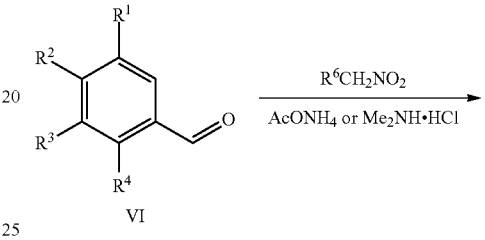

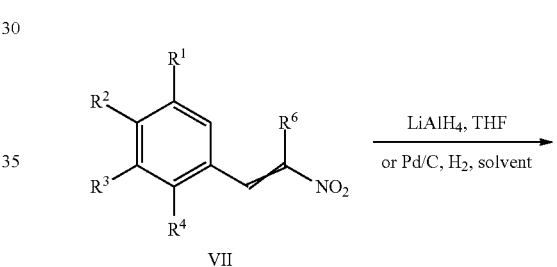

Intermediates can be prepared according to Scheme 1.

By Method 1), coupling reaction of II with III affords IV. The reaction can be carried out in the presence of Pd catalyst such as $Pd_2(dba)_3$, $Pd(PPh_3)_4$ or $PdCl_2(PPh_3)_2$, a ligand such as Xantphos, and a suitable base such as t-BuONa, $Na_2CO_3$ or $Cs_2CO_3$, in a suitable solvent such as THF, toluene or 1,4-dioxane at room temperature to 130° C. Reductive amination of IV affords Compound V.

By Method 2), Compound VI reacts with nitroalkane in the presence of ammonium acetate or dimethylamine hydrochloride affords VII, which is reduced by $LiAlH_4$ or undergoes hydrogenation in the presence of Pd/C to give V-1.

General Synthetic Route for Compounds I, Ia, Ib, Ic and Id (Scheme 2)

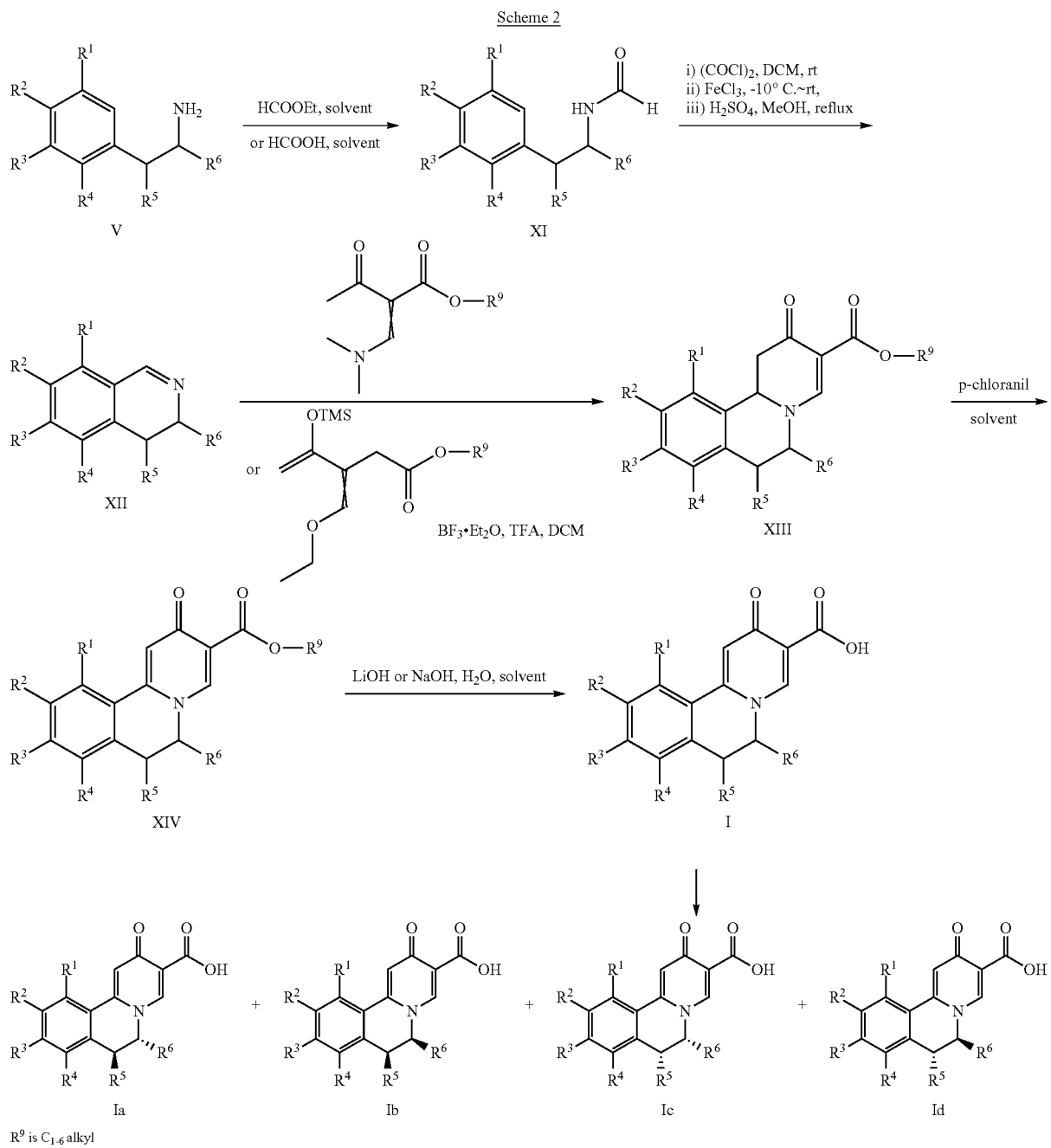

The compound of formula I, Ia, Ib, Ic and Id can be prepared according to Scheme 2. Compound V is heated with ethyl formate or formic acid in a solvent such as ethanol or dioxane affords Compound XI. Compound XI is treated with oxalyl chloride followed by $FeCl_3$ at −10° C. to room temperature, and then after separation, the intermediate is heated with a solution of concentrated $H_2SO_4$ in methanol to give Compound XII. Compound XII reacts with $C_{1-6}$alkyl 2-(dimethylaminomethylene)-3-oxo-butanoate in a solvent such as DMSO, DMF, ethanol, or reacts with $C_{1-6}$alkyl 3-(ethoxymethylene)-4-trimethylsilyloxy-pent-4-enoate, $BF_3 \cdot Et_2O$ and TFA in DCM to give Compound XIII. After dehydrogenation by p-chloranil, Compound XIV is obtained. Hydrolyzation of XIV by lithium hydroxide or sodium hydroxide in a suitable solvent such as $THF/H_2O$, $EtOH/H_2O$ or $MeOH/H_2O$ affords Compound I. Compound I can be separated by preparative HPLC and chiral HPLC to give Compounds Ia, Ib, Ic and Id.

General Synthetic Route for Compounds I-1 (Scheme 3)

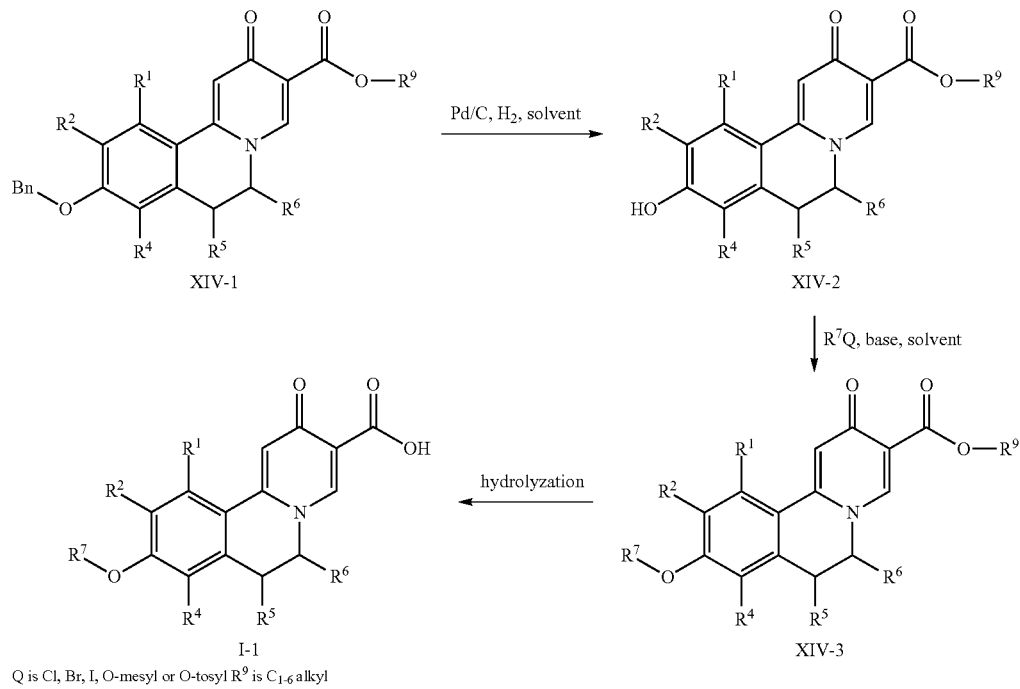

Q is Cl, Br, I, O-mesyl or O-tosyl R$^9$ is C$_{1-6}$ alkyl

The compound of formula I-1 can be prepared according to Scheme 3. Debenzylation of Compound XIV-1 by hydrogen is carried out in the presence of Pd/C in a solvent such as ethanol, THF or methanol to afford XIV-2. Then XIV-2 reacts with halides, mesylates or tosylates in the presence of a base such as K$_2$CO$_3$ and Cs$_2$CO$_3$ in a solvent such as acetone or DMF to give XIV-3. Hydrolyzation of XIV-3 by a base such as lithium hydroxide or sodium hydroxide in a suitable solvent such as THF/H$_2$O, EtOH/H$_2$O or MeOH/H$_2$O affords I-1.

This invention also relates to a process for the preparation of a compound of formula I comprising (a) hydrolysis of a compound of formula (A)

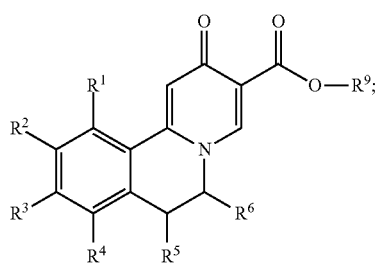

(b) hydrolysis of a compound of formula (B)

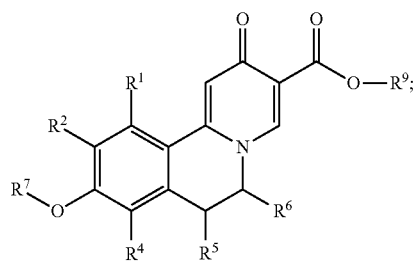

wherein R$^1$ to R$^7$ and R$^9$ are defined above unless otherwise indicated.

In step (a) and step (b) a base such as lithium hydroxide or sodium hydroxide can be for example used.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

Combination Therapy

The compounds of the invention can be combined with other anti HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti HBV agents such as HBV RNA replication inhibitor, HBsAg secretion inhibitors, HBV capsid inhibitors, antisense oligomer, siRNA, HBV therapeutic vaccine, HBV prophylactic vaccine, HBV antibody therapy (monoclonal or polyclonal) and TLR 2, 3, 7, 8 and 9 agonists for the treatment or prophylaxis of HBV.

EXAMPLES

Figure 1:
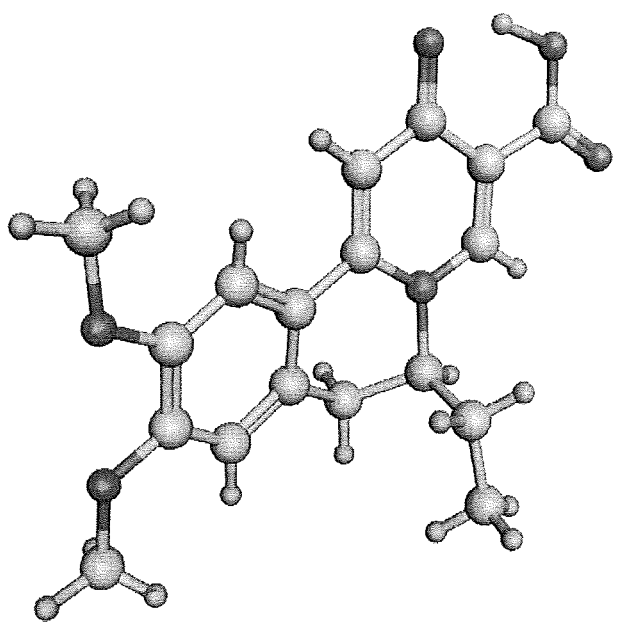
FIG. 1. X-ray structure of Example 72

The invention will be more fully understood by reference to the following examples. They should not, however, be construed as limiting the scope of the invention.

Abbreviations used herein are as follows:

μL: microliter
μm: micrometer
μM: micromoles per liter
AcOK: potassium acetate
AcOH: acetic acid
Ar: argon
BSA: bovine serum albumin
BnBr: bromomethylbenzene
CDI: di(imidazol-1-yl)methanone
DCM: dichloromethane
DIPEA: N,N-diisopropylethylamine
DMAP 4-Dimethylaminopyridine
DME: 1,2-dimethoxyethane
DMF: dimethylformamide
DMSO-d6: deuterated dimethylsulfoxide
DTT: dithiothreitol
EtOAc: ethyl acetate
EGTA: ethylene glycol tetraacetic acid
g: gram
h or hr: hour
hrs: hours
$IC_{50}$: the half maximal inhibitory concentration
HATU: 2-(7-aza-1H-benzotriazole-1-yl)-1,1,3,3-tetramethyluronium hexafluorophosphate
HCMV: human cytomegalovirus
HIV: human immunodeficiency
HSV: herpes simplex virus
HPV: human papillomavirus
HPLC: high performance liquid chromatography
LC/MS: Liquid chromatography/mass spectrometry
m-CPBA: m-chloroperoxybenzoic acid
MeOH: methanol
METHANOL-$d_4$: perdeuteromethanol
M: molarity
mg: milligram
MHz: megahertz
min: minute
mins: minutes
mL: milliliter
mM: millimoles per liter
mm: millimeter
mmol: millimole
MS (ESI): mass spectroscopy (electron spray ionization)
nM: nanomoles per liter
nm: nanometer
NMR: nuclear magnetic resonance
$N_2$: nitrogen
OD: optical density
rt: room temperature
PCC pyridinium chlorochromate
Pd/C: palladium on activated carbon
Pd(PPh$_3$)$_4$: tetrakis(triphenylphosphine)palladium
Pd(PPh$_3$)$_2$Cl$_2$: bis(triphenylphosphine)palladium(II) chloride
Pd(dppf)Cl$_2$: [1,1'-bis(diphenylphosphino)ferrocene]dichloropalladium(II)
PE or Pet: petroleum ether
prep-HPLC: preparative high performance liquid chromatography
rac. racemic
SFC: supercritical fluid chromatography
TEA: triethylamine
TFA: trifluoroacetic acid
THF: tetrahydrofuran
TLC: thin layer chromatography
δ: chemical shift
Xantphos: 9,9-dimethyl-4,5-bis(diphenylphosphino)xanthene
Pd$_2$(dba)$_3$: tris(dibenzylideneacetone)dipalladium(0)
t-BuONa: sodium t-butoxide General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™

Perp C$_{18}$ (5 μm, OBD™ 30×100 mm) column or SunFire™ Perp C$_{18}$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;

Basic condition: A: 0.05% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty or CEM Discover.

NMR Spectra were obtained using Bruker Avance 400 MHz.

A single crystal was mounted in a loop and cooled to 160 K in a nitrogen stream. Data were collected on a Gemini R Ultra diffractometer (Oxford Diffraction, UK) with Cu-K-alpha-radiation (1.54178 Å) and processed with the Crysalis-package. Structure solution and refinement was performed using the ShelXTL software (Bruker AXS, Karlsruhe).

All reactions involving air-sensitive reagents were performed under an argon atmosphere. Reagents were used as received from commercial suppliers without further purification unless otherwise noted.

Preparative Examples

Example 1: 9-benzyloxy-10-methoxy-6-methyl-2-oxo-6,7-dihydrobenzo[a]quinolizine-3-carboxylic acid

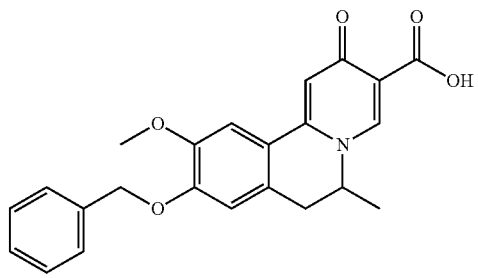 [SMILES: COc1cc2c(cc1OCc1ccccc1)CC(C)n1cc(C(=O)O)c(=O)cc1-2]

Step 1: Preparation of 2-benzyloxy-1-methoxy-4-[2-nitroprop-1-enyl]benzene

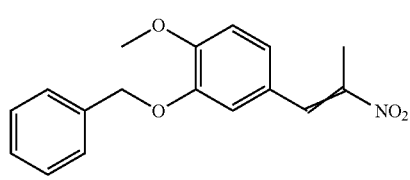 [SMILES: COc1ccc(C=C(C)[N+](=O)[O-])cc1OCc1ccccc1]

A mixture of 3-benzyloxy-4-methoxy-benzaldehyde (3.0 g, 12.4 mmol) and ammonium acetate (0.95 g, 12.4 mmol) in toluene (40 mL) was refluxed with a Dean-Stark trap for 2 hours. Then nitroethane (4.7 g, 62 mmol) was added and the resultant mixture was refluxed for additional 36 hours. The mixture was concentrated under reduced pressure, and the residue was dissolved in ethyl acetate (100 mL). The resultant solution was washed with water (60 mL), and then dried over anhydrous Na$_2$SO$_4$ and then concentrated. The residue was purified by column chromatography to give 2-benzyloxy-1-methoxy-4-[2-nitroprop-1-enyl]benzene (3.5 g).

Step 2: Preparation of 1-(3-benzyloxy-4-methoxy-phenyl)propan-2-amine

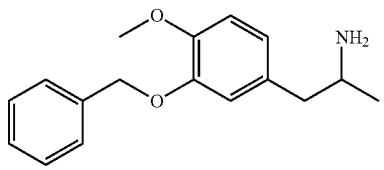 [SMILES: COc1ccc(CC(C)N)cc1OCc1ccccc1]

To a mixture of LiAlH$_4$ (1.1 g, 30 mmol) in THF (15 mL) was added a solution of 2-benzyloxy-1-methoxy-4-[2-nitroprop-1-enyl]benzene (3 g, 10 mmol) in THF (20 mL) dropwise in an ice-water bath. The mixture was refluxed for 6 hours and then stirred at room temperature for additional 16 hours. Then water (1.1 g) was added dropwise at 0° C., and then followed by addition of 15% NaOH aqueous solution (1.1 mL) and water (3.3 mL). The resultant mixture was filtered, and the filtrate was concentrated to afford crude 1-(3-benzyloxy-4-methoxy-phenyl)propan-2-amine (2.5 g) which was used in the next step without further purification.

Step 3: Preparation of N-[2-(3-benzyloxy-4-methoxy-phenyl)-1-methyl-ethyl]formamide

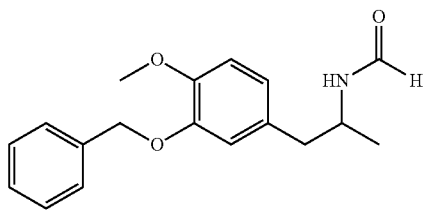 [SMILES: COc1ccc(CC(C)NC=O)cc1OCc1ccccc1]

A mixture of 1-(3-benzyloxy-4-methoxy-phenyl)propan-2-amine (2.5 g, 9.2 mmol) and formic acid (1.7 g, 37 mmol) in dioxane (200 mL) was refluxed for 16 hours and then concentrated under reduced pressure to afford the crude N-[2-(3-benzyloxy-4-methoxy-phenyl)-1-methyl-ethyl]formamide (2.7 g), which was used in the next step without purification.

Step 4: Preparation of 6-benzyloxy-7-methoxy-3-methyl-3,4-dihydroisoquinoline

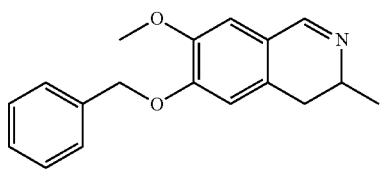 [SMILES: COc1cc2c(cc1OCc1ccccc1)CC(C)N=C2]

To a solution of N-[2-(3-benzyloxy-4-methoxy-phenyl)-1-methyl-ethyl]formamide (2.7 g, 9.0 mmol) in acetonitrile (50 mL) was added POCl₃ (2.3 g, 15.3 mmol) dropwise at 0-5° C. The resultant mixture was refluxed for 4 hours and then concentrated. Ethyl acetate (50 mL) was added to the mixture, and then followed by addition of ammonia to adjust the pH of the aqueous solution to around 11. The aqueous layer was extracted with ethyl acetate (50 mL×3). The organic layers were combined and concentrated. The residue was purified by column chromatography to give 6-benzyloxy-7-methoxy-3-methyl-3,4-dihydroisoquinoline (1.8 g).

Step 5: Preparation of ethyl 9-benzyloxy-10-methoxy-6-methyl-2-oxo-1,6,7,11b-tetrahydrobenzo[a]quinolizine-3-carboxylate

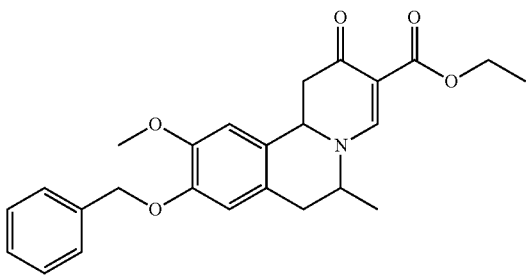

A mixture of 6-benzyloxy-7-methoxy-3-methyl-3,4-dihydroisoquinoline (1.8 g, 6.4 mmol) and ethyl 2-(ethoxymethylene)-3-oxo-butanoate (1.3 g, 7.0 mmol) in EtOH (20 mL) was refluxed overnight. The mixture was concentrated to give crude ethyl 9-benzyloxy-10-methoxy-6-methyl-2-oxo-1,6,7,11b-tetrahydrobenzo[a]quinolizine-3-carboxylate as dark brown oil which was used in the next step without purification.

Step 6: Preparation of ethyl 9-benzyloxy-10-methoxy-6-methyl-2-oxo-6,7-dihydrobenzo[a]quinolizine-3-carboxylate

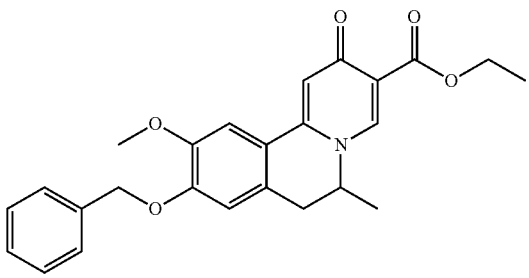 [SMILES: CCOC(=O)C1=CN2C(C)Cc3cc(OCc4ccccc4)c(OC)cc3C2CC1=O]

A mixture of crude ethyl 9-benzyloxy-10-methoxy-6-methyl-2-oxo-1,6,7,11b-tetrahydrobenzo[a]quinolizine-3-carboxylate from Step 5 and p-chloranil (1.0 g, 4.2 mmol) in DME (10 mL) was refluxed for 2 hours. After being cooled to room temperature, the suspension was filtered with suction. The filter cake was washed with cold DME and then dried under vacuum to give ethyl 9-benzyloxy-10-methoxy-6-methyl-2-oxo-6,7-dihydrobenzo[a]quinolizine-3-carboxylate as a yellow solid (0.5 g).

Step 7: Preparation of 9-benzyloxy-10-methoxy-6-methyl-2-oxo-6,7-dihydrobenzo[a]quinolizine-3-carboxylic acid

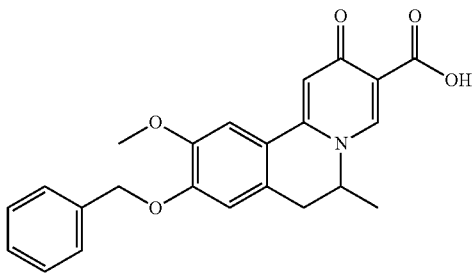 [SMILES: COc1cc2c(cc1OCc1ccccc1)CC(C)n1cc(C(=O)O)c(=O)cc1-2]

To a solution of ethyl 9-benzyloxy-10-methoxy-6-methyl-2-oxo-6,7-dihydrobenzo[a]quinolizine-3-carboxylate (50 mg, 0.13 mmol) in THF (2 mL), was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous Na₂SO₄ and then concentrated. The residue was purified by prep-HPLC to give 9-benzyloxy-10-methoxy-6-methyl-2-oxo-6,7-dihydrobenzo[a]quinolizine-3-carboxylic acid (20 mg) as a light yellow solid. $^1$H NMR (400 MHz, DMSO-$d_6$): δ 8.84 (s, 1H), 7.56 (s, 1H), 7.48-7.35 (m, 6H), 7.15 (s, 1H), 5.18 (s, 2H), 5.01-4.91 (m, 1H), 3.89 (s, 3H), 3.41-3.37 (m, 1H), 2.91-2.87 (m, 1H), 1.20 (d, 3H). MS obsd. (ESI⁺) [(M+H)⁺]: 392.

Example 2: 9-hydroxy-10-methoxy-6-methyl-2-oxo-6,7-dihydrobenzo[a]quinolizine-3-carboxylic acid

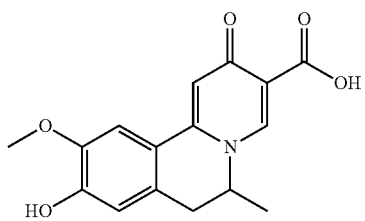 [SMILES: COc1cc2c(cc1O)CC(C)n1cc(C(=O)O)c(=O)cc1-2]

A mixture of 9-benzyloxy-10-methoxy-6-methyl-2-oxo-6,7-dihydrobenzo[a]quinolizine-3-carboxylic acid (200 mg, 0.5 mmol) and 10% palladium on carbon (50 mg) in THF/MeOH (10 mL, V/V=1/1) was stirred under hydrogen atmosphere for 12 hours. The mixture was filtered through celite pad, and the filtrate was concentrated under reduced pressure. The residue was purified by prep-HPLC to afford 9-hydroxy-10-methoxy-6-methyl-2-oxo-6,7-dihydrobenzo[a]quinolizine-3-carboxylic acid (80 mg) as a light yellow solid. $^1$H NMR (400 MHz, MeOD-$d_4$): δ 8.80 (s, 1H), 7.47 (s, 1H), 7.33 (s, 1H), 6.83 (s, 1H), 4.91-4.83 (m, 1H), 3.99 (s, 3H), 3.45-3.39 (m, 1H), 2.91-2.87 (m, 1H), 1.35 (d, 3H). MS obsd. (ESI⁺) [(M+H)⁺]: 302.

Example 3: 9,11-dimethoxy-6-methyl-2-oxo-6,7-dihydrobenzo[a]quinolizine-3-carboxylic acid

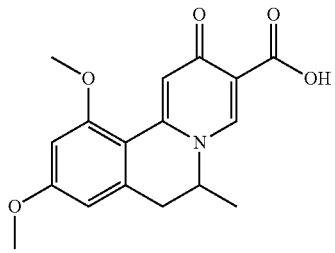 [SMILES: COc1cc2c(c(OC)c1)-c1cc(=O)c(C(=O)O)cn1C(C)C2]

Step 1: Preparation of 1,3-dimethoxy-5-[2-nitroprop-1-enyl]benzene

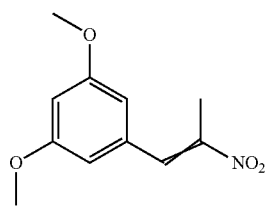 [SMILES: COc1cc(C=C(C)[N+](=O)[O-])cc(OC)c1]

A mixture of 3,5-dimethoxybenzaldehyde (10.0 g, 60.2 mmol) and ammonium acetate (4.6 g, 60.2 mmol) in toluene (30 mL) was refluxed with a Dean-Stark trap for 2 hours. Then nitroethane (23 g, 300 mmol) was added and the resultant mixture was refluxed for additional 36 hours. The mixture was concentrated under reduced pressure, and the residue was dissolved in ethyl acetate (100 mL). The resultant solution was washed with water (60 mL), and then dried over anhydrous $Na_2SO_4$ and then concentrated. The residue was purified by column chromatography to give 1,3-dimethoxy-5-[2-nitroprop-1-enyl]benzene (12 g).

Step 2: Preparation of 1-(3,5-dimethoxyphenyl)propan-2-amine

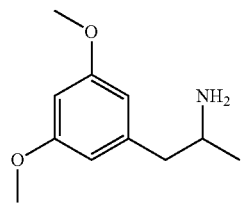

To a mixture of $LiAlH_4$ (6.1 g, 161 mmol) in THF (30 mL) was added a solution of 1,3-dimethoxy-5-[2-nitroprop-1-enyl]benzene (12 g, 53.8 mmol) in THF (120 mL) dropwise in an ice-water bath. The mixture was refluxed for 6 hours and then stirred at room temperature for additional 16 hours. Then water (6.1 g) was added dropwise at 0° C. to the mixture, and then followed by addition of 15% NaOH aqueous solution (6.1 mL) and water (18.3 mL). The resultant mixture was filtered, and the filtrate was concentrated to afford crude 1-(3,5-dimethoxyphenyl)propan-2-amine (8.6 g) which was used in the next step without further purification.

Step 3: Preparation of N-[2-(3,5-dimethoxyphenyl)-1-methyl-ethyl]formamide

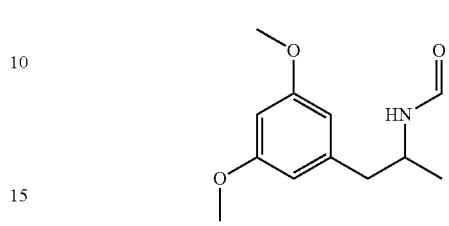

A mixture of 1-(3,5-dimethoxyphenyl)propan-2-amine (2.4 g, 12.2 mmol) and formic acid (2.2 g, 49 mmol) in dioxane (30 mL) was refluxed for 16 hours and then concentrated under reduced pressure to afford the crude N-[2-(3,5-dimethoxyphenyl)-1-methyl-ethyl]formamide (2.7 g) which was used in the next step without purification.

Step 4: Preparation of 6,8-dimethoxy-3-methyl-3,4-dihydroisoquinoline

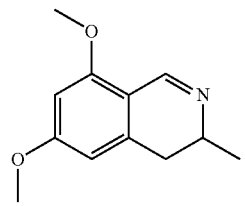

To a solution of N-[2-(3,5-dimethoxyphenyl)-1-methyl-ethyl]formamide (2.7 g, 12.2 mmol) in acetonitrile (30 mL) was added $POCl_3$ (2.2 g, 14.6 mmol) dropwise at 0-5° C. The resultant mixture was refluxed for 4 hours and then concentrated. Ethyl acetate (50 mL) was added to the mixture, and then followed by addition of ammonia to adjust the pH of the aqueous solution to around 11. The aqueous layer was extracted with ethyl acetate (50 mL×3). The organic layers were combined and concentrated. The residue was purified by column chromatography to give 6,8-dimethoxy-3-methyl-3,4-dihydroisoquinoline (1.4 g).

Step 5: Preparation of ethyl 9,11-dimethoxy-6-methyl-2-oxo-1,6,7,11b-tetrahydrobenzo[a]quinolizine-3-carboxylate

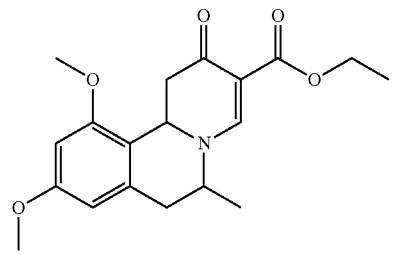 [SMILES: CCOC(=O)C1=CN2C(C)Cc3cc(OC)cc(OC)c3C2CC1=O]

A mixture of 6,8-dimethoxy-3-methyl-3,4-dihydroisoquinoline (1.4 g, 6.8 mmol) and ethyl 2-(ethoxymethylene)-3-oxo-butanoate (1.9 g, 10.2 mmol) in EtOH (20 mL) was refluxed overnight. The mixture was concentrated to give crude ethyl 9,11-dimethoxy-6-methyl-2-oxo-1,6,7,11b-tetrahydrobenzo[a]quinolizine-3-carboxylate as dark brown oil which was used in the next step without purification.

Step 6: Preparation of ethyl 9,11-dimethoxy-6-methyl-2-oxo-6,7-dihydrobenzo[a]quinolizine-3-carboxylate

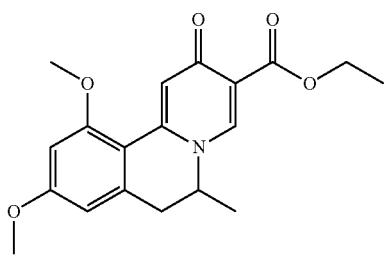 [SMILES: CCOC(=O)c1cn2c(cc1=O)-c1c(cc(OC)cc1OC)CC2C]

A mixture of crude ethyl 9,11-dimethoxy-6-methyl-2-oxo-1,6,7,11b-tetrahydrobenzo[a]quinolizine-3-carboxylate from Step 5 and p-chloranil (1.0 g, 4.2 mmol) in DME (10 mL) was refluxed for 2 hours. After being cooled to room temperature, the suspension was filtered with suction. The filter cake was washed with cold DME and then dried under vacuum to give ethyl 9,11-dimethoxy-6-methyl-2-oxo-6,7-dihydrobenzo[a]quinolizine-3-carboxylate as a yellow solid (0.5 g).

Step 7: Preparation of 9,11-dimethoxy-6-methyl-2-oxo-6,7-dihydrobenzo[a]quinolizine-3-carboxylic acid

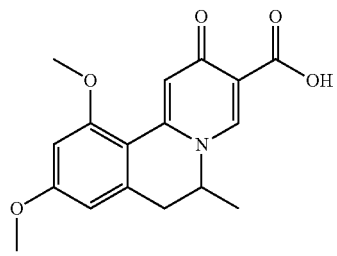 [SMILES: COc1cc2c(c(OC)c1)-c1cc(=O)c(C(=O)O)cn1C(C)C2]

To a solution of ethyl 9,11-dimethoxy-6-methyl-2-oxo-6,7-dihydrobenzo[a]quinolizine-3-carboxylate (50 mg, 0.14 mmol) in THF (2 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous $Na_2SO_4$ and then concentrated. The residue was purified by prep-HPLC to give 9,11-dimethoxy-6-methyl-2-oxo-6,7-dihydrobenzo[a]quinolizine-3-carboxylic acid (30 mg) as a light yellow solid. $^1$H NMR (400 MHz, DMSO-$d_6$): δ 8.83 (s, 1H), 7.54 (s, 1H), 6.69 (d, 1H), 6.64 (d, 1H), 4.91-4.88 (m, 1H), 3.95 (s, 3H), 3.88 (s, 3H), 3.34-3.30 (m, 1H), 2.93-2.89 (m, 1H), 1.17 (d, 3H). MS obsd. (ESI$^+$) [(M+H)$^+$]: 316.

Example 4: 9-ethoxy-10-methoxy-6-methyl-2-oxo-6,7-dihydrobenzo[a]quinolizine-3-carboxylic acid

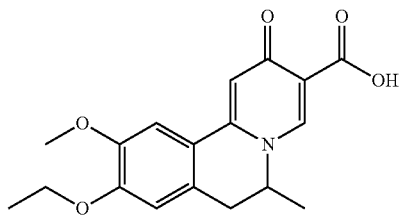 [SMILES: CCOc1cc2c(cc1OC)-c1cc(=O)c(C(=O)O)cn1C(C)C2]

Step 1: Preparation of ethyl 9-hydroxy-10-methoxy-6-methyl-2-oxo-6,7-dihydrobenzo[a]quinolizine-3-carboxylate

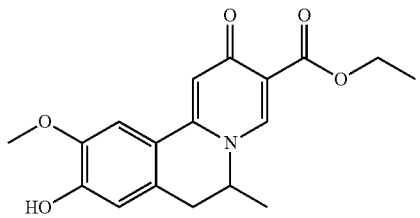 [SMILES: CCOC(=O)c1cn2c(cc1=O)-c1cc(OC)c(O)cc1CC2C]

A mixture of ethyl 9-benzyloxy-10-methoxy-6-methyl-2-oxo-6,7-dihydrobenzo[a]quinolizine-3-carboxylate (500 mg, 1.2 mmol) and 10% palladium on carbon (20 mg) in THF/MeOH (1/1, 5 mL) was stirred under hydrogen atmosphere for 12 hours. The mixture was filtered through celite pad, and the filtrate was concentrated under reduced pressure. The residue was purified by prep-HPLC to afford ethyl 9-hydroxy-10-methoxy-6-methyl-2-oxo-6,7-dihydrobenzo[a]quinolizine-3-carboxylate (350 mg) as a light yellow solid.

Step 2: Preparation of ethyl 9-ethoxy-10-methoxy-6-methyl-2-oxo-6,7-dihydrobenzo[a]quinolizine-3-carboxylate

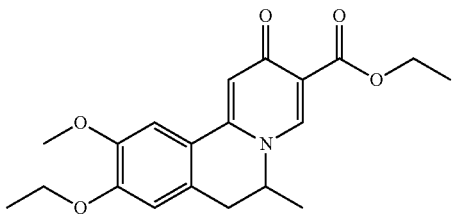 [SMILES: CCOC(=O)c1cn2c(cc1=O)-c1cc(OC)c(OCC)cc1CC2C]

A mixture of ethyl 9-hydroxy-10-methoxy-6-methyl-2-oxo-6,7-dihydrobenzo[a]quinolizine-3-carboxylate (350 mg, 1.0 mmol), bromoethane (327 mg, 3.0 mmol) and $K_2CO_3$ (414 mg, 3.0 mmol) in DMF (2 mL) was stirred at 80° C. for 2 hours. Water was added and then the mixture was extracted with ethyl acetate. The organic phase was dried over anhydrous $Na_2SO_4$ and then concentrated. The residue was purified by column chromatography to give ethyl 9-ethoxy-10-methoxy-6-methyl-2-oxo-6,7-dihydrobenzo[a]quinolizine-3-carboxylate (340 mg).

Step 3: Preparation of 9-ethoxy-10-methoxy-6-methyl-2-oxo-6,7-dihydrobenzo[a]quinolizine-3-carboxylic acid

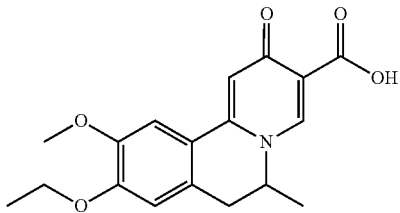 [SMILES: CCOc1cc2c(cc1OC)-c1cc(=O)c(C(=O)O)cn1C(C)C2]

To a solution of ethyl 9-ethoxy-10-methoxy-6-methyl-2-oxo-6,7-dihydrobenzo[a]quinolizine-3-carboxylate (50 mg, 0.13 mmol) in THF (2 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous $Na_2SO_4$ and then concentrated. The residue was purified by prep-HPLC to give 9-ethoxy-10-methoxy-6-methyl-2-oxo-6,7-dihydrobenzo[a]quinolizine-3-carboxylic acid (30 mg) as a light yellow solid. $^1$H NMR (400 MHz, DMSO-$d_6$): δ 8.82 (s, 1H), 7.52 (s, 1H), 7.46 (s, 1H), 7.00 (s, 1H), 4.97-4.91 (m, 1H), 4.11 (q, 2H), 3.88 (s, 3H), 3.34-3.30 (m, 1H), 2.91-2.87 (m, 1H), 1.37 (t, 3H), 1.19 (d, 3H). MS obsd. (ESI$^+$) [(M+H)$^+$]: 330.

Example 5: 9,10-diethoxy-6-ethyl-2-oxo-6,7-dihydrobenzo[a]quinolizine-3-carboxylic acid

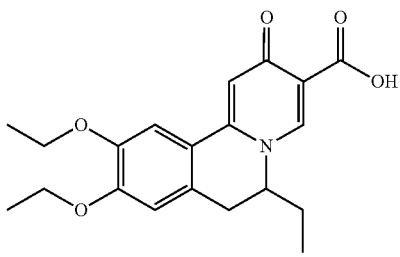 [SMILES: CCOc1cc2c(cc1OCC)-c1cc(=O)c(C(=O)O)cn1C(CC)C2]

Step 1: Preparation of 1,2-diethoxy-4-[2-nitrobut-1-enyl]benzene

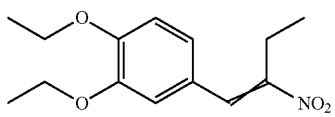 [SMILES: CCOc1ccc(C=C(CC)[N+](=O)[O-])cc1OCC]

A mixture of 3,4-diethoxybenzaldehyde (10 g, 51.5 mmol) and ammonium acetate (4.0 g, 51.5 mmol) in toluene (100 mL) was refluxed with a Dean-Stark trap for 2 hours. Then nitropropane (13.7 g, 154 mmol) was added and then the resultant mixture was refluxed for additional 36 hours. The mixture was concentrated under reduced pressure, and the residue was dissolved in ethyl acetate (200 mL). The resultant solution was washed with water (100 mL), and then dried over anhydrous $Na_2SO_4$ and concentrated. The residue was purified by column chromatography to give 1,2-diethoxy-4-[2-nitrobut-1-enyl]benzene (11.9 g).

Step 2: Preparation of 1-(3,4-diethoxyphenyl)butan-2-amine

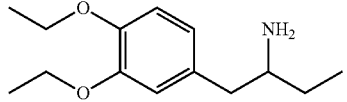 [SMILES: CCOc1ccc(CC(N)CC)cc1OCC]

To a mixture of LiAlH$_4$ (5.1 g, 135 mmol) in THF (100 mL) was added a solution of 1,2-diethoxy-4-[2-nitrobut-1-enyl]benzene (11.9 g, 45 mmol) in THF (100 mL) dropwise in an ice-water bath. The mixture was refluxed for 6 hours and then stirred at room temperature for additional 16 hours. Then water (5.1 g) was added dropwise to the mixture at 0° C., and then followed by addition of 15% NaOH aqueous (5.1 mL) and water (15.3 mL). The resultant mixture was filtered, and the filtrate was concentrated to afford crude 1-(3,4-diethoxyphenyl)butan-2-amine (11 g) which was used in the next step without further purification.

Step 3: Preparation of N-[1-[(3,4-diethoxyphenyl)methyl]propyl]formamide

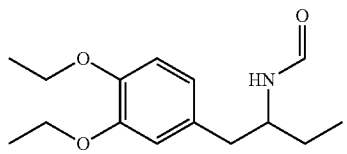 [SMILES: CCOc1ccc(CC(CC)NC=O)cc1OCC]

A mixture of 1-(3,4-diethoxyphenyl)butan-2-amine (11 g, 46 mmol) and formic acid (6.4 g, 0.14 mol) in dioxane (100 mL) was refluxed for 16 hours and then concentrated under reduce pressure to afford the crude N-[1-[(3,4-diethoxyphenyl)methyl]propyl]formamide (11 g) which was used in the next step without purification.

Step 4: Preparation of 6,7-diethoxy-3-ethyl-3,4-dihydroisoquinoline

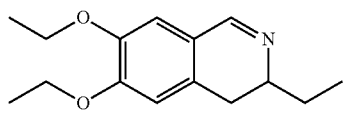 [SMILES: CCOc1cc2c(cc1OCC)CC(CC)N=C2]

To a solution of N-[1-[(3,4-diethoxyphenyl)methyl]propyl]formamide (11 g, 41.5 mmol) in acetonitrile (100 mL) was added POCl$_3$ (9.5 g, 62.2 mol) dropwise at 0-5° C. The resultant mixture was refluxed for 4 hours and then concentrated. Ethyl acetate (200 mL) was added to the mixture, and then followed by addition of ammonia to adjust the pH of the aqueous solution to around 11. The aqueous layer was extracted with ethyl acetate (200 mL×3). The organic layers were combined and then concentrated. The residue was purified by column chromatography to give 6,7-diethoxy-3-ethyl-3,4-dihydroisoquinoline (8.3 g).

Step 5: Preparation of ethyl 9,10-diethoxy-6-ethyl-2-oxo-1,6,7,11b-tetrahydrobenzo[a]quinolizine-3-carboxylate

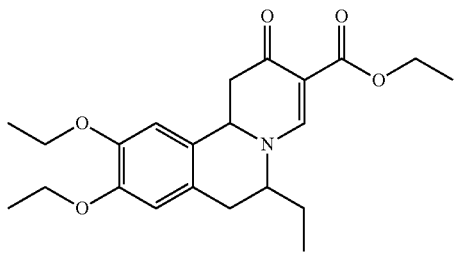 [SMILES: CCOC(=O)C1=CN2C(CC)Cc3cc(OCC)c(OCC)cc3C2CC1=O]

A mixture of 6,7-diethoxy-3-ethyl-3,4-dihydroisoquinoline (8.3 g, 21.4 mmol) and ethyl 2-(ethoxymethylene)-3-oxo-butanoate (6.0 g, 32.2 mmol) in EtOH (100 mL) was refluxed overnight. The mixture was concentrated to give crude ethyl 9, 10-diethoxy-6-ethyl-2-oxo-1,6,7,11b-tetrahydrobenzo[a]quinolizine-3-carboxylate as dark brown oil which was used in the next step without purification.

Step 6: Preparation of ethyl 9,10-diethoxy-6-ethyl-2-oxo-6,7-dihydrobenzo[a]quinolizine-3-carboxylate

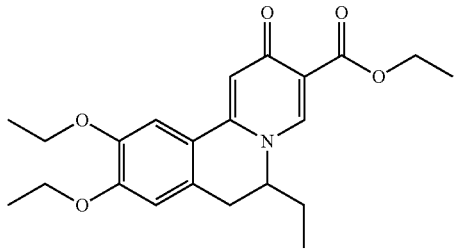 [SMILES: CCOC(=O)c1cn2c(cc1=O)-c1cc(OCC)c(OCC)cc1CC2CC]

A mixture of crude ethyl 9,10-diethoxy-6-ethyl-2-oxo-1,6,7,11b-tetrahydrobenzo[a]quinolizine-3-carboxylate from Step 5 and p-chloranil (4.97 g, 20.4 mmol) in DME (40 mL) was refluxed for 2 hours. After being cooled to room temperature, the suspension was filtered with suction. The filter cake was washed with cold DME and then dried under vacuum to give ethyl 9,10-diethoxy-6-ethyl-2-oxo-6,7-dihydrobenzo[a]quinolizine-3-carboxylate as a yellow solid (5.4 g).

Step 7: Preparation of 9,10-diethoxy-6-ethyl-2-oxo-6,7-dihydrobenzo[a]quinolizine-3-carboxylic acid

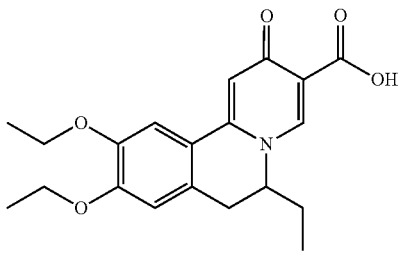 [SMILES: CCOc1cc2c(cc1OCC)-c1cc(=O)c(C(=O)O)cn1C(CC)C2]

To a solution of ethyl 9,10-diethoxy-6-ethyl-2-oxo-6,7-dihydrobenzo[a]quinolizine-3-carboxylate (2 g, 5.2 mmol) in THF (20 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2). The combined organic layers were washed with brine, and then dried over anhydrous $Na_2SO_4$ and then concentrated. The residue was purified by prep-HPLC to give 9,10-diethoxy-6-ethyl-2-oxo-6,7-dihydrobenzo[a]quinolizine-3-carboxylic acid (1.4 g) as a light yellow solid. $^1$H NMR (400 MHz, $CDCl_3$): δ 8.50 (s, 1H), 7.19 (s, 1H), 7.06 (s, 1H), 6.74 (s, 1H), 4.23-4.21 (m, 1H), 4.20-4.12 (m, 4H), 3.40 (dd, 1H), 2.92 (d, 1H), 1.70-1.59 (m, 2H), 1.51 (t, 3H), 1.50 (t, 3H), 0.92 (t, 3H). MS obsd. (ESI$^+$) [(M+H)$^+$]: 358

Example 6 and 7

(+)-9,10-diethoxy-6-ethyl-2-oxo-6,7-dihydrobenzo[a]quinolizine-3-carboxylic acid and (−)-9,10-diethoxy-6-ethyl-2-oxo-6,7-dihydrobenzo[a]quinolizine-3-carboxylic acid

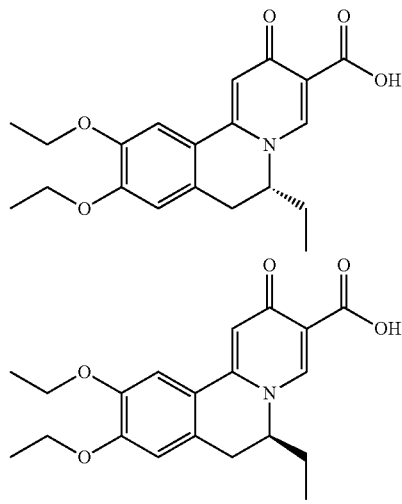

Separation of the racemic 9,10-diethoxy-6-ethyl-2-oxo-6,7-dihydrobenzo[a]quinolizine-3-carboxylic acid (40 mg) by chiral HPLC afforded (+)-9,10-diethoxy-6-ethyl-2-oxo-6,7-dihydrobenzo[a]quinolizine-3-carboxylic acid (11 mg) and (−)-9,10-diethoxy-6-ethyl-2-oxo-6,7-dihydrobenzo[a]quinolizine-3-carboxylic acid (12 mg).

Example 6

$^1$H NMR (400 MHz, $CDCl_3$): δ 8.50 (s, 1H), 7.19 (s, 1H), 7.06 (s, 1H), 6.74 (s, 1H), 4.23-4.21 (m, 1H), 4.20-4.12 (m, 4H), 3.40 (dd, 1H), 2.92 (d, 1H), 1.70-1.59 (m, 2H), 1.51 (t, 3H), 1.50 (t, 3H), 0.92 (t, 3H). MS obsd. (ESI$^+$) [(M+H)$^+$]: 358. $[α]_D20=+94°$ (0.05%, methanol)

Example 7

$^1$H NMR (400 MHz, $CDCl_3$): δ 8.50 (s, 1H), 7.19 (s, 1H), 7.06 (s, 1H), 6.74 (s, 1H), 4.23-4.21 (m, 1H), 4.20-4.12 (m, 4H), 3.40 (dd, 1H), 2.92 (d, 1H), 1.70-1.59 (m, 2H), 1.51 (t, 3H), 1.50 (t, 3H), 0.92 (t, 3H). MS obsd. (ESI$^+$) [(M+H)$^+$]: 358.

Example 8: 9-benzyloxy-6-ethyl-10-methoxy-2-oxo-6,7-dihydrobenzo[a]quinolizine-3-carboxylic acid

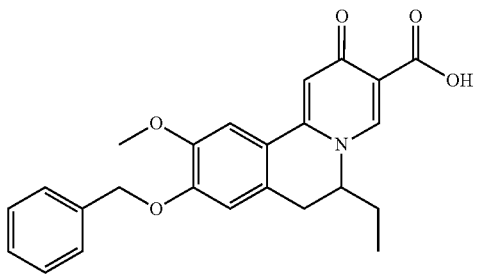 [SMILES: CCC1Cc2cc(OCc3ccccc3)c(OC)cc2-c2cc(=O)c(C(=O)O)cn21]

Step 1: Preparation of 3-benzyloxy-4-methoxy-benzaldehyde

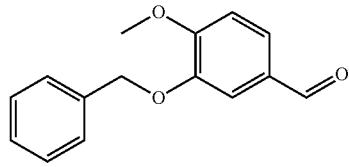 [SMILES: COc1ccc(C=O)cc1OCc1ccccc1]

A 5 L round-bottomed flask was charged with 3-hydroxy-4-methoxy-benzaldehyde (304 g, 2 mol), bromomethylbenzene (445 g, 2.6 mol), $K_2CO_3$ (608 g, 4.4 mol) and acetone (3 L). The resultant mixture was stirred at 20° C. for 16 hours, and then filtered and then concentrated to give yellow oil which was stood for 16 hours at room temperature. Then petroleum ether (1 L) was added and the mixture was stirred for 30 minutes and then filtered. The filter cake was dried to give 3-benzyloxy-4-methoxy-benzaldehyde (400 g).

Step 2: Preparation of 2-benzyloxy-1-methoxy-4-[2-nitrobut-1-enyl]benzene

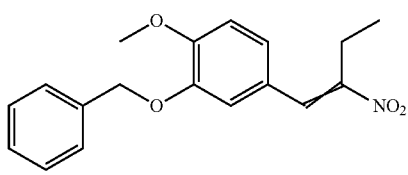 [SMILES: CCC(=Cc1ccc(OC)c(OCc2ccccc2)c1)[N+](=O)[O-]]

A mixture of 3-benzyloxy-4-methoxy-benzaldehyde (300 g, 1.24 mol) and ammonium acetate (95 g, 1.24 mol) in toluene (4 L) was refluxed with a Dean-Stark trap for 2 hours. Then nitropropane (552 g, 6.19 mol) was added and the resultant mixture was refluxed for additional 36 hours. The mixture was concentrated under reduced pressure, and then the residue was dissolved in ethyl acetate (2 L). The resultant solution was washed with water (1 L), and then dried over anhydrous $Na_2SO_4$ and then concentrated. The residue was purified by column chromatography to give 2-benzyloxy-1-methoxy-4-[2-nitrobut-1-enyl]benzene (270 g).

Step 3: Preparation of 1-(3-benzyloxy-4-methoxy-phenyl)butan-2-amine

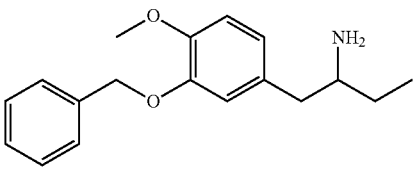 [SMILES: CCC(N)Cc1ccc(OC)c(OCc2ccccc2)c1]

To a mixture of $LiAlH_4$ (101 g, 2.67 mol) in THF (1500 mL) was added a solution of 2-benzyloxy-1-methoxy-4-[2-nitrobut-1-enyl]benzene (270 g, 862 mmol) in THF (1000 mL) dropwise in an ice-water bath. The mixture was refluxed for 6 hours and then stirred at room temperature for additional 16 hours. Then water (101 g) was added dropwise to the mixture at 0° C., and then followed by addition of 15% NaOH aqueous solution (101 mL) and water (303 mL). The resultant mixture was filtered, and the filtrate was concentrated to afford crude 1-(3-benzyloxy-4-methoxy-phenyl)butan-2-amine (224 g) which was used in the next step without further purification.

Step 4: Preparation of N-[1-[(3-benzyloxy-4-methoxy-phenyl)methyl]propyl]formamide

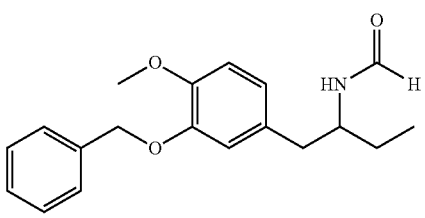 [SMILES: CCC(Cc1ccc(OC)c(OCc2ccccc2)c1)NC=O]

A mixture of 1-(3-benzyloxy-4-methoxy-phenyl)butan-2-amine (224 g, 785 mmol) and formic acid (145 g, 3.14 mol) in dioxane (2 L) was refluxed for 16 hours and then concentrated under reduce pressure to afford the crude N-[1-[(3-benzyloxy-4-methoxy-phenyl)methyl]propyl]formamide (230 g), which was used in the next step without purification.

Step 5: Preparation of 6-benzyloxy-3-ethyl-7-methoxy-3,4-dihydroisoquinoline

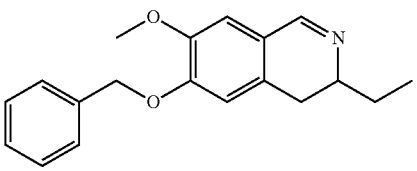 [SMILES: CCC1Cc2cc(OCc3ccccc3)c(OC)cc2C=N1]

To a solution of N-[1-[(3-benzyloxy-4-methoxy-phenyl)methyl]propyl]formamide (230 g, 734 mmol) in acetonitrile (2000 mL) was added $POCl_3$ (189.16 g, 1.23 mol) dropwise at 0-5° C. The resultant mixture was refluxed for 4 hours and then concentrated. Ethyl acetate (3 L) was added to the mixture, and then followed by addition of ammonia to adjust the pH of the aqueous solution to around 11. The aqueous layer was extracted with ethyl acetate (2 L×3). The organic layers were combined and then concentrated. The residue was purified by column chromatography to give 6-benzyloxy-3-ethyl-7-methoxy-3,4-dihydroisoquinoline (90 g).

Step 6: Preparation of ethyl 9-benzyloxy-6-ethyl-10-methoxy-2-oxo-1,6,7,11b-tetrahydrobenzo[a]quinolizine-3-carboxylate

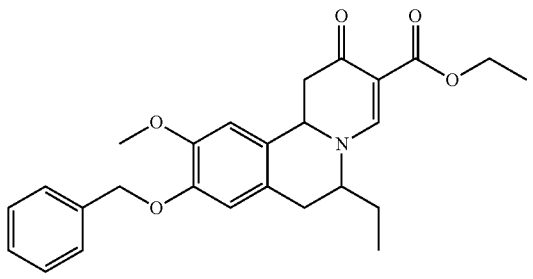 [SMILES: CCOC(=O)C1=CN2C(CC)Cc3cc(OCc4ccccc4)c(OC)cc3C2CC1=O]

A mixture of 6-benzyloxy-3-ethyl-7-methoxy-3,4-dihydroisoquinoline (10 g, 34 mmol) and ethyl 2-(ethoxymethylene)-3-oxo-butanoate (6.9 g, 37.4 mmol) in EtOH (150 mL) was refluxed overnight. The mixture was concentrated to give crude ethyl 9-benzyloxy-6-ethyl-10-methoxy-2-oxo-1,6,7,11b-tetrahydrobenzo[a]quinolizine-3-carboxylate as dark brown oil which was used in the next step without purification.

Step 7: Preparation of ethyl 9-benzyloxy-6-ethyl-10-methoxy-2-oxo-6,7-dihydrobenzo[a]quinolizine-3-carboxylate

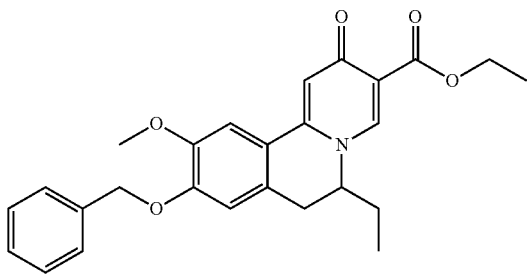 [SMILES: CCOC(=O)c1cn2c(cc1=O)-c1cc(OC)c(OCc3ccccc3)cc1CC2CC]

A mixture of crude ethyl 9-benzyloxy-6-ethyl-10-methoxy-2-oxo-1,6,7,11b-tetrahydrobenzo[a]quinolizine-3-carboxylate from Step 6 and p-chloranil (4.97 g, 20.4 mmol) in DME (40 mL) was refluxed for 2 hours. After being cooled to room temperature, the suspension was filtered with suction. The filter cake was washed with cold DME and then dried under vacuum to give ethyl 9-benzyloxy-6-ethyl-10-methoxy-2-oxo-6,7-dihydrobenzo[a]quinolizine-3-carboxylate as a yellow solid (5.2 g).

Step 8: Preparation of 9-benzyloxy-6-ethyl-10-methoxy-2-oxo-6,7-dihydrobenzo[a]quinolizine-3-carboxylic acid

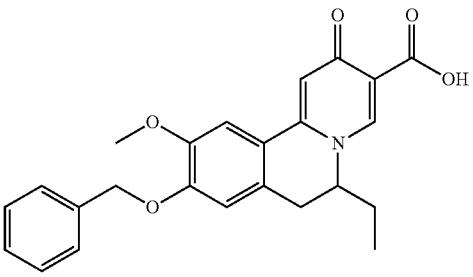 [SMILES: CCC1Cc2cc(OCc3ccccc3)c(OC)cc2-c2cc(=O)c(C(=O)O)cn21]

To a solution of ethyl 9-benzyloxy-6-ethyl-10-methoxy-2-oxo-6,7-dihydrobenzo[a]quinolizine-3-carboxylate (2 g, 4.6 mmol) in THF (20 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous $Na_2SO_4$ and then concentrated. The residue was purified by prep-HPLC to give 9-benzyloxy-6-ethyl-10-methoxy-2-oxo-6,7-dihydrobenzo[a]quinolizine-3-carboxylic acid (1.5 g) as a light yellow solid. $^1$H NMR (400 MHz, $CDCl_3$): δ 8.50 (s, 1H), 7.46-7.30 (m, 5H), 7.21 (s, 1H), 7.10 (s, 1H), 6.78 (s, 1H), 5.22 (d, 2H), 4.24-4.19 (m, 1H), 3.96 (s, 3H), 3.37 (d, 1H), 2.88 (d, 1H), 1.86-1.59 (m, 2H), 0.90 (t, 3H). MS obsd. (ESI$^+$) [(M+H)$^+$]: 406.

Example 9 and 10

(+)-9-benzyloxy-6-ethyl-10-methoxy-2-oxo-6,7-dihydrobenzo[a]quinolizine-3-carboxylic acid and
(−)-9-benzyloxy-6-ethyl-10-methoxy-2-oxo-6,7-dihydrobenzo[a]quinolizine-3-carboxylic acid

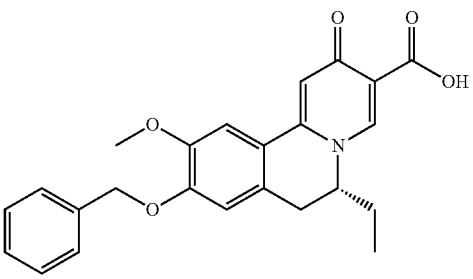

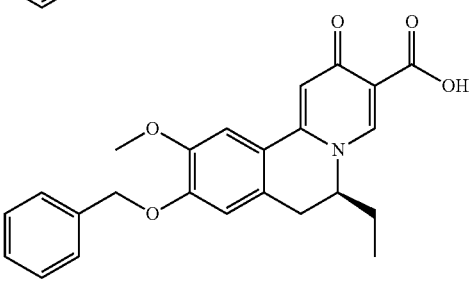

Separation of the racemic 9-benzyloxy-6-ethyl-10-methoxy-2-oxo-6,7-dihydrobenzo[a]quinolizine-3-carboxylic acid (200 mg) by chiral HPLC afforded (+)-9-benzyloxy-6-ethyl-10-methoxy-2-oxo-6,7-dihydrobenzo[a]quinolizine-3-carboxylic acid (62 mg) and (−)-9-benzyloxy-6-ethyl-10-methoxy-2-oxo-6,7-dihydrobenzo[a]quinolizine-3-carboxylic acid (68 mg).

Example 9

$^1$H NMR (400 MHz, CDCl$_3$): δ 8.50 (s, 1H), 7.46-7.30 (m, 5H), 7.21 (s, 1H), 7.10 (s, 1H), 6.78 (s, 1H), 5.22 (d, 2H), 4.24-4.19 (m, 1H), 3.96 (s, 3H), 3.37 (d, 1H), 2.88 (d, 1H), 1.86-1.59 (m, 2H), 0.90 (t, 3H). MS obsd. (ESI$^+$) [(M+H)$^+$]: 406. $[α]_D^{20}$=+78° (0.10%, CH$_3$CN)

Example 10

$^1$H NMR (400 MHz, CDCl$_3$): δ 8.50 (s, 1H), 7.46-7.30 (m, 5H), 7.21 (s, 1H), 7.10 (s, 1H), 6.78 (s, 1H), 5.22 (d, 2H), 4.24-4.19 (m, 1H), 3.96 (s, 3H), 3.37 (d, 1H), 2.88 (d, 1H), 1.86-1.59 (m, 2H), 0.90 (t, 3H). MS obsd. (ESI$^+$) [(M+H)$^+$]: 406.

Example 11 and 12

(+)-6-ethyl-10-methoxy-2-oxo-9-(2,2,2-trifluoroethoxy)-6,7-dihydrobenzo[a]quinolizine-3-carboxylic acid and (−)-6-ethyl-10-methoxy-2-oxo-9-(2,2,2-trifluoroethoxy)-6,7-dihydrobenzo[a]quinolizine-3-carboxylic acid

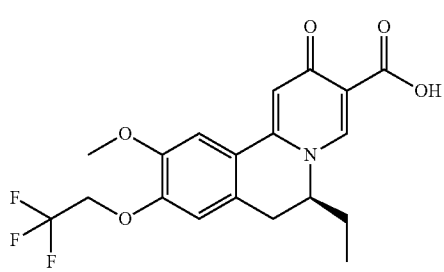

Step 1: Preparation of ethyl 6-ethyl-9-hydroxy-10-methoxy-2-oxo-6,7-dihydrobenzo[a]quinolizine-3-carboxylate

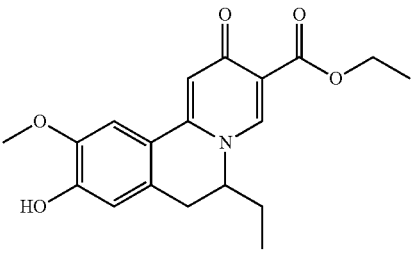 [SMILES: CCOC(=O)c1cn2c(cc1=O)-c1cc(OC)c(O)cc1CC2CC]

A mixture of ethyl 9-benzyloxy-6-ethyl-10-methoxy-2-oxo-6,7-dihydrobenzo[a]quinolizine-3-carboxylate (5.2 g) and 10% palladium on carbon (300 mg) in THF/MeOH (1/1, 40 mL) was stirred under hydrogen atmosphere for 12 hours. The mixture was filtered through celite pad, and filtrate was concentrated under reduced pressure to afford ethyl 6-ethyl-9-hydroxy-10-methoxy-2-oxo-6,7-dihydrobenzo[a]quinolizine-3-carboxylate as yellow solid (4.2 g).

Step 2: Preparation of ethyl 6-ethyl-10-methoxy-2-oxo-9-(2,2,2-trifluoroethoxy)-6,7-dihydrobenzo[a]quinolizine-3-carboxylate

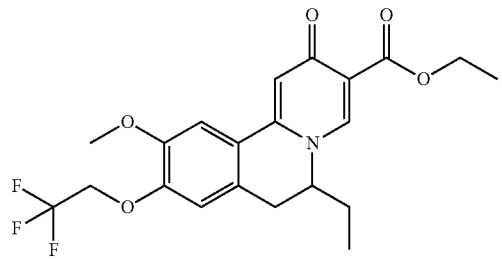 [SMILES: CCOC(=O)c1cn2c(cc1=O)-c1cc(OC)c(OCC(F)(F)F)cc1CC2CC]

To a solution of ethyl 6-ethyl-9-hydroxy-10-methoxy-2-oxo-6,7-dihydrobenzo[a]quinolizine-3-carboxylate (4.2 g, 12 mmol) in DMF (40 mL) was added potassium carbonate (2.5 g, 18 mmol) and 2-iodo-1,1,1-trifluoroethane (3.78 g, 18 mmol). The resultant mixture was heated at 110° C. for 12 hours. After being cooled to room temperature, the dark-brown mixture was poured into water (500 mL) and the aqueous solution was extracted with EtOAc (250 mL×2). The organic layers were combined and washed with brine, and then dried over anhydrous Na$_2$SO$_4$, and then concentrated under reduced pressure to give crude ethyl 6-ethyl-10-methoxy-2-oxo-9-(2,2,2-trifluoroethoxy)-6,7-dihydrobenzo[a]quinolizine-3-carboxylate, which was used in the next step without purification.

Step 3: Preparation of 6-ethyl-10-methoxy-2-oxo-9-(2,2,2-trifluoroethoxy)-6,7-dihydrobenzo[a]quinolizine-3-carboxylic acid

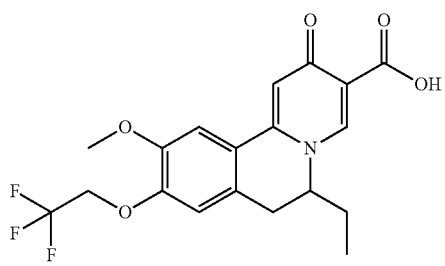 [SMILES: CCC1Cc2cc(OCC(F)(F)F)c(OC)cc2-c2cc(=O)c(C(=O)O)cn21]

To a solution of ethyl 6-ethyl-10-methoxy-2-oxo-9-(2,2,2-trifluoroethoxy)-6,7-dihydrobenzo[a]quinolizine-3-carboxylate in THF (40 mL) was added 10% NaOH aqueous solution dropwise at room temperature. The resultant mixture was stirred for 2 hours, and then acidified to pH 1-2 with 2 M hydrochloric acid. The mixture was extracted with DCM (200 mL×2), and the combined organic layers were washed with brine, and then dried over anhydrous $Na_2SO_4$ and then concentrated to give a light yellow solid, which was recrystallized from EtOH to afford 6-ethyl-10-methoxy-2-oxo-9-(2,2,2-trifluoroethoxy)-6,7-dihydrobenzo[a]quinolizine-3-carboxylic acid as a white solid (2.3 g).

Step 4: Preparation of (+)-6-ethyl-10-methoxy-2-oxo-9-(2,2,2-trifluoroethoxy)-6,7-dihydrobenzo[a]quinolizine-3-carboxylic acid and (−)-6-ethyl-10-methoxy-2-oxo-9-(2,2,2-trifluoroethoxy)-6,7-dihydrobenzo[a]quinolizine-3-carboxylic acid

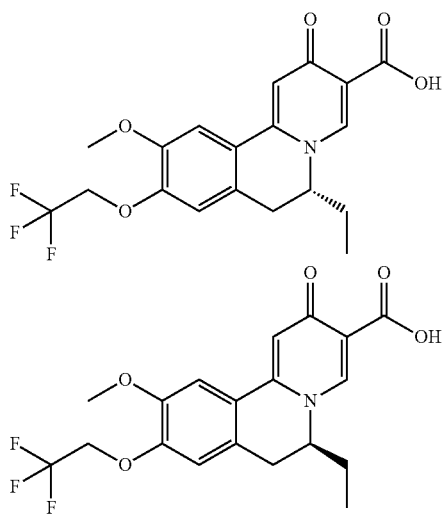

Separation of the racemic 6-ethyl-10-methoxy-2-oxo-9-(2,2,2-trifluoroethoxy)-6,7-dihydrobenzo[a]quinolizine-3-carboxylic acid (200 mg) by chiral HPLC afforded (+)-6-ethyl-10-methoxy-2-oxo-9-(2,2,2-trifluoroethoxy)-6,7-dihydrobenzo[a]quinolizine-3-carboxylic acid (68 mg) and (−)-6-ethyl-10-methoxy-2-oxo-9-(2,2,2-trifluoroethoxy)-6,7-dihydrobenzo[a]quinolizine-3-carboxylic acid (63 mg).

Example 11

$^1$H NMR (400 MHz, DMSO-$d_6$): δ 8.33 (s, 1H), 7.62 (s, 1H), 7.53 (s, 1H), 7.18 (s, 1H), 4.80 (m, 2H), 4.72 (m, 1H), 3.92 (s, 3H), 3.36 (m, 1H), 2.97 (d, 1H), 1.47 (m, 2H), 0.80 (t, 3H). MS obsd. (ESI$^+$) [(M+H)$^+$]: 398. [α]$_D^{20}$=+112.70° (0.126%, $CH_3CN$).

Example 12

$^1$H NMR (400 MHz, DMSO-$d_6$): δ 8.33 (s, 1H), 7.62 (s, 1H), 7.53 (s, 1H), 7.18 (s, 1H), 4.80 (m, 2H), 4.72 (m, 1H), 3.92 (s, 3H), 3.36 (m, 1H), 2.97 (d, 1H), 1.47 (m, 2H), 0.80 (t, 3H). MS obsd. (ESI$^+$) [(M+H)$^+$]: 398.

Example 13: 6-ethyl-9-isopropoxy-10-methoxy-2-oxo-6,7-dihydrobenzo[a]quinolizine-3-carboxylic acid

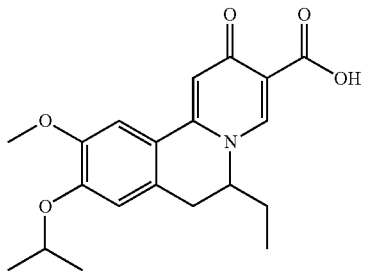 [SMILES: CCC1Cc2cc(OC(C)C)c(OC)cc2-c2cc(=O)c(C(=O)O)cn21]

Step 1: Preparation of ethyl 6-ethyl-9-isopropoxy-10-methoxy-2-oxo-6,7-dihydrobenzo[a]quinolizine-3-carboxylate

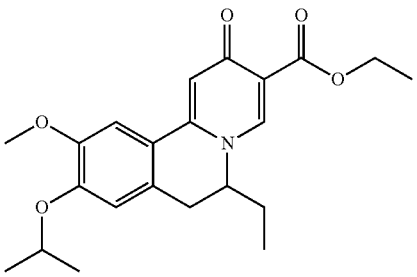 [SMILES: CCOC(=O)c1cn2c(cc1=O)-c1cc(OC)c(OC(C)C)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 2-bromopropane (37 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-9-isopropoxy-10-methoxy-2-oxo-6,7-dihydrobenzo[a]quinolizine-3-carboxylate (70 mg) which was used in the next step without purification.

Step 2: Preparation of 6-ethyl-9-isopropoxy-10-methoxy-2-oxo-6,7-dihydrobenzo[a]quinolizine-3-carboxylic acid

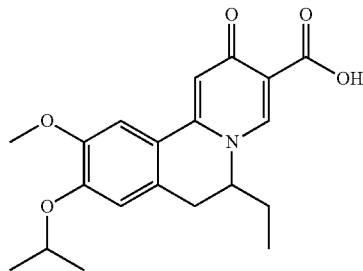 [SMILES: CCC1Cc2cc(OC(C)C)c(OC)cc2-c2cc(=O)c(C(=O)O)cn21]

To a solution of ethyl 6-ethyl-9-isopropoxy-10-methoxy-2-oxo-6,7-dihydrobenzo[a]quinolizine-3-carboxylate (60 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-9-isopropoxy-10-methoxy-2-oxo-6,7-dihydrobenzo[a]quinolizine-3-carboxylic acid (29 mg) as a white solid. $^1$H NMR (400 MHz, $CDCl_3$): δ 8.51 (s, 1H), 7.19 (s, 1H), 7.09 (s, 1H), 6.76 (s, 1H), 4.68-4.65 (m, 1H), 4.25-4.21 (m, 1H), 3.93 (s, 3H), 3.40 (d, 1H), 2.92 (d, 1H), 1.69-1.60 (m, 2H), 1.45 (d, 3H), 1.43 (d, 3H), 0.93 (t, 3H). MS obsd. (ESI$^+$) [(M+H)$^+$]: 358.

Example 14: 6-ethyl-10-methoxy-2-oxo-9-(2-phenylethoxy)-6,7-dihydrobenzo[a]quinolizine-3-carboxylic acid

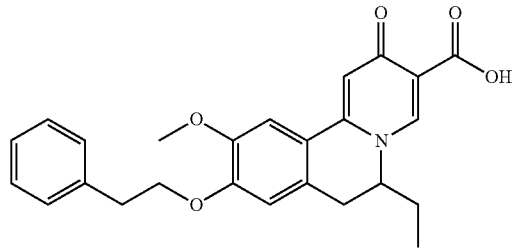 [SMILES: CCC1Cc2cc(OCCc3ccccc3)c(OC)cc2-c2cc(=O)c(C(=O)O)cn21]

Step 1: Preparation of ethyl 6-ethyl-10-methoxy-2-oxo-9-(2-phenylethoxy)-6,7-dihydrobenzo[a]quinolizine-3-carboxylate

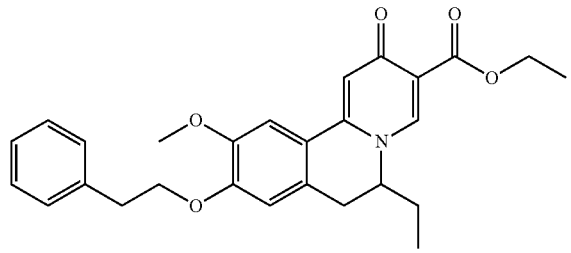 [SMILES: CCOC(=O)c1cn2c(cc1=O)-c1cc(OC)c(OCCc3ccccc3)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 2-bromoethylbenzene (55 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-10-methoxy-2-oxo-9-(2-phenylethoxy)-6,7-dihydrobenzo[a]quinolizine-3-carboxylate (79 mg) which was used in the next step without purification.

Step 2: Preparation of 6-ethyl-10-methoxy-2-oxo-9-(2-phenylethoxy)-6,7-dihydrobenzo[a]quinolizine-3-carboxylic acid

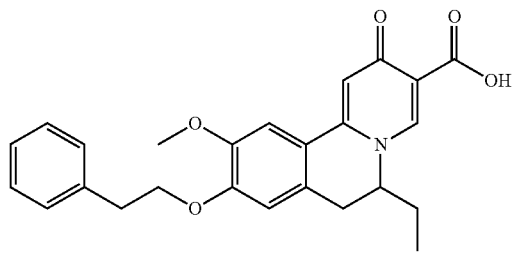 [SMILES: CCC1Cc2cc(OCCc3ccccc3)c(OC)cc2-c2cc(=O)c(C(=O)O)cn21]

To a solution of ethyl 6-ethyl-10-methoxy-2-oxo-9-(2-phenylethoxy)-6,7-dihydrobenzo[a]quinolizine-3-carboxylate (79 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-10-methoxy-2-oxo-9-(2-phenylethoxy)-6,7-dihydrobenzo[a]quinolizine-3-carboxylic acid (37 mg) as a white solid. $^1$H NMR (400 MHz, $CDCl_3$): δ 8.56 (s, 1H), 7.37-7.25 (m, 5H), 7.19 (s, 1H), 7.12 (s, 1H), 6.71 (s, 1H), 4.30-4.27 (m, 3H), 3.94 (s, 3H), 3.40 (d, 1H), 3.22 (t, 2H), 2.88 (dd, 1H), 1.66-1.58 (m, 2H), 0.92 (t, 3H). MS obsd. (ESI$^+$) [(M+H)$^+$]: 420.

Example 15: 9-butoxy-6-ethyl-10-methoxy-2-oxo-6,7-dihydrobenzo[a]quinolizine-3-carboxylic acid

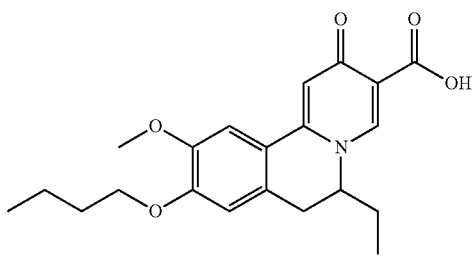 [SMILES: CCCCOc1cc2c(cc1OC)-c1cc(=O)c(C(=O)O)cn1C(CC)C2]

Step 1: Preparation of ethyl 9-butoxy-6-ethyl-10-methoxy-2-oxo-6,7-dihydrobenzo[a]quinolizine-3-carboxylate

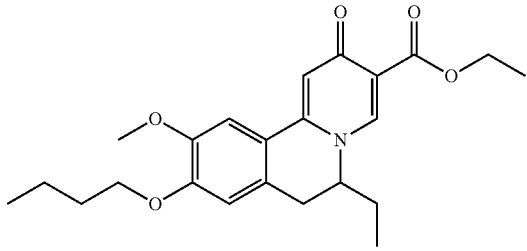 [SMILES: CCCCOc1cc2c(cc1OC)-c1cc(=O)c(C(=O)OCC)cn1C(CC)C2]

A mixture of ethyl 6-ethyl-9-hydroxy-10-methoxy-2-oxo-6,7-dihydrobenzo[a]quinolizine-3-carboxylate (50 mg, 0.15 mmol), 1-bromobutane (41 mg, 0.3 mmol) and K$_2$CO$_3$ (62 mg, 0.45 mmol) in DMF (2 mL) was stirred at 80° C. for 2 hours. Water was added and the mixture was extracted with ethyl acetate. The organic phase was dried over anhydrous Na$_2$SO$_4$ and then concentrated in vacuo to give crude ethyl 9-butoxy-6-ethyl-10-methoxy-2-oxo-6,7-dihydrobenzo[a]quinolizine-3-carboxylate (64 mg) which was used in the next step without purification.

Step 2: Preparation of 9-butoxy-6-ethyl-10-methoxy-2-oxo-6,7-dihydrobenzo[a]quinolizine-3-carboxylic acid

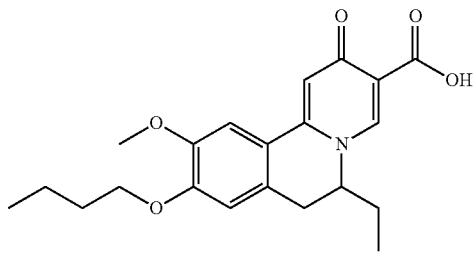 [SMILES: CCCCOc1cc2c(cc1OC)-c1cc(=O)c(C(=O)O)cn1C(CC)C2]

To a solution of ethyl 9-butoxy-6-ethyl-10-methoxy-2-oxo-6,7-dihydrobenzo[a]quinolizine-3-carboxylate (64 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na$_2$SO$_4$ and then concentrated. The residue was purified by prep-HPLC to give 9-butoxy-6-ethyl-10-methoxy-2-oxo-6,7-dihydrobenzo[a]quinolizine-3-carboxylic acid (33 mg) as a white solid. $^1$H NMR (400 MHz, CDCl$_3$): δ 8.51 (s, 1H), 7.18 (s, 1H), 7.09 (s, 1H), 6.75 (s, 1H), 4.25-4.21 (m, 1H), 4.10 (dt, 2H), 3.94 (s, 3H), 3.41 (d, 1H), 2.93 (d, 1H), 1.92-1.85 (m, 2H), 1.70-1.58 (m, 2H), 1.58-1.49 (m, 2H), 1.01 (t, 3H), 0.93 (t, 3H). MS obsd. (ESI$^+$) [(M+H)$^+$]: 372.

Example 16: 9-(2-cyclohexylethoxy)-6-ethyl-10-methoxy-2-oxo-6,7-dihydrobenzo[a]quinolizine-3-carboxylic acid

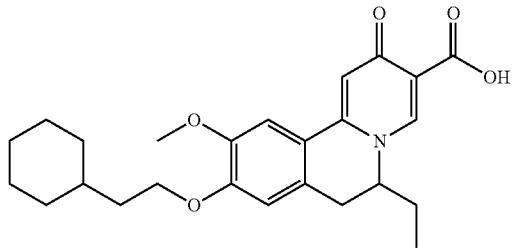 [SMILES: CCC1Cc2cc(OCCC3CCCCC3)c(OC)cc2-c2cc(=O)c(C(=O)O)cn21]

Step 1: Preparation of ethyl 9-(2-cyclohexylethoxy)-6-ethyl-10-methoxy-2-oxo-6,7-dihydrobenzo[a]quinolizine-3-carboxylate

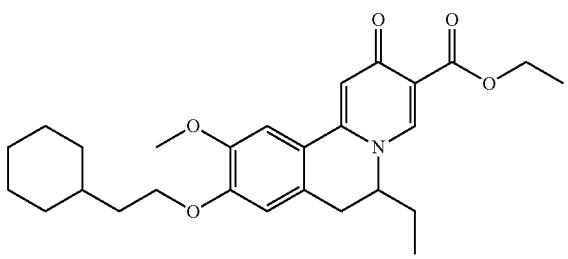 [SMILES: CCOC(=O)c1cn2c(cc1=O)-c1cc(OC)c(OCCC3CCCCC3)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 2-bromoethylcyclohexane (57 mg, 0.3 mmol) and K$_2$CO$_3$ (62 mg, 0.45 mmol) in DMF (2 mL) was stirred at 80° C. for 2 hours. Water was added and the mixture was extracted with ethyl acetate. The organic phase was dried over anhydrous Na$_2$SO$_4$ and then concentrated in vacuo to give crude ethyl 9-(2-cyclohexylethoxy)-6-ethyl-10-methoxy-2-oxo-6,7-dihydrobenzo[a]quinolizine-3-carboxylate (69 mg) which was used in the next step without purification.

Step 2: Preparation of 9-(2-cyclohexylethoxy)-6-ethyl-10-methoxy-2-oxo-6,7-dihydrobenzo[a]quinolizine-3-carboxylic acid

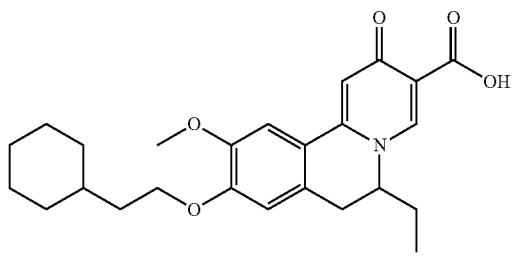 [SMILES: CCC1Cc2cc(OCCC3CCCCC3)c(OC)cc2-c2cc(=O)c(C(=O)O)cn21]

To a solution of ethyl 9-(2-cyclohexylethoxy)-6-ethyl-10-methoxy-2-oxo-6,7-dihydrobenzo[a]quinolizine-3-carboxylate (69 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na₂SO₄ and then concentrated. The residue was purified by prep-HPLC to give 9-(2-cyclohexylethoxy)-6-ethyl-10-methoxy-2-oxo-6,7-dihydrobenzo[a]quinolizine-3-carboxylic acid (33 mg) as a white solid. ¹H NMR (400 MHz, CDCl₃): δ 8.50 (s, 1H), 7.18 (s, 1H), 7.08 (s, 1H), 6.74 (s, 1H), 4.25-4.20 (m, 1H), 4.11 (dt, 2H), 3.93 (s, 3H), 3.41 (dd, 1H), 2.92 (d, 1H), 1.82-1.52 (m, 9H), 1.34-1.17 (m, 4H), 1.05-0.97 (m, 2H), 0.93 (t, 3H). MS obsd. (ESI⁺) [(M+H)⁺]: 426.

Example 17: 6-ethyl-10-methoxy-2-oxo-9-prop-2-ynoxy-6,7-dihydrobenzo[a]quinolizine-3-carboxylic acid

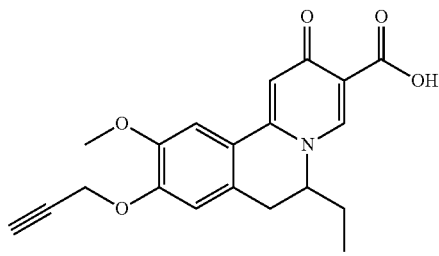 [SMILES: C#CCOc1cc2c(cc1OC)-c1cc(=O)c(C(=O)O)cn1C(CC)C2]

Step 1: Preparation of ethyl 6-ethyl-10-methoxy-2-oxo-9-prop-2-ynoxy-6,7-dihydrobenzo[a]quinolizine-3-carboxylate

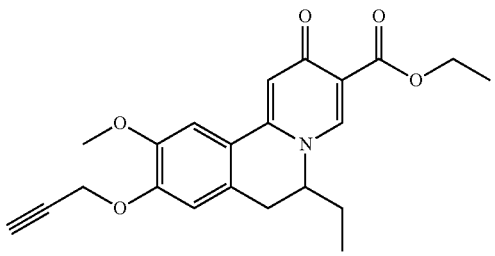 [SMILES: C#CCOc1cc2c(cc1OC)-c1cc(=O)c(C(=O)OCC)cn1C(CC)C2]

A mixture of ethyl 6-ethyl-9-hydroxy-10-methoxy-2-oxo-6,7-dihydrobenzo[a]quinolizine-3-carboxylate (50 mg, 0.15 mmol), 3-bromoprop-1-yne (36 mg, 0.3 mmol) and K₂CO₃ (62 mg, 0.45 mmol) in DMF (2 mL) was stirred at 80° C. for 2 hours. Water was added and the mixture was extracted with ethyl acetate. The organic phase was dried over anhydrous Na₂SO₄ and then concentrated in vacuo to give crude ethyl 6-ethyl-10-methoxy-2-oxo-9-prop-2-ynoxy-6,7-dihydrobenzo[a]quinolizine-3-carboxylate (57 mg) which was used in the next step without purification.

Step 2: Preparation of 6-ethyl-10-methoxy-2-oxo-9-prop-2-ynoxy-6,7-dihydrobenzo[a]quinolizine-3-carboxylic acid

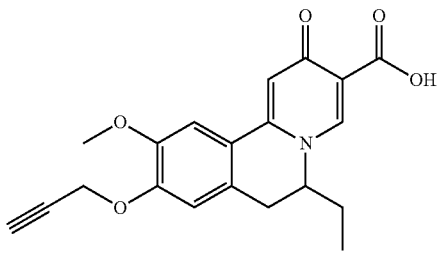 [SMILES: C#CCOc1cc2c(cc1OC)-c1cc(=O)c(C(=O)O)cn1C(CC)C2]

To a solution of ethyl 6-ethyl-10-methoxy-2-oxo-9-prop-2-ynoxy-6,7-dihydrobenzo[a]quinolizine-3-carboxylate (57 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na₂SO₄ and then concentrated. The residue was purified by prep-HPLC to give 6-ethyl-10-methoxy-2-oxo-9-prop-2-ynoxy-6,7-dihydrobenzo[a]quinolizine-3-carboxylic acid (22 mg) as a white solid. ¹H NMR (400 MHz, CDCl₃): δ 8.52 (s, 1H), 7.22 (s, 1H), 7.10 (s, 1H), 6.92 (s, 1H), 4.86 (d, 2H), 4.28-4.22 (m, 1H), 3.95 (s, 3H), 3.42 (dd, 1H), 2.96 (d, 1H), 2.59 (t, 1H), 1.72-1.58 (m, 2H), 0.93 (t, 3H). MS obsd. (ESI⁺) [(M+H)⁺]: 354

Example 18: 6-ethyl-10-methoxy-2-oxo-9-(2-oxo-2-pyrrolidin-1-yl-ethoxy)-6,7-dihydrobenzo[a]quinolizine-3-carboxylic acid

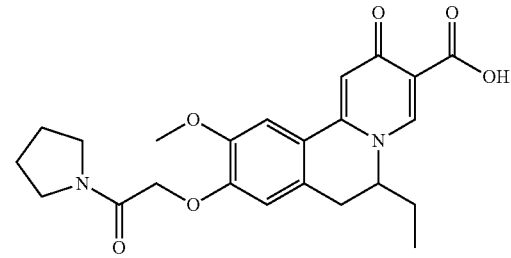 [SMILES: CCC1Cc2cc(OCC(=O)N3CCCC3)c(OC)cc2-c2cc(=O)c(C(=O)O)cn21]

Step 1: Preparation of ethyl 6-ethyl-10-methoxy-2-oxo-9-(2-oxo-2-pyrrolidin-1-yl-ethoxy)-6,7-dihydrobenzo[a]quinolizine-3-carboxylate

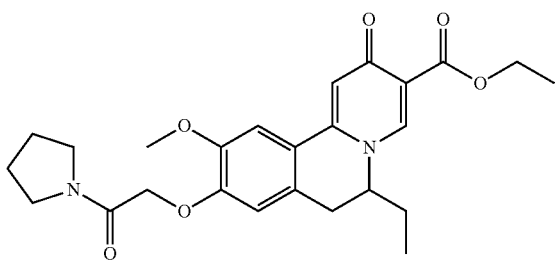 [SMILES: CCOC(=O)c1cn2c(cc1=O)-c1cc(OC)c(OCC(=O)N3CCCC3)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 2-bromo-1-pyrrolidin-1-yl-ethanone (57 mg, 0.3 mmol) and K₂CO₃ (62 mg, 0.45 mmol) in DMF (2 mL) was stirred at 80° C. for 2 hours. Water was added and the mixture was extracted with ethyl acetate. The organic phase was dried over anhydrous Na₂SO₄ and then concentrated in vacuo to give crude ethyl 6-ethyl-10-methoxy-2-oxo-9-(2-oxo-2-pyrrolidin-1-yl-ethoxy)-6,7-dihydrobenzo[a]quinolizine-3-carboxylate (68 mg) which was used in the next step without purification.

Step 2: Preparation of 6-ethyl-10-methoxy-2-oxo-9-(2-oxo-2-pyrrolidin-1-yl-ethoxy)-6,7-dihydrobenzo[a]quinolizine-3-carboxylic acid

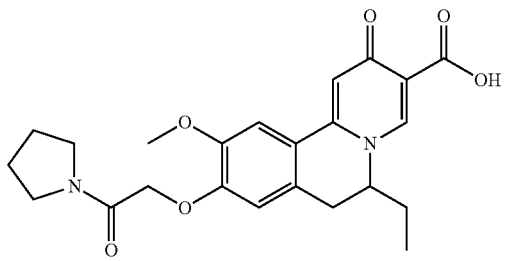 [SMILES: CCC1Cc2cc(OCC(=O)N3CCCC3)c(OC)cc2-c2cc(=O)c(C(=O)O)cn21]

To a solution of ethyl 6-ethyl-10-methoxy-2-oxo-9-(2-oxo-2-pyrrolidin-1-yl-ethoxy)-6,7-dihydrobenzo[a]quinolizine-3-carboxylate (68 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na₂SO₄ and then concentrated. The residue was purified by prep-HPLC to give 6-ethyl-0-methoxy-2-oxo-9-(2-oxo-2-pyrrolidin-1-yl-ethoxy)-6,7-dihydrobenzo[a]quinolizine-3-carboxylic acid (30 mg) as a white solid. $^1$H NMR (400 MHz, CDCl₃): δ 8.49 (s, 1H), 7.21 (s, 1H), 7.09 (s, 1H), 6.87 (s, 1H), 4.78 (s, 2H), 4.24-4.19 (m, 1H), 3.60-3.53 (m, 4H), 3.38 (dd, 1H), 2.93 (d, 1H), 2.04-1.97 (m, 2H), 1.91-1.85 (m, 2H), 1.68-1.60 (m, 2H), 0.91 (t, 3H). MS obsd. (ESI⁺) [(M+H)⁺]: 427.

Example 19: 6-ethyl-10-methoxy-9-[2-(2-methoxyethoxy)ethoxy]-2-oxo-6,7-dihydrobenzo[a]quinolizine-3-carboxylic acid

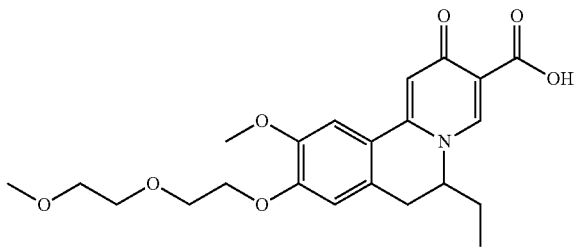 [SMILES: CCC1Cc2cc(OCCOCCOC)c(OC)cc2-c2cc(=O)c(C(=O)O)cn21]

Step 1: Preparation of ethyl 6-ethyl-10-methoxy-9-[2-(2-methoxyethoxy)ethoxy]-2-oxo-6,7-dihydrobenzo[a]quinolizine-3-carboxylate

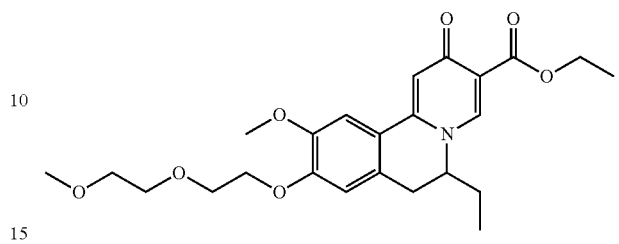

A mixture of ethyl 6-ethyl-9-hydroxy-10-methoxy-2-oxo-6,7-dihydrobenzo[a]quinolizine-3-carboxylate (50 mg, 0.15 mmol), 1-(2-bromoethoxy)-2-methoxy-ethane (55 mg, 0.3 mmol) and K₂CO₃ (62 mg, 0.45 mmol) in DMF (2 mL) was stirred at 80° C. for 2 hours. Water was added and the mixture was extracted with ethyl acetate. The organic phase was dried over anhydrous Na₂SO₄ and then concentrated in vacuo to give crude ethyl 6-ethyl-10-methoxy-2-oxo-9-(2-oxo-2-pyrrolidin-1-yl-ethoxy)-6,7-dihydrobenzo[a]quinolizine-3-carboxylate (67 mg) which was used in the next step without purification.

Step 2: Preparation of 6-ethyl-10-methoxy-9-[2-(2-methoxyethoxy)ethoxy]-2-oxo-6,7-dihydrobenzo[a]quinolizine-3-carboxylic acid

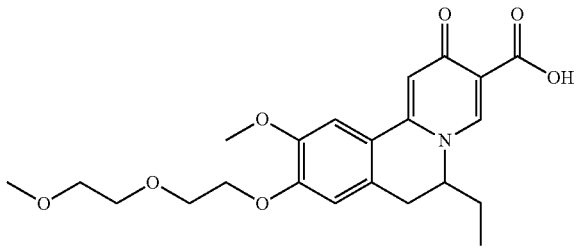 [SMILES: CCC1Cc2cc(OCCOCCOC)c(OC)cc2-c2cc(=O)c(C(=O)O)cn21]

To a solution of ethyl 6-ethyl-10-methoxy-2-oxo-9-(2-oxo-2-pyrrolidin-1-yl-ethoxy)-6,7-dihydrobenzo[a]quinolizine-3-carboxylate (67 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na₂SO₄ and then concentrated. The residue was purified by prep-HPLC to give 6-ethyl-10-methoxy-9-[2-(2-methoxyethoxy)ethoxy]-2-oxo-6,7-dihydrobenzo[a]quinolizine-3-carboxylic acid (37 mg) as a white solid. $^1$H NMR (400 MHz, CDCl₃): δ 8.50 (s, 1H), 7.18 (s, 1H), 7.08 (s, 1H), 6.81 (s, 1H), 4.29-4.26 (m, 2H), 4.24-4.19 (m, 1H), 3.95-3.92 (m, 2H), 3.93 (s, 3H), 3.76-3.73 (m, 2H), 3.60-3.57 (m, 2H), 3.42-3.37 (m, 1H), 3.40 (s, 3H), 2.92 (dd, 1H), 1.70-1.64 (m, 2H), 0.92 (t, 3H). MS obsd. (ESI⁺) [(M+H)⁺]: 418.

Example 20: 6-ethyl-10-methoxy-9-(2-morpholinoethoxy)-2-oxo-6,7-dihydrobenzo[a]quinolizine-3-carboxylic acid

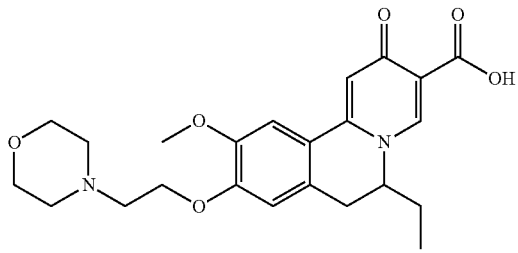 [SMILES: CCC1Cc2cc(OCCN3CCOCC3)c(OC)cc2-c2cc(=O)c(C(=O)O)cn21]

Step 1: Preparation of ethyl 6-ethyl-10-methoxy-9-(2-morpholinoethoxy)-2-oxo-6,7-dihydrobenzo[a]quinolizine-3-carboxylate

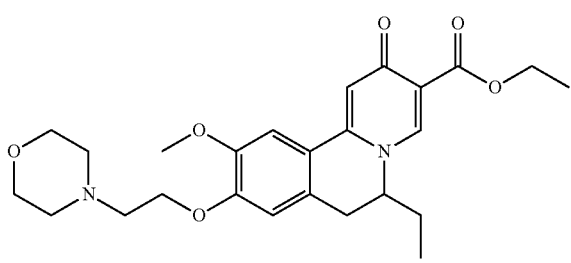 [SMILES: CCOC(=O)c1cn2c(cc1=O)-c1cc(OC)c(OCCN3CCOCC3)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 4-(2-bromoethyl)morpholine hydrobromide (82 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-10-methoxy-9-(2-morpholinoethoxy)-2-oxo-6,7-dihydrobenzo[a]quinolizine-3-carboxylate (68 mg) which was used in the next step without purification.

Step 2: Preparation of 6-ethyl-10-methoxy-9-(2-morpholinoethoxy)-2-oxo-6,7-dihydrobenzo[a]quinolizine-3-carboxylic acid

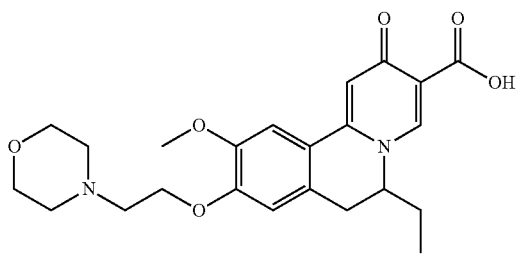 [SMILES: CCC1Cc2cc(OCCN3CCOCC3)c(OC)cc2-c2cc(=O)c(C(=O)O)cn21]

To a solution of ethyl 6-ethyl-10-methoxy-9-(2-morpholinoethoxy)-2-oxo-6,7-dihydrobenzo[a]quinolizine-3-carboxylate (68 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-10-methoxy-9-(2-morpholinoethoxy)-2-oxo-6,7-dihydrobenzo[a]quinolizine-3-carboxylic acid (32 mg) as a white solid. $^1$H NMR (400 MHz, DMSO-$d_6$): δ 8.83 (s, 1H), 7.59 (s, 1H), 7.51 (s, 1H), 7.13 (s, 1H), 4.75-4.70 (m, 1H), 4.45 (t, 2H), 3.91 (s, 3H), 3.62-3.50 (m, 10H), 3.36 (dd, 1H), 3.01 (d, 1H), 1.54-1.42 (m, 2H), 0.81 (t, 3H). MS obsd. (ESI$^+$) [(M+H)$^+$]: 429.

Example 21: 6-ethyl-9-(2-hydroxyethoxy)-10-methoxy-2-oxo-6,7-dihydrobenzo[a]quinolizine-3-carboxylic acid

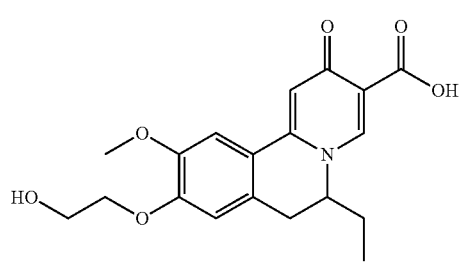 [SMILES: CCC1Cc2cc(OCCO)c(OC)cc2-c2cc(=O)c(C(=O)O)cn21]

Step 1: Preparation of ethyl 6-ethyl-9-(2-hydroxyethoxy)-10-methoxy-2-oxo-6,7-dihydrobenzo[a]quinolizine-3-carboxylate

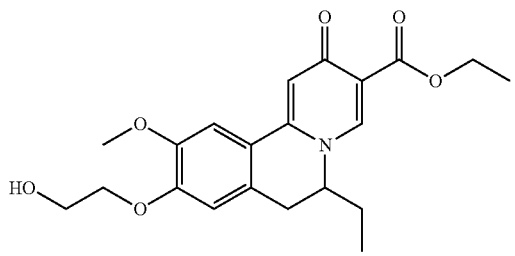 [SMILES: CCOC(=O)c1cn2c(cc1=O)-c1cc(OC)c(OCCO)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 2-bromoethanol (37 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-9-(2-hydroxyethoxy)-10-methoxy-2-oxo-6,7-dihydrobenzo[a]quinolizine-3-carboxylate (58 mg) which was used in the next step without purification.

Step 2: Preparation of 6-ethyl-9-(2-hydroxyethoxy)-10-methoxy-2-oxo-6,7-dihydrobenzo[a]quinolizine-3-carboxylic acid

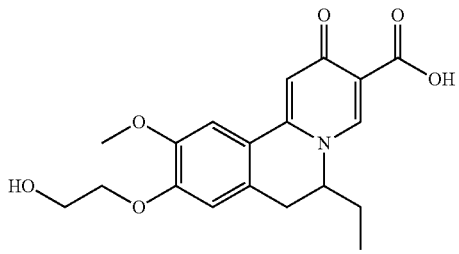 [SMILES: CCC1Cc2cc(OCCO)c(OC)cc2-c2cc(=O)c(C(=O)O)cn21]

To a solution of ethyl 6-ethyl-9-(2-hydroxyethoxy)-10-methoxy-2-oxo-6,7-dihydrobenzo[a]quinolizine-3-carboxylate (58 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-9-(2-hydroxyethoxy)-10-methoxy-2-oxo-6,7-dihydrobenzo[a]quinolizine-3-carboxylic acid (20 mg) as a white solid. $^1$H NMR (400 MHz, MeOD-$d_4$): δ 8.72 (s, 1H), 7.47 (s, 1H), 7.30 (s, 1H), 7.03 (s, 1H), 4.60-4.58 (m, 1H), 4.20-4.17 (m, 2H), 3.97 (s, 3H), 3.96-3.93 (m, 1H), 3.42 (dd, 1H), 3.37 (s, 1H), 3.09 (d, 1H), 1.70-1.59 (m, 2H), 0.93 (t, 3H). MS obsd. (ESI$^+$) [(M+H)$^+$]: 360.

Example 22: 6-ethyl-9-(3-hydroxy-2,2-dimethyl-propoxy)-10-methoxy-2-oxo-6,7-dihydrobenzo[a]quinolizine-3-carboxylic acid

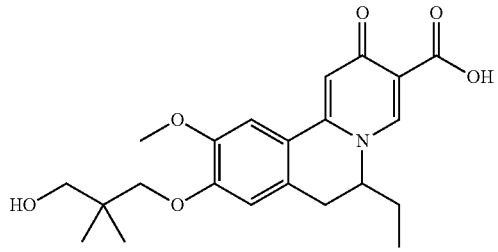 [SMILES: CCC1Cc2cc(OCC(C)(C)CO)c(OC)cc2-c2cc(=O)c(C(=O)O)cn21]

Step 1: Preparation of ethyl 6-ethyl-9-(3-hydroxy-2,2-dimethyl-propoxy)-10-methoxy-2-oxo-6,7-dihydrobenzo[a]quinolizine-3-carboxylate

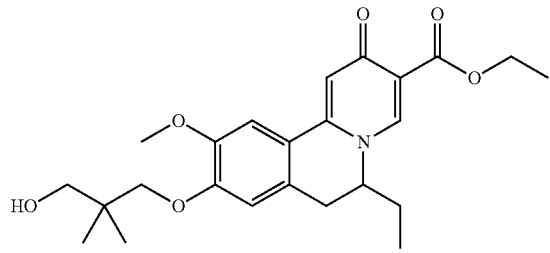 [SMILES: CCOC(=O)c1cn2c(cc1=O)-c1cc(OC)c(OCC(C)(C)CO)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 3-bromo-2,2-dimethyl-propan-1-ol (50 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-9-(3-hydroxy-2,2-dimethyl-propoxy)-10-methoxy-2-oxo-6,7-dihydrobenzo[a]quinolizine-3-carboxylate (65 mg) which was used in the next step without purification.

Step 2: Preparation of 6-ethyl-9-(3-hydroxy-2,2-dimethyl-propoxy)-10-methoxy-2-oxo-6,7-dihydrobenzo[a]quinolizine-3-carboxylic acid

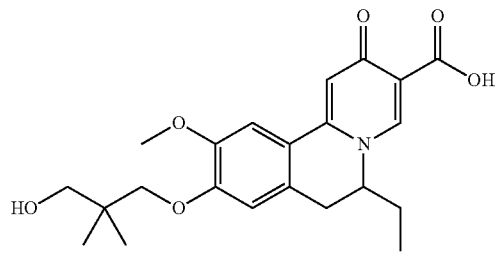 [SMILES: CCC1Cc2cc(OCC(C)(C)CO)c(OC)cc2-c2cc(=O)c(C(=O)O)cn21]

To a solution of ethyl 6-ethyl-9-(3-hydroxy-2,2-dimethyl-propoxy)-10-methoxy-2-oxo-6,7-dihydrobenzo[a]quinolizine-3-carboxylate (65 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-9-(3-hydroxy-2,2-dimethyl-propoxy)-10-methoxy-2-oxo-6,7-dihydrobenzo[a]quinolizine-3-carboxylic acid (30 mg) as a white solid. $^1$H NMR (400 MHz, DMSO-$d_6$): δ 8.80 (s, 1H), 7.52 (s, 1H), 7.45 (s, 1H), 7.04 (s, 1H), 4.72-4.68 (m, 1H), 4.63 (t, 1H), 3.89 (s, 3H), 3.78 (q, 2H), 3.32-3.29 (m, 2H), 3.02 (d, 1H), 1.55-1.41 (m, 2H), 0.95 (s, 6H), 0.81 (t, 3H). MS obsd. (ESI$^+$) [(M+H)$^+$]: 402.

Example 23 and 24

(+)-6-ethyl-9-(3-hydroxy-2,2-dimethyl-propoxy)-10-methoxy-2-oxo-6,7-dihydrobenzo[a]quinolizine-3-carboxylic acid and (−)-6-ethyl-9-(3-hydroxy-2,2-dimethyl-propoxy)-10-methoxy-2-oxo-6,7-dihydrobenzo[a]quinolizine-3-carboxylic acid

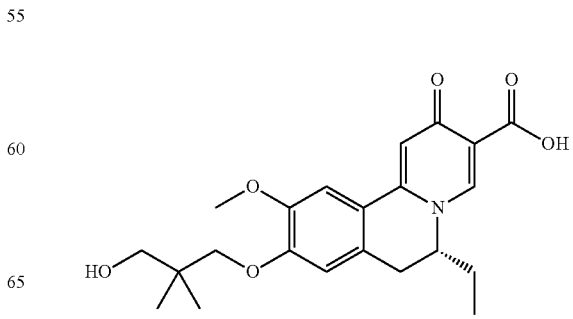

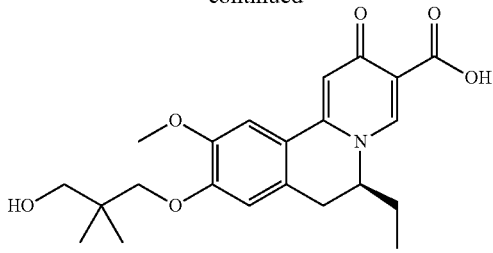

Separation of the racemic 6-ethyl-9-(3-hydroxy-2,2-dimethyl-propoxy)-10-methoxy-2-oxo-6,7-dihydrobenzo[a]quinolizine-3-carboxylic acid (60 mg) by chiral HPLC afforded (+)-6-ethyl-9-(3-hydroxy-2,2-dimethyl-propoxy)-10-methoxy-2-oxo-6,7-dihydrobenzo[a]quinolizine-3-carboxylic acid (21 mg) and (−)-6-ethyl-9-(3-hydroxy-2,2-dimethyl-propoxy)-10-methoxy-2-oxo-6,7-dihydrobenzo[a]quinolizine-3-carboxylic acid (18 mg).

Example 23

$^1$H NMR (400 MHz, DMSO-d$_6$): δ 8.80 (s, 1H), 7.52 (s, 1H), 7.45 (s, 1H), 7.04 (s, 1H), 4.72-4.68 (m, 1H), 4.63 (t, 1H), 3.89 (s, 3H), 3.78 (q, 2H), 3.32-3.29 (m, 2H), 3.02 (d, 1H), 1.55-1.41 (m, 2H), 0.95 (s, 6H), 0.81 (t, 3H). MS obsd. (ESI$^+$) [(M+H)$^+$]: 402. [α]$_D$20=+72° (0.05%, methanol).

Example 24

$^1$H NMR (400 MHz, DMSO-d$_6$): δ 8.80 (s, 1H), 7.52 (s, 1H), 7.45 (s, 1H), 7.04 (s, 1H), 4.72-4.68 (m, 1H), 4.63 (t, 1H), 3.89 (s, 3H), 3.78 (q, 2H), 3.32-3.29 (m, 2H), 3.02 (d, 1H), 1.55-1.41 (m, 2H), 0.95 (s, 6H), 0.81 (t, 3H). MS obsd. (ESI$^+$) [(M+H)$^+$]: 402.

Example 25: 6-ethyl-9-(3-hydroxypropoxy)-10-methoxy-2-oxo-6,7-dihydrobenzo[a]quinolizine-3-carboxylic acid

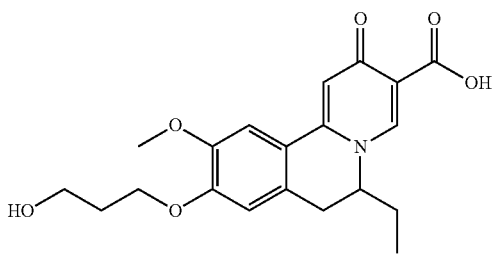 [SMILES: CCC1Cc2cc(OCCCO)c(OC)cc2-c2cc(=O)c(C(=O)O)cn21]

Step 1: Preparation of ethyl 6-ethyl-9-(3-hydroxypropoxy)-10-methoxy-2-oxo-6,7-dihydrobenzo[a]quinolizine-3-carboxylate

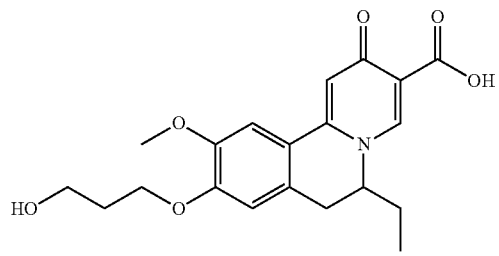 [SMILES: CCC1Cc2cc(OCCCO)c(OC)cc2-c2cc(=O)c(C(=O)O)cn21]

A mixture of ethyl 6-ethyl-9-hydroxy-10-methoxy-2-oxo-6,7-dihydrobenzo[a]quinolizine-3-carboxylate (50 mg, 0.15 mmol), 3-bromopropan-1-ol (42 mg, 0.3 mmol) and K$_2$CO$_3$ (62 mg, 0.45 mmol) in DMF (2 mL) was stirred at 80° C. for 2 hours. Water was added and the mixture was extracted with ethyl acetate. The organic phase was dried over anhydrous Na$_2$SO$_4$ and then concentrated in vacuo to give crude ethyl 6-ethyl-9-(3-hydroxypropoxy)-10-methoxy-2-oxo-6,7-dihydrobenzo[a]quinolizine-3-carboxylate (60 mg) which was used in the next step without purification.

Step 2: Preparation of 6-ethyl-9-(3-hydroxypropoxy)-10-methoxy-2-oxo-6,7-dihydrobenzo[a]quinolizine-3-carboxylic acid

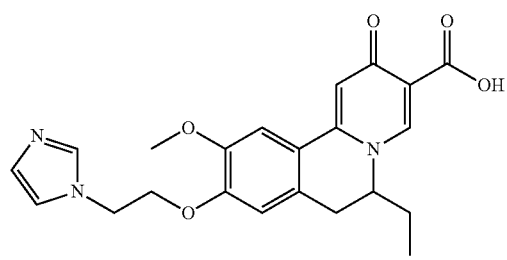 [SMILES: CCC1Cc2cc(OCCn3ccnc3)c(OC)cc2-c2cc(=O)c(C(=O)O)cn21]

To a solution of ethyl 6-ethyl-9-(3-hydroxypropoxy)-10-methoxy-2-oxo-6,7-dihydrobenzo[a]quinolizine-3-carboxylate (60 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous Na$_2$SO$_4$ and then concentrated. The residue was purified by prep-HPLC to give 6-ethyl-9-(3-hydroxypropoxy)-10-methoxy-2-oxo-6,7-dihydrobenzo[a]quinolizine-3-carboxylic acid (23 mg) as a white solid. $^1$H NMR (400 MHz, DMSO-d$_6$): δ 8.81 (s, 1H), 7.52 (s, 1H), 7.46 (s, 1H), 7.05 (s, 1H), 4.73-4.68 (m, 1H), 4.57 (t, 1H), 4.15-4.09 (m, 2H), 3.88 (s, 3H), 3.59-3.55 (m, 2H), 3.35-3.30 (m, 2H), 3.01 (d, 1H), 1.93-1.87 (m, 2H), 1.53-1.43 (m, 2H), 0.80 (t, 3H). MS obsd. (ESI$^+$) [(M+H)$^+$]: 374.

Example 26: 6-ethyl-9-(2-imidazol-1-ylethoxy)-10-methoxy-2-oxo-6,7-dihydrobenzo[a]quinolizine-3-carboxylic acid Step 1: Preparation of ethyl 6-ethyl-9-(2-imidazol-1-ylethoxy)-10-methoxy-2-oxo-6,7-dihydrobenzo[a]quinolizine-3-carboxylate

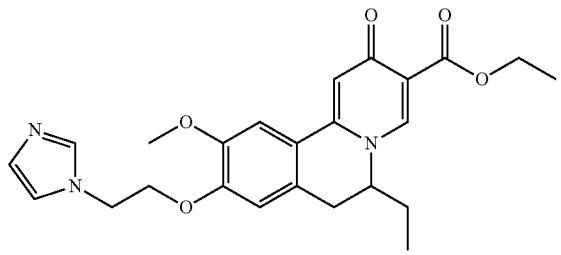 [SMILES: CCOC(=O)c1cn2c(cc1=O)-c1cc(OC)c(OCCn3ccnc3)cc1CC2CC]

A mixture of ethyl 6-ethyl-9-hydroxy-10-methoxy-2-oxo-6,7-dihydrobenzo[a]quinolizine-3-carboxylate (50 mg, 0.15 mmol), 1-(2-bromoethyl)imidazole (53 mg, 0.3 mmol) and $K_2CO_3$ (62 mg, 0.45 mmol) in DMF (2 mL) was stirred at 80° C. for 2 hours. Water was added and the mixture was extracted with ethyl acetate. The organic phase was dried over anhydrous $Na_2SO_4$ and then concentrated in vacuo to give crude ethyl 6-ethyl-9-(2-imidazol-1-ylethoxy)-10-methoxy-2-oxo-6,7-dihydrobenzo[a]quinolizine-3-carboxylate (66 mg) which was used in the next step without purification.

Step 2: Preparation of 6-ethyl-9-(2-imidazol-1-ylethoxy)-10-methoxy-2-oxo-6,7-dihydrobenzo[a]quinolizine-3-carboxylic acid

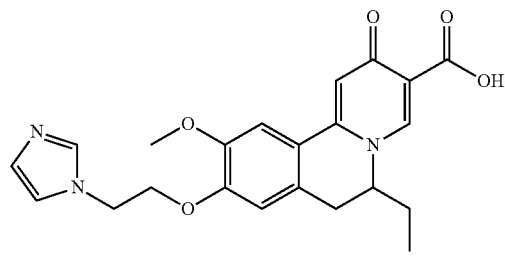 [SMILES: CCC1Cc2cc(OCCn3ccnc3)c(OC)cc2-c2cc(=O)c(C(=O)O)cn21]

To a solution of ethyl 6-ethyl-9-(2-imidazol-1-ylethoxy)-10-methoxy-2-oxo-6,7-dihydrobenzo[a]quinolizine-3-carboxylate (66 mg, 0.15 mmol) in THF (5 mL) was added 10% NaOH aqueous solution dropwise at room temperature. The resultant mixture was stirred for 2 hours, and then acidified to pH 1-2 with 2 M hydrochloric acid. The mixture was extracted with DCM (10 mL×2), and the combined organic layers were washed with brine, and then dried over anhydrous $Na_2SO_4$ and then concentrated. The residue was purified by prep-HPLC to give 6-ethyl-9-(2-imidazol-1-ylethoxy)-10-methoxy-2-oxo-6,7-dihydrobenzo[a]quinolizine-3-carboxylic acid (31 mg) as a white solid. $^1$H NMR (400 MHz, DMSO-$d_6$): δ 8.81 (s, 1H), 7.72 (s, 1H), 7.55 (s, 1H), 7.48 (s, 1H), 7.27 (t, 1H), 7.02 (s, 1H), 6.91 (t, 1H), 4.72-4.67 (m, 1H), 4.42 (t, 2H), 4.33 (t, 2H), 3.89 (s, 3H), 3.34-3.29 (m, 1H), 2.98 (d, 1H), 1.52-1.41 (m, 2H), 0.79 (t, 3H). MS obsd. (ESI$^+$) [(M+H)$^+$]: 410.

Example 27: 6-ethyl-10-methoxy-9-(2-methoxyethoxy)-2-oxo-6,7-dihydrobenzo[a]quinolizine-3-carboxylic acid

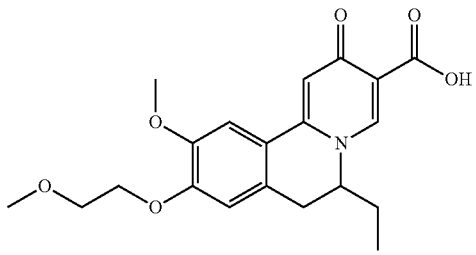

Step 1: Preparation of ethyl 6-ethyl-10-methoxy-9-(2-methoxyethoxy)-2-oxo-6,7-dihydrobenzo[a]quinolizine-3-carboxylate

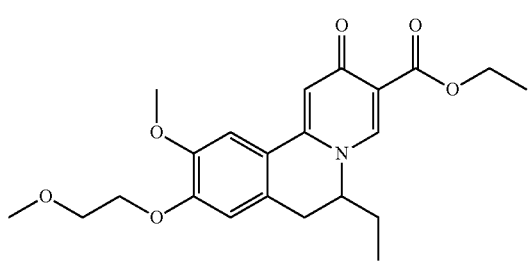

To a solution of ethyl 6-ethyl-9-hydroxy-10-methoxy-2-oxo-6,7-dihydrobenzo[a]quinolizine-3-carboxylate (1.0 g, 2.9 mmol) in DMF was added 1-bromo-2-methoxy-ethane (1.21 g, 8.7 mmol) and $K_2CO_3$ (0.8 g, 5.8 mmol). The reaction mixture was stirred for 3 hours at 80° C. and then filtered. The filtrate was concentrated in vacuo and the residue was used for the next step without further purification.

Step 2: Preparation of 6-ethyl-10-methoxy-9-(2-methoxyethoxy)-2-oxo-6,7-dihydrobenzo[a]quinolizine-3-carboxylic acid

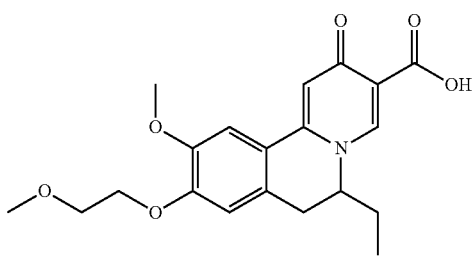

To a solution of crude ethyl 6-ethyl-10-methoxy-9-(2-methoxyethoxy)-2-oxo-6,7-dihydrobenzo[a]quinolizine-3-carboxylate from Step 1 in MeOH (30 mL) and water (10 mL) was added LiOH.$H_2O$ (0.37 g, 8.7 mmol). The mixture was stirred for 2 hours at room temperature and then concentrated under reduced pressure. The residue was dissolved in water (10 mL) and acidified with 6 M hydrochloric acid. The mixture was filtered and the filter cake was dried in vacuo to give 6-ethyl-10-methoxy-9-(2-methoxyethoxy)-2-oxo-6,7-dihydrobenzo[a]quinolizine-3-carboxylic acid (540 mg). ¹H NMR (400 MHz, DMSO-d₆) δ 8.81 (s, 1H), 7.53 (s, 1H), 7.47 (s, 1H), 7.05 (s, 1H), 4.71 (q, 1H), 4.24-4.12 (m, 2H), 3.89 (s, 3H), 3.70 (t, 2H), 3.37-3.33 (m, 4H), 2.99 (d, 1H), 1.58-1.38 (m, 2H), 0.80 (t, 3H). MS obsd. (ESI⁺) [(M+H)⁺]: 374.

Example 28 and 29

(+)-6-ethyl-10-methoxy-9-(2-methoxyethoxy)-2-oxo-6,7-dihydrobenzo[a]quinolizine-3-carboxylic acid and (−)-6-ethyl-10-methoxy-9-(2-methoxyethoxy)-2-oxo-6,7-dihydrobenzo[a]quinolizine-3-carboxylic acid

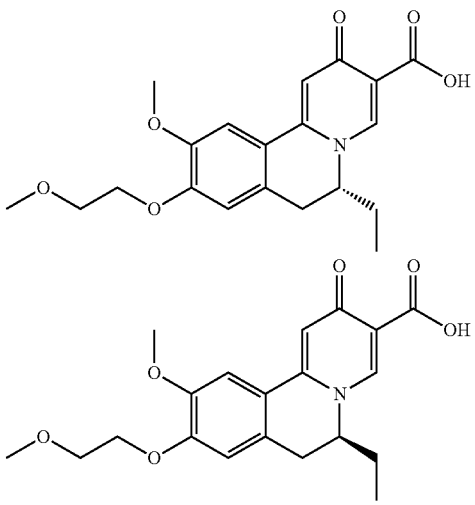

Separation of the racemic 6-ethyl-10-methoxy-9-(2-methoxyethoxy)-2-oxo-6,7-dihydrobenzo[a]quinolizine-3-carboxylic acid (160 mg) by chiral HPLC afforded (+)-6-ethyl-10-methoxy-9-(2-methoxyethoxy)-2-oxo-6,7-dihydrobenzo[a]quinolizine-3-carboxylic acid (21 mg) and (−)-6-ethyl-10-methoxy-9-(2-methoxyethoxy)-2-oxo-6,7-dihydrobenzo[a]quinolizine-3-carboxylic acid (20 mg).

Example 28

¹H NMR (400 MHz, DMSO-d₆) δ 8.81 (s, 1H), 7.53 (s, 1H), 7.47 (s, 1H), 7.05 (s, 1H), 4.71 (q, 1H), 4.24-4.12 (m, 2H), 3.89 (s, 3H), 3.70 (t, 2H), 3.37-3.33 (m, 4H), 2.99 (d, 1H), 1.58-1.38 (m, 2H), 0.80 (t, 3H). MS obsd. (ESI⁺) [(M+H)⁺]: 374. [α]$_D^{20}$=+100.00° (0.070/0%, CH₃CN)

Example 29

¹H NMR (400 MHz, DMSO-d₆) δ 8.81 (s, 1H), 7.53 (s, 1H), 7.47 (s, 1H), 7.05 (s, 1H), 4.71 (q, 1H), 4.24-4.12 (m, 2H), 3.89 (s, 3H), 3.70 (t, 2H), 3.37-3.33 (m, 4H), 2.99 (d, 1H), 1.58-1.38 (m, 2H), 0.80 (t, 3H). MS obsd. (ESI⁺) [(M+H)⁺]: 374.

Example 30: 9-(cyclopropylmethoxy)-6-ethyl-10-methoxy-2-oxo-6,7-dihydrobenzo[a]quinolizine-3-carboxylic acid

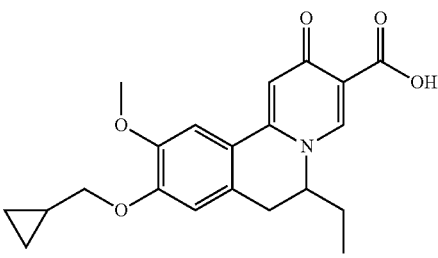 [SMILES: CCC1Cc2cc(OCC3CC3)c(OC)cc2-c2cc(=O)c(C(=O)O)cn21]

Step 1: Preparation of ethyl 9-(cyclopropylmethoxy)-6-ethyl-10-methoxy-2-oxo-6,7-dihydrobenzo[a]quinolizine-3-carboxylate

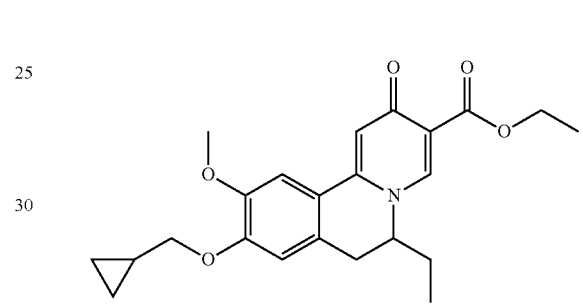

To a solution of ethyl 6-ethyl-9-hydroxy-10-methoxy-2-oxo-6,7-dihydrobenzo[a]quinolizine-3-carboxylate (60 mg, 0.17 mmol) in DMF was added bromomethylcyclopropane (68.9 mg, 0.51 mmol) and K₂CO₃ (46.9 mg, 0.34 mmol). The mixture was stirred for 3 hours at 80° C. and then filtered. The filtrate was concentrated in vacuo to give crude ethyl 9-(cyclopropylmethoxy)-6-ethyl-10-methoxy-2-oxo-6,7-dihydrobenzo[a]quinolizine-3-carboxylate which was used for the next step without further purification.

Step 2: Preparation of 9-(cyclopropylmethoxy)-6-ethyl-10-methoxy-2-oxo-6,7-dihydrobenzo[a]quinolizine-3-carboxylic acid

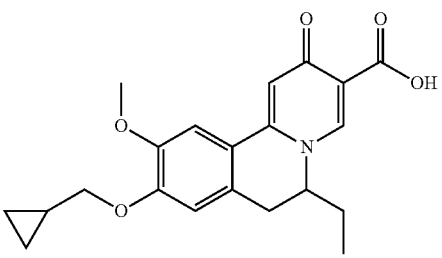 [SMILES: CCC1Cc2cc(OCC3CC3)c(OC)cc2-c2cc(=O)c(C(=O)O)cn21]

To a solution of crude ethyl 9-(cyclopropylmethoxy)-6-ethyl-10-methoxy-2-oxo-6,7-dihydrobenzo[a]quinolizine-3-carboxylate from Step 1 in MeOH (9 mL) and water (3 mL) was added LiOH.H₂O (36.7 mg). The mixture was stirred for 2 hours, and then concentrated under reduced pressure. The residue was dissolved in water (5 mL) and acidified with 6 M hydrochloric acid. The mixture was filtered and the filter cake was dried in vacuo to give 9-(cyclopropylmethoxy)-6-ethyl-10-methoxy-2-oxo-6,7-dihydrobenzo[a]quinolizine-3-carboxylic acid (18 mg). $^1$H NMR (400 MHz, CDCl$_3$) δ 8.51 (s, 1H), 7.20 (s, 1H), 7.10 (s, 1H), 6.74 (s, 1H), 4.23 (q, 1H), 4.00-3.90 (m, 5H), 3.40 (s, 1H), 2.93 (d, 1H), 1.74-1.63 (m, 2H), 1.44-1.34 (m, 1H), 0.94 (t, 3H), 0.77-0.69 (m, 2H), 0.46-0.38 (m, 2H). MS obsd. (ESI$^+$) [(M+H)$^+$]: 370.

Example 31 and 32

(+)-9-(cyclopropylmethoxy)-6-ethyl-10-methoxy-2-oxo-6,7-dihydrobenzo[a]quinolizine-3-carboxylic acid and (−)-9-(cyclopropylmethoxy)-6-ethyl-10-methoxy-2-oxo-6,7-dihydrobenzo[a]quinolizine-3-carboxylic acid

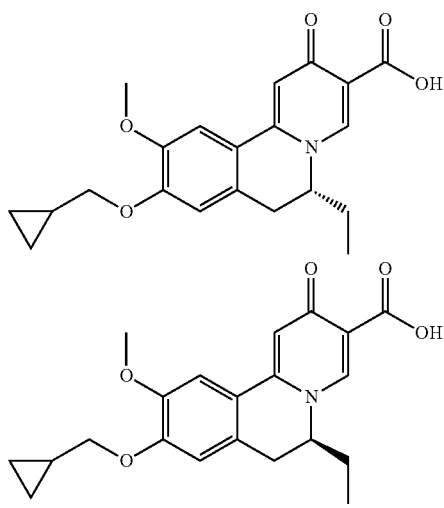

Separation of the racemic 6-ethyl-10-methoxy-9-(2-methoxyethoxy)-2-oxo-6,7-dihydrobenzo[a]quinolizine-3-carboxylic acid (10 mg) by chiral HPLC afforded (+)-9-(cyclopropylmethoxy)-6-ethyl-10-methoxy-2-oxo-6,7-dihydrobenzo[a]quinolizine-3-carboxylic acid (3 mg) and (−)-9-(cyclopropylmethoxy)-6-ethyl-10-methoxy-2-oxo-6,7-dihydrobenzo[a]quinolizine-3-carboxylic acid (3 mg).

Example 31

$^1$H NMR (400 MHz, CDCl$_3$) δ 8.51 (s, 1H), 7.20 (s, 1H), 7.10 (s, 1H), 6.74 (s, 1H), 4.23 (q, 1H), 4.00-3.90 (m, 5H), 3.40 (s, 1H), 2.93 (d, 1H), 1.74-1.63 (m, 2H), 1.44-1.34 (m, 1H), 0.94 (t, 3H), 0.77-0.69 (m, 2H), 0.46-0.38 (m, 2H). MS obsd. (ESI$^+$) [(M+H)$^+$]: 370. [α]$_D^{20}$=+88.80° (0.05%, DMSO)

Example 32

$^1$H NMR (400 MHz, CDCl$_3$) δ 8.51 (s, 1H), 7.20 (s, 1H), 7.10 (s, 1H), 6.74 (s, 1H), 4.23 (q, 1H), 4.00-3.90 (m, 5H), 3.40 (s, 1H), 2.93 (d, 1H), 1.74-1.63 (m, 2H), 1.44-1.34 (m, 1H), 0.94 (t, 3H), 0.77-0.69 (m, 2H), 0.46-0.38 (m, 2H). MS obsd. (ESI$^+$) [(M+H)$^+$]: 370.

Example 33: 6-ethyl-9-isobutoxy-10-methoxy-2-oxo-6,7-dihydrobenzo[a]quinolizine-3-carboxylic acid

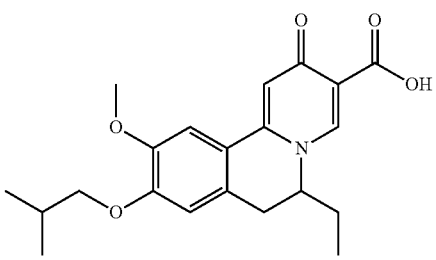 [SMILES: CCC1Cc2cc(OCC(C)C)c(OC)cc2-c2cc(=O)c(C(=O)O)cn21]

Step 1: Preparation of ethyl 6-ethyl-9-isobutoxy-10-methoxy-2-oxo-6,7-dihydrobenzo[a]quinolizine-3-carboxylate

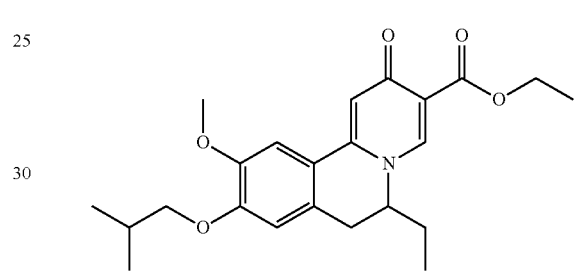

To a solution of ethyl 6-ethyl-9-hydroxy-10-methoxy-2-oxo-6,7-dihydrobenzo[a]quinolizine-3-carboxylate (100 mg, 0.29 mmol) in DMF was added 1-bromo-2-methyl-propane (119.2 mg, 0.87 mmol) and K$_2$CO$_3$ (80 mg, 0.58 mmol). The mixture was stirred for 3 hours at 80° C., and then cooled to room temperature and filtered. The filtrate was concentrated in vacuo to give crude ethyl 6-ethyl-9-isobutoxy-10-methoxy-2-oxo-6,7-dihydrobenzo[a]quinolizine-3-carboxylate which was used for the next step without further purification.

Step 2: Preparation of 6-ethyl-9-isobutoxy-10-methoxy-2-oxo-6,7-dihydrobenzo[a]quinolizine-3-carboxylic acid

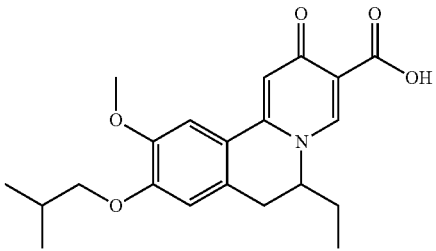 [SMILES: CCC1Cc2cc(OCC(C)C)c(OC)cc2-c2cc(=O)c(C(=O)O)cn21]

To a solution of crude ethyl 6-ethyl-9-isobutoxy-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL) and acidified with 6 M hydrochloric acid. The mixture was filtered and the filter cake was dried in vacuo to give 6-ethyl-9-isobutoxy-10-methoxy-2-oxo-6,7-dihydrobenzo[a]quinolizine-3-carboxylic acid (38 mg). $^1$H NMR (400 MHz, CDCl$_3$) δ 8.50 (s, 1H), 7.20 (s, 1H), 7.09 (s, 1H), 6.75 (s, 1H), 4.27-4.17 (m, 1H), 3.95 (s, 3H), 3.86 (d, 2H), 3.46-3.36 (m, 1H), 2.97-2.90 (m, 1H), 2.28-2.17 (m, 1H), 1.74-1.62 (m, 2H), 1.10 (d, 6H), 0.94 (t, 3H). MS obsd. (ESI$^+$) [(M+H)$^+$]: 372.

Example 34 and 35

(+)-6-ethyl-9-isobutoxy-10-methoxy-2-oxo-6,7-dihydrobenzo[a]quinolizine-3-carboxylic acid and (−)-6-ethyl-9-isobutoxy-10-methoxy-2-oxo-6,7-dihydrobenzo[a]quinolizine-3-carboxylic acid

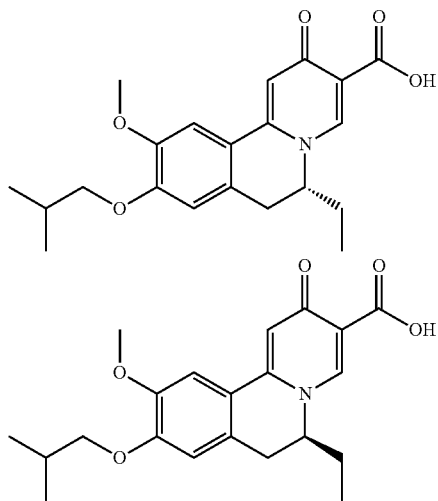

Separation of the racemic 6-ethyl-9-isobutoxy-10-methoxy-2-oxo-6,7-dihydrobenzo[a]quinolizine-3-carboxylic acid (30 mg) by chiral HPLC afforded (+)-6-ethyl-9-isobutoxy-10-methoxy-2-oxo-6,7-dihydrobenzo[a]quinolizine-3-carboxylic acid (8 mg) and (−)-6-ethyl-9-isobutoxy-10-methoxy-2-oxo-6,7-dihydrobenzo[a]quinolizine-3-carboxylic acid (8.6 mg).

Example 34

$^1$H NMR (400 MHz, CDCl$_3$) δ 8.50 (s, 1H), 7.20 (s, 1H), 7.09 (s, 1H), 6.75 (s, 1H), 4.27-4.17 (m, 1H), 3.95 (s, 3H), 3.86 (d, 2H), 3.46-3.36 (m, 1H), 2.97-2.90 (m, 1H), 2.28-2.17 (m, 1H), 1.74-1.62 (m, 2H), 1.10 (d, 6H), 0.94 (t, 3H). MS obsd. (ESI$^+$) [(M+H)$^+$]: 372. [α]$_D$20=+78.40° (0.125%, CH$_3$CN)

Example 35

$^1$H NMR (400 MHz, CDCl$_3$) δ 8.50 (s, 1H), 7.20 (s, 1H), 7.09 (s, 1H), 6.75 (s, 1H), 4.27-4.17 (m, 1H), 3.95 (s, 3H), 3.86 (d, 2H), 3.46-3.36 (m, 1H), 2.97-2.90 (m, 1H), 2.28-2.17 (m, 1H), 1.74-1.62 (m, 2H), 1.10 (d, 6H), 0.94 (t, 3H). MS obsd. (ESI$^+$) [(M+H)$^+$]: 372.

Example 36: 9-ethoxy-6-ethyl-10-methoxy-2-oxo-6,7-dihydrobenzo[a]quinolizine-3-carboxylic acid

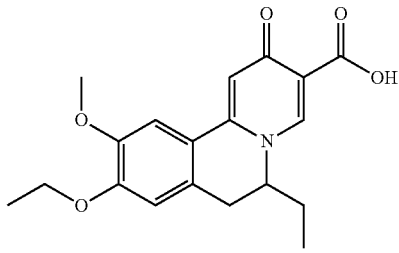 [SMILES: CCOc1cc2c(cc1OC)-c1cc(=O)c(C(=O)O)cn1C(CC)C2]

Step 1: Preparation of ethyl 9-ethoxy-6-ethyl-10-methoxy-2-oxo-6,7-dihydrobenzo[a]quinolizine-3-carboxylate

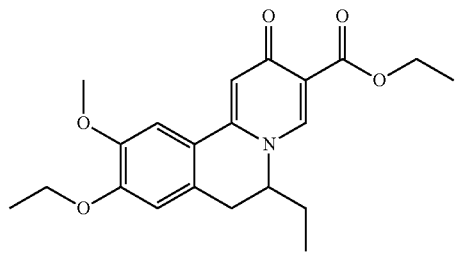 [SMILES: CCOC(=O)c1cn2c(cc1=O)-c1cc(OC)c(OCC)cc1CC2CC]

To a solution of ethyl 6-ethyl-9-hydroxy-10-methoxy-2-oxo-6,7-dihydrobenzo[a]quinolizine-3-carboxylate (100 mg, 0.29 mmol) in DMF was added bromoethane (316 mg, 29 mmol) and K$_2$CO$_3$ (80 mg, 0.58 mmol). The mixture was stirred for 16 hours at 60° C., and then cooled to room temperature and filtered. The filtrate was concentrated in vacuo to give crude ethyl 9-ethoxy-6-ethyl-10-methoxy-2-oxo-6,7-dihydrobenzo[a]quinolizine-3-carboxylate was used for the next step without further purification.

Step 2: Preparation of 9-ethoxy-6-ethyl-10-methoxy-2-oxo-6,7-dihydrobenzo[a]quinolizine-3-carboxylic acid

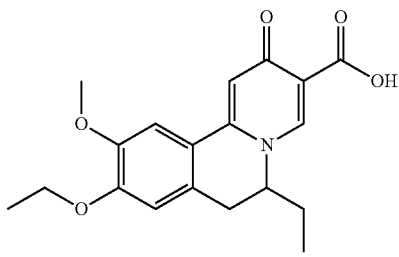 [SMILES: CCOc1cc2c(cc1OC)-c1cc(=O)c(C(=O)O)cn1C(CC)C2]

To a solution of crude ethyl 9-ethoxy-6-ethyl-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL), and then acidified with 6 M hydrochloric acid and then filtered. The filter cake was dried in vacuo to give 9-ethoxy-6-ethyl-10-methoxy-2-oxo-6,7-dihydrobenzo[a]quinolizine-3-carboxylic acid (26 mg). $^1$H NMR (400 MHz, CDCl$_3$) δ 8.52 (s, 1H), 7.20 (s, 1H), 7.10 (s, 1H), 6.76 (s, 1H), 4.31-4.15 (m, 3H), 3.96 (s, 3H), 3.42 (dd, 1H), 2.94 (d, 1H), 1.66-1.62 (m, 2H), 1.54 (t, 3H), 0.94 (t, 3H). MS obsd. (ESI$^+$) [(M+H)$^+$]: 344.

Example 37 and 38

(+)-9-ethoxy-6-ethyl-10-methoxy-2-oxo-6,7-dihydrobenzo[a]quinolizine-3-carboxylic acid and (−)-9-ethoxy-6-ethyl-10-methoxy-2-oxo-6,7-dihydrobenzo[a]quinolizine-3-carboxylic acid

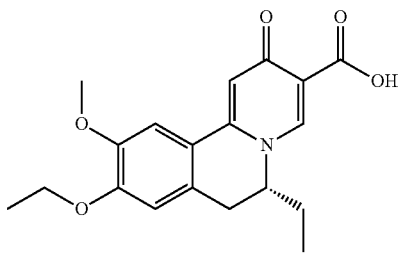

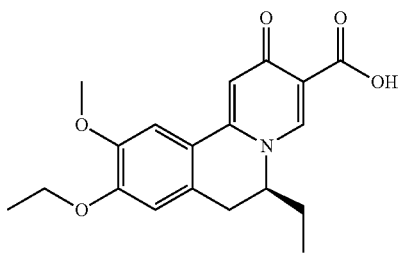

Separation of the racemic 9-ethoxy-6-ethyl-10-methoxy-2-oxo-6,7-dihydrobenzo[a]quinolizine-3-carboxylic acid (15 mg) by chiral HPLC afforded (+)-9-ethoxy-6-ethyl-10-methoxy-2-oxo-6,7-dihydrobenzo[a]quinolizine-3-carboxylic acid (4 mg) and (−)-9-ethoxy-6-ethyl-10-methoxy-2-oxo-6,7-dihydrobenzo[a]quinolizine-3-carboxylic acid (4.6 mg).

Example 37

$^1$H NMR (400 MHz, CDCl$_3$) δ 8.52 (s, 1H), 7.20 (s, 1H), 7.10 (s, 1H), 6.76 (s, 1H), 4.31-4.15 (m, 3H), 3.96 (s, 3H), 3.42 (dd, 1H), 2.94 (d, 1H), 1.66-1.62 (m, 2H), 1.54 (t, 3H), 0.94 (t, 3H). MS obsd. (ESI$^+$) [(M+H)$^+$]: 344. [α]$_D$20=+96.00° (0.05%, DMSO)

Example 38

$^1$H NMR (400 MHz, CDCl$_3$) δ 8.52 (s, 1H), 7.20 (s, 1H), 7.10 (s, 1H), 6.76 (s, 1H), 4.31-4.15 (m, 3H), 3.96 (s, 3H), 3.42 (dd, 1H), 2.94 (d, 1H), 1.66-1.62 (m, 2H), 1.54 (t, 3H), 0.94 (t, 3H). MS obsd. (ESI$^+$) [(M+H)$^+$]: 344.

Example 39: 6-ethyl-10-methoxy-9-(3-methoxypropoxy)-2-oxo-6,7-dihydrobenzo[a]quinolizine-3-carboxylic acid

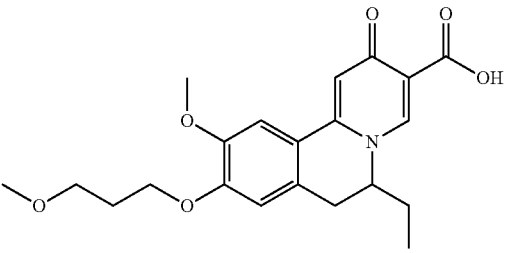 [SMILES: CCC1Cc2cc(OCCCOC)c(OC)cc2-c2cc(=O)c(C(=O)O)cn21]

Step 1: Preparation of ethyl 6-ethyl-10-methoxy-9-(3-methoxypropoxy)-2-oxo-6,7-dihydrobenzo[a]quinolizine-3-carboxylate

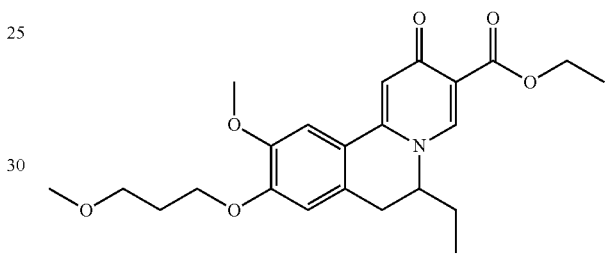

To a solution of ethyl 6-ethyl-9-hydroxy-10-methoxy-2-oxo-6,7-dihydrobenzo[a]quinolizine-3-carboxylate (100 mg, 0.29 mmol) in DMF was added 1-bromo-3-methoxypropane (133.1 mg, 0.87 mmol) and K$_2$CO$_3$ (80 mg, 0.58 mmol). The mixture was stirred for 2 hours at 80° C., and then cooled to room temperature and filtered. The filtrate was concentrated in vacuo to give crude ethyl 6-ethyl-10-methoxy-9-(3-methoxypropoxy)-2-oxo-6,7-dihydrobenzo[a]quinolizine-3-carboxylate which was used for the next step without further purification.

Step 2: Preparation of 6-ethyl-10-methoxy-9-(3-methoxypropoxy)-2-oxo-6,7-dihydrobenzo[a]quinolizine-3-carboxylic acid

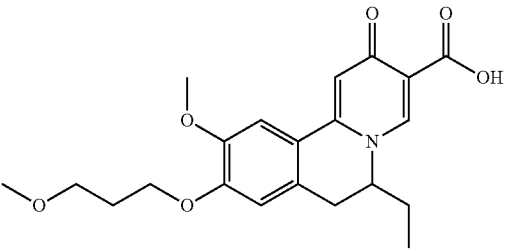 [SMILES: CCC1Cc2cc(OCCCOC)c(OC)cc2-c2cc(=O)c(C(=O)O)cn21]

To a solution of crude ethyl 6-ethyl-10-methoxy-9-(3-methoxypropoxy)-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL), and then acidified with 6 M hydrochloric acid and filtered. The filter cake was dried in vacuo to give 6-ethyl-10-methoxy-9-(3-methoxypropoxy)-2-oxo-6,7-dihydrobenzo[a]quinolizine-3-carboxylic acid (45 mg). $^1$H NMR (400 MHz, CDCl$_3$) δ 8.51 (s, 1H), 7.19 (s, 1H), 7.09 (s, 1H), 6.80 (s, 1H), 4.23-4.19 (m, 3H), 3.95 (s, 3H), 3.66-3.56 (m, 2H), 3.46-3.37 (m, 4H), 2.94 (d, 1H), 2.17 (q, 2H), 1.81-1.66 (m, 2H), 0.94 (t, 3H). MS obsd. (ESI$^+$) [(M+H)$^+$]: 388.

Example 40 and 41

(+)-6-ethyl-10-methoxy-9-(3-methoxypropoxy)-2-oxo-6,7-dihydrobenzo[a]quinolizine-3-carboxylic acid and (−)-6-ethyl-10-methoxy-9-(3-methoxypropoxy)-2-oxo-6,7-dihydrobenzo[a]quinolizine-3-carboxylic acid

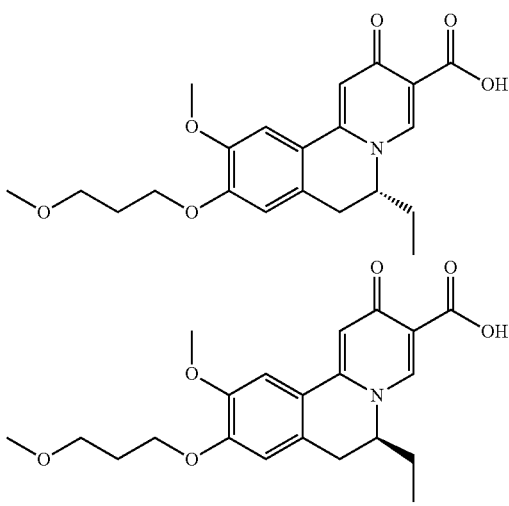

Separation of the racemic 6-ethyl-10-methoxy-9-(3-methoxypropoxy)-2-oxo-6,7-dihydrobenzo[a]quinolizine-3-carboxylic acid (35 mg) by chiral HPLC afforded (+)-6-ethyl-10-methoxy-9-(3-methoxypropoxy)-2-oxo-6,7-dihydrobenzo[a]quinolizine-3-carboxylic acid (10.6 mg) and (−)-6-ethyl-10-methoxy-9-(3-methoxypropoxy)-2-oxo-6,7-dihydrobenzo[a]quinolizine-3-carboxylic acid (7 mg).

Example 40

$^1$H NMR (400 MHz, CDCl$_3$) δ 8.51 (s, 1H), 7.19 (s, 1H), 7.09 (s, 1H), 6.80 (s, 1H), 4.23-4.19 (m, 3H), 3.95 (s, 3H), 3.66-3.56 (m, 2H), 3.46-3.37 (m, 4H), 2.94 (d, 1H), 2.17 (q, 2H), 1.81-1.66 (m, 2H), 0.94 (t, 3H). MS obsd. (ESI$^+$) [(M+H)$^+$]: 388. [α]$_D$20=+96.97° (0.099%, CH$_3$CN)

Example 41

$^1$H NMR (400 MHz, CDCl$_3$) δ 8.51 (s, 1H), 7.19 (s, 1H), 7.09 (s, 1H), 6.80 (s, 1H), 4.23-4.19 (m, 3H), 3.95 (s, 3H), 3.66-3.56 (m, 2H), 3.46-3.37 (m, 4H), 2.94 (d, 1H), 2.17 (q, 2H), 1.81-1.66 (m, 2H), 0.94 (t, 3H). MS obsd. (ESI$^+$) [(M+H)$^+$]: 388.

Example 42: 9-(2-ethoxyethoxy)-6-ethyl-10-methoxy-2-oxo-6,7-dihydrobenzo[a]quinolizine-3-carboxylic acid

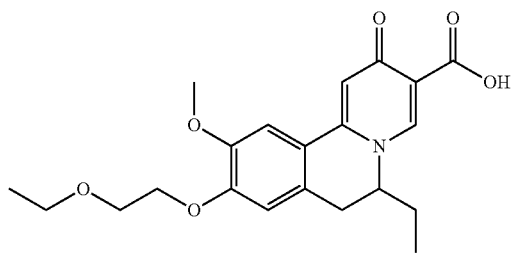 [SMILES: CCOCCOc1cc2c(cc1OC)-c1cc(=O)c(C(=O)O)cn1C(CC)C2]

Step 1: Preparation of ethyl 9-(2-ethoxyethoxy)-6-ethyl-10-methoxy-2-oxo-6,7-dihydrobenzo[a]quinolizine-3-carboxylate

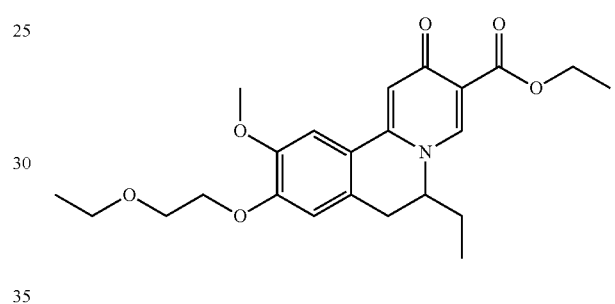

To a solution of ethyl 6-ethyl-9-hydroxy-10-methoxy-2-oxo-6,7-dihydrobenzo[a]quinolizine-3-carboxylate (100 mg, 0.29 mmol) in DMF was added 1-bromo-2-ethoxyethane (133.10 mg, 0.87 mmol) and K$_2$CO$_3$ (80 mg, 0.58 mmol). The mixture was stirred for 2 hours at 80° C., and then cooled to room temperature and filtered. The filtrate was concentrated in vacuo to give crude ethyl 9-(2-ethoxyethoxy)-6-ethyl-10-methoxy-2-oxo-6,7-dihydrobenzo[a]quinolizine-3-carboxylate which was used for the next step without further purification.

Step 2: Preparation of 9-(2-ethoxyethoxy)-6-ethyl-10-methoxy-2-oxo-6,7-dihydrobenzo[a]quinolizine-3-carboxylic acid

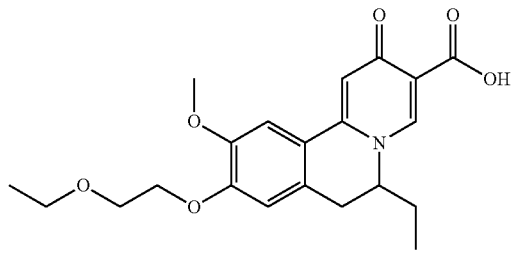 [SMILES: CCOCCOc1cc2c(cc1OC)-c1cc(=O)c(C(=O)O)cn1C(CC)C2]

To a solution of crude ethyl 9-(2-ethoxyethoxy)-6-ethyl-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL), and then acidified with 6 M hydrochloric acid and filtered. The filter cake was dried in vacuo to give 9-(2-ethoxyethoxy)-6-ethyl-10-methoxy-2-oxo-6,7-dihydrobenzo[a]quinolizine-3-carboxylic acid (44 mg). $^1$H NMR (400 MHz, CDCl$_3$) δ 8.51 (s, 1H), 7.20 (s, 1H), 7.10 (s, 1H), 6.84 (s, 1H), 4.34-4.18 (m, 3H), 3.95 (s, 3H), 3.88 (t, 2H), 3.64 (q, 2H), 3.42 (dd, 1H), 2.93 (d, 1H), 1.76-1.64 (m, 2H), 1.26 (t, 3H), 0.94 (t, 3H). MS obsd. (ESI$^+$) [(M+H)$^+$]: 388.

Example 43 and 44

(+)-9-(2-ethoxyethoxy)-6-ethyl-10-methoxy-2-oxo-6,7-dihydrobenzo[a]quinolizine-3-carboxylic acid and (−)-9-(2-ethoxyethoxy)-6-ethyl-10-methoxy-2-oxo-6,7-dihydrobenzo[a]quinolizine-3-carboxylic acid

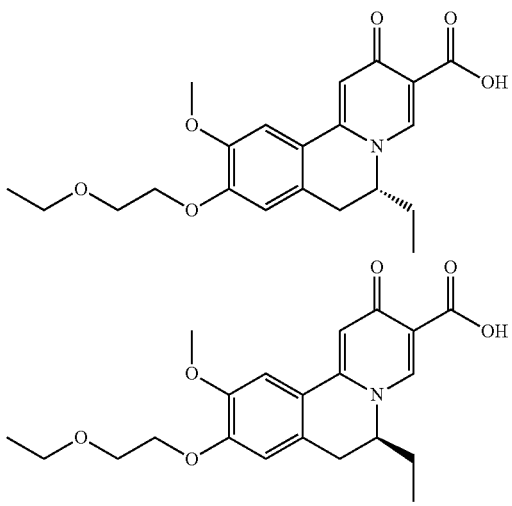

Separation of the racemic 9-(2-ethoxyethoxy)-6-ethyl-10-methoxy-2-oxo-6,7-dihydrobenzo[a]quinolizine-3-carboxylic acid (35 mg) by chiral HPLC afforded (+)-9-(2-ethoxyethoxy)-6-ethyl-10-methoxy-2-oxo-6,7-dihydrobenzo[a]quinolizine-3-carboxylic acid (9.8 mg) and (−)-9-(2-ethoxyethoxy)-6-ethyl-10-methoxy-2-oxo-6,7-dihydrobenzo[a]quinolizine-3-carboxylic acid (9.5 mg).

Example 43

$^1$H NMR (400 MHz, CDCl$_3$) δ 8.51 (s, 1H), 7.20 (s, 1H), 7.10 (s, 1H), 6.84 (s, 1H), 4.34-4.18 (m, 3H), 3.95 (s, 3H), 3.88 (t, 2H), 3.64 (q, 2H), 3.42 (dd, 1H), 2.93 (d, 1H), 1.76-1.64 (m, 2H), 1.26 (t, 3H), 0.94 (t, 3H). MS obsd. (ESI$^+$) [(M+H)$^+$]: 388. [α]$_D$20=+83.20 (0.100%, CH$_3$CN)

Example 44

$^1$H NMR (400 MHz, CDCl$_3$) δ 8.51 (s, 1H), 7.20 (s, 1H), 7.10 (s, 1H), 6.84 (s, 1H), 4.34-4.18 (m, 3H), 3.95 (s, 3H), 3.88 (t, 2H), 3.64 (q, 2H), 3.42 (dd, 1H), 2.93 (d, 1H), 1.76-1.64 (m, 2H), 1.26 (t, 3H), 0.94 (t, 3H). MS obsd. (ESI$^+$) [(M+H)$^+$]: 388.

Example 45: 9-(2,2-difluoroethoxy)-6-ethyl-10-methoxy-2-oxo-6,7-dihydrobenzo[a]quinolizine-3-carboxylic acid

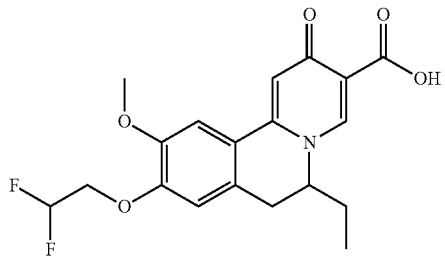

Step 1: Preparation of ethyl 9-(2,2-difluoroethoxy)-6-ethyl-10-methoxy-2-oxo-6,7-dihydrobenzo[a]quinolizine-3-carboxylate

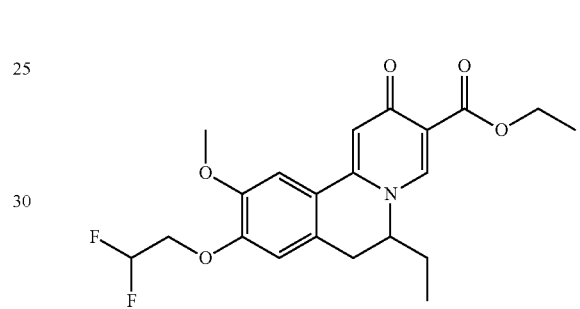

To a solution of ethyl 6-ethyl-9-hydroxy-10-methoxy-2-oxo-6,7-dihydrobenzo[a]quinolizine-3-carboxylate (100 mg, 0.29 mmol) in DMF was added 2-bromo-1,1-difluoroethane (126 mg, 0.87 mmol) and K$_2$CO$_3$ (80 mg, 0.58 mmol). The mixture was stirred for 2 hours at 80° C., and then cooled to room temperature and filtered. The filtrate was concentrated in vacuo to give crude ethyl 9-(2,2-difluoroethoxy)-6-ethyl-10-methoxy-2-oxo-6,7-dihydrobenzo[a]quinolizine-3-carboxylate which was used for the next step without further purification.

Step 2: Preparation of 9-(2,2-difluoroethoxy)-6-ethyl-10-methoxy-2-oxo-6,7-dihydrobenzo[a]quinolizine-3-carboxylic acid

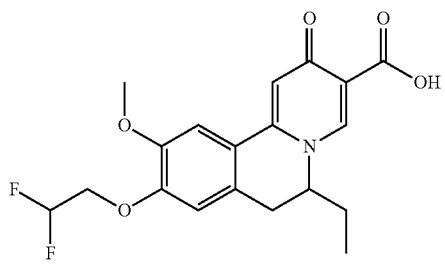 [SMILES: CCC1Cc2cc(OCC(F)F)c(OC)cc2-c2cc(=O)c(C(=O)O)cn21]

To a solution of crude ethyl 9-(2,2-difluoroethoxy)-6-ethyl-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL), and then acidified with 6 M hydrochloric acid and filtered. The filter cake was dried in vacuo to give 9-(2,2-difluoroethoxy)-6-ethyl-10-methoxy-2-oxo-6,7-dihydrobenzo[a]quinolizine-3-carboxylic acid (37 mg). ¹H NMR (400 MHz, CDCl₃) δ 8.53 (s, 1H), 7.25 (s, 1H), 7.12 (s, 1H), 6.83 (s, 1H), 6.32 (t, 0.3H), 6.19 (t, 0.53H), 6.05 (t, 0.32H), 4.41-4.17 (m, 3H), 3.96 (s, 3H), 3.43 (d, 1H), 2.96 (d, 1H), 1.84-1.65 (m, 2H), 0.94 (t, 3H). MS obsd. (ESI⁺) [(M+H)⁺]: 380.

Example 46 and 47

(+)-9-(2,2-difluoroethoxy)-6-ethyl-10-methoxy-2-oxo-6,7-dihydrobenzo[a]quinolizine-3-carboxylic acid and (−)-9-(2,2-difluoroethoxy)-6-ethyl-10-methoxy-2-oxo-6,7-dihydrobenzo[a]quinolizine-3-carboxylic acid

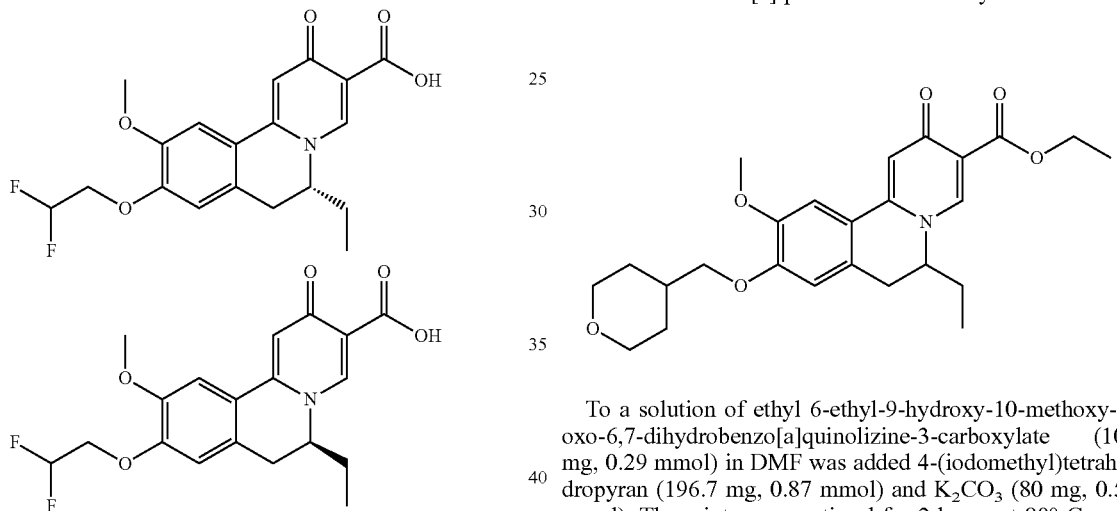

Separation of the racemic 9-(2,2-difluoroethoxy)-6-ethyl-10-methoxy-2-oxo-6,7-dihydrobenzo[a]quinolizine-3-carboxylic acid (28 mg) by chiral HPLC afforded (+)-9-(2,2-difluoroethoxy)-6-ethyl-10-methoxy-2-oxo-6,7-dihydrobenzo[a]quinolizine-3-carboxylic acid (5.7 mg) and (−)-9-(2,2-difluoroethoxy)-6-ethyl-10-methoxy-2-oxo-6,7-dihydrobenzo[a]quinolizine-3-carboxylic acid (5.6 mg).

Example 46

¹H NMR (400 MHz, CDCl₃) δ 8.53 (s, 1H), 7.25 (s, 1H), 7.12 (s, 1H), 6.83 (s, 1H), 6.32 (t, 0.3H), 6.19-6.05 (m, 1H), 4.41-4.17 (m, 3H), 3.96 (s, 3H), 3.43 (d, 1H), 2.96 (d, 1H), 1.84-1.65 (m, 2H), 0.94 (t, 3H). MS obsd. (ESI⁺) [(M+H)⁺]: 380. $[\alpha]_D^{20}$=+75.20° (0.05%, DMSO)

Example 47

¹H NMR (400 MHz, CDCl₃) δ 8.53 (s, 1H), 7.25 (s, 1H), 7.12 (s, 1H), 6.83 (s, 1H), 6.32 (t, 0.3H), 6.19-6.05 (m, 1H), 4.41-4.17 (m, 3H), 3.96 (s, 3H), 3.43 (d, 1H), 2.96 (d, 1H), 1.84-1.65 (m, 2H), 0.94 (t, 3H). MS obsd. (ESI⁺) [(M+H)⁺]: 380.

Example 48: 6-ethyl-10-methoxy-2-oxo-9-(tetrahydropyran-4-ylmethoxy)-6,7-dihydrobenzo[a]quinolizine-3-carboxylic acid

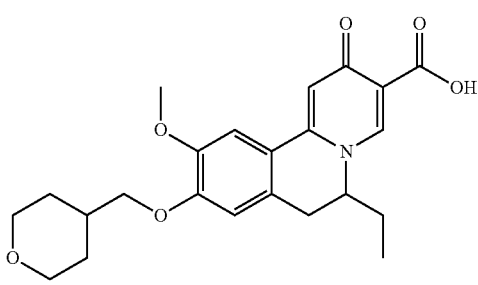 [SMILES: CCC1Cc2cc(OCC3CCOCC3)c(OC)cc2-c2cc(=O)c(C(=O)O)cn21]

Step 1: Preparation of ethyl 6-ethyl-10-methoxy-2-oxo-9-(tetrahydropyran-4-ylmethoxy)-6,7-dihydrobenzo[a]quinolizine-3-carboxylate

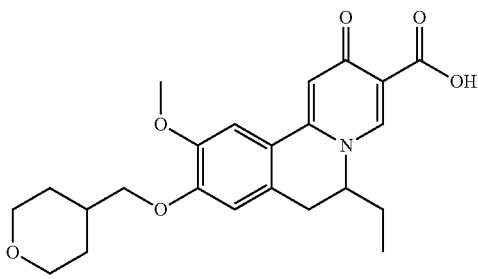 [SMILES: CCC1Cc2cc(OCC3CCOCC3)c(OC)cc2-c2cc(=O)c(C(=O)O)cn21]

To a solution of ethyl 6-ethyl-9-hydroxy-10-methoxy-2-oxo-6,7-dihydrobenzo[a]quinolizine-3-carboxylate (100 mg, 0.29 mmol) in DMF was added 4-(iodomethyl)tetrahydropyran (196.7 mg, 0.87 mmol) and K₂CO₃ (80 mg, 0.58 mmol). The mixture was stirred for 2 hours at 80° C., and then cooled to room temperature and filtered. The filtrate was concentrated in vacuo to give crude ethyl 6-ethyl-10-methoxy-2-oxo-9-(tetrahydropyran-4-ylmethoxy)-6,7-dihydrobenzo[a]quinolizine-3-carboxylate which was used for the next step without further purification.

Step 2: Preparation of 6-ethyl-10-methoxy-2-oxo-9-(tetrahydropyran-4-ylmethoxy)-6,7-dihydrobenzo[a]quinolizine-3-carboxylic acid To a solution of crude ethyl 6-ethyl-10-methoxy-2-oxo-9-(tetrahydropyran-4-ylmethoxy)-6,7-dihydrobenzo[a]quinolizine-3-carboxylate from Step 1 in MeOH (9 mL) and water (3 mL) was added LiOH.H₂O (36.7 mg). The mixture was stirred for 2 hours and then concentrated under reduced pressure. The residue was dissolved in water (5 mL), and then acidified with 6 M hydrochloric acid and filtered. The filter cake was dried in vacuo to give 6-ethyl-10-methoxy-2-oxo-9-(tetrahydropyran-4-ylmethoxy)-6,7-dihydrobenzo[a]quinolizine-3-carboxylic acid (48 mg). $^1$H NMR (400 MHz, CDCl$_3$) δ 8.52 (s, 1H), 7.20 (s, 1H), 7.11 (s, 1H), 6.75 (s, 1H), 4.25 (br. s., 1H), 4.06 (dd, 2H), 3.99-3.88 (m, 5H), 3.58-3.34 (m, 3H), 2.94 (d, 1H), 2.29-2.15 (m, 1H), 1.89-1.79 (m, 2H), 1.71-1.58 (m, 2H), 1.57-1.43 (m, 2H), 0.94 (t, 3H). MS obsd. (ESI$^+$) [(M+H)$^+$]: 414.

Example 49 and 50

(+)-6-ethyl-10-methoxy-2-oxo-9-(tetrahydropyran-4-ylmethoxy)-6,7-dihydrobenzo[a]quinolizine-3-carboxylic acid and (−)-6-ethyl-10-methoxy-2-oxo-9-(tetrahydropyran-4-ylmethoxy)-6,7-dihydrobenzo[a]quinolizine-3-carboxylic acid

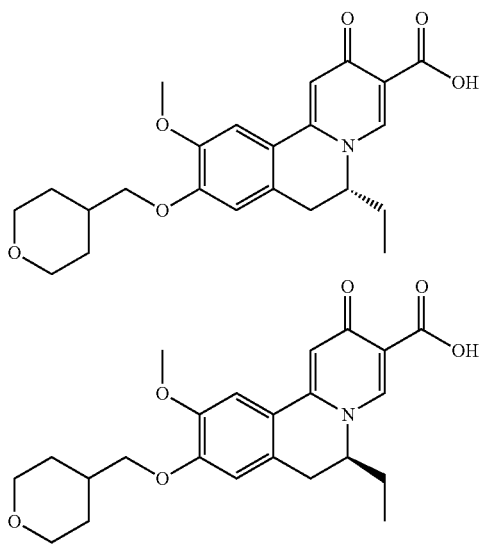

Separation of the racemic 6-ethyl-10-methoxy-2-oxo-9-(tetrahydropyran-4-ylmethoxy)-6,7-dihydrobenzo[a]quinolizine-3-carboxylic acid (40 mg) by chiral HPLC afforded (+)-6-ethyl-10-methoxy-2-oxo-9-(tetrahydropyran-4-ylmethoxy)-6,7-dihydrobenzo[a]quinolizine-3-carboxylic acid (12 mg) and (−)-6-ethyl-10-methoxy-2-oxo-9-(tetrahydropyran-4-ylmethoxy)-6,7-dihydrobenzo[a]quinolizine-3-carboxylic acid (11.8 mg).

Example 49

$^1$H NMR (400 MHz, CDCl$_3$) δ 8.52 (s, 1H), 7.20 (s, 1H), 7.11 (s, 1H), 6.75 (s, 1H), 4.25 (br. s., 1H), 4.06 (dd, 2H), 3.99-3.88 (m, 5H), 3.58-3.34 (m, 3H), 2.94 (d, 1H), 2.29-2.15 (m, 1H), 1.89-1.79 (m, 2H), 1.71-1.58 (m, 2H), 1.57-1.43 (m, 2H), 0.94 (t, 3H). MS obsd. (ESI$^+$) [(M+H)$^+$]: 414. [α]$_D$20=+88.73° (0.11%, CH$_3$CN).

Example 50

$^1$H NMR (400 MHz, CDCl$_3$) δ 8.52 (s, 1H), 7.20 (s, 1H), 7.11 (s, 1H), 6.75 (s, 1H), 4.25 (br. s., 1H), 4.06 (dd, 2H), 3.99-3.88 (m, 5H), 3.58-3.34 (m, 3H), 2.94 (d, 1H), 2.29-2.15 (m, 1H), 1.89-1.79 (m, 2H), 1.71-1.58 (m, 2H), 1.57-1.43 (m, 2H), 0.94 (t, 3H). MS obsd. (ESI$^+$) [(M+H)$^+$]: 414.

Example 51: 6-ethyl-10-methoxy-2-oxo-9-(2-pyrrolidin-1-ylethoxy)-6,7-dihydrobenzo[a]quinolizine-3-carboxylic acid

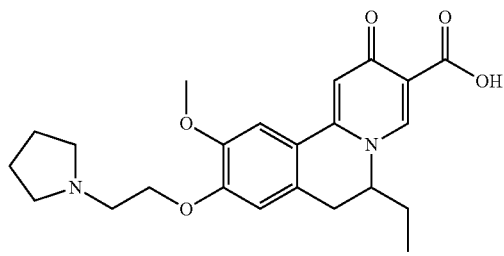 [SMILES: CCC1Cc2cc(OCCN3CCCC3)c(OC)cc2-c2cc(=O)c(C(=O)O)cn21]

Step 1: Preparation of ethyl 6-ethyl-10-methoxy-2-oxo-9-(2-pyrrolidin-1-ylethoxy)-6,7-dihydrobenzo[a]quinolizine-3-carboxylate

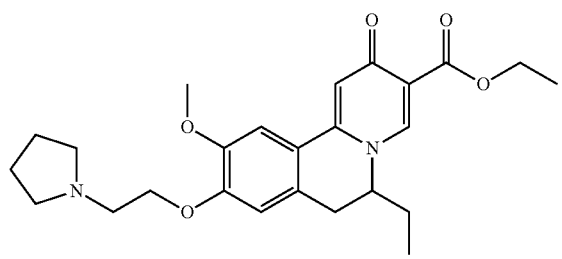 [SMILES: CCOC(=O)c1cn2c(cc1=O)-c1cc(OC)c(OCCN3CCCC3)cc1CC2CC]

To a solution of ethyl 6-ethyl-9-hydroxy-10-methoxy-2-oxo-6,7-dihydrobenzo[a]quinolizine-3-carboxylate (100 mg, 0.29 mmol) in DMF was added 1-(2-Chloroethyl)pyrrolidine hydrochloride (148 mg, 0.87 mmol) and K$_2$CO$_3$ (200.1 mg, 1.45 mmol). The mixture was stirred for 48 hours at 80° C., and then cooled to room temperature and filtered. The filtrate was concentrated in vacuo to give crude ethyl 6-ethyl-10-methoxy-2-oxo-9-(2-pyrrolidin-1-yl ethoxy)-6,7-dihydrobenzo[a]quinolizine-3-carboxylate which was used for the next step without further purification.

Step 2: Preparation of 6-ethyl-10-methoxy-2-oxo-9-(2-pyrrolidin-1-ylethoxy)-6,7-dihydrobenzo[a]quinolizine-3-carboxylic acid

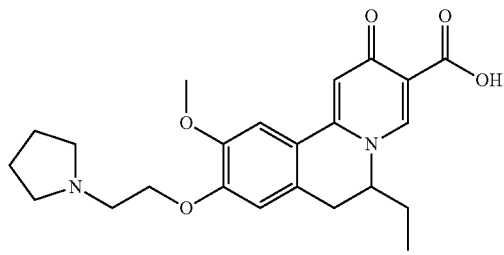 [SMILES: CCC1Cc2cc(OCCN3CCCC3)c(OC)cc2-c2cc(=O)c(C(=O)O)cn21]

To a solution of crude ethyl 6-ethyl-10-methoxy-2-oxo-9-(2-pyrrolidin-1-ylethoxy)-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and concentrated under reduced pressure. The residue was dissolved in water (5 mL) and then acidified with 6 M hydrochloric acid. The mixture was purified by prep-HPLC to give 6-ethyl-10-methoxy-2-oxo-9-(2-pyrrolidin-1-ylethoxy)-6,7-dihydrobenzo[a]quinolizine-3-carboxylic acid (8 mg). $^1$H NMR (400 MHz, MeOD-d$_4$) δ 8.68 (s, 1H), 7.44 (s, 1H), 7.24 (s, 1H), 7.02 (s, 1H), 4.56 (d, 1H), 4.29 (br. s, 2H), 3.96 (s, 3H), 3.46-3.35 (m, 1H), 3.21-3.01 (m, 3H), 2.92 (br. s, 4H), 1.93 (br. s, 4H), 1.74-1.52 (m, 2H), 0.92 (t, 3H). MS obsd. (ESI$^+$) [(M+H)$^+$]: 413.

Example 52: 9-(3-cyanopropoxy)-6-ethyl-10-methoxy-2-oxo-6,7-dihydrobenzo[a]quinolizine-3-carboxylic acid

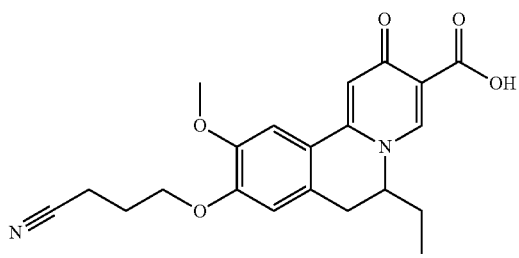 [SMILES: CCC1Cc2cc(OCCCC#N)c(OC)cc2-c2cc(=O)c(C(=O)O)cn21]

Step 1: Preparation of ethyl 9-(3-cyanopropoxy)-6-ethyl-10-methoxy-2-oxo-6,7-dihydrobenzo[a]quinolizine-3-carboxylate

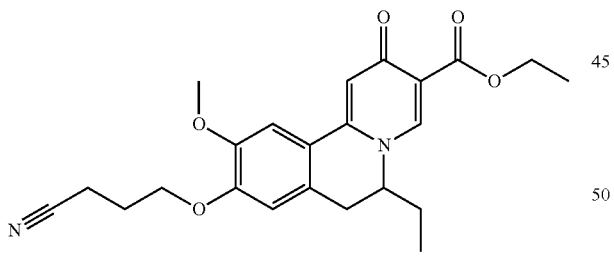

To a solution of ethyl 6-ethyl-9-hydroxy-10-methoxy-2-oxo-6,7-dihydrobenzo[a]quinolizine-3-carboxylate (100 mg, 0.29 mmol) in DMF was added 4-bromobutanenitrile (214.6 mg, 1.45 mmol) and K$_2$CO$_3$ (80 mg, 0.58 mmol). The mixture was stirred for 4 hours at 80° C., and then cooled to room temperature and filtered. The filtrate was concentrated in vacuo to give crude ethyl 9-(3-cyanopropoxy)-6-ethyl-10-methoxy-2-oxo-6,7-dihydrobenzo[a]quinolizine-3-carboxylate which was used for the next step without further purification.

Step 2: Preparation of 9-(3-cyanopropoxy)-6-ethyl-10-methoxy-2-oxo-6,7-dihydrobenzo[a]quinolizine-3-carboxylic acid

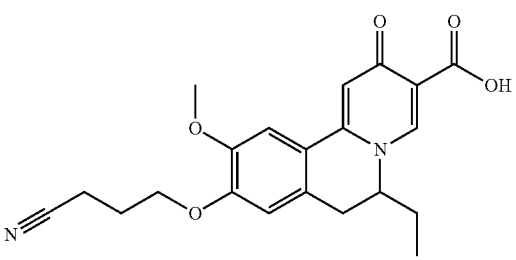 [SMILES: CCC1Cc2cc(OCCCC#N)c(OC)cc2-c2cc(=O)c(C(=O)O)cn21]

To a solution of crude ethyl 9-(3-cyanopropoxy)-6-ethyl-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and concentrated under reduced pressure. The residue was dissolved in water (5 mL) and then acidified with 6 M hydrochloric acid. The mixture was purified by prep-HPLC to give 9-(3-cyanopropoxy)-6-ethyl-10-methoxy-2-oxo-6,7-dihydrobenzo[a]quinolizine-3-carboxylic acid (10 mg). $^1$H NMR (400 MHz, CDCl$_3$) δ 8.52 (s, 1H), 7.21 (s, 1H), 7.11 (s, 1H), 6.79 (s, 1H), 4.32-4.15 (m, 3H), 3.95 (s, 3H), 3.43 (dd, 1H), 2.95 (d, 1H), 2.74-2.64 (m, 2H), 2.34-2.17 (m, 2H), 1.77-1.64 (m, 2H), 0.95 (t, 3H). MS obsd. (ESI$^+$) [(M+H)$^+$]: 383.

Example 53: 6-ethyl-10-methoxy-9-(2-methylsulfonylethoxy)-2-oxo-6,7-dihydrobenzo[a]quinolizine-3-carboxylic acid

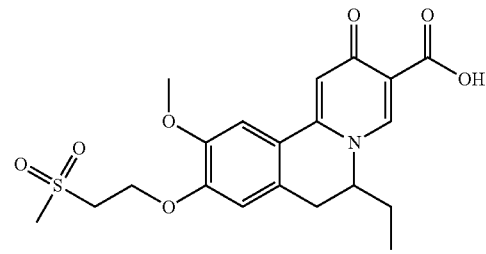 [SMILES: CCC1Cc2cc(OCCS(C)(=O)=O)c(OC)cc2-c2cc(=O)c(C(=O)O)cn21]

Step 1: Preparation of ethyl 6-ethyl-10-methoxy-9-(2-methylsulfanylethoxy)-2-oxo-6,7-dihydrobenzo[a]quinolizine-3-carboxylate

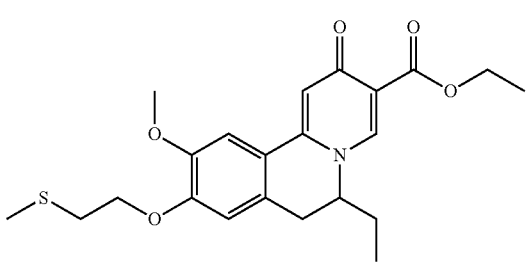 [SMILES: CCOC(=O)c1cn2c(cc1=O)-c1cc(OC)c(OCCSC)cc1CC2CC]

To a solution of ethyl 6-ethyl-9-hydroxy-10-methoxy-2-oxo-6,7-dihydrobenzo[a]quinolizine-3-carboxylate (100 mg, 0.29 mmol) in DMF was added 1-bromo-2-methylsulfanyl-ethane (134.9 mg, 0.87 mmol) and K$_2$CO$_3$ (80 mg, 0.58 mmol). The mixture was stirred for 3 hours at 80° C., and then cooled to room temperature and filtered. The filtrate was concentrated in vacuo to give crude ethyl 6-ethyl-10-methoxy-9-(2-methylsulfanylethoxy)-2-oxo-6,7-dihydrobenzo[a]quinolizine-3-carboxylate which was used for the next step without further purification.

Step 2: Preparation of 6-ethyl-10-methoxy-9-(2-methylsulfanylethoxy)-2-oxo-6,7-dihydrobenzo[a]quinolizine-3-carboxylic acid

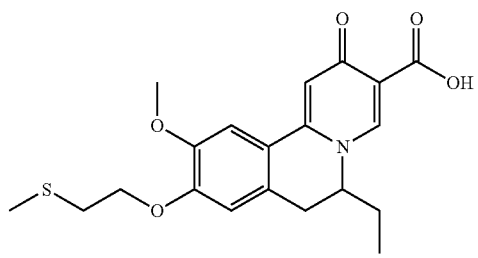

To a solution of crude ethyl 6-ethyl-10-methoxy-9-(2-methylsulfanylethoxy)-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL), and then acidified with 6 M hydrochloric acid and filtered. The filter cake was dried in vacuo to give 6-ethyl-10-methoxy-9-(2-methylsulfanylethoxy)-2-oxo-6,7-dihydrobenzo[a]quinolizine-3-carboxylic acid (40 mg).

Step 3: Preparation of 6-ethyl-10-methoxy-9-(2-methylsulfonylethoxy)-2-oxo-6,7-dihydrobenzo[a]quinolizine-3-carboxylic acid

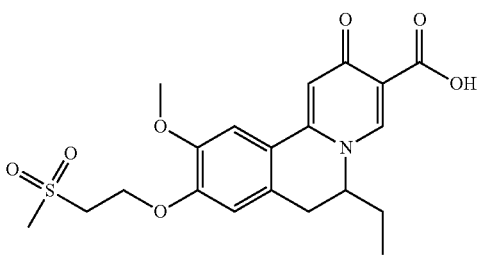 [SMILES: CCC1Cc2cc(OCCS(C)(=O)=O)c(OC)cc2-c2cc(=O)c(C(=O)O)cn21]

To a solution of 6-ethyl-10-methoxy-9-(2-methylsulfanyl ethoxy)-2-oxo-6,7-dihydrobenzo[a]quinolizine-3-carboxylic acid (40 mg, 0.1 mmol) in DCM (5 mL) was added m-CPBA (34.5 mg, 0.2 mmol) at 0° C. The reaction was stirred for 2 hours and then concentrated under reduced pressure. The residue was purified by preparative HPLC to give 6-ethyl-10-methoxy-9-(2-methylsulfonylethoxy)-2-oxo-6,7-dihydrobenzo[a]quinolizine-3-carboxylic acid (8 mg). $^1$H NMR (400 MHz, CDCl$_3$) δ 8.51 (s, 1H), 7.22 (s, 1H), 7.11 (s, 1H), 6.80 (s, 1H), 4.60-4.48 (m, 2H), 4.31-4.20 (m, 1H), 3.93 (s, 3H), 3.59-3.39 (m, 3H), 3.22 (s, 3H), 2.96 (d, 1H), 1.75-1.64 (m, 2H), 0.95 (t, 3H). MS obsd. (ESI$^+$) [(M+H)$^+$]: 422.

Example 54: 6-ethyl-10-methoxy-2-oxo-9-[2-(2-oxopyrrolidin-1-yl)ethoxy]-6,7-dihydrobenzo[a]quinolizine-3-carboxylic acid

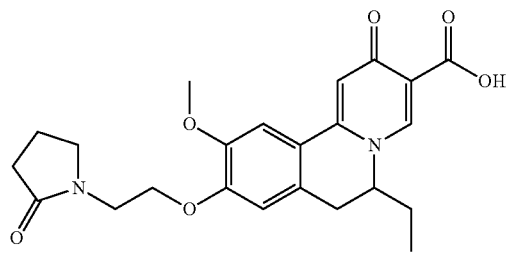 [SMILES: CCC1Cc2cc(OCCN3CCCC3=O)c(OC)cc2-c2cc(=O)c(C(=O)O)cn21]

Step 1: Preparation of 2-(2-oxopyrrolidin-1-yl)ethyl 4-methylbenzenesulfonate

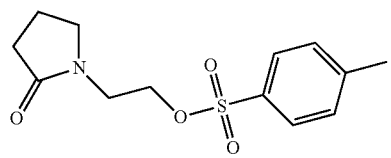 [SMILES: Cc1ccc(S(=O)(=O)OCCN2CCCC2=O)cc1]

To a solution of 1-(2-hydroxyethyl)pyrrolidin-2-one (6.0 g, 46.4 mmol) in DCM was added DMAP (11.3 g, 92.8 mmol) at 0° C. The mixture was stirred for 30 minutes, and then 4-methylbenzenesulfonyl chloride (9.3 g, 48.8 mmol) was added. The mixture was stirred for 14 hours at room temperature and then washed with 4 M hydrochloric acid and saturated aqueous solution of NaHCO$_3$ in turn, and then dried over anhydrous Na$_2$SO$_4$ and then concentrated in vacuo to give 2-(2-oxopyrrolidin-1-yl)ethyl 4-methylbenzenesulfonate (9.99 g).

Step 2: Preparation of ethyl 6-ethyl-10-methoxy-2-oxo-9-[2-(2-oxopyrrolidin-1-yl)ethoxy]-6,7-dihydrobenzo[a]quinolizine-3-carboxylate

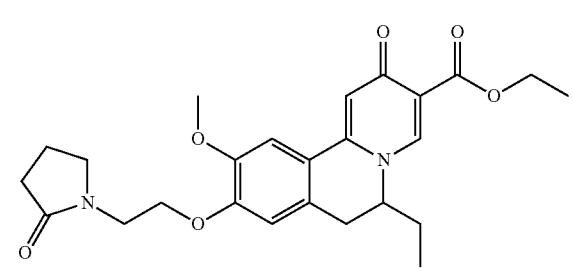 [SMILES: CCOC(=O)c1cn2c(cc1=O)-c1cc(OC)c(OCCN3CCCC3=O)cc1CC2CC]

To a solution of ethyl 6-ethyl-9-hydroxy-10-methoxy-2-oxo-6,7-dihydrobenzo[a]quinolizine-3-carboxylate (100 mg, 0.29 mmol) in DMF was added 2-(2-oxopyrrolidin-1-yl)ethyl 4-methylbenzenesulfonate (246.6 mg, 0.87 mmol) and K$_2$CO$_3$ (80 mg, 0.58 mmol). The mixture was stirred for 3 hours at 80° C., and then cooled to room temperature and filtered. The filtrate was concentrated in vacuo to give crude ethyl 6-ethyl-10-methoxy-2-oxo-9-[2-(2-oxopyrrolidin-1-yl)ethoxy]-6,7-dihydrobenzo[a]quinolizine-3-carboxylate which was used for the next step without further purification.

Step 3: Preparation of 6-ethyl-10-methoxy-2-oxo-9-[2-(2-oxopyrrolidin-1-yl)ethoxy]-6,7-dihydrobenzo[a]quinolizine-3-carboxylic acid

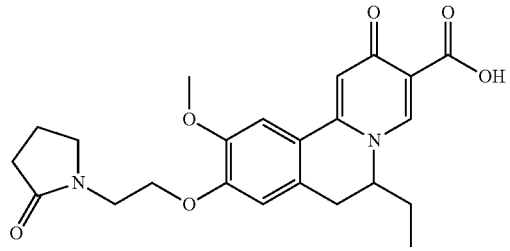 [SMILES: CCC1Cc2cc(OCCN3CCCC3=O)c(OC)cc2-c2cc(=O)c(C(=O)O)cn21]

To a solution of crude ethyl 6-ethyl-10-methoxy-2-oxo-9-[2-(2-oxopyrrolidin-1-yl)ethoxy]-6,7-dihydrobenzo[a]quinolizine-3-carboxylate from Step 2 in MeOH (9 mL) and water (3 mL) was added LiOH.H$_2$O (36.7 mg). The mixture was stirred for 2 hours and then concentrated under reduced pressure. The residue was dissolved in water (5 mL) and acidified with 6 M hydrochloric acid. The mixture was purified by preparative HPLC to give 6-ethyl-10-methoxy-2-oxo-9-[2-(2-oxopyrrolidin-1-yl)ethoxy]-6,7-dihydrobenzo[a]quinolizine-3-carboxylic acid (42 mg). $^1$H NMR (400 MHz, CDCl$_3$) δ 8.50 (s, 1H), 7.20 (s, 1H), 7.10 (s, 1H), 6.79 (s, 1H), 4.27-4.22 (m, 3H), 3.94 (s, 3H), 3.80-3.74 (m, 2H), 3.72-3.63 (m, 2H), 3.41 (dd, 1H), 2.95 (dd, 1H), 2.42 (t, 2H), 2.13-2.02 (m, 2H), 1.74-1.63 (m, 2H), 0.94 (t, 3H). MS obsd. (ESI$^+$) [(M+H)$^+$]: 427.

Example 55: (+)-6-ethyl-10-methoxy-2-oxo-9-[2-(2-oxopyrrolidin-1-yl)ethoxy]-6,7-dihydrobenzo[a]quinolizine-3-carboxylic acid

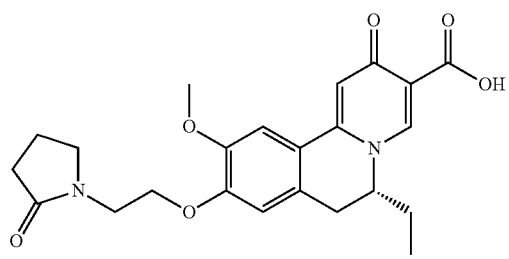 [SMILES: CC[C@@H]1Cc2cc(OCCN3CCCC3=O)c(OC)cc2-c2cc(=O)c(C(=O)O)cn21]

Separation of the racemic 6-ethyl-10-methoxy-2-oxo-9-[2-(2-oxopyrrolidin-1-yl)ethoxy]-6,7-dihydrobenzo[a]quinolizine-3-carboxylic acid (36 mg) by chiral HPLC afforded (+)-6-ethyl-10-methoxy-2-oxo-9-[2-(2-oxopyrrolidin-1-yl)ethoxy]-6,7-dihydrobenzo[a]quinolizine-3-carboxylic acid (12 mg). $^1$H NMR (400 MHz, CDCl$_3$) δ 8.50 (s, 1H), 7.20 (s, 1H), 7.10 (s, 1H), 6.79 (s, 1H), 4.27-4.22 (m, 3H), 3.94 (s, 3H), 3.80-3.74 (m, 2H), 3.72-3.63 (m, 2H), 3.41 (dd, 1H), 2.95 (dd, 1H), 2.42 (t, 2H), 2.13-2.02 (m, 2H), 1.74-1.63 (m, 2H), 0.94 (t, 3H). MS obsd. (ESI$^+$) [(M+H)$^+$]: 427.

Example 56: 6-ethyl-9-[2-(methanesulfonamido)ethoxy]-10-methoxy-2-oxo-6,7-dihydrobenzo[a]quinolizine-3-carboxylic acid

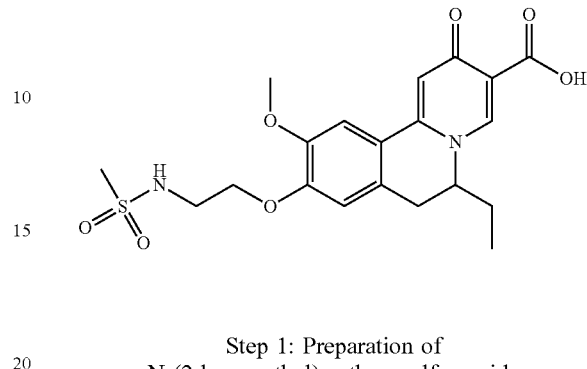

Step 1: Preparation of N-(2-bromoethyl)methanesulfonamide

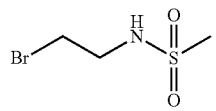

To a solution of 2-aminoethylbromide hydrobromide (2.0 g, 9.8 mmol) in DCM was added Et$_3$N (2.78 mL, 19.6 mmol). The mixture was stirred for 10 minutes, then mesyl chloride (0.91 mL, 11.8 mmol) was slowly added to the solution at 0° C. The reaction mixture was stirred for 2 hours, and then washed with 2 M hydrochloric acid and brine, and then dried over anhydrous Na$_2$SO$_4$ and then concentrated in vacuo to give N-(2-bromoethyl)methanesulfonamide (1.64 g).

Step 2: Preparation of ethyl 6-ethyl-9-[2-(methanesulfonamido)ethoxy]-10-methoxy-2-oxo-6,7-dihydrobenzo[a]quinolizine-3-carboxylate

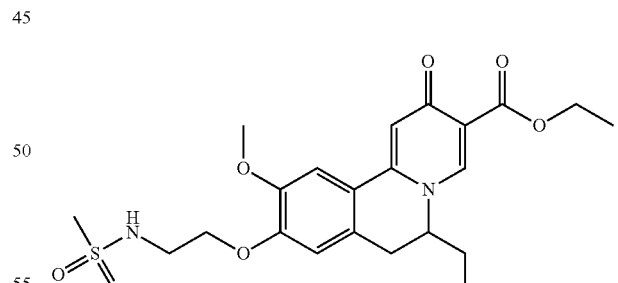

To a solution of ethyl 6-ethyl-9-hydroxy-10-methoxy-2-oxo-6,7-dihydrobenzo[a]quinolizine-3-carboxylate (100 mg, 0.29 mmol) in DMF was added N-(2-bromoethyl)methanesulfonamide (117.2 mg, 0.58 mmol) and K$_2$CO$_3$ (80 mg, 0.58 mmol). The mixture was stirred for 16 hours at 100° C., and then cooled to room temperature and filtered. The filtrate was concentrated in vacuo to give crude ethyl 6-ethyl-9-[2-(methanesulfonamido)ethoxy]-10-methoxy-2-oxo-6,7-dihydrobenzo[a]quinolizine-3-carboxylate which was used for the next step without further purification.

Step 3: Preparation of 6-ethyl-9-[2-(methanesulfonamido)ethoxy]-10-methoxy-2-oxo-6,7-dihydrobenzo[a]quinolizine-3-carboxylic acid

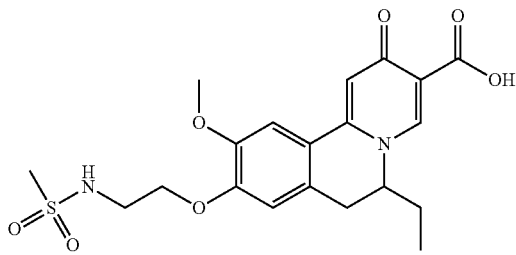 [SMILES: CCC1Cc2cc(OCCNS(C)(=O)=O)c(OC)cc2-c2cc(=O)c(C(=O)O)cn21]

To a solution of crude ethyl 6-ethyl-9-[2-(methanesulfonamido)ethoxy]-10-methoxy-2-oxo-6,7-dihydrobenzo[a]quinolizine-3-carboxylate from Step 2 in MeOH (9 mL) and water (3 mL) was added LiOH.H$_2$O (36.7 mg). The mixture was stirred for 2 hours and then concentrated under reduced pressure. The residue was dissolved in water (5 mL) and then acidified with 6 M hydrochloric acid. The mixture was purified by preparative HPLC to give 6-ethyl-9-[2-(methanesulfonamido)ethoxy]-10-methoxy-2-oxo-6,7-dihydrobenzo[a]quinolizine-3-carboxylic acid (14 mg). $^1$H NMR (400 MHz, DMSO-d$_6$) δ 8.81 (s, 1H), 7.55 (s, 1H), 7.48 (s, 1H), 7.36-7.26 (m, 1H), 7.10-7.04 (m, 1H), 4.77-4.64 (m, 1H), 4.18-4.06 (m, 2H), 3.89 (s, 3H), 3.47-3.34 (m, 3H), 3.18 (d, 1H), 3.00 (s, 3H), 1.60-1.40 (m, 2H), 0.81 (t, 3H). MS obsd. (ESI$^+$) [(M+H)$^+$]: 437.

Example 57: 9-[(1-cyanocyclopropyl)methoxy]-6-ethyl-10-methoxy-2-oxo-6,7-dihydrobenzo[a]quinolizine-3-carboxylic acid

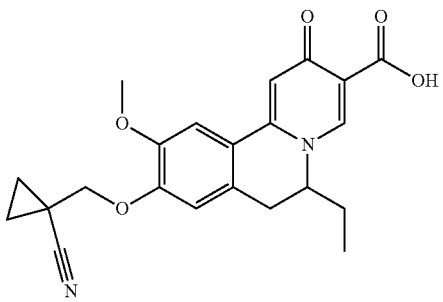 [SMILES: CCC1Cc2cc(OCC3(C#N)CC3)c(OC)cc2-c2cc(=O)c(C(=O)O)cn21]

Step 1: Preparation of ethyl 9-[(1-cyanocyclopropyl)methoxy]-6-ethyl-10-methoxy-2-oxo-6,7-dihydrobenzo[a]quinolizine-3-carboxylate

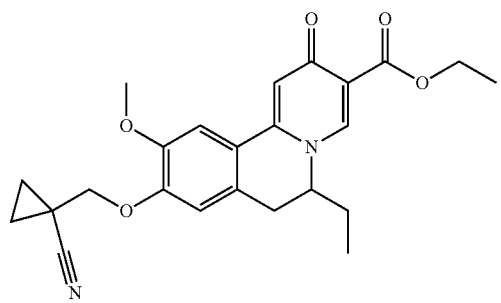 [SMILES: CCOC(=O)c1cn2c(cc1=O)-c1cc(OC)c(OCC3(C#N)CC3)cc1CC2CC]

To a solution of ethyl 6-ethyl-9-hydroxy-10-methoxy-2-oxo-6,7-dihydrobenzo[a]quinolizine-3-carboxylate (100 mg, 0.29 mmol) in DMF was added (1-cyanocyclopropyl)methyl 4-methylbenzenesulfonate (137.6 mg, 0.58 mmol) and K$_2$CO$_3$ (80 mg, 0.58 mmol). The mixture was stirred for 16 hours at 80° C., and then cooled to room temperature and filtered. The filtrate was concentrated in vacuo to give crude ethyl 9-[(1-cyanocyclopropyl)methoxy]-6-ethyl-10-methoxy-2-oxo-6,7-dihydrobenzo[a]quinolizine-3-carboxylate which was used for the next step without further purification.

Step 2: Preparation of 9-[(1-cyanocyclopropyl)methoxy]-6-ethyl-10-methoxy-2-oxo-6,7-dihydrobenzo[a]quinolizine-3-carboxylic acid

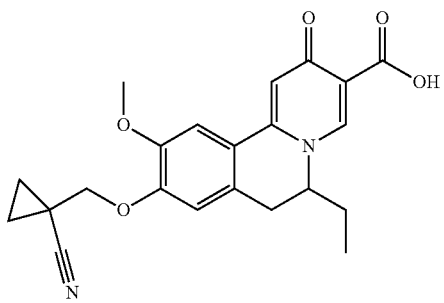 [SMILES: CCC1Cc2cc(OCC3(C#N)CC3)c(OC)cc2-c2cc(=O)c(C(=O)O)cn21]

To a solution of crude ethyl 9-[(1-cyanocyclopropyl)methoxy]-6-ethyl-10-methoxy-2-oxo-6,7-dihydrobenzo[a]quinolizine-3-carboxylate from Step 1 in MeOH (9 mL) and water (3 mL) was added LiOH.H$_2$O (36.7 mg). The mixture was stirred for 2 hours and then concentrated under reduced pressure. The residue was dissolved in water (5 mL) and then acidified with 6 M hydrochloric acid. The mixture was purified by preparative HPLC to give 9-[(1-cyanocyclopropyl)methoxy]-6-ethyl-10-methoxy-2-oxo-6,7-dihydrobenzo[a]quinolizine-3-carboxylic acid (19 mg). $^1$H NMR (400 MHz, CDCl$_3$ plus MeOD-d$_4$) δ 8.44 (s, 1H), 7.18 (s, 1H), 7.02 (s, 1H), 6.74 (s, 1H), 4.34-4.12 (m, 1H), 4.00 (d, 2H), 3.85 (s, 3H), 3.37-3.27 (m, 1H), 2.85 (d, 1H), 1.52 (d, 2H), 1.34 (br. s., 2H), 1.09 (br. s., 2H), 0.81 (br. s., 3H). MS obsd. (ESI$^+$) [(M+H)$^+$]: 395.

Example 58: 9-(2-acetamidoethoxy)-6-ethyl-10-methoxy-2-oxo-6,7-dihydrobenzo[a]quinolizine-3-carboxylic acid

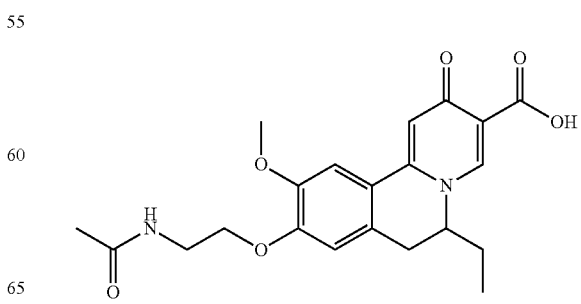

Step 1: Preparation of ethyl 9-[2-(2,5-dioxopyrrolidin-1-yl)ethoxy]-6-ethyl-10-methoxy-2-oxo-6,7-dihydrobenzo[a]quinolizine-3-carboxylate

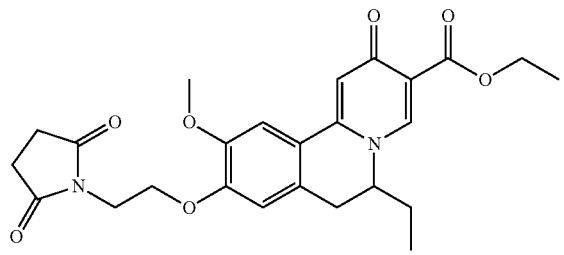 [SMILES: CCOC(=O)c1cn2c(cc1=O)-c1cc(OC)c(OCCN3C(=O)CCC3=O)cc1CC2CC]

To a solution of ethyl 6-ethyl-9-hydroxy-10-methoxy-2-oxo-6,7-dihydrobenzo[a]quinolizine-3-carboxylate (150 mg, 0.44 mmol) in DMF (5 mL) was added 1-(2-bromoethyl)pyrrolidine-2,5-dione (166.5 mg, 0.66 mmol) and $K_2CO_3$ (121.4 mg, 0.88 mmol). The mixture was stirred for 16 hours at 100° C., and then cooled to room temperature and then filtered. The filtrate was concentrated in vacuo and the residue was purified by column chromatography to give ethyl 9-[2-(2, 5-dioxopyrrolidin-1-yl)ethoxy]-6-ethyl-10-methoxy-2-oxo-6,7-dihydrobenzo[a]quinolizine-3-carboxylate (100 mg).

Step 2: Preparation of ethyl 9-(2-aminoethoxy)-6-ethyl-10-methoxy-2-oxo-6,7-dihydrobenzo[a]quinolizine-3-carboxylate

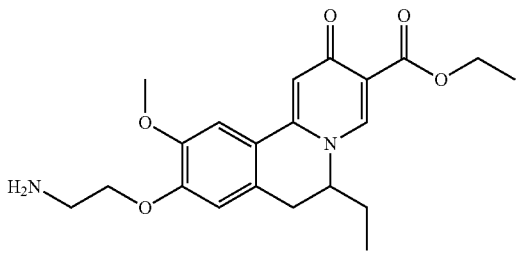 [SMILES: CCOC(=O)c1cn2c(cc1=O)-c1cc(OC)c(OCCN)cc1CC2CC]

To a solution of ethyl 9-[2-(2,5-dioxopyrrolidin-1-yl)ethoxy]-6-ethyl-10-methoxy-2-oxo-6,7-dihydrobenzo[a]quinolizine-3-carboxylate (100 mg, 0.21 mmol) in EtOH was added $N_2H_4 \cdot H_2O$ (37.6 mg, 0.63 mmol). The mixture was stirred for 2 hours at 60° C., and then cooled to room temperature and filtered. The filtrate was concentrated in vacuo to give crude ethyl 9-(2-aminoethoxy)-6-ethyl-10-methoxy-2-oxo-6,7-dihydrobenzo[a]quinolizine-3-carboxylate (50 mg).

Step 3: Preparation of ethyl 9-(2-acetamidoethoxy)-6-ethyl-10-methoxy-2-oxo-6,7-dihydrobenzo[a]quinolizine-3-carboxylate

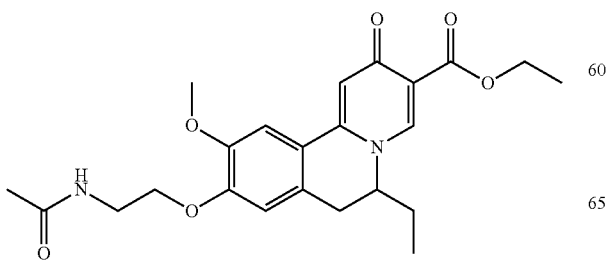

To a solution of crude ethyl 9-(2-aminoethoxy)-6-ethyl-10-methoxy-2-oxo-6,7-dihydrobenzo[a]quinolizine-3-carboxylate (30 mg, 0.08 mmol) in MeCN (2 mL) was added $Et_3N$ (16.2 mg, 0.16 mmol). The mixture was stirred for 10 minutes, and then acetyl chloride (8.2 mg, 0.10 mmol) was added. The resultant mixture was stirred for 2 hours and then concentrated under reduced pressure to give ethyl 9-(2-acetamidoethoxy)-6-ethyl-10-methoxy-2-oxo-6,7-dihydrobenzo[a]quinolizine-3-carboxylate which was used for the next step without further purification.

Step 4: Preparation of 9-(2-acetamidoethoxy)-6-ethyl-10-methoxy-2-oxo-6,7-dihydrobenzo[a]quinolizine-3-carboxylic acid

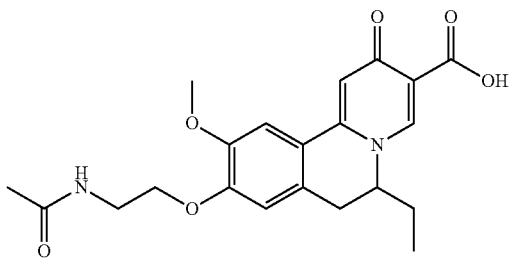 [SMILES: CCC1Cc2cc(OCCNC(C)=O)c(OC)cc2-c2cc(=O)c(C(=O)O)cn21]

To a solution of crude ethyl 9-(2-acetamidoethoxy)-6-ethyl-10-methoxy-2-oxo-6,7-dihydrobenzo[a]quinolizine-3-carboxylate from Step 3 in the mixture solvent of MeOH (9 mL) and water (3 mL) was added $LiOH \cdot H_2O$ (10 mg). The mixture was stirred for 2 hours and then concentrated under reduced pressure. The residue was dissolved in water (5 mL) and acidified with 6 M hydrochloric acid. The mixture was purified by preparative HPLC to give 9-(2-acetamidoethoxy)-6-ethyl-10-methoxy-2-oxo-6,7-dihydrobenzo[a]quinolizine-3-carboxylic acid (5.6 mg). $^1H$ NMR (400 MHz, $CDCl_3$) δ 8.51 (s, 1H), 7.21 (s, 1H), 7.10 (s, 1H), 6.81 (s, 1H), 6.24 (br. s, 1H), 4.34-4.09 (m, 3H), 3.96 (s, 3H), 3.83-3.64 (m, 2H), 3.49-3.32 (m, 1H), 2.95 (d, 1H), 2.04 (s, 3H), 1.64-1.53 (m, 2H), 0.94 (t, 3H). MS obsd. ($ESI^+$) [$(M+H)^+$]: 401.

Example 59 and 60

9-bromo-6-methyl-2-oxo-6,7-dihydrobenzo[a]quinolizine-3-carboxylic acid and 11-bromo-6-methyl-2-oxo-6,7-dihydrobenzo[a]quinolizine-3-carboxylic acid Example 59

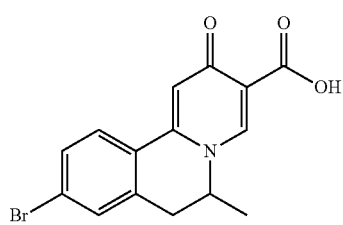

Example 60

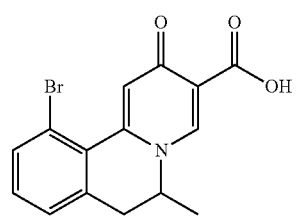

Step 1: Preparation of 1-bromo-3-[2-nitroprop-1-enyl]benzene

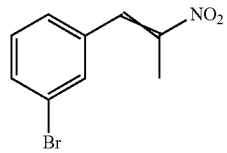

To a solution of 3-bromobenzaldehyde (20 g, 0.11 mol) in nitroethane (150 mL) was added ammonium acetate (5.4 g, 0.07 mol). The reaction was refluxing for 3 hours at 130° C., and then concentrated under reduced pressure. The residue was dissolved in DCM, and the solution was washed with brine, and then dried over anhydrous $Na_2SO_4$ and then concentrated in vacuo to give 1-bromo-3-[2-nitroprop-1-enyl]benzene (22.7 g).

Step 2: Preparation of 1-(3-bromophenyl)propan-2-amine

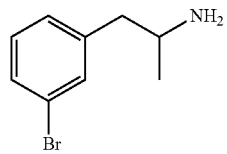

To a solution of 1-bromo-3-[2-nitroprop-1-enyl]benzene (10 g, 41.3 mmol) in THF (100 mL) was added $LiAlH_4$ (4.7 g, 123.9 mmol) in portions at 0° C., then the reaction was slowly warmed to 60° C. and stirred for 1 hour. After 1-bromo-3-[2-nitroprop-1-enyl]benzene was consumed completely, the reaction was cooled to room temperature and then quenched with water and aqueous NaOH (10%). The mixture was filtered and the filtrate was concentrated under reduced pressure to give the crude 1-(3-bromophenyl)propan-2-amine (5.7 g).

Step 3: Preparation of N-[2-(3-bromophenyl)-1-methyl-ethyl]formamide

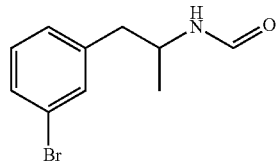

To a solution of 1-(3-bromophenyl)propan-2-amine in dioxane (30 mL) was added ethyl formate (30 mL). The mixture was refluxed. After 1-(3-bromophenyl)propan-2-amine was consumed completely, the reaction mixture was concentrated under reduced pressure to give the crude product N-[2-(3-bromophenyl)-1-methyl-ethyl]formamide which was used in next step without further purification.

Step 4: Preparation of 6-bromo-3-methyl-3,4-dihydroisoquinoline and 8-bromo-3-methyl-3,4-dihydroisoquinoline

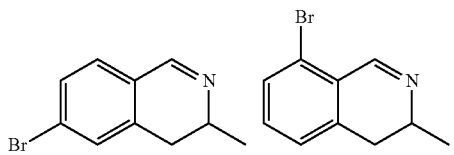

To a solution of N-[2-(3-bromophenyl)-1-methyl-ethyl]formamide (2.0 g, 8.3 mmol) in DCM was added oxalyl chloride (1.2 g, 9.1 mmol) at room temperature under argon atmosphere, then the reaction was cooled to −10° C. and $FeCl_3$ (1.6 g, 10.0 mmol) was added. The reaction was slowly warmed to room temperature and then stirred for 24 hours. The reaction was quenched with 2 M hydrochloric acid. The organic layer was washed with brine, and then dried over anhydrous $Na_2SO_4$ and then concentrated in vacuo. The residue was dissolved in concentrated $H_2SO_4$/MeOH (1/19, 20 mL). The mixture was stirred for 2 hours at 70° C., and then cooled to room temperature and then concentrated under reduced pressure. The residue was dissolved in water and basified with $NaHCO_3$. The mixture was extracted in DCM. The organic layer was dried over anhydrous $Na_2SO_4$ and then concentrated under reduced pressure to afford the crude 6-bromo-3-methyl-3,4-dihydroisoquinoline and 8-bromo-3-methyl-3,4-dihydroisoquinoline (1.0 g), which was used for the next step without purification.

Step 5: Preparation of ethyl 3-(ethoxymethylene)-4-trimethylsilyloxy-pent-4-enoate

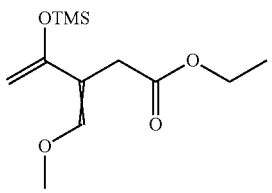

To a solution of $Et_3N$ (19.4 mL, 139 mmol) in toluene (150 mL) was added catalytic amount fused zinc chloride (0.26 g), the reaction was stirred for 1 hour at room temperature under argon atmosphere. Then ethyl 3-(ethoxymethylene)-4-oxo-pentanoate (11.8 g, 63.3 mmol) was added to the mixture. After stirring for 10 minutes, TMSCl (16.1 mL, 126.6 mmol) was slowly added. The mixture was heated to 40° C. for 20 hours and then filtered. The filtrate was concentrated in vacuo to give ethyl 3-(ethoxymethylene)-4-trimethylsilyloxy-pent-4-enoate (16.2 g).

Step 6: Preparation of ethyl 9-bromo-6-methyl-2-oxo-1,6,7,11b-tetrahydrobenzo[a]quinolizine-3-carboxylate and ethyl 11-bromo-6-methyl-2-oxo-1,6,7,11b-tetrahydrobenzo[a]quinolizine-3-carboxylate

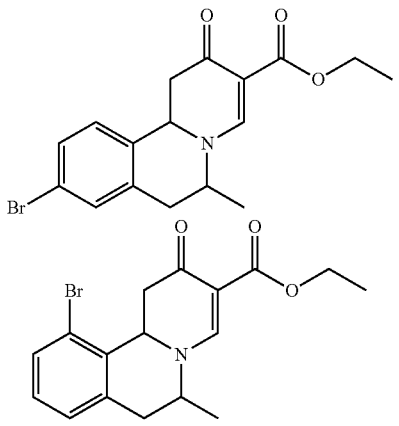

To a mixture of 6-bromo-3-methyl-3,4-dihydroisoquinoline and 8-bromo-3-methyl-3,4-dihydroisoquinoline (1.0 g, 4.46 mmol) in DCM was added TFA (0.34 mL, 4.46 mmol). The mixture was stirred for 5 minutes, then BF$_3$-Et$_2$O (0.54 mL, 4.46 mmol) was added. After another 5 minutes, ethyl 3-(ethoxymethylene)-4-trimethylsilyloxy-pent-4-enoate (1.73 g, 6.70 mmol) was added and the mixture was stirred at room temperature. After 6-bromo-3-methyl-3,4-dihydroisoquinoline and 8-bromo-3-methyl-3,4-dihydroisoquinoline was consumed completely, the reaction mixture was washed with brine, and then dried over anhydrous Na$_2$SO$_4$ and then concentrated in vacuo. The residue was purified by column chromatography to give 0.2 g of the mixture of 9-bromo-6-methyl-2-oxo-1,6,7,11b-tetrahydrobenzo[a]quinolizine-3-carboxylate and ethyl 11-bromo-6-methyl-2-oxo-1,6,7,11b-tetrahydrobenzo[a]quinolizine-3-carboxylate.

Step 7: Preparation of ethyl 9-bromo-6-methyl-2-oxo-6,7-dihydrobenzo[a]quinolizine-3-carboxylate and ethyl 11-bromo-6-methyl-2-oxo-6,7-dihydrobenzo[a]quinolizine-3-carboxylate

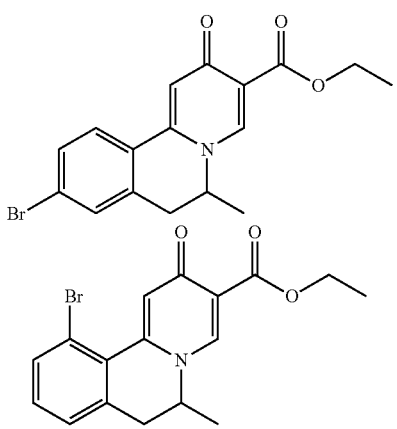

To a mixture of 9-bromo-6-methyl-2-oxo-1,6,7,11b-tetrahydrobenzo[a]quinolizine-3-carboxylate and ethyl 11-bromo-6-methyl-2-oxo-1,6,7,11b-tetrahydrobenzo[a]quinolizine-3-carboxylate (200 mg, 0.55 mmol) in DME and toluene (5 mL, V/V=1/1) was added p-chloranil (135 mg, 20.4 mmol). The mixture was stirred for 20 minutes at 135° C. under microwave, and then concentrated under reduced pressure. The residue was used for the next step without further purification.

Step 8: Preparation of 9-bromo-6-methyl-2-oxo-6,7-dihydrobenzo[a]quinolizine-3-carboxylic acid and 11-bromo-6-methyl-2-oxo-6,7-dihydrobenzo[a]quinolizine-3-carboxylic acid Example 59

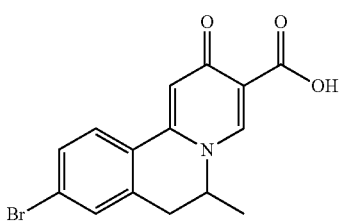 [SMILES: C[C@@H]1Cc2cc(Br)ccc2-c2cc(=O)c(C(=O)O)cn21]

Example 60

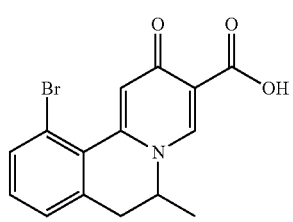

To a crude mixture of ethyl 9-bromo-6-methyl-2-oxo-6,7-dihydrobenzo[a]quinolizine-3-carboxylate and ethyl 11-bromo-6-methyl-2-oxo-6,7-dihydrobenzo[a]quinolizine-3-carboxylate in MeOH (9 mL) and water (3 mL) was added LiOH.H$_2$O (69.6 mg). The mixture was stirred for 1 hour and then concentrated in vacuo. The residue was dissolved in water (5 mL). The aqueous solution was acidified with hydrochloric acid and then purified by prep-HPLC to give 9-bromo-6-methyl-2-oxo-6,7-dihydrobenzo[a]quinolizine-3-carboxylic acid (8 mg) and 11-bromo-6-methyl-2-oxo-6,7-dihydrobenzo[a]quinolizine-3-carboxylic acid (7 mg).

Example 59

$^1$H NMR (400 MHz, CDCl$_3$) δ 8.59 (s, 1H), 7.71-7.58 (m, 2H), 7.54 (s, 1H), 7.19 (s, 1H), 4.65-4.54 (m, 1H), 3.55-3.43 (m, 1H), 2.95 (dd, 1H), 1.39 (d, 3H). MS obsd. (ESI$^+$) [(M+H)$^+$]: 334.

Example 60

$^1$H NMR (400 MHz, CDCl$_3$) δ 8.63 (s, 1H), 7.85 (s, 1H), 7.77 (d, 1H), 7.37-7.31 (m, 2H), 4.56-4.50 (m, 1H), 3.42-3.35 (m, 1H), 2.98-2.91 (m, 1H), 1.37 (d, 3H). MS obsd. (ESI$^+$) [(M+H)$^+$]: 334.

Example 61: (+)-9-bromo-6-methyl-2-oxo-6,7-dihydrobenzo[a]quinolizine-3-carboxylic acid

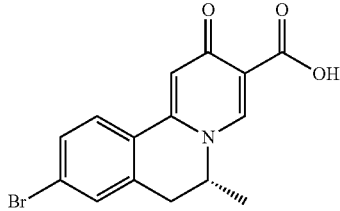

The title compound (39 mg) was obtained through the separation of the racemic 9-bromo-6-methyl-2-oxo-6,7-dihydrobenzo[a]quinolizine-3-carboxylic acid (120 mg) by chiral HPLC. $^1$H NMR (400 MHz, CDCl$_3$) δ 8.59 (s, 1H), 7.71-7.58 (m, 2H), 7.54 (s, 1H), 7.19 (s, 1H), 4.65-4.54 (m, 1H), 3.55-3.43 (m, 1H), 2.95 (dd, 1H), 1.39 (d, 3H). MS obsd. (ESI$^+$) [(M+H)$^+$]: 334.

Example 62: 9-(4-tert-butoxycarbonylpiperazin-1-yl)-6-methyl-2-oxo-6,7-dihydrobenzo[a]quinolizine-3-carboxylic acid

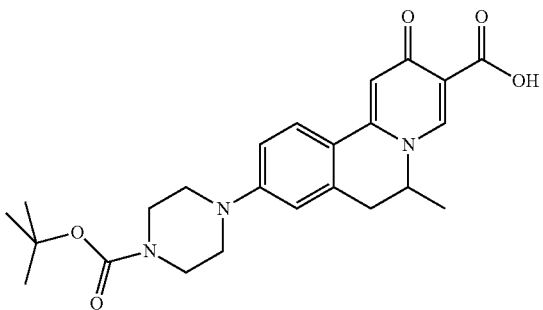 [SMILES: CC1Cc2cc(N3CCN(C(=O)OC(C)(C)C)CC3)ccc2-c2cc(=O)c(C(=O)O)cn21]

To a solution of 9-bromo-6-methyl-2-oxo-6,7-dihydrobenzo[a]quinolizine-3-carboxylic acid (100 mg, 0.30 mmol) in DMSO (3 mL) was added tert-butyl piperazine-1-carboxylate (67 mg, 0.36 mmol), K$_2$CO$_3$ (82.8 mg, 0.60 mmol), CuI (5.7 mg, 0.03 mmol) and L-proline (6.9 mg, 0.06 mmol). The mixture was stirred for 18 hours at 100° C. under argon atmosphere, and then purified by prep-HPLC to give 9-(4-tert-butoxycarbonylpiperazin-1-yl)-6-methyl-2-oxo-6,7-dihydrobenzo[a]quinolizine-3-carboxylic acid (5 mg). $^1$H NMR (400 MHz, MeOD-d$_4$) δ 8.76 (s, 1H), 7.83 (d, 1H), 7.23 (s, 1H), 7.03 (d, 1H), 6.93 (s, 1H), 6.97-6.90 (m, 1H), 4.84-4.78 (m, 1H), 3.64-3.58 (m, 4H), 3.44-3.41 (m, 4H), 3.27-3.18 (m, 1H), 2.96 (d, 1H), 1.51 (s, 9H), 1.33 (d, 3H). MS obsd. (ESI$^+$) [(M+H)$^+$]: 440.

Example 63: 9-[benzyl(methyl)amino]-6-methyl-2-oxo-6,7-dihydrobenzo[a]quinolizine-3-carboxylic acid

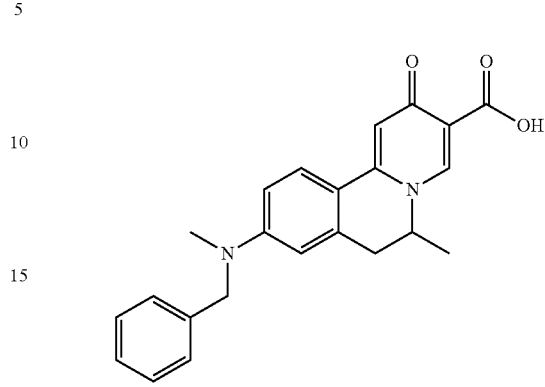

To a solution of 9-bromo-6-methyl-2-oxo-6,7-dihydrobenzo[a]quinolizine-3-carboxylic acid (100 mg, 0.30 mmol) in DMSO (3 mL) was added N-methyl-1-phenylmethanamine (43.6 mg, 0.36 mmol), K$_2$CO$_3$ (82.8 mg, 0.60 mmol), CuI (5.7 mg, 0.03 mmol) and L-proline (6.9 mg, 0.06 mmol). The mixture was stirred for 18 hours at 100° C. under argon atmosphere, and then purified by prep-HPLC to give 9-[benzyl(methyl)amino]-6-methyl-2-oxo-6,7-dihydrobenzo[a]quinolizine-3-carboxylic acid (4.5 mg). $^1$H NMR (400 MHz, MeOD-d$_4$) δ 8.70 (s, 1H), 7.84 (s, 1H), 7.75 (d, 1H), 7.33 (d, 2H), 7.28-7.18 (m, 3H), 6.83 (dd, 1H), 6.70 (d, 1H), 4.82-4.77 (m, 1H), 4.73 (s, 2H), 3.46-3.38 (m, 1H), 3.20 (s, 3H), 2.93-2.84 (m, 1H), 1.34 (d, 3H). MS obsd. (ESI$^+$) [(M+H)$^+$]: 375.

Example 64: 6-methyl-11-(methylamino)-2-oxo-6,7-dihydrobenzo[a]quinolizine-3-carboxylic acid

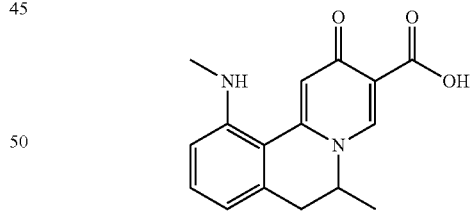

To a mixture of 9-bromo-6-methyl-2-oxo-6,7-dihydrobenzo[a]quinolizine-3-carboxylic acid and 11-bromo-6-methyl-2-oxo-6,7-dihydrobenzo[a]quinolizine-3-carboxylic acid (100 mg, 0.30 mmol) in DMSO (3 mL) was added a solution of methylamine in MeOH (7 M, 2 mL), K$_2$CO$_3$ (82.8 mg, 0.60 mmol), CuI (5.7 mg, 0.03 mmol) and L-proline (6.9 mg, 0.06 mmol). The mixture was stirred for 18 hours at 100° C. under argon atmosphere, and then purified by prep-HPLC to give the title compound (8 mg). $^1$H NMR (400 MHz, MeOD-d$_4$) δ 8.88 (br. s, 1H), 7.78 (br. s, 1H), 7.40-7.33 (m, 2H), 6.80 (d, 1H), 6.68 (d, 1H), 4.81-4.74 (m, 1H), 3.30-3.25 (m, 1H), 2.87 (m, 4H), 1.35 (d, 3H). MS obsd. (ESI$^+$) [(M+H)$^+$]: 285.

Example 65: 10-chloro-9-methoxy-6-methyl-2-oxo-6,7-dihydrobenzo[a]quinolizine-3-carboxylic acid

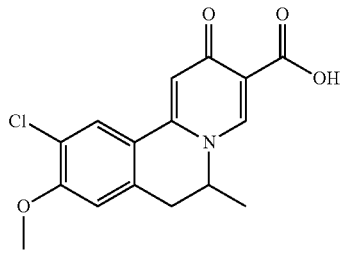 [SMILES: COc1cc2c(cc1Cl)-c1cc(=O)c(C(=O)O)cn1C(C)C2]

Step 1: Preparation of 1-chloro-2-methoxy-4-[2-nitroprop-1-enyl]benzene

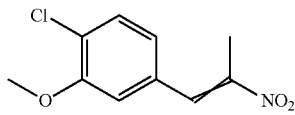

To a solution of 4-chloro-3-methoxy-benzaldehyde (25 g, 150 mmol) in toluene (300 mL) was added nitroethane (27 g, 300 mol), dimethylamine hydrochloride (36.5 g, 450 mmol) and potassium fluoride (8.7 g, 150 mmol). The mixture was refluxed for 20 hours with a Dean-Stark trap. The reaction mixture was diluted with ethyl acetate (500 mL) and then quenched with 10% HCl (150 mL). The organic layer was separated, washed with water (150 mL) and brine (150 mL), and then dried over anhydrous Na$_2$SO$_4$ and then concentrated under reduced pressure. The residue was purified by column chromatography to give 1-chloro-2-methoxy-4-[2-nitroprop-1-enyl]benzene (20 g) as a yellow solid.

Step 2: Preparation of 1-(4-chloro-3-methoxy-phenyl)propan-2-amine

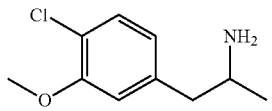

LiAlH$_4$ (11.4 g, 300 mmol) was dissolved in anhydrous THF (200 mL) and the solution of 1-chloro-2-methoxy-4-[2-nitroprop-1-enyl]benzene (20 g, 84 mmol) in THF (200 mL) was added dropwise at 0° C. After addition, the reaction mixture was refluxed slightly. After 1-chloro-2-methoxy-4-[2-nitroprop-1-enyl]benzene was consumed completely, the reaction was quenched with water and aqueous NaOH (10%). The mixture was filtered and the filtrate was concentrated in vacuo to give crude 1-(4-chloro-3-methoxy-phenyl)propan-2-amine which was directly used for the next step without purification.

Step 3: Preparation of N-[2-(4-chloro-3-methoxy-phenyl)-1-methyl-ethyl]formamide

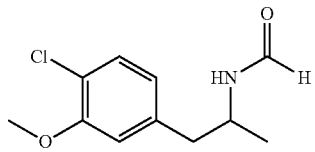

To a solution of 1-(4-chloro-3-methoxy-phenyl)propan-2-amine (10.35 g, 50 mmol) in EtOH (300 mL) was added ethyl formate (200 mL) and Et$_3$N (20 mL,) dropwise under nitrogen atmosphere. The resultant mixture was refluxed for 2 days, and then concentrated under reduced pressure. The residue was purified by column chromatography to give N-[2-(4-chloro-3-methoxy-phenyl)-1-methyl-ethyl]formamide (10 g, yield 84%).

Step 4: Preparation of 7-chloro-6-methoxy-3-methyl-3,4-dihydroisoquinoline

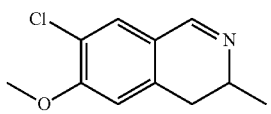

To a solution of N-[2-(4-chloro-3-methoxy-phenyl)-1-methyl-ethyl]formamide (227 mg, 1 mmol) in MeCN (100 mL) was added POCl$_3$ (2.3 g, 15 mmol). The mixture was refluxed for 1 hour, and then cooled to room temperature and poured into water. The mixture was basified with ammonia to pH>10 and then extracted with EtOAc. The organic layer was dried over anhydrous Na$_2$SO$_4$, and then concentrated in vacuo and the residue was purified by column chromatography to give 7-chloro-6-methoxy-3-methyl-3,4-dihydroisoquinoline (65 mg).

Step 5: Preparation of ethyl 10-chloro-9-methoxy-6-methyl-2-oxo-1,6,7,11b-tetrahydrobenzo[a]quinolizine-3-carboxylate

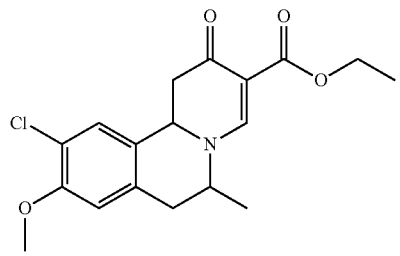 [SMILES: CCOC(=O)C1=CN2C(C)Cc3cc(OC)c(Cl)cc3C2CC1=O]

To a solution of 7-chloro-6-methoxy-3-methyl-3,4-dihydroisoquinoline (80 mg, 0.38 mmol) in DCM was added TFA (0.03 mL, 0.38 mmol). The reaction mixture was stirred for 5 minutes, then BF3.Et$_2$O (0.05 mL, 0.38 mmol) was added. After stirring for another 5 minutes, ethyl 3-(ethoxymethylene)-4-trimethylsilyloxy-pent-4-enoate (147.2 mg, 0.57 mmol) was added and the resultant mixture was stirred for 2 hours at room temperature. After 7-chloro- 6-methoxy-3-methyl-3,4-dihydroisoquinoline was consumed completely, the mixture was washed with brine, and then dried over anhydrous Na₂SO₄ and then concentrated in vacuo. The residue was purified by column chromatography to give ethyl 10-chloro-9-methoxy-6-methyl-2-oxo-1,6,7,11b-tetrahydrobenzo[a]quinolizine-3-carboxylate (30 mg).

Step 6: Preparation of ethyl 10-chloro-9-methoxy-6-methyl-2-oxo-6,7-dihydrobenzo[a]quinolizine-3-carboxylate

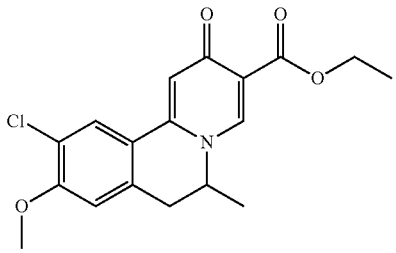 [SMILES: CCOC(=O)c1cn2c(cc1=O)-c1cc(Cl)c(OC)cc1CC2C]

To a solution of ethyl 10-chloro-9-methoxy-6-methyl-2-oxo-1,6,7,11b-tetrahydrobenzo[a]quinolizine-3-carboxylate (30 mg, 0.09 mmol) in DME (1 mL) and toluene (1 mL) was added p-chloranil (22.12 mg, 0.09 mmol). The mixture was stirred for 20 minutes at 135° C. under microwave and then concentrated under reduced pressure. The residue was used for the next step without further purification.

Step 7: Preparation of 10-chloro-9-methoxy-6-methyl-2-oxo-6,7-dihydrobenzo[a]quinolizine-3-carboxylic acid

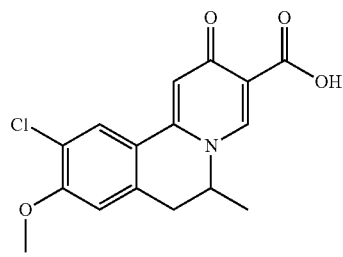 [SMILES: COc1cc2c(cc1Cl)-c1cc(=O)c(C(=O)O)cn1C(C)C2]

To a mixture of crude ethyl 10-chloro-9-methoxy-6-methyl-2-oxo-6,7-dihydrobenzo[a]quinolizine-3-carboxylate in MeOH (3 mL) and water (1 mL) was added LiOH.H₂O (9 mg). The mixture was stirred for 1 hour, and then concentrated in vacuo. The residue was dissolved in water (3 mL), and then acidified with hydrochloric acid and then purified by prep-HPLC to give 10-chloro-9-methoxy-6-methyl-2-oxo-6,7-dihydrobenzo[a]quinolizine-3-carboxylic acid (3.5 mg). $^1$H NMR (400 MHz, CDCl₃) δ 8.29 (br. s, 1H), 7.51 (s, 1H), 6.75 (s, 1H), 6.61 (br. s, 1H), 4.25-4.18 (m, 1H), 3.55 (s, 3H), 3.07-2.97 (m, 1H), 2.62-2.50 (m, 1H), 0.90 (br. s, 3H). MS obsd. (ESI⁺) [(M+H)⁺]: 320.

Example 66: 9,10-dimethoxy-6-methyl-2-oxo-6,7-dihydrobenzo[a]quinolizine-3-carboxylic acid

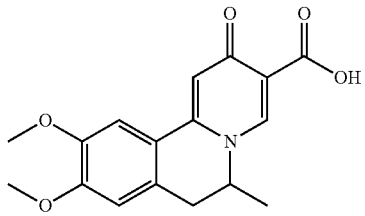 [SMILES: COc1cc2c(cc1OC)-c1cc(=O)c(C(=O)O)cn1C(C)C2]

Step 1: Preparation of 1,2-dimethoxy-4-[2-nitroprop-1-enyl]benzene

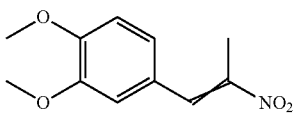

A mixture of 3,4-dimethoxy-benzaldehyde (25 g, 150 mmol), 1-nitroethane (27 g, 360 mol), dimethylamine hydrochloride (36.5 g, 450 mmol) and potassium fluoride (8.7 g, 150 mmol) in toluene (300 mL) was heated to reflux with a Dean-Stark trap for 20 hours. The reaction mixture was diluted with ethyl acetate (500 mL) and then quenched with 10% hydrochloric acid (150 mL). The organic layer was separated, and then washed with water (150 mL) and brine (150 mL), and then dried over anhydrous Na₂SO₄, and then concentrated under reduced pressure. The residue was purified by chromatography to give 1,2-dimethoxy-4-[2-nitroprop-1-enyl]benzene (20 g) as a yellow solid.

Step 2: Preparation of 1-(3,4-dimethoxyphenyl)propan-2-amine

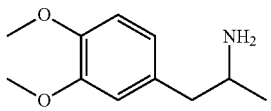

To a mixture of LiAlH₄ (11.4 g, 300 mmol) in THF (200 mL) was added a solution of 1,2-dimethoxy-4-[2-nitroprop-1-enyl]benzene (20 g, 84 mmol) in THF (200 mL) dropwise at a rate that the mixture refluxed slightly. After the addition, the mixture was refluxed for additional 3 hours and then stirred at room temperature overnight. Water (60 mL) was added dropwise, and then the mixture was filtered. The organic layer was dried over anhydrous MgSO₄ and then concentrated in vacuo to give 1-(3,4-dimethoxyphenyl)propan-2-amine.

Step 3: Preparation of N-[2-(3,4-dimethoxyphenyl)-1-methyl-ethyl]formamide

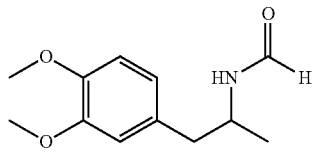 [SMILES: COc1ccc(CC(C)NC=O)cc1OC]

1-(3,4-Dimethoxyphenyl)propan-2-amine (10.45 g, 50 mmol) was dissolved in ethanol (300 mL) under nitrogen atmosphere. Ethyl formate (200 mL) and triethylamine (20 mL,) were added dropwise. The resultant mixture was refluxed for 2 days. The reaction mixture was concentrated, and the residue was purified by column chromatography to give N-[2-(3,4-dimethoxyphenyl)-1-methyl-ethyl]formamide (10 g).

Step 4: Preparation of 6,7-dimethoxy-3-methyl-3,4-dihydroisoquinoline

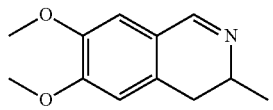

To a solution of N-[2-(3,4-dimethoxyphenyl)-1-methyl-ethyl]formamide (2.37 g, 10 mmol) in acetonitrile (100 mL) was added POCl$_3$ (2.3 g, 15 mmol). The mixture was refluxed for 1 hour. After being cooled to room temperature, the mixture was poured into water slowly. The resultant mixture was basified to pH>10 with ammonia and then extracted with ethyl acetate. The organic layer was concentrated in vacuo and the residue was purified by column chromatography to give 6,7-dimethoxy-3-methyl-3,4-dihydroisoquinoline (0.9 g).

Step 5: Preparation of ethyl 9,10-dimethoxy-6-methyl-2-oxo-1,6,7,11b-tetrahydrobenzo[a]quinolizine-3-carboxylate

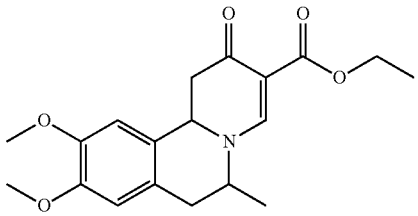 [SMILES: CCOC(=O)C1=CN2C(C)Cc3cc(OC)c(OC)cc3C2CC1=O]

A mixture of 6,7-dimethoxy-3-methyl-3,4-dihydroisoquinoline (800 g, 3.9 mmol) and ethyl 2-(dimethylaminomethylene)-3-oxo-butanoate (1.12 g, 6 mmol) in tert-butanol (15 mL) was heated under microwave irradiation at 150° C. for 80 minutes. Then the mixture was purified by flash column chromatography to give 9,10-dimethoxy-6-methyl-2-oxo-1,6,7,11b-tetrahydrobenzo[a]quinolizine-3-carboxylate (650 mg) as viscous solid.

Step 6: Preparation of ethyl 9,10-dimethoxy-6-methyl-2-oxo-6,7-dihydrobenzo[a]quinolizine-3-carboxylate

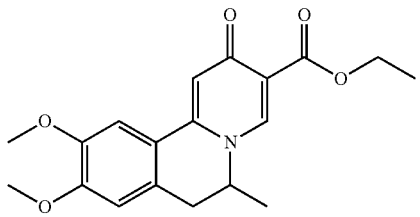 [SMILES: CCOC(=O)c1cn2c(cc1=O)-c1cc(OC)c(OC)cc1CC2C]

A mixture of 9,10-dimethoxy-6-methyl-2-oxo-1,6,7,11b-tetrahydrobenzo[a]quinolizine-3-carboxylate (250 mg, 0.72 mmol) and chloranil (355 mg, 1.44 mmol) in toluene (3 mL) and DME (3 mL) was heated under microwave irradiation at 135° C. for 20 minutes. The reaction mixture was diluted with ethyl acetate. The resultant mixture was washed with NaOH aqueous solution and brine, and then concentrated. The residue was purified by flash column chromatography to give ethyl 9,10-dimethoxy-6-methyl-2-oxo-6,7-dihydrobenzo[a]quinolizine-3-carboxylate as a brown viscous solid.

Step 7: Preparation of 9,10-dimethoxy-6-methyl-2-oxo-6,7-dihydrobenzo[a]quinolizine-3-carboxylic acid

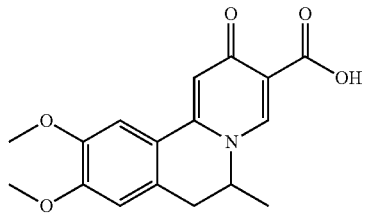 [SMILES: COc1cc2c(cc1OC)-c1cc(=O)c(C(=O)O)cn1C(C)C2]

A mixture of ethyl 9,10-dimethoxy-6-methyl-2-oxo-6,7-dihydrobenzo[a]quinolizine-3-carboxylate (350 mg, 1 mmol) and lithium hydroxide monohydrate (84 mg, 2 mmol) in ethanol (4 mL) and water (2 mL) was stirred at room temperature for 1 hour. The mixture was acidified by diluted hydrochloric acid solution and then extracted with ethyl acetate. The organic layer was washed with brine, and then dried over anhydrous Na$_2$SO$_4$ and then concentrated to give 9,10-dimethoxy-6-methyl-2-oxo-6,7-dihydrobenzo[a]quinolizine-3-carboxylic acid (110 mg). $^1$H NMR (400 MHz, DMSO-d$_6$): δ 8.83 (s, 1H), 7.54 (s, 1H), 7.47 (s, 1H), 7.02 (s, 1H), 4.95 (m, 1H), 3.89 (s, 3H), 3.86 (s, 3H), 3.40-3.28 (m, 1H), 2.91 (dd, 1H), 1.20 (d, 3H). MS obsd. (ESI$^+$) [(M+H)$^+$]: 316.

Example 67 and 68

(+)-9,10-dimethoxy-6-methyl-2-oxo-6,7-dihydrobenzo[a]quinolizine-3-carboxylic acid and (−)-9,10-dimethoxy-6-methyl-2-oxo-6,7-dihydrobenzo[a]quinolizine-3-carboxylic acid

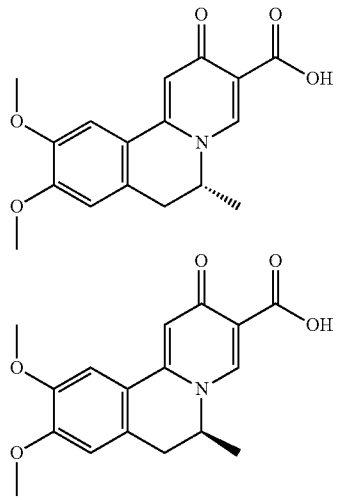

Separation of the racemic 9,10-dimethoxy-6-methyl-2-oxo-6,7-dihydrobenzo[a]quinolizine-3-carboxylic acid (100 mg) by chiral HPLC afforded (+)-9,10-dimethoxy-6-methyl-2-oxo-6,7-dihydrobenzo[a]quinolizine-3-carboxylic acid (21 mg) and (−)-9,10-dimethoxy-6-methyl-2-oxo-6,7-dihydrobenzo[a]quinolizine-3-carboxylic acid (21 mg).

Example 67

$^1$H NMR (400 MHz, CDCl$_3$): δ 8.56 (s, 1H), 7.21 (s, 1H), 7.11 (s, 1H), 6.78 (s, 1H), 4.56 (br, 1H), 3.99 (d, 6H), 3.48-3.45 (m, 1H), 2.86 (d, 1H), 1.30 (d, 3H). MS obsd. (ESI$^)$ [(M+H)$^+$]: 316. [α]$_D^{20}$=+96.26° (0.155%, CH$_3$CN).

Example 68

$^1$H NMR (400 MHz, CDCl$_3$): δ 8.56 (s, 1H), 7.21 (s, 1H), 7.11 (s, 1H), 6.78 (s, 1H), 4.56 (br, 1H), 3.99 (d, 6H), 3.48-3.45 (m, 1H), 2.86 (d, 1H), 1.30 (d, 3H). MS obsd. (ESI$^+$) [(M+H)$^+$]: 316.

Example 69: 9,10-dimethoxy-7-methyl-2-oxo-6,7-dihydrobenzo[a]quinolizine-3-carboxylic acid

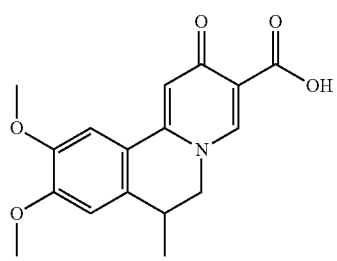

Step 1: Preparation of ethyl 2-(3,4-dimethoxyphenyl)propanoate

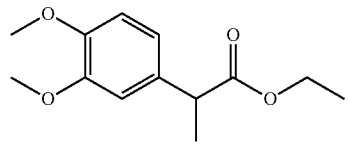 [SMILES: CCOC(=O)C(C)c1ccc(OC)c(OC)c1]

To a solution of ethyl 3,4-dimethoxyphenyl acetate (18.8 g, 0.084 mol) and hexamethylphosphoric triamide (14 g, 0.084 mol) in anhydrous tetrahydrofuran (200 mL) was added dropwise a solution of lithium diisopropylamide (2 M, 42 mL, 0.084 mole) while maintaining the temperature below −70° C. After 30 minutes at −78° C., iodomethane (26.6 g, 0.186 mol) was added dropwise while maintaining the temperature below −70° C. The resultant mixture was allowed to warm to room temperature and stirred for 18 hours, and then quenched by addition of saturated NH$_4$Cl solution (100 mL). The organic layer was separated. The aqueous layer was diluted with water (100 mL) and then extracted with ethyl acetate (100 mL×2). All organic layers were combined, and then dried over anhydrous Na$_2$SO$_4$ and then concentrated in vacuo. The residue was purified by column chromatography to give ethyl 2-(3,4-dimethoxyphenyl)propanoate as colorless oil (17 g).

Step 2: Preparation of 2-(3,4-dimethoxyphenyl)propanoic acid

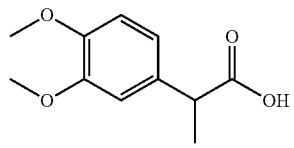

To a solution of ethyl 2-(3,4-dimethoxyphenyl)propanoate (17 g, 71.3 mmol) in THF (60 mL) and methanol (40 mL) was added a solution of NaOH (6.1 g, 0.15 mol) in water (60 mL). The resultant mixture was stirred for 4 hours at room temperature, and then extracted with DCM (50 mL). The aqueous layer was acidified with 6 N HCl till pH 1, and then extracted with DCM (50 mL×3). The organic layer was concentrated in vacuo to give 2-(3,4-dimethoxyphenyl)propanoic acid (14 g) as light yellow oil.

Step 3: Preparation of 2-(3,4-dimethoxyphenyl)propanamide

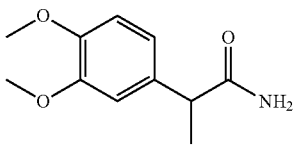

To a solution of 2-(3,4-dimethoxyphenyl)propanoic acid (0.52 g, 2.5 mmol) in DCM (20 mL) was added SOCl$_2$ (1.2 g, 10 mmol) dropwise at 0° C. The resultant mixture was stirred at room temperature for 30 minutes, and then refluxed

Step 4: Preparation of 2-(3,4-dimethoxyphenyl)propan-1-amine for 2 hours. After concentrated in vacuo, the residue was dissolved in DCM (5 mL) and then added dropwise into a NH₃ solution in DCM at 0° C. The resultant mixture was then allowed to warm to room temperature, stirred for 3 hours and then concentrated in vacuo to give crude 2-(3,4-dimethoxyphenyl)propanamide (0.42 g) as a light yellow solid.

Step 4: Preparation of 2-(3,4-dimethoxyphenyl)propan-1-amine

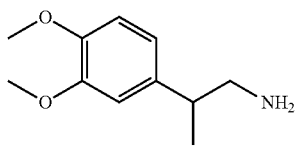

In a three-neck round-bottom flask was added 2-(3,4-dimethoxyphenyl)propanamide (10.4 g, 50 mmol) and dry THF (250 mL). The mixture was heated to reflux. To the mixture was added a solution of BH₃ in THF (1 M, 250 mL) dropwise. The resultant mixture was refluxed for 12 hours, and then cooled to 0° C. Methanol (150 mL) was added dropwise. The mixture was concentrated in vacuo, and the residue was dissolved in 1,4-dioxane (50 mL) and then followed by addition of hydrochloric acid (6 M, 175 mL). The resultant mixture was refluxed for 2 hours, and then cooled to room temperature, then diluted with water (200 mL) and extracted with DCM (200 mL). The aqueous layer was basified and then extracted with DCM (200 mL×3). The organic layers were combined, and then washed with water (200 mL), then dried over anhydrous Na₂SO₄, and concentrated. The residue was purified by column chromatography to give 2-(3,4-dimethoxyphenyl)propan-1-amine (7 g) as light brown oil.

Step 5: Preparation of N-[2-(3,4-dimethoxyphenyl)propyl]formamide

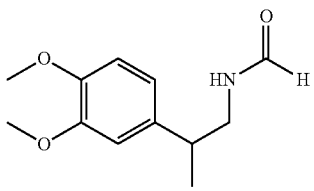 [SMILES: COc1ccc(C(C)CNC=O)cc1OC]

2-(3,4-Dimethoxyphenyl)propan-1-amine (0.72 g, 4 mmol) was dissolved in ethanol (2 mL) under nitrogen atmosphere. Ethyl formate (3 mL, 40 mmol) and triethylamine (0.02 mL, 0.175 mmol) was added dropwise successively. The resultant mixture was refluxed for 2 days. The reaction mixture was concentrated to give N-[2-(3,4-dimethoxyphenyl)propyl]formamide (0.83 g) which was used without further purification.

Step 6: Preparation of 6,7-dimethoxy-4-methyl-3,4-dihydroisoquinoline

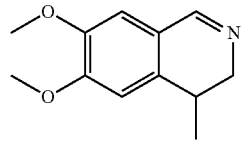

To a solution of N-[2-(3,4-dimethoxyphenyl)propyl]formamide (3.3 g, 1.5 mmol) in acetonitrile (20 mL) was added POCl₃ (3.9 g, 2.5 mmol). The mixture was refluxed for 1 hour. After being cooled to room temperature, the mixture was poured into water slowly. The resultant mixture was basified to pH>10 with ammonia and then extracted with ethyl acetate. The organic layer was concentrated in vacuo and the residue was purified by column chromatography to give 6,7-dimethoxy-4-methyl-3,4-dihydroisoquinoline (1.6 g).

Step 7: Preparation of 9,10-dimethoxy-7-methyl-2-oxo-6,7-dihydrobenzo[a]quinolizine-3-carboxylic acid

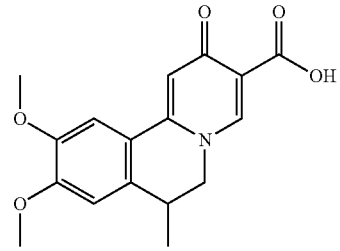 [SMILES: COc1cc2c(cc1OC)C(C)Cn1cc(C(=O)O)c(=O)cc1-2]

A mixture of 6,7-dimethoxy-4-methyl-3,4-dihydroisoquinoline (250 mg, 1.2 mmol), hydrochloric acid in dioxane (0.5 mmol) and ethyl 2-(dimethylaminomethylene)-3-oxobutanoate (300 mg, 1.3 mmol) in DMSO (1.5 mL) was heated under microwave irradiation at 130° C. for 3 hours. To this mixture was added MnO₂ (435 mg, 5 mmol), and then heated for additional 1 hour. Then additional MnO₂ (218 mg, 2.5 mmol) was added and the mixture was heated for 1 hour. The mixture was partitioned between DCM and water, and the aqueous layer was acidified by hydrochloric acid. The organic layer was dried over anhydrous Na₂SO₄ and then concentrated. The residue was purified by column chromatography to give 9,10-dimethoxy-7-methyl-2-oxo-6,7-dihydrobenzo[a]quinolizine-3-carboxylic acid (20 mg). ¹H NMR (400 MHz, DMSO-d₆): δ 8.79 (s, 1H), 7.52 (s, 1H), 7.47 (s, 1H), 7.04 (s, 1H), 4.32 (d, 2H), 3.88 (s, 3H), 3.87 (s, 3H), 3.26 (m, 1H), 1.18 (d, 3H). MS obsd. (ESI⁺) [(M+H)⁺]: 316.

Example 70: 6-ethyl-9,10-dimethoxy-2-oxo-6,7-dihydrobenzo[a]quinolizine-3-carboxylic acid

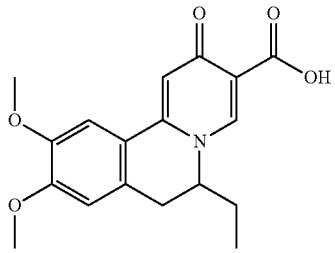

Step 1: Preparation of 1,2-dimethoxy-4-[2-nitrobut-1-enyl]benzene

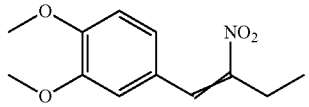 [SMILES: CCC(=Cc1ccc(OC)c(OC)c1)[N+](=O)[O-]]

A mixture of 3,4-dimethoxybenzaldehyde (112.5 g, 677 mmol), nitropropane (122 g, 1355 mol), dimethylamine HCl (164 g, 2.33 mmol) and potassium fluoride (39.1 g, 677 mmol) in toluene (1500 mL) was refluxed with a Dean-Stark trap for 20 hours. Then the reaction mixture was diluted with ethyl acetate (800 mL) and then quenched with 10% hydrochloric acid (250 mL). The organic layer was separated, and then washed with water (250 mL) and brine (250 mL), then dried over anhydrous $Na_2SO_4$ and concentrated under reduced pressure. The residue was purified by column chromatography to give 1,2-dimethoxy-4-[2-nitrobut-1-enyl]benzene (120 g) as a yellow solid.

Step 2: Preparation of 1-(3,4-dimethoxyphenyl)butan-2-amine

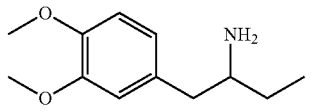

To a solution of 1,2-dimethoxy-4-[2-nitrobut-1-enyl]benzene (108 g, 454 mmol) in methanol (500 mL) was added Pd/C (10.0 g). The mixture was stirred at 50° C. under 50 psi of $H_2$ atmosphere for 60 hours, and then filtered through a celite pad. The filtrate was concentrated to give 1-(3,4-dimethoxyphenyl)butan-2-amine (54.0 g) as a white solid.

Step 3: Preparation of N-[1-[(3,4-dimethoxyphenyl)methyl]propyl]formamide

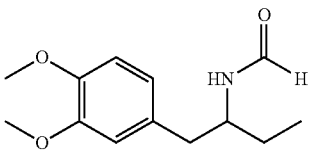 [SMILES: CCC(Cc1ccc(OC)c(OC)c1)NC=O]

1-(3,4-Dimethoxyphenyl)butan-2-amine (54 g, 258 mmol) was dissolved in ethanol (250 mL) under nitrogen atmosphere. Ethyl formate (300 mL) and triethylamine (20 mL) was added dropwise successively. The resultant mixture was refluxed for 2 days. The mixture was concentrated in vacuo to give N-[1-[(3,4-dimethoxyphenyl)methyl]propyl]formamide (50.0 g).

Step 4: Preparation of 3-ethyl-6,7-dimethoxy-3,4-dihydroisoquinoline

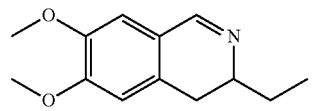 [SMILES: CCC1Cc2cc(OC)c(OC)cc2C=N1]

To a solution of N-[1-[(3,4-dimethoxyphenyl)methyl]propyl]formamide (50.0 g, 211 mmol) in acetonitrile (100 mL) was added $POCl_3$ (48.4 g, 316.4 mmol) dropwise. The resultant mixture was refluxed for 1 hour. The resultant mixture was basified to pH>10 with ammonia and then extracted with ethyl acetate. The organic layer was concentrated in vacuo and the residue was purified by column chromatography to give 3-ethyl-6,7-dimethoxy-3,4-dihydroisoquinoline.

Step 5: Preparation of 6-ethyl-9,10-dimethoxy-2-oxo-6,7-dihydrobenzo[a]quinolizine-3-carboxylic acid

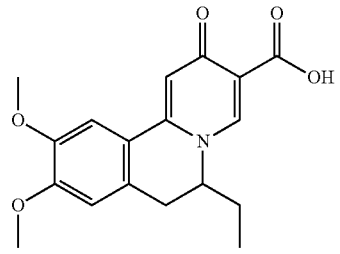 [SMILES: CCC1Cc2cc(OC)c(OC)cc2-c2cc(=O)c(C(=O)O)cn21]

A mixture of 3-ethyl-6,7-dimethoxy-3,4-dihydroisoquinoline (4 g, 18 mmol), hydrochloric acid in dioxane (5 M, 2 mL, 10 mmol) and ethyl 2-(dimethylaminomethylene)-3-oxo-butanoate (4, 21.6 mmol) in DMSO (20 mL) was heated under microwave irradiation at 125° C. for 1 hour. To this mixture was added $MnO_2$ (4.7 g, 54 mmol), and then the mixture was heated at 120° C. for 5 hours. Then additional $MnO_2$ (1.6 g, 18 mmol) was added and the mixture was heated for additional 2 hours. The mixture was partitioned between DCM and water, and the aqueous layer was acidified by hydrochloric acid to pH 1. The organic layer was washed with brine, and then dried over anhydrous $Na_2SO_4$ and concentrated. The residue was purified by column chromatography and then recrystallized in ethanol to give 6-ethyl-9,10-dimethoxy-2-oxo-6,7-dihydrobenzo[a]quinolizine-3-carboxylic acid as a white solid (1.8 g). $^1$H NMR (400 MHz, DMSO-$d_6$): δ 8.81 (s, 1H), 7.53 (s, 1H), 7.47 (s, 1H), 7.04 (s, 1H), 4.72 (m, 1H), 3.88 (s, 3H), 3.85 (s, 3H), 3.36 (dd, 1H), 3.02 (d, 1H), 1.52-1.44 (m, 2H), 0.81 (t, 3H). MS obsd. (ESI$^+$) [(M+H)$^+$]: 330.

Example 71 and 72

(6R)-(+)-6-ethyl-9,10-dimethoxy-2-oxo-6,7-dihydrobenzo[a]quinolizine-3-carboxylic acid and (6S)-(−)-6-ethyl-9,10-dimethoxy-2-oxo-6,7-dihydrobenzo[a]quinolizine-3-carboxylic acid Example 71

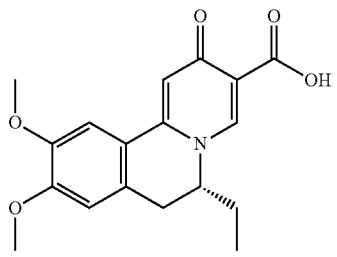

Example 72

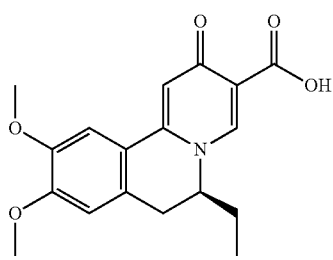

Separation of the racemic 6-ethyl-9,10-dimethoxy-2-oxo-6,7-dihydrobenzo[a]quinolizine-3-carboxylic acid (50 mg) by chiral HPLC afforded (6R)-(+)-6-ethyl-9,10-dimethoxy-2-oxo-6,7-dihydrobenzo[a]quinolizine-3-carboxylic acid (10 mg) and (6S)-(−)-6-ethyl-9,10-dimethoxy-2-oxo-6,7-dihydrobenzo[a]quinolizine-3-carboxylic acid (10 mg).

Example 71

$^1$H NMR (400 MHz, DMSO-d$_6$): δ 8.81 (s, 1H), 7.53 (s, 1H), 7.47 (s, 1H), 7.04 (s, 1H), 4.72 (m, 1H), 3.88 (s, 3H), 3.85 (s, 3H), 3.36 (dd, 1H), 3.02 (d, 1H), 1.52-1.44 (m, 2H), 0.81 (t, 3H). MS obsd. (ESI$^+$) [(M+H)$^+$]: 330. [α]$_D^{20}$=+121.21 (0.165%, CH$_3$CN), the absolute stereochemistry was determined by the X-ray diffraction study of its (6S)-enantiomer Example 72.

Example 72

$^1$H NMR (400 MHz, DMSO-d$_6$): δ 8.81 (s, 1H), 7.53 (s, 1H), 7.47 (s, 1H), 7.04 (s, 1H), 4.72 (m, 1H), 3.88 (s, 3H), 3.85 (s, 3H), 3.36 (dd, 1H), 3.02 (d, 1H), 1.52-1.44 (m, 2H), 0.81 (t, 3H). MS obsd. (ESI$^+$) [(M+H)$^+$]: 330, the absolute stereochemistry was determined by X-ray diffraction study (FIG. 1).

Example 73: 9-methoxy-6,10-dimethyl-2-oxo-6,7-dihydrobenzo[a]quinolizine-3-carboxylic acid

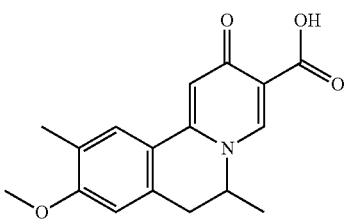

Step 1: Preparation of 2-methoxy-1-methyl-4-[2-nitroprop-1-enyl]benzene

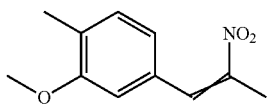

A mixture of 3-methoxy-4-methyl-benzaldehyde (20 g, 133 mmol), nitroethane (250 g, 3.3 mol) and NH$_4$OAc (51 g, 665 mmol) was heated at 110° C. for 2 hours. After being cooled to room temperature, the mixture was poured into ice-water (1000 mL) and then extracted with ethyl acetate (400 mL×3). The combined organic layers were washed with water (400 mL) and brine (400 mL), and then dried over anhydrous Na$_2$SO$_4$ and filtered. The filtrate was concentrated under reduced pressure, and the residue was purified by column chromatography to afford 2-methoxy-1-methyl-4-[2-nitroprop-1-enyl]benzene as a solid (10 g).

Step 2: Preparation of 1-(3-methoxy-4-methyl-phenyl)propan-2-amine

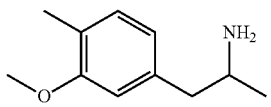

A mixture of 2-methoxy-1-methyl-4-[2-nitroprop-1-enyl]benzene (14 g, 67.5 mmol) and Pd/C (2 g) in methanol (150 mL) was stirred at 50° C. under 50 psi of H$_2$ atmosphere overnight. The reaction mixture was filtered, and the filter cake was washed with methanol (30 mL×3). The combined methanol solution was concentrated to give a residue, which was dissolved in 2 N hydrochloric acid (150 mL) and then extracted with ethyl acetate (50 mL×3). The aqueous solution was adjusted to pH 12 with NaOH solution, and then extracted with ethyl acetate (50 mL×4). The combined organic layers were dried over anhydrous Na$_2$SO$_4$, and concentrated in vacuo and then purified by column chromatography to give 1-(3-methoxy-4-methyl-phenyl)propan-2-amine (3.6 g) as colorless oil.

Step 3: Preparation of N-[2-(3-methoxy-4-methyl-phenyl)-1-methyl-ethyl]formamide

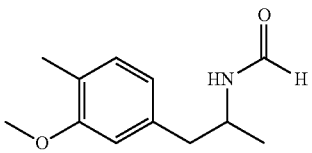

1-(3-Methoxy-4-methyl-phenyl)propan-2-amine (3.6 g, 20 mmol) was dissolved in ethanol (12 mL) under nitrogen atmosphere. Ethyl formate (24 mL, 300 mmol) and triethylamine (1 mL, 7 mmol) were added dropwise successively, and the resultant mixture was refluxed for 2 days. The mixture was concentrated and to give N-[2-(3-methoxy-4-methyl-phenyl)-1-methyl-ethyl]formamide (3 g).

Step 4: Preparation of 8-methoxy-5,9-dimethyl-6,10b-dihydro-5H-oxazolo[2,3-a]isoquinoline-2,3-dione

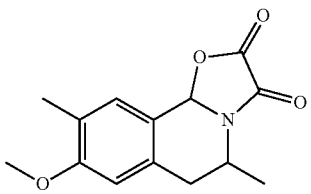 [SMILES: COc1cc2c(cc1C)C1OC(=O)C(=O)N1C(C)C2]

To a solution of N-[2-(3-methoxy-4-methyl-phenyl)-1-methyl-ethyl]formamide (3 g, 15 mmol) in DCM (100 mL) was added oxalyl chloride (2.1 g, 16.5 mmol). The solution was stirred at room temperature for 30 minutes, then cooled to −10° C. Iron(III) chloride (2.9 g, 18 mmol) was added. The mixture was allowed to warm to room temperature, and then stirred overnight, and filtered. The filtrate was washed with water and brine, and then dried over anhydrous Na$_2$SO$_4$, filtered and concentrated under reduced pressure to give 8-methoxy-5,9-dimethyl-6, 10b-dihydro-5H-oxazolo[2,3-a]isoquinoline-2,3-dione as dark oil (3.5 g).

Step 5: Preparation of 6-methoxy-3,7-dimethyl-3,4-dihydroisoquinoline

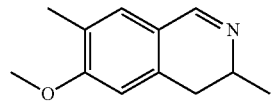

A mixture of 8-methoxy-5,9-dimethyl-6,10b-dihydro-5H-oxazolo[2,3-a]isoquinoline-2,3-dione (3.5 g, 11.5 mmol) in concentrated H$_2$SO$_4$/MeOH (1/19, 80 mL) was refluxed for 20 hours. After being cooled to room temperature, the mixture was concentrated under reduced pressure. The dark red residue was dissolved in water (100 mL), and then basified with ammonia and then extracted with DCM (3×50 mL). The combined organic layers were washed with brine (100 mL), and then dried over anhydrous Na$_2$SO$_4$ and filtered. The filtrate was concentrated and the residue was purified by column chromatography to give 6-methoxy-3,7-dimethyl-3,4-dihydroisoquinoline as light yellow oil (0.9 g).

Step 6: Preparation of ethyl 9-methoxy-6,10-dimethyl-2-oxo-6,7-dihydrobenzo[a]quinolizine-3-carboxylate

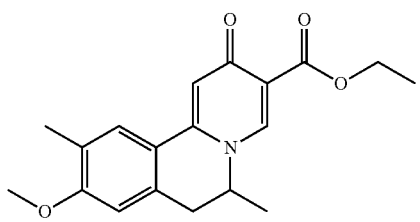 [SMILES: CCOC(=O)c1cn2c(cc1=O)-c1cc(C)c(OC)cc1CC2C]

A mixture of 6-methoxy-3,7-dimethyl-3,4-dihydroisoquinoline (300 mg, 1.59 mmol) and ethyl 2-(dimethylaminomethylene)-3-oxo-butanoate (350 mg, 1.89 mmol) in DMF (2 mL) was heated under microwave irradiation at 170° C. for 4.5 hours. Then the mixture was partitioned between ethyl acetate and water. The organic layer was washed with water, and then dried over anhydrous Na$_2$SO$_4$ and concentrated to give a residue. The residue was dissolved in toluene (2.5 mL) and DME (2.5 mL) with chloranil (245 mg, 1 mmol). The mixture was heated at 135° C. for 10 minutes, and then concentrated to crude ethyl 9-methoxy-6,10-dimethyl-2-oxo-6,7-dihydrobenzo[a]quinolizine-3-carboxylate (1.2 g) which was used in next step without purification.

Step 7: Preparation of 9-methoxy-6,10-dimethyl-2-oxo-6,7-dihydrobenzo[a]quinolizine-3-carboxylic acid

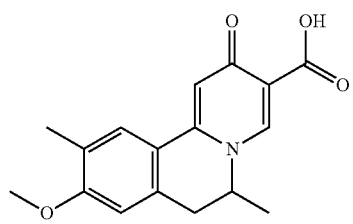 [SMILES: COc1cc2c(cc1C)-c1cc(=O)c(C(=O)O)cn1C(C)C2]

A mixture of crude ethyl 9-methoxy-6,10-dimethyl-2-oxo-6,7-dihydrobenzo[a]quinolizine-3-carboxylate (1.2 g) and lithium hydroxide monohydrate (126 mg, 3 mmol) in methanol (5 mL) and water (2 mL) was stirred at room temperature for 1 hour. The mixture was acidified by diluted hydrochloric acid solution to pH 1, partitioned between ethyl acetate and water. The organic layer was dried over anhydrous Na$_2$SO$_4$ and then concentrated. The residue was purified by column chromatography to give 9-methoxy-6,10-dimethyl-2-oxo-6,7-dihydrobenzo[a]quinolizine-3-carboxylic acid (30 mg). $^1$H NMR (400 MHz, DMSO-d$_6$): δ 8.83 (s, 1H), 7.91 (s, 1H), 7.30 (s, 1H), 6.99 (s, 1H), 4.96 (m, 1H), 3.89 (s, 3H), 3.39 (dd, 1H), 2.95 (d, 1H), 2.21 (s, 3H), 1.20 (d, 3H). MS obsd. (ESI$^+$) [(M+H)$^+$]: 300.

Example 74: 9,10-diethoxy-6-methyl-2-oxo-6,7-dihydrobenzo[a]quinolizine-3-carboxylic acid

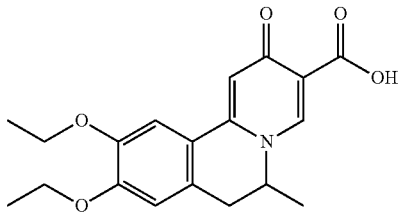 [SMILES: CCOc1cc2c(cc1OCC)-c1cc(=O)c(C(=O)O)cn1C(C)C2]

Step 1: Preparation of 1,2-diethoxy-4-[2-nitroprop-1-enyl]benzene

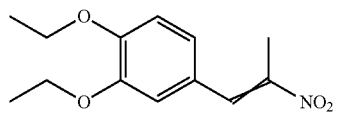 [SMILES: CCOc1ccc(C=C(C)[N+](=O)[O-])cc1OCC]

A mixture of 3,4-diethoxy-benzaldehyde (19.4 g, 100 mmol), 1-nitroethane (27 g, 360 mol), dimethylamine hydrochloride (36.5 g, 450 mmol) and potassium fluoride (8.7 g, 150 mmol) in toluene (300 mL) was refluxed with a Dean-Stark trap for 20 hours. The mixture was diluted with ethyl acetate (500 mL) and then quenched with 10% hydrochloric acid (150 mL). The organic layer was washed with water (150 mL) and brine (150 mL), and then dried over anhydrous $Na_2SO_4$ and filtered. The filtrate was concentrated under reduced pressure and the residue was purified by column chromatography to give 1,2-diethoxy-4-[2-nitroprop-1-enyl]benzene (10 g) as a yellow solid.

Step 2: Preparation of 1-(3,4-diethoxyphenyl)propan-2-amine

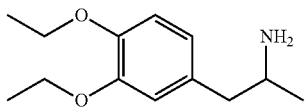 [SMILES: CCOc1ccc(CC(C)N)cc1OCC]

To a mixture of $LiAlH_4$ (11.4 g, 300 mmol) in THF (200 mL) was added a solution of 1,2-diethoxy-4-[2-nitroprop-1-enyl]benzene (10 g, 40 mmol) in THF (200 mL) dropwise at a rate that the mixture was refluxed slightly. After the addition was completed, the mixture was refluxed for additional 3 hours, and then stirred at room temperature overnight. Water (60 mL) was added dropwise and the resultant mixture was filtered. The organic layer was dried over $MgSO_4$ and then concentrated in vacuo to give crude 1-(3,4-diethoxyphenyl)propan-2-amine, which was used directly in the next step without any further purification.

Step 3: Preparation of N-[2-(3,4-diethoxyphenyl)-1-methyl-ethyl]formamide

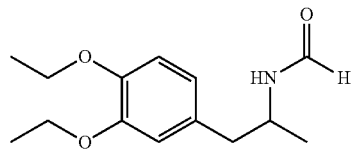 [SMILES: CCOc1ccc(CC(C)NC=O)cc1OCC]

1-(3,4-Diethoxyphenyl)propan-2-amine (2.23 g, 10 mmol) was dissolved in ethanol (30 mL) under nitrogen atmosphere. Ethyl formate (20 mL) and triethylamine (2 mL) was added dropwise successively. The resultant mixture was refluxed for 2 days. The mixture was concentrated in vacuo and the residue was purified by column chromatography to give N-[2-(3,4-diethoxyphenyl)-1-methyl-ethyl]formamide (2 g).

Step 4: Preparation of 8,9-diethoxy-5-ethyl-6,10b-dihydro-5H-oxazolo[2,3-a]isoquinoline-2,3-dione and 8-ethoxy-5-ethyl-9-hydroxy-6,10b-dihydro-5H-oxazolo[2,3-a]isoquinoline-2,3-dione

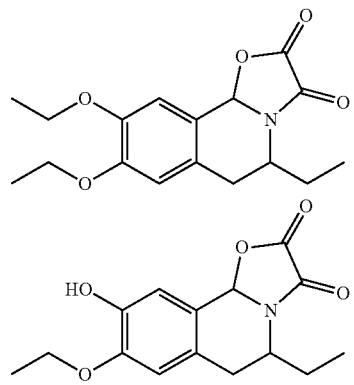

To a solution of N-[2-(3,4-diethoxyphenyl)-1-methyl-ethyl]formamide (2 g, 7.5 mmol) in DCM (100 mL) was added oxalyl chloride (1.05 g, 8.25 mmol). The mixture was stirred at room temperature for 30 minutes, and then cooled to −10° C. Iron (III) chloride (1.45 g, 9 mmol) was added to the mixture. The mixture was allowed to warm to room temperature and then stirred overnight, and then filtered. The filtrate was washed with water and brine, and then dried over anhydrous $Na_2SO_4$, filtered and concentrated under reduced pressure to give dark oil (2 g), which was used in next step without purification.

Step 5: Preparation of 6,7-diethoxy-3-methyl-3,4-dihydroisoquinoline and 6-ethoxy-3-methyl-3,4-dihydroisoquinolin-7-ol

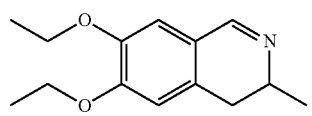

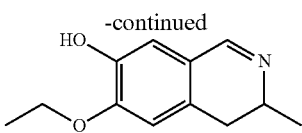

A mixture of 8,9-diethoxy-5-ethyl-6,10b-dihydro-5H-oxazolo[2,3-a]isoquinoline-2,3-dione and 8-ethoxy-5-ethyl-9-hydroxy-6,10b-dihydro-5H-oxazolo[2,3-a]isoquinoline-2,3-dione (2 g) in acetonitrile (10 mL) and concentrated $H_2SO_4$/MeOH (1/19, 40 mL) was refluxed for 20 hours. After being cooled to room temperature, the mixture was concentrated under reduced pressure. The residue was purified by prep-HPLC to give 6,7-diethoxy-3-methyl-3,4-dihydroisoquinoline (58 mg) and 6-ethoxy-3-methyl-3,4-dihydroisoquinolin-7-ol (450 mg).

Step 6: Preparation of ethyl 9,10-diethoxy-6-methyl-2-oxo-6,7-dihydrobenzo[a]quinolizine-3-carboxylate

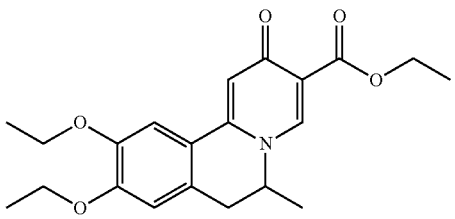 [SMILES: CCOC(=O)c1cn2c(cc1=O)-c1cc(OCC)c(OCC)cc1CC2C]

A mixture of 6,7-diethoxy-3-methyl-3,4-dihydroisoquinoline (55 mg, 0.24 mmol) and ethyl 2-(dimethylaminomethylene)-3-oxo-butanoate (57 mg, 0.31 mmol) in DMF (0.8 mL) was heated under microwave irradiation at 170° C. for 90 minutes. Then the mixture was partitioned between ethyl acetate and water. The organic layer was washed with water, and then dried over anhydrous $Na_2SO_4$ and concentrated to give a residue, which was dissolved in toluene (1 mL) and DME (1 mL) with chloranil (40 mg, 0.17 mmol). The mixture was heated at 130° C. for 10 minutes, and then partitioned between ethyl acetate and water. The organic layer was washed with brine and then concentrated to crude ethyl 9, 10-dimethoxy-6-methyl-2-oxo-6,7-dihydrobenzo[a]quinolizine-3-carboxylate which was used in next step without purification.

Step 7: Preparation of 9,10-diethoxy-6-methyl-2-oxo-6,7-dihydrobenzo[a]quinolizine-3-carboxylic acid

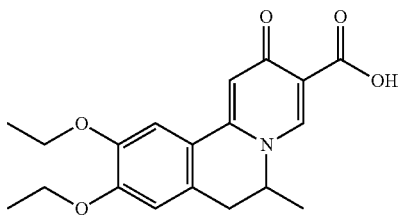 [SMILES: CCOc1cc2c(cc1OCC)-c1cc(=O)c(C(=O)O)cn1C(C)C2]

A mixture of crude ethyl 9,10-dimethoxy-6-methyl-2-oxo-6,7-dihydrobenzo[a]quinolizine-3-carboxylate (110 mg) and lithium hydroxide monohydrate (40 mg, 1 mmol) in methanol (3 mL) and water (1 mL) was stirred at room temperature for 2 hours. The mixture was acidified by diluted hydrochloric acid solution, and then partitioned between ethyl acetate and water. The organic layer was dried over anhydrous $Na_2SO_4$ and then concentrated. The residue was purified by column chromatography to give 9, 10-diethoxy-6-methyl-2-oxo-6,7-dihydrobenzo[a]quinolizine-3-carboxylic acid (4 mg). $^1$H NMR (400 MHz, MeOD-$d_4$): δ 8.79 (s, 1H), 7.46 (s, 1H), 7.28 (s, 1H), 6.99 (s, 1H), 4.84 (m, 1H), 4.22-4.15 (m, 4H), 3.45 (dd, 1H), 2.96 (dd, 1H), 1.50-1.45 (m, 6H), 1.35 (d, 3H). MS obsd. (ESI$^+$) [(M+H)$^+$]: 344.

Example 75: 9-ethoxy-6-methyl-10-hydroxy-2-oxo-6,7-dihydrobenzo[a]quinolizine-3-carboxylic acid

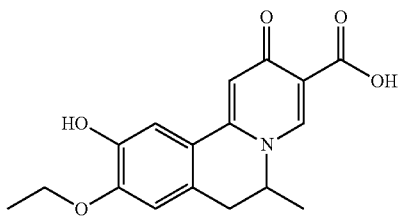 [SMILES: CCOc1cc2c(cc1O)-c1cc(=O)c(C(=O)O)cn1C(C)C2]

Step 1: Preparation of ethyl 9-ethoxy-10-hydroxy-6-methyl-2-oxo-1,6,7,11b-tetrahydrobenzo[a]quinolizine-3-carboxylate

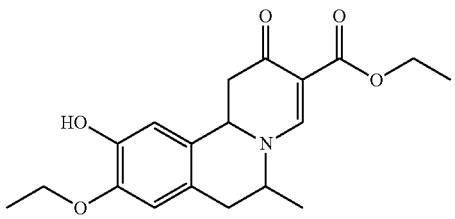 [SMILES: CCOC(=O)C1=CN2C(C)Cc3cc(OCC)c(O)cc3C2CC1=O]

A mixture of 6-ethoxy-3-methyl-3,4-dihydroisoquinolin-7-ol (350 mg, 1.70 mmol) and ethyl 2-(dimethylaminomethylene)-3-oxo-butanoate (472 mg, 2.55 mmol) in DMF (2 mL) was heated to 170° C. for 1.5 hours under microwave. The mixture was diluted with $H_2O$ (20 mL), and then extracted with EtOAc (30 mL×3). The combined organic layers were washed with brine, and then dried over anhydrous $Na_2SO_4$, then concentrated to give crude product. The crude product was purified by flash chromatography to afford ethyl 9-ethoxy-10-hydroxy-6-methyl-2-oxo-1,6,7,11b-tetrahydrobenzo[a]quinolizine-3-carboxylate (300 mg) as brown oil which was directly used for next step without further purification.

Step 2: Preparation of 9-ethoxy-10-hydroxy-6-methyl-2-oxo-6,7-dihydrobenzo[a]quinolizine-3-carboxylic acid

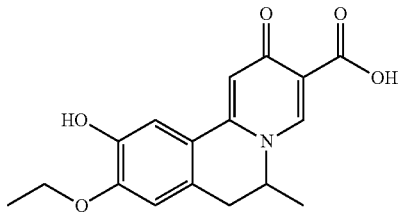 [SMILES: CCOc1cc2c(cc1O)-c1cc(=O)c(C(=O)O)cn1C(C)C2]

A mixture of ethyl 9-ethoxy-10-hydroxy-6-methyl-2-oxo-1,6,7,11b-tetrahydrobenzo[a]quinolizine-3-carboxylate (300 mg, 0.87 mmol) and p-chloranil (213 mg, 0.87 mmol) in DME (1 mL) and toluene (1 mL) was heated to 135° C. for 20 minutes under microwave. After being cooled to room temperature, the mixture was concentrated under reduced pressure. The residue was purified by flash column chromatography to afford a mixture of ester and carboxylic acid (163 mg). Then the mixture was dissolved in $CH_3OH$ (4 mL) and $H_2O$ (1 mL), and then lithium hydroxide monohydrate (84 mg, 2.0 mmol) was added. The resultant mixture was stirred at room temperature overnight. The mixture was diluted with $H_2O$ (10 mL) and acidified by 1 M hydrochloric acid to pH 2. Then the mixture was extracted with $CH_2Cl_2$ (20 mL×3), the combined layers were washed with brine, and then dried over anhydrous $Na_2SO_4$ and concentrated. The residue was washed with $EtOH/Et_2O$ to afford 9-ethoxy-10-hydroxy-6-methyl-2-oxo-6,7-dihydrobenzo[a]quinolizine-3-carboxylic acid (130 mg) as a yellow solid. $^1H$ NMR (400 MHz, DMSO-$d_6$) δ 9.26 (br. s, 1H), 8.81 (s, 1H), 7.36 (s, 1H), 7.04 (s, 1H), 6.96 (s, 1H), 4.92 (t, 1H), 4.13 (q, 2H), 3.32 (dd, 1H), 2.89-2.81 (m, 1H), 1.38 (t, 3H), 1.19 (d, 3H). MS obsd. (ESI$^+$) [(M+H)$^+$]: 316.

Example 76: 9,10-diethoxy-2-oxo-6,7-dihydrobenzo[a]quinolizine-3-carboxylic acid

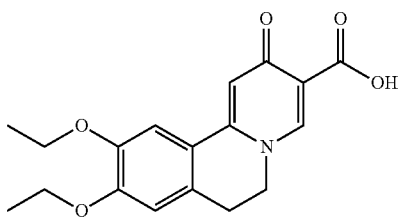 [SMILES: CCOc1cc2c(cc1OCC)-c1cc(=O)c(C(=O)O)cn1CC2]

Step 1: Preparation of tert-butyl N-[2-(3,4-diethoxyphenyl)ethyl]carbamate

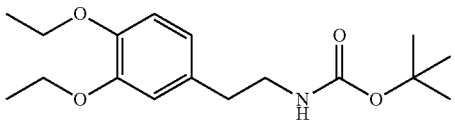 [SMILES: CCOc1ccc(CCNC(=O)OC(C)(C)C)cc1OCC]

To a solution of [2-(3,4-dihydroxy-phenyl)-ethyl]-carbamic acid tert-butyl ester (2.53 g, 10 mmol) in DMF (20 mL) was added potassium carbonate (2.1 g) and iodoethane (3.12 g, 20 mmol). The reaction mixture was stirred overnight at room temperature and then concentrated in vacuo. Saturated ammonium chloride solution was added to the residue and the mixture was extracted with ethyl acetate (3×50 mL). The organic phases were combined and washed with water and brine, and then dried over anhydrous magnesium sulfate and then concentrated in vacuo. The residue was purified by flash column chromatography to give tert-butyl N-[2-(3, 4-diethoxyphenyl)ethyl]carbamate (2.8 g).

Step 2: Preparation of 2-(3,4-diethoxyphenyl)ethanamine

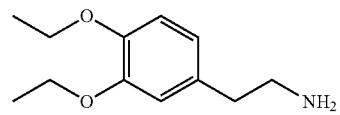

To a solution of tert-butyl N-[2-(3, 4-diethoxyphenyl)ethyl]carbamate (3.09 g) in dichloromethane (20 mL) was added trifluoroacetic acid (5 mL) at 0° C. The reaction mixture was stirred at room temperature for 30 minutes and then another batch of trifluoroacetic acid (5 mL) was added. Then the mixture was stirred for another 2 hours. An aqueous solution of sodium hydroxide (1 M) was added dropwise. The mixture was extracted with dichloromethane. The organic layers were combined and washed with water and brine, and then dried over anhydrous magnesium sulfate and then concentrated in vacuo to give 2-(3,4-diethoxyphenyl)-ethylamine (1.8 g) as yellow oil.

Step 3: Preparation of methyl 3-[2-(3,4-diethoxyphenyl)ethylamino]prop-2-enoate

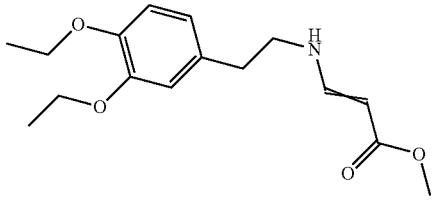 [SMILES: CCOc1ccc(CCNC=CC(=O)OC)cc1OCC]

A mixture of 2-(3,4-diethoxyphenyl)ethanamine (1.8 g, 9 mmol) and methyl prop-2-ynoate (0.84 g, 10 mmol) in dichloromethane was stirred at room temperature overnight. After reaction was completed, the solvent was removed. The residue was purified by flash column chromatography to give methyl 3-[2-(3,4-diethoxyphenyl)ethylamino]prop-2-enoate (2.0 g).

Step 4: Preparation of methyl 1-[2-(3,4-diethoxyphenyl)ethyl]-4,6-dioxo-pyridine-3-carboxylate

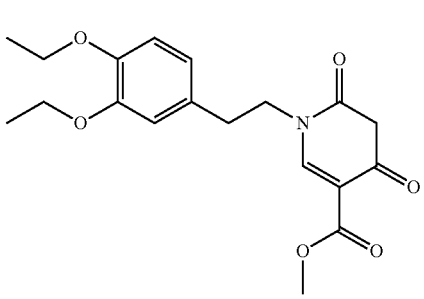 [SMILES: CCOc1ccc(CCN2C=C(C(=O)OC)C(=O)CC2=O)cc1OCC]

To a solution of methyl 3-[2-(3,4-diethoxyphenyl)ethyl-amino]prop-2-enoate (2.0 g, 6.2 mmol) in dichloromethane (25 mL) was added malonyl dichloride (0.98 g, 6.8 mmol) slowly at 50° C. The reaction mixture was then stirred for 2 hours and then concentrated. The residue was purified by flash column chromatography to afford methyl 1-[2-(3,4-diethoxyphenyl)ethyl]-4,6-dioxo-pyridine-3-carboxylate (400 mg).

Step 5: Preparation of 9,10-diethoxy-2-oxo-6,7-dihydrobenzo[a]quinolizine-3-carboxylic acid

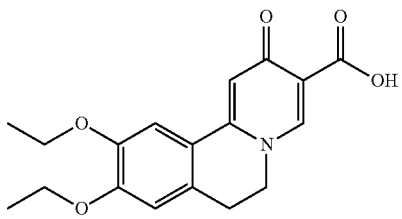 [SMILES: CCOc1cc2c(cc1OCC)-c1cc(=O)c(C(=O)O)cn1CC2]

To a solution of methyl 1-[2-(3,4-diethoxyphenyl)ethyl]-4,6-dioxo-pyridine-3-carboxylate (200 mg, 0.55 mmol) in xylene (2 mL) was added POCl$_3$ (2 mL) dropwise at 0-5° C. The resultant mixture was refluxed for 1 hour. Then the solvent was removed, and then THF/water (10 mL, V/V=5/1) and lithium hydroxide monohydrate (1.96 g, 40 mmol) were added to the mixture. The mixture was heated at 50° C. for 1 hour. After reaction was completed, the organic solvent was removed, then the mixture was acidified to pH 1-2 with 2 M hydrochloric acid. The mixture was extracted with dichloromethane (10 mL×2). The combined organic layers were washed with brine, and then dried over anhydrous sodium sulfate and then concentrated to give a light yellow solid, which was purified by prep-HPLC to give of 9,10-diethoxy-2-oxo-6,7-dihydrobenzo[a]quinolizine-3-carboxylic acid (18 mg). $^1$H NMR (400 MHz, DMSO-d$_6$): δ 8.77 (s, 1H), 7.52 (s, 1H), 7.41 (s, 1H), 7.01 (s, 1H), 4.35 (m, 4H), 4.14 (m, 2H), 3.04 (t, 2H), 1.36 (t, 6H). MS obsd. (ESI$^+$) [(M+H)$^+$]: 330.

Example 77: 2-oxo-9,10-dipropoxy-6,7-dihydrobenzo[a]quinolizine-3-carboxylic acid

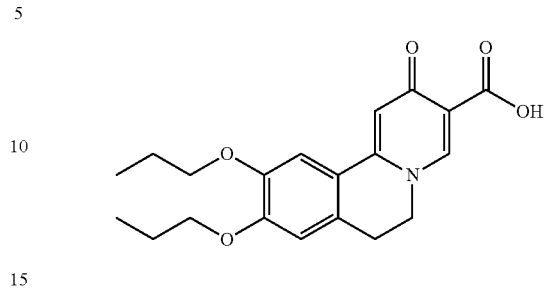

Step 1: Preparation of tert-butyl N-[2-(3,4-dipropoxyphenyl)ethyl]carbamate

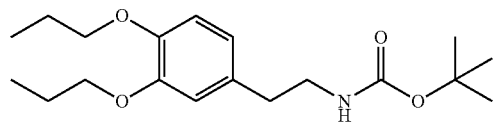 [SMILES: CCCOc1ccc(CCNC(=O)OC(C)(C)C)cc1OCCC]

To a solution of [2-(3,4-dihydroxy-phenyl)-ethyl]-carbamic acid tert-butyl ester (2.53 g) in DMF (20 mL) was added K$_2$CO$_3$ (2.1) and bromopropane (3.0 g, 24.0 mmol). The reaction mixture was stirred at 80° C. for 3 hours, and then concentrated in vacuo. Saturated NH$_4$Cl solution was added to the residue and the mixture was extracted with EtOAc (3×50 mL). The organic phases were washed with water and brine, and then dried over anhydrous MgSO$_4$ and concentrated in vacuo. The residue was purified by flash column chromatography to give tert-butyl N-[2-(3,4-dipropoxyphenyl)ethyl]carbamate (3.2 g) as yellow oil.

Step 2: Preparation of 2-(3,4-dipropoxyphenyl)ethanamine

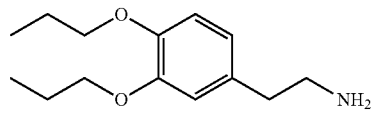

To a solution of tert-butyl N-[2-(3, 4-dipropoxyphenyl)ethyl]carbamate (3.0 g) in DCM (20 mL) was added TFA (5 mL) at 0° C. The reaction mixture was stirred at room temperature for 30 minutes and then another 5 mL of TFA was added to the mixture. After being stirred for 2 hours, an aqueous solution of NaOH (1 M) was added dropwise. The mixture was extracted with DCM. The organic layer was washed with water and brine, and then dried over anhydrous MgSO$_4$ and then concentrated in vacuo to give 2-(3,4-dipropoxy-phenyl)-ethylamine (2.0 g) as yellow oil.

Step 3: Preparation of methyl 3-[2-(3,4-dipropoxy-phenyl)ethylamino]prop-2-enoate

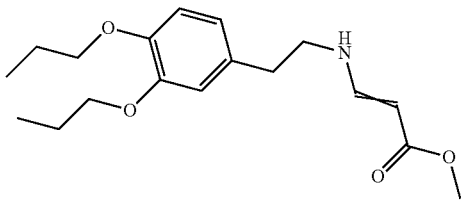 [SMILES: CCCOc1ccc(CCNC=CC(=O)OC)cc1OCCC]

A mixture of 2-(3,4-dipropoxyphenyl)ethanamine (2.37 g, 10 mmol) and methyl prop-2-ynoate (0.84 g, 10 mmol) in dichloromethane was stirred at room temperature overnight. After reaction was completed, the solvent was removed. The residue was purified by column chromatography to give methyl 3-[2-(3,4-dipropoxyphenyl)ethylamino]prop-2-enoate (2.6 g).

Step 4: Preparation of methyl 1-[2-(3,4-dipropoxy-phenyl)ethyl]-4,6-dioxo-pyridine-3-carboxylate

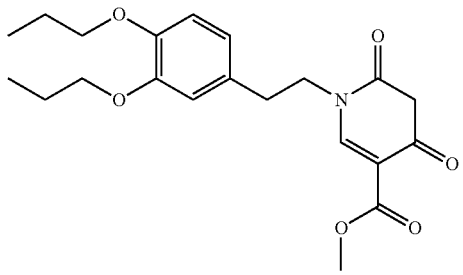 [SMILES: CCCOc1ccc(CCN2C=C(C(=O)OC)C(=O)CC2=O)cc1OCCC]

To a solution of methyl 3-[2-(3,4-dipropoxyphenyl)eth-ylamino]prop-2-enoate (2.0 g, 6.2 mmol) in dichloromethane (25 mL) was added malonyl dichloride (0.98 g, 6.8 mmol) slowly at 50° C. The reaction mixture was then stirred for 2 hours and then concentrated. The residue was purified by flash column chromatography to afford methyl 1-[2-(3,4-dipropoxyphenyl)ethyl]-4,6-dioxo-pyridine-3-carboxylate (400 mg).

Step 5: Preparation of 9,10-dipropoxy-2-oxo-6,7-dihydrobenzo[a]quinolizine-3-carboxylic acid

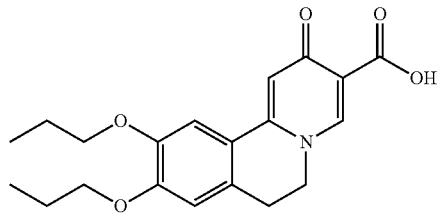 [SMILES: CCCOc1cc2c(cc1OCCC)-c1cc(=O)c(C(=O)O)cn1CC2]

To a solution of methyl 1-[2-(3,4-dipropoxyphenyl) ethyl]-4,6-dioxo-pyridine-3-carboxylate (400 mg, 1.07 mmol) in xylene (10 mL) was added POCl$_3$ (2 mL) dropwise at 0-5° C. The resultant mixture was refluxed for 1 hour and then the reaction mixture was concentrated. To the residue was added THF/water (V/V=5/1) and lithium hydroxide monohydrate (1.96 g, 40 mmol). The mixture was refluxed for 1 hour. After reaction was completed, the organic solvent was removed, then acidified to pH 1-2 with 2 M hydrochloric acid. The mixture was extracted with dichloromethane (10 mL×2). The combined organic layers were washed with brine, and then dried over anhydrous Na$_2$SO$_4$ and then concentrated to give a light yellow solid, which was purified to give 9,10-dipropoxy-2-oxo-6,7-dihydrobenzo[a]quinolizine-3-carboxylic acid (21 mg). $^1$H NMR (400 MHz, DMSO-d$_6$): δ 8.77 (s, 1H), 7.54 (s, 1H), 7.41 (s, 1H), 7.01 (s, 1H), 4.35 (m, 2H), 4.04 (m, 4H), 3.64 (t, 2H), 1.76 (m, 4H), 1.00 (m, 6H). MS obsd. (ESI$^+$) [(M+H)$^+$]: 358.

Example 78: 6-ethyl-10-methoxy-2-oxo-9-propoxy-6,7-dihydrobenzo[a]quinolizine-3-carboxylic acid

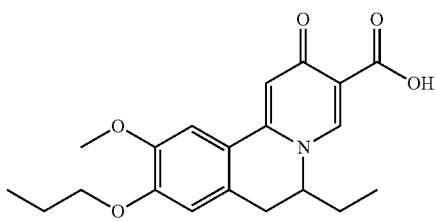 [SMILES: CCCOc1cc2c(cc1OC)-c1cc(=O)c(C(=O)O)cn1C(CC)C2]

Step 1: Preparation of 4-methoxy-3-propoxy-benzaldehyde

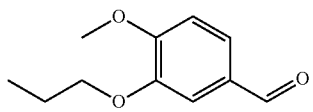

To a stirred mixture of 3-hydroxy-4-methoxy-benzaldehyde (10.0 g, 66 mmol) and potassium carbonate (30 g, 217 mmol) in dimethylformamide (50 mL) was added 1-bromopropane (18.4 g, 150 mmol) at room temperature. The mixture was stirred at 100° C. for 12 hours, and then cooled to room temperature. The mixture was diluted with water (100 mL) and then extracted with ethyl acetate (150 mL). The organic layer was washed with water (100 mL) and brine (100 mL), and then dried over anhydrous magnesium sulfate, and then concentrated. 4-Methoxy-3-propoxy-benzaldehyde (10.0 g) was obtained without further purification.

Step 2: Preparation of 1-methoxy-4-[2-nitrobut-1-enyl]-2-propoxy-benzene

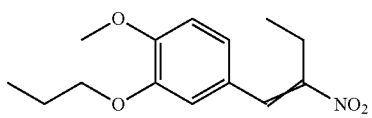 [SMILES: CCCOc1cc(C=C(CC)[N+](=O)[O-])ccc1OC]

A mixture of 4-methoxy-3-propoxy-benzaldehyde (2.0 g, 10.3 mmol) and ammonium acetate (0.5 g, 6.5 mmol) in nitropropane (10 mL) was refluxed for 24 hours. The mixture was concentrated under reduced pressure, and the residue was dissolved in ethyl acetate (100 mL). The resultant solution was washed with water (100 mL), and then dried over anhydrous sodium sulfate and concentrated. The residue was purified by column chromatography to give 1-methoxy-4-[2-nitrobut-1-enyl]-2-propoxy-benzene (1.7 g).

Step 3: Preparation of 1-(4-methoxy-3-propoxy-phenyl)butan-2-amine

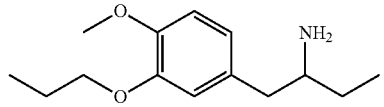 [SMILES: CCCOc1cc(CC(N)CC)ccc1OC]

To a solution of LiAlH$_4$ (28.0 mmol, 2 M in THF) was added concentrated sulfuric acid (95%, 0.74 mL) dropwise. After being stirred for 10 minutes, a solution of 1-methoxy-4-[2-nitrobut-1-enyl]-2-propyl-benzene (1.6 g, 6.5 mmol) in THF (12 mL) was added dropwise at 0° C. The mixture was stirred for additional 10 minutes. After being cooled to 0° C., isopropanol (4.6 mL) and aqueous solution of NaOH (2.0 M, 3.2 mL) were added dropwise successively. After addition, the mixture was stirred at room temperature for another 1 hour, then filtered. The filtrate was concentrated to give 1-(4-methoxy-3-propoxy-phenyl)butan-2-amine, which was used without further purification.

Step 4: Preparation of N-[1-[(4-methoxy-3-propoxy-phenyl)methyl]propyl]formamide

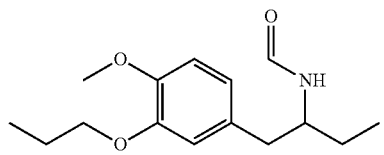 [SMILES: CCCOc1cc(CC(CC)NC=O)ccc1OC]

A mixture of 1-(4-methoxy-3-propoxyphenyl)butan-2-amine (1.0 g, 4.2 mmol) and ethyl formate (10 mL) was refluxed for 16 hours and then concentrated under reduce pressure to afford the crude N-[1-[(4-methoxy-3-propoxy-phenyl)methyl]propyl]formamide (1.1 g), which was used in the next step without purification.

Step 5: Preparation of 3-ethyl-7-methoxy-6-propoxy-3,4-dihydroisoquinoline

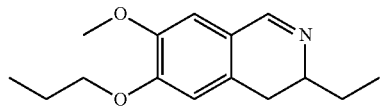 [SMILES: CCCOc1cc2c(cc1OC)C=NC(CC)C2]

To a solution of N-[1-[(4-methoxy-3-propoxyphenyl)methyl]propyl]formamide (500 mg, 2 mmol) in acetonitrile (10 mL) was added POCl$_3$ (307 mg, 2 mmol) dropwise at 0-5° C. The resultant mixture was refluxed for 2 hours and then concentrated. Ethyl acetate was added to the mixture, and then the mixture was washed with sodium bicarbonate. The organic phase was dried over Na$_2$SO$_4$ and then concentrated to give 3-ethyl-7-methoxy-6-propxy-3,4-dihydroisoquinoline (400 mg), which was used in next step without further purification.

Step 6: Preparation of ethyl 6-ethyl-10-methoxy-2-oxo-9-propoxy-1,6,7,11b-tetrahydrobenzo[a]quinolizine-3-carboxylate

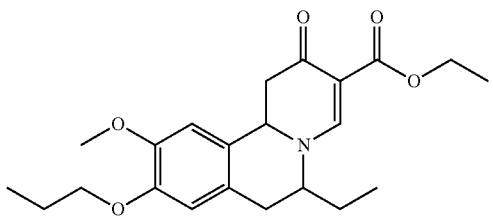 [SMILES: CCCOc1cc2c(cc1OC)C1CC(=O)C(C(=O)OCC)=CN1C(CC)C2]

A mixture of 3-ethyl-7-methoxy-6-propxyl-3,4-dihydroisoquinoline (494 mg, 2 mmol) and ethyl 2-(ethoxymethylene)-3-oxo-butanoate (465.5 mg, 2.5 mmol) in EtOH (10 mL) was refluxed overnight. The mixture was concentrated and the residue was purified by column chromatography to give ethyl 6-ethyl-10-methoxy-2-oxo-9-propoxyl-1,6,7,11b-tetrahydrobenzo[a]quinolizine-3-carboxylate (300 mg).

Step 7: Preparation of ethyl 6-ethyl-10-methoxy-2-oxo-9-propoxy-6,7-dihydrobenzo[a]quinolizine-3-carboxylate

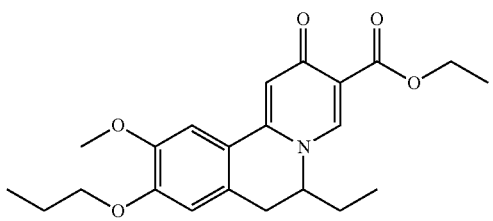 [SMILES: CCCOc1cc2c(cc1OC)-c1cc(=O)c(C(=O)OCC)cn1C(CC)C2]

A mixture of ethyl 6-ethyl-10-methoxy-2-oxo-9-propyl-1,6,7,11b-tetrahydrobenzo[a]quinolizine-3-carboxylate (300 mg, 0.77 mmol) and p-chloranil (300 mg, 1.2 mmol) in dimethoxyethane and toluene (40 mL, V/V=1/1) was refluxed for 2 hours. After being cooled to room temperature, the reaction mixture was concentrated. The residue was purified by flash column chromatography to give ethyl 6-ethyl-10-methoxy-2-oxo-9-propoxyl-6,7-dihydrobenzo[a]quinolizine-3-carboxylate as a yellow solid (200 mg).

Step 8: Preparation of 6-ethyl-10-methoxy-2-oxo-9-propoxy-6,7-dihydrobenzo[a]quinolizine-3-carboxylic acid

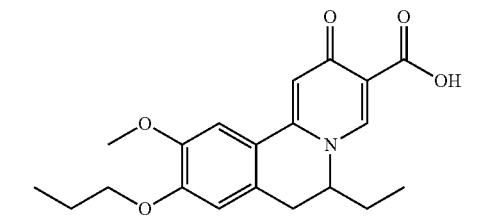 [SMILES: CCCOc1cc2c(cc1OC)-c1cc(=O)c(C(=O)O)cn1C(CC)C2]

To a solution of ethyl 6-ethyl-10-methoxy-2-oxo-9-propoxyl-6,7-dihydrobenzo[a]quinolizine-3-carboxylate (200 mg, 0.52 mmol) in methanol and water (20 mL, V/V=1) was added lithium hydroxide monohydrate (480 mg, 10 mmol) at room temperature. The resultant mixture was stirred for 2 hours, and then acidified to pH 1-2 with 2 M hydrochloric acid. The mixture was extracted with dichloromethane (10 mL×2). The combined organic layers were washed with brine, and then dried over anhydrous sodium sulfate and concentrated. The residue was purified by prep-HPLC to give 6-ethyl-10-methoxy-2-oxo-9-propoxy-6,7-dihydrobenzo[a]quinolizine-3-carboxylic acid (100 mg). $^1$H NMR (400 MHz, DMSO-d$_6$): δ 8.81 (s, 1H), 7.52 (s, 1H), 7.46 (s, 1H), 7.04 (s, 1H), 4.70 (m, 1H), 4.04-3.98 (m, 2H), 3.88 (s, 3H), 3.33 (d, 1H), 3.00 (d, 1H), 1.77 (m, 2H), 1.55-1.35 (m, 2H), 0.99 (t, 3H), 0.87 (m, 3H). MS obsd. (ESI$^+$) [(M+H)$^+$]: 358.

Example 79 and 80

(+)-6-ethyl-10-methoxy-2-oxo-9-propoxyl-6,7-dihydrobenzo[a]quinolizine-3-carboxylic acid and (−)-6-ethyl-10-methoxy-2-oxo-9-propoxyl-6,7-dihydrobenzo[a]quinolizine-3-carboxylic acid

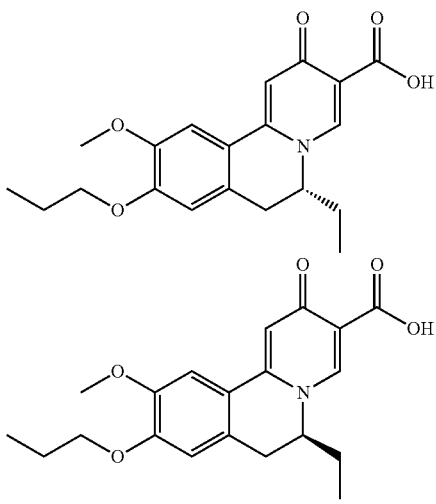

Separation of the racemic 6-ethyl-10-methoxy-2-oxo-9-propoxyl-6,7-dihydrobenzo[a]quinolizine-3-carboxylic acid (100 mg) by chiral HPLC afforded (+)-6-ethyl-10-methoxy-2-oxo-9-propoxyl-6,7-dihydrobenzo[a]quinolizine-3-carboxylic acid (26.9 mg) and (−)-6-ethyl-10-methoxy-2-oxo-9-propoxyl-6,7-dihydrobenzo[a]quinolizine-3-carboxylic acid (28.3 mg).

Example 79

$^1$H NMR (400 MHz, DMSO-d$_6$): δ 8.81 (s, 1H), 7.52 (s, 1H), 7.46 (s, 1H), 7.04 (s, 1H), 4.70 (m, 1H), 4.04-3.98 (m, 2H), 3.88 (s, 3H), 3.33 (d, 1H), 3.00 (d, 1H), 1.77 (m, 2H), 1.55-1.35 (m, 2H), 0.99 (t, 3H), 0.87 (m, 3H). MS obsd. (ESI$^+$) [(M+H)$^+$]: 358. [α]$_D$20=+90.9° (0.025%, CH$_3$CN).

Example 80

$^1$H NMR (400 MHz, DMSO-d$_6$): δ 8.81 (s, 1H), 7.52 (s, 1H), 7.46 (s, 1H), 7.04 (s, 1H), 4.70 (m, 1H), 4.04-3.98 (m, 2H), 3.88 (s, 3H), 3.33 (d, 1H), 3.00 (d, 1H), 1.77 (m, 2H), 1.55-1.35 (m, 2H), 0.99 (t, 3H), 0.87 (m, 3H). MS obsd. (ESI$^+$) [(M+H)$^+$]: 358.

Example 81: 6-ethyl-10-methoxy-2-oxo-9-propyl-6,7-dihydrobenzo[a]quinolizine-3-carboxylic acid

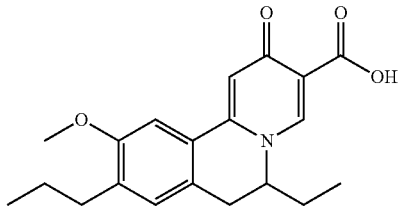 [SMILES: CCCc1cc2c(cc1OC)-c1cc(=O)c(C(=O)O)cn1C(CC)C2]

Step 1: Preparation of 1-methoxy-2-propyl-benzene

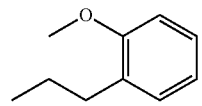

To a stirred mixture of 2-n-propylphenol (13.6 g, 100 mmol) and NaH (60% w/w in mineral oil, 4.0 g, 100 mmol) in DMF (70 mL) was added iodomethane (21.0 g, 150 mmol) at room temperature. The mixture was stirred at room temperature for 3 hours, and then diluted with H$_2$O (100 mL) and then extracted with diethyl ether (150 mL). The organic layer was washed with H$_2$O (100 mL) and brine (100 mL), and then dried over anhydrous MgSO$_4$ and concentrated in vacuo. The residue was purified by column to give 1-methoxy-2-propyl-benzene (15.0 g) as colorless oil.

Step 2: Preparation of 4-methoxy-3-propyl-benzaldehyde

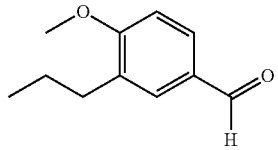

A solution of 1-methoxy-2-propyl-benzene (7.5 g, 50.0 mmol) in dry DMF (4.2 mL, 52.8 mol) was cooled to −5° C. and then POCl$_3$ (6.0 mL, 64.2 mmol) was added to the mixture dropwise. The resultant suspension was allowed to warm to room temperature over 2 hours and then was refluxed overnight. The reaction was cooled to room temperature. Then water (100 mL) was added. The reaction mixture was extracted with diethyl ether (3×100 mL). The combined organic layers were washed with water and brine, and then dried over anhydrous magnesium sulfate and then concentrated under reduced pressure. The residue was purified by flash column chromatography to give 4-methoxy-3-propyl-benzaldehyde (1.6 g).

Step 3: Preparation of 1-methoxy-4-[2-nitrobut-1-enyl]-2-propyl-benzene

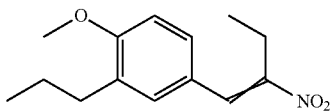 [SMILES: CCCc1cc(C=C(CC)[N+](=O)[O-])ccc1OC]

A mixture of 4-methoxy-3-propyl-benzaldehyde (2.0 g, 11.2 mmol) and ammonium acetate (0.5 g, 6.5 mmol) in nitropropane (10 mL) was refluxed for 24 hours. The mixture was concentrated under reduced pressure, and the residue was dissolved in ethyl acetate (100 mL). The resultant solution was washed with water (100 mL). The organic layer was dried over anhydrous sodium sulfate and then concentrated. The residue was purified by column chromatography to give 1-methoxy-4-[2-nitrobut-1-enyl]-2-propyl-benzene (1.6 g).

Step 4: Preparation of 1-(4-methoxy-3-propyl-phenyl)butan-2-amine

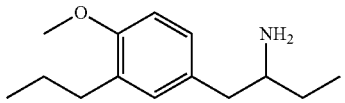 [SMILES: CCCc1cc(CC(N)CC)ccc1OC]

To a solution of LiAlH$_4$ (28.0 mmol) in THF (50 mL) was added concentrated sulfuric acid (95%, 0.74 mL) dropwise. After 10 minutes, a solution of 1-methoxy-4-[2-nitrobut-1-enyl]-2-propyl-benzene (1.6 g, 6.5 mmol) in THF (12 mL) was added to the mixture dropwise at 0° C. The mixture was stirred for additional 10 minutes. After being cooled to 0° C., isopropanol (4.6 mL) and an aqueous solution of NaOH (2.0 M, 3.2 mL) were added dropwise. The resultant mixture was filtered, and the filtrate was concentrated to give 1-(4-methoxy-3-propyl-phenyl)butan-2-amine, which was used in the next step without further purification.

Step 5: Preparation of N-[1-[(4-methoxy-3-propyl-phenyl)methyl]propyl]formamide

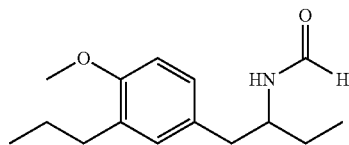 [SMILES: CCCc1cc(CC(CC)NC=O)ccc1OC]

A mixture of 1-(4-methoxy-3-propyl-phenyl)butan-2-amine (1.2 g, 5.4 mmol) and ethyl formate (20 mL) was refluxed for 16 hours and then concentrated under reduced pressure to afford the crude N-[1-[(4-methoxy-3-propyl-phenyl)methyl]propyl]formamide, which was used in the next step without purification.

Step 6: Preparation of 3-ethyl-7-methoxy-6-propyl-3,4-dihydroisoquinoline

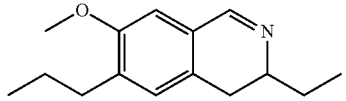 [SMILES: CCCc1cc2c(cc1OC)C=NC(CC)C2]

To a solution of N-[1-[(4-methoxy-3-propyl-phenyl)methyl]propyl]formamide (125 mg, 0.5 mmol) in acetonitrile (3 mL) was added POCl$_3$ (80 mg, 0.52 mmol) dropwise at 0-5° C. The resultant mixture was refluxed for 2 hours and then concentrated. To the residue was added diluted hydrochloric acid (2 M), and the resultant mixture was washed with EtOAc. The aqueous layer was neutralized with lithium hydroxide monohydrate and then extracted with ethyl acetate (50 mL×3). The organic phase was dried over Na$_2$SO$_4$ and then concentrated to give 3-ethyl-7-methoxy-6-propyl-3,4-dihydroisoquinoline (57 mg), which was used in the next step without further purification.

Step 7: Preparation of ethyl 6-ethyl-10-methoxy-2-oxo-9-propyl-1,6,7,11b-tetrahydrobenzo[a]quinolizine-3-carboxylate

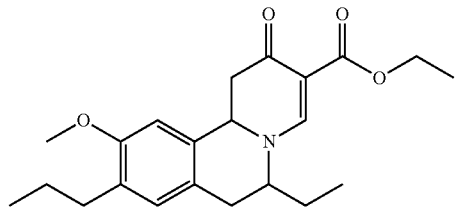 [SMILES: CCCc1cc2c(cc1OC)C1CC(=O)C(C(=O)OCC)=CN1C(CC)C2]

A mixture of 3-ethyl-7-methoxy-6-propyl-3,4-dihydroisoquinoline (57 mg, 0.25 mmol) and ethyl 2-(ethoxymethylene)-3-oxo-butanoate (138 mg, 0.75 mmol) in ethanol (2 mL) was refluxed overnight. The mixture was concentrated to give crude ethyl 6-ethyl-10-methoxy-2-oxo-9-propyl-1,6,7,11b-tetrahydrobenzo[a]quinolizine-3-carboxylate as dark brown oil, which was used in the next step without purification.

Step 8: Preparation of ethyl 6-ethyl-10-methoxy-2-oxo-9-propyl-6,7-dihydrobenzo[a]quinolizine-3-carboxylate

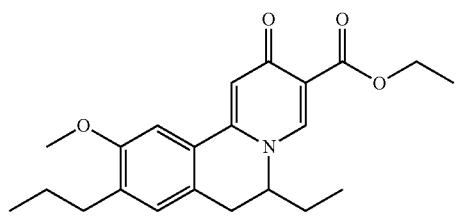 [SMILES: CCCc1cc2c(cc1OC)-c1cc(=O)c(C(=O)OCC)cn1C(CC)C2]

A mixture of ethyl 6-ethyl-10-methoxy-2-oxo-9-propyl-1,6,7,11b-tetrahydrobenzo[a]quinolizine-3-carboxylate (30 mg, 0.08 mmol) and p-chloranil (20 mg, 0.081 mmol) in DME (40 mL) was refluxed for 2 hours. The reaction mixture was cooled to room temperature, and then concentrated. The residue was purified by flash column chromatography to give ethyl 6-ethyl-10-methoxy-2-oxo-9-propyl-6,7-dihydrobenzo[a]quinolizine-3-carboxylate as a yellow solid (25 mg).

Step 9: Preparation of 6-ethyl-10-methoxy-2-oxo-9-propyl-6,7-dihydrobenzo[a]quinolizine-3-carboxylic acid

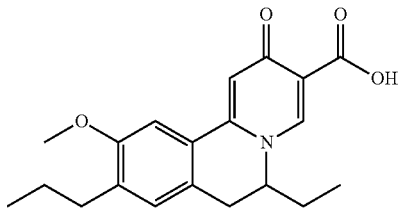 [SMILES: CCCc1cc2c(cc1OC)-c1cc(=O)c(C(=O)O)cn1C(CC)C2]

To a mixture of ethyl 6-ethyl-10-methoxy-2-oxo-9-propyl-6,7-dihydrobenzo[a]quinolizine-3-carboxylate (25 mg) in THF and water (10 mL, V/V=1/1) was added lithium hydroxide monohydrate (48 mg, 1.1 mmol) at room temperature. The resultant mixture was stirred for 2 hours, and then acidified to pH 1-2 with 2 M hydrochloric acid. The mixture was extracted with dichloromethane (10 mL×2). The combined organic layers were washed with brine, and then dried over anhydrous sodium sulfate and then concentrated. The residue was purified by column chromatography to give 6-ethyl-10-methoxy-2-oxo-9-propyl-6,7-dihydrobenzo[a]quinolizine-3-carboxylic acid (8 mg). $^1$H NMR (400 MHz, DMSO-$d_6$): δ 8.84 (s, 1H), 7.57 (s, 1H), 7.51 (s, 1H), 7.19 (s, 1H), 4.73 (m, 2H), 3.91 (s, 3H), 2.99 (d, 1H), 1.62-1.53 (m, 2H), 1.51-1.39 (m, 5H), 0.94-0.88 (m, 2H), 0.79 (m, 3H). MS obsd. (ESI$^+$) [(M+H)$^+$]: 342.

Example 82: 8-chloro-9-methoxy-6-methyl-2-oxo-6,7-dihydrobenzo[a]quinolizine-3-carboxylic acid

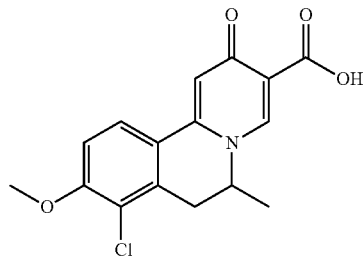 [SMILES: COc1ccc2c(c1Cl)CC(C)n1cc(C(=O)O)c(=O)cc1-2]

Step 1: Preparation of 2-chloro-1-methoxy-3-[2-nitroprop-1-enyl]benzene

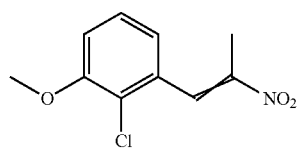

A mixture of 2-chloro-3-methoxy-benzaldehyde (1.8 g, 10.5 mol) and ammonium acetate (520 mg, 6.75 mol) in nitroethane (30 mL) was refluxed for 3 hours. The solvent was removed under reduced pressure, and the yellow residue was partitioned between DCM (50 mL) and water (50 mL). The aqueous layer was extracted with DCM (2×50 mL), and the combined layers were washed with brine, and then dried over anhydrous Na$_2$SO$_4$, and then filtered. The filtrate was evaporated to afford 2-chloro-1-methoxy-3-[2-nitroprop-1-enyl]benzene as a yellow solid (2.2 g).

Step 2: Preparation of 1-(2-chloro-3-methoxy-phenyl)propan-2-amine

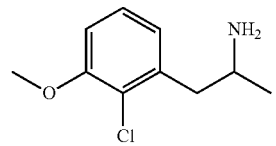

To a mixture of LiAlH$_4$ (15 mL, 30 mmol) in THF (30 mL) was added a solution of 2-chloro-1-methoxy-3-[2-nitroprop-1-enyl]benzene (2.2 g, 10 mmol) in THF (20 mL) dropwise in an ice-water bath. The mixture was refluxed for 1 hour and then water (40 mL) was added dropwise at 0° C. Then 15% NaOH aqueous solution (20 mL) was added to the mixture. The resultant mixture was filtered, and the filtrate was concentrated to afford crude 1-(2-chloro-3-methoxy-phenyl)propan-2-amine (1.8 g) which was used in the next step without further purification.

Step 3: Preparation of N-[2-(2-chloro-3-methoxy-phenyl)-1-methyl-ethyl]formamide

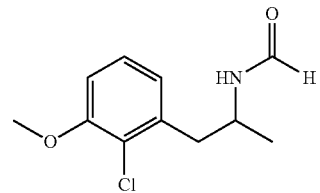

A mixture of 1-(2-chloro-3-methoxy-phenyl)propan-2-amine (1.8 g, 9 mmol) and ethyl formate (20 mL) in dioxane (20 mL) was refluxed for 16 hours and then concentrated under reduce pressure to afford the crude N-[2-(2-chloro-3-methoxy-phenyl)-1-methyl-ethyl]formamide (2.04 g), which was used in the next step without purification.

Step 4: Preparation of 5-chloro-6-methoxy-3-methyl-3,4-dihydroisoquinoline

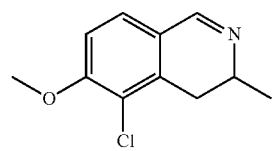

To a solution of N-[2-(2-chloro-3-methoxy-phenyl)-1-methyl-ethyl]formamide (2.04 g, 9 mmol) in DCM (30 mL) under N₂ atmosphere was added oxalyl chloride (9.9 mmol, 882 µL) and the solution was stirred at room temperature for 30 minutes. The solution was cooled to −10° C., and then anhydrous ferric chloride (1.78 g, 10.8 mmol) was added. The mixture was slowly warmed to room temperature and then stirred for 20 hours. Hydrochloric acid (2 M, 50 mL) was added to quench the reaction and the mixture was stirred at room temperature for 1 hour. After the solvent was removed, saturated NaHCO₃ aqueous solution was added to the residue to adjust pH>7. Then the mixture was extracted with EtOAc (30 mL×2). The organic layers were combined, and then washed with brine, and then concentrated in vacuo to afford 5-chloro-6-methoxy-3-methyl-3,4-dihydroisoquinoline as a grey solid (1.6 g).

Step 5: Preparation of ethyl 8-chloro-9-methoxy-6-methyl-2-oxo-1,6,7,11b-tetrahydrobenzo[a]quinolizine-3-carboxylate

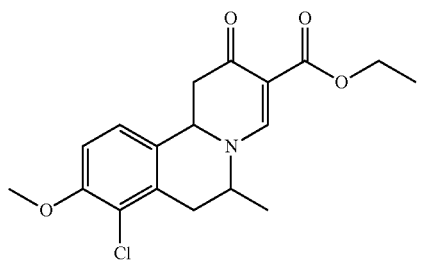 [SMILES: CCOC(=O)C1=CN2C(C)Cc3c(ccc(OC)c3Cl)C2CC1=O]

A mixture of 5-chloro-6-methoxy-3-methyl-3,4-dihydroisoquinoline (209 mg, 1 mmol) and ethyl 2-(ethoxymethylene)-3-oxo-butanoate (372 mg, 2 mmol) in EtOH (15 mL) was refluxed overnight. The mixture was concentrated to give crude ethyl 8-chloro-9-methoxy-6-methyl-2-oxo-1,6,7,11b-tetrahydrobenzo[a]quinolizine-3-carboxylate as dark brown oil which was used in the next step without purification.

Step 6: Preparation of ethyl 8-chloro-9-methoxy-6-methyl-2-oxo-6,7-dihydrobenzo[a]quinolizine-3-carboxylate

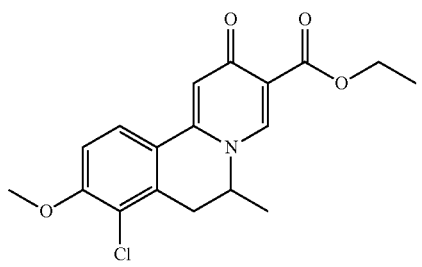 [SMILES: CCOC(=O)c1cn2c(cc1=O)-c1ccc(OC)c(Cl)c1CC2C]

A mixture of crude ethyl 8-chloro-9-methoxy-6-methyl-2-oxo-1,6,7,11b-tetrahydrobenzo[a]quinolizine-3-carboxylate from Step 5 and p-chloranil (244 mg, 1 mmol) in DME (15 mL) was refluxed for 2 hours. After being cooled to room temperature, the suspension was filtered with suction. The filter cake was washed with cold DME and then dried under vacuum to give ethyl 8-chloro-9-methoxy-6-methyl-2-oxo-6,7-dihydrobenzo[a]quinolizine-3-carboxylate as a yellow solid (120 mg).

Step 7: Preparation of 8-chloro-9-methoxy-6-methyl-2-oxo-6,7-dihydrobenzo[a]quinolizine-3-carboxylic acid

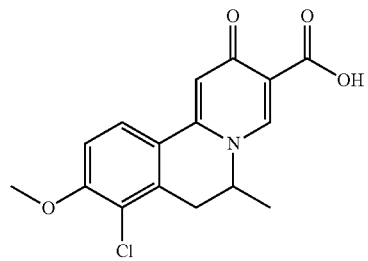 [SMILES: COc1ccc2c(c1Cl)CC(C)n1cc(C(=O)O)c(=O)cc1-2]

To a solution of ethyl 8-chloro-9-methoxy-6-methyl-2-oxo-6,7-dihydrobenzo[a]quinolizine-3-carboxylate in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2). The combined organic layers were washed with brine, and then dried over anhydrous Na₂SO₄ and then concentrated to give a light yellow solid, which was purified by prep-HPLC to afford 8-chloro-9-methoxy-6-methyl-2-oxo-6,7-dihydrobenzo[a]quinolizine-3-carboxylic acid (10 mg). ¹H NMR (400 MHz, CDCl₃): δ 8.60 (s, 1H), 7.74 (d, 1H), 7.07 (s, 1H), 7.04 (d, 1H), 4.61 (m, 1H), 4.06 (s, 3H), 3.46 (m, 1H), 3.27 (m, 1H), 1.38 (d, 3H). MS obsd. (ESI⁺) [(M+H)⁺]: 320.

Example 83: 8-chloro-9,10-dimethoxy-6-methyl-2-oxo-6,7-dihydrobenzo[a]quinolizine-3-carboxylic acid

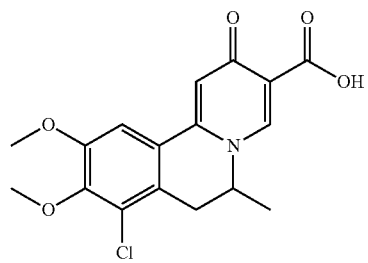 [SMILES: COc1cc2c(c(Cl)c1OC)CC(C)n1cc(C(=O)O)c(=O)cc1-2]

Step 1: Preparation of 3-chloro-1,2-dimethoxy-4-[2-nitroprop-1-enyl]benzene

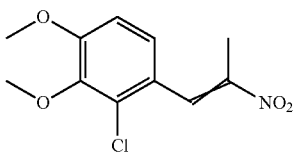 [SMILES: COc1ccc(C=C(C)[N+](=O)[O-])c(Cl)c1OC]

A mixture of 2-chloro-3,4-dimethoxy-benzaldehyde (2.1 g, 10.5 mol) and ammonium acetate (520 mg, 6.75 mol) in nitroethane (30 mL) was refluxed for 3 hours. The solvent was removed under reduced pressure, and the yellow residue was partitioned between DCM (50 mL) and water (50 mL). The aqueous layer was extracted with DCM (2×50 mL). The combined layers were washed with brine, and then dried over anhydrous $Na_2SO_4$, and then filtered. The filtrate was evaporated to afford 3-chloro-1,2-dimethoxy-4-[2-nitroprop-1-enyl]benzene as a yellow solid (2.6 g).

Step 2: Preparation of 1-(2-chloro-3,4-dimethoxy-phenyl)propan-2-amine

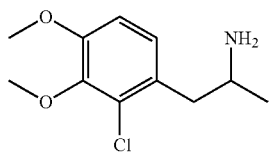

To a mixture of $LiAlH_4$ (15 mL, 30 mmol) in THF (30 mL) was added a solution of 3-chloro-1,2-dimethoxy-4-[2-nitroprop-1-enyl]benzene (2.6 g, 10 mmol) in THF (20 mL) dropwise in an ice-water bath. The mixture was refluxed for 1 hour and then water (40 mL) was added dropwise at 0° C., and then 15% NaOH aqueous solution (20 mL) was added to the mixture. The resultant mixture was filtered, and the filtrate was concentrated to afford crude 1-(2-chloro-3,4-dimethoxy-phenyl)propan-2-amine (2.0 g) which was used in the next step without further purification.

Step 3: Preparation of N-[2-(2-chloro-3,4-dimethoxy-phenyl)-1-methyl-ethyl]formamide

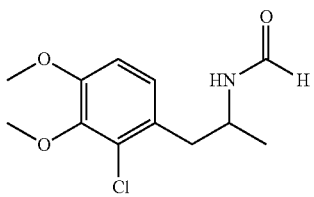 [SMILES: COc1ccc(CC(C)NC=O)c(Cl)c1OC]

A mixture of 1-(2-chloro-3,4-dimethoxy-phenyl)propan-2-amine (2.0 g, 9 mmol) and ethyl formate (20 mL) in dioxane (20 mL) was refluxed for 16 hours and then concentrated under reduce pressure to afford the crude N-[2-(2-chloro-3,4-dimethoxy-phenyl)-1-methyl-ethyl]formamide (2.3 g), which was used in the next step without purification.

Step 4: Preparation of 5-chloro-6,7-dimethoxy-3-methyl-3,4-dihydroisoquinoline

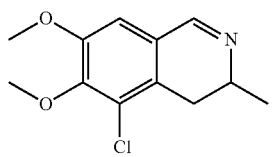

To a solution of N-[2-(2-chloro-3,4-dimethoxy-phenyl)-1-methyl-ethyl]formamide (2.3 g, 9 mmol) in DCM (30 mL) under $N_2$ atmosphere was added oxalyl chloride (9.9 mmol, 882 µL) and the solution was stirred at room temperature for 30 minutes. The solution was cooled to −10° C., and anhydrous ferric chloride (1.78 g, 10.8 mmol) was added. The mixture was slowly warmed to room temperature and then stirred for 20 hours. Hydrochloric acid (2 M, 50 mL) was added to quench the reaction and the biphasic mixture was stirred at room temperature for 1 hour. After the solvent was removed, saturated $NaHCO_3$ aqueous solution was added to the residue to adjust pH>7. Then the mixture was extracted with EtOAc (30 mL×2). The organic layers were combined, and then washed with brine, and then concentrated in vacuo to afford 5-chloro-6,7-dimethoxy-3-methyl-3,4-dihydroisoquinoline as a grey solid (1.5 g).

Step 5: Preparation of ethyl 8-chloro-9,10-dimethoxy-6-methyl-2-oxo-1,6,7,11b-tetrahydrobenzo[a]quinolizine-3-carboxylate

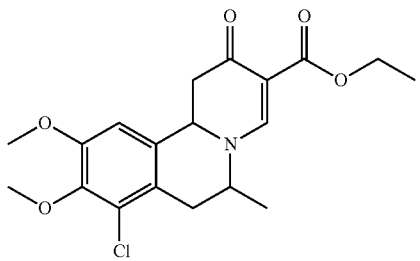 [SMILES: CCOC(=O)C1=CN2C(C)Cc3c(cc(OC)c(OC)c3Cl)C2CC1=O]

A mixture of 5-chloro-6,7-dimethoxy-3-methyl-3,4-dihydroisoquinoline (239 mg, 1 mmol) and ethyl 2-(ethoxymethylene)-3-oxo-butanoate (372 mg, 2 mmol) in EtOH (15 mL) was refluxed overnight. The mixture was concentrated to give crude ethyl 8-chloro-9,10-dimethoxy-6-methyl-2-oxo-1,6,7,11b-tetrahydrobenzo[a]quinolizine-3-carboxylate as dark brown oil which was used in the next step without purification.

Step 6: Preparation of ethyl 8-chloro-9,10-dimethoxy-6-methyl-2-oxo-6,7-dihydrobenzo[a]quinolizine-3-carboxylate

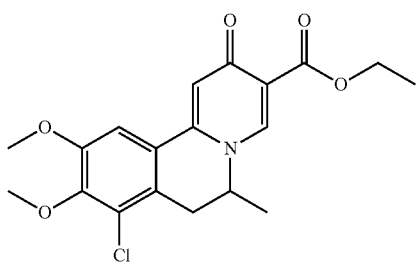 [SMILES: CCOC(=O)c1cn2c(cc1=O)-c1cc(OC)c(OC)c(Cl)c1CC2C]

A mixture of crude ethyl 8-chloro-9,10-dimethoxy-6-methyl-2-oxo-1,6,7,11b-tetrahydrobenzo[a]quinolizine-3-carboxylate from Step 5 and p-chloranil (244 mg, 1 mmol) in DME (15 mL) was refluxed for 2 hours. After being cooled to room temperature, the suspension was filtered with suction. The filter cake was washed with cold DME and then dried under vacuum to give ethyl 8-chloro-9,10-dimethoxy- 6-methyl-2-oxo-6,7-dihydrobenzo[a]quinolizine-3-carboxylate as a yellow solid (110 mg).

Step 7: Preparation of 8-chloro-9,10-dimethoxy-6-methyl-2-oxo-6,7-dihydrobenzo[a]quinolizine-3-carboxylic acid

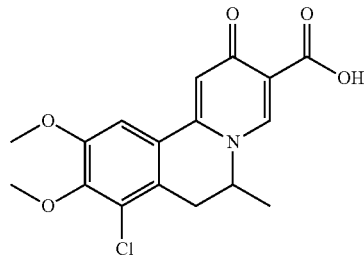 [SMILES: COc1cc2c(c(Cl)c1OC)CC(C)n1cc(C(=O)O)c(=O)cc1-2]

To a solution of ethyl 8-chloro-9,10-dimethoxy-6-methyl-2-oxo-6,7-dihydrobenzo[a]quinolizine-3-carboxylate from Step 6 in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2). The combined organic layers were washed with brine, and then dried over anhydrous $Na_2SO_4$ and then concentrated to give a light yellow solid, which was purified by prep-HPLC to afford 8-chloro-9,10-dimethoxy-6-methyl-2-oxo-6,7-dihydrobenzo[a]quinolizine-3-carboxylic acid (13 mg). $^1$H NMR (400 MHz, $CDCl_3$): δ 8.60 (s, 1H), 7.24 (s, 1H), 7.16 (s, 1H), 4.60 (m, 1H), 4.06 (s, 6H), 3.30 (m, 2H), 1.38 (d, 3H). MS obsd. (ESI$^+$) [(M+H)$^+$]: 350.

Example 84: 10-methoxy-6-methyl-2-oxo-6,7-dihydrobenzo[a]quinolizine-3-carboxylic acid

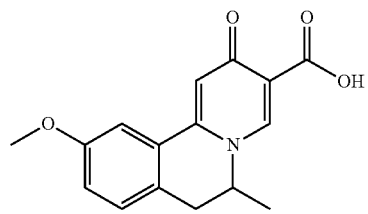 [SMILES: COc1ccc2c(c1)-c1cc(=O)c(C(=O)O)cn1C(C)C2]

Step 1: Preparation of 1-methoxy-4-[2-nitroprop-1-enyl]benzene

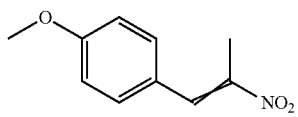

A mixture of 4-methoxy-benzaldehyde (1.4 g, 10.5 mol) and ammonium acetate (520 mg, 6.75 mol) in nitroethane (30 mL) was refluxed for 3 hours. The solvent was removed under reduced pressure, and the yellow residue was partitioned between DCM (50 mL) and water (50 mL). The aqueous layer was extracted with DCM (2×50 mL), and the combined organic layers were washed with brine, and then dried over anhydrous $Na_2SO_4$ and then filtered. The filtrate was evaporated to afford 1-methoxy-4-[2-nitroprop-1-enyl]benzene as a yellow solid (1.8 g).

Step 2: Preparation of 1-(4-methoxyphenyl)propan-2-amine

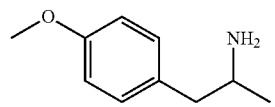

To a mixture of $LiAlH_4$ (15 mL, 30 mmol) in THF (30 mL) was added a solution of 1-methoxy-4-[2-nitroprop-1-enyl]benzene (1.8 g, 9.3 mmol) in THF (20 mL) dropwise in an ice-water bath. The mixture was refluxed for 1 hour and then water (40 mL) was added dropwise at 0° C., and then 15% NaOH aqueous (20 mL) was added to the mixture. The resultant mixture was filtered, and the filtrate was concentrated to afford crude 1-(4-methoxyphenyl)propan-2-amine (1.2 g) which was used in the next step without further purification.

Step 3: Preparation of N-[2-(4-methoxyphenyl)-1-methyl-ethyl]formamide

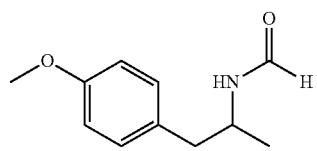

A mixture of 1-(4-methoxyphenyl)propan-2-amine (1.2 g, 7.2 mmol) and ethyl formate (20 mL) in dioxane (20 mL) was refluxed for 16 hours and then concentrated under reduced pressure to afford crude N-[2-(4-methoxyphenyl)-1-methyl-ethyl]formamide (2.04 g), which was used in the next step without purification.

Step 4: Preparation of 7-methoxy-3-methyl-3,4-dihydroisoquinoline

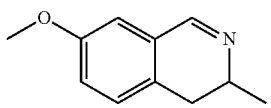

To a solution of N-[2-(4-methoxyphenyl)-1-methyl-ethyl] formamide (1.4 g, 7.2 mmol) in DCM (30 mL) under $N_2$ atmosphere was added oxalyl chloride (9.9 mmol, 882 μL) and the solution was stirred at room temperature for 30 minutes. The solution was cooled to −10° C., and anhydrous ferric chloride (1.78 g, 10.8 mmol) was added. The mixture was slowly warmed to room temperature and then stirred for 20 hours. Hydrochloric acid (2 M, 50 mL) was added to quench the reaction and the biphasic mixture was stirred at room temperature for 1 hour. After the solvent was removed, saturated $NaHCO_3$ aqueous solution was added to the residue to adjust pH>7. The mixture was extracted with EtOAc (30 mL×2). The organic layers were washed with brine and then concentrated in vacuo to afford 7-methoxy-3-methyl-3,4-dihydroisoquinoline as grey solid (1.1 g).

Step 5: Preparation of ethyl 10-methoxy-6-methyl-2-oxo-1,6,7,11b-tetrahydrobenzo[a]quinolizine-3-carboxylate

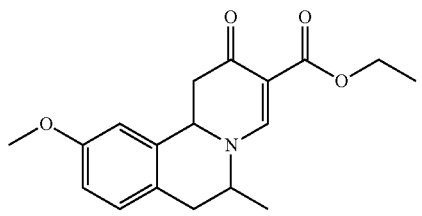 [SMILES: CCOC(=O)C1=CN2C(C)Cc3ccc(OC)cc3C2CC1=O]

A mixture of 7-methoxy-3-methyl-3,4-dihydroisoquinoline (175 mg, 1 mmol) and ethyl 2-(ethoxymethylene)-3-oxo-butanoate (372 mg, 2 mmol) in EtOH (15 mL) was refluxed overnight. The mixture was concentrated to give crude ethyl 10-methoxy-6-methyl-2-oxo-1,6,7,11b-tetrahydrobenzo[a]quinolizine-3-carboxylate as dark brown oil which was used in the next step without purification.

Step 6: Preparation of ethyl 10-methoxy-6-methyl-2-oxo-6,7-dihydrobenzo[a]quinolizine-3-carboxylate

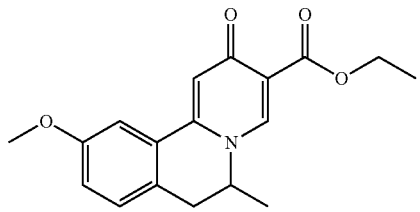 [SMILES: CCOC(=O)c1cn2c(cc1=O)-c1cc(OC)ccc1CC2C]

A mixture of crude ethyl 10-methoxy-6-methyl-2-oxo-1,6,7,11b-tetrahydrobenzo[a]quinolizine-3-carboxylate from Step 5 and p-chloranil (243 mg, 1 mmol) in DME (15 mL) was refluxed for 2 hours. After being cooled to room temperature, the suspension was filtered with suction. The filter cake was washed with cold DME and then dried under vacuum to give ethyl 10-methoxy-6-methyl-2-oxo-6,7-dihydrobenzo[a]quinolizine-3-carboxylate as a yellow solid (72 mg).

Step 7: Preparation of 10-methoxy-6-methyl-2-oxo-6,7-dihydrobenzo[a]quinolizine-3-carboxylic acid

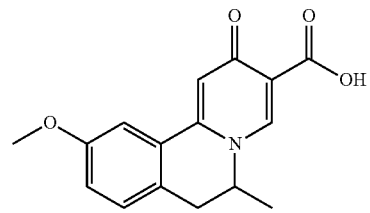 [SMILES: COc1ccc2c(c1)-c1cc(=O)c(C(=O)O)cn1C(C)C2]

To a solution of ethyl 10-methoxy-6-methyl-2-oxo-6,7-dihydrobenzo[a]quinolizine-3-carboxylate from Step 6 in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2). The combined organic layers were washed with brine, and then dried over anhydrous $Na_2SO_4$ and then concentrated to give a light yellow solid, which was purified by prep-HPLC to afford 10-methoxy-6-methyl-2-oxo-6,7-dihydrobenzo[a]quinolizine-3-carboxylic acid (12 mg). $^1$H NMR (400 MHz, $CDCl_3$): δ 8.60 (s, 1H), 7.26 (d, 2H), 7.21 (s, 1H), 7.09 (dd, 1H), 4.58 (m, 1H), 3.90 (s, 3H), 3.43 (dd, 1H), 2.90 (d, 1H), 1.38 (d, 3H). MS obsd. (ESI$^+$) [(M+H)$^+$]: 286.

Example 85: 10-benzyloxy-9-methoxy-6-methyl-2-oxo-6,7-dihydrobenzo[a]quinolizine-3-carboxylic acid

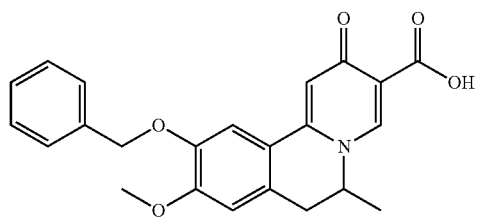 [SMILES: COc1cc2c(cc1OCc1ccccc1)-c1cc(=O)c(C(=O)O)cn1C(C)C2]

Step 1: Preparation of 4-benzyloxy-3-methoxy-benzaldehyde

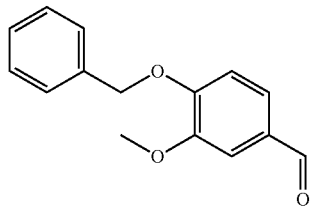 [SMILES: COc1cc(C=O)ccc1OCc1ccccc1]

A 500 mL round-bottomed flask was charged with 4-hydroxy-3-methoxy-benzaldehyde (30.4 g, 0.2 mol), bromomethylbenzene (44.5 g, 0.26 mol), $K_2CO_3$ (60.8 g, 0.44 mol) and acetone (300 mL). The resultant mixture was stirred at 20° C. for 16 hours and then filtered. The filtrate was concentrated to give yellow oil which was stood for 16 hours at room temperature. Then petroleum ether (500 mL) was added and the mixture was stirred for 30 minutes and then filtered. The filter cake was dried to give 4-benzyloxy-3-methoxy-benzaldehyde (40 g).

Step 2: Preparation of 1-benzyloxy-2-methoxy-4-[2-nitroprop-1-enyl]benzene

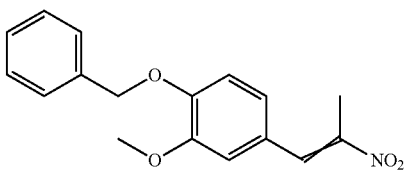 [SMILES: COc1cc(C=C(C)[N+](=O)[O-])ccc1OCc1ccccc1]

A mixture of 4-benzyloxy-3-methoxy-benzaldehyde (30 g, 0.124 mol) and ammonium acetate (9.5 g, 0.124 mol) in toluene (400 mL) was refluxed with a Dean-Stark trap for 2 hours. Then nitroethane (46.4 g, 0.619 mol) was added and the resultant mixture was refluxed for additional 36 hours. The mixture was concentrated under reduced pressure, and the residue was dissolved in ethyl acetate (200 mL). The resultant solution was washed with water (100 mL), and then dried over anhydrous Na₂SO₄ and then concentrated. The residue was purified by column chromatography to give 1-benzyloxy-2-methoxy-4-[2-nitroprop-1-enyl]benzene (27 g).

Step 3: Preparation of 1-(4-benzyloxy-3-methoxy-phenyl)propan-2-amine

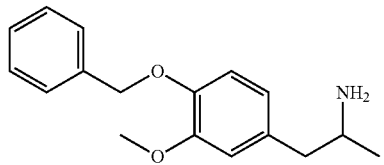 [SMILES: COc1cc(CC(C)N)ccc1OCc1ccccc1]

To a mixture of LiAlH₄ (10.1 g, 0.267 mol) in THF (150 mL) was added a solution of 1-benzyloxy-2-methoxy-4-[2-nitroprop-1-enyl]benzene (25.7 g, 0.862 mol) in THF (100 mL) dropwise in an ice-water bath. The mixture was refluxed for 6 hours and then stirred at room temperature for additional 16 hours. Then water (200 mL) was added dropwise at 0° C., and then 15% NaOH aqueous solution (100 mL) and water (100 mL) were added to the mixture. The resultant mixture was filtered, and the filtrate was concentrated to afford crude 1-(4-benzyloxy-3-methoxy-phenyl)propan-2-amine (16 g) which was used in the next step without further purification.

Step 4: Preparation of N-[2-(4-benzyloxy-3-methoxy-phenyl)-1-methyl-ethyl]formamide

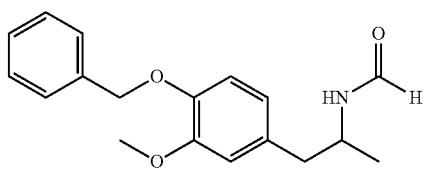 [SMILES: COc1cc(CC(C)NC=O)ccc1OCc1ccccc1]

A mixture of 1-(4-benzyloxy-3-methoxy-phenyl)propan-2-amine (16 g, 59 mmol) and formic acid (4.8 g, 0.106 mol) in dioxane (150 mL) was refluxed for 16 hours and then concentrated under reduce pressure to afford crude N-[2-(4-benzyloxy-3-methoxy-phenyl)-1-methyl-ethyl]formamide (17 g), which was used in the next step without purification.

Step 5: Preparation of 7-benzyloxy-6-methoxy-3-methyl-3,4-dihydroisoquinoline

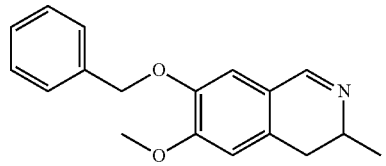 [SMILES: COc1cc2c(cc1OCc1ccccc1)C=NC(C)C2]

To a solution of N-[2-(4-benzyloxy-3-methoxy-phenyl)-1-methyl-ethyl]formamide (17 g, 56.8 mmol) in acetonitrile (100 mL) was added POCl₃ (19 g, 123 mmol) dropwise at 0-5° C. The resultant mixture was refluxed for 4 hours and then concentrated. Ethyl acetate (0.3 L) was added, and then ammonia was added to the mixture to adjust the pH>10. The aqueous layer was extracted with ethyl acetate (0.2 L×3). The organic layers were combined and then concentrated to give 7-benzyloxy-6-methoxy-3-methyl-3,4-dihydroisoquinoline (9.2 g).

Step 6: Preparation of ethyl 10-benzyloxy-9-methoxy-6-methyl-2-oxo-1,6,7,11b-tetrahydrobenzo[a]quinolizine-3-carboxylate

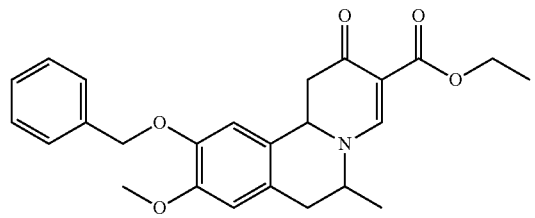 [SMILES: CCOC(=O)C1=CN2C(C)Cc3cc(OC)c(OCc4ccccc4)cc3C2CC1=O]

A mixture of 7-benzyloxy-6-methoxy-3-methyl-3,4-dihydroisoquinoline (9 g, 32 mmol) and ethyl 2-(ethoxymethylene)-3-oxo-butanoate (6.9 g, 37.4 mmol) in EtOH (50 mL) was refluxed overnight. The mixture was concentrated to give crude ethyl 10-benzyloxy-9-methoxy-6-methyl-2-oxo-1,6,7,11b-tetrahydrobenzo[a]quinolizine-3-carboxylate as dark brown oil which was used in the next step without purification.

Step 7: Preparation of ethyl 10-benzyloxy-9-methoxy-6-methyl-2-oxo-6,7-dihydrobenzo[a]quinolizine-3-carboxylate

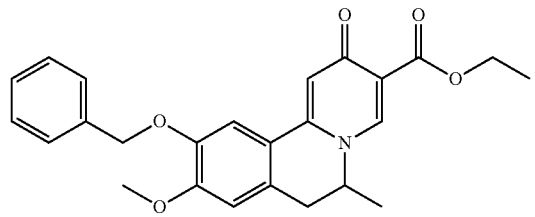 [SMILES: CCOC(=O)c1cn2c(cc1=O)-c1cc(OCc3ccccc3)c(OC)cc1CC2C]

A mixture of crude ethyl 10-benzyloxy-9-methoxy-6-methyl-2-oxo-1,6,7,11b-tetrahydrobenzo[a]quinolizine-3-carboxylate from Step 6 and p-chloranil (4.97 g, 20.4 mmol)

in DME (40 mL) was refluxed for 2 hours. After being cooled to room temperature, the suspension was filtered with suction. The filter cake was washed with cold DME and then dried under vacuum to give ethyl 10-benzyloxy-9-methoxy-6-methyl-2-oxo-6,7-dihydrobenzo[a]quinolizine-3-carboxylate (4.8 g).

Step 8: Preparation of 10-benzyloxy-9-methoxy-6-methyl-2-oxo-6,7-dihydrobenzo[a]quinolizine-3-carboxylic acid

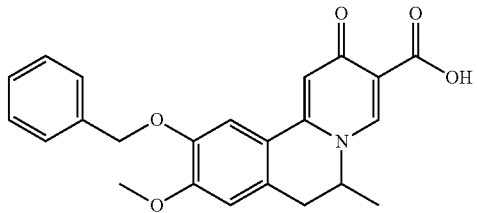 [SMILES: COc1cc2c(cc1OCc1ccccc1)-c1cc(=O)c(C(=O)O)cn1C(C)C2]

To a solution of ethyl 10-benzyloxy-9-methoxy-6-methyl-2-oxo-6,7-dihydrobenzo[a]quinolizine-3-carboxylate (500 mg) in THF (30 mL) was added 10% NaOH aqueous solution dropwise at room temperature. The resultant mixture was stirred for 2 hours, and then acidified to pH 1-2 with 2 M hydrochloric acid. The mixture was extracted with DCM (200 mL×2). The combined organic layers were washed with brine, and then dried over anhydrous Na$_2$SO$_4$ and then concentrated to give a light yellow solid, which was purified by prep-HPLC to afford 10-benzyloxy-9-methoxy-6-methyl-2-oxo-6,7-dihydrobenzo[a]quinolizine-3-carboxylic acid (14 mg). $^1$H NMR (400 MHz, CDCl$_3$): δ 8.56 (s, 1H), 7.44 (m, 5H), 7.25 (s, 1H), 6.95 (s, 1H), 6.79 (s, 1H), 5.22 (s, 2H), 4.55 (m, 1H), 3.99 (s, 3H), 3.43 (dd, 1H), 2.85 (d, 1H), 1.38 (d, 3H). MS obsd. (ESI$^+$) [(M+H)$^+$]: 392.

Example 86: 10-ethoxy-9-methoxy-6-methyl-2-oxo-6,7-dihydrobenzo[a]quinolizine-3-carboxylic acid

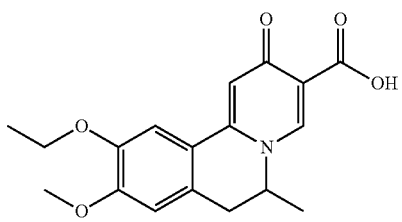 [SMILES: CCOc1cc2c(cc1OC)CC(C)n1cc(C(=O)O)c(=O)cc1-2]

Step 1: Preparation of ethyl 10-hydroxy-9-methoxy-6-methyl-2-oxo-6,7-dihydrobenzo[a]quinolizine-3-carboxylate

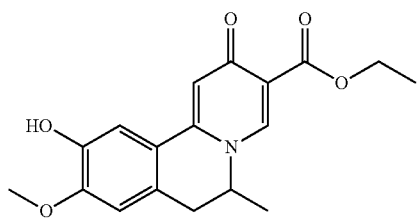 [SMILES: CCOC(=O)c1cn2c(cc1=O)-c1cc(O)c(OC)cc1CC2C]

A mixture of ethyl 10-benzyloxy-9-methoxy-6-methyl-2-oxo-1,6,7,11b-tetrahydrobenzo[a]quinolizine-3-carboxylate (4.3 g) and 10% palladium on carbon (300 mg) in THF/MeOH (1/1, 40 mL) was stirred under hydrogen atmosphere for 12 hours. The mixture was filtered through celite pad, and the filtrate was concentrated under reduced pressure to afford ethyl 10-hydroxy-9-methoxy-6-methyl-2-oxo-6,7-dihydrobenzo[a]quinolizine-3-carboxylate as yellow solid (4.0 g).

Step 2: Preparation of ethyl 10-ethoxy-9-methoxy-6-methyl-2-oxo-6,7-dihydrobenzo[a]quinolizine-3-carboxylate

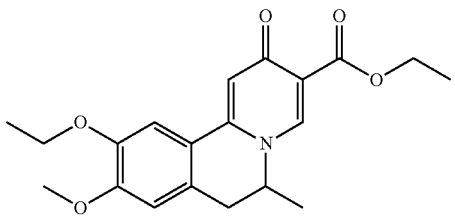 [SMILES: CCOC(=O)c1cn2c(cc1=O)-c1cc(OCC)c(OC)cc1CC2C]

To a solution of ethyl 10-hydroxy-9-methoxy-6-methyl-2-oxo-6,7-dihydrobenzo[a]quinolizine-3-carboxylate (329 mg, 1 mmol) in DMF (15 mL) was added potassium carbonate (278 mg, 2 mmol) and iodoethane (312 mg, 2 mmol). The resultant mixture was heated at 110° C. for 2 hours. After being cooled to room temperature, the mixture was poured into water (20 mL) and the aqueous solution was extracted with EtOAc (20 mL×2). The organic layers were combined and washed with brine, and then dried over anhydrous Na$_2$SO$_4$, and then concentrated under reduced pressure to give crude ethyl 10-ethoxy-9-methoxy-6-methyl-2-oxo-6,7-dihydrobenzo[a]quinolizine-3-carboxylate which was used in the next step without purification.

Step 3: Preparation of 10-ethoxy-9-methoxy-6-methyl-2-oxo-6,7-dihydrobenzo[a]quinolizine-3-carboxylic acid

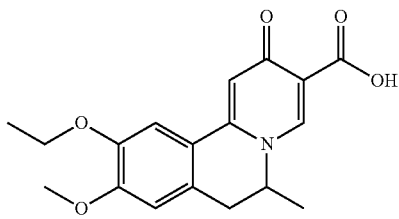 [SMILES: CCOc1cc2c(cc1OC)CC(C)n1cc(C(=O)O)c(=O)cc1-2]

To a solution of ethyl 10-ethoxy-9-methoxy-6-methyl-2-oxo-6,7-dihydrobenzo[a]quinolizine-3-carboxylate from Step 2 in THF (20 mL), was added 10% NaOH aqueous solution dropwise at room temperature. The resultant mixture was stirred for 2 hours, and then acidified to pH 1-2 with 2 M hydrochloric acid. The mixture was extracted with DCM (20 mL×2). The combined organic layers were washed with brine, and then dried over anhydrous Na$_2$SO$_4$ and then concentrated to give a light yellow solid, which was purified by prep-HPLC to afford 10-ethoxy-9-methoxy-6-methyl-2-oxo-6,7-dihydrobenzo[a]quinolizine-3-carboxylic acid (5 mg). $^1$H NMR (400 MHz, MeOD-d$_4$): δ 8.80 (s, 1H), 7.45 (s, 1H), 7.29 (s, 1H), 7.02 (s, 1H), 4.18 (m, 2H), 3.95 (s, 3H), 3.43 (m, 2H), 2.90 (m, 1H), 1.47 (t, 3H), 1.35 (d, 3H). MS obsd. (ESI$^+$) [(M+H)$^+$]: 330.

Example 87: 9-methoxy-6-methyl-2-oxo-10-propoxy-6,7-dihydrobenzo[a]quinolizine-3-carboxylic acid

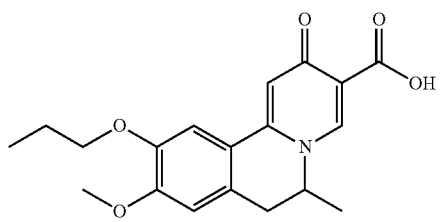 [SMILES: CCCOc1cc2c(cc1OC)CC(C)n1cc(C(=O)O)c(=O)cc1-2]

Step 1: Preparation of ethyl 9-methoxy-6-methyl-2-oxo-10-propoxy-6,7-dihydrobenzo[a]quinolizine-3-carboxylate

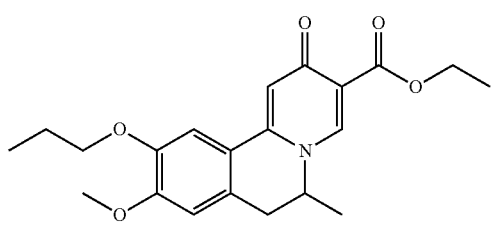 [SMILES: CCCOc1cc2c(cc1OC)CC(C)n1cc(C(=O)OCC)c(=O)cc1-2]

To a solution of ethyl 10-hydroxy-9-methoxy-6-methyl-2-oxo-6,7-dihydrobenzo[a]quinolizine-3-carboxylate (329 mg, 1 mmol) in DMF (15 mL) was added potassium carbonate (278 mg, 2 mmol) and 1-iodopropane (340 mg, 2 mmol). The resultant mixture was heated at 110° C. for 2 hours. After being cooled to room temperature, the mixture was poured into water (20 mL) and the aqueous solution was extracted with EtOAc (25 mL×2). The organic layers were combined and then washed with brine, and then dried over anhydrous Na$_2$SO$_4$, and then concentrated under reduced pressure to give crude ethyl 9-methoxy-6-methyl-2-oxo-10-propoxy-6,7-dihydrobenzo[a]quinolizine-3-carboxylate which was used in next step without purification.

Step 2: Preparation of 9-methoxy-6-methyl-2-oxo-10-propoxy-6,7-dihydrobenzo[a]quinolizine-3-carboxylic acid

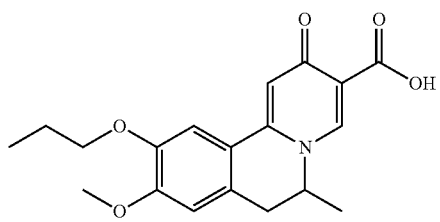 [SMILES: CCCOc1cc2c(cc1OC)CC(C)n1cc(C(=O)O)c(=O)cc1-2]

To a solution of crude ethyl 9-methoxy-6-methyl-2-oxo-10-propoxy-6,7-dihydrobenzo[a]quinolizine-3-carboxylate from Step 1 in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (15 mL×2). The combined organic layers were washed with brine, and then dried over anhydrous Na$_2$SO$_4$ and then concentrated to give a light yellow solid, which was purified by prep-HPLC to afford 9-methoxy-6-methyl-2-oxo-10-propoxy-6,7-dihydrobenzo[a]quinolizine-3-carboxylic acid (10 mg). $^1$H NMR (400 MHz, CDCl$_3$): δ 8.56 (s, 1H), 7.22 (s, 1H), 7.10 (s, 1H), 6.77 (s, 1H), 4.56 (m, 1H), 4.05 (t, 2H), 3.97 (s, 3H), 3.43 (m, 1H), 2.85 (m, 1H), 1.94 (m, 2H), 1.40 (d, 3H), 1.11 (t, 3H). MS obsd. (ESI$^+$) [(M+H)$^+$]: 344.

Example 88: 6,10-diethyl-9-methoxy-2-oxo-6,7-dihydrobenzo[a]quinolizine-3-carboxylic acid

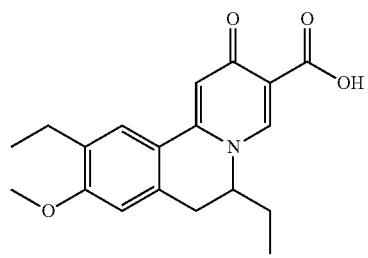 [SMILES: CCc1cc2c(cc1OC)CC(CC)n1cc(C(=O)O)c(=O)cc1-2]

Step 1: Preparation of 4-ethyl-3-methoxy-benzaldehyde

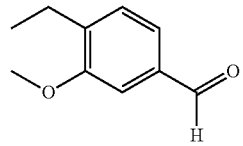

To a mixture of 4-bromo-3-methoxy-benzaldehyde (5.0 g, 23.38 mmol), ethylboronic acid (5.2 g, 71 mmol) and potassium phosphate (17.3 g, 81.83 mmol) in toluene (100 mL) was added water (10 mL), tricyclohexylphosphine (0.65 g, 2.33 mmol) and palladium (II) acetate (260 mg, 1.16 mmol). The reaction mixture was heated at reflux under argon atmosphere overnight. The reaction was cooled, and then diluted with ethyl acetate. The organic layer was washed with water and brine, and then dried over anhydrous sodium sulfate and then concentrated in vacuo. The residue was purified by column chromatography to give 4-ethyl-3-methoxy-benzaldehyde (2 g).

Step 2: Preparation of 1-ethyl-2-methoxy-4-[2-nitrobut-1-enyl]benzene

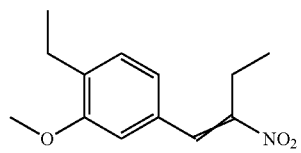 [SMILES: CCC(=Cc1ccc(CC)c(OC)c1)[N+](=O)[O-]]

A mixture of 4-ethyl-3-methoxy-benzaldehyde (2 g, 12.4 mmol) and ammonium acetate (950 mg, 12.4 mmol) in nitropropane (20 mL) was refluxed for 3 hours. The mixture was concentrated under reduced pressure, and the residue was dissolved in ethyl acetate (20 mL). The resultant solution was washed with water (20 mL), and then dried over anhydrous Na₂SO₄ and then concentrated. The residue was purified by column chromatography to give 1-ethyl-2-methoxy-4-[2-nitrobut-1-enyl]benzene (2.3 g).

Step 3: Preparation of
1-(4-ethyl-3-methoxy-phenyl)butan-2-amine

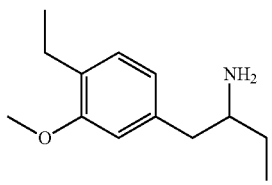

To a mixture of LiAlH₄ (10 mL, 2 M in THF) in THF (15 mL) was added a solution of 1-ethyl-2-methoxy-4-[2-nitrobut-1-enyl]benzene (2.3 g, 9.8 mmol) in THF (15 mL) dropwise in an ice-water bath. The mixture was refluxed for 1 hour. Then water (10 mL) was added dropwise at 0° C., and then 15% NaOH aqueous (20 mL) and water (30 mL) were added to the mixture. The resultant mixture was filtered, and the filtrate was concentrated to afford crude 1-(4-ethyl-3-methoxy-phenyl)butan-2-amine (1.8 g) which was used in the next step without further purification.

Step 4: Preparation of N-[1-[(4-ethyl-3-methoxy-phenyl)methyl]propyl]formamide

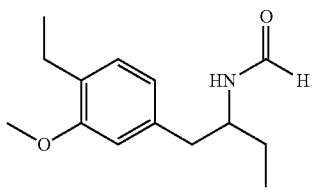 [SMILES: CCc1ccc(CC(CC)NC=O)cc1OC]

A mixture of 1-(4-ethyl-3-methoxy-phenyl)butan-2-amine (1.8 g, 8.7 mmol) and ethyl formate (7.6 g, 87 mmol) in dioxane (30 mL) was refluxed for 16 hours and then concentrated under reduced pressure to afford crude N-[1-[(4-ethyl-3-methoxy-phenyl)methyl]propyl]formamide (2 g), which was used in the next step without purification.

Step 5: Preparation of
3,7-diethyl-6-methoxy-3,4-dihydroisoquinoline

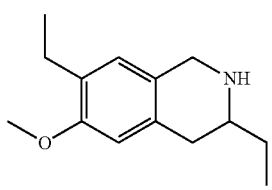 [SMILES: CCc1cc2c(cc1OC)CC(CC)NC2]

To a solution of N-[1-[(4-ethyl-3-methoxy-phenyl)methyl]propyl]formamide (2 g, 8.5 mmol) in acetonitrile (20 mL) was added POCl₃ (2 g, 14 mmol) dropwise at 0-5° C. The resultant mixture was refluxed for 1 hour and then concentrated. Ethyl acetate (30 mL) was added, and then ammonia was added to the mixture to adjust the pH of the aqueous solution to around 11. The aqueous layer was extracted with ethyl acetate (20 mL×3). The organic layers were combined and then concentrated. The residue was purified by column chromatography to give 3,7-diethyl-6-methoxy-3,4-dihydroisoquinoline (1.1 g).

Step 6: Preparation of ethyl 6,10-diethyl-9-methoxy-2-oxo-1,6,7,11b-tetrahydrobenzo[a]quinolizine-3-carboxylate

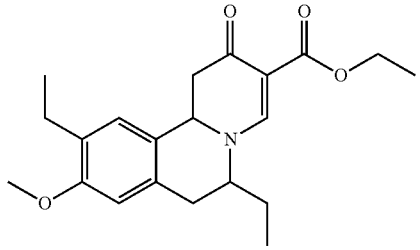 [SMILES: CCOC(=O)C1=CN2C(CC)Cc3cc(OC)c(CC)cc3C2CC1=O]

A mixture of 3,7-diethyl-6-methoxy-3,4-dihydroisoquinoline (1.1 g, 5 mmol) and ethyl 2-(ethoxymethylene)-3-oxo-butanoate (1.1 g, 6 mmol) in EtOH (20 mL) was refluxed overnight. The mixture was concentrated to give crude ethyl 6,10-diethyl-9-methoxy-2-oxo-1,6,7,11b-tetrahydrobenzo[a]quinolizine-3-carboxylat as dark brown oil which was used in the next step without purification.

Step 7: Preparation of ethyl 6,10-diethyl-9-methoxy-2-oxo-6,7-dihydrobenzo[a]quinolizine-3-carboxylate

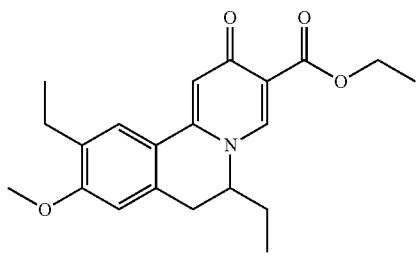 [SMILES: CCOC(=O)c1cn2c(cc1=O)-c1cc(CC)c(OC)cc1CC2CC]

A mixture of crude ethyl 6,10-diethyl-9-methoxy-2-oxo-1,6,7,11b-tetrahydrobenzo[a]quinolizine-3-carboxylat from Step 6 and tetrachloro-1,4-benzoquinone (732 mg, 3 mmol) in DME (20 mL) was refluxed for 2 hours. After being cooled to room temperature, the suspension was filtered with suction. The filter cake was washed with cold DME and then dried under vacuum to give ethyl 6,10-diethyl-9-methoxy-2-oxo-6,7-dihydrobenzo[a]quinolizine-3-carboxylate (400 mg).

Step 8: Preparation of 6,10-diethyl-9-methoxy-2-oxo-6,7-dihydrobenzo[a]quinolizine-3-carboxylic acid

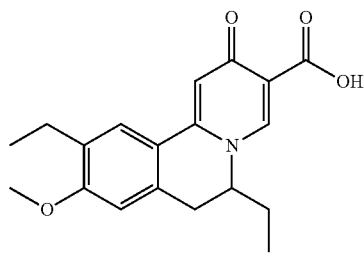 [SMILES: CCc1cc2c(cc1OC)CC(CC)n1cc(C(=O)O)c(=O)cc1-2]

To a solution of ethyl 6,10-diethyl-9-methoxy-2-oxo-6,7-dihydrobenzo[a]quinolizine-3-carboxylate in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous $Na_2SO_4$ and then concentrated to give a light yellow solid, which was purified by prep-HPLC to afford 6,10-diethyl-9-methoxy-2-oxo-6,7-dihydrobenzo[a]quinolizine-3-carboxylic acid (16 mg). $^1$H NMR (400 MHz, MeOD-$d_4$): δ 8.74 (s, 1H), 7.74 (s, 1H), 7.28 (s, 1H), 6.99 (s, 1H), 4.59 (m, 1H), 3.97 (s, 3H), 3.43 (m, 1H), 3.13 (d, 1H), 2.73 (m, 2H), 1.64 (m, 2H), 1.24 (t, 3H), 0.93 (t, 3H). MS obsd. (ESI$^+$) [(M+H)$^+$]: 328.

Example 89: 10-cyclopropyl-6-ethyl-9-methoxy-2-oxo-6,7-dihydrobenzo[a]quinolizine-3-carboxylic acid

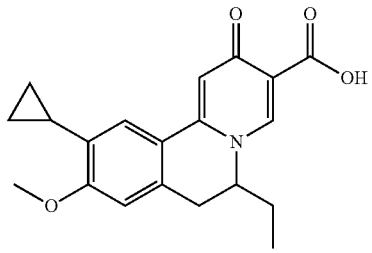 [SMILES: CCC1Cc2cc(OC)c(C3CC3)cc2-c2cc(=O)c(C(=O)O)cn21]

Step 1: Preparation of 4-cyclopropyl-3-methoxy-benzaldehyde

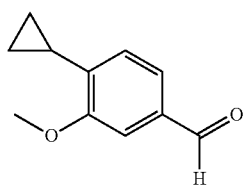

To a mixture of 4-bromo-3-methoxy-benzaldehyde (5.0 g, 23.38 mmol), cyclopropylboronic acid (3 g, 35 mmol) and potassium phosphate (17.3 g, 81.83 mmol) in toluene (100 mL) was added water (10 mL), tricyclohexylphosphine (0.65 g, 2.33 mmol) and palladium (II) acetate (260 mg, 1.16 mmol). The reaction mixture was heated at reflux under argon atmosphere overnight. The reaction was cooled, and then diluted with ethyl acetate. The organic layer was washed with water and brine, and then dried over anhydrous sodium sulfate and then concentrated in vacuo. The residue was purified by column chromatography to give 4-cyclopropyl-3-methoxy-benzaldehyde (3.3 g).

Step 2: Preparation of 1-cyclopropyl-2-methoxy-4-[2-nitrobut-1-enyl]benzene

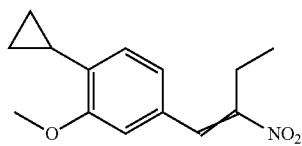 [SMILES: CCC(=Cc1ccc(C2CC2)c(OC)c1)[N+](=O)[O-]]

A mixture of 4-cyclpropyl-3-methoxy-benzaldehyde (3.3 g, 18.7 mmol) and ammonium acetate (1.4 g, 18.7 mmol) in nitropropane (20 mL) was refluxed for 3 hours. The mixture was concentrated under reduced pressure, and the residue was dissolved in ethyl acetate (20 mL). The resultant solution was washed with water (20 mL), and then dried over anhydrous $Na_2SO_4$ and then concentrated. The residue was purified by column chromatography to give 1-cyclopropyl-2-methoxy-4-[2-nitrobut-1-enyl]benzene (4.2 g).

Step 3: Preparation of 1-(4-cyclopropyl-3-methoxy-phenyl)butan-2-amine

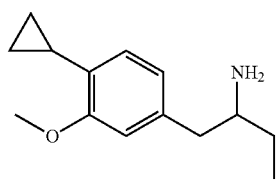 [SMILES: CCC(N)Cc1ccc(C2CC2)c(OC)c1]

To a mixture of LiAlH$_4$ (10 mL, 2 M in THF) in THF (15 mL) was added a solution of 1-cyclopropyl-2-methoxy-4-[2-nitrobut-1-enyl]benzene (2.47 g, 10 mmol) in THF (15 mL) dropwise in an ice-water bath. The mixture was refluxed for 1 hour. Then water (10 mL) was added dropwise at 0° C., and then 15% NaOH aqueous (20 mL) and water (30 mL) were added to the mixture. The resultant mixture was filtered, and the filtrate was concentrated to afford crude 1-(4-cyclopropyl-3-methoxy-phenyl)butan-2-amine (1.3 g) which was used in the next step without further purification.

Step 4: Preparation of N-[1-[(4-cyclopropyl-3-methoxy-phenyl)methyl]propyl]formamide

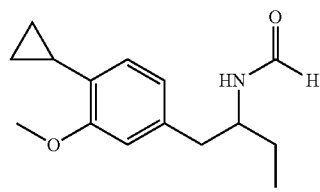 [SMILES: CCC(Cc1ccc(C2CC2)c(OC)c1)NC=O]

A mixture of 1-(4-cyclopropyl-3-methoxy-phenyl)butan-2-amine (1.3 g, 6 mmol) and ethyl formate (7.6 g, 87 mmol) in dioxane (30 mL) was refluxed for 16 hours and then concentrated under reduced pressure to afford crude N-[1-[(4-cyclopropyl-3-methoxy-phenyl)methyl]propyl]formamide (1.4 g), which was used in the next step without purification.

Step 5: Preparation of 7-cyclopropyl-3-ethyl-6-methoxy-3,4-dihydroisoquinoline

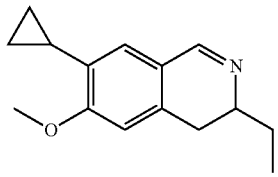 [SMILES: CCC1Cc2cc(OC)c(C3CC3)cc2C=N1]

To a solution of N-[1-[(4-cyclopropyl-3-methoxy-phenyl)methyl]propyl]formamide (1.4 g, 6 mmol) in acetonitrile (20 mL) was added POCl$_3$ (2 g, 14 mmol) dropwise at 0-5° C. The resultant mixture was refluxed for 1 hour and then concentrated. Ethyl acetate (30 mL) was added, and then ammonia was added to the mixture to adjust the pH of the aqueous solution to around 11. The aqueous layer was extracted with ethyl acetate (20 mL×3). The organic layers were combined and then concentrated to give 7-cyclopropyl-3-ethyl-6-methoxy-3,4-dihydroisoquinoline (1.2 g).

Step 6: Preparation of ethyl 10-cyclopropyl-6-ethyl-9-methoxy-2-oxo-1,6,7,11b-tetrahydrobenzo[a]quinolizine-3-carboxylate

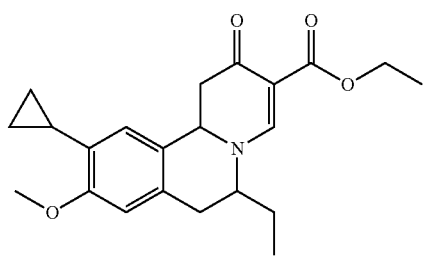 [SMILES: CCOC(=O)C1=CN2C(CC)Cc3cc(OC)c(C4CC4)cc3C2CC1=O]

A mixture of 7-cyclopropyl-3-ethyl-6-methoxy-3,4-dihydroisoquinoline (1.2 g, 5.2 mmol) and ethyl 2-(ethoxymethylene)-3-oxo-butanoate (1.1 g, 6 mmol) in EtOH (20 mL) was refluxed overnight. The mixture was concentrated to give crude ethyl 10-cyclopropyl-6-ethyl-9-methoxy-2-oxo-1,6,7,11b-tetrahydrobenzo[a]quinolizine-3-carboxylate as dark brown oil which was used in the next step without purification.

Step 7: Preparation of ethyl 10-cyclopropyl-6-ethyl-9-methoxy-2-oxo-6,7-dihydrobenzo[a]quinolizine-3-carboxylate

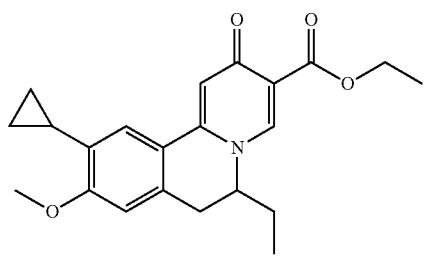 [SMILES: CCOC(=O)c1cn2c(cc1=O)-c1cc(C3CC3)c(OC)cc1CC2CC]

A mixture of crude ethyl 10-cyclopropyl-6-ethyl-9-methoxy-2-oxo-1,6,7,11b-tetrahydrobenzo[a]quinolizine-3-carboxylate from Step 6 and p-chloranil (732 mg, 3 mmol) in DME (20 mL) was refluxed for 2 hours. After being cooled to room temperature, the suspension was filtered with suction. The filter cake was washed with cold DME and then dried under vacuum to give ethyl 10-cyclopropyl-6-ethyl-9-methoxy-2-oxo-6,7-dihydrobenzo[a]quinolizine-3-carboxylate (500 mg).

Step 8: Preparation of 10-cyclopropyl-6-ethyl-9-methoxy-2-oxo-6,7-dihydrobenzo[a]quinolizine-3-carboxylic acid

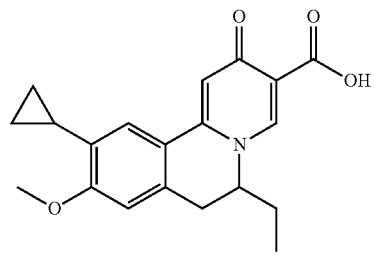 [SMILES: CCC1Cc2cc(OC)c(C3CC3)cc2-c2cc(=O)c(C(=O)O)cn21]

To a solution of ethyl 10-cyclopropyl-6-ethyl-9-methoxy-2-oxo-6,7-dihydrobenzo[a]quinolizine-3-carboxylate in THF (15 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, and then dried over anhydrous Na$_2$SO$_4$ and then concentrated to give a light yellow solid, which was purified by prep-HPLC to afford 10-cyclopropyl-6-ethyl-9-methoxy-2-oxo-6,7-dihydrobenzo[a]quinolizine-3-carboxylic acid (25 mg). $^1$H NMR (400 MHz, CDCl$_3$): δ 8.49 (s, 1H), 7.23 (s, 1H), 7.08 (s, 1H), 6.73 (s, 1H), 4.23 (m, 1H), 3.97 (s, 3H), 3.42 (m, 1H), 2.98 (m, 1H), 2.17 (m, 1H), 1.64 (m, 2H), 1.03 (m, 2H), 0.95 (t, 3H), 0.70 (m, 2H). MS obsd. (ESI$^+$) [(M+H)$^+$]: 340.

Example 90 and 91

(+)-10-cyclopropyl-6-ethyl-9-methoxy-2-oxo-6,7-dihydrobenzo[a]quinolizine-3-carboxylic acid and (−)-10-cyclopropyl-6-ethyl-9-methoxy-2-oxo-6,7-dihydrobenzo[a]quinolizine-3-carboxylic acid

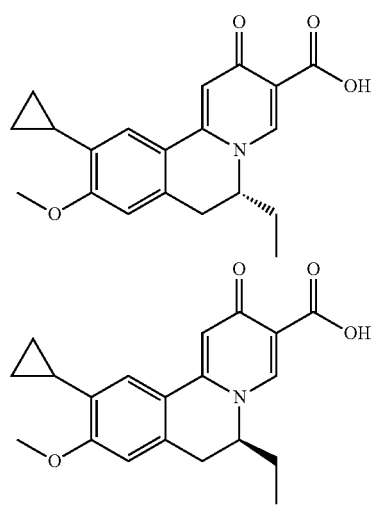

Separation of the racemic 10-cyclopropyl-6-ethyl-9-methoxy-2-oxo-6,7-dihydrobenzo[a]quinolizine-3-carboxylic acid (20 mg) by chiral HPLC afforded (+)-10-cyclopropyl-6-ethyl-9-methoxy-2-oxo-6,7-dihydrobenzo[a]quinolizine-3-carboxylic acid (2.5 mg) and (−)-10-cyclopropyl-6-ethyl-9-methoxy-2-oxo-6,7-dihydrobenzo[a]quinolizine-3-carboxylic acid (2.5 mg).

Example 90

$^1$H NMR (400 MHz, CDCl$_3$): δ 8.49 (s, 1H), 7.23 (s, 1H), 7.08 (s, 1H), 6.73 (s, 1H), 4.23 (m, 1H), 3.97 (s, 3H), 3.42 (m, 1H), 2.98 (m, 1H), 2.17 (m, 1H), 1.64 (m, 2H), 1.03 (m, 2H), 0.95 (t, 3H), 0.70 (m, 2H). MS obsd. (ESI$^+$) [(M+H)$^+$]: 340. [α]$_D^{20}$=+102.30° (0.126%, CH$_3$CN).

Example 91

$^1$H NMR (400 MHz, CDCl$_3$): δ 8.49 (s, 1H), 7.23 (s, 1H), 7.08 (s, 1H), 6.73 (s, 1H), 4.23 (m, 1H), 3.97 (s, 3H), 3.42 (m, 1H), 2.98 (m, 1H), 2.17 (m, 1H), 1.64 (m, 2H), 1.03 (m, 2H), 0.95 (t, 3H), 0.70 (m, 2H). MS obsd. (ESI$^+$) [(M+H)$^+$]: 340.

Example 92: 9-bromo-6-ethyl-10-methoxy-2-oxo-6,7-dihydrobenzo[a]quinolizine-3-carboxylic acid

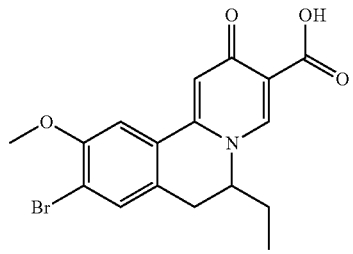 [SMILES: CCC1Cc2cc(Br)c(OC)cc2-c2cc(=O)c(C(=O)O)cn21]

Step 1: Preparation of methyl 2-(3-bromo-4-hydroxy-phenyl)acetate

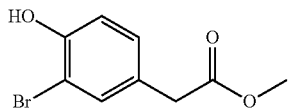

To a mixture of methyl 4-hydroxyphenylacetate (60 g, 0.36 mol) in acetic acid (300 mL) was added a solution of bromine (17 mL, 0.342 mol) in acetic acid (100 mL) dropwise in an ice-water bath. The mixture was stirred for 1 hour at 0° C. and then stirred at room temperature for additional 2 hours. The mixture was concentrated under reduced pressure, and the residue was dissolved in ethyl acetate (500 mL). The resultant solution was washed with aqueous solution of sodium thiosulfate (300 mL×2), water (500 mL) and brine, and then dried over anhydrous Na$_2$SO$_4$ and then concentrated to give methyl 2-(3-bromo-4-hydroxy-phenyl) acetate as a white solid (86 g) which was used in the next step without further purification.

Step 2: Preparation of methyl 2-(3-bromo-4-methoxy-phenyl) acetate

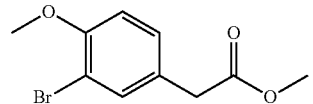

A 500 mL round-bottomed flask was charged with methyl 2-(3-bromo-4-hydroxy-phenyl) acetate (86 g, 0.35 mol), iodomethane (57.3 g, 0.40 mol), K$_2$CO$_3$ (96.8 g, 0.70 mol) and DMF (300 mL). The mixture was stirred at 90° C. for 3 hours. The resultant mixture was filtered, and the filtrate was concentrated under reduced pressure. The residue was dissolved in ethyl acetate (600 mL). The resultant solution was washed with water (500 mL×2) and brine, and then dried over anhydrous Na$_2$SO$_4$ and then concentrated. The residue was purified by column chromatography to give methyl 2-(3-bromo-4-methoxy-phenyl) acetate (85 g).

Step 3: Preparation of 2-(3-bromo-4-methoxy-phenyl) acetic acid

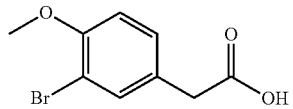

To a solution of methyl 2-(3-bromo-4-methoxy-phenyl) acetate (85 g, 0.33 mol) in methanol (100 mL), THF (35 mL) and water (5 mL) was added lithium hydroxide monohydrate (42 g, 1.0 mol). The resultant mixture was stirred overnight at room temperature and then acidified to pH 1-2 with 2 M hydrochloric acid. The suspension was filtered with suction. The filter cake was washed with cold water and then dried under vacuum to give 2-(3-bromo-4-methoxy-phenyl) acetic acid as a white solid (65 g).

Step 4: Preparation of 2-(3-bromo-4-methoxy-phenyl)-N-methoxy-N-methyl-acetamide

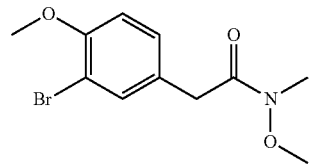

To a solution of 2-(3-bromo-4-methoxy-phenyl) acetic acid (49 g, 0.20 mol) in DCM (500 mL) was added CDI (45 g, 0.28 mol) in batches at 0° C. and then the mixture was stirred for 2 hours. N, O-dimethylhydroxylamine hydrochloride (49 g, 0.20 mol) and Et$_3$N (80.8 g, 0.80 mol) were added into the reaction mixture and the mixture was stirred overnight. The suspension was filtered with suction, and the filtrate was washed with 2 M hydrochloric acid (200 mL×2) and brine (200 mL), and then dried over anhydrous Na$_2$SO$_4$ and then concentrated. The residue was purified by column chromatography to give 2-(3-bromo-4-methoxy-phenyl)-N-methoxy-N-methyl-acetamide as a yellow solid (40 g).

Step 5: Preparation of
1-(3-bromo-4-methoxy-phenyl)butan-2-one

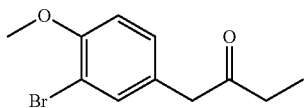

To a solution of 2-(3-bromo-4-methoxy-phenyl)-N-methoxy-N-methyl-acetamide (28.8 g, 0.1 mol) in anhydrous THF (200 mL) was added 1.0 M ethylmagnesium bromide in THF (200 mL) dropwise at −78° C. The resultant mixture was stirred for 2 hours at −78° C. and then stirred overnight at room temperature. The reaction was quenched with water, the solvent was removed under reduced pressure. The residue was dissolved in ethyl acetate (300 mL). The resultant solution was washed with water (200 mL×2) and brine, and then dried over anhydrous $Na_2SO_4$ and then concentrated. The residue was purified by column chromatography to give 1-(3-bromo-4-methoxy-phenyl)butan-2-one (18.5 g).

Step 6: Preparation of
1-(3-bromo-4-methoxy-phenyl)butan-2-amine

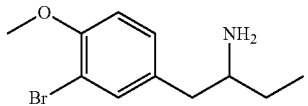

To a solution of 1-(3-bromo-4-methoxy-phenyl)butan-2-one (18.5 g, 72 mmol) in methanol (200 mL) was added ammonium acetate (88 g, 1.08 mol) and $NaBH_3CN$ (9.0 g, 144 mmol). The resultant mixture was stirred overnight at room temperature. The reaction was quenched with water, and then 2.0 M NaOH aqueous solution (100 mL) was added, The mixture was stirred for 1 hour. The mixture was extracted with ethyl acetate (300 mL). The organic layer was washed with water (200 mL×2) and brine, and then dried over anhydrous $Na_2SO_4$ and then concentrated to give 1-(3-bromo-4-methoxy-phenyl)butan-2-amine (11.5 g) which was used in the next step without further purification.

Step 7: Preparation of N-[1-[(3-bromo-4-methoxy-phenyl)methyl]propyl]formamide

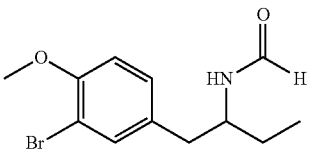 [SMILES: CCC(Cc1ccc(OC)c(Br)c1)NC=O]

A mixture of 1-(3-bromo-4-methoxy-phenyl)butan-2-amine (8.5 g, 33 mmol) and formic acid (4.6 g, 100 mmol) in 1,4-dioxane (150 mL) was refluxed for 12 hours and then concentrated under reduce pressure to afford crude N-[1-[(3-bromo-4-methoxy-phenyl)methyl]propyl]formamide (6.15 g), which was used in the next step without purification.

Step 8: Preparation of
6-bromo-3-ethyl-7-methoxy-3,4-dihydroisoquinoline

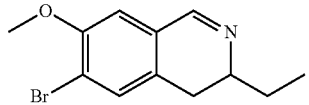

To a solution of N-[1-[(3-bromo-4-methoxy-phenyl)methyl]propyl]formamide (6.15 g, 22.7 mmol) in DCM (100 mL) under $N_2$ atmosphere was added oxalyl chloride (3.6 g, 28.4 mmol).

The solution was stirred at room temperature for 1 hour and then cooled to −10° C., and then iron(III) chloride (5.2 g, 31.8 mmol) was added. The mixture was slowly warmed to room temperature and stirred for 20 hours. 2 M hydrochloride (50 mL) was added to quench the reaction. The biphasic mixture was stirred for 1 hour. The organic layer was washed with water and brine, and then dried over anhydrous $Na_2SO_4$ and then concentrated to give dark red oil. The oil was dissolved in methanol (100 mL) and concentrated $H_2SO_4$ (5 mL), and the mixture was refluxed for 20 hours. After being cooled to room temperature, the solvent was removed under reduced pressure, and the residue was dissolved in ethyl acetate (100 mL). Then ammonia was added to adjust the aqueous solution to pH around 11. The aqueous layer was extracted with ethyl acetate (100 mL×3). The organic layers were combined and then concentrated. The residue was purified by column chromatography to give 6-bromo-3-ethyl-7-methoxy-3,4-dihydroisoquinoline (5.1 g).

Step 9: Preparation of ethyl 9-bromo-6-ethyl-10-methoxy-2-oxo-1,6,7,11b-tetrahydrobenzo[a]quinolizine-3-carboxylate

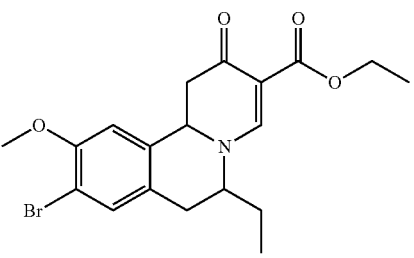 [SMILES: CCOC(=O)C1=CN2C(CC)Cc3cc(Br)c(OC)cc3C2CC1=O]

A mixture of 6-bromo-3-ethyl-7-methoxy-3,4-dihydroisoquinoline (3.5 g, 13 mmol) and ethyl 2-(ethoxymethylene)-3-oxo-butanoate (7.3 g, 39 mmol) in ethanol (50 mL) was refluxed overnight. The mixture was concentrated to give crude ethyl 9-bromo-6-ethyl-10-methoxy-2-oxo-1,6,7,11b-tetrahydrobenzo[a]quinolizine-3-carboxylate as dark brown oil which was used in the next step without purification.

Step 10: Preparation of ethyl 9-bromo-6-ethyl-10-methoxy-2-oxo-6,7-dihydrobenzo[a]quinolizine-3-carboxylate

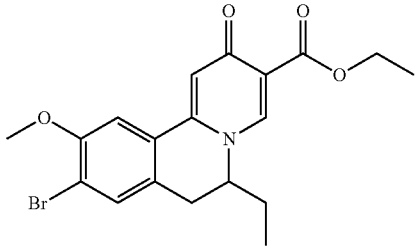

A mixture of crude ethyl 9-bromo-6-ethyl-10-methoxy-2-oxo-1,6,7,11b-tetrahydrobenzo[a]quinolizine-3-carboxylate from Step 9 and p-chloranil (2.7 g, 11 mmol) in DME (40 mL) was refluxed for 2 hours. After being cooled to room temperature, the suspension was filtered with suction. The filter cake was washed with cold DME and then dried under vacuum to give ethyl 9-bromo-6-ethyl-10-methoxy-2-oxo-6,7-dihydrobenzo[a]quinolizine-3-carboxylate as a yellow solid (3.2 g).

Step 11: Preparation of 9-bromo-6-ethyl-10-methoxy-2-oxo-6,7-dihydrobenzo[a]quinolizine-3-carboxylic acid

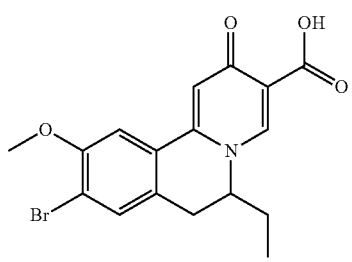 [SMILES: CCC1Cc2cc(Br)c(OC)cc2-c2cc(=O)c(C(=O)O)cn21]

To a solution of ethyl 9-bromo-6-ethyl-10-methoxy-2-oxo-6,7-dihydrobenzo[a]quinolizine-3-carboxylate (0.2 g, 0.5 mmol) in THF (2 mL) and methanol (6 mL) was added 1.0 M lithium hydroxide (1.5 mL) aqueous solution at room temperature. The resultant mixture was stirred for 4 hours, and then acidified to pH 1-2 with 2 M hydrochloric acid. The mixture was extracted with DCM (50 mL×2). The combined organic layers were washed with brine, and then dried over anhydrous $Na_2SO_4$ and then concentrated to give a yellow solid, which was purified by prep-HPLC to give 9-bromo-6-ethyl-10-methoxy-2-oxo-6,7-dihydrobenzo[a]quinolizine-3-carboxylic acid (58 mg). $^1$H NMR (400 MHz, $CDCl_3$): δ 15.72 (s, 1H), 8.54 (s, 1H), 7.53 (s, 1H), 7.21 (s, 1H), 7.19 (s, 1H), 4.30 (m, 1H), 3.92 (s, 3H), 3.41 (m, 1H), 2.98 (d, 1H), 1.59 (m, 2H), 0.93 (t, 3H). MS obsd. ($ESI^+$) [(M+H)$^+$]: 378.

Example 93: 9-cyano-6-ethyl-10-methoxy-2-oxo-6,7-dihydrobenzo[a]quinolizine-3-carboxylic acid

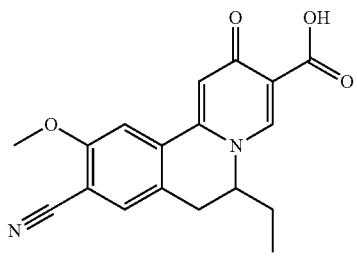 [SMILES: CCC1Cc2cc(C#N)c(OC)cc2-c2cc(=O)c(C(=O)O)cn21]

Step 1: Preparation of ethyl 9-cyano-6-ethyl-10-methoxy-2-oxo-6,7-dihydrobenzo[a]quinolizine-3-carboxylate

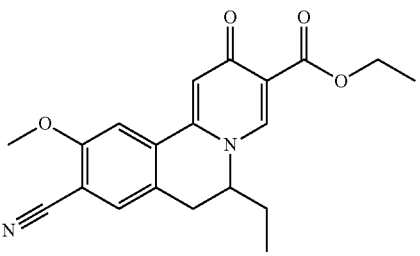 [SMILES: CCOC(=O)c1cn2c(cc1=O)-c1cc(OC)c(C#N)cc1CC2CC]

To a solution of ethyl 9-bromo-6-ethyl-10-methoxy-2-oxo-6,7-dihydrobenzo[a]quinolizine-3-carboxylate (0.12 g, 0.3 mmol) in DMF (10 mL) was added zinc cyanide (53 mg, 0.45 mmol) and tetrakis(triphenylphosphine) palladium(0) (70 mg, 0.06 mmol). The resultant mixture was stirred at 100° C. for 10 hours. After being cooled to room temperature, the mixture was concentrated under reduced pressure, and the residue was dissolved in ethyl acetate (50 mL). The resultant solution was washed with water (25 mL×2) and brine, and then dried over anhydrous $Na_2SO_4$ and then concentrated to give ethyl 9-cyano-6-ethyl-10-methoxy-2-oxo-6,7-dihydrobenzo[a]quinolizine-3-carboxylate (100 mg) which was used in the next step without purification.

Step 2: Preparation of 9-cyano-6-ethyl-10-methoxy-2-oxo-6,7-dihydrobenzo[a]quinolizine-3-carboxylic acid

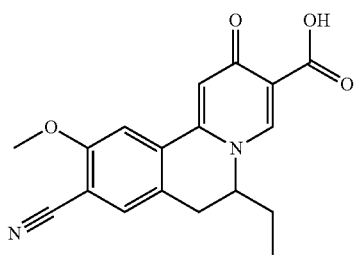 [SMILES: CCC1Cc2cc(C#N)c(OC)cc2-c2cc(=O)c(C(=O)O)cn21]

To a solution of ethyl 9-cyano-6-ethyl-10-methoxy-2-oxo-6,7-dihydrobenzo[a]quinolizine-3-carboxylate (0.1 g, 0.3 mmol) in THF (2 mL) and methanol (6 mL) was added 1.0 M LiOH (0.9 mL) aqueous solution at room temperature. The resultant mixture was stirred for 4 hours, and then acidified to pH 1-2 with 2 M hydrochloric acid. The mixture was extracted with DCM (50 mL×2), and the combined organic layers were washed with brine, and then dried over anhydrous Na$_2$SO$_4$ and then concentrated to give a yellow solid, which was purified by prep-HPLC to give 9-cyano-6-ethyl-10-methoxy-2-oxo-6,7-dihydrobenzo[a]quinolizine-3-carboxylic acid (6 mg). $^1$H NMR (400 MHz, DMSO-d$_6$): δ 16.35 (s, 1H), 8.91 (s, 1H), 7.86 (s, 1H), 7.82 (s, 1H), 7.79 (s, 1H), 4.80 (m, 1H), 4.10 (s, 3H), 3.35 (m, 1H) 3.11 (m, 1H), 1.41 (m, 2H), 0.80 (t, 3H). MS obsd. (ESI$^+$) [(M+H)$^+$]: 325.

Example 94: 8-bromo-11-ethoxy-6-ethyl-2-oxo-6,7-dihydrobenzo[a]quinolizine-3-carboxylic acid

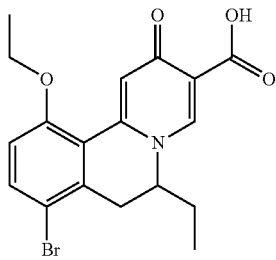 [SMILES: CCOc1ccc(Br)c2c1-c1cc(=O)c(C(=O)O)cn1C(CC)C2]

Step 1: Preparation of methyl 2-(2-bromo-5-hydroxy-phenyl)acetate

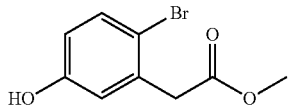

To a mixture of methyl 2-(3-hydroxyphenyl)acetate (55 g, 0.33 mol) in acetic acid (800 mL) was added a solution of bromine (15 mL, 0.298 mol) in acetic acid (270 mL) dropwise in an ice-water bath. The mixture was stirred for 0.5 hour at 0° C. and then stirred at room temperature for additional 2 hours. The mixture was concentrated under reduced pressure, and the residue was dissolved in ethyl acetate (500 mL). The resultant solution was washed aqueous solution of sodium thiosulfate (300 mL×2), water (500 mL) and brine, and then dried over anhydrous Na$_2$SO$_4$ and then concentrated to give methyl 2-(2-bromo-5-hydroxy-phenyl)acetate as a solid (83 g) which was used in the next step without further purification.

Step 2: Preparation of methyl 2-(2-bromo-5-ethoxy-phenyl)acetate

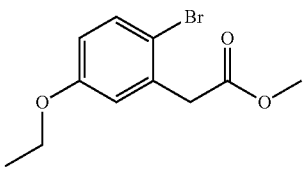

A 500 mL round-bottomed flask was charged with methyl 2-(2-bromo-5-hydroxy-phenyl) acetate (90 g, 0.369 mol), iodoethane (63.3 g, 0.406 mol), K$_2$CO$_3$ (101.8 g, 0.738 mol) and DMF (450 mL). The mixture was stirred at 90° C. for 3 hours. The resultant mixture was filtered, and the filtrate was concentrated under reduced pressure. The residue was dissolved in ethyl acetate (600 mL). The resultant solution was washed with water (500 mL×2) and brine, and then dried over anhydrous Na$_2$SO$_4$ and concentrated. The residue was purified by column chromatography to give methyl 2-(2-bromo-5-ethoxy-phenyl)acetate (74 g).

Step 3: Preparation of 2-(2-bromo-5-ethoxy-phenyl)acetic acid

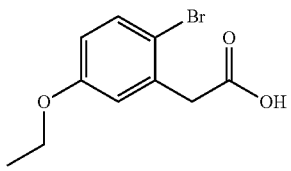

To a solution of methyl 2-(2-bromo-5-ethoxy-phenyl) acetate (74 g, 0.272 mol) in methanol (300 mL), THF (105 mL) and water (15 mL) was added lithium hydroxide monohydrate (57 g, 1.36 mol). The resultant mixture was stirred overnight at room temperature and then acidified to pH 1-2 with 2 M hydrochloric acid. The suspension was filtered with suction. The filter cake was washed with cold water and then dried under vacuum to give 2-(2-bromo-5-ethoxy-phenyl)acetic acid as a white solid (68 g).

Step 4: Preparation of 2-(2-bromo-5-ethoxy-phenyl)-N-methoxy-N-methyl-acetamide

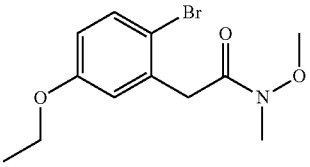 [SMILES: CCOc1ccc(Br)c(CC(=O)N(C)OC)c1]

To a solution of 2-(2-bromo-5-ethoxy-phenyl)acetic acid (46 g, 0.178 mol) in DCM (950 mL) was added CDI (40.5 g, 0.25 mol) in batches at 0° C. and then the mixture was stirred for 2 hours. N, O-dimethylhydroxylamine hydrochloride (52.2 g, 0.535 mol) and Et$_3$N (72 g, 0.713 mol) were added and the resultant solution was stirred overnight. The mixture was concentrated and the residue was purified by column chromatography to give 2-(2-bromo-5-ethoxy-phenyl)-N-methoxy-N-methyl-acetamide as a solid (45 g).

Step 5: Preparation of 1-(2-bromo-5-ethoxy-phenyl)butan-2-one

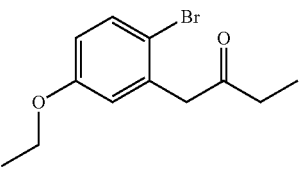

To a solution of 2-(2-bromo-5-ethoxy-phenyl)-N-methoxy-N-methyl-acetamide (36 g, 0.12 mol) in anhydrous THF (200 mL) was added 3.0 M ethylmagnesium bromide in ether (80 mL) dropwise at −78° C. The resultant mixture was stirred for 2 hours at −78° C. and then stirred overnight at room temperature. The reaction was quenched with 1 M hydrochloric acid at −78° C.

Then the solution was warmed to room temperature and stirred for 1 hour. The solution was concentrated under reduced pressure, and the residue was dissolved in ethyl acetate (300 mL). The resultant solution was washed with water (200 mL×2) and brine, and then dried over anhydrous Na₂SO₄ and then concentrated. The residue was purified by column chromatography to give 1-(2-bromo-5-ethoxy-phenyl)butan-2-one (16.2 g).

Step 6: Preparation of
1-(2-bromo-5-ethoxy-phenyl)butan-2-amine

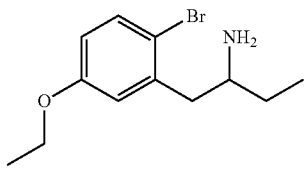

To a solution of 1-(2-bromo-5-ethoxy-phenyl)butan-2-one (16.2 g, 60 mmol) in methanol (400 mL) was added ammonium acetate (69.4 g, 0.9 mol) and NaBH₃CN (7.54 g, 120 mmol). The resultant mixture was stirred overnight at room temperature. The reaction was quenched with water. Then 2.0 M NaOH aqueous solution (100 mL) was added and the reaction mixture was stirred for 1 hour. The mixture was extracted with ethyl acetate (300 mL). The organic layer was washed with water (200 mL×2) and brine, and then dried over anhydrous Na₂SO₄ and then concentrated to give 1-(2-bromo-5-ethoxy-phenyl)butan-2-amine (11 g) which was used in the next step without further purification.

Step 7: Preparation of N-[1-[(2-bromo-5-ethoxy-phenyl)methyl]propyl]formamide

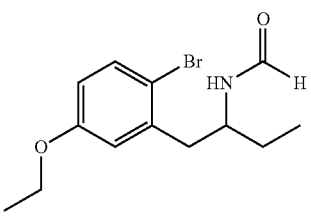 [SMILES: CCOc1ccc(Br)c(CC(CC)NC=O)c1]

A mixture of 1-(2-bromo-5-ethoxy-phenyl)butan-2-amine (11 g, 40.59 mmol) and formic acid (4.6 g, 100 mmol) in 1,4-dioxane (400 mL) was refluxed for 6 hours and then concentrated under reduced pressure. The residue was dissolved in EtOAc and the mixture was washed with NaHCO₃ aqueous solution and water. The organic layer was dried over anhydrous Na₂SO₄ and then concentrated to give crude N-[1-[(2-bromo-5-ethoxy-phenyl)methyl]propyl]formamide as a yellow solid (11.57 g) which was used in the next step without purification.

Step 8: Preparation of
5-bromo-8-ethoxy-3-ethyl-3,4-dihydroisoquinoline

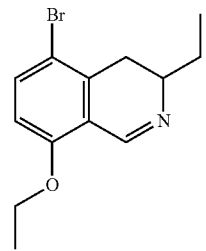 [SMILES: CCOc1ccc(Br)c2c1C=NC(CC)C2]

A mixture of N-[1-[(2-bromo-5-ethoxy-phenyl)methyl]propyl]formamide (11.5 g, 38.46 mmol), POCl₃ (7.08 g, 46.15 mmol) in CH₃CN (400 mL) was heated at 85° C. for 2 hours. Then the mixture was concentrated and the residue was dissolved in CH₃CN (20 mL). The pH of the mixture was adjusted to around 9 by addition of ammonia at 0° C. Then aqueous layer was extracted with CH₂Cl₂ (100 mL×3). The combined organic layers were washed with water, and then dried over anhydrous Na₂SO₄ and then concentrated to give crude 5-bromo-8-ethoxy-3-ethyl-3,4-dihydroisoquinoline as dark green oil (11 g) which was used in the next step without purification.

Step 9: Preparation of ethyl 8-bromo-11-ethoxy-6-ethyl-2-oxo-1,6,7,11b-tetrahydrobenzo[a]quinolizine-3-carboxylate

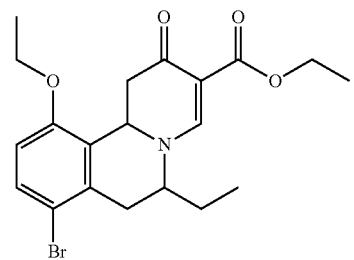 [SMILES: CCOC(=O)C1=CN2C(CC)Cc3c(Br)ccc(OCC)c3C2CC1=O]

A mixture of 5-bromo-8-ethoxy-3-ethyl-3,4-dihydroisoquinoline (10.5 g, 37.4 mmol) and ethyl 2-(ethoxymethylene)-3-oxo-butanoate (20.85 g, 112 mmol) in ethanol (300 mL) was refluxed overnight. The mixture was concentrated and the residue was purified by column chromatography to give crude ethyl 8-bromo-11-ethoxy-6-ethyl-2-oxo-1,6,7,11b-tetrahydrobenzo[a]quinolizine-3-carboxylate (4.8 g).

Step 10: Preparation of ethyl 8-bromo-11-ethoxy-6-ethyl-2-oxo-6,7-dihydrobenzo[a]quinolizine-3-carboxylate

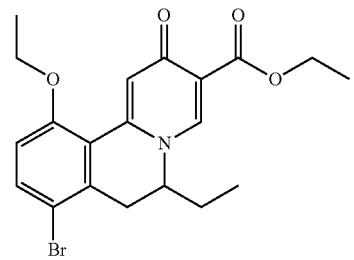 [SMILES: CCOC(=O)c1cn2c(cc1=O)-c1c(OCC)ccc(Br)c1CC2CC]

A mixture of crude ethyl 8-bromo-11-ethoxy-6-ethyl-2-oxo-1,6,7,11b-tetrahydrobenzo[a]quinolizine-3-carboxylate (4.8 g, 11.4 mmol) from Step 9 and p-chloranil (2.8 g, 11.4 mmol) in DME (40 mL) was refluxed for 4 hours. Then CH$_2$Cl$_2$ was added. The organic layer was washed with NaHCO$_3$ aqueous solution (50 mL×6), and then dried and then concentrated to give crude ethyl 8-bromo-11-ethoxy-6-ethyl-2-oxo-6,7-dihydrobenzo[a]quinolizine-3-carboxylate (4 g).

Step 11: Preparation of 8-bromo-11-ethoxy-6-ethyl-2-oxo-6,7-dihydrobenzo[a]quinolizine-3-carboxylic acid

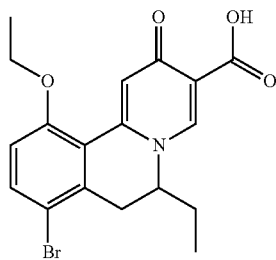 [SMILES: CCOc1ccc(Br)c2c1-c1cc(=O)c(C(=O)O)cn1C(CC)C2]

To a solution of ethyl 8-bromo-11-ethoxy-6-ethyl-2-oxo-6,7-dihydrobenzo[a]quinolizine-3-carboxylate (0.2 g, 0.48 mmol) in THF (3 mL), methanol (5 mL) and H$_2$O (1 mL) was added lithium hydroxide monohydrate (60 mg, 1.43 mmol) at room temperature. The mixture was stirred for 4 hours, and then acidified to pH 1-2 with 2 M hydrochloric acid. The mixture was extracted with DCM (50 mL×2). The combined organic layers were washed with brine, and then dried over anhydrous Na$_2$SO$_4$ and then concentrated. The residue was purified by prep-HPLC to give 8-bromo-11-ethoxy-6-ethyl-2-oxo-6,7-dihydrobenzo[a]quinolizine-3-carboxylic acid (12 mg). $^1$H NMR (400 MHz, DMSO-d$_6$): δ 8.88 (s, 1H), 7.79 (d, 1H), 7.71 (s, 1H), 7.18 (d, 1H), 4.76 (d, 1H), 4.29 (dd, 1H), 4.15 (dd, 1H), 4.05 (br. s., 1H), 3.28-3.22 (m, 1H), 1.52 (dd, 1H), 1.41 (t, 3H), 1.37-1.25 (m, 1H), 0.80 (t, 3H). MS obsd. (ESI$^+$) [(M+H)$^+$]: 392.

Example 95: 8-cyano-11-ethoxy-6-ethyl-2-oxo-6,7-dihydrobenzo[a]quinolizine-3-carboxylic acid

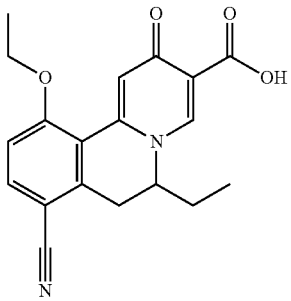 [SMILES: CCOc1ccc(C#N)c2c1-c1cc(=O)c(C(=O)O)cn1C(CC)C2]

To a solution of ethyl 8-bromo-11-ethoxy-6-ethyl-2-oxo-6,7-dihydrobenzo[a]quinolizine-3-carboxylate (0.2 g, 0.48 mmol) in DMF (5 mL) was added zinc cyanide (112 mg, 0.95 mmol) and tetrakis(triphenylphosphine) palladium(0) (110 mg, 0.095 mmol). The reaction was carried out under microwave irradiation at 150° C. for 25 minutes. After being cooled to room temperature, the mixture was acidified to pH 1-2 with 2 M hydrochloric acid. Then the mixture was extracted with DCM (50 mL×2), and the combined organic layers were washed with brine, and then dried over anhydrous Na$_2$SO$_4$ and then concentrated to give crude product which was purified by prep-HPLC to give 8-cyano-11-ethoxy-6-ethyl-2-oxo-6,7-dihydrobenzo[a]quinolizine-3-carboxylic acid (11 mg). $^1$H NMR (400 MHz, DMSO-d$_6$): δ 8.90 (s, 1H), 8.03 (d, 1H), 7.72 (s, 1H), 7.37 (d, 1H), 4.87-4.76 (m, 1H), 4.48-4.35 (m, 1H), 4.26 (qd, 1H), 3.53 (dd, 1H), 3.23 (dd, 1H), 1.59-1.48 (m, 1H), 1.44 (t, 3H), 1.41-1.33 (m, 1H), 0.81 (t, 3H). MS obsd. (ESI$^+$) [(M+H)$^+$]: 339

Example 96: 9,10-dimethoxy-2-oxo-6-propyl-6,7-dihydrobenzo[a]quinolizine-3-carboxylic acid

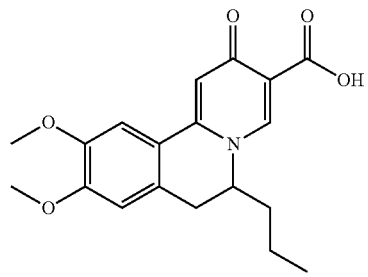 [SMILES: CCCC1Cc2cc(OC)c(OC)cc2-c2cc(=O)c(C(=O)O)cn21]

Step 1: Preparation of 2-(3,4-dimethoxyphenyl)-N-methoxy-N-methyl-acetamide

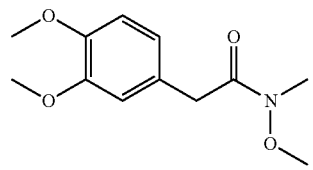

To a solution of 2-(3,4-dimethoxyphenyl)acetic acid (25.2 g, 129 mmol) in CH$_2$Cl$_2$ (300 mL) was added di(imidazol-1-yl)methanone (25.1 g, 155 mmol) in portions at 0° C. The resultant mixture was stirred at 0° C. to room temperature for 2 hours. Then N,O-dimethylhydroxylamine hydrochloride (37.9 g, 387 mmol) was added at 0° C., and then Et$_3$N (52.1 g, 516 mmol) was added to the mixture in dropwise. The resultant mixture was stirred at 0° C. at room temperature overnight. The reaction mixture was diluted with 2 M hydrochloric acid (100 mL) and extracted with EtOAc. The organic layer was washed with 2 M hydrochloric acid (50 mL×5) and brine, and then dried over anhydrous Na$_2$SO$_4$ and then concentrated to give 2-(3,4-dimethoxyphenyl)-N-methoxy-N-methyl-acetamide (31.2 g) as an orange oil.

Step 2: Preparation of 1-(3,4-dimethoxyphenyl)pentan-2-one

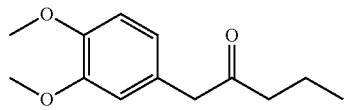 [SMILES: CCCC(=O)Cc1ccc(OC)c(OC)c1]

To a solution of 2-(3,4-dimethoxyphenyl)-N-methoxy-N-methyl-acetamide (4.78 g, 20 mmol) in THF (50 mL) was added propylmagnesium bromide (20 mL, 40 mmol) dropwise at −78° C. The resultant mixture was stirred from −78° C. to room temperature overnight. The reaction was quenched by 1 M hydrochloric acid at −78° C., and then warmed to room temperature. The mixture was extracted with Et$_2$O (100 mL×3). The combined organic layers were washed with brine, and then dried over anhydrous Na$_2$SO$_4$ and then concentrated to give crude 1-(3,4-dimethoxyphenyl)pentan-2-one (4.56 g) which was directly used for the next step without purification.

Step 3: Preparation of 1-(3,4-dimethoxyphenyl)pentan-2-amine

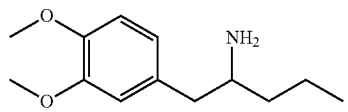 [SMILES: CCCC(N)Cc1ccc(OC)c(OC)c1]

To a mixture of 1-(3,4-dimethoxyphenyl)pentan-2-one (4.56 g, 20 mmol) and ammonium acetate (25.1 g, 300 mmol) in CH$_3$OH (60 mL) was added NaBH$_3$CN (2.52 g, 40 mmol). The resultant mixture was stirred at room temperature overnight. The reaction mixture was diluted with H$_2$O, and then acidified by concentrated hydrochloric acid to pH 2 and then concentrated under vacuum. The residue was basified by aqueous solution of NaOH to pH 14. Then the mixture was extracted with CH$_2$Cl$_2$ (100 mL×3). The combined organic layers were washed with brine, and then dried over anhydrous Na$_2$SO$_4$ and then concentrated to give 1-(3,4-dimethoxyphenyl)pentan-2-amine (4.0 g) as yellow oil which was directly used for the next step without further purification.

Step 4: Preparation of N-[1-[(3,4-dimethoxyphenyl)methyl]butyl]formamide

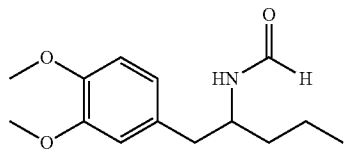 [SMILES: CCCC(Cc1ccc(OC)c(OC)c1)NC=O]

A solution of 1-(3,4-dimethoxyphenyl)pentan-2-amine (4.0 g, 18 mmol) in ethyl formate (30 mL) was heated at 65° C. overnight. Then 1,4-dioxane (30 mL) was added and the mixture was heated at 90° C. for 1 hour. After removal of the solvent, N-[1-[(3,4-dimethoxyphenyl)methyl]butyl]formamide (4.32 g) was obtained as yellow oil which was directly used for the next step without purification.

Step 5: Preparation of 6,7-dimethoxy-3-propyl-3,4-dihydroisoquinoline

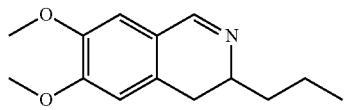 [SMILES: CCCC1Cc2cc(OC)c(OC)cc2C=N1]

To a solution of N-[1-[(3,4-dimethoxyphenyl)methyl]butyl]formamide (4.32 g, 17.2 mmol) in acetonitrile (50 mL) was added POCl$_3$ (3.15 g, 20.6 mmol). The resultant mixture was heated to 85° C. for 1 hour. After removal of the solvent and excess POCl$_3$, yellow oil was obtained. The oil was dissolved in acetonitrile (10 mL), and then cooled to 0° C. Ammonium hydroxide was added dropwise at 0° C. to basify the mixture, and then H$_2$O was added to the mixture. The reaction mixture was stirred at 0° C. for 30 minutes. The mixture was extracted with CH$_2$Cl$_2$ (100 mL×3), and the combined organic layers were washed with brine, and then dried over anhydrous Na$_2$SO$_4$ and then concentrated. The residue was purified by flash column chromatography to afford 6,7-dimethoxy-3-propyl-3,4-dihydroisoquinoline (2.60 g) as yellow oil which was directly used for the next step without further purification.

Step 6: Preparation of ethyl 9,10-dimethoxy-2-oxo-6-propyl-1,6,7,11b-tetrahydrobenzo[a]quinolizine-3-carboxylate

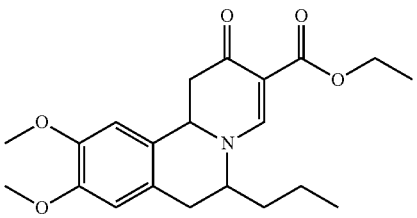 [SMILES: CCCC1Cc2cc(OC)c(OC)cc2C2CC(=O)C(C(=O)OCC)=CN12]

A mixture of 6,7-dimethoxy-3-propyl-3,4-dihydroisoquinoline (699 mg, 3 mmol) and ethyl 2-(dimethylaminomethylene)-3-oxo-butanoate (833 mg, 4.5 mmol) in DMF (3 mL) was heated to 170° C. for 6 hours under microwave, then the mixture was heated to 180° C. for 2 hours under microwave. The mixture was diluted with H$_2$O and then extracted with EtOAc (50 mL×3). The combined organic layers were washed with brine, and then dried over anhydrous Na$_2$SO$_4$ and then concentrated in vacuo. The residue was purified by flash column chromatography to afford crude ethyl 9,10-dimethoxy-2-oxo-6-propyl-1,6,7,11b-tetrahydrobenzo[a]quinolizine-3-carboxylate (780 mg) as red oil which was directly used for the next step without further purification.

Step 7: Preparation of ethyl 9,10-dimethoxy-2-oxo-6-propyl-6,7-dihydrobenzo[a]quinolizine-3-carboxylate

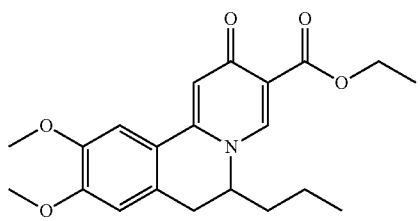 [SMILES: CCCC1Cc2cc(OC)c(OC)cc2-c2cc(=O)c(C(=O)OCC)cn21]

A mixture of ethyl 9,10-dimethoxy-2-oxo-6-propyl-1,6,7,11b-tetrahydrobenzo[a]quinolizine-3-carboxylate (780 mg, crude) and p-chloranil (490 mg, 2 mmol) in DME (3 mL) and toluene (3 mL) was heated to 135° C. for 20 minutes under microwave. After removing solvent, the residue was purified by flash column chromatography to afford ethyl 9,10-dimethoxy-2-oxo-6-propyl-6,7-dihydrobenzo[a]quinolizine-3-carboxylate (70 mg) as brown oil which was directly used for the next step without further purification.

Step 8: Preparation of 9,10-dimethoxy-2-oxo-6-propyl-6,7-dihydrobenzo[a]quinolizine-3-carboxylic acid

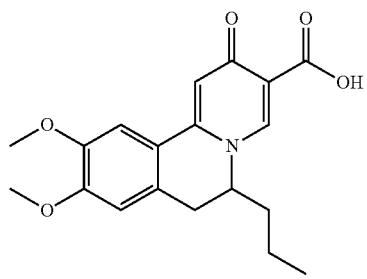 [SMILES: CCCC1Cc2cc(OC)c(OC)cc2-c2cc(=O)c(C(=O)O)cn21]

To a solution of ethyl 9,10-dimethoxy-2-oxo-6-propyl-6,7-dihydrobenzo[a]quinolizine-3-carboxylate (70 mg, 0.2 mmol) in CH$_3$OH (3 mL) and H$_2$O (1 mL) was added lithium hydroxide monohydrate (37 mg, 0.8 mmol). The resultant reaction mixture was stirred at room temperature overnight. The mixture was diluted with H$_2$O (10 mL) and acidified by 2 M hydrochloric acid to pH 2-3. Then the mixture was extracted with CH$_2$Cl$_2$ (20 mL×3), and the combined organic layers were washed with brine, and then dried over anhydrous Na$_2$SO$_4$ and then concentrated in vacuo. The residue was washed with EtOAc/petroleum ether to afford 9,10-dimethoxy-2-oxo-6-propyl-6,7-dihydrobenzo[a]quinolizine-3-carboxylic acid (19 mg) as a yellow solid. $^1$H NMR (400 MHz, CDCl$_3$): δ 8.51 (s, 1H), 7.21 (s, 1H), 7.11 (s, 1H), 6.77 (s, 1H), 4.40-4.26 (m, 1H), 3.99 (s, 3H), 3.98 (s, 3H), 3.44 (dd, 1H), 2.94 (d, 1H), 1.70-1.51 (m, 2H), 1.40-1.19 (m, 2H), 0.90 (t, 3H). MS obsd. (ESI$^+$) [(M+H)$^+$]: 344.

Example 97: 6-cyclopropyl-9,10-dimethoxy-2-oxo-6,7-dihydrobenzo[a]quinolizine-3-carboxylic acid

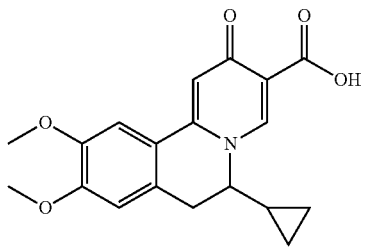 [SMILES: COc1cc2c(cc1OC)-c1cc(=O)c(C(=O)O)cn1C(C1CC1)C2]

Step 1: Preparation of 1-cyclopropyl-2-(3,4-dimethoxyphenyl)ethanone

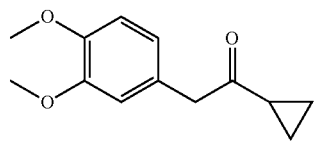 [SMILES: COc1ccc(CC(=O)C2CC2)cc1OC]

To a solution of 2-(3,4-dimethoxyphenyl)-N-methoxy-N-methyl-acetamide (2.39 g, 10 mmol) in THF (20 mL) was added cyclopropylmagnesium bromide (30 mL, 21 mmol) dropwise at −78° C. The resultant solution was stirred from −78° C. to room temperature for 6 hours. The reaction was quenched by saturated aqueous NH$_4$Cl solution at −78° C., then warmed to room temperature. The mixture was extracted with EtOAc (50 mL×3). The combined organic layers were washed with brine, and then dried over anhydrous Na$_2$SO$_4$ and then concentrated to give crude 1-cyclopropyl-2-(3,4-dimethoxyphenyl)ethanone (2.53 g) as yellow oil which was used for the next step without purification.

Step 2: Preparation of 1-cyclopropyl-2-(3,4-dimethoxyphenyl)ethanamine

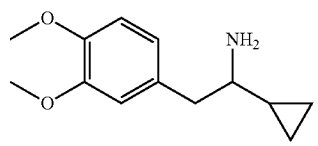 [SMILES: COc1ccc(CC(N)C2CC2)cc1OC]

To a mixture of crude 1-cyclopropyl-2-(3,4-dimethoxyphenyl)ethanamine (2.53 g, 10 mmol) and ammonium acetate (11.6 g, 150 mmol) in CH$_3$OH (30 mL) was added NaBH$_3$CN (1.26 g, 20 mmol). The resultant mixture was stirred at room temperature overnight. The reaction mixture was basified by 2 M aqueous NaOH solution to pH 12-14 and then extracted with CH$_2$Cl$_2$ (50 mL×3). The combined organic layers were acidified by 1 M hydrochloric acid to pH 2. The separated aqueous layer was basified by 2 M aqueous NaOH solution to pH 12-14, then extracted with CH$_2$Cl$_2$ (60 mL×3). The combined organic layers were washed with brine, and then dried over anhydrous Na$_2$SO$_4$ and then concentrated to give 1-cyclopropyl-2-(3,4-dimethoxyphenyl)ethanamine (1.44 g) as yellow oil which was directly used for the next step without further purification.

Step 3: Preparation of N-[1-cyclopropyl-2-(3,4-dimethoxyphenyl)ethyl]formamide

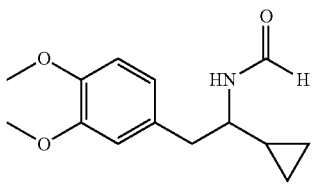 [SMILES: COc1ccc(CC(NC=O)C2CC2)cc1OC]

A solution of 1-cyclopropyl-2-(3,4-dimethoxyphenyl) ethanamine (1.44 g, 6.5 mmol) in ethyl formate (15 mL) and 1,4-dioxane (15 mL) was heated to 90° C. for 16 hours. After removing the solvent, N-[1-cyclopropyl-2-(3,4-dimethoxyphenyl)ethyl]formamide (1.69 g) was obtained as yellow oil which was directly used for the next step without purification.

Step 4: Preparation of 3-cyclopropyl-6,7-dimethoxy-3,4-dihydroisoquinoline

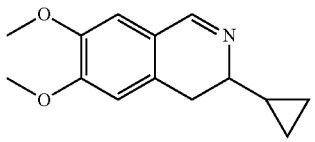 [SMILES: COc1cc2c(cc1OC)CC(C1CC1)N=C2]

To a solution of N-[1-cyclopropyl-2-(3,4-dimethoxyphenyl)ethyl]formamide (1.57 g, 6.3 mmol) in acetonitrile (15 mL) was added $POCl_3$ (1.16 g, 7.6 mmol). The resultant mixture was heated to 50° C. for 1.5 hours. After removing the solvent and excess $POCl_3$, yellow oil was obtained. The oil was dissolved in acetonitrile (10 mL), and then cooled to 0° C. Ammonium hydroxide was added dropwise at 0° C. to basify the mixture. The mixture was extracted with $CH_2Cl_2$ (60 mL×3), and the combined organic layers were washed with brine, and then dried over anhydrous $Na_2SO_4$ and then concentrated to give crude 3-cyclopropyl-6,7-dimethoxy-3,4-dihydroisoquinoline (1.32 g) as yellow oil which was directly used for the next step without purification.

Step 5: Preparation of 6-cyclopropyl-9,10-dimethoxy-2-oxo-6,7-dihydrobenzo[a]quinolizine-3-carboxylic acid

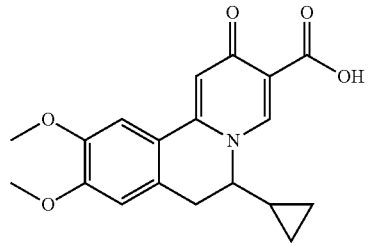 [SMILES: COc1cc2c(cc1OC)-c1cc(=O)c(C(=O)O)cn1C(C1CC1)C2]

To a solution of 3-cyclopropyl-6,7-dimethoxy-3,4-dihydroisoquinoline (231 mg, 1 mmol) and ethyl 2-(dimethylaminomethylene)-3-oxo-butanoate (204 mg, 1.1 mmol) in DMSO (2 mL) was added 5 M HCl in dioxane (40 µL, 0.2 mmol). The resultant mixture was heated to 130° C. for 1 hour under microwave. After the mixture was cooled to room temperature, $MnO_2$ (445 mg, 5 mmol) was added and the resultant mixture was heated to 140° C. for 5 hours. The reaction mixture was cooled to room temperature, and then diluted with $CH_2Cl_2$ (20 mL) and $H_2O$ (20 mL). The mixture was extracted with $CH_2Cl_2$ (50 mL×3). The combined organic layers were washed with brine, and then dried over anhydrous $Na_2SO_4$ and then concentrated. The residue was purified by flash column chromatography to afford 6-cyclopropyl-9,10-dimethoxy-2-oxo-6,7-dihydrobenzo[a]quinolizine-3-carboxylic acid (25 mg) as a yellow solid. $^1H$ NMR (400 MHz, $CDCl_3$): δ 8.62 (s, 1H), 7.23 (s, 1H), 7.12 (s, 1H), 6.82 (s, 1H), 4.00 (s, 3H), 3.98 (s, 3H), 3.47-3.37 (m, 2H), 3.15-3.06 (m, 1H), 1.19-1.09 (m, 1H), 0.77-0.66 (m, 2H), 0.65-0.56 (m, 1H), 0.50-0.41 (m, 1H). MS obsd. ($ESI^+$) $[(M+H)^+]$: 342.

Example 98: 6-isopropyl-9,10-dimethoxy-2-oxo-6,7-dihydrobenzo[a]quinolizine-3-carboxylic acid

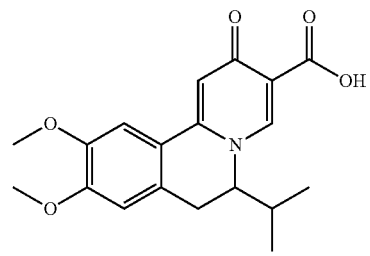 [SMILES: COc1cc2c(cc1OC)-c1cc(=O)c(C(=O)O)cn1C(C(C)C)C2]

Step 1: Preparation of 1-(3,4-dimethoxyphenyl)-3-methyl-butan-2-one

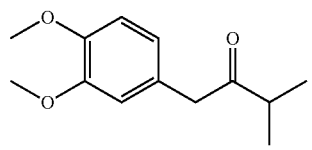 [SMILES: COc1ccc(CC(=O)C(C)C)cc1OC]

To a mixture of 4-bromo-1,2-dimethoxy-benzene (2.17 g, 10 mmol), tris(dibenzylideneacetone)dipalladium(0) (92 mg, 0.1 mmol), 9,9-dimethyl-4,5-bis(diphenylphosphino) xanthene (116 mg, 0.2 mmol) and t-BuONa (1.25 g, 13 mmol) in THF (10 mL) was added 3-methylbutan-2-one (1.03 g, 12 mmol). The resultant mixture was heated at 70° C. overnight under argon atmosphere. After being cooled to room temperature, the mixture was diluted with EtOAc (20 mL) and $H_2O$ (30 mL), and then extracted with EtOAc (50 mL×3). The combined organic layers were washed with brine, and then dried over anhydrous $Na_2SO_4$ and then concentrated. The residue was purified by flash column chromatography to afford 1-(3,4-dimethoxyphenyl)-3-methyl-butan-2-one (1.45 g) which was directly used for the next step without further purification.

Step 2: Preparation of 1-(3,4-dimethoxyphenyl)-3-methyl-butan-2-amine

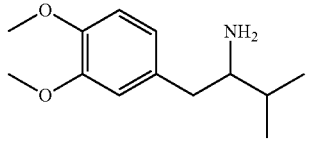 [SMILES: COc1ccc(CC(N)C(C)C)cc1OC]

To a mixture of 1-(3,4-dimethoxyphenyl)-3-methyl-butan-2-one (1.45 g, 6.5 mmol) and ammonium acetate (7.55 g, 98 mmol) in CH$_3$OH (15 mL) was added NaBH$_3$CN (819 mg, 13 mmol). The resultant mixture was stirred at room temperature overnight. The reaction mixture was basified by 2 M NaOH solution to pH 12-14 and then extracted with CH$_2$Cl$_2$ (50 mL×3). The combined organic layers were acidified by 1 M HCl aqueous solution to pH 2. The separated aqueous layer was basified by 2 M NaOH aqueous solution to pH 12-14, and then extracted with CH$_2$Cl$_2$ (60 mL×3). The combined organic layers were washed with brine, and then dried over anhydrous Na$_2$SO$_4$ and concentrated to give 1-(3,4-dimethoxyphenyl)-3-methyl-butan-2-amine (1.19 g) as yellow oil which was directly used for the next step without further purification.

Step 3: Preparation of N-[1-[(3,4-dimethoxyphenyl)methyl]-2-methyl-propyl]formamide

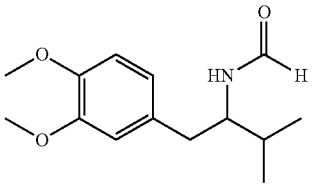 [SMILES: COc1ccc(CC(NC=O)C(C)C)cc1OC]

A solution of 1-(3,4-dimethoxyphenyl)-3-methyl-butan-2-amine (1.19 g, 5.3 mmol) in ethyl formate (6 mL) and 1,4-dioxane (6 mL) was heated to 90° C. for 16 hours. After removing the solvent, N-[1-[(3,4-dimethoxyphenyl) methyl]-2-methyl-propyl]formamide (845 mg) was obtained as yellow oil which was directly used for the next step without purification.

Step 4: Preparation of 3-isopropyl-6,7-dimethoxy-3,4-dihydroisoquinoline

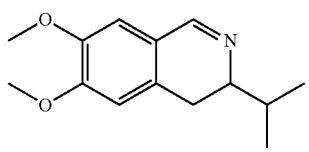 [SMILES: COc1cc2c(cc1OC)CC(C(C)C)N=C2]

To a solution of N-[1-[(3,4-dimethoxyphenyl)methyl]-2-methyl-propyl]formamide (845 g, 3.4 mmol) in acetonitrile (10 mL) was added POCl$_3$ (627 mg, 4.1 mmol). The resultant mixture was heated to 50° C. for 1 hour and then concentrated. The residue was dissolved in acetonitrile (10 mL), and then cooled to 0° C. Ammonium hydroxide was added dropwise at 0° C. to basify the mixture. The mixture was extracted with CH$_2$Cl$_2$ (50 mL×3), and the combined organic layers were washed with brine, and then dried over anhydrous Na$_2$SO$_4$ and then concentrated to give crude 3-isopropyl-6,7-dimethoxy-3,4-dihydroisoquinoline (727 mg) as yellow oil which was directly used for the next step without purification.

Step 5: Preparation of 6-isopropyl-9,10-dimethoxy-2-oxo-6,7-dihydrobenzo[a]quinolizine-3-carboxylic acid

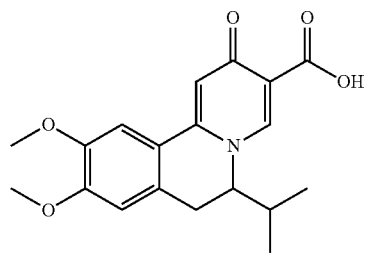 [SMILES: COc1cc2c(cc1OC)-c1cc(=O)c(C(=O)O)cn1C(C(C)C)C2]

To a solution of 3-isopropyl-6,7-dimethoxy-3,4-dihydroisoquinoline (280 mg, 1.2 mmol) and ethyl 2-(dimethylaminomethylene)-3-oxo-butanoate (333 mg, 1.8 mmol) in DMSO (2 mL) was added 5 M HCl in dioxane (50 µL, 0.24 mmol). The resultant mixture was heated at 130° C. for 4 hours under microwave. After the mixture was cooled to room temperature, MnO$_2$ (445 mg, 5 mmol) was added and the mixture was heated at 130° C. for 8 hours. The reaction mixture was cooled to room temperature, and then diluted with CH$_2$Cl$_2$ (20 mL) and H$_2$O (20 mL), and then extracted with CH$_2$Cl$_2$ (50 mL×3). The combined organic layers were washed with brine, and then dried over anhydrous Na$_2$SO$_4$ and then concentrated. The residue was purified by flash column chromatography to afford 6-isopropyl-9,10-dimethoxy-2-oxo-6,7-dihydrobenzo[a]quinolizine-3-carboxylic acid (78 mg) as a light-yellow solid. $^1$H NMR (400 MHz, DMSO-d$_6$): δ 8.78 (s, 1H), 7.52 (s, 1H), 7.46 (s, 1H), 7.08 (s, 1H), 4.45 (dd, 1H), 3.88 (s, 3H), 3.85 (s, 3H), 3.31-3.27 (m, 1H), 3.19-3.12 (m, 1H), 1.64 (m, 1H), 0.89 (d, 3H), 0.71 (d, 3H). MS obsd. (ESI$^+$) [(M+H)$^+$]: 344

Example 99 and 100

(+)-6-isopropyl-9,10-dimethoxy-2-oxo-6,7-dihydrobenzo[a]quinolizine-3-carboxylic acid and (−)-6-isopropyl-9,10-dimethoxy-2-oxo-6,7-dihydrobenzo[a]quinolizine-3-carboxylic acid

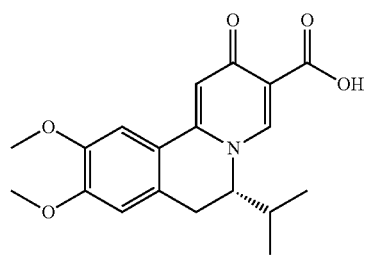

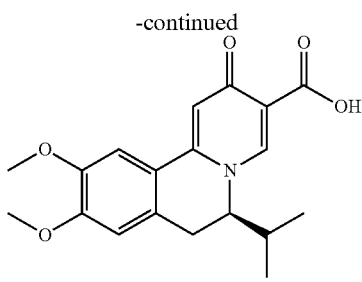

Separation of the racemic 6-isopropyl-9,10-dimethoxy-2-oxo-6,7-dihydrobenzo[a]quinolizine-3-carboxylic acid (60 mg) by chiral HPLC afforded (+)-6-isopropyl-9,10-dimethoxy-2-oxo-6,7-dihydrobenzo[a]quinolizine-3-carboxylic acid (20 mg) and (−)-6-isopropyl-9,10-dimethoxy-2-oxo-6,7-dihydrobenzo[a]quinolizine-3-carboxylic acid (20 mg).

Example 99

$^1$H NMR (400 MHz, DMSO-d$_6$): δ 8.78 (s, 1H), 7.52 (s, 1H), 7.46 (s, 1H), 7.08 (s, 1H), 4.45 (dd, 1H), 3.88 (s, 3H), 3.85 (s, 3H), 3.31-3.27 (m, 1H), 3.19-3.12 (m, 1H), 1.64 (m, 1H), 0.89 (d, 3H), 0.71 (d, 3H). MS obsd. (ESI$^+$) [(M+H)$^+$]: 344. [α]$_D^{20}$=+98.7° (0.075%, CH$_3$CN).

Example 100

$^1$H NMR (400 MHz, DMSO-d$_6$): δ 8.78 (s, 1H), 7.52 (s, 1H), 7.46 (s, 1H), 7.08 (s, 1H), 4.45 (dd, 1H), 3.88 (s, 3H), 3.85 (s, 3H), 3.31-3.27 (m, 1H), 3.19-3.12 (m, 1H), 1.64 (m, 1H), 0.89 (d, 3H), 0.71 (d, 3H). MS obsd. (ESI$^+$) [(M+H)$^+$]: 344.

Example 101: 6-isobutyl-9,10-dimethoxy-2-oxo-6,7-dihydrobenzo[a]quinolizine-3-carboxylic acid

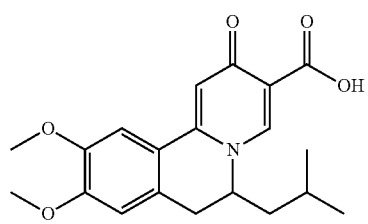 [SMILES: COc1cc2c(cc1OC)-c1cc(=O)c(C(=O)O)cn1C(CC(C)C)C2]

Step 1: Preparation of 1-(3,4-dimethoxyphenyl)-4-methyl-pentan-2-one

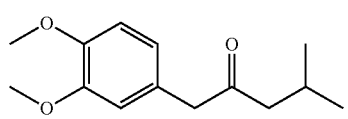

To a mixture of 4-bromo-1,2-dimethoxy-benzene (2.17 g, 10 mmol), tris(dibenzylideneacetone)dipalladium(0) (92 mg, 0.1 mmol), 9,9-dimethyl-4,5-bis(diphenylphosphino)xanthene (116 mg, 0.2 mmol) and t-BuONa (1.25 g, 13 mmol) in THF (10 mL) was added 4-methylpentan-2-one (1.2 g, 12 mmol). The resultant mixture was heated to 70° C. overnight under argon atmosphere. After being cooled to room temperature, the mixture was diluted with EtOAc (20 mL) and H$_2$O (30 mL), and then extracted with EtOAc (50 mL×3).

The combined organic layers were washed with brine, and then dried and then concentrated. The residue was purified by flash chromatography to afford 1-(3,4-dimethoxyphenyl)-4-methyl-pentan-2-one (1.12 g) which was directly used for the next step without further purification.

Step 2: Preparation of 1-(3,4-dimethoxyphenyl)-4-methyl-pentan-2-amine

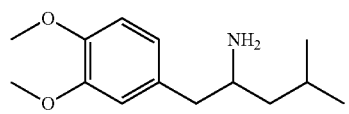

To a mixture of 1-(3,4-dimethoxyphenyl)-4-methyl-pentan-2-one (1.45 g, 4.8 mmol) and ammonium acetate (5.54 g, 72 mmol) in CH$_3$OH (15 mL) was added NaBH$_3$CN (605 mg, 9.6 mmol). The resultant mixture was stirred at room temperature overnight and then basified by 2 M NaOH aqueous solution to pH 12-14. The mixture was extracted with CH$_2$Cl$_2$ (50 mL×3), and the combined organic layers were acidified by 1 M hydrochloric acid to pH 2. The separated aqueous layer was basified by 2 M NaOH aqueous solution to pH 12-14, then extracted with CH$_2$Cl$_2$ (60 mL×3). The combined organic layers were washed with brine, and then dried over anhydrous Na$_2$SO$_4$, and then concentrated to give 1-(3,4-dimethoxyphenyl)-4-methyl-pentan-2-amine (879 mg) as yellow oil which was directly used for the next step without further purification.

Step 3: Preparation of N-[1-[(3,4-dimethoxyphenyl)methyl]-3-methyl-butyl]formamide

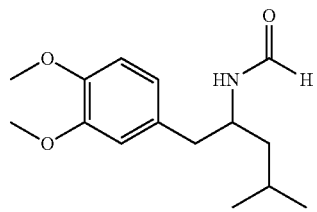 [SMILES: COc1ccc(CC(CC(C)C)NC=O)cc1OC]

A solution of 1-(3,4-dimethoxyphenyl)-4-methyl-pentan-2-amine (879 mg, 3.7 mmol) in ethyl formate (6 mL) and 1,4-dioxane (6 mL) was heated at 90° C. for 16 hours. After removing the solvent, N-[1-[(3,4-dimethoxyphenyl)methyl]-3-methyl-butyl]formamide (1.02 g) was obtained as yellow oil which was directly used for the next step without purification.

Step 4: Preparation of 3-isobutyl-6,7-dimethoxy-3,4-dihydroisoquinoline

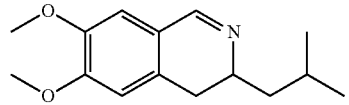 [SMILES: COc1cc2c(cc1OC)CC(CC(C)C)N=C2]

To a solution of N-[1-[(3,4-dimethoxyphenyl)methyl]-3-methyl-butyl]formamide (1.02 g, 3.8 mmol) in acetonitrile (10 mL) was added POCl₃ (704 mg, 4.6 mmol). The resultant mixture was heated to 50° C. for 1 hour and then concentrated. The residue was dissolved in acetonitrile (10 mL), and then cooled to 0° C. Ammonium hydroxide was added dropwise at 0° C. to basify the mixture. The mixture was extracted with CH₂Cl₂ (50 mL×3). The combined organic layers were washed with brine, and then dried over anhydrous Na₂SO₄ and concentrated to give crude 3-isobutyl-6,7-dimethoxy-3,4-dihydroisoquinoline (900 mg) as yellow oil which was directly used for the next step without purification.

Step 5: Preparation of 6-isobutyl-9,10-dimethoxy-2-oxo-6,7-dihydrobenzo[a]quinolizine-3-carboxylic acid

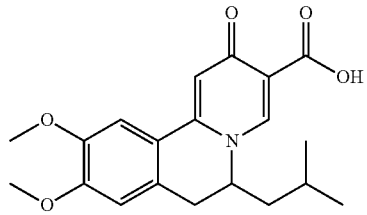 [SMILES: COc1cc2c(cc1OC)-c1cc(=O)c(C(=O)O)cn1C(CC(C)C)C2]

To a solution of 3-isobutyl-6,7-dimethoxy-3,4-dihydroisoquinoline (247 mg, 1 mmol) and ethyl 2-(dimethylaminomethylene)-3-oxo-butanoate (278 mg, 1.5 mmol) in DMSO (2 mL) was added 5N HCl in dioxane (40 μL, 0.2 mmol). The resultant mixture was heated at 130° C. for 4 hours under microwave. After the mixture was cooled to room temperature, MnO₂ (445 mg, 5 mmol) was added and the mixture was heated to 130° C. for 8 hours. The reaction mixture was cooled to room temperature, then diluted with CH₂Cl₂ (20 mL) and H₂O (20 mL) and then extracted with CH₂Cl₂ (50 mL×3). The combined organic layers were washed with brine, and then dried over anhydrous Na₂SO₄ and concentrated. The residue was purified by flash column chromatography to afford 6-isobutyl-9,10-dimethoxy-2-oxo-6,7-dihydrobenzo[a]quinolizine-3-carboxylic acid (63 mg) as a light-yellow solid. ¹H NMR (400 MHz, DMSO-d₆): δ 8.76 (s, 1H), 7.53 (s, 1H), 7.48 (s, 1H), 7.05 (s, 1H), 4.88 (m, 1H), 3.88 (s, 3H), 3.85 (s, 3H), 3.31 (d, 1H), 2.99 (d, 1H), 1.46 (qd, 1H), 1.34 (t, 2H), 0.88 (d, 3H), 0.83 (d, 3H). MS obsd. (ESI⁺) [(M+H)⁺]: 358.

Example 102 and 103

(+)-6-isobutyl-9,10-dimethoxy-2-oxo-6,7-dihydrobenzo[a]quinolizine-3-carboxylic acid and (−)-6-isobutyl-9,10-dimethoxy-2-oxo-6,7-dihydrobenzo[a]quinolizine-3-carboxylic acid

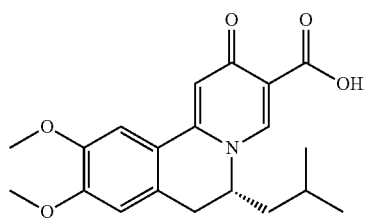

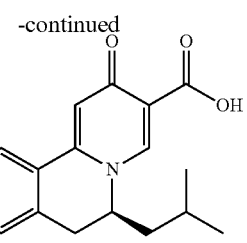

Separation of the racemic 6-isobutyl-9,10-dimethoxy-2-oxo-6,7-dihydrobenzo[a]quinolizine-3-carboxylic acid (40 mg) by chiral HPLC afforded (+)-6-isobutyl-9,10-dimethoxy-2-oxo-6,7-dihydrobenzo[a]quinolizine-3-carboxylic acid (9 mg) and (−)-6-isobutyl-9,10-dimethoxy-2-oxo-6,7-dihydrobenzo[a]quinolizine-3-carboxylic acid (9 mg).

Example 102

¹H NMR (400 MHz, DMSO-d₆): δ 8.76 (s, 1H), 7.53 (s, 1H), 7.48 (s, 1H), 7.05 (s, 1H), 4.88 (m, 1H), 3.88 (s, 3H), 3.85 (s, 3H), 3.31 (d, 1H), 2.99 (d, 1H), 1.46 (qd, 1H), 1.34 (t, 2H), 0.88 (d, 3H), 0.83 (d, 3H). MS obsd. (ESI⁺) [(M+H)⁺]: 358. [α]$_D^{20}$=+93.30 (0.075%, CH₃CN)

Example 103

¹H NMR (400 MHz, DMSO-d₆): δ 8.76 (s, 1H), 7.53 (s, 1H), 7.48 (s, 1H), 7.05 (s, 1H), 4.88 (m, 1H), 3.88 (s, 3H), 3.85 (s, 3H), 3.31 (d, 1H), 2.99 (d, 1H), 1.46 (qd, 1H), 1.34 (t, 2H), 0.88 (d, 3H), 0.83 (d, 3H). MS obsd. (ESI⁺) [(M+H)⁺]: 358.

Example 104: 10-chloro-6-isobutyl-9-(2-methoxyethoxy)-2-oxo-6,7-dihydrobenzo[a]quinolizine-3-carboxylic acid

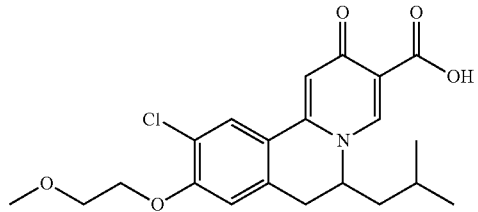 [SMILES: COCCOc1cc2c(cc1Cl)-c1cc(=O)c(C(=O)O)cn1C(CC(C)C)C2]

Step 1: Preparation of 4-bromo-1-chloro-2-(2-methoxyethoxy)benzene

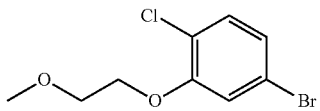

To a mixture of 5-bromo-2-chloro-phenol (28.2 g, 136 mmol) and K₂CO₃ (56.3 g, 408 mmol) in DMF (300 mL) was added 1-bromo-2-methoxy-ethane (56.7 g, 408 mmol). The resultant mixture was stirred at room temperature overnight, and then diluted with H₂O (1.5 L) and then extracted with EtOAc (400 mL×3). The combined organic layers were washed with water and brine, and then dried over anhydrous Na$_2$SO$_4$ and then concentrated to give 4-bromo-1-chloro-2-(2-methoxyethoxy)benzene (38.0 g) as yellow oil which was directly used for the next step without purification.

Step 2: Preparation of 1-[4-chloro-3-(2-methoxyethoxy)phenyl]-4-methyl-pentan-2-one

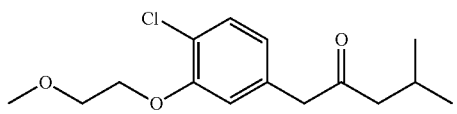 [SMILES: COCCOc1cc(CC(=O)CC(C)C)ccc1Cl]

To a mixture of 4-bromo-1-chloro-2-(2-methoxyethoxy) benzene (21.2 g, 80 mmol), tris(dibenzylideneacetone)dipalladium(0) (736 mg, 0.8 mmol), 9,9-dimethyl-4,5-bis(diphenylphosphino)xanthene (928 mg, 1.6 mmol) and t-BuONa (25.4 g, 264 mmol) in THF (200 mL) was added 4-methylpentan-2-one (24.0 g, 240 mmol). The resultant mixture was heated to 50° C. for 3 hours under argon atmosphere, and then cooled to room temperature and filtered. The filtrate was concentrated under reduced pressure. The residue was purified by column to afford 1-[4-chloro-3-(2-methoxyethoxy)phenyl]-4-methyl-pentan-2-one (16.9 g) as brown oil which was directly used for the next step without further purification.

Step 3: Preparation of 1-[4-chloro-3-(2-methoxyethoxy)phenyl]-4-methyl-pentan-2-amine

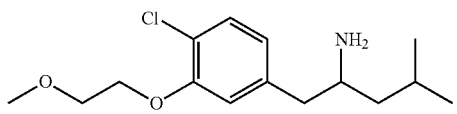 [SMILES: COCCOc1cc(CC(N)CC(C)C)ccc1Cl]

To a mixture of 1-[4-chloro-3-(2-methoxyethoxy)phenyl]-4-methyl-pentan-2-one (16.3 g, 57.4 mmol) and ammonium acetate (66.3 g, 861 mmol) in CH$_3$OH (160 mL) was added NaBH$_3$CN (7.23 g, 114.8 mmol) in portions at 0° C. The resultant mixture was stirred from 0° C. to room temperature overnight and then basified by 2 M NaOH aqueous solution to pH 12-14. The mixture was extracted with CH$_2$Cl$_2$ (300 mL×3), and the combined organic layers were washed with brine, and then dried over anhydrous Na$_2$SO$_4$ and then concentrated to give 1-[4-chloro-3-(2-methoxyethoxy)phenyl]-4-methyl-pentan-2-amine (15.5 g) as yellow oil which was directly used for the next step without purification.

Step 4: Preparation of N-[1-[[4-chloro-3-(2-methoxyethoxy)phenyl]methyl]-3-methyl-butyl]formamide

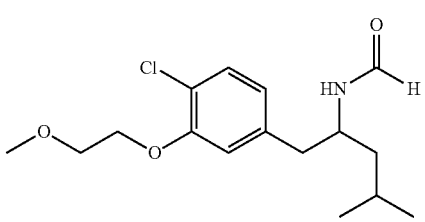 [SMILES: COCCOc1cc(CC(CC(C)C)NC=O)ccc1Cl]

A solution of 1-[4-chloro-3-(2-methoxyethoxy)phenyl]-4-methyl-pentan-2-amine (15.5 g, 54.4 mmol) and formic acid (1 mL) in ethyl formate (100 mL) was heated at 90° C. overnight, and then concentrated to give N-[1-[[4-chloro-3-(2-methoxyethoxy)phenyl]methyl]-3-methyl-butyl]formamide (16.3 g) as yellow oil which was directly used for the next step without purification.

Step 5: Preparation of 7-chloro-3-isobutyl-6-(2-methoxyethoxy)-3,4-dihydroisoquinoline

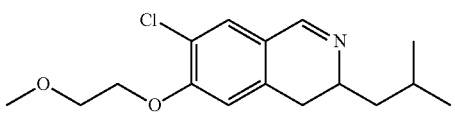 [SMILES: COCCOc1cc2c(cc1Cl)C=NC(CC(C)C)C2]

To a solution of N-[1-[[4-chloro-3-(2-methoxyethoxy)phenyl]methyl]-3-methyl-butyl]formamide (16.3 g, 52 mmol) in acetonitrile (150 mL) was added POCl$_3$ (9.49 g, 62.4 mmol). The resultant mixture was heated at 90° C. for 2 hours and then concentrated. The residue was dissolved in acetonitrile (50 mL), and then cooled to 0° C. Ammonium hydroxide was added dropwise at 0° C. to basify the mixture. The mixture was extracted with CH$_2$Cl$_2$ (200 mL×5), and the combined organic layers were washed with brine, and then dried over anhydrous Na$_2$SO$_4$ and then concentrated to give crude 7-chloro-3-isobutyl-6-(2-methoxyethoxy)-3,4-dihydroisoquinoline (13.6 g) as dark-green oil which was directly used for the next step without purification.

Step 6: Preparation of ethyl 10-chloro-6-isobutyl-9-(2-methoxyethoxy)-2-oxo-1,6,7,11b-tetrahydrobenzo[a]quinolizine-3-carboxylate

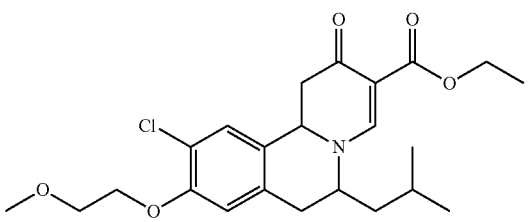

A mixture of 7-chloro-3-isobutyl-6-(2-methoxyethoxy)-3,4-dihydroisoquinoline (13.6 g, 46 mmol) and ethyl 2-(ethoxymethylene)-3-oxo-butanoate (25.7 g, 138 mmol) in EtOH (150 mL) was heated to 100° C. overnight. The mixture was concentrated, and the residue was purified by flash column chromatography to afford ethyl 10-chloro-6-isobutyl-9-(2-methoxyethoxy)-2-oxo-1,6,7,11b-tetrahydrobenzo[a]quinolizine-3-carboxylate (10.9 g) as red oil which was directly used in the next step without further purification.

Step 7: Preparation of ethyl 10-chloro-6-isobutyl-9-(2-methoxyethoxy)-2-oxo-6,7-dihydrobenzo[a]quinolizine-3-carboxylate

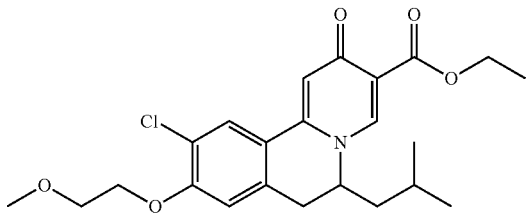 [SMILES: CCOC(=O)C1=CN2C(CC(C)C)Cc3cc(OCCOC)c(Cl)cc3C2CC1=O]

A mixture of ethyl 10-chloro-6-isobutyl-9-(2-methoxyethoxy)-2-oxo-1,6,7,11b-tetrahydrobenzo[a]quinolizine-3-carboxylate (10.9 g, 25 mmol) and p-chloranil (6.02 g, 25 mmol) in DME (100 mL) was heated to 70° C. for 3 hours under argon atmosphere. After being cooled to room temperature, the mixture was filtered to give ethyl 10-chloro-6-isobutyl-9-(2-methoxyethoxy)-2-oxo-6,7-dihydrobenzo[a]quinolizine-3-carboxylate (2.1 g). The filtrate was concentrated. The residue was dissolved in $CH_2Cl_2$ (150 mL) and then washed with saturated $NaHCO_3$ aqueous solution (100 mL×5). The separated organic layer was washed with water and brine, and then dried over anhydrous $Na_2SO_4$, and then concentrated. The residue was purified by flash column chromatography to afford ethyl 10-chloro-6-isobutyl-9-(2-methoxyethoxy)-2-oxo-6,7-dihydrobenzo[a]quinolizine-3-carboxylate (5.2 g) as brown oil which was directly used for the next step without further purification.

Step 8: Preparation of 10-chloro-6-isobutyl-9-(2-methoxyethoxy)-2-oxo-6,7-dihydrobenzo[a]quinolizine-3-carboxylic acid

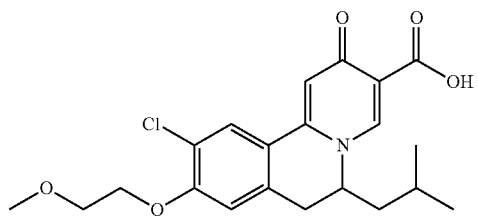 [SMILES: COCCOc1cc2c(cc1Cl)-c1cc(=O)c(C(=O)O)cn1C(CC(C)C)C2]

To a mixture of ethyl 10-chloro-6-isobutyl-9-(2-methoxyethoxy)-2-oxo-6,7-dihydrobenzo[a]quinolizine-3-carboxylate (2.1 g, 4.8 mmol) in $CH_3OH$ (32 mL) and $H_2O$ (8 mL) was added lithium hydroxide monohydrate (806 mg, 19.2 mmol). The resultant reaction mixture was stirred at room temperature for 3 hours. The mixture was diluted with $CH_2Cl_2$, and then acidified by 1 M hydrochloric acid to pH 2-3, and then extracted with $CH_2Cl_2$ (100 mL×3). The combined organic layers were washed with brine, and then dried over anhydrous $Na_2SO_4$ and then concentrated. The residue was washed with $EtOH/Et_2O$ to afford 10-chloro-6-isobutyl-9-(2-methoxyethoxy)-2-oxo-6,7-dihydrobenzo[a]quinolizine-3-carboxylic acid (1.71 g) as a yellow solid. $^1H$ NMR (400 MHz, DMSO-$d_6$): δ 8.79 (s, 1H), 8.21 (s, 1H), 7.43 (s, 1H), 7.28 (s, 1H), 4.91 (q, 1H), 4.35-4.24 (m, 2H), 3.73 (t, 2H), 3.42-3.36 (m, 1H), 3.35 (s, 3H), 3.06 (d, 1H), 1.48 (m, 1H), 1.33 (m, 2H), 0.87 (d, 3H), 0.84 (d, 3H). MS obsd. (ESI$^+$) [(M+H)$^+$]: 406.

Example 105 and 106

(+)-10-chloro-6-isobutyl-9-(2-methoxyethoxy)-2-oxo-6,7-dihydrobenzo[a]quinolizine-3-carboxylic acid and (−)-10-chloro-6-isobutyl-9-(2-methoxyethoxy)-2-oxo-6,7-dihydrobenzo[a]quinolizine-3-carboxylic acid

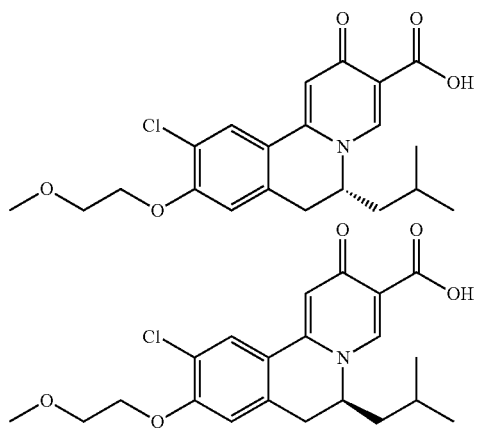

Separation of the racemic 10-chloro-6-isobutyl-9-(2-methoxyethoxy)-2-oxo-6,7-dihydrobenzo[a]quinolizine-3-carboxylic acid (1.7 g) by chiral HPLC afforded (+)-10-chloro-6-isobutyl-9-(2-methoxyethoxy)-2-oxo-6,7-dihydrobenzo[a]quinolizine-3-carboxylic acid (0.55 g) and (−)-10-chloro-6-isobutyl-9-(2-methoxyethoxy)-2-oxo-6,7-dihydrobenzo[a]quinolizine-3-carboxylic acid (0.56 g).

Example 105

$^1H$ NMR (400 MHz, DMSO-$d_6$): δ 8.79 (s, 1H), 8.21 (s, 1H), 7.43 (s, 1H), 7.28 (s, 1H), 4.91 (q, 1H), 4.35-4.24 (m, 2H), 3.73 (t, 2H), 3.42-3.36 (m, 1H), 3.35 (s, 3H), 3.06 (d, 1H), 1.48 (m, 1H), 1.33 (m, 2H), 0.87 (d, 3H), 0.84 (d, 3H). MS obsd. (ESI$^+$) [(M+H)$^+$]: 406. [α]$_D$20=+121.2° (0.115%, MeOH).

Example 106

$^1H$ NMR (400 MHz, DMSO-$d_6$): δ 8.79 (s, 1H), 8.21 (s, 1H), 7.43 (s, 1H), 7.28 (s, 1H), 4.91 (q, 1H), 4.35-4.24 (m, 2H), 3.73 (t, 2H), 3.42-3.36 (m, 1H), 3.35 (s, 3H), 3.06 (d, 1H), 1.48 (m, 1H), 1.33 (m, 2H), 0.87 (d, 3H), 0.84 (d, 3H). MS obsd. (ESI$^+$) [(M+H)$^+$]: 406.

Example 107: 10-chloro-6-isopropyl-9-(2-methoxyethoxy)-2-oxo-6,7-dihydrobenzo[a]quinolizine-3-carboxylic acid

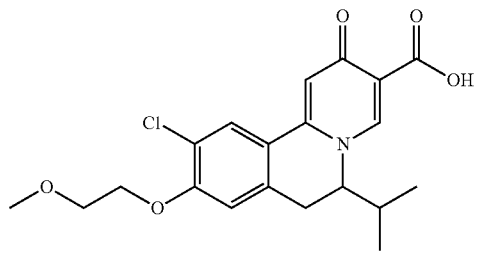

Step 1: Preparation of 1-[4-chloro-3-(2-methoxy-ethoxy)phenyl]-3-methyl-butan-2-one

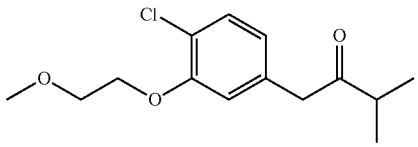

To a mixture of 4-bromo-1-chloro-2-(2-methoxyethoxy)benzene (60.0 g, 0.23 mol), tris(dibenzylideneacetone)dipalladium (0) (4.14 g, 0.005 mol), 9,9-dimethyl-4,5-bis(diphenylphosphino)xanthene (5.23 g, 0.009 mol) and t-BuONa (39.1 g, 0.41 mol) in THF (600 mL) was added 3-methylbutan-2-one (29.2 g, 0.34 mol). The resultant mixture was heated at 50° C. for 6 hours under nitrogen atmosphere, and then cooled to room temperature and filtered.

The filtrate was concentrated under reduced pressure. The residue was purified by column chromatography to afford 1-[4-chloro-3-(2-methoxyethoxy)phenyl]-3-methyl-butan-2-one (46.0 g) as yellow oil which was directly used for the next step without further purification.

Step 2: Preparation of 1-[4-chloro-3-(2-methoxy-ethoxy)phenyl]-3-methyl-butan-2-amine

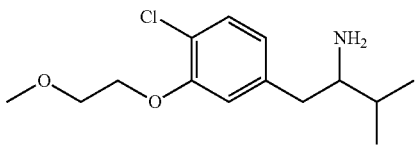

A mixture of 1-[4-chloro-3-(2-methoxyethoxy)phenyl]-3-methyl-butan-2-one (46.0 g, 0.17 mol) and ammonium acetate (91.7 g, 1.19 mol) in CH$_3$OH (160 mL) was stirred at room temperature for 1 hour. NaBH$_3$CN (13.9 g, 0.22 mol) was added in portions. The resultant mixture was stirred at room temperature overnight. The reaction was quenched by saturated NH$_4$Cl aqueous solution and then concentrated. The residue was diluted with EtOAc and then washed with brine. The organic phase was separated, and then dried over anhydrous Na$_2$SO$_4$ and then concentrated to give 1-[4-chloro-3-(2-methoxyethoxy)phenyl]-3-methyl-butan-2-amine (50.0 g) as a crude product and used directly in the next step without purification.

Step 3: Preparation of N-[1-[[4-chloro-3-(2-methoxyethoxy)phenyl]methyl]-2-methyl-propyl]formamide

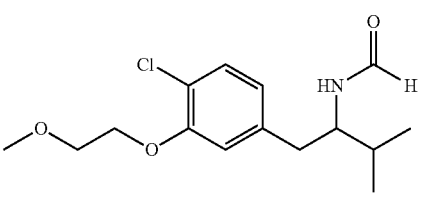 [SMILES: COCCOc1cc(CC(NC=O)C(C)C)ccc1Cl]

A solution of 1-[4-chloro-3-(2-methoxyethoxy)phenyl]-3-methyl-butan-2-amine (50.0 g, 0.18 mol) and formic acid (33.9 g, 0.72 mol) in 1,4-dioxane (500 mL) was refluxed overnight and then concentrated. The residue was purified by the flash column chromatography to afford N-[1-[[4-chloro-3-(2-methoxyethoxy)phenyl]methyl]-2-methyl-propyl]formamide (30.9 g) as a white solid.

Step 4: Preparation of 7-chloro-3-isopropyl-6-(2-methoxyethoxy)-3,4-dihydroisoquinoline

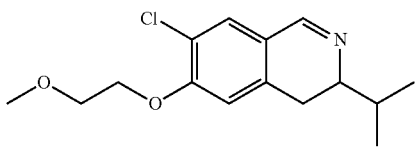

A stirred solution of N-[1-[[4-chloro-3-(2-methoxyethoxy)phenyl]methyl]-2-methyl-propyl]formamide (30.9 g, 0.10 mol) in CH$_2$Cl$_2$ (300 mL) was cooled to 0° C., and then POCl$_3$ (19.00 g, 0.12 mol) was added slowly. The reaction was warmed up to room temperature, and then heated at 50° C. for 2 hours, and then poured into a stirred mixture of NH$_4$OH and CH$_2$Cl$_2$ (50 mL). The separated organic phase was washed with brine, and then dried over anhydrous Na$_2$SO$_4$ and then concentrated. The residue was purified by flash column chromatography to afford 7-chloro-3-isopropyl-6-(2-methoxyethoxy)-3,4-dihydroisoquinoline (11.08 g) as a brown solid.

Step 5: Preparation of ethyl 10-chloro-6-isopropyl-9-(2-methoxyethoxy)-2-oxo-1,6,7,11b-tetrahydrobenzo[a]quinolizine-3-carboxylate

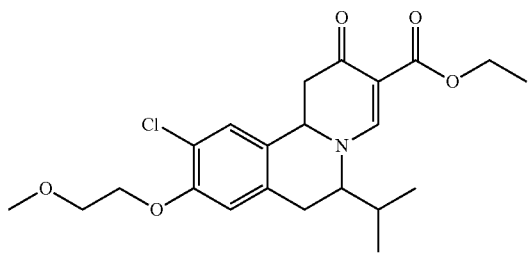 [SMILES: CCOC(=O)C1=CN2C(CC1=O)c1cc(Cl)c(OCCOC)cc1CC2C(C)C]

A mixture of 7-chloro-3-isopropyl-6-(2-methoxyethoxy)-3,4-dihydroisoquinoline (11.0 g, 40 mmol) and ethyl 2-(ethoxymethylene)-3-oxo-butanoate (22.3 g, 120 mmol) in EtOH (100 mL) was refluxed overnight. The mixture was concentrated, and the residue was purified by flash column chromatography to afford ethyl 10-chloro-6-isopropyl-9-(2-methoxyethoxy)-2-oxo-1,6,7,11b-tetrahydrobenzo[a]quinolizine-3-carboxylate (14.2 g) as dark-red oil which was directly used in the next step without further purification.

Step 6: Preparation of ethyl 10-chloro-6-isopropyl-9-(2-methoxyethoxy)-2-oxo-6,7-dihydrobenzo[a]quinolizine-3-carboxylate

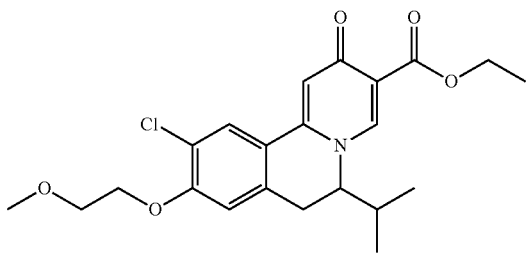 [SMILES: CCOC(=O)c1cn2c(cc1=O)-c1cc(Cl)c(OCCOC)cc1CC2C(C)C]

A mixture of ethyl 10-chloro-6-isopropyl-9-(2-methoxyethoxy)-2-oxo-1,6,7,11b-tetrahydrobenzo[a]quinolizine-3-carboxylate (14.2 g, 34 mmol) and p-chloranil (6.64 g, 27 mmol) in DME (100 mL) was heated to 70° C. for 3 hours under argon atmosphere. After being cooled to room temperature, the mixture was partitioned between $CH_2Cl_2$ (500 mL) and $H_2O$ (200 mL). The organic layer was washed with saturated $NaHCO_3$ (200 mL×6) and brine, and then dried over anhydrous $Na_2SO_4$ and then concentrated to give brown solid. To the brown solid was added EtOAc, then the resultant precipitation was filtered to give ethyl 10-chloro-6-isopropyl-9-(2-methoxyethoxy)-2-oxo-6,7-dihydrobenzo[a]quinolizine-3-carboxylate (7.26 g) as a pale solid. The mother liquid was concentrated under reduced pressure to afford additional crude ethyl 10-chloro-6-isopropyl-9-(2-methoxyethoxy)-2-oxo-6,7-dihydrobenzo[a]quinolizine-3-carboxylate (4.5 g) as dark oil.

Step 7: Preparation of 10-chloro-6-isopropyl-9-(2-methoxyethoxy)-2-oxo-6,7-dihydrobenzo[a]quinolizine-3-carboxylic acid

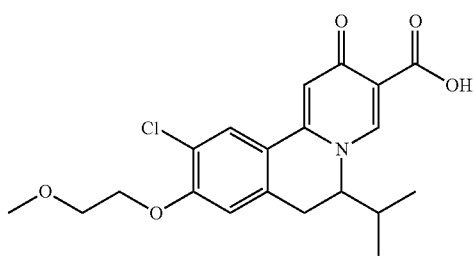 [SMILES: COCCOc1cc2c(cc1Cl)-c1cc(=O)c(C(=O)O)cn1C(C(C)C)C2]

To a mixture of ethyl 10-chloro-6-isopropyl-9-(2-methoxyethoxy)-2-oxo-6,7-dihydrobenzo[a]quinolizine-3-carboxylate (7.26 g, 17.3 mmol) in $CH_3OH$ (60 mL) and $H_2O$ (15 mL) was added lithium hydroxide monohydrate (2.91 g, 69.2 mmol). The resultant mixture was stirred at room temperature overnight, then acidified by 1 M hydrochloric acid to pH 2-3. The resultant suspension was stirred at room temperature for 15 minutes and then filtered. The filter cake was dried to give 10-chloro-6-isopropyl-9-(2-methoxyethoxy)-2-oxo-6,7-dihydrobenzo[a]quinolizine-3-carboxylic acid (6.63 g) as a yellow solid. $^1$H NMR (400 MHz, DMSO-$d_6$): δ 8.80 (s, 1H), 8.20 (s, 1H), 7.41 (s, 1H), 7.32 (s, 1H), 4.49 (dd, 1H), 4.36-4.23 (m, 2H), 3.73 (t, 2H), 3.42-3.34 (m, 1H), 3.35 (s, 3H), 3.19 (d, 1H), 1.60 (td, 1H), 0.88 (d, 3H), 0.71 (d, 3H). MS obsd. (ESI$^+$) [(M+H)$^+$]: 392.

Example 108 and 109

(+)-10-chloro-6-isopropyl-9-(2-methoxyethoxy)-2-oxo-6,7-dihydrobenzo[a]quinolizine-3-carboxylic acid and (−)-10-chloro-6-isopropyl-9-(2-methoxyethoxy)-2-oxo-6,7-dihydrobenzo[a]quinolizine-3-carboxylic acid

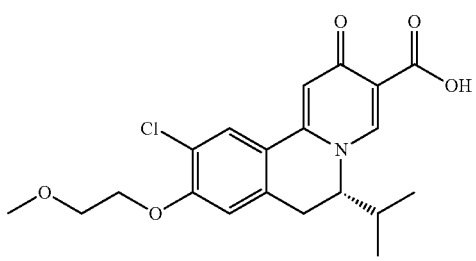 [SMILES: COCCOc1cc2c(cc1F)-c1cc(=O)c(C(=O)O)cn1C(C(C)C)C2]

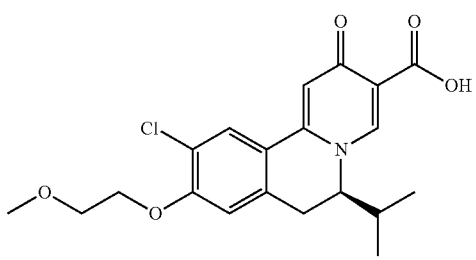

Separation of the racemic 10-chloro-6-isopropyl-9-(2-methoxyethoxy)-2-oxo-6,7-dihydrobenzo[a]quinolizine-3-carboxylic acid (2.0 g) by chiral HPLC afforded (+)-10-chloro-6-isopropyl-9-(2-methoxyethoxy)-2-oxo-6,7-dihydrobenzo[a]quinolizine-3-carboxylic acid (850 mg) and (−)-10-chloro-6-isopropyl-9-(2-methoxyethoxy)-2-oxo-6,7-dihydrobenzo[a]quinolizine-3-carboxylic acid (922 mg).

Example 108

$^1$H NMR (400 MHz, DMSO-$d_6$): δ 8.80 (s, 1H), 8.20 (s, 1H), 7.41 (s, 1H), 7.32 (s, 1H), 4.49 (dd, 1H), 4.36-4.23 (m, 2H), 3.73 (t, 2H), 3.42-3.34 (m, 1H), 3.35 (s, 3H), 3.19 (d, 1H), 1.60 (td, 1H), 0.88 (d, 3H), 0.71 (d, 3H). MS obsd. (ESI$^+$) [(M+H)$^+$]: 392. [α]$_D$20=+105.88° (0.085%, MeOH).

Example 109

$^1$H NMR (400 MHz, DMSO-$d_6$): δ 8.80 (s, 1H), 8.20 (s, 1H), 7.41 (s, 1H), 7.32 (s, 1H), 4.49 (dd, 1H), 4.36-4.23 (m, 2H), 3.73 (t, 2H), 3.42-3.34 (m, 1H), 3.35 (s, 3H), 3.19 (d, 1H), 1.60 (td, 1H), 0.88 (d, 3H), 0.71 (d, 3H). MS obsd. (ESI$^+$) [(M+H)$^+$]: 392.

Example 110: 10-fluoro-6-isopropyl-9-(2-methoxyethoxy)-2-oxo-6,7-dihydrobenzo[a]quinolizine-3-carboxylic acid

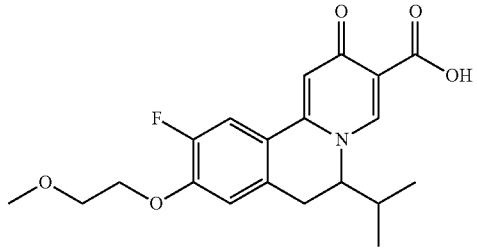

Step 1: Preparation of 4-bromo-1-fluoro-2-(2-methoxyethoxy)benzene

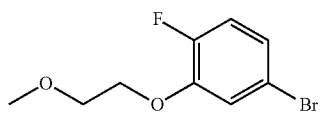

To a mixture of 5-bromo-2-fluoro-phenol (10 g, 52.4 mmol) in MeCN (100 mL) was added 1-bromo-2-methoxyethane (10.9 g, 78.5 mmol) and Cs$_2$CO$_3$ (34.1 g, 105 mmol). The resultant mixture was heated at 80° C. for 12 hours, and then cooled room temperature and filtered. The filtrate was concentrated under reduced pressure and the residue was purified by column chromatography to give 4-bromo-1-fluoro-2-(2-methoxyethoxy)benzene (12.2 g) as colorless oil.

Step 2: Preparation of 1-[4-fluoro-3-(2-methoxyethoxy)phenyl]-3-methyl-butan-2-one

To a mixture of 4-bromo-1-fluoro-2-(2-methoxyethoxy)benzene (11.2 g, 45 mmol), tris(dibenzylideneacetone)dipalladium(0) (823 mg, 0.899 mmol), 9,9-dimethyl-4,5-bis(diphenylphosphino)xanthene (1.04 g, 1.80 mmol) and t-BuONa (7.78 g, 80.9 mmol) in THF (100 mL) was added 3-methylbutan-2-one (5.81 g, 67.5 mmol). The resultant mixture was heated at 80° C. for 12 hours under nitrogen atmosphere, and then cooled to room temperature and filtered. The filtrate was concentrated under reduced pressure, and the residue was purified by column to afford 1-[4-fluoro-3-(2-methoxyethoxy)phenyl]-3-methyl-butan-2-one (6.6 g) as colorless oil which was directly used for the next step without further purification.

Step 3: Preparation of 1-[4-fluoro-3-(2-methoxyethoxy)phenyl]-3-methyl-butan-2-amine

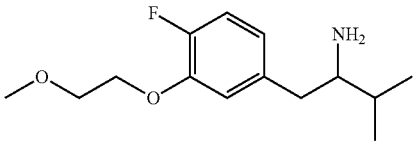 [SMILES: COCCOc1cc(CC(N)C(C)C)ccc1F]

A mixture of 1-[4-fluoro-3-(2-methoxyethoxy)phenyl]-3-methyl-butan-2-one (5.3 g, 20.8 mmol) and ammonium acetate (11.25 g, 146 mmol) in CH$_3$OH (50 mL) was stirred at room temperature for 1 hour. Then NaBH$_3$CN (1.7 g, 27.1 mmol) was added at 0° C., and the resultant mixture was stirred at room temperature for 12 hours, and then concentrated. The residue was partitioned between H$_2$O (20 mL) and CH$_2$Cl$_2$ (100 mL). The organic layer was washed with brine (20 mL), and then dried over anhydrous Na$_2$SO$_4$ and then concentrated under reduced pressure to afford 1-[4-fluoro-3-(2-methoxyethoxy)phenyl]-3-methyl-butan-2-amine (6 g, crude) as yellow oil.

Step 4: Preparation of N-[1-[[4-fluoro-3-(2-methoxyethoxy)phenyl]methyl]-2-methyl-propyl]formamide

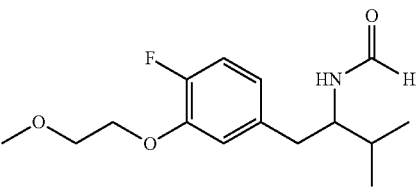 [SMILES: COCCOc1cc(CC(NC=O)C(C)C)ccc1F]

A solution of 1-[4-fluoro-3-(2-methoxyethoxy)phenyl]-3-methyl-butan-2-amine (7.3 g, 28.6 mmol) and formic acid (5.26 g, 114 mmol) in 1,4-dioxane (80 mL) was heated to reflux for 12 hours. The reaction solution was diluted with H$_2$O (50 mL) and then extracted with EtOAc (50 mL×3). The organic layers were dried over anhydrous Na$_2$SO$_4$ and then concentrated. The residue was purified by column chromatography to give N-[1-[[4-fluoro-3-(2-methoxyethoxy)phenyl]methyl]-2-methyl-propyl]formamide (4.8 g) as a yellow solid.

Step 5: Preparation of 7-fluoro-3-isopropyl-6-(2-methoxyethoxy)-3,4-dihydroisoquinoline

A stirred solution of N-[1-[[4-fluoro-3-(2-methoxyethoxy)phenyl]methyl]-2-methyl-propyl]formamide (4.0 g, 14.1 mmol) in CH$_2$Cl$_2$ (40 mL) was cooled to 0° C., and then POCl$_3$ (6.56 g, 43.1 mmol) was added slowly. The reaction mixture was refluxed for 2 hours. After being cooled down, the mixture was poured into a solution of NH₄OH (40 mL) in H₂O (200 mL), and then stirred for 0.5 hour. The mixture was extracted with CH₂Cl₂ (200 mL). The organic layer was washed with brine (200 mL), and then dried over anhydrous Na₂SO₄ and then concentrated. The residue was purified by column chromatography to give 7-fluoro-3-isopropyl-6-(2-methoxyethoxy)-3,4-dihydroisoquinoline (1.16 g) as colorless oil.

Step 6: Preparation of ethyl 10-fluoro-6-isopropyl-9-(2-methoxyethoxy)-2-oxo-1,6,7,11b-tetrahydrobenzo[a]quinolizine-3-carboxylate

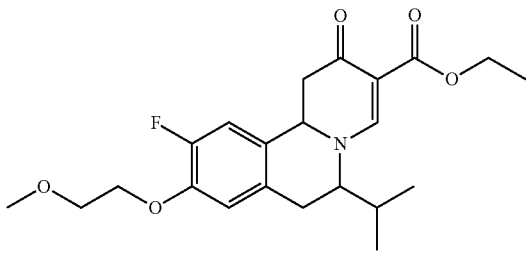

To a mixture of 7-fluoro-3-isopropyl-6-(2-methoxyethoxy)-3,4-dihydroisoquinoline (1.06 g, 4 mmol) and ethyl 2-(dimethylaminomethylene)-3-oxo-butanoate (1.11 g, 6 mmol) in DMSO (8 mL) was added 4 M HCl in dioxane (0.3 mL, 1.2 mmol). The resultant mixture was heated at 130° C. for 5 hours under microwave. The reaction was cooled to room temperature, and then diluted with EtOAc and H₂O. The separated aqueous layer was extracted with EtOAc. The combined organic layers were washed with brine, and then dried over anhydrous Na₂SO₄ and then concentrated to give crude ethyl 10-fluoro-6-isopropyl-9-(2-methoxyethoxy)-2-oxo-1,6,7,11b-tetrahydrobenzo[a]quinolizine-3-carboxylate (1.56 g) as brown oil which was directly used in the next step without purification.

Step 7: Preparation of ethyl 10-fluoro-6-isopropyl-9-(2-methoxyethoxy)-2-oxo-6,7-dihydrobenzo[a]quinolizine-3-carboxylate

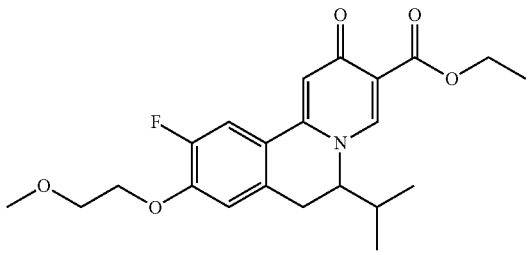

A mixture of crude ethyl 10-fluoro-6-isopropyl-9-(2-methoxyethoxy)-2-oxo-1,6,7,11b-tetrahydrobenzo[a]quinolizine-3-carboxylate (1.57 g, 4 mmol) and p-chloranil (787 mg, 3.2 mmol) in DME (10 mL) was heated at 70° C. for 3 hours under argon atmosphere. After being cooled to room temperature, the resultant precipitation was filtered. The filter cake was dissolved in CH₃OH, then concentrated under reduced pressure to give crude ethyl 10-fluoro-6-isopropyl-9-(2-methoxyethoxy)-2-oxo-6,7-dihydrobenzo[a]quinolizine-3-carboxylate (757 mg) as a yellow solid.

Step 8: Preparation of 10-fluoro-6-isopropyl-9-(2-methoxyethoxy)-2-oxo-6,7-dihydrobenzo[a]quinolizine-3-carboxylic acid

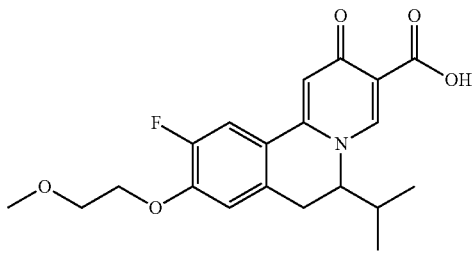 [SMILES: COCCOc1cc2c(cc1F)-c1cc(=O)c(C(=O)O)cn1C(C(C)C)C2]

To a mixture of ethyl 10-fluoro-6-isopropyl-9-(2-methoxyethoxy)-2-oxo-6,7-dihydrobenzo[a]quinolizine-3-carboxylate (757 mg, 1.87 mmol) in CH₃OH (8 mL) and H₂O (2 mL) was added lithium hydroxide monohydrate (314 mg, 7.48 mmol). The resultant mixture was stirred at room temperature for 1 hour, and then acidified by 1 M hydrochloric acid to pH 2-3.

The resulting precipitation was filtered. The filter cake was dissolved in CH₂Cl₂ and then concentrated to give 10-fluoro-6-isopropyl-9-(2-methoxyethoxy)-2-oxo-6,7-dihydrobenzo[a]quinolizine-3-carboxylic acid (489 mg) as a yellow solid. ¹H NMR (400 MHz, DMSO-d₆): δ 8.80 (s, 1H), 8.03 (d, 1H), 7.37 (s, 1H), 7.33 (d, 1H), 4.48 (dd, 1H), 4.35-4.22 (m, 2H), 3.72 (t, 2H), 3.31-3.38 (m, 1H), 3.33 (s, 3H), 3.24-3.16 (m, 1H), 1.62 (td, 1H), 0.88 (d, 3H), 0.71 (d, 3H). MS obsd. (ESI⁺) [(M+H)⁺]: 376.

Example 111: 11-chloro-6-isopropyl-9-(2-methoxyethoxy)-2-oxo-6,7-dihydrobenzo[a]quinolizine-3-carboxylic acid

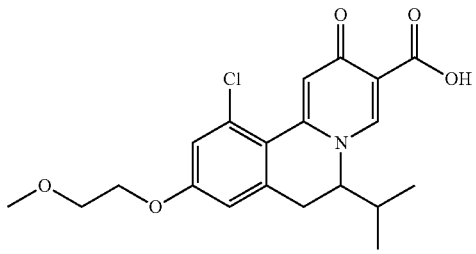 [SMILES: COCCOc1cc(Cl)c2c(c1)CC(C(C)C)n1cc(C(=O)O)c(=O)cc1-2]

Step 1: Preparation of 1-bromo-3-chloro-5-(2-methoxyethoxy)benzene

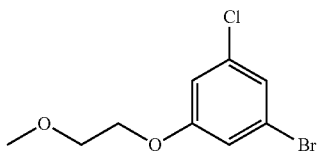

To a mixture of 3-bromo-5-chloro-phenol (14.0 g, 67.5 mmol) in MeCN (150 mL) was added 1-bromo-2-methoxyethane (12.6 g, 90.7 mmol) and Cs₂CO₃ (34.1 g, 105 mmol). The resultant mixture was heated at 80° C. for 12 hours, and then cooled to room temperature and then filtered. The filtrate was evaporated under reduced pressure, and the residue was purified by column chromatography to give 1-bromo-3-chloro-5-(2-methoxyethoxy)benzene (17.0 g) as colorless oil.

Step 2: Preparation of 1-[3-chloro-5-(2-methoxyethoxy)phenyl]-3-methyl-butan-2-one

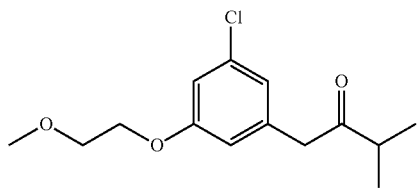 [SMILES: COCCOc1cc(Cl)cc(CC(=O)C(C)C)c1]

To a mixture of 1-bromo-3-chloro-5-(2-methoxyethoxy)benzene (14.8 g, 55.7 mmol), tris(dibenzylideneacetone)dipalladium(0) (1.02 g, 1.11 mmol), 9,9-dimethyl-4,5-bis(diphenylphosphino)xanthene (1.29 g, 2.22 mmol) and t-BuONa (9.62 g, 100 mmol) in THF (150 mL) was added 3-methylbutan-2-one (7.18 g, 83.4 mmol). The resultant mixture was heated at 50° C. for 12 hours under nitrogen atmosphere, and then cooled to room temperature and then filtered. The filtrate was concentrated under reduced pressure, and the residue was purified by column chromatography to afford 1-[3-chloro-5-(2-methoxyethoxy)phenyl]-3-methyl-butan-2-one (13.0 g) as colorless oil which was directly used for the next step without further purification.

Step 3: Preparation of 1-[3-chloro-5-(2-methoxyethoxy)phenyl]-3-methyl-butan-2-amine

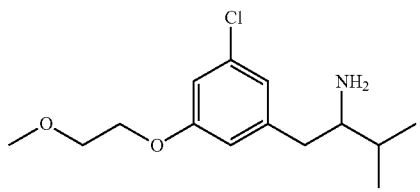 [SMILES: COCCOc1cc(Cl)cc(CC(N)C(C)C)c1]

A mixture of 1-[3-chloro-5-(2-methoxyethoxy)phenyl]-3-methyl-butan-2-one (15.2 g, 56.1 mmol) and ammonium acetate (30.3 g, 393 mmol) in CH₃OH (150 mL) was stirred at room temperature for 1 hour. NaBH₃CN (4.59 g, 73 mmol) was added at 0° C. The resultant mixture was stirred at room temperature for 12 hours and then concentrated. The residue was diluted with H₂O (20 mL) and then extracted with CH₂Cl₂ (500 mL). The organic layer was washed with brine (100 mL), and then dried over anhydrous Na₂SO₄ and then evaporated under reduced pressure to afford 1-[3-chloro-5-(2-methoxyethoxy)phenyl]-3-methyl-butan-2-amine (19.0 g, crude) as light yellow oil which was directly used for the next step without purification.

Step 4: Preparation of N-[1-[[3-chloro-5-(2-methoxyethoxy)phenyl]methyl]-2-methyl-propyl]formamide

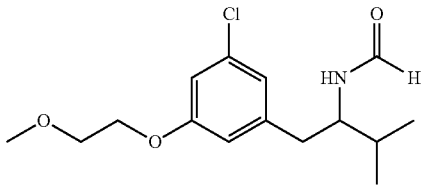 [SMILES: COCCOc1cc(Cl)cc(CC(NC=O)C(C)C)c1]

A solution of 1-[3-chloro-5-(2-methoxyethoxy)phenyl]-3-methyl-butan-2-amine (17.0 g, 62.6 mmol) and formic acid (11.5 g, 250 mmol) in 1,4-dioxane (200 mL) was heated to reflux for 12 hours. The reaction solution was diluted with H₂O (200 mL) and then extracted with EtOAc (200 mL×2). The organic layer was dried over anhydrous Na₂SO₄ and then concentrated. The residue was purified by column chromatography to give N-[1-[[3-chloro-5-(2-methoxyethoxy)phenyl]methyl]-2-methyl-propyl]formamide (10.0 g) as light yellow oil.

Step 5: Preparation of 8-chloro-3-isopropyl-6-(2-methoxyethoxy)-3,4-dihydroisoquinoline

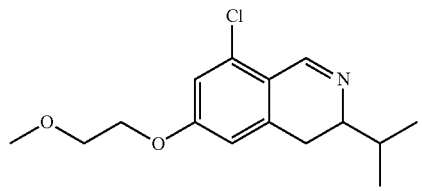 [SMILES: COCCOc1cc(Cl)c2c(c1)CC(C(C)C)N=C2]

A stirred solution of N-[1-[[3-chloro-5-(2-methoxyethoxy)phenyl]methyl]-2-methyl-propyl]formamide (9.0 g, 30.0 mmol) in CH₂Cl₂ (100 mL) was cooled to 0° C., and then POCl₃ (5.31 g, 34.5 mmol) was added slowly. Then the mixture was refluxed for 2 hours. After being cooled down, the mixture was poured into a solution of NH₄OH (50 mL) in H₂O (200 mL), and then stirred for 0.5 hour. The mixture was extracted with CH₂Cl₂ (500 mL). The organic layer was washed with brine (200 mL), and then dried over anhydrous Na₂SO₄ and then evaporated under reduced pressure. The residue was purified by column chromatography to give 8-chloro-3-isopropyl-6-(2-methoxyethoxy)-3,4-dihydroisoquinoline (2.02 g) as yellow oil.

Step 6: Preparation of ethyl 11-chloro-6-isopropyl-9-(2-methoxyethoxy)-2-oxo-1,6,7,11b-tetrahydrobenzo[a]quinolizine-3-carboxylate

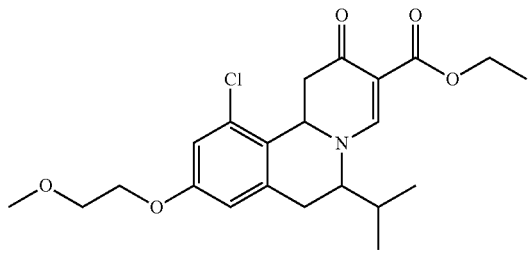 [SMILES: CCOC(=O)C1=CN2C(CC1=O)c1c(Cl)cc(OCCOC)cc1CC2C(C)C]

To a mixture of 8-chloro-3-isopropyl-6-(2-methoxyethoxy)-3,4-dihydroisoquinoline (843 mg, 3 mmol) and ethyl 2-(dimethylaminomethylene)-3-oxo-butanoate (851 mg, 6 mmol) in DMSO (5 mL) was added 4 M HCl in dioxane (0.15 mL, 0.6 mmol). The resultant mixture was heated at 130° C. for 8 hours under microwave, and then cooled to chromatography and diluted with EtOAc and H₂O. The separated aqueous layer was extracted with EtOAc. The combined organic layers were washed with brine, and then dried over anhydrous Na₂SO₄, and then concentrated to give crude ethyl 11-chloro-6-isopropyl-9-(2-methoxyethoxy)-2-oxo-1,6,7,11b-tetrahydrobenzo[a]quinolizine-3-carboxylate (1.35 g) as a yellow solid which was directly used in the next step without purification.

Step 7: Preparation of 11-chloro-6-isopropyl-9-(2-methoxyethoxy)-2-oxo-6,7-dihydrobenzo[a]quinolizine-3-carboxylic acid

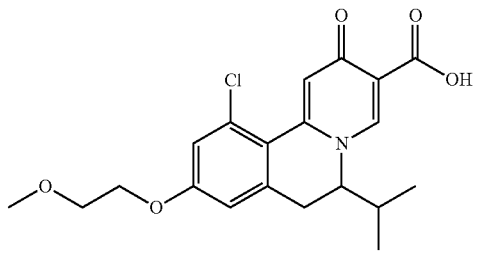 [SMILES: COCCOc1cc(Cl)c2c(c1)CC(C(C)C)n1cc(C(=O)O)c(=O)cc1-2]

A mixture of crude ethyl 11-chloro-6-isopropyl-9-(2-methoxyethoxy)-2-oxo-1,6,7,11b-tetrahydrobenzo[a]quinolizine-3-carboxylate (1.35 g, 3 mmol) and p-chloranil (590 mg, 2.4 mmol) in DME (10 mL) was heated at 70° C. for 3 hours, then heated at 100° C. for 16 hours, and then heated to 130° C. for 1 hour under microwave under argon atmosphere. After being cooled to room temperature, the resultant mixture was concentrated. The residue was purified by flash column chromatography and washed with EtOH/Et₂O to afford 11-chloro-6-isopropyl-9-(2-methoxyethoxy)-2-oxo-6,7-dihydrobenzo[a]quinolizine-3-carboxylic acid (247 mg) as a yellow solid. ¹H NMR (400 MHz, DMSO-d₆): δ 16.38 (s, 1H), 8.83 (s, 1H), 7.48 (s, 1H), 7.20 (s, 1H), 7.16 (s, 1H), 4.46 (d, 1H), 4.24 (m, 2H), 3.68 (br. s., 2H), 3.32 (s, 3H), 3.25-3.16 (m, 2H), 1.45 (m, 1H), 1.11-0.97 (m, 1H), 0.85 (d, 3H), 0.79 (d, 3H). MS obsd. (ESI⁺) [(M+H)⁺]: 392.

Example 112 and 113

6-ethyl-9,10-dimethyl-2-oxo-6,7-dihydrobenzo[a]quinolizine-3-carboxylic acid and 6-ethyl-8,9-dimethyl-2-oxo-6,7-dihydrobenzo[a]quinolizine-3-carboxylic acid Example 112

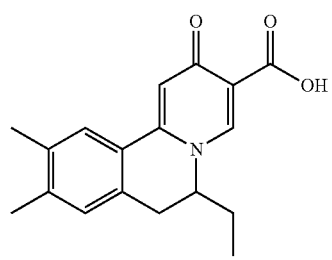

Example 113

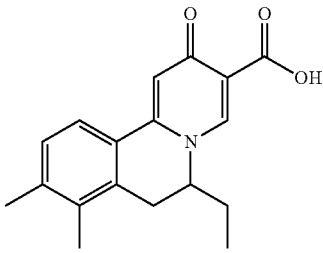

Step 1: Preparation of 1,2-dimethyl-4-[2-nitrobut-1-enyl]benzene

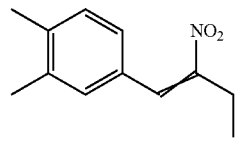

A mixture of 3,4-dimethylbenzaldehyde (20 g, 150 mmol), 1-nitropropane (27 g, 300 mol), dimethyamine hydrochloride (36.5 g, 450 mmol) and potassium fluoride (8.7 g, 150 mmol) in toluene (300 mL) was refluxed with a Dean-Stark trap for 20 hours. The reaction mixture was diluted with ethyl acetate (500 mL) and then quenched with 10% hydrochloric acid (150 mL). The organic layer was washed with water (150 mL) and brine (150 mL), and then dried over anhydrous Na₂SO₄, and then concentrated under reduced pressure. The residue was purified by chromatography to give 1,2-dimethyl-4-[2-nitrobut-1-enyl]benzene (25 g) as a yellow solid.

Step 2: Preparation of 1-(3,4-dimethylphenyl)butan-2-amine

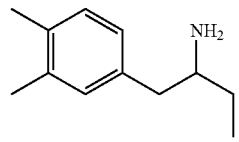

A mixture of 1,2-dimethyl-4-[2-nitrobut-1-enyl]benzene (25 g, 122 mmol) and Pd/C (5 g) in methanol (300 mL) was stirred at 50° C. under 50 psi of H₂ for 20 hours. The mixture was filtered through a celite pad, and the filtrate was concentrated in vacuo to give 1-(3,4-dimethylphenyl)butan-2-amine (15 g).

Step 3: Preparation of N-[1-[(3,4-dimethylphenyl)methyl]propyl]formamide

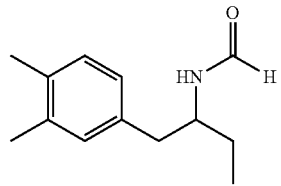

1-(3,4-Dimethylphenyl)butan-2-amine (10 g, 56.5 mmol) was dissolved in ethanol (40 mL) under nitrogen atmosphere. Ethyl formate (60 mL) and triethylamine (3 mL) were added successively, and the resultant mixture was refluxed for 2 days. The reaction mixture was concentrated, and the residue was purified by column chromatography to give N-[1-[(3,4-dimethylphenyl)methyl]propyl]formamide (8 g).

Step 4: Preparation of 3-ethyl-6,7-dimethyl-3,4-dihydroisoquinoline and 3-ethyl-5,6-dimethyl-3,4-dihydroisoquinoline

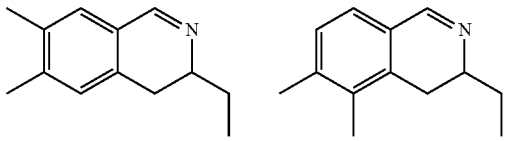

To a solution of N-[1-[(3,4-dimethylphenyl)methyl]propyl]formamide (1.02 g, 5 mmol) in acetonitrile (10 mL) was added $POCl_3$ (920 mg, 12 mmol). The resultant mixture was heated to 90° C. for 4 hours under microwave, and then concentrated. The residue was purified by flash column chromatography to afford a mixture of 3-ethyl-6,7-dimethyl-3,4-dihydroisoquinoline and 3-ethyl-5,6-dimethyl-3,4-dihydroisoquinoline (521 mg) which was directly used for the next step without further purification.

Step 5: Preparation of ethyl 6-ethyl-9,10-dimethyl-2-oxo-1,6,7,11b-tetrahydrobenzo[a]quinolizine-3-carboxylate and ethyl 6-ethyl-8,9-dimethyl-2-oxo-1,6,7,11b-tetrahydrobenzo[a]quinolizine-3-carboxylate

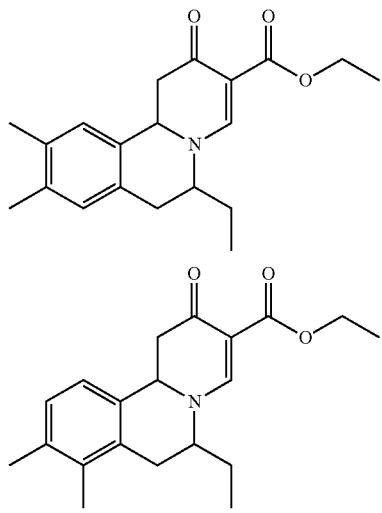

To a solution of the mixture (521 mg, 2.8 mmol) of 3-ethyl-6,7-dimethyl-3,4-dihydroisoquinoline and 3-ethyl-5,6-dimethyl-3,4-dihydroisoquinoline and ethyl 2-(dimethylaminomethylene)-3-oxo-butanoate (777 mg, 4.2 mmol) in DMSO (5 mL) was added 5 M HCl in dioxane (112 µL, 0.56 mmol). The resultant mixture was heated at 130° C. for 1 hour under microwave. After being cooled to room temperature, the reaction mixture was diluted with EtOAc and $H_2O$. The separated aqueous layer was extracted with EtOAc. The combined organic layers were washed with brine, and then dried over anhydrous $Na_2SO_4$ and concentrated to give a mixture (1.0 g) of ethyl 6-ethyl-9,10-dimethyl-2-oxo-1,6,7,11b-tetrahydrobenzo[a]quinolizine-3-carboxylate and ethyl 6-ethyl-8,9-dimethyl-2-oxo-1,6,7,11b-tetrahydrobenzo[a]quinolizine-3-carboxylate as brown oil, which was directly used for the next step without purification.

Step 6: Preparation of ethyl 6-ethyl-9,10-dimethyl-2-oxo-6,7-dihydrobenzo[a]quinolizine-3-carboxylate and ethyl 6-ethyl-8,9-dimethyl-2-oxo-6,7-dihydrobenzo[a]quinolizine-3-carboxylate

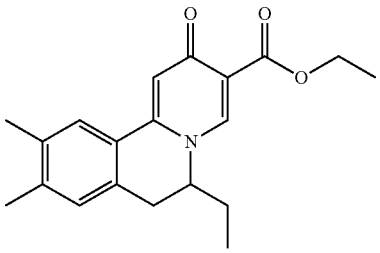

The mixture (1.0 g, 2.8 mmol) of crude ethyl 6-ethyl-9,10-dimethyl-2-oxo-1,6,7,11b-tetrahydrobenzo[a]quinolizine-3-carboxylate and ethyl 6-ethyl-8,9-dimethyl-2-oxo-1,6,7,11b-tetrahydrobenzo[a]quinolizine-3-carboxylate was dissolved in DME (5 mL), then p-chloranil (551 mg, 2.24 mmol) was added. The resultant mixture was heated at 80° C. for 3 hours under argon atmosphere. After being cooled to room temperature, the mixture was diluted with $CH_2Cl_2$ and $H_2O$, and then extracted with $CH_2Cl_2$. The combined organic layers were washed with brine, and then dried over anhydrous $Na_2SO_4$, and then concentrated to give a mixture (1.39 g) of ethyl 6-ethyl-9,10-dimethyl-2-oxo-6,7-dihydrobenzo[a]quinolizine-3-carboxylate and ethyl 6-ethyl-8,9-dimethyl-2-oxo-6,7-dihydrobenzo[a]quinolizine-3-carboxylate as a dark solid, which was directly used for the next step without purification.

Step 7: Preparation of 6-ethyl-9,10-dimethyl-2-oxo-6,7-dihydrobenzo[a]quinolizine-3-carboxylic acid and 6-ethyl-8,9-dimethyl-2-oxo-6,7-dihydrobenzo[a]quinolizine-3-carboxylic acid Example 112

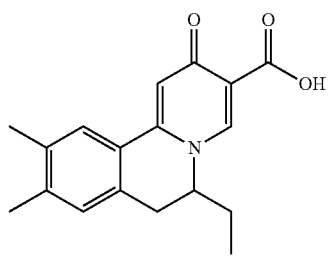

Example 113

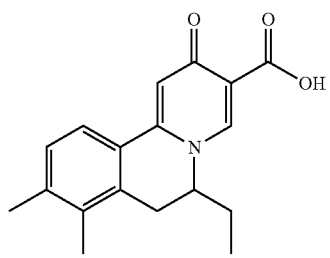

To a mixture of crude ethyl 6-ethyl-9,10-dimethyl-2-oxo-6,7-dihydrobenzo[a]quinolizine-3-carboxylate and ethyl 6-ethyl-8,9-dimethyl-2-oxo-6,7-dihydrobenzo[a]quinolizine-3-carboxylate (1.39 g, 2.8 mmol) in CH$_3$OH (8 mL) and H$_2$O (2 mL) was added lithium hydroxide monohydrate (470 mg, 11.2 mmol). The resultant mixture was stirred at room temperature overnight, and then acidified by 1 M hydrochloric acid to pH 2-3. The mixture was extracted with CH$_2$Cl$_2$ (50 mL×3). The combined organic layers were washed with brine, and then dried over anhydrous Na$_2$SO$_4$ and then concentrated. The residue was directly purified by prep-HPLC to afford 6-ethyl-9,10-dimethyl-2-oxo-6,7-dihydrobenzo[a]quinolizine-3-carboxylic acid (54 mg) and 6-ethyl-8,9-dimethyl-2-oxo-6,7-dihydrobenzo[a]quinolizine-3-carboxylic acid (15 mg) as a yellow solid.

Example 112

$^1$H NMR (400 MHz, DMSO-d$_6$): δ 8.83 (s, 1H), 7.88 (s, 1H), 7.38 (s, 1H), 7.20 (s, 1H), 4.73 (d, 1H), 3.37-3.31 (d, 1H), 3.00 (d, 1H), 2.29 (d, 6H), 1.55-1.33 (m, 3H), 0.79 (t, 3H). MS obsd. (ESI$^+$) [(M+H)$^+$]: 298.

Example 113

$^1$H NMR (400 MHz, DMSO-d$_6$): δ 8.89 (s, 1H), 7.33 (d, 1H), 7.18 (d, 1H), 6.97 (s, 1H), 4.75-4.64 (m, 1H), 3.30-3.22 (m, 2H), 3.05-2.95 (m, 1H), 2.46 (s, 3H), 2.32 (s, 3H), 1.47 (m, 2H), 0.80 (t, 3H). MS obsd. (ESI$^+$) [(M+H)$^+$]: 298.

Example 114: 9,10-dimethoxy-2-oxo-6-(trifluoromethyl)-6,7-dihydrobenzo[a]quinolizine-3-carboxylic acid

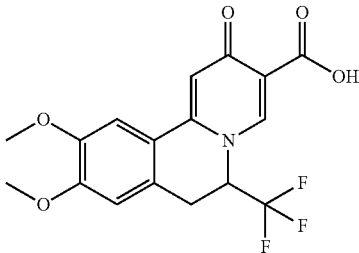 [SMILES: COc1cc2c(cc1OC)-c1cc(=O)c(C(=O)O)cn1C(C(F)(F)F)C2]

Step 1: Preparation of 3-(3,4-dimethoxyphenyl)-1,1,1-trifluoro-propan-2-one

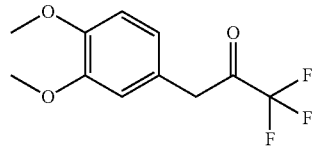 [SMILES: COc1ccc(CC(=O)C(F)(F)F)cc1OC]

To a mixture of 2-(3,4-dimethoxyphenyl)acetic acid (3.92 g, 20 mmol) in THF (60 mL) was added lithium diisopropylamide (22 mL, 44 mmol, 2M in THF) dropwise at −20° C. The resultant mixture was stirred at 20° C. for 5 hours, then the mixture was added to a solution of methyl trifluoroacetate (7.2 mL, 60 mmol) in THF (20 mL) at −65° C. Upon the completion of the addition, the mixture was stirred at −65° C. for additional 15 minutes. Then the reaction was quenched by 6 M hydrochloric acid (40 mL) and stirred for 15 minutes. The mixture was diluted with EtOAc (40 mL) and then stirred at room temperature overnight. The separated organic layer was washed with brine, and then dried over anhydrous Na$_2$SO$_4$ and concentrated. The residue was purified by flash chromatography to afford 3-(3,4-dimethoxyphenyl)-1,1,1-trifluoro-propan-2-one (1.92 g) as yellow oil which was directly used for the next step without further purification.

Step 2: Preparation of 3-(3,4-dimethoxyphenyl)-1,1,1-trifluoro-propan-2-one oxime

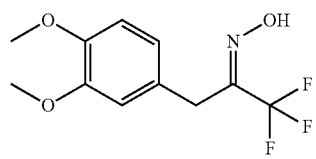 [SMILES: COc1ccc(C/C(=N/O)C(F)(F)F)cc1OC]

The mixture of 3-(3,4-dimethoxyphenyl)-1,1,1-trifluoropropan-2-one (1.81 g, 7.3 mmol), hydroxylamine hydrochloride (3.73 g, 54 mmol) and sodium acetate (4.43 g, 54 mmol) in EtOH (5 mL) and H$_2$O (20 mL) was heated at 100° C. for 2 hours. After being cooled to room temperature, the reaction mixture was extracted with CHCl$_3$ (80 mL×3). The combined organic layers were washed with brine, and then dried over anhydrous Na₂SO₄ and then concentrated to give 3-(3,4-dimethoxyphenyl)-1,1,1-trifluoro-propan-2-one oxime (1.78 g) as a yellow solid.

Step 3: Preparation of 3-(3,4-dimethoxyphenyl)-1,1,1-trifluoro-propan-2-amine

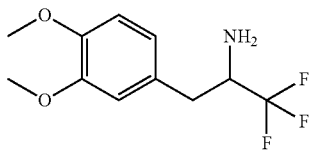 [SMILES: COc1ccc(CC(N)C(F)(F)F)cc1OC]

To a mixture of 3-(3,4-dimethoxyphenyl)-1,1,1-trifluoro-propan-2-one oxime (526 mg, 2 mmol) in THF (30 mL) was added LiAlH₄ (2 mL, 4 mmol, 2 M in THF). The resultant mixture was stirred at 70° C. overnight under argon atmosphere. After being cooled to room temperature, the reaction was quenched by H₂O and 10% NaOH (5 mL), and then extracted with CH₂Cl₂ (60 mL×3). The combined organic layers were washed with brine, and then dried over anhydrous Na₂SO₄ and then concentrated to give crude 3-(3,4-dimethoxyphenyl)-1,1,1-trifluoro-propan-2-amine (543 mg) as yellow oil which was directly used for the next step without purification.

Step 4: Preparation of N-[1-[(3,4-dimethoxyphenyl)methyl]-2,2,2-trifluoro-ethyl]formamide

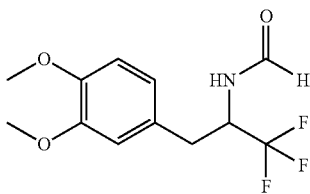 [SMILES: COc1ccc(CC(NC=O)C(F)(F)F)cc1OC]

A solution of 3-(3,4-dimethoxyphenyl)-1,1,1-trifluoro-propan-2-amine (475 mg, 2 mmol) in ethyl formate (10 mL) and HOAc (1 mL) was heated at 90° C. overnight, and then cooled to room temperature and then concentrated to give crude N-[1-[(3,4-dimethoxyphenyl)methyl]-2,2,2-trifluoro-ethyl]formamide (621 mg) as orange oil which was directly used for the next step without purification.

Step 5: Preparation of 6,7-dimethoxy-3-(trifluoromethyl)-3,4-dihydroisoquinoline

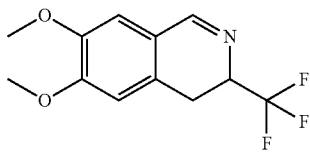 [SMILES: COc1cc2c(cc1OC)CC(C(F)(F)F)N=C2]

To a solution of crude N-[1-[(3,4-dimethoxyphenyl)methyl]-2,2,2-trifluoro-ethyl]formamide (621 mg, 2 mmol) in acetonitrile (5 mL) was added POCl₃ (368 mg, 2.4 mmol).

The resultant mixture was heated at 80° C. for 8 hours and then concentrated. The residue was purified by column chromatography to afford 6,7-dimethoxy-3-(trifluoromethyl)-3,4-dihydroisoquinoline (309 mg) as yellow oil which was directly used for the next step without further purification.

Step 6: Preparation of ethyl 9,10-dimethoxy-2-oxo-6-(trifluoromethyl)-1,6,7,11b-tetrahydrobenzo[a]quinolizine-3-carboxylate

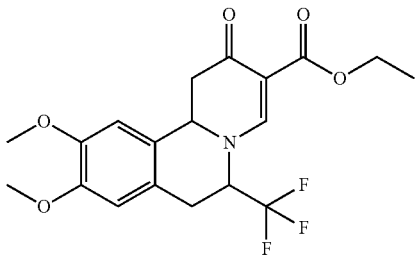 [SMILES: CCOC(=O)C1=CN2C(CC1=O)c1cc(OC)c(OC)cc1CC2C(F)(F)F]

To a solution of 6,7-dimethoxy-3-(trifluoromethyl)-3,4-dihydroisoquinoline (309 mg, 1.2 mmol) and ethyl 2-(dimethylaminomethylene)-3-oxo-butanoate (222 mg, 1.2 mmol) in DMSO (2 mL) was added 5 M HCl in dioxane (50 µL, 0.24 mmol). The resultant mixture was heated at 130° C. for 4 hours under microwave. After being cooled to room temperature, the reaction mixture was diluted with EtOAc and H₂O. The separated aqueous layer was extracted with EtOAc. The combined organic layers were washed with brine, and then dried over anhydrous Na₂SO₄ and then concentrated to give crude ethyl 9,10-dimethoxy-2-oxo-6-(trifluoromethyl)-1,6,7,11b-tetrahydrobenzo[a]quinolizine-3-carboxylate (630 mg) as brown oil, which was directly used for the next step without purification.

Step 7: Preparation of ethyl 9,10-dimethoxy-2-oxo-6-(trifluoromethyl)-6,7-dihydrobenzo[a]quinolizine-3-carboxylate

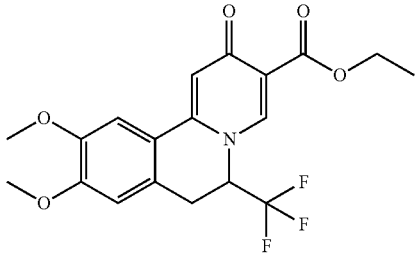 [SMILES: CCOC(=O)c1cn2c(cc1=O)-c1cc(OC)c(OC)cc1CC2C(F)(F)F]

To a solution of crude ethyl 9,10-dimethoxy-2-oxo-6-(trifluoromethyl)-1,6,7,11b-tetrahydrobenzo[a]quinolizine-3-carboxylate (630 mg, 1.2 mmol) in DME (1 mL) and toluene (1 mL) was added p-chloranil (148 mg, 0.6 mmol). The resultant mixture was heated at 135° C. for 15 minutes under microwave. After being cooled to room temperature, the mixture was diluted with CH₂Cl₂ and H₂O, and then extracted with CH₂Cl₂. The combined organic layers were washed with brine, and then dried over anhydrous Na₂SO₄ and then concentrated to give crude ethyl 9,10-dimethoxy-2-oxo-6-(trifluoromethyl)-6,7-dihydrobenzo[a]quinolizine- 3-carboxylate (751 mg) as brown oil, which was directly used for the next step without purification.

Step 8: Preparation of 9,10-dimethoxy-2-oxo-6-(trifluoromethyl)-6,7-dihydrobenzo[a]quinolizine-3-carboxylic acid

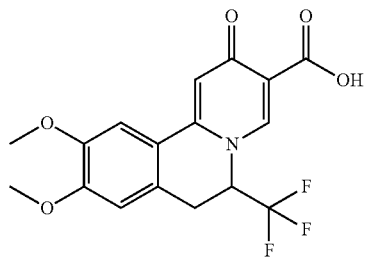 [SMILES: COc1cc2c(cc1OC)-c1cc(=O)c(C(=O)O)cn1C(C(F)(F)F)C2]

To a solution of crude ethyl 9,10-dimethoxy-2-oxo-6-(trifluoromethyl)-6,7-dihydrobenzo[a]quinolizine-3-carboxylate (751 mg, 1.2 mmol) in CH$_3$OH (4 mL) and H$_2$O (1 mL) was added lithium hydroxide monohydrate (202 mg, 4.8 mmol). The resultant mixture was stirred at room temperature overnight, and then acidified by 1 M hydrochloric acid to pH 2-3, and then extracted with CH$_2$Cl$_2$ (50 mL×3). The combined organic layers were washed with brine, and then dried over anhydrous Na$_2$SO$_4$ and then concentrated. The residue was washed with EtOH/Et$_2$O to afford 9,10-dimethoxy-2-oxo-6-(trifluoromethyl)-6,7-dihydrobenzo[a]quinolizine-3-carboxylic acid (30 mg) as a yellow solid. $^1$H NMR (400 MHz, DMSO-d$_6$): δ 16.11 (s, 1H), 8.91 (s, 1H), 7.56 (s, 1H), 7.55 (s, 1H), 7.10 (s, 1H), 5.94-5.77 (m, 1H), 3.88 (s, 3H), 3.85 (s, 3H), 3.78-3.69 (m, 1H), 3.39 (br. s., 1H). MS obsd. (ESI$^+$) [(M+H)$^+$]: 370.

Example 115: 9-benzyloxy-6-ethyl-10-methyl-2-oxo-6,7-dihydrobenzo[a]quinolizine-3-carboxylic acid

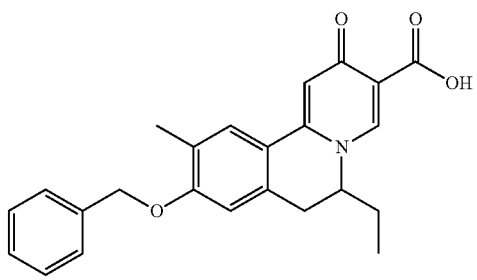 [SMILES: CCC1Cc2cc(OCc3ccccc3)c(C)cc2-c2cc(=O)c(C(=O)O)cn21]

Step 1: Preparation of methyl 3-hydroxy-4-methyl-benzoate

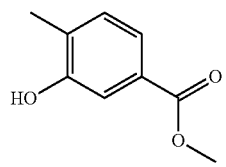

A 500 mL round bottomed flask was charged with 3-hydroxy-4-methyl-benzoate (30 g, 0.2 mmol), 200 mL of MeOH and 10 mL of H$_2$SO$_4$. The resultant mixture was refluxed for 2 hours and then concentrated. Then ethyl acetate and water was added. The organic phase was dried over anhydrous Na$_2$SO$_4$ and then concentrated to give methyl 3-hydroxy-4-methyl-benzoate which used directly in the next step.

Step 2: Preparation of methyl 3-benzyloxy-4-methyl-benzoate

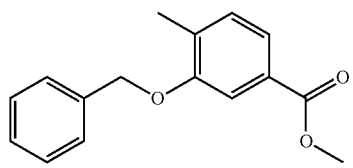 [SMILES: COC(=O)c1ccc(C)c(OCc2ccccc2)c1]

A 250 mL round-bottomed flask was charged with 3-hydroxy-4-methyl-benzaldehyde (33 g, 0.2 mol), bromomethylbenzene (37.6 g, 0.22 mol), K$_2$CO$_3$ (60.7 g, 0.44 mol) and DMF (50 mL). The resultant mixture was stirred at 50° C. for 6 hours, and then ethyl acetate and water were added. The organic phase was dried over anhydrous Na$_2$SO$_4$ and then concentrated to give 3-benzyloxy-4-methyl-benzoate (46 g).

Step 3: Preparation of (3-benzyloxy-4-methyl-phenyl)methanol

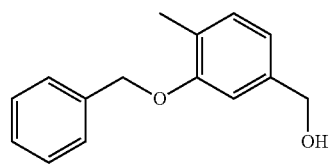 [SMILES: Cc1ccc(CO)cc1OCc1ccccc1]

To a mixture of LiAlH$_4$ solution (100 mL, 2 M in THF) in THF (100 mL) was added a solution of 3-benzyloxy-4-methyl-benzoate (46 g, 0.2 mol) in THF (100 mL) dropwise at −30° C. The mixture was warmed slowly to room temperature and then stirred for additional 2 hours. Then 50 mL of saturated Na$_2$SO$_4$ solution was added dropwise at 0° C. to quench the reaction. The resultant mixture was filtered, and the filtrate was concentrated to afford crude (3-benzyloxy-4-methyl-phenyl)methanol (41 g) which was used in the next step without further purification.

Step 4: Preparation of 3-benzyloxy-4-methyl-benzaldehyde

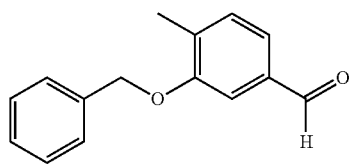 [SMILES: Cc1ccc(C=O)cc1OCc1ccccc1]

A 500 mL round-bottomed flask was charged with (3-benzyloxy-4-methyl-phenyl)methanol (41 g, 0.18 mol) in 200 mL of DCM. Then PCC (39 g, 0.18 mmol) was added. The resultant mixture was stirred at room temperature for 4 hours, and then filtered and the filtrate was concentrated to give yellow oil which was purified by silica gel column chromatography to give 3-benzyloxy-4-methyl-benzaldehyde (28.5 g).

Step 5: Preparation of 2-benzyloxy-1-methyl-4-[2-nitrobut-1-enyl]benzene

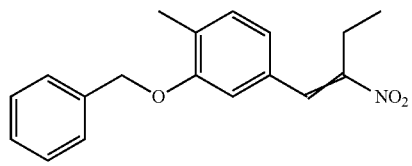 [SMILES: CCC(=Cc1ccc(C)c(OCc2ccccc2)c1)[N+](=O)[O-]]

A mixture of 3-benzyloxy-4-methyl-benzaldehyde (2.2 g, 10 mmol) and ammonium acetate (770 mg, 10 mmol) in nitropropane (30 mL) was stirred at 100° C. for 36 hours. The mixture was concentrated under reduced pressure, and the residue was dissolved in ethyl acetate. The resultant solution was washed with water, and then dried over anhydrous Na$_2$SO$_4$ and then concentrated. The residue was purified by column chromatography to give crude 2-benzyloxy-1-methyl-4-[2-nitrobut-1-enyl]benzene which was used in the next step without further purification.

Step 6: Preparation of 1-(3-benzyloxy-4-methyl-phenyl)butan-2-amine

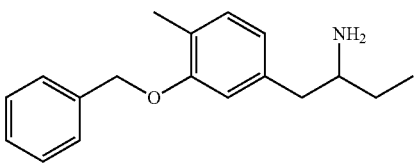 [SMILES: CCC(N)Cc1ccc(C)c(OCc2ccccc2)c1]

To a mixture of LiAlH$_4$ solution (20 mL, 2 M in THF) in THF (20 mL) was added a solution of 2-benzyloxy-1-methyl-4-[2-nitrobut-1-enyl]benzene (10 mmol) in THF (20 mL) dropwise in an ice-water bath. The mixture was refluxed for 6 hours and stirred at room temperature for additional 16 hours. Then water was added dropwise at 0° C., and then 15% NaOH aqueous was added to the mixture. The resultant mixture was filtered, and the filtrate was concentrated to afford 1-(3-benzyloxy-4-methyl-phenyl)butan-2-amine which was used in the next step without further purification.

Step 7: Preparation of N-[1-[(3-benzyloxy-4-methyl-phenyl)methyl]propyl]formamide

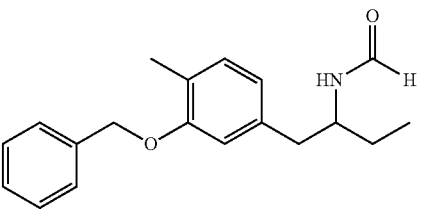 [SMILES: CCC(Cc1ccc(C)c(OCc2ccccc2)c1)NC=O]

A mixture of 1-(3-benzyloxy-4-methyl-phenyl)butan-2-amine (10 mmol) and formic acid (1.4 g, 30 mol) in dioxane (100 mL) was refluxed for 16 hours and then concentrated under reduced pressure to afford crude N-[1-[(3-benzyloxy-4-methyl-phenyl)methyl]propyl]formamide, which was used in the next step without purification.

Step 8: Preparation of 6-benzyloxy-3-ethyl-7-methyl-3,4-dihydroisoquinoline

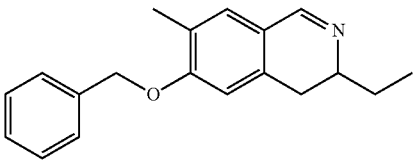 [SMILES: CCC1Cc2cc(OCc3ccccc3)c(C)cc2C=N1]

To a solution of N-[1-[(3-benzyloxy-4-methyl-phenyl)methyl]propyl]formamide (10 mmol) in acetonitrile (100 mL) was added POCl$_3$ (3 g, 20 mmol) dropwise at 0-5° C. The resultant mixture was refluxed for 4 hours and then concentrated. Ethyl acetate was added, and then ammonia was added to adjust the pH of the aqueous solution to around 11. The aqueous layer was extracted with ethyl acetate. The organic layers were combined and then concentrated. The residue was purified by column chromatography to give 6-benzyloxy-3-ethyl-7-methyl-3,4-dihydroisoquinoline (700 mg).

Step 9: Preparation of 9-benzyloxy-6-ethyl-10-methyl-2-oxo-6,7-dihydrobenzo[a]quinolizine-3-carboxylic acid

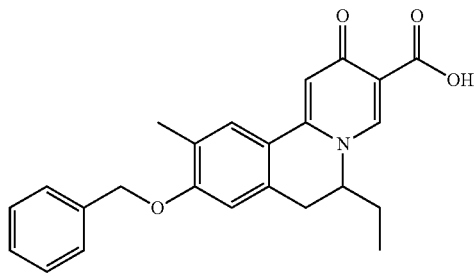 [SMILES: CCC1Cc2cc(OCc3ccccc3)c(C)cc2-c2cc(=O)c(C(=O)O)cn21]

A mixture of 6-benzyloxy-3-ethyl-7-methyl-3,4-dihydroisoquinoline (700 mg, 2.5 mmol) and ethyl 2-(ethoxymethylene)-3-oxo-butanoate (1.38 g, 7.5 mmol) in DMSO (20 mL) was stirred at 110° C. overnight. Then MnO$_2$ (1.1 g, 12.5 mmol) was added and the mixture was stirred at 130° C. for 10 hours. The mixture was extracted with DCM, and the combined organic layers were washed with brine, and then dried over anhydrous Na$_2$SO$_4$ and then concentrated. The residue was purified by column chromatography and recrystallized from EtOH/ethyl ether to afford 9-benzyloxy-6-ethyl-10-methyl-2-oxo-6,7-dihydrobenzo[a]quinolizine-3-carboxylic acid (200 mg) as a white solid. $^1$H NMR (400 MHz, DMSO-d$_6$): δ 8.81 (s, 1H), 7.93 (s, 1H), 7.48-7.53 (m, 2H), 7.33-7.46 (m, 3H), 7.31 (s, 1H), 7.14 (s, 1H), 5.22 (d, 2H), 4.72 (d, 1H), 3.35-3.45 (m, 1H), 3.04 (d, 1H), 2.24 (s, 3H), 1.33-1.63 (m, 2H), 0.80 (t, 3H). MS obsd. (ESI$^+$) [(M+H)$^+$]: 390.

Example 116 and 117

(+)-9-benzyloxy-6-ethyl-10-methyl-2-oxo-6,7-dihydrobenzo[a]quinolizine-3-carboxylic acid and (−)-9-benzyloxy-6-ethyl-10-methyl-2-oxo-6,7-dihydrobenzo[a]quinolizine-3-carboxylic acid

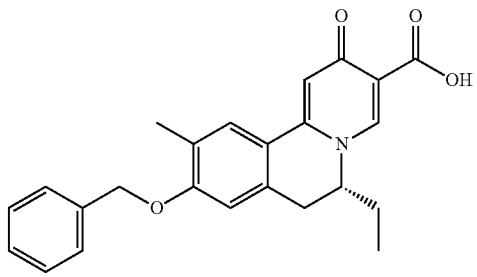

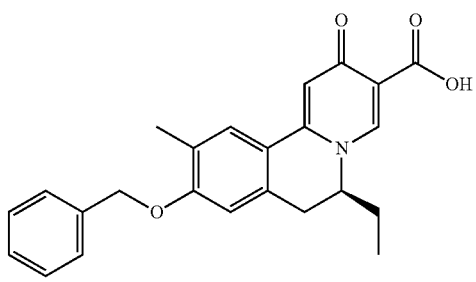

Separation of the racemic 9-benzyloxy-6-ethyl-10-methyl-2-oxo-6,7-dihydrobenzo[a]quinolizine-3-carboxylic acid (140 mg) by chiral HPLC afforded (+)-9-benzyloxy-6-ethyl-10-methyl-2-oxo-6,7-dihydrobenzo[a]quinolizine-3-carboxylic acid (28 mg) and (−)-9-benzyloxy-6-ethyl-10-methyl-2-oxo-6,7-dihydrobenzo[a]quinolizine-3-carboxylic acid (55 mg).

Example 116

$^1$H NMR (400 MHz, DMSO-d$_6$): δ 8.81 (s, 1H), 7.93 (s, 1H), 7.48-7.53 (m, 2H), 7.33-7.46 (m, 3H), 7.31 (s, 1H), 7.14 (s, 1H), 5.22 (d, 2H), 4.72 (d, 1H), 3.35-3.45 (m, 1H), 3.04 (d, 1H), 2.24 (s, 3H), 1.33-1.63 (m, 2H), 0.80 (t, 3H). MS obsd. (ESI$^+$) [(M+H)$^+$]: 390. [α]$_D$20=+97.39° (0.115%, CH$_3$CN).

Example 117

$^1$H NMR (400 MHz, DMSO-d$_6$): δ 8.81 (s, 1H), 7.93 (s, 1H), 7.48-7.53 (m, 2H), 7.33-7.46 (m, 3H), 7.31 (s, 1H), 7.14 (s, 1H), 5.22 (d, 2H), 4.72 (d, 1H), 3.35-3.45 (m, 1H), 3.04 (d, 1H), 2.24 (s, 3H), 1.33-1.63 (m, 2H), 0.80 (t, 3H). MS obsd. (ESI$^+$) [(M+H)$^+$]: 390.

Example 118 and 119

(+)-10-chloro-9-ethoxy-6-ethyl-2-oxo-6,7-dihydrobenzo[a]quinolizine-3-carboxylic acid and (−)-10-chloro-9-ethoxy-6-ethyl-2-oxo-6,7-dihydrobenzo[a]quinolizine-3-carboxylic acid

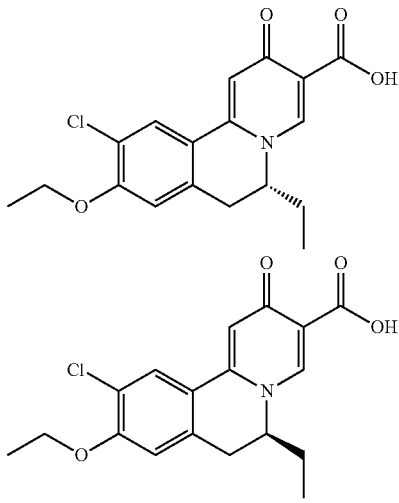

Step 1: Preparation of methyl 4-chloro-3-hydroxy-benzoate

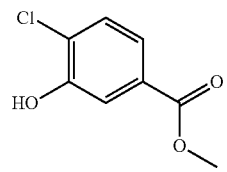

A 500 mL round bottomed flask was charged with 4-chloro-3-hydroxy-benzoic acid (30 g, 0.175 mmol), 200 mL of MeOH and 10 mL of H$_2$SO$_4$. The resultant mixture was refluxed for 2 hours and then concentrated. Then ethyl acetate and water was added. The organic phase was dried over anhydrous Na$_2$SO$_4$ and then concentrated to give methyl 4-chloro-3-hydroxy-benzoate which used directly in the next step.

Step 2: Preparation of methyl 4-chloro-3-ethoxy-benzoate

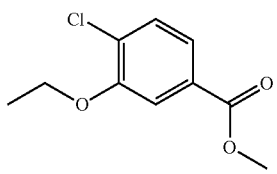

A 250 mL round-bottomed flask was charged with 3-hydroxy-4-methyl-benzaldehyde (32 g, 0.175 mol), iodoethane (32.8 g, 0.21 mol), K$_2$CO$_3$ (60.7 g, 0.44 mol) and DMF (50 mL). The resultant mixture was stirred at 50° C. for 3 hours, and then ethyl acetate and water were added. The organic phase was separated, and then dried over anhydrous Na₂SO₄ and then concentrated to give methyl 4-chloro-3-ethoxy-benzoate (34 g).

Step 3: Preparation of (4-chloro-3-ethoxy-phenyl)methanol

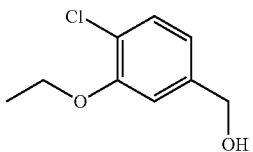

To a mixture of LiAlH₄ solution (80 mL, 2 M in THF) in THF (100 mL) was added a solution of methyl 4-chloro-3-ethoxy-benzoate (34 g, 0.16 mol) in THF (100 mL) dropwise at −30° C. The mixture was warmed slowly to room temperature and then stirred for additional 2 hours. Then 50 mL of saturated Na₂SO₄ solution was added dropwise at 0° C. to quench the reaction. The resultant mixture was filtered, and the filtrate was concentrated to afford crude (4-chloro-3-ethoxy-phenyl)methanol (24 g) which was used in the next step without further purification.

Step 4: Preparation of 4-chloro-3-ethoxy-benzaldehyde

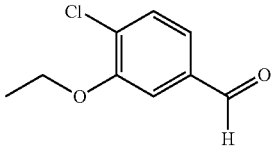

A 500 mL round-bottomed flask was charged with (4-chloro-3-ethoxy-phenyl)methanol (24 g, 0.13 mol) in 200 mL of DCM. Then PCC (28 g, 0.13 mmol) was added. The resultant mixture was stirred at room temperature for 4 hours, and then filtered and then concentrated to give yellow oil which was purified by silica gel column chromatography to give 4-chloro-3-ethoxy-benzaldehyde (18 g).

Step 5: Preparation of 1-chloro-2-ethoxy-4-[2-nitrobut-1-enyl]benzene

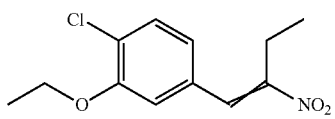 [SMILES: CCOc1cc(C=C(CC)[N+](=O)[O-])ccc1Cl]

A mixture of 4-chloro-3-ethoxy-benzaldehyde (8 g, 43 mmol) and ammonium acetate (2 g, 26 mmol) in nitropropane (12 g, 130 mmol) was stirred at 100° C. for 36 hours. The mixture was concentrated under reduced pressure, and the residue was dissolved in ethyl acetate. The resultant solution was washed with water, and then dried over anhydrous Na₂SO₄ and concentrated. The residue was purified by column chromatography to give crude 1-chloro-2-ethoxy-4-[2-nitrobut-1-enyl]benzene which was used in the next step without further purification.

Step 6: Preparation of 1-(4-chloro-3-ethoxy-phenyl)butan-2-amine

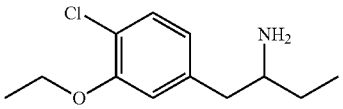

To a mixture of solution LiAlH₄ (55 mL, 2M in THF) in THF (50 mL) was added a solution of 1-chloro-2-ethoxy-4-[2-nitrobut-1-enyl]benzene (12.4 g, 55 mmol) in THF (50 mL) dropwise in an ice-water bath. The mixture was refluxed for 6 hours and then stirred at room temperature for additional 16 hours. Then water was added dropwise at 0° C., and then 15% NaOH solution was added to the mixture. The resultant mixture was filtered, and the filtrate was concentrated to afford 1-(4-chloro-3-ethoxy-phenyl)butan-2-amine which was used in the next step without further purification.

Step 7: Preparation of N-[1-[(4-chloro-3-ethoxy-phenyl)methyl]propyl]formamide

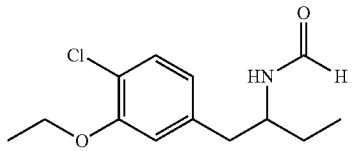 [SMILES: CCOc1cc(CC(CC)NC=O)ccc1Cl]

A mixture of 1-(4-chloro-3-ethoxy-phenyl)butan-2-amine (55 mmol) and formic acid (1.4 g, 30 mol) in dioxane (100 mL) was refluxed for 16 hours and then concentrated under reduced pressure to afford crude N-[1-[(4-chloro-3-ethoxy-phenyl)methyl]propyl]formamide which was used in the next step without purification.

Step 8: Preparation of 7-chloro-6-ethoxy-3-ethyl-3,4-dihydroisoquinoline

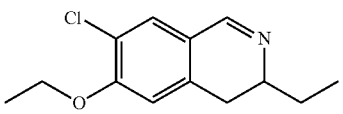 [SMILES: CCOc1cc2c(cc1Cl)C=NC(CC)C2]

To a solution of N-[1-[(4-chloro-3-ethoxy-phenyl)methyl]propyl]formamide (6 g, 23 mmol) in acetonitrile (100 mL) was added POCl₃ (4.4 g, 28 mmol) dropwise at 0-5° C. The resultant mixture was refluxed for 4 hours and then concentrated. Ethyl acetate was added, and then ammonia was added to adjust the pH of the aqueous solution to around 11. The aqueous layer was extracted with ethyl acetate. The organic layers were combined and concentrated. The residue was purified by column chromatography to give 7-chloro-6-ethoxy-3-ethyl-3,4-dihydroisoquinoline (2.5 g).

Step 9: Preparation of ethyl 10-chloro-9-ethoxy-6-ethyl-2-oxo-1,6,7,11b-tetrahydrobenzo[a]quinolizine-3-carboxylate

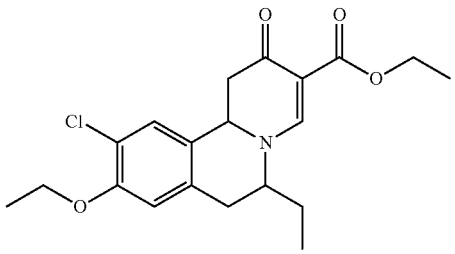

A mixture of 7-chloro-6-ethoxy-3-ethyl-3,4-dihydroisoquinoline (1.7 g, 7.2 mmol) and ethyl 2-(ethoxymethylene)-3-oxo-butanoate (4.0 g, 21.6 mmol) in EtOH (10 mL) was stirred at 110° C. overnight. The mixture was concentrated to give crude ethyl 10-chloro-9-ethoxy-6-ethyl-2-oxo-1,6,7,11b-tetrahydrobenzo[a]quinolizine-3-carboxylate as dark brown oil which was used in the next step without purification.

Step 10: Preparation of ethyl 10-chloro-9-ethoxy-6-ethyl-2-oxo-6,7-dihydrobenzo[a]quinolizine-3-carboxylate

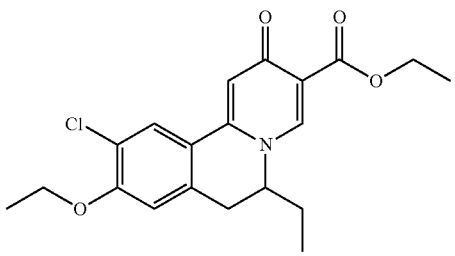 [SMILES: CCOC(=O)C1=CN2C(CC)Cc3cc(OCC)c(Cl)cc3C2CC1=O]

A mixture of crude ethyl 10-chloro-9-ethoxy-6-ethyl-2-oxo-1,6,7,11b-tetrahydrobenzo[a]quinolizine-3-carboxylate (700 mg, 1.85 mmol) and p-chloranil (450 mg, 1.83 mmol) in DME (20 mL) was refluxed for 2 hours. After being cooled to room temperature, the mixture was concentrated under vacuum to give crude ethyl 10-chloro-9-ethoxy-6-ethyl-2-oxo-6,7-dihydrobenzo[a]quinolizine-3-carboxylate as brown oil.

Step 11: Preparation of 10-chloro-9-ethoxy-6-ethyl-2-oxo-6,7-dihydrobenzo[a]quinolizine-3-carboxylic acid

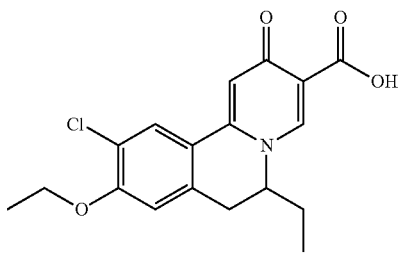 [SMILES: CCOc1cc2c(cc1Cl)-c1cc(=O)c(C(=O)O)cn1C(CC)C2]

To a solution of crude ethyl 10-chloro-9-ethoxy-6-ethyl-2-oxo-6,7-dihydrobenzo[a]quinolizine-3-carboxylate from Step 10 in THF (20 mL) was added 10% NaOH aqueous solution dropwise at room temperature. The resultant mixture was stirred for 2 hours, and then acidified to pH 1-2 with 2 M hydrochloric acid. The mixture was extracted with DCM, and the combined organic layers were washed with brine, and then dried over anhydrous $Na_2SO_4$ and then concentrated. The residue was purified by column chromatography and recrystallization from EtOH/ethyl ether to afford 10-chloro-9-ethoxy-6-ethyl-2-oxo-6,7-dihydrobenzo[a]quinolizine-3-carboxylic acid (200 mg) as a white solid.

Step 12: Preparation of (+)-10-chloro-9-ethoxy-6-ethyl-2-oxo-6,7-dihydrobenzo[a]quinolizine-3-carboxylic acid and (−)-10-chloro-9-ethoxy-6-ethyl-2-oxo-6,7-dihydrobenzo[a]quinolizine-3-carboxylic acid

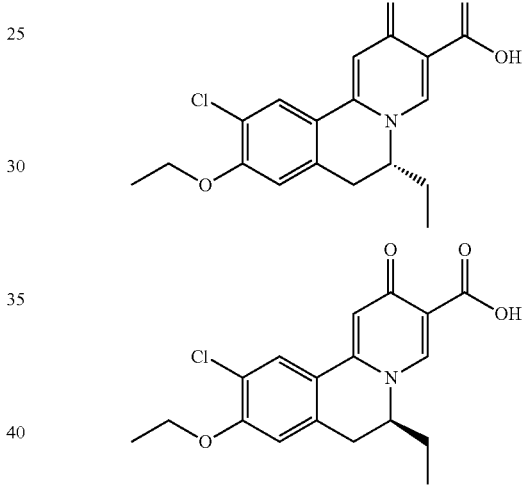

Separation of the racemic 10-chloro-9-ethoxy-6-ethyl-2-oxo-6,7-dihydrobenzo[a]quinolizine-3-carboxylic acid (110 mg) by chiral HPLC afforded (+)-10-chloro-9-ethoxy-6-ethyl-2-oxo-6,7-dihydrobenzo[a]quinolizine-3-carboxylic acid (38 mg) and (−)-10-chloro-9-ethoxy-6-ethyl-2-oxo-6,7-dihydrobenzo[a]quinolizine-3-carboxylic acid (38 mg).

Example 118

$^1$H NMR (400 MHz, DMSO-$d_6$): δ 8.83 (s, 1H), 8.20 (s, 1H), 7.42 (s, 1H), 7.25 (s, 1H), 4.74 (q, 1H), 4.23 (dd, 2H), 3.36-3.45 (m, 1H), 3.11 (d, 1H), 1.40 (t, 3H), 0.81 (t, 3H). MS obsd. (ESI$^+$) [(M+H)$^+$]: 348. [α]$_D^{20}$=+136.00° (0.070%, $CH_3CN$)

Example 119

$^1$H NMR (400 MHz, DMSO-$d_6$): δ 8.83 (s, 1H), 8.20 (s, 1H), 7.42 (s, 1H), 7.25 (s, 1H), 4.74 (q, 1H), 4.23 (dd, 2H), 3.36-3.45 (m, 1H), 3.11 (d, 1H), 1.40 (t, 3H), 0.81 (t, 3H). MS obsd. (ESI$^+$) [(M+H)$^+$]: 348.

Example 120: 10-chloro-6-isopropyl-9-(3-methoxypropoxy)-2-oxo-6,7-dihydrobenzo[a]quinolizine-3-carboxylic acid

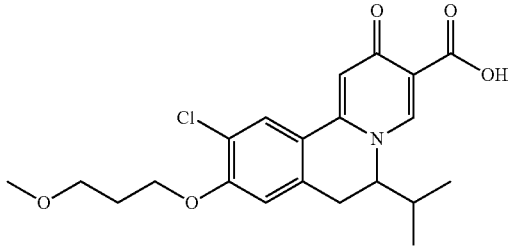 [SMILES: COCCCOc1cc2c(cc1Cl)-c1cc(=O)c(C(=O)O)cn1C(C(C)C)C2]

Step 1: Preparation of 4-bromo-1-chloro-2-(3-methoxypropoxy)benzene

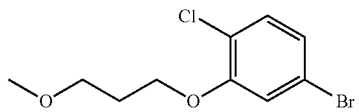

A 250 mL round-bottomed flask was charged with 5-bromo-2-chloro-phenol (22 g, 106 mmol), 1-bromo-3-methoxy-propane (19.5 g, 127 mmol), $K_2CO_3$ (30 g, 212 mmol) and DMF (50 mL). The resultant mixture was stirred at 50° C. for 3 hours, then ethyl acetate and water were added. The organic phase was separated, and then dried over anhydrous $Na_2SO_4$ and then concentrated to give 4-bromo-1-chloro-2-(3-methoxypropoxy)benzene (30 g).

Step 2: Preparation of 1-[4-chloro-3-(3-methoxypropoxy)phenyl]-3-methyl-butan-2-one

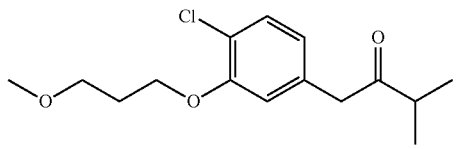 [SMILES: COCCCOc1cc(CC(=O)C(C)C)ccc1Cl]

A mixture of 4-bromo-1-chloro-2-(3-methoxypropoxy)benzene (28 g, 0.1 mol), 3-methylbutan-2-one (26 g, 0.3 mol), $Pd_2(dba)_3$ (1.4 g, 1.5 mmol), Xantphos (1.8 g, 3 mmol) and t-BuONa (32 g, 0.33 mol) in 500 mL of THF was stirred at 70° C. overnight. Then ethyl acetate and water were added. The separated organic phase was washed with brine, and then dried over anhydrous $Na_2SO_4$ and then concentrated. The residue was purified by column chromatography to give 1-[4-chloro-3-(3-methoxypropoxy)phenyl]-3-methyl-butan-2-one (19.6 g).

Step 3: Preparation of 1-[4-chloro-3-(3-methoxypropoxy)phenyl]-3-methyl-butan-2-amine

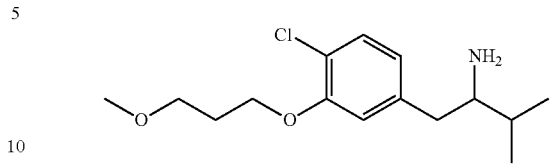

1-[4-Chloro-3-(3-methoxypropoxy)phenyl]-3-methyl-butan-2-one (10 g, 35 mmol) was dissolved in MeOH (100 mL). Then $NH_4OAc$ (40 g, 525 mmol) and $NaBH_3CN$ (4.4 g, 70 mmol) were added. The mixture was stirred at room temperature overnight. Then 20% NaOH aqueous solution (50 mL) was added, and the mixture was stirred for 20 minutes. The mixture was extracted with ethyl acetate, and the organic layer was dried over anhydrous $Na_2SO_4$ and then concentrated to afford 1-[4-chloro-3-(3-methoxypropoxy)phenyl]-3-methyl-butan-2-amine (8 g) which was used in the next step without further purification.

Step 4: Preparation of N-[1-[[4-chloro-3-(3-methoxypropoxy)phenyl]methyl]-2-methyl-propyl]formamide

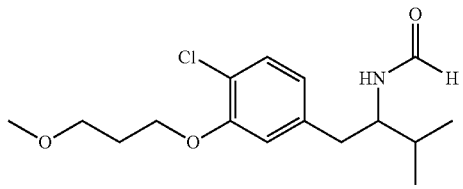 [SMILES: COCCCOc1cc(CC(NC=O)C(C)C)ccc1Cl]

A mixture of 1-(4-chloro-3-ethoxy-phenyl)butan-2-amine (35 mmol) and formic acid (20 mL) in dioxane (100 mL) was refluxed for 16 hours and then concentrated under reduced pressure to afford the crude N-[1-[[4-chloro-3-(3-methoxypropoxy)phenyl]methyl]-2-methyl-propyl]formamide which was used in the next step without purification.

Step 5: Preparation of 7-chloro-3-isopropyl-6-(3-methoxypropoxy)-3,4-dihydroisoquinoline

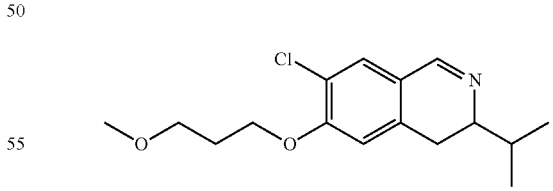

To a solution of N-[1-[[4-chloro-3-(3-methoxypropoxy)phenyl]methyl]-2-methyl-propyl]formamide (7.6 g, 24 mmol) in acetonitrile (100 mL) was added $POCl_3$ (3.8 g, 24 mmol) dropwise at 0-5° C. The resultant mixture was refluxed for 4 hours and then concentrated. Ethyl acetate was added, and then ammonia was added to the mixture to adjust the pH of the aqueous solution to around 11. The aqueous layer was extracted with ethyl acetate. The organic layers were combined and then concentrated. The residue was purified by column chromatography to give 7-chloro-3-isopropyl-6-(3-methoxypropoxy)-3,4-dihydroisoquinoline (4.6 g).

Step 6: Preparation of ethyl 10-chloro-6-isopropyl-9-(3-methoxypropoxy)-2-oxo-1,6,7,11b-tetrahydrobenzo[a]quinolizine-3-carboxylate

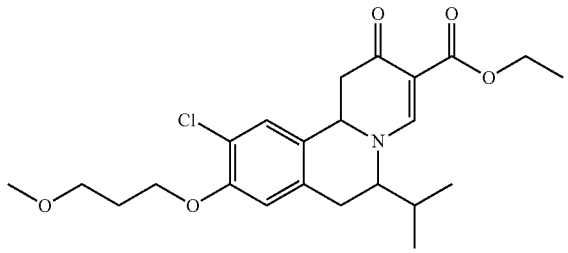 [SMILES: CCOC(=O)C1=CN2C(CC1=O)c1cc(Cl)c(OCCCOC)cc1CC2C(C)C]

A mixture of 7-chloro-3-isopropyl-6-(3-methoxypropoxy)-3,4-dihydroisoquinoline (4.6 g, 15 mmol) and ethyl 2-(ethoxymethylene)-3-oxo-butanoate (8.3 g, 45 mmol) in EtOH (20 mL) was stirred at 110° C. overnight. The mixture was concentrated to give crude ethyl 10-chloro-6-isopropyl-9-(3-methoxypropoxy)-2-oxo-1,6,7,11b-tetrahydrobenzo[a]quinolizine-3-carboxylate as dark brown oil which was used in the next step without purification.

Step 7: Preparation of ethyl 10-chloro-6-isopropyl-9-(3-methoxypropoxy)-2-oxo-6,7-dihydrobenzo[a]quinolizine-3-carboxylate

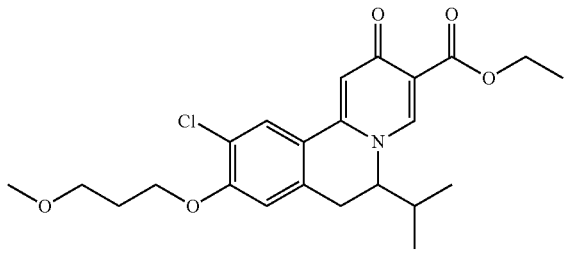 [SMILES: CCOC(=O)c1cn2c(cc1=O)-c1cc(Cl)c(OCCCOC)cc1CC2C(C)C]

A mixture of crude ethyl 10-chloro-6-isopropyl-9-(3-methoxypropoxy)-2-oxo-1,6,7,11b-tetrahydrobenzo[a]quinolizine-3-carboxylate (15 mmol) and p-chloranil (3.6 g, 15 mmol) in DME (20 mL) was refluxed for 2 hours. After being cooled to room temperature, the mixture was concentrated under vacuum to give crude ethyl 10-chloro-6-isopropyl-9-(3-methoxypropoxy)-2-oxo-6,7-dihydrobenzo[a]quinolizine-3-carboxylate as brown oil.

Step 8: Preparation of 10-chloro-6-isopropyl-9-(3-methoxypropoxy)-2-oxo-6,7-dihydrobenzo[a]quinolizine-3-carboxylic acid

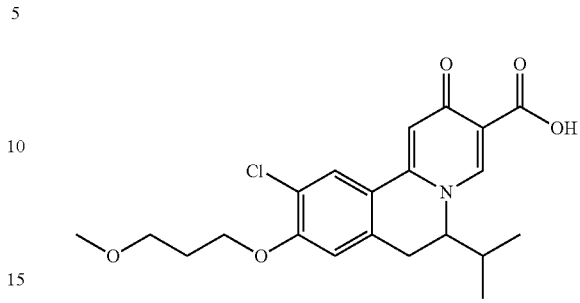

To a solution of crude ethyl 10-chloro-6-isopropyl-9-(3-methoxypropoxy)-2-oxo-6,7-dihydrobenzo[a]quinolizine-3-carboxylate from Step 7 in EtOH (50 mL) was added 10% NaOH aqueous solution dropwise at room temperature. The resultant mixture was stirred for 2 hours, and then acidified to pH 1-2 with 2M hydrochloric acid. The mixture was extracted with DCM, and the combined organic layers were washed with brine, and then dried over anhydrous $Na_2SO_4$ and then concentrated. The residue was purified by column chromatography and recrystallization from EtOH/ethyl ether to afford 10-chloro-6-isopropyl-9-(3-methoxypropoxy)-2-oxo-6,7-dihydrobenzo[a]quinolizine-3-carboxylic acid (1.7 g) as a white solid. $^1$H NMR (400 MHz, DMSO-$d_6$): δ 8.80 (s, 1H), 8.19 (s, 1H), 7.41 (s, 1H), 7.32 (s, 1H), 4.48 (dd, 1H), 4.21 (m, 2H), 3.52 (t, 2H), 3.26-3.42 (m, 5H), 2.02 (m, 2H), 1.54-1.68 (m, 1H), 0.88 (d, 3H), 0.71 (d, 3H). MS obsd. (ESI$^+$) [(M+H)$^+$]: 406.

Example 121 and 122

(+)-10-chloro-6-isopropyl-9-(3-methoxypropoxy)-2-oxo-6,7-dihydrobenzo[a]quinolizine-3-carboxylic acid and (−)-10-chloro-6-isopropyl-9-(3-methoxypropoxy)-2-oxo-6,7-dihydrobenzo[a]quinolizine-3-carboxylic acid

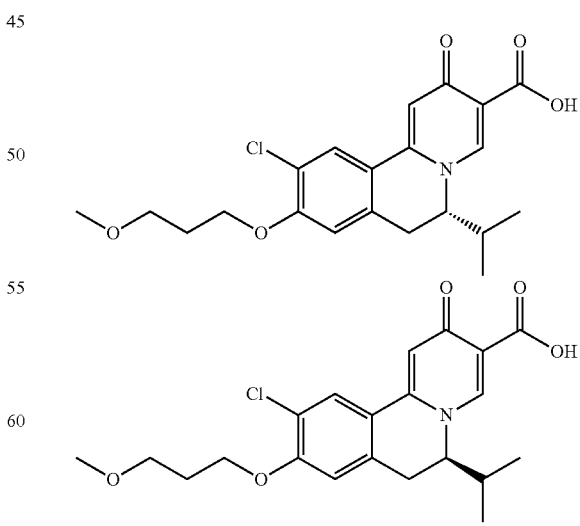

Separation of the racemic 10-chloro-6-isopropyl-9-(3-methoxypropoxy)-2-oxo-6,7-dihydrobenzo[a]quinolizine- 3-carboxylic acid (1.3 g) by chiral HPLC afforded (+)-10-chloro-6-isopropyl-9-(3-methoxypropoxy)-2-oxo-6,7-dihydrobenzo[a]quinolizine-3-carboxylic acid (465 mg) and (−)-10-chloro-6-isopropyl-9-(3-methoxypropoxy)-2-oxo-6,7-dihydrobenzo[a]quinolizine-3-carboxylic acid (506 mg).

Example 121

$^1$H NMR (400 MHz, DMSO-d$_6$): δ 8.80 (s, 1H), 8.19 (s, 1H), 7.41 (s, 1H), 7.32 (s, 1H), 4.48 (dd, 1H), 4.21 (m, 2H), 3.52 (t, 2H), 3.26-3.42 (m, 5H), 2.02 (m, 2H), 1.54-1.68 (m, 1H), 0.88 (d, 3H), 0.71 (d, 3H). MS obsd. (ESI$^+$) [(M+H)$^+$]: 406. [α]$_D$20=+118.44° (0.103%, MeOH).

Example 122

$^1$H NMR (400 MHz, DMSO-d$_6$): δ 8.80 (s, 1H), 8.19 (s, 1H), 7.41 (s, 1H), 7.32 (s, 1H), 4.48 (dd, 1H), 4.21 (m, 2H), 3.52 (t, 2H), 3.26-3.42 (m, 5H), 2.02 (m, 2H), 1.54-1.68 (m, 1H), 0.88 (d, 3H), 0.71 (d, 3H). MS obsd. (ESI$^+$) [(M+H)$^+$]: 406.

Example 123: 10-methoxy-6-isopropyl-9-(3-methoxypropoxy)-2-oxo-6,7-dihydrobenzo[a]quinolizine-3-carboxylic acid

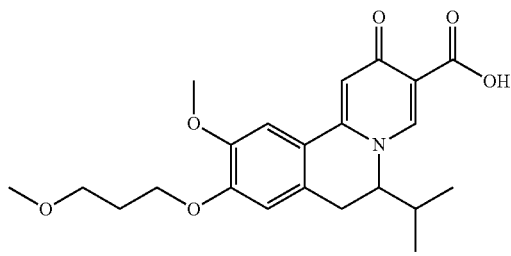 [SMILES: COCCCOc1cc2c(cc1OC)-c1cc(=O)c(C(=O)O)cn1C(C(C)C)C2]

Step 1: Preparation of 4-bromo-1-methoxy-2-(3-methoxypropoxy)benzene

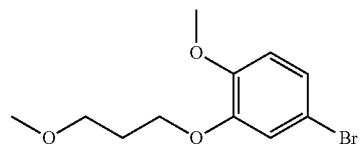

A 250 mL round-bottomed flask was charged with 5-bromo-2-methoxy-phenol (15.5 g, 76.4 mmol), 1-bromo-3-methoxy-propane (12.9 g, 84 mmol), K$_2$CO$_3$ (22 g, 2153 mmol) and DMF (50 mL). The resultant mixture was stirred at 50° C. for 3 hours, and then ethyl acetate and water was added. The organic phase was separated, and then dried over anhydrous Na$_2$SO$_4$ and then concentrated to give 4-bromo-1-methoxy-2-(3-methoxypropoxy)benzene (23 g).

Step 2: Preparation of 1-[4-methoxy-3-(3-methoxypropoxy)phenyl]-3-methyl-butan-2-one

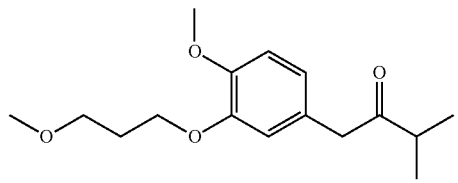 [SMILES: COCCCOc1cc(CC(=O)C(C)C)ccc1OC]

A mixture of 4-bromo-1-methoxy-2-(3-methoxypropoxy)benzene (20 g, 73 mmol), 3-methylbutan-2-one (19 g, 219 mmol), Pd$_2$(dba)$_3$ (1 g, 1.2 mmol), Xantphos (1.3 g, 2.4 mmol) and t-BuONa (23 g, 241 mol) in 500 mL of THF was stirred at 70° C. overnight. Then ethyl acetate and water were added. The separated organic phase was washed with brine, and then dried over anhydrous Na$_2$SO$_4$ and then concentrated. The residue was purified by column chromatography to give 1-[4-methoxy-3-(3-methoxypropoxy)phenyl]-3-methyl-butan-2-one (19 g)

Step 3: Preparation of 1-[4-methoxy-3-(3-methoxypropoxy)phenyl]-3-methyl-butan-2-amine

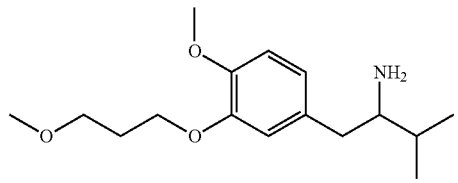 [SMILES: COCCCOc1cc(CC(N)C(C)C)ccc1OC]

1-[4-Methoxy-3-(3-methoxypropoxy)phenyl]-3-methyl-butan-2-one (19 g, 73 mmol) was dissolved in MeOH (150 mL). Then NH$_4$OAc (84 g, 1.1 mol) and NaBH$_3$CN (9.2 g, 146 mmol) were added. The mixture was stirred at room temperature overnight. 20% NaOH aqueous solution (100 mL) was added to the mixture. The reaction mixture was stirred for 20 minutes. The mixture was extracted with ethyl acetate, and the organic layer was dried over anhydrous Na$_2$SO$_4$ and $_{then}$ concentrated to afford 1-[4-methoxy-3-(3-methoxypropoxy)phenyl]-3-methyl-butan-2-amine (8 g) which was used in the next step without further purification.

Step 4: Preparation of N-[1-[[4-methoxy-3-(3-methoxypropoxy)phenyl]methyl]-2-methyl-propyl]formamide

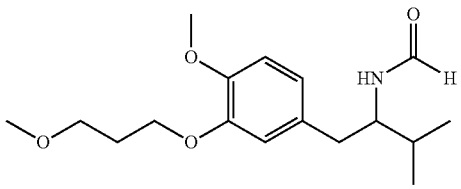 [SMILES: COCCCOc1cc(CC(NC=O)C(C)C)ccc1OC]

A mixture of 1-(4-methoxy-3-ethoxy-phenyl)butan-2-amine (73 mmol) and formic acid (40 mL) in dioxane (150 mL) was refluxed for 16 hours and then concentrated under reduced pressure to afford crude N-[1-[[4-methoxy-3-(3-methoxypropoxy)phenyl]methyl]-2-methyl-propyl]formamide which was used in the next step without purification.

Step 5: Preparation of 7-methoxy-3-isopropyl-6-(3-methoxypropoxy)-3,4-dihydroisoquinoline

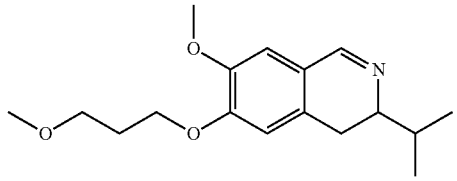 [SMILES: COCCCOc1cc2c(cc1OC)C=NC(C(C)C)C2]

To a solution of N-[1-[[4-methoxy-3-(3-methoxypropoxy)phenyl]methyl]-2-methyl-propyl]formamide (64.7 mmol) in acetonitrile (150 mL) was added POCl$_3$ (10.1 g, 64.7 mmol) dropwise at 0-5° C. The resultant mixture was refluxed for 4 hours and then concentrated. Ethyl acetate was added, followed by addition of ammonia water to adjust the pH of the aqueous solution to around 11. The aqueous layer was extracted with ethyl acetate. The organic layers were combined and then concentrated. The residue was purified by column chromatography to give 7-methoxy-3-isopropyl-6-(3-methoxypropoxy)-3,4-dihydroisoquinoline (16 g).

Step 6: Preparation of ethyl 10-methoxy-6-isopropyl-9-(3-methoxypropoxy)-2-oxo-1,6,7,11b-tetrahydrobenzo[a]quinolizine-3-carboxylate

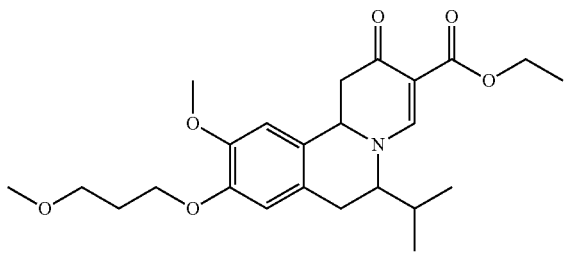 [SMILES: CCOC(=O)C1=CN2C(CC1=O)c1cc(OC)c(OCCCOC)cc1CC2C(C)C]

A mixture of 7-methoxy-3-isopropyl-6-(3-methoxypropoxy)-3,4-dihydroisoquinoline (16 g, 55 mmol) and ethyl 2-(ethoxymethylene)-3-oxo-butanoate (30 g, 165 mmol) in EtOH (150 mL) was stirred at 100° C. overnight. The mixture was concentrated to give crude ethyl 10-methoxy-6-isopropyl-9-(3-methoxypropoxy)-2-oxo-1,6,7,11b-tetrahydrobenzo[a]quinolizine-3-carboxylate as dark brown oil which was used in the next step without purification.

Step 7: Preparation of ethyl 10-methoxy-6-isopropyl-9-(3-methoxypropoxy)-2-oxo-6,7-dihydrobenzo[a]quinolizine-3-carboxylate

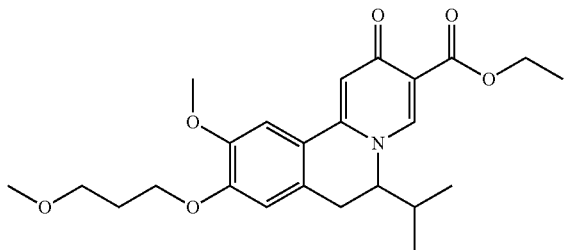 [SMILES: CCOC(=O)c1cn2c(cc1=O)-c1cc(OC)c(OCCCOC)cc1CC2C(C)C]

A mixture of crude ethyl 10-methoxy-6-isopropyl-9-(3-methoxypropoxy)-2-oxo-1,6,7,11b-tetrahydrobenzo[a]quinolizine-3-carboxylate (55 mmol) and p-chloranil (13.4 g, 55 mmol) in DME (100 mL) was refluxed for 2 hours. After being cooled to room temperature, the mixture was concentrated under vacuum to give crude ethyl 10-methoxy-6-isopropyl-9-(3-methoxypropoxy)-2-oxo-6,7-dihydrobenzo[a]quinolizine-3-carboxylate as brown oil.

Step 8: Preparation of 10-methoxy-6-isopropyl-9-(3-methoxypropoxy)-2-oxo-6,7-dihydrobenzo[a]quinolizine-3-carboxylic acid

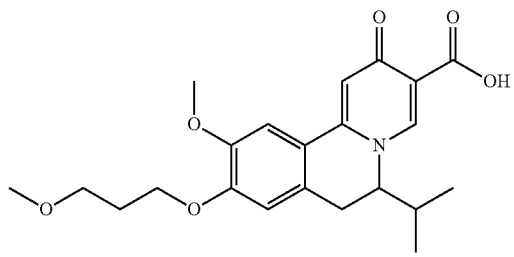 [SMILES: COCCCOc1cc2c(cc1OC)-c1cc(=O)c(C(=O)O)cn1C(C(C)C)C2]

To a solution of crude ethyl 10-methoxy-6-isopropyl-9-(3-methoxypropoxy)-2-oxo-6,7-dihydrobenzo[a]quinolizine-3-carboxylate from Step 7 in EtOH (100 mL) was added 10% NaOH aqueous solution dropwise at room temperature. The resultant mixture was stirred for 2 hours, and then acidified to pH 1-2 with 2M hydrochloric acid. The mixture was extracted with DCM, and the combined organic layers were washed with brine, and then dried over anhydrous Na$_2$SO$_4$ and then concentrated. The residue was purified by column chromatography and recrystallization from EtOH/ethyl ether to afford 10-methoxy-6-isopropyl-9-(3-methoxypropoxy)-2-oxo-6,7-dihydrobenzo[a]quinolizine-3-carboxylic acid (8.7 g) as a white solid. $^1$H NMR (400 MHz, DMSO-d$_6$): δ 8.76 (s, 1H), 7.52 (s, 1H), 7.45 (s, 1H), 7.09 (s, 1H), 4.43 (dd, 1H), 4.08 (m, 2H), 3.88 (s, 3H), 3.48 (t, 2H), 3.13-3.17 (m, 2H), 2.01 (m, 2H), 1.61-1.66 (m, 1H), 0.88 (d, 3H), 0.71 (d, 3H). MS obsd. (ESI$^+$) [(M+H)$^+$]: 402.

Example 124 and 125

(+)-10-methoxy-6-isopropyl-9-(3-methoxypropoxy)-2-oxo-6,7-dihydrobenzo[a]quinolizine-3-carboxylic acid and (−)-10-methoxy-6-isopropyl-9-(3-methoxypropoxy)-2-oxo-6,7-dihydrobenzo[a]quinolizine-3-carboxylic acid Example 124

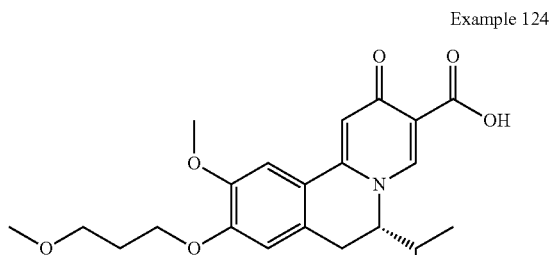

Example 125

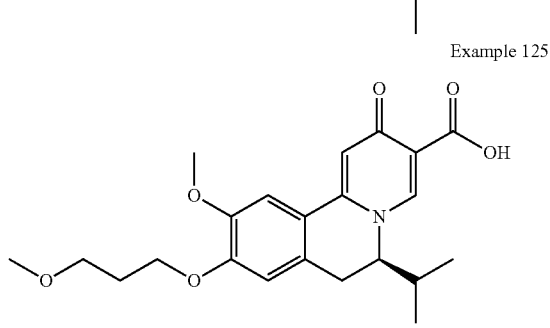

Separation of the racemic 10-methoxy-6-isopropyl-9-(3-methoxypropoxy)-2-oxo-6,7-dihydrobenzo[a]quinolizine-3-carboxylic acid (2.0 g) by chiral HPLC afforded (+)-10-methoxy-6-isopropyl-9-(3-methoxypropoxy)-2-oxo-6,7-dihydrobenzo[a]quinolizine-3-carboxylic acid (840 mg) and (−)-10-methoxy-6-isopropyl-9-(3-methoxypropoxy)-2-oxo-6,7-dihydrobenzo[a]quinolizine-3-carboxylic acid (1.0 g).

Example 124

$^1$H NMR (400 MHz, DMSO-d$_6$): δ 8.76 (s, 1H), 7.52 (s, 1H), 7.45 (s, 1H), 7.09 (s, 1H), 4.43 (dd, 1H), 4.08 (m, 2H), 3.88 (s, 3H), 3.48 (t, 2H), 3.13-3.17 (m, 2H), 2.01 (m, 2H), 1.61-1.66 (m, 1H), 0.88 (d, 3H), 0.71 (d, 3H). MS obsd. (ESI$^+$) [(M+H)$^+$]: 402. [α]$_D$20=+71.19° (0.059%, CH$_3$CN).

Example 125

$^1$H NMR (400 MHz, DMSO-d$_6$): δ 8.76 (s, 1H), 7.52 (s, 1H), 7.45 (s, 1H), 7.09 (s, 1H), 4.43 (dd, 1H), 4.08 (m, 2H), 3.88 (s, 3H), 3.48 (t, 2H), 3.13-3.17 (m, 2H), 2.01 (m, 2H), 1.61-1.66 (m, 1H), 0.88 (d, 3H), 0.71 (d, 3H). MS obsd. (ESI$^+$) [(M+H)$^+$]: 402.

Example 126: 6-isopropyl-10-methoxy-2-oxo-9-(2,2,2-trifluoroethoxy)-6,7-dihydrobenzo[a]quinolizine-3-carboxylic acid

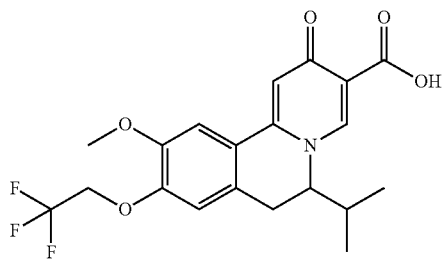 [SMILES: COc1cc2c(cc1OCC(F)(F)F)CC(C(C)C)n1cc(C(=O)O)c(=O)cc1-2]

Step 1: Preparation of 2-benzyloxy-4-bromo-1-methoxy-benzene

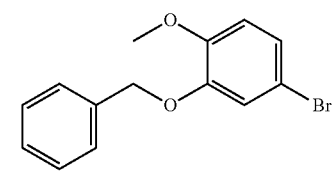 [SMILES: COc1ccc(Br)cc1OCc1ccccc1]

To a mixture of 5-bromo-2-methoxy-phenol (125 g, 615 mmol) in acetone (1.5 L) was added K$_2$CO$_3$ (128 g, 923 mmol) and bromomethylbenzene (126 g, 740 mmol). The mixture was refluxed for 16 h. The reaction was carried out again at the same scale, and then the two batches of mixtures were combined and filtered. The filter cake was washed with acetone. The filtrate was concentrated to give a white solid, which was washed with petroleum ether to give 2-benzyloxy-4-bromo-1-methoxy-benzene (330 g) as a white solid.

Step 2: Preparation of 1-(3-benzyloxy-4-methoxy-phenyl)-3-methyl-butan-2-one

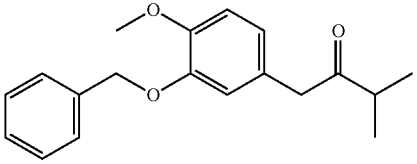 [SMILES: COc1ccc(CC(=O)C(C)C)cc1OCc1ccccc1]

A mixture of 2-benzyloxy-4-bromo-1-methoxy-benzene (110 g, 375 mmol), 3-methyl-2-butanone (42 g, 488 mmol), t-BuONa (54 g, 563 mmol), Xantphos (9 g, 15 mmol) and Pd$_2$(dba)$_3$ (7 g, 7.5 mmol) in THF (1.2 L) was stirred at 50° C. under N$_2$ for 6 h. The reaction was conducted at the same scale totally three times in parallel. Then the reaction mixtures were combined and filtered. The filtrate was concentrated, and the residue was purified by column chromatography to give 1-(3-benzyloxy-4-methoxy-phenyl)-3-methyl-butan-2-one (159 g).

Step 3: Preparation of 1-(3-benzyloxy-4-methoxy-phenyl)-3-methyl-butan-2-amine

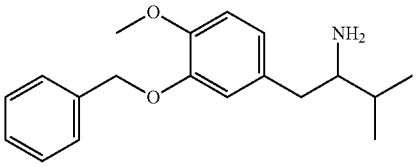 [SMILES: COc1ccc(CC(N)C(C)C)cc1OCc1ccccc1]

To a mixture of 1-(3-benzyloxy-4-methoxy-phenyl)-3-methyl-butan-2-one (53 g, 178 mmol) in MeOH (600 mL) was added NH$_4$OAc (96 g, 1.25 mol) at 25° C. The reaction mixture was stirred at rt for 1 h and then cooled to 0° C. To the cooled mixture was added NaBH$_3$CN (14.5 g, 231 mmol) at 0° C. The resulting mixture was warmed naturally to 25° C. and stirred at 25° C. for 12 h, and then the reaction was quenched with NH$_4$Cl aqueous solution (200 mL). The reaction was conducted at the same scale for totally three times in parallel. The combined mixtures were concentrated under reduced pressure to remove MeOH, and the residual mixture was extracted with DCM (600 mL). The combined organic layers were washed with brine (300 mL), dried over anhydrous Na$_2$SO$_4$ and concentrated under reduced pressure to afford crude 1-(3-benzyloxy-4-methoxy-phenyl)-3-methyl-butan-2-amine (180 g) as a yellow oil, which was used directly in the next step without further purification.

Step 4: Preparation of N-[1-[(3-benzyloxy-4-methoxy-phenyl)methyl]-2-methyl-propyl]formamide

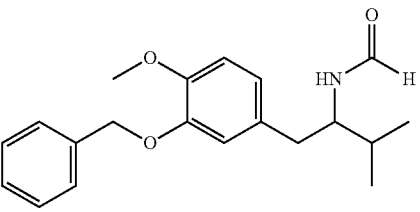 [SMILES: COc1ccc(CC(NC=O)C(C)C)cc1OCc1ccccc1]

To a mixture of 1-(3-benzyloxy-4-methoxy-phenyl)-3-methyl-butan-2-amine (180 g, 601 mmol) in dioxane (1.5 L) was added formic acid (194 g, 4.21 mol) at 30° C. The mixture was refluxed for 12 h and concentrated. The residue was diluted with EtOAc (1.5 L), and the solution was washed with H₂O (500 mL), brine (500 mL), dried over anhydrous Na₂SO₄, and concentrated. The residue was purified by column chromatography to give N-[1-[(3-benzyloxy-4-methoxy-phenyl)methyl]-2-methyl-propyl]formamide (130 g, yield: 82%) as a yellow solid.

Step 5: Preparation of 6-benzyloxy-3-isopropyl-7-methoxy-3,4-dihydroisoquinoline

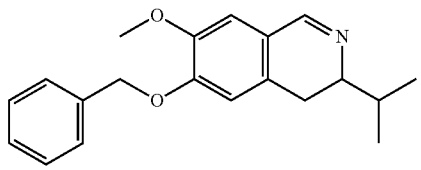 [SMILES: COc1cc2c(cc1OCc1ccccc1)CC(C(C)C)N=C2]

To a mixture of N-[1-[(3-benzyloxy-4-methoxy-phenyl)methyl]-2-methyl-propyl]formamide (65 g, 199 mmol) in dry DCM (500 mL) was added POCl₃ (46 g, 298 mmol) dropwise at 0° C. Then the mixture was refluxed for 2 h. The reaction was conducted again at the same scale, and the combined two batches of mixtures were poured into a solution of ammonia water (100 mL) in ice (500 g), and stirred for 0.5 h. Then the mixture was extracted with DCM (2 L). The organic layer was washed with brine (500 mL), dried over anhydrous Na₂SO₄ and concentrated under reduced pressure to give a yellow solid, which was washed with methyl tert-butyl ether and purified by column chromatography to give 6-benzyloxy-3-isopropyl-7-methoxy-3,4-dihydroisoquinoline (99 g).

Step 6: Preparation of ethyl 9-benzyloxy-6-isopropyl-10-methoxy-2-oxo-1,6,7,11b-tetrahydrobenzo[a]quinolizine-3-carboxylate

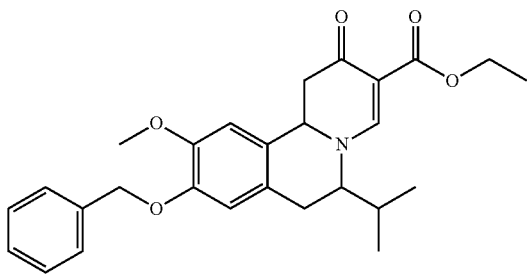 [SMILES: CCOC(=O)C1=CN2C(CC1=O)c1cc(OC)c(OCc3ccccc3)cc1CC2C(C)C]

A mixture of 6-benzyloxy-3-isopropyl-7-methoxy-3,4-dihydroisoquinoline (15 g, 48.4 mmol) and ethyl 2-(ethoxymethylene)-3-oxo-butanoate (10 g, 53.2 mmol) in EtOH (150 ml) was refluxed overnight. The mixture was concentrated to give crude ethyl 9-benzyloxy-6-isopropyl-10-methoxy-2-oxo-1,6,7,11b-tetrahydrobenzo[a]quinolizine-3-carboxylate as a dark brown oil which was used in the next step without purification.

Step 7: Preparation of ethyl 9-benzyloxy-6-isopropyl-10-methoxy-2-oxo-6,7-dihydrobenzo[a]quinolizine-3-carboxylate

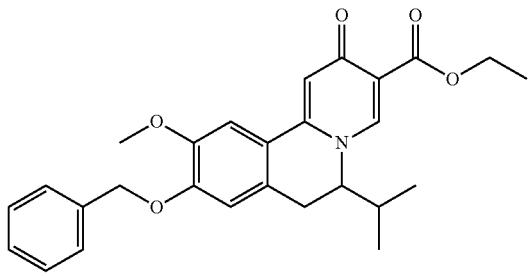 [SMILES: CCOC(=O)c1cn2c(cc1=O)-c1cc(OC)c(OCc3ccccc3)cc1CC2C(C)C]

A mixture of crude ethyl 9-benzyloxy-6-isopropyl-10-methoxy-2-oxo-1,6,7,11b-tetrahydrobenzo[a]quinolizine-3-carboxylate and p-chloranil (7.14 g, 29 mmol) in DME (60 mL) was refluxed for 2 h. After being cooled to rt, the resulting suspension was filtered with suction.

The filter cake was washed with cold DME and dried under reduced pressure to give ethyl 9-benzyloxy-6-isopropyl-10-methoxy-2-oxo-6,7-dihydrobenzo[a]quinolizine-3-carboxylate as a yellow solid (15 g, 69% yield over 2 steps).

Step 8: Preparation of ethyl 9-hydroxy-6-isopropyl-10-methoxy-2-oxo-6,7-dihydrobenzo[a]quinolizine-3-carboxylate

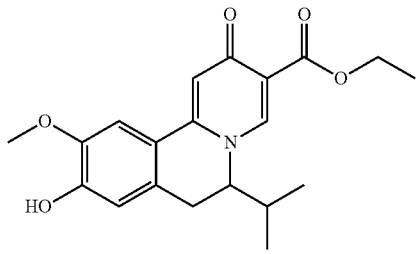 [SMILES: CCOC(=O)c1cn2c(cc1=O)-c1cc(OC)c(O)cc1CC2C(C)C]

To a solution of ethyl 9-benzyloxy-6-isopropyl-10-methoxy-2-oxo-6,7-dihydrobenzo[a]quinolizine-3-carboxylate (15 g, 33.5 mmol) in ethanol (150 mL) was added palladium on carbon (10%, 450 mg). The resulting mixture was stirred under hydrogen (1 atm) at room temperature for 10 hours. The mixture was filtered and the filtrate was concentrated to afford ethyl 9-hydroxy-6-isopropyl-10-methoxy-2-oxo-6,7-dihydrobenzo[a]quinolizine-3-carboxylate (11.8 g, 99% yield).

Step 9: Preparation of ethyl 6-isopropyl-10-methoxy-2-oxo-9-(2,2,2-trifluoroethoxy)-6,7-dihydrobenzo[a]quinolizine-3-carboxylate

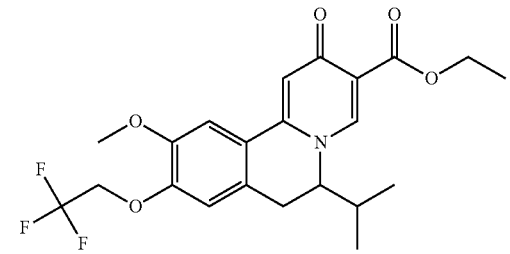 [SMILES: CCOC(=O)c1cn2c(cc1=O)-c1cc(OC)c(OCC(F)(F)F)cc1CC2C(C)C]

A mixture of ethyl 9-hydroxy-6-isopropyl-10-methoxy-2-oxo-6,7-dihydrobenzo[a]quinolizine-3-carboxylate (11.8 g, 33 mmol), 1,1,1-trifluoro-2-iodo-ethane (10.9 g, 52 mmol) and K$_2$CO$_3$ (7.2 g, 52 mmol) in DMF (150 mL) was stirred at 80° C. for 2 hours. The resulting mixture was diluted with water and extracted with ethyl acetate. The organic phase was dried over anhydrous Na$_2$SO$_4$ and concentrated in vacuo to give crude ethyl 6-isopropyl-10-methoxy-2-oxo-9-(2,2,2-trifluoroethoxy)-6,7-dihydrobenzo[a]quinolizine-3-carboxylate which was used in the next step without purification.

Step 10: Preparation of 6-isopropyl-10-methoxy-2-oxo-9-(2,2,2-trifluoroethoxy)-6,7-dihydrobenzo[a]quinolizine-3-carboxylic acid

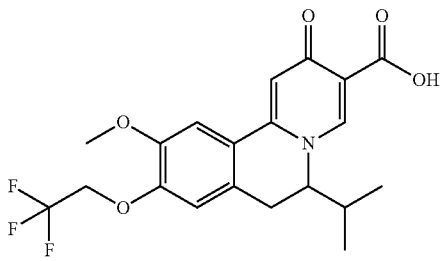

To a solution of ethyl 6-isopropyl-10-methoxy-2-oxo-9-(2,2,2-trifluoroethoxy)-6,7-dihydrobenzo[a]quinolizine-3-carboxylate (1 g, 2.2 mmol) in THF (10 mL) was added 10% aqueous solution of NaOH aqueous solution dropwise at rt. The resultant mixture was stirred for 2 h, and then acidified to pH=1-2 with 2 M hydrochloric acid. The mixture was extracted with DCM (20 mL×2), and the combined organic layers were washed with brine, dried over anhydrous Na$_2$SO$_4$ and concentrated. The residue was purified by HPLC to give 6-isopropyl-10-methoxy-2-oxo-9-(2,2,2-trifluoroethoxy)-6,7-dihydrobenzo[a]quinolizine-3-carboxylic acid (780 mg, 84% yield) as a light yellow solid. $^1$H NMR (400 MHz, DMSO-d6): δ 8.80 (s, 1H), 7.61 (s, 1H), 7.52 (s, 1H), 7.22 (s, 1H), 4.84 (q, 2H), 4.46 (dd, 1H), 3.92 (s, 3H), 3.31 (d, 1H), 3.12 (d, 1H), 1.64-1.59 (m, 1H), 0.88 (d, 3H), 0.71 (d, 3H). MS obsd. (ESI$^+$) [(M+H)$^+$]: 412.

Example 127 and 128

(+)-6-isopropyl-10-methoxy-2-oxo-9-(2,2,2-trifluoroethoxy)-6,7-dihydrobenzo[a]quinolizine-3-carboxylic acid and (−)-6-isopropyl-10-methoxy-2-oxo-9-(2,2,2-trifluoroethoxy)-6,7-dihydrobenzo[a]quinolizine-3-carboxylic acid

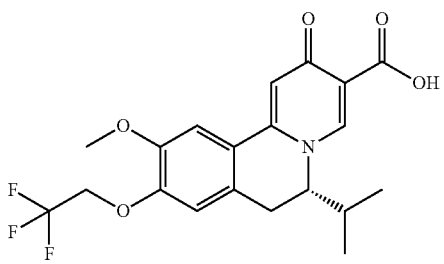 [SMILES: COc1cc2c(cc1OCC(F)(F)F)CC(C(C)C)n1cc(C(=O)O)c(=O)cc1-2]

-continued

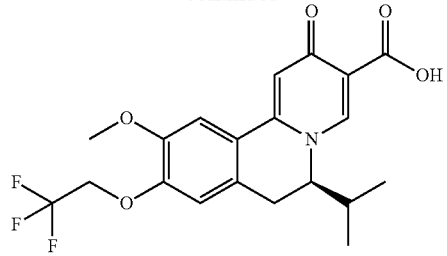

Separation of 6-isopropyl-10-methoxy-2-oxo-9-(2,2,2-trifluoroethoxy)-6,7-dihydrobenzo[a]quinolizine-3-carboxylic acid by chiral HPLC provided (+)-6-isopropyl-10-methoxy-2-oxo-9-(2,2,2-trifluoroethoxy)-6,7-dihydrobenzo[a]quinolizine-3-carboxylic acid and (−)-6-isopropyl-10-methoxy-2-oxo-9-(2,2,2-trifluoroethoxy)-6,7-dihydrobenzo[a]quinolizine-3-carboxylic acid.

Example 127

$^1$H NMR (400 MHz, DMSO-d6): δ 8.80 (s, 1H), 7.61 (s, 1H), 7.52 (s, 1H), 7.22 (s, 1H), 4.84 (q, 2H), 4.46 (dd, 1H), 3.92 (s, 3H), 3.31 (d, 1H), 3.12 (d, 1H), 1.64-1.59 (m, 1H), 0.88 (d, 3H), 0.71 (d, 3H). MS obsd. (ESI$^+$) [(M+H)$^+$]: 412. [α]$_D$20=+121.7° (0.1%, CH$_3$CN).

Example 128

$^1$H NMR (400 MHz, DMSO-d6): δ 8.80 (s, 1H), 7.61 (s, 1H), 7.52 (s, 1H), 7.22 (s, 1H), 4.84 (q, 2H), 4.46 (dd, 1H), 3.92 (s, 3H), 3.31 (d, 1H), 3.12 (d, 1H), 1.64-1.59 (m, 1H), 0.88 (d, 3H), 0.71 (d, 3H). MS obsd. (ESI$^+$) [(M+H)$^+$]: 412.

Example 129 and 130

(+)-6-isopropyl-10-methoxy-9-(2-methoxyethoxy)-2-oxo-6,7-dihydrobenzo[a]quinolizine-3-carboxylic acid and (−)-6-isopropyl-10-methoxy-9-(2-methoxyethoxy)-2-oxo-6,7-dihydrobenzo[a]quinolizine-3-carboxylic acid

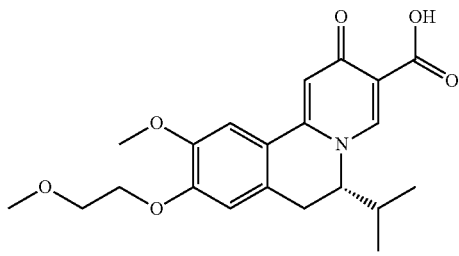

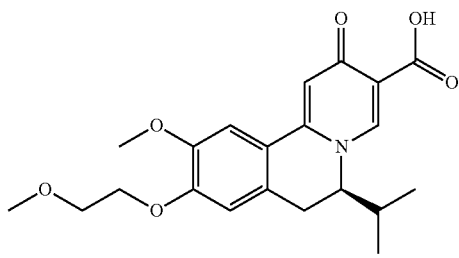

Step 1: Preparation of ethyl 9-benzyloxy-6-isopropyl-10-methoxy-2-oxo-1,6,7,11b-tetrahydrobenzo[a]quinolizine-3-carboxylate

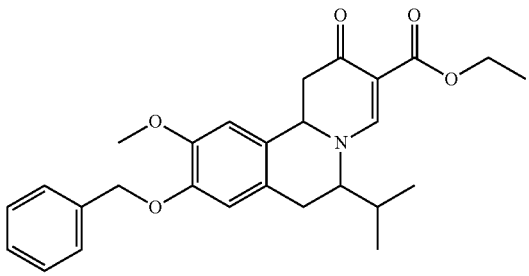 [SMILES: CCOC(=O)C1=CN2C(CC1=O)c1cc(OC)c(OCc3ccccc3)cc1CC2C(C)C]

A mixture of 6-benzyloxy-3-isopropyl-7-methoxy-3,4-dihydroisoquinoline (15.5 g, 50 mmol) and ethyl 2-(ethoxymethylene)-3-oxo-butanoate (28.0 g, 150 mmol, Sinopharm Chemical) in ethanol (150 mL) was refluxed for 24 h. The mixture was concentrated to give crude ethyl 9-benzyloxy-6-isopropyl-10-methoxy-2-oxo-1,6,7,11b-tetrahydrobenzo[a]quinolizine-3-carboxylate (22 g) as a dark brown oil which was used in the next step without further purification.

Step 2: Preparation of ethyl 9-benzyloxy-6-isopropyl-10-methoxy-2-oxo-6,7-dihydrobenzo[a]quinolizine-3-carboxylate

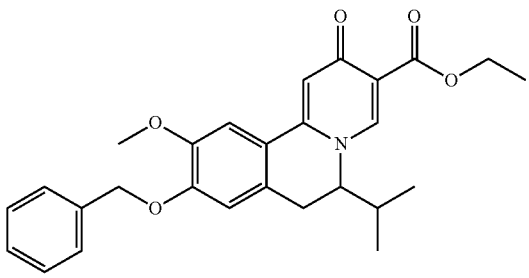 [SMILES: CCOC(=O)c1cn2c(cc1=O)-c1cc(OC)c(OCc3ccccc3)cc1CC2C(C)C]

A mixture of crude ethyl 9-benzyloxy-6-isopropyl-10-methoxy-2-oxo-1,6,7,11b-tetrahydrobenzo[a]quinolizine-3-carboxylate (22 g, 49 mmol) and p-chloranil (8.6 g, 35 mmol, TCI) in DME (100 mL) was refluxed for 2 h. After being cooled to room temperature, the resulting suspension was filtered with suction. The filter cake was washed with cold DME and dried under reduced pressure to give ethyl 9-benzyloxy-6-isopropyl-10-methoxy-2-oxo-6,7-dihydrobenzo[a]quinolizine-3-carboxylate (19 g) as a yellow solid.

Step 3: Preparation of ethyl 9-hydroxy-6-isopropyl-10-methoxy-2-oxo-6,7-dihydrobenzo[a]quinolizine-3-carboxylate

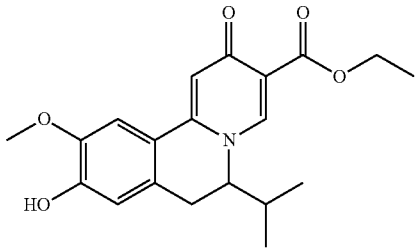 [SMILES: CCOC(=O)c1cn2c(cc1=O)-c1cc(OC)c(O)cc1CC2C(C)C]

A mixture of ethyl 9-benzyloxy-6-isopropyl-10-methoxy-2-oxo-6,7-dihydrobenzo[a]quinolizine-3-carboxylate (19 g, 42.5 mmol) and 10% palladium on carbon (500 mg) in ethanol (150 mL) was stirred under hydrogen atmosphere for 12 h. The mixture was filtered through celite and the filtrate was concentrated under reduced pressure to afford ethyl 9-hydroxy-6-isopropyl-10-methoxy-2-oxo-6,7-dihydrobenzo[a]quinolizine-3-carboxylate (13.6 g) as a yellow solid which was used in the next step without further purification.

Step 4: Preparation of ethyl 6-isopropyl-10-methoxy-9-(2-methoxyethoxy)-2-oxo-6,7-dihydrobenzo[a]quinolizine-3-carboxylate

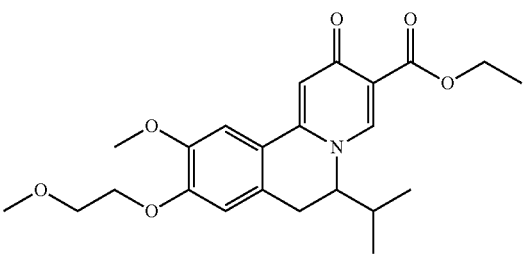 [SMILES: CCOC(=O)c1cn2c(cc1=O)-c1cc(OC)c(OCCOC)cc1CC2C(C)C]

To a solution of ethyl 9-hydroxy-6-isopropyl-10-methoxy-2-oxo-6,7-dihydrobenzo[a]quinolizine-3-carboxylate (12.5 g, 35 mmol) in DMF (100 mL) was added potassium carbonate (9.6 g, 70 mmol) and 1-bromo-2-methoxy-ethane (14.6 g, 105 mmol, Sinopharm Chemical). The resulting mixture was heated at 90° C. for 6 h. After being cooled to room temperature, the resulting dark-brown mixture was poured into water (300 mL) and the aqueous mixture was extracted with DCM (300 mL×2). The organic layers were combined and washed with brine, dried over anhydrous $Na_2SO_4$, and concentrated under reduced pressure to give crude ethyl 6-isopropyl-10-methoxy-9-(2-methoxyethoxy)-2-oxo-6,7-dihydrobenzo[a]quinolizine-3-carboxylate (13 g), which was used directly in the next step without further purification.

Step 5: Preparation of 6-isopropyl-10-methoxy-9-(2-methoxyethoxy)-2-oxo-6,7-dihydrobenzo[a]quinolizine-3-carboxylic acid

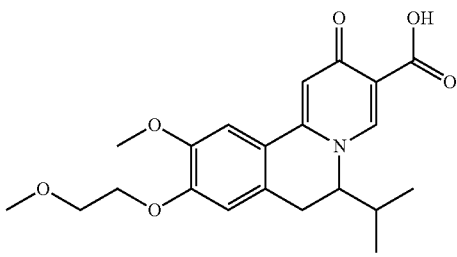 [SMILES: COCCOc1cc2c(cc1OC)-c1cc(=O)c(C(=O)O)cn1C(C(C)C)C2]

To a solution of ethyl 6-isopropyl-10-methoxy-9-(2-methoxyethoxy)-2-oxo-6,7-dihydrobenzo[a]quinolizine-3-carboxylate (13 g, 31.5 mmol) in THF (150 mL) and ethanol (30 mL) was added 2.0 M LiOH (50 mL) aqueous solution at room temperature. The resulting mixture was stirred for 4 h, and then acidified to pH=1-2 with 2 M hydrochloric acid. The mixture was extracted with DCM (200 mL×2). The combined organic layers were washed with water and brine, dried over anhydrous $Na_2SO_4$ and concentrated to give a yellow solid, which was purified by flash column chromatography on silica gel to give 6-isopropyl-10-methoxy-9-(2-methoxyethoxy)-2-oxo-6,7-dihydrobenzo[a]quinolizine-3-carboxylic acid (4.35 g).

Step 6: Preparation of (+)-6-isopropyl-10-methoxy-9-(2-methoxyethoxy)-2-oxo-6,7-dihydrobenzo[a]quinolizine-3-carboxylic acid and (−)-6-isopropyl-10-methoxy-9-(2-methoxyethoxy)-2-oxo-6,7-dihydrobenzo[a]quinolizine-3-carboxylic acid

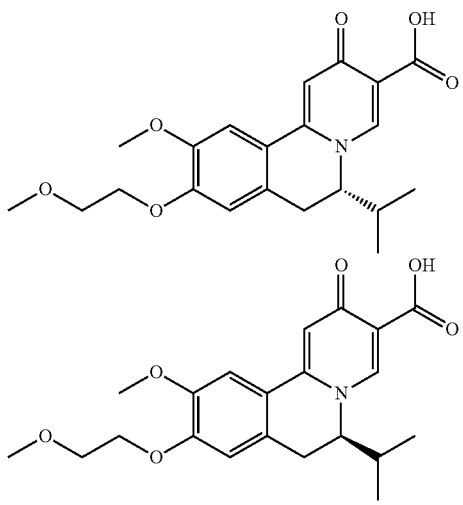

Separation of 6-isopropyl-10-methoxy-9-(2-methoxyethoxy)-2-oxo-6,7-dihydrobenzo[a]quinolizine-3-carboxylic acid by chiral HPLC provided (+)-6-isopropyl-10-methoxy-9-(2-methoxyethoxy)-2-oxo-6,7-dihydrobenzo[a]quinolizine-3-carboxylic acid and (−)-6-isopropyl-10-methoxy-9-(2-methoxyethoxy)-2-oxo-6,7-dihydrobenzo[a]quinolizine-3-carboxylic acid.

Example 129

$^1$H NMR (400 MHz, CDCl$_3$): δ 16.03 (s, 1H), 8.45-8.50 (s, 1H), 7.18-7.20 (s, 1H), 7.06-7.11 (s, 1H), 6.79-6.84 (s, 1H), 4.21-4.32 (m, 2H), 3.95 (s, 3H), 3.88-3.91 (m, 1H), 3.83-3.87 (m, 2H), 3.49 (s, 3H), 3.32-3.39 (m, 1H), 3.05-3.13 (m, 1H), 1.78-1.88 (m, 1H), 0.96 (d, 3H), 0.81-0.88 (d, 3H). MS obsd. (ESI$^+$) [(M+H)$^+$]: 388. [α]$_D^{20}$=+78.0° (0.100%, CH$_3$CN).

Example 130

$^1$H NMR (400 MHz, CDCl$_3$): δ 16.03 (s, 1H), 8.45-8.50 (s, 1H), 7.18-7.20 (s, 1H), 7.06-7.11 (s, 1H), 6.79-6.84 (s, 1H), 4.21-4.32 (m, 2H), 3.95 (s, 3H), 3.88-3.91 (m, 1H), 3.83-3.87 (m, 2H), 3.49 (s, 3H), 3.32-3.39 (m, 1H), 3.05-3.13 (m, 1H), 1.78-1.88 (m, 1H), 0.96 (d, 3H), 0.81-0.88 (d, 3H). MS obsd. (ESI$^+$) [(M+H)$^+$]: 388.

Example 131: 6-tert-butyl-10-methoxy-9-(3-methoxypropoxy)-2-oxo-6,7-dihydrobenzo[a]quinolizine-3-carboxylic acid

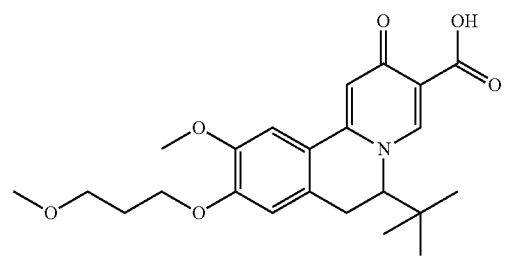 [SMILES: COCCCOc1cc2c(cc1OC)-c1cc(=O)c(C(=O)O)cn1C(C(C)(C)C)C2]

Step 1: Preparation of 1-[4-methoxy-3-(3-methoxypropoxy)phenyl]-3,3-dimethyl-butan-2-one

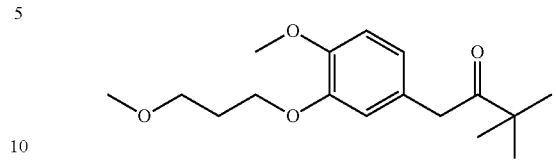

To a solution of 4-bromo-1-methoxy-2-(3-methoxypropoxy)benzene (27.5 g, 0.1 mol) in THF (300 mL) was added 3,3-dimethyl-2-butanone (30 g, 0.3 mol), Pd$_2$(dba)$_3$ (1.37 g, 1.5 mmol), Xantphos (1.74 g, 3.0 mmol) and sodium tert-butoxide (31.7 g, 0.33 mol). The resulting mixture was stirred for 8 h at 60° C. under argon atmosphere. After being cooled to room temperature, the resulting suspension was filtered with suction, the filter cake was poured into water and acidified to pH=3 with 2 M hydrochloride acid. The mixture was extracted with ethyl acetate (400 mL×2) and the combined organic layers were washed with water (200 mL) and brine, dried over anhydrous Na$_2$SO$_4$ and concentrated to give 1-[4-methoxy-3-(3-methoxypropoxy)phenyl]-3,3-dimethyl-butan-2-one (23 g) as a yellow oil.

Step 2: Preparation of 1-[4-methoxy-3-(3-methoxypropoxy)phenyl]-3,3-dimethyl-butan-2-amine

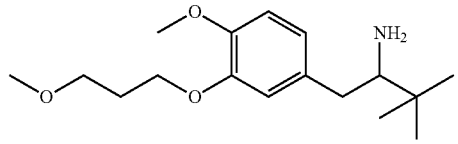 [SMILES: COCCCOc1cc(CC(N)C(C)(C)C)ccc1OC]

To a solution of 1-[4-methoxy-3-(3-methoxypropoxy)phenyl]-3,3-dimethyl-butan-2-one (23 g, 78 mmol) in methanol (230 mL) was added ammonium acetate (90 g, 1.17 mol) and NaBH$_3$CN (9.8 g, 156 mmol). The resulting mixture was stirred for 12 h at room temperature. The reaction was quenched with water and 2.0 M NaOH aqueous solution (150 mL). The resulting mixture was stirred for 1 h and then extracted with ethyl acetate (450 mL). The organic layer was washed with water (200 mL×2) and brine, dried over anhydrous Na$_2$SO$_4$ and concentrated to give 1-[4-methoxy-3-(3-methoxypropoxy)phenyl]-3,3-dimethyl-butan-2-amine (20 g) which was used directly in the next step without further purification.

Step 3: Preparation of N-[1-[[4-methoxy-3-(3-methoxypropoxy)phenyl]methyl]-2,2-dimethyl-propyl]formamide

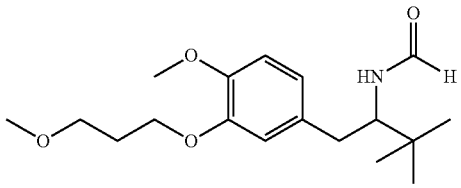 [SMILES: COCCCOc1cc(CC(NC=O)C(C)(C)C)ccc1OC]

A mixture of 1-[4-methoxy-3-(3-methoxypropoxy)phenyl]-3,3-dimethyl-butan-2-amine (20 g, 67.8 mmol) and formic acid (9.3 g, 203 mmol) in 1,4-dioxane (200 mL) was refluxed for 12 h and then concentrated under reduced pressure to give a red oil, which was dissolved in ethyl acetate (300 mL). The solution was washed with water (100 mL×2) and brine, dried over anhydrous Na₂SO₄ and concentrated to give N-[1-[[4-methoxy-3-(3-methoxypropoxy)phenyl]methyl]-2,2-dimethyl-propyl]formamide (20.6 g).

Step 4: Preparation of 3-tert-butyl-7-methoxy-6-(3-methoxypropoxy)-3,4-dihydroisoquinoline

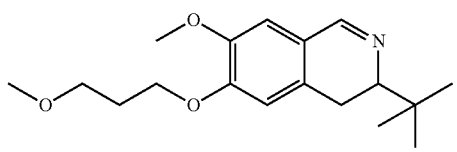 [SMILES: COCCCOc1cc2c(cc1OC)C=NC(C(C)(C)C)C2]

To a solution of N-[1-[[4-methoxy-3-(3-methoxypropoxy)phenyl]methyl]-2,2-dimethyl-propyl]formamide (20.6 g, 62 mmol) in acetonitrile (100 mL) was added POCl₃ (14.2 g, 93 mol) dropwise at 0-5° C. The resulting mixture was refluxed for 3 h. After being cooled to room temperature, the mixture was concentrated under reduced pressure to remove the solvent and the residue was dissolved in ethyl acetate (100 mL). The aqueous phase of the mixture was adjusted to around pH=11 with ammonia water. The mixture was extracted with ethyl acetate (200 mL×2), and the organic layers were combined and concentrated. The residue was purified by column chromatography to give 3-tert-butyl-7-methoxy-6-(3-methoxypropoxy)-3,4-dihydroisoquinoline (18 g).

Step 5: Preparation of ethyl 6-tert-butyl-10-methoxy-9-(3-methoxypropoxy)-2-oxo-1,6,7,11b-tetrahydrobenzo[a]quinolizine-3-carboxylate

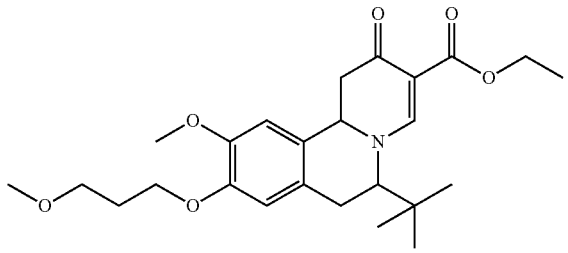 [SMILES: CCOC(=O)C1=CN2C(CC1=O)c1cc(OC)c(OCCCOC)cc1CC2C(C)(C)C]

A mixture of 3-tert-butyl-7-methoxy-6-(3-methoxypropoxy)-3,4-dihydroisoquinoline (18 g, 60 mmol) and ethyl 2-(ethoxymethylene)-3-oxo-butanoate (33.5 g, 180 mmol) in ethanol (200 mL) was refluxed overnight. The mixture was concentrated to give crude ethyl 6-tert-butyl-10-methoxy-9-(3-methoxypropoxy)-2-oxo-1,6,7,11b-tetrahydrobenzo[a]quinolizine-3-carboxylate (26.7 g) as a dark brown oil which was used in the next step without purification.

Step 6: Preparation of ethyl 6-tert-butyl-10-methoxy-9-(3-methoxypropoxy)-2-oxo-6,7-dihydrobenzo[a]quinolizine-3-carboxylate

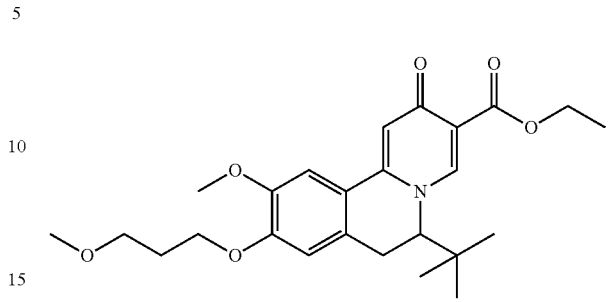

A mixture of crude ethyl 6-tert-butyl-10-methoxy-9-(3-methoxypropoxy)-2-oxo-1,6,7,11b-tetrahydrobenzo[a]quinolizine-3-carboxylate (26.7 g, 60 mmol, from step 5) and p-chloranil (11 g, 45 mmol) in DME (85 mL) was refluxed for 2 h. After being cooled to room temperature, the resulting suspension was filtered with suction. The filter cake was washed with cold DME and dried under vacuum to give ethyl 6-tert-butyl-10-methoxy-9-(3-methoxypropoxy)-2-oxo-6,7-dihydrobenzo[a]quinolizine-3-carboxylate as a yellow solid (15.5 g).

Step 7: Preparation of 6-tert-butyl-10-methoxy-9-(3-methoxypropoxy)-2-oxo-6,7-dihydrobenzo[a]quinolizine-3-carboxylic acid

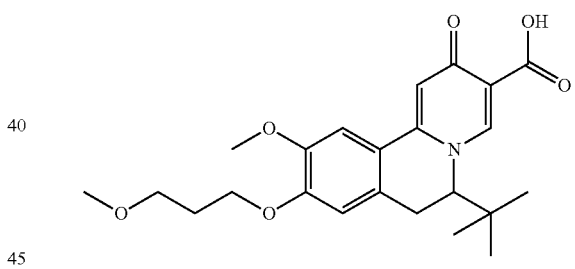

To a solution of ethyl 6-tert-butyl-10-methoxy-9-(3-methoxypropoxy)-2-oxo-6,7-dihydrobenzo[a]quinolizine-3-carboxylate (15.5 g, 35 mmol) in THF (150 mL) and methanol (30 mL) was added 2.0 M LiOH (70 mL) aqueous solution at rt. The resulting mixture was stirred for 4 h, and then acidified to pH=1-2 with 2 M hydrochloric acid. The mixture was extracted with DCM (200 mL×2), the combined organic layers were washed with water and brine, dried over anhydrous Na₂SO₄ and concentrated to give a yellow solid, which was purified by column chromatography to give 6-tert-butyl-10-methoxy-9-(3-methoxypropoxy)-2-oxo-6,7-dihydrobenzo[a]quinolizine-3-carboxylic acid (8.5 g) as an off-white solid. $^1$H NMR (400 MHz, CDCl₃): δ 15.97-16.02 (s, 1H), 8.37-8.53 (s, 1H), 7.14-7.17 (s, 1H), 7.06-7.09 (s, 1H), 6.74-6.78 (s, 1H), 4.15-4.24 (m, 2H), 4.02-4.06 (m, 1H), 3.92-3.96 (s, 3H), 3.58-3.64 (m, 2H), 3.41-3.48 (m, 1H), 3.37-3.40 (s, 3H), 3.15-3.23 (m, 1H), 2.13-2.21 (m, 2H), 0.84 (s, 9H). MS obsd. (ESI⁺) [(M+H)⁺]: 416.

Example 132 and 133

(+)-6-tert-butyl-10-methoxy-9-(3-methoxypropoxy)-2-oxo-6,7-dihydrobenzo[a]quinolizine-3-carboxylic acid and (−)-6-tert-butyl-10-methoxy-9-(3-methoxypropoxy)-2-oxo-6,7-dihydrobenzo[a]quinolizine-3-carboxylic acid

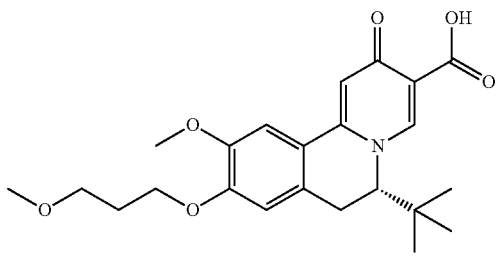

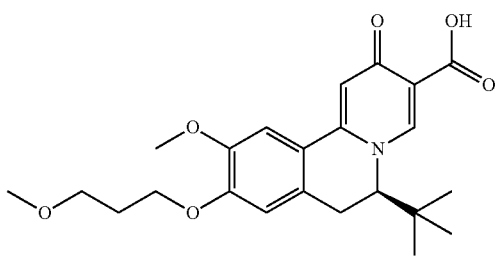

Separation of 6-tert-butyl-10-methoxy-9-(3-methoxypropoxy)-2-oxo-6,7-dihydrobenzo[a]quinolizine-3-carboxylic acid by chiral HPLC provided (+)-6-tert-butyl-10-methoxy-9-(3-methoxypropoxy)-2-oxo-6,7-dihydrobenzo[a]quinolizine-3-carboxylic acid and (−)-6-tert-butyl-10-methoxy-9-(3-methoxypropoxy)-2-oxo-6,7-dihydrobenzo[a]quinolizine-3-carboxylic acid.

Example 132

$^1$H NMR (400 MHz, CDCl$_3$): δ 15.98-16.05 (s, 1H), 8.48-8.51 (s, 1H), 7.14-7.17 (s, 1H), 7.06-7.10 (s, 1H), 6.75-6.79 (s, 1H), 4.16-4.24 (m, 2H), 4.04-4.08 (m, 1H), 3.92-3.95 (s, 3H), 3.58-3.64 (m, 2H), 3.41-3.48 (m, 1H), 3.39 (s, 3H), 3.15-3.23 (m, 1H), 2.13-2.21 (m, 2H), 0.84 (s, 9H). MS obsd. (ESI$^+$) [(M+H)$^+$]: 416. [α]$_D^{20}$=+98.2° (0.110%, CH$_3$CN).

Example 133

$^1$H NMR (400 MHz, CDCl$_3$): δ 15.98-16.05 (s, 1H), 8.48-8.51 (s, 1H), 7.14-7.17 (s, 1H), 7.06-7.10 (s, 1H), 6.75-6.79 (s, 1H), 4.16-4.24 (m, 2H), 4.04-4.08 (m, 1H), 3.92-3.95 (s, 3H), 3.58-3.64 (m, 2H), 3.41-3.48 (m, 1H), 3.39 (s, 3H), 3.15-3.23 (m, 1H), 2.13-2.21 (m, 2H), 0.84 (s, 9H). MS obsd. (ESI$^+$) [(M+H)$^+$]: 416.

Example 134: 10-methoxy-9-(2-methoxyethoxy)-6-(1-methylcyclopropyl)-2-oxo-6,7-dihydrobenzo[a]quinolizine-3-carboxylic acid

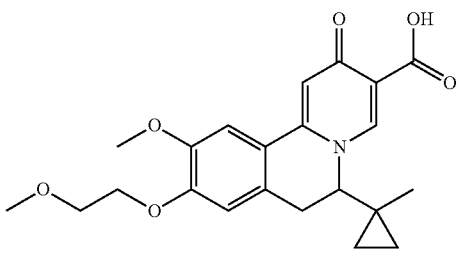 [SMILES: COCCOc1cc2c(cc1OC)-c1cc(=O)c(C(=O)O)cn1C(C1(C)CC1)C2]

Step 1: Preparation of 4-bromo-1-methoxy-2-(2-methoxyethoxy)benzene

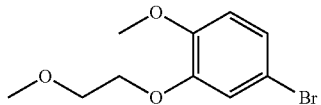

To a solution of 5-bromo-2-methoxyphenol (50 g, 0.25 mol, Accela) in DMF (200 ml) was added potassium carbonate (70 g, 0.5 mol) and 1-bromo-2-methoxy-ethane (42 g, 0.3 mol, Sinopharm Chemical). The resulting mixture was heated at 90° C. for 8 h. After being cooled to room temperature, the mixture was poured into water (500 mL) and the aqueous solution was extracted with ethyl acetate (400 mL×2). The organic layers were combined and washed with water and brine, dried over anhydrous Na$_2$SO$_4$, and concentrated under reduced pressure to give 4-bromo-1-methoxy-2-(2-methoxyethoxy)benzene (45 g) as a white solid, which was used directly in the next step without further purification.

Step 2: Preparation of 2-[4-methoxy-3-(2-methoxyethoxy)phenyl]-1-(1-methylcyclopropyl)ethanone

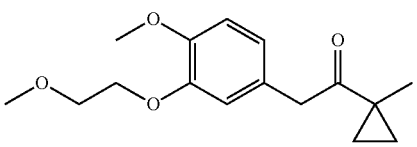

To a solution of 4-bromo-1-methoxy-2-(2-methoxyethoxy)benzene (21.4 g, 82 mmol) in THF (300 mL) was added 1-(1-methylcyclopropyl)ethanone (16 g, 164 mmol, TCI), Pd$_2$(dba)$_3$ (1.13 g, 1.23 mmol), Xantphos (1.42 g, 2.46 mmol) and sodium tert-butoxide (26.0 g, 270 mmol). The resulting mixture was stirred for 8 h at 60° C. under argon atmosphere. After being cooled to room temperature, the resulting suspension was filtered with suction, the filter cake was poured into water and acidified to pH=3 with 2 M hydrochloride acid. The mixture was extracted with ethyl acetate (400 mL×2) and the combined organic layers were washed with water (200 mL) and brine, dried over anhydrous Na$_2$SO$_4$ and concentrated to give 2-[4-methoxy-3-(2-methoxyethoxy)phenyl]-1-(1-methylcyclopropyl)ethanone (25 g) as a yellow oil.

Step 3: Preparation of 2-[4-methoxy-3-(2-methoxyethoxy)phenyl]-1-(1-methylcyclopropyl)ethanamine

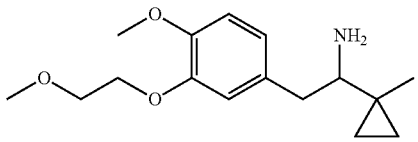

To a solution of 2-[4-methoxy-3-(2-methoxyethoxy)phenyl]-1-(1-methylcyclopropyl)ethanone (25 g, 82 mmol) in methanol (250 mL) was added ammonium acetate (104 g, 1.35 mol) and NaBH$_3$CN (10.3 g, 164 mmol). The resulting mixture was stirred for 12 h at room temperature.

The reaction was quenched with water, and to the resulting mixture was added 2.0 M NaOH aqueous solution (200 mL). The resulting mixture was stirred for 1 h and then extracted with ethyl acetate (500 mL). The organic layer was washed with water (200 mL×2) and brine, dried over anhydrous Na$_2$SO$_4$ and concentrated to give 2-[4-methoxy-3-(2-methoxyethoxy)phenyl]-1-(1-methylcyclopropyl)ethanamine (21 g) which was used in the next step without purification.

Step 4: Preparation of N-[2-[4-methoxy-3-(2-methoxyethoxy)phenyl]-1-(1-methylcyclopropyl)ethyl]formamide

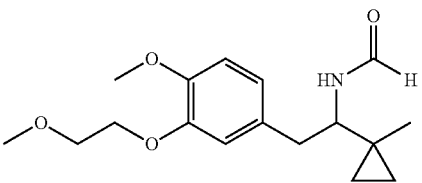 [SMILES: COCCOc1cc(CC(NC=O)C2(C)CC2)ccc1OC]

A mixture of 2-[4-methoxy-3-(2-methoxyethoxy)phenyl]-1-(1-methylcyclopropyl)ethanamine (21 g, 75 mmol) and formic acid (10.35 g, 225 mmol) in 1,4-dioxane (150 mL) was refluxed for 12 h and then concentrated under reduced pressure to give a red oil, which was dissolved in ethyl acetate (300 mL). The solution was washed with water (100 mL×2) and brine, dried over anhydrous Na$_2$SO$_4$ and concentrated to give N-[2-[4-methoxy-3-(2-methoxyethoxy)phenyl]-1-(1-methylcyclopropyl)ethyl]formamide. (23 g)

Step 5: Preparation of 7-methoxy-6-(2-methoxyethoxy)-3-(1-methylcyclopropyl)-3,4-dihydroisoquinoline

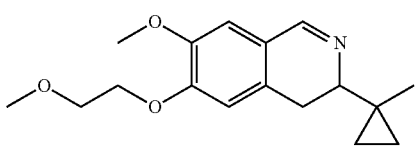

To a solution of N-[2-[4-methoxy-3-(2-methoxyethoxy)phenyl]-1-(1-methylcyclopropyl)ethyl]formamide (23.0 g, 75 mmol) in acetonitrile (165 mL) was added POCl$_3$ (17.5 g, 112.5 mol) at 0-5° C. The mixture was refluxed for 3 h. After being cooled to room temperature, the mixture was concentrated to remove the solvent and the residue was dissolved in ethyl acetate (100 mL). The aqueous phase of the mixture was adjusted to pH around 11 with ammonia water. The resulting mixture was extracted with ethyl acetate (200 mL×2), and the organic layers were combined and concentrated. The residue was purified by column chromatography to give 7-methoxy-6-(2-methoxyethoxy)-3-(1-methylcyclopropyl)-3,4-dihydroisoquinoline (20 g).

Step 6: Preparation of ethyl 10-methoxy-9-(2-methoxyethoxy)-6-(1-methylcyclopropyl)-2-oxo-1,6,7,11b-tetrahydrobenzo[a]quinolizine-3-carboxylate

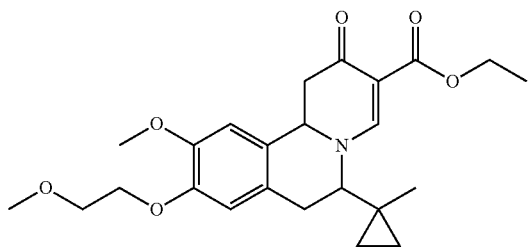 [SMILES: CCOC(=O)C1=CN2C(CC1=O)c1cc(OC)c(OCCOC)cc1CC2C1(C)CC1]

A mixture of 7-methoxy-6-(2-methoxyethoxy)-3-(1-methylcyclopropyl)-3,4-dihydroisoquinoline (20 g, 70 mmol) and ethyl 2-(ethoxymethylene)-3-oxo-butanoate (39 g, 210 mmol, Sinopharm Chemical) in ethanol (200 mL) was refluxed overnight. The mixture was concentrated to give crude ethyl 10-methoxy-9-(2-methoxyethoxy)-6-(1-methylcyclopropyl)-2-oxo-1,6,7,11b-tetrahydrobenzo[a]quinolizine-3-carboxylate (30 g) as a dark brown oil which was used in the next step without further purification.

Step 7: Preparation of ethyl 10-methoxy-9-(2-methoxyethoxy)-6-(1-methylcyclopropyl)-2-oxo-6,7-dihydrobenzo[a]quinolizine-3-carboxylate

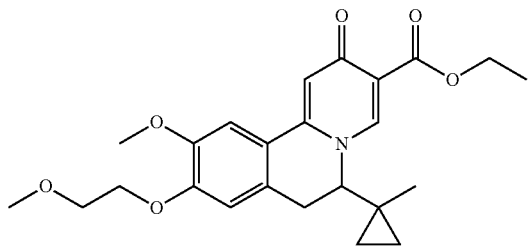

A mixture of crude ethyl 10-methoxy-9-(2-methoxyethoxy)-6-(1-methylcyclopropyl)-2-oxo-1,6,7,11b-tetrahydrobenzo[a]quinolizine-3-carboxylate (30 g, 70 mmol) an) from step 6 and p-chloranil (13 g, 52.5 mmol) in DME (100 mL) was refluxed for 2 h. After being cooled to room temperature, the resulting suspension was filtered with suction. The filter cake was washed with cold DME and dried under vacuum to give ethyl 10-methoxy-9-(2-methoxyethoxy)-6-(1-methylcyclopropyl)-2-oxo-6,7-dihydrobenzo[a]quinolizine-3-carboxylate (25.6 g)

Step 8: Preparation of 10-methoxy-9-(2-methoxy-ethoxy)-6-(1-methylcyclopropyl)-2-oxo-6,7-dihydrobenzo[a]quinolizine-3-carboxylic acid

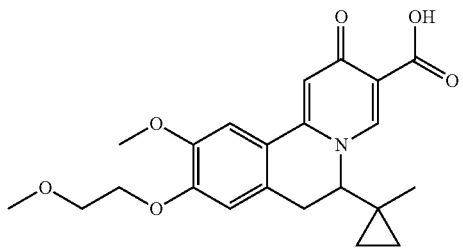 [SMILES: COCCOc1cc2c(cc1OC)-c1cc(=O)c(C(=O)O)cn1C(C1(C)CC1)C2]

To a solution of ethyl 10-methoxy-9-(2-methoxyethoxy)-6-(1-methylcyclopropyl)-2-oxo-6,7-dihydrobenzo[a]quinolizine-3-carboxylate (25.6 g, 60 mmol) in THF (200 mL) and methanol (40 mL) was added 2.0 M LiOH aqueous solution (105 mL) at rt. The resulting mixture was stirred for 4 h, and then acidified to pH=1-2 with 2 M hydrochloric acid, extracted with DCM (250 mL×2). The combined organic layers were washed with water and brine, dried over anhydrous $Na_2SO_4$ and concentrated to give a yellow solid, which was purified by flash column chromatography to give 10-methoxy-9-(2-methoxyethoxy)-6-(1-methylcyclopropyl)-2-oxo-6,7-dihydrobenzo[a]quinolizine-3-carboxylic acid (9.5 g). $^1$H NMR (400 MHz, $CDCl_3$): δ 15.99-16.09 (s, 1H), 8.72-8.77 (s, 1H), 7.15-7.21 (s, 1H), 7.07-7.13 (s, 1H), 6.77-6.85 (s, 1H), 4.22-4.32 (m, 2H), 3.94 (s, 3H), 3.81-3.88 (m, 2H), 3.52-3.58 (m, 1H), 3.48 (s, 3H), 3.30-3.39 (m, 1H), 3.14-3.22 (m, 1H), 0.84 (s, 3H), 0.75-0.81 (m, 1H), 0.63-0.70 (m, 1H), 0.52-0.61 (m, 2H). MS obsd. ($ESI^+$) [(M+H)$^+$]: 400

Example 135 and 136

(+)-10-methoxy-9-(2-methoxyethoxy)-6-(1-methylcyclopropyl)-2-oxo-6,7-dihydrobenzo[a]quinolizine-3-carboxylic acid and (−)-10-methoxy-9-(2-methoxyethoxy)-6-(1-methylcyclopropyl)-2-oxo-6,7-dihydrobenzo[a]quinolizine-3-carboxylic acid

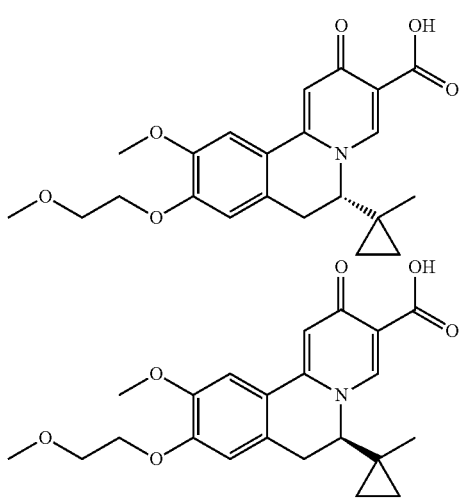

Separation of 10-methoxy-9-(2-methoxyethoxy)-6-(1-methylcyclopropyl)-2-oxo-6,7-dihydrobenzo[a]quinolizine-3-carboxylic acid by chiral HPLC provided (+)-10-methoxy-9-(2-methoxyethoxy)-6-(1-methylcyclopropyl)-2-oxo-6,7-dihydrobenzo[a]quinolizine-3-carboxylic acid and (−)-10-methoxy-9-(2-methoxyethoxy)-6-(1-methylcyclopropyl)-2-oxo-6,7-dihydrobenzo[a]quinolizine-3-carboxylic acid.

Example 135

$^1$H NMR (400 MHz, $CDCl_3$): δ 16.07-16.01 (s, 1H), 8.74 (s, 1H), 7.16-7.19 (s, 1H), 7.08-7.13 (s, 1H), 6.81 (s, 1H), 4.23-4.30 (m, 2H), 3.94 (s, 3H), 3.82-3.87 (m, 2H), 3.52-3.57 (m, 1H), 3.48 (s, 3H), 3.30-3.38 (m, 1H), 3.14-3.22 (m, 1H), 0.83-0.86 (m, 3H), 0.74-0.81 (m, 1H), 0.64-0.70 (m, 1H), 0.52-0.59 (m, 2H). MS obsd. ($ESI^+$) [(M+H)$^+$]: 400. $[α]_D^{20}$=+72.0° (0.100%, $CH_3CN$).

Example 136

$^1$H NMR (400 MHz, $CDCl_3$): δ 16.07-16.01 (s, 1H), 8.74 (s, 1H), 7.16-7.19 (s, 1H), 7.08-7.13 (s, 1H), 6.81 (s, 1H), 4.23-4.30 (m, 2H), 3.94 (s, 3H), 3.82-3.87 (m, 2H), 3.52-3.57 (m, 1H), 3.48 (s, 3H), 3.30-3.38 (m, 1H), 3.14-3.22 (m, 1H), 0.83-0.86 (m, 3H), 0.74-0.81 (m, 1H), 0.64-0.70 (m, 1H), 0.52-0.59 (m, 2H). MS obsd. ($ESI^+$) [(M+H)$^+$]: 400.

Example 137: 11-chloro-10-fluoro-6-isopropyl-9-(3-methoxypropoxy)-2-oxo-6,7-dihydrobenzo[a]quinolizine-3-carboxylic acid

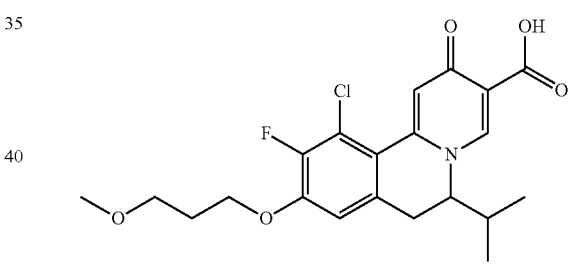

Step 1: Preparation of 5-bromo-1-chloro-2-fluoro-3-(3-methoxypropoxy)benzene

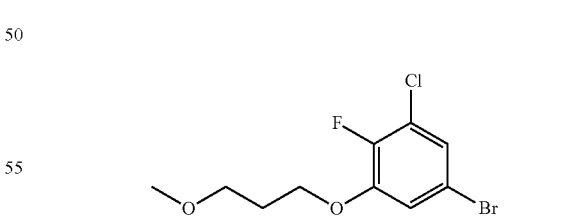

To a solution of 5-bromo-3-chloro-2-fluoro-phenol (5 g, 22.5 mmol, TCI) in DMF (25 ml) was added potassium carbonate (6.2 g, 45 mmol) and 1-bromo-3-methoxy-propane (42 g, 27 mmol, Accela). The resulting mixture was heated at 90° C. for 5 h. After being cooled to room temperature, the mixture was poured into water (200 mL) and the aqueous solution was extracted with ethyl acetate (200 mL×2). The organic layers were combined and washed with water and brine, dried over anhydrous $Na_2SO_4$ and concentrated under reduced pressure to give 5-bromo-1-chloro-2-fluoro-3-(3-methoxypropoxy)benzene (5.6 g) as a red oil which was used directly in the next step without further purification.

Step 2: Preparation of 1-[3-chloro-4-fluoro-5-(3-methoxypropoxy)phenyl]-3-methyl-butan-2-one

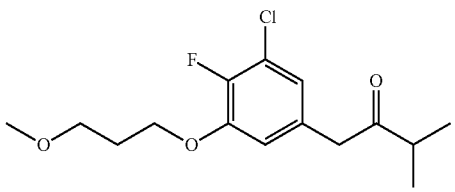 [SMILES: COCCCOc1cc(CC(=O)C(C)C)cc(Cl)c1F]

To a solution of 5-bromo-1-chloro-2-fluoro-3-(3-methoxypropoxy)benzene (5.6 g, 19 mmol) in THF (300 mL) was added 3-methylbutan-2-one (4.9 g, 57 mmol, Accela), $Pd_2(dba)_3$ (260 mg, 0.285 mmol), Xantphos (330 mg, 0.57 mmol) and sodium tert-butoxide (6 g, 62.7 mmol). The resulting mixture was stirred for 8 h at 60° C. under argon atmosphere. After being cooled to room temperature, the resulting suspension was filtered with suction. The filter cake was poured into water and the resulting mixture was acidified to pH=3 with 2 M hydrochloride acid, then extracted with ethyl acetate (200 mL×2). The combined organic layers were washed with water (200 mL) and brine, dried over anhydrous $Na_2SO_4$ and concentrated to give 1-[3-chloro-4-fluoro-5-(3-methoxypropoxy)phenyl]-3-methyl-butan-2-one (6 g) as a yellow oil.

Step 3: Preparation of 1-[3-chloro-4-fluoro-5-(3-methoxypropoxy)phenyl]-3-methyl-butan-2-amine

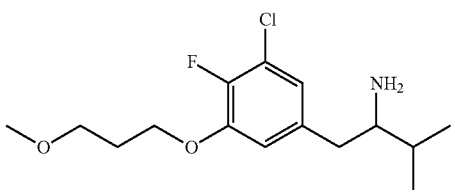 [SMILES: COCCCOc1cc(CC(N)C(C)C)cc(Cl)c1F]

To a solution of 1-[3-chloro-4-fluoro-5-(3-methoxypropoxy)phenyl]-3-methyl-butan-2-one (6 g, 20 mmol) in methanol (90 mL) was added ammonium acetate (23.1 g, 0.3 mol) and $NaBH_3CN$ (2.5 g, 40 mmol). The resulting mixture was stirred for 12 h at room temperature. The reaction was quenched with water and to the resulting mixture was added 2.0 M NaOH aqueous solution (200 mL). The mixture was stirred for 2 h, and then extracted with ethyl acetate (150 mL). The organic layer was washed with water (100 mL×2) and brine, dried over anhydrous $Na_2SO_4$ and concentrated to give 1-[3-chloro-4-fluoro-5-(3-methoxypropoxy)phenyl]-3-methyl-butan-2-amine (4.5 g) which was used directly in the next step without further purification.

Step 4: Preparation of N-[1-[[3-chloro-4-fluoro-5-(3-methoxypropoxy)phenyl]methyl]-2-methyl-propyl]formamide

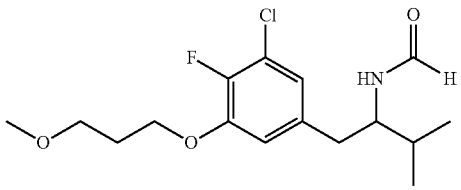 [SMILES: COCCCOc1cc(CC(NC=O)C(C)C)cc(Cl)c1F]

A mixture of 1-[3-chloro-4-fluoro-5-(3-methoxypropoxy)phenyl]-3-methyl-butan-2-amine (4.5 g, 15 mmol) and formic acid (2 g, 45 mmol) in 1,4-dioxane (50 mL) was refluxed for 12 h and then concentrated under reduced pressure to give a red oil, which was dissolved in ethyl acetate (100 mL). The organic solution was washed with water (50 mL×2) and brine, dried over anhydrous $Na_2SO_4$ and concentrated to give N-[1-[[3-chloro-4-fluoro-5-(3-methoxypropoxy)phenyl]methyl]-2-methyl-propyl]formamide. (4.5 g)

Step 5: Preparation of 8-chloro-7-fluoro-3-isopropyl-6-(3-methoxypropoxy)-3,4-dihydroisoquinoline

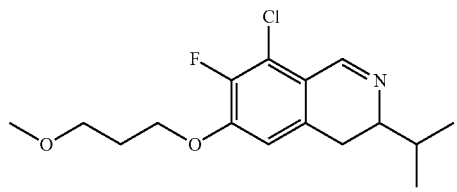

To a solution of N-[1-[[3-chloro-4-fluoro-5-(3-methoxypropoxy)phenyl]methyl]-2-methyl-propyl]formamide (4.5 g, 13.6 mmol) in acetonitrile (50 mL) was added $POCl_3$ (4.2 g, 27.2 mmol) at 0-5° C. and then the resulting mixture was refluxed for 3 h. After being cooled to room temperature, the resulting mixture was concentrated to remove the solvent and the residue was dissolved in ethyl acetate (100 mL). The aqueous phase of the mixture was adjusted to pH around 11 with ammonia water. The mixture was extracted with ethyl acetate (100 mL×2), and the organic layers were combined and concentrated. The residue was purified by column chromatography to give 8-chloro-7-fluoro-3-isopropyl-6-(3-methoxypropoxy)-3,4-dihydroisoquinoline (2.5 g).

Step 6: Preparation of ethyl 11-chloro-10-fluoro-6-isopropyl-9-(3-methoxypropoxy)-2-oxo-1,6,7,11b-tetrahydrobenzo[a]quinolizine-3-carboxylate

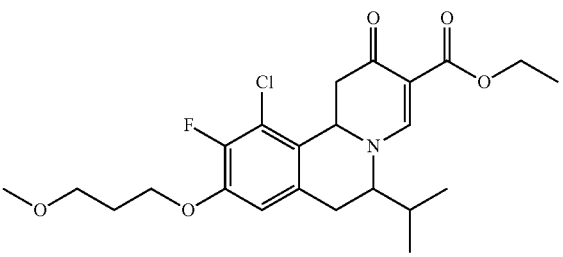 [SMILES: CCOC(=O)C1=CN2C(CC1=O)c1c(cc(OCCCOC)c(F)c1Cl)CC2C(C)C]

A mixture of 8-chloro-7-fluoro-3-isopropyl-6-(3-methoxypropoxy)-3,4-dihydroisoquinoline (2.5 g, 8 mmol) and ethyl 2-(ethoxymethylene)-3-oxo-butanoate (4.5 g, 24 mmol) in ethanol (50 mL) was refluxed overnight. The mixture was concentrated to give crude ethyl 11-chloro-10-fluoro-6-isopropyl-9-(3-methoxypropoxy)-2-oxo-1,6,7,11b-tetrahydrobenzo[a]quinolizine-3-carboxylate (3.6 g) as dark a brown oil which was used in the next step without further purification.

Step 7: Preparation of ethyl 11-chloro-10-fluoro-6-isopropyl-9-(3-methoxypropoxy)-2-oxo-6,7-dihydrobenzo[a]quinolizine-3-carboxylate

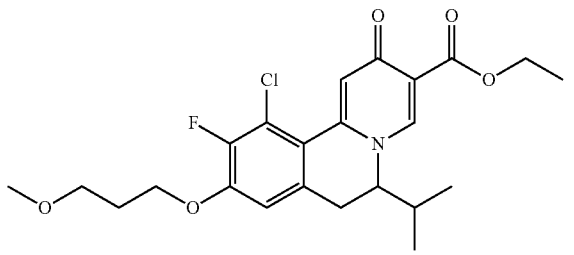 [SMILES: CCOC(=O)c1cn2c(cc1=O)-c1c(cc(OCCCOC)c(F)c1Cl)CC2C(C)C]

A mixture of crude ethyl 11-chloro-10-fluoro-6-isopropyl-9-(3-methoxypropoxy)-2-oxo-1,6,7,11b-tetrahydrobenzo[a]quinolizine-3-carboxylate e (3.6 g, 8 mmol) from step 6 and p-chloranil (1.5 g, 6 mmol) in DME (35 mL) was refluxed for 2 h. After being cooled to room temperature, the resulting suspension was filtered with suction. The filter cake was washed with cold DME and dried under vacuum to give ethyl 11-chloro-10-fluoro-6-isopropyl-9-(3-methoxypropoxy)-2-oxo-6,7-dihydrobenzo[a]quinolizine-3-carboxylate (1.0 g) Step 8: Preparation of 11-chloro-10-fluoro-6-isopropyl-9-(3-methoxypropoxy)-2-oxo-6,7-dihydrobenzo[a]quinolizine-3-carboxylic acid

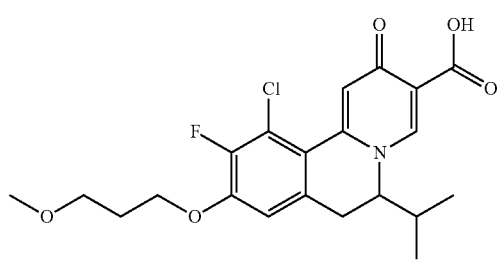

To a solution of ethyl 11-chloro-10-fluoro-6-isopropyl-9-(3-methoxypropoxy)-2-oxo-6,7-dihydrobenzo[a]quinolizine-3-carboxylate (1.0 g, 2.2 mmol) in THF (25 mL) and methanol (5 mL) was added 2.0 M LiOH (5.5 mL) aqueous solution at room temperature. The resulting mixture was stirred for 4 h, and then acidified to pH=1-2 with 2 M hydrochloric acid. The mixture was extracted with DCM (100 mL×2). The combined organic layers were washed with water and brine, dried over anhydrous $Na_2SO_4$ and concentrated to give a yellow solid, which was purified by flash column chromatography to give 11-chloro-10-fluoro-6-isopropyl-9-(3-methoxypropoxy)-2-oxo-6,7-dihydrobenzo[a]quinolizine-3-carboxylic acid (0.8 g) as an off-white solid. $^1$H NMR (400 MHz, $CDCl_3$): δ 15.83-15.90 (s, 1H), 8.50 (s, 1H), 7.67-7.73 (s, 1H), 6.83-6.89 (s, 1H), 4.19-4.30 (m, 2H), 3.84-3.90 (m, 1H), 3.56-3.66 (m, 2H), 3.39 (s, 3H), 3.25-3.33 (m, 1H), 3.08-3.14 (m, 1H), 2.10-2.20 (m, 2H), 1.67-1.75 (m, 1H), 0.94 (dd, 6H). MS obsd. (ESI$^+$) [(M+H)$^+$]: 424

Example 138 and 139

(+)-11-chloro-10-fluoro-6-isopropyl-9-(3-methoxypropoxy)-2-oxo-6,7-dihydrobenzo[a]quinolizine-3-carboxylic acid and (−)-11-chloro-10-fluoro-6-isopropyl-9-(3-methoxypropoxy)-2-oxo-6,7-dihydrobenzo[a]quinolizine-3-carboxylic acid

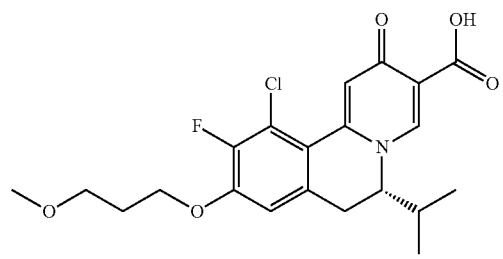 [SMILES: COCCCOc1cc2c(c(Cl)c1F)-c1cc(=O)c(C(=O)O)cn1C(C(C)C)C2]

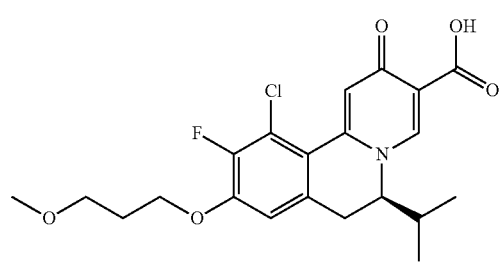

Separation of 11-chloro-10-fluoro-6-isopropyl-9-(3-methoxypropoxy)-2-oxo-6,7-dihydrobenzo[a]quinolizine-3-carboxylic acid by chiral HPLC provided (+)-11-chloro-10-fluoro-6-isopropyl-9-(3-methoxypropoxy)-2-oxo-6,7-dihydrobenzo[a]quinolizine-3-carboxylic acid and (−)-11-chloro-10-fluoro-6-isopropyl-9-(3-m ethoxypropoxy)-2-oxo-6,7-dihydrobenzo[a]quinolizine-3-carboxylic acid.

Example 138

$^1$H NMR (400 MHz, $CDCl_3$): δ 15.86-15.90 (s, 1H), 8.49-8.53 (s, 1H), 7.68-7.71 (s, 1H), 6.83-6.89 (s, 1H), 4.19-4.30 (m, 2H), 3.84-3.91 (m, 1H), 3.56-3.64 (m, 2H), 3.39 (s, 3H), 3.25-3.33 (m, 1H), 3.08-3.14 (m, 1H), 2.12-2.19 (m, 2H), 1.68-1.74 (m, 1H), 0.94 (dd, 6H). MS obsd. (ESI$^+$) [(M+H)$^+$]: 424. [α]$_D$20=+135.7° (0.115%, $CH_3CN$).

Example 139

$^1$H NMR (400 MHz, $CDCl_3$): δ 15.86-15.90 (s, 1H), 8.49-8.53 (s, 1H), 7.68-7.71 (s, 1H), 6.83-6.89 (s, 1H), 4.19-4.30 (m, 2H), 3.84-3.91 (m, 1H), 3.56-3.64 (m, 2H), 3.39 (s, 3H), 3.25-3.33 (m, 1H), 3.08-3.14 (m, 1H), 2.12-2.19 (m, 2H), 1.68-1.74 (m, 1H), 0.94 (dd, 6H). MS obsd. (ESI$^+$) [(M+H)$^+$]: 424

Example 140: 10-fluoro-6-isopropyl-9-(3-methoxy-propoxy)-2-oxo-6,7-dihydrobenzo[a]quinolizine-3-carboxylic acid

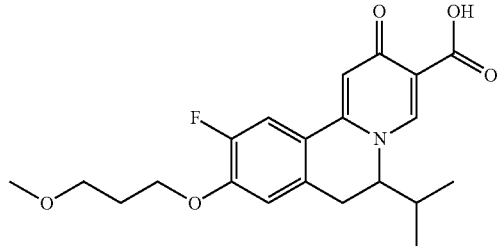 [SMILES: COCCCOc1cc2c(cc1F)-c1cc(=O)c(C(=O)O)cn1C(C(C)C)C2]

Step 1: Preparation of 4-bromo-1-fluoro-2-(3-methoxypropoxy)benzene

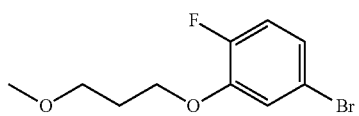

To a mixture of 5-bromo-2-fluoro-phenol (90 g, 471 mmol) in acetonitrile (1 L) was added 1-bromo-3-methoxy-propane (93.7 g, 613 mmol) and $Cs_2CO_3$ (307 g, 942 mmol). After being heated at 80° C. for 12 h, the mixture was filtered. The filtrate was concentrated to give a colorless oil, which was purified by column chromatography to give 4-bromo-1-fluoro-2-(3-methoxypropoxy)benzene (123 g).

Step 2: Preparation of 1-[4-fluoro-3-(3-methoxy-propoxy)phenyl]-3-methyl-butan-2-one

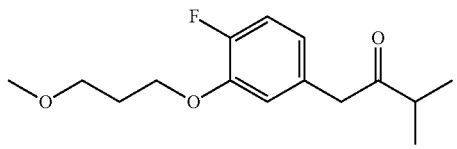 [SMILES: COCCCOc1cc(CC(=O)C(C)C)ccc1F]

To a mixture of 4-bromo-1-fluoro-2-(3-methoxypropoxy) benzene (41 g, 155 mmol) in THF (500 mL) was added 3-methylbutan-2-one (17.5 g, 202 mmol), t-BuONa (27.0 g, 280 mmol), $Pd_2(dba)_3$ (11.4 g, 12.5 mmol) and Xantphos (3.61 g, 6.23 mmol). The mixture was heated at 50° C. for 12 h. The reaction was conducted at the same scale for additional two times. The three batches were combined and filtered. The filtrate was concentrated and the residue was partitioned between $H_2O$ and DCM. The separated organic layer was washed with brine, dried over anhydrous $Na_2SO_4$ and concentrated to leave a brown oil, which was purified by column chromatography to give crude 1-[4-fluoro-3-(3-methoxypropoxy)phenyl]-3-methyl-butan-2-one (115 g) as a light yellow oil.

Step 3: Preparation of 1-[4-fluoro-3-(3-methoxy-propoxy)phenyl]-3-methyl-butan-2-amine

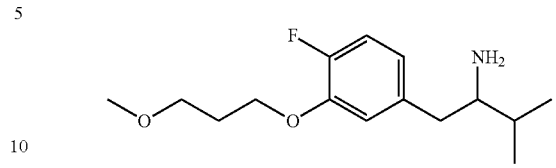

To a mixture of 1-[4-fluoro-3-(3-methoxypropoxy)phenyl]-3-methyl-butan-2-one (46.7 g, 174 mmol) in MeOH (500 mL) was added $NH_4OAc$ (93.9 g, 1.22 mol) at rt. Then the mixture was cooled to 0° C. and to the cooled solution was added $NaBH_3CN$ (14.2 g, 226 mmol) at 0° C. The resulting mixture was stirred at rt for 12 h. The reaction was carried out again as the same procedure with 1-[4-fluoro-3-(3-methoxypropoxy)phenyl]-3-methyl-butan-2-one (69.6 g, 259 mmol), MeOH (700 mL), $NH_4OAc$ (140 g, 1.82 mol) and $NaBH_3CN$ (21.2 g, 337 mmol). Then the two batches mixtures were combined and concentrated. The residue was diluted with $H_2O$ (200 mL), the resulting mixture was extracted with DCM (500 mL×2). The combined organic layers were washed with brine (100 mL), dried and concentrated under reduced pressure. The residue was purified by column chromatography to give 1-[4-fluoro-3-(3-methoxypropoxy)phenyl]-3-methyl-butan-2-amine (70 g) as a white solid.

Step 4: Preparation of N-[1-[[4-fluoro-3-(3-methoxypropoxy)phenyl]methyl]-2-methyl-propyl]formamide

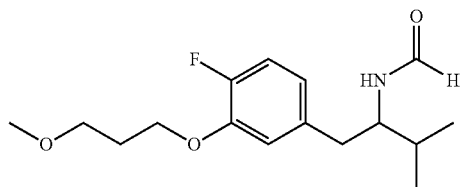 [SMILES: COCCCOc1cc(CC(NC=O)C(C)C)ccc1F]

To a mixture of 1-[4-fluoro-3-(3-methoxypropoxy)phenyl]-3-methyl-butan-2-amine (70 g, 260 mmol) in dioxane (700 mL) was added formic acid (47.8 g, 1.04 mol) at rt. The mixture was refluxed for 12 h, then diluted with $H_2O$ (200 mL) and extracted with EtOAc (2×200 mL). The organic layer was dried over anhydrous $Na_2SO_4$ and concentrated. The residue was purified by column chromatography to give N-[1-[[4-fluoro-3-(3-methoxypropoxy)phenyl]methyl]-2-methyl-propyl]formamide (55 g) as light yellow oil.

Step 5: Preparation of 7-fluoro-3-isopropyl-6-(3-methoxypropoxy)-3,4-dihydroisoquinoline

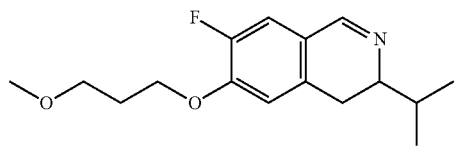 [SMILES: COCCCOc1cc2c(cc1F)C=NC(C(C)C)C2]

To a mixture of N-[1-[[4-fluoro-3-(3-methoxypropoxy)phenyl]methyl]-2-methyl-propyl]formamide (55 g, 185 mmol) in dry DCM (600 mL) was added POCl₃ (41.02 g, 268 mmol) dropwise at 0° C. The mixture was refluxed for 2 h. After being cooled to rt, the mixture was poured into a solution of ammonium hydroxide (100 mL) in H₂O (300 mL). The resulting mixture was stirred for 0.5 h and extracted with DCM (500 mL). The organic layer was washed with brine (200 mL), dried over anhydrous Na₂SO₄ and concentrated. The residue was purified by column chromatography to give 7-fluoro-3-isopropyl-6-(3-methoxypropoxy)-3,4-dihydroisoquinoline (20.2 g) as light yellow oil.

Step 6: Preparation of ethyl 10-fluoro-6-isopropyl-9-(3-methoxypropoxy)-2-oxo-1,6,7,11b-tetrahydrobenzo[a]quinolizine-3-carboxylate

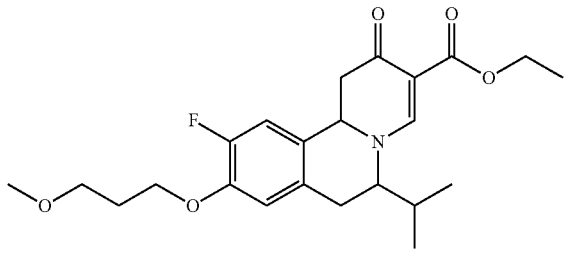 [SMILES: CCOC(=O)C1=CN2C(CC1=O)c1cc(F)c(OCCCOC)cc1CC2C(C)C]

A mixture of 7-fluoro-3-isopropyl-6-(3-methoxypropoxy)-3,4-dihydroisoquinoline (5.6 g, 20 mmol) and ethyl 2-(ethoxymethylene)-3-oxo-butanoate (11.2 g, 60 mmol) in ethanol (100 mL) was refluxed overnight. The mixture was concentrated to give crude ethyl 10-fluoro-6-isopropyl-9-(3-methoxypropoxy)-2-oxo-1,6,7,11b-tetrahydrobenzo[a]quinolizine-3-carboxylate (8.4 g) as dark brown oil which was used in the next step without further purification.

Step 7: Preparation of ethyl 10-methoxy-9-(2-methoxyethoxy)-6-(1-methylcyclopropyl)-2-oxo-6,7-dihydrobenzo[a]quinolizine-3-carboxylate

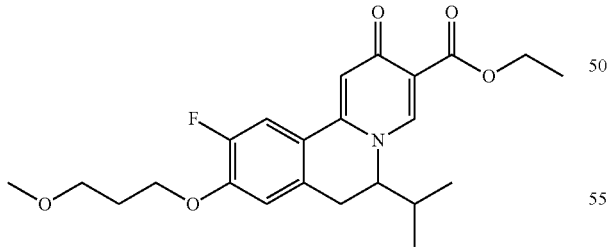

A mixture of crude ethyl 10-fluoro-6-isopropyl-9-(3-methoxypropoxy)-2-oxo-1,6,7,11b-tetrahydrobenzo[a]quinolizine-3-carboxylate (8.4 g, 20 mmol) an) and p-chloranil (3.7 g, 15 mmol) in DME (50 mL) was refluxed for 2 h. After being cooled to room temperature, the resulting suspension was filtered with suction. The filter cake was washed with cold DME and dried under vacuum to give ethyl 10-fluoro-6-isopropyl-9-(3-methoxypropoxy)-2-oxo-6,7-dihydrobenzo[a]quinolizine-3-carboxylate (7.5 g).

Step 8: Preparation of 10-fluoro-6-isopropyl-9-(3-methoxypropoxy)-2-oxo-6,7-dihydrobenzo[a]quinolizine-3-carboxylic acid

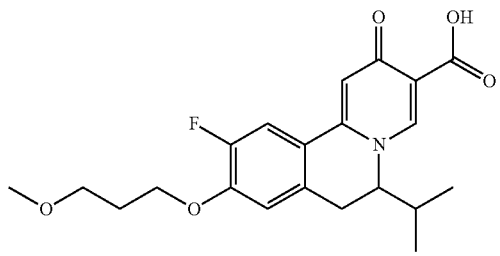 [SMILES: COCCCOc1cc2c(cc1F)-c1cc(=O)c(C(=O)O)cn1C(C(C)C)C2]

To a solution of ethyl 10-fluoro-6-isopropyl-9-(3-methoxypropoxy)-2-oxo-6,7-dihydrobenzo[a]quinolizine-3-carboxylate (7.5 g, 18 mmol) in THF (75 mL) and methanol (15 mL) was added 2.0 M LiOH (45 mL) aqueous solution at room temperature. The resulting mixture was stirred for 4 h, and then acidified to pH=1-2 with 2 M hydrochloric acid. The mixture was extracted with DCM (250 mL×2). The combined organic layers were washed with water and brine, dried over anhydrous Na₂SO₄ and concentrated to give a yellow solid, which was purified by flash column chromatography to give 10-fluoro-6-isopropyl-9-(3-methoxypropoxy)-2-oxo-6,7-dihydrobenzo[a]quinolizine-3-carboxylic acid (2.5 g). ¹H NMR (400 MHz, CDCl₃): δ 15.89-15.98 (s, 1H), 8.46-8.51 (s, 1H), 7.44-7.50 (s, 1H), 6.97-7.04 (s, 1H), 6.86-6.93 (s, 1H), 4.18-4.28 (m, 2H), 3.89-3.97 (m, 1H), 3.57-3.66 (m, 2H), 3.39 (s, 3H), 3.34-3.37 (m, 1H), 3.09-3.17 (m, 1H), 2.11-2.19 (m, 2H), 1.77-1.87 (m, 1H), 0.94-1.01 (m, 3H), 0.82-0.88 (m, 3H). MS obsd. (ESI⁺) [(M+H)⁺]: 390.

Example 141: 6-tert-butyl-9-(2,2-difluoro-3-hydroxy-propoxy)-10-methoxy-2-oxo-6,7-dihydrobenzo[a]quinolizine-3-carboxylic acid

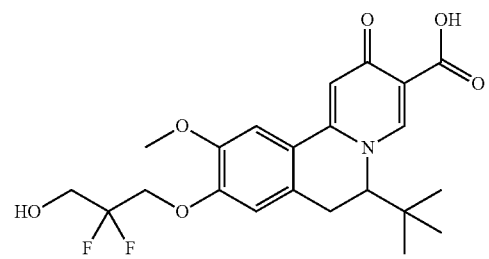 [SMILES: COc1cc2c(cc1OCC(F)(F)CO)CC(C(C)(C)C)n1cc(C(=O)O)c(=O)cc1-2]

Step 1: Preparation of (2,2-difluoro-3-hydroxy-propyl) 4-methylbenzenesulfonate

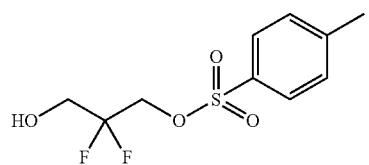 [SMILES: Cc1ccc(S(=O)(=O)OCC(F)(F)CO)cc1]

To a solution of 2,2-difluoropropane-1,3-diol (1.1 g, 10 mmol, PharmaBlock) in DCM (30 mL) was added triethylamine (5 g, 50 mmol) and 4-toluene sulfonyl chloride (1.14 g, 6 mmol). The resulting mixture was stirred for 10 h at room temperature. To the resulting mixture was added water, and then the organic layer was separated, washed with brine, dried over anhydrous Na₂SO₄ and concentrated to give crude (2,2-difluoro-3-hydroxy-propyl) 4-methylbenzenesulfonate (1.2 g) as a yellow oil.

Step 2: Preparation of 2-benzyloxy-4-bromo-1-methoxy-benzene

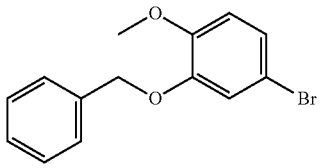 [SMILES: COc1ccc(Br)cc1OCc1ccccc1]

To a mixture of 5-bromo-2-methoxy-phenol (150 g, 739 mmol) in acetone (1.5 L) was added K₂CO₃ (153 g, 1.11 mol) and bromomethylbenzene (152 g, 887 mmol). The mixture was refluxed for 16 h and filtered. The filter cake was washed with acetone. The filtrate was concentrated. The residue was washed with petroleum ether to give 2-benzyloxy-4-bromo-1-methoxy-benzene (170 g) as a white solid.

Step 3: Preparation of 1-(3-benzyloxy-4-methoxy-phenyl)-3,3-dimethyl-butan-2-one

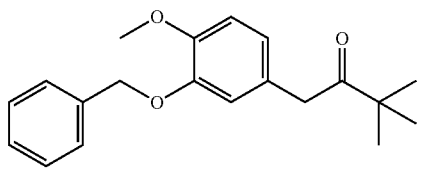 [SMILES: COc1ccc(CC(=O)C(C)(C)C)cc1OCc1ccccc1]

A mixture of 2-benzyloxy-4-bromo-1-methoxy-benzene (140 g, 478 mmol), 3,3-dimethylbutan-2-one (144 g, 1.43 mol), t-BuONa (151 g, 1.58 mol), Xantphos (27.6 g, 47.8 mmol) and Pd₂(dba)₃ (21.9 g, 23.9 mmol) in dioxane (2 L) was heated at 100° C. for 1 h. The reaction mixture was cooled to rt and filtered. The filtrate was concentrated and the residue was purified by the flash column chromatography to afford 1-(3-benzyloxy-4-methoxy-phenyl)-3,3-dimethyl-butan-2-one (110 g) as a yellow oil.

Step 4: Preparation of 1-(3-benzyloxy-4-methoxy-phenyl)-3,3-dimethyl-butan-2-amine

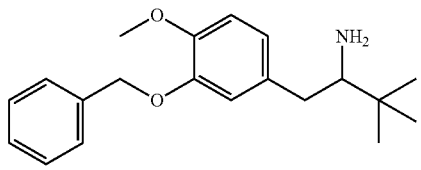

To a solution of 1-(3-benzyloxy-4-methoxy-phenyl)-3,3-dimethyl-butan-2-one (105 g, 112 mmol) in MeOH (350 mL) was added NH₄OAc (86.4 g, 1.12 mol) at 15° C. After the mixture being stirred for 1 h, NaBH₃CN (10.6 g, 168 mmol) was added to the mixture at 0° C. Then the resulting mixture was stirred at 40° C. for 48 h and then concentrated. The residue was diluted with H₂O (300 mL), and the aqueous mixture was extracted with DCM (1 L×2). The organic layers were combined, washed with brine (200 mL), dried over anhydrous Na₂SO₄ and concentrated under reduced pressure to afford 1-(3-benzyloxy-4-methoxy-phenyl)-3,3-dimethyl-butan-2-amine (95 g) as yellow oil.

Step 5: Preparation of N-[1-[(3-benzyloxy-4-methoxy-phenyl)methyl]-2,2-dimethyl-propyl]formamide

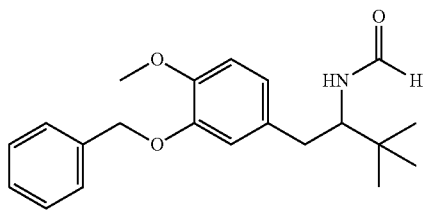 [SMILES: COc1ccc(CC(NC=O)C(C)(C)C)cc1OCc1ccccc1]

To a mixture of 1-(3-benzyloxy-4-methoxy-phenyl)-3,3-dimethyl-butan-2-amine (95 g, 303 mmol) in dioxane (1 L) was added formic acid (97.7 g, 2.12 mol) at 15° C. Then the mixture was heated at 120° C. for 24 h and then concentrated. The residue was dissolved in EtOAc (1 L), and then the organic solution was washed with H₂O (500 mL) and brine (500 mL×2), dried over anhydrous Na₂SO₄ and concentrated. The residue was purified by column chromatography to give N-[1-[(3-benzyloxy-4-methoxy-phenyl)methyl]-2,2-dimethyl-propyl]formamide (55 g) as a yellow oil.

Step 6: Preparation of 6-benzyloxy-3-tert-butyl-7-methoxy-3,4-dihydroisoquinoline

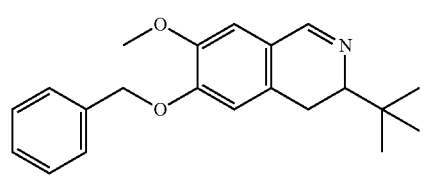

To a solution of N-[1-[(3-benzyloxy-4-methoxy-phenyl)methyl]-2,2-dimethyl-propyl]formamide (55 g, 161 mmol) in DCM (500 mL) was added POCl₃ (54.54 g, 356 mmol) at rt. The resulting mixture was stirred at 40° C. for 12 h. After being cooled to rt, the mixture was basified with ammonia water and extracted with DCM (1 L). The organic layer was concentrated to afford crude 6-benzyloxy-3-tert-butyl-7-methoxy-3,4-dihydroisoquinoline (50 g) as a yellow solid.

Step 7: Preparation of ethyl 9-benzyloxy-6-tert-butyl-10-methoxy-2-oxo-1,6,7,11b-tetrahydrobenzo[a]quinolizine-3-carboxylate

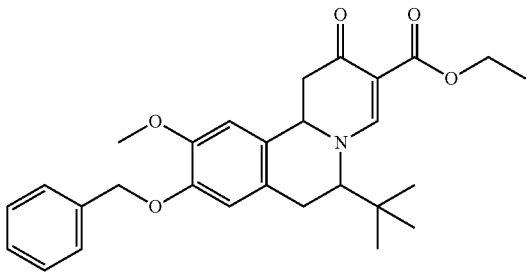 [SMILES: CCOC(=O)C1=CN2C(CC1=O)c1cc(OC)c(OCc3ccccc3)cc1CC2C(C)(C)C]

A solution of 6-benzyloxy-3-tert-butyl-7-methoxy-3,4-dihydroisoquinoline (18 g, 55.7 mmol) and ethyl 2-(ethoxymethylene)-3-oxo-butanoate (36 g, 195 mmol) in EtOH (150 mL) was heated at 100° C. for 48 h. After being cooled to rt, the mixture was concentrated to give crude ethyl 9-benzyloxy-6-tert-butyl-10-methoxy-2-oxo-1,6,7,11b-tetrahydrobenzo[a]quinolizine-3-carboxylate which was used in the next step without purification.

Step 8: Preparation of ethyl 9-benzyloxy-6-tert-butyl-10-methoxy-2-oxo-6,7-dihydrobenzo[a]quinolizine-3-carboxylate

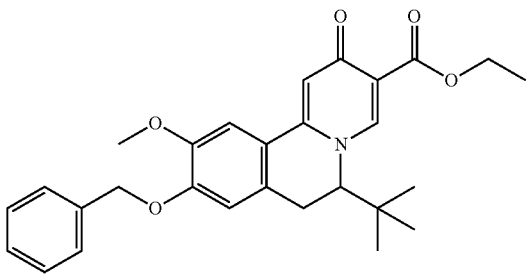 [SMILES: CCOC(=O)c1cn2c(cc1=O)-c1cc(OC)c(OCc3ccccc3)cc1CC2C(C)(C)C]

To a solution of ethyl 9-benzyloxy-6-tert-butyl-10-methoxy-2-oxo-1,6,7,11b-tetrahydrobenzo[a]quinolizine-3-carboxylate (77 g, 166 mmol) in DME (700 mL) was added p-chloranil (34.7 g, 141 mmol). The mixture was heated at 70° C. for 3 h. After being cooled to rt, the mixture was filtered. The filter cake was washed with cold DME and dried in vacuo to afford ethyl 9-benzyloxy-6-tert-butyl-10-methoxy-2-oxo-6,7-dihydrobenzo[a]quinolizine-3-carboxylate (24 g) as a yellow solid.

Step 9: Preparation of ethyl 6-tert-butyl-9-hydroxy-10-methoxy-2-oxo-6,7-dihydrobenzo[a]quinolizine-3-carboxylate

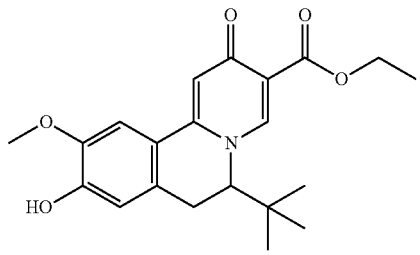 [SMILES: CCOC(=O)c1cn2c(cc1=O)-c1cc(OC)c(O)cc1CC2C(C)(C)C]

A mixture of ethyl 9-benzyloxy-6-tert-butyl-10-methoxy-2-oxo-6,7-dihydrobenzo[a]quinolizine-3-carboxylate (22 g, 47.7 mmol) and Pd/C (3 g) in EtOH (250 mL) was stirred under hydrogen atmosphere (30 psi) at 30° C. for 12 h. The mixture was filtered and the filtrate was concentrated under reduced pressure. The residue was washed with a mixture solvent of PE/EA=1/1 (60 mL), dried under reduced pressure to afford ethyl 6-tert-butyl-9-hydroxy-10-methoxy-2-oxo-6,7-dihydrobenzo[a]quinolizine-3-carboxylate (16.4 g) as a yellow solid.

Step 10: Preparation of ethyl 6-tert-butyl-9-(2,2-difluoro-3-hydroxy-propoxy)-10-methoxy-2-oxo-6,7-dihydrobenzo[a]quinolizine-3-carboxylate

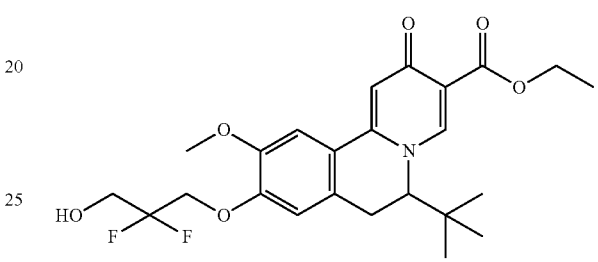

To a solution of ethyl 6-tert-butyl-9-hydroxy-10-methoxy-2-oxo-6,7-dihydrobenzo[a]quinolizine-3-carboxylate (250 mg, 0.67 mmol) in DMF (10 mL) was added potassium carbonate (185 mg, 1.34 mmol) and (2,2-difluoro-3-hydroxy-propyl) 4-methylbenzenesulfonate (180 mg, 0.67 mmol). The resulting mixture was heated at 90° C. for 3 h. After being cooled to room temperature, the dark-brown mixture was poured into water (30 mL) and the resulting mixture was extracted with DCM (75 mL×2). The organic layers were combined and washed with brine, dried over anhydrous Na₂SO₄, and concentrated under reduced pressure to give crude ethyl 6-tert-butyl-9-(2,2-difluoro-3-hydroxy-propoxy)-10-methoxy-2-oxo-6,7-dihydrobenzo[a]quinolizine-3-carboxylate (230 mg), which was used directly in the next step without further purification.

Step 11: Preparation of 6-tert-butyl-9-(2,2-difluoro-3-hydroxy-propoxy)-10-methoxy-2-oxo-6,7-dihydrobenzo[a]quinolizine-3-carboxylic acid

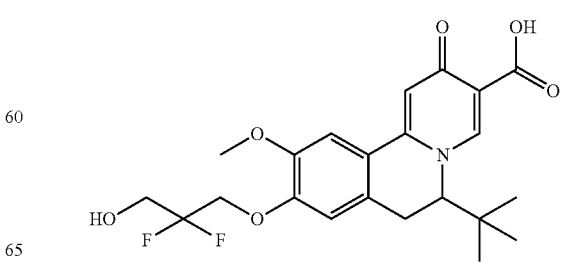

To a solution of ethyl 6-tert-butyl-9-(2,2-difluoro-3-hydroxy-propoxy)-10-methoxy-2-oxo-6,7-dihydrobenzo[a]quinolizine-3-carboxylate (220 mg, 0.50 mmol) in THF (10 mL) and ethanol (2 mL) was added 2.0 M LiOH (1.25 mL) aqueous solution at room temperature. The resulting mixture was stirred for 4 h, and then acidified to pH=1-2 with 2 M hydrochloric acid. The resulting mixture was extracted with DCM (30 mL×2). The combined organic layers were washed with water and brine, dried over anhydrous $Na_2SO_4$ and concentrated to give a yellow solid, which was purified by prep-HPLC to give 6-tert-butyl-9-(2,2-difluoro-3-hydroxy-propoxy)-10-methoxy-2-oxo-6,7-dihydrobenzo[a]quinolizine-3-carboxylic acid (3 mg). $^1$H NMR (400 MHz, MeOD): δ 8.68-8.73 (s, 1H), 7.44-7.49 (s, 1H), 7.27-7.34 (s, 1H), 7.05-7.14 (s, 1H), 4.31-4.53 (m, 2H), 4.04-4.15 (m, 1H), 3.96 (m, 4H), 3.70-3.80 (m, 1H), 3.45 (s, 2H), 0.85 (s, 9H). MS obsd. (ESI$^+$) [(M+H)$^+$]: 438.

Example 142 and 143

(+)-9-(2,2-difluoroethoxy)-6-isopropyl-10-methoxy-2-oxo-6,7-dihydrobenzo[a]quinolizine-3-carboxylic acid and (−)-9-(2,2-difluoroethoxy)-6-isopropyl-10-methoxy-2-oxo-6,7-dihydrobenzo[a]quinolizine-3-carboxylic acid

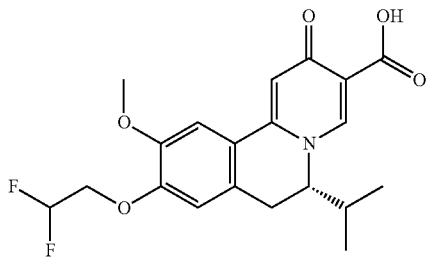

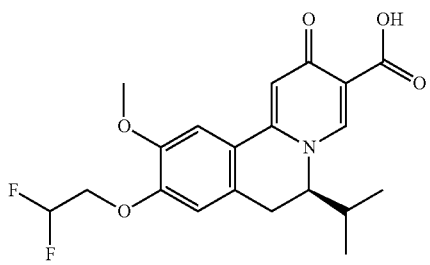

Step 1: Preparation of ethyl 9-(2,2-difluoroethoxy)-6-isopropyl-10-methoxy-2-oxo-6,7-dihydrobenzo[a]quinolizine-3-carboxylate

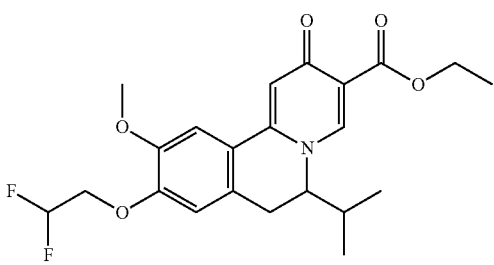 [SMILES: CCOC(=O)c1cn2c(cc1=O)-c1cc(OC)c(OCC(F)F)cc1CC2C(C)C]

To a solution of ethyl 9-hydroxy-6-isopropyl-10-methoxy-2-oxo-6,7-dihydrobenzo[a]quinolizine-3-carboxylate (7.0 g, 20.0 mmol) in DMF (70 mL) was added 2-bromo-1,1-difluoro-ethane (14.5 g, 100.0 mmol) and $K_2CO_3$ (5.5 g, 40.0 mmol). The reaction mixture was stirred for 3 hours at 80° C., and then filtered. The filtrate was concentrated to give crude ethyl 9-(2,2-difluoroethoxy)-6-isopropyl-10-methoxy-2-oxo-6,7-dihydrobenzo[a]quinolizine-3-carboxylate which was directly used in the next step without further purification.

Step 2: Preparation of 9-(2, 2-difluoroethoxy)-6-isopropyl-10-methoxy-2-oxo-6,7-dihydrobenzo[a]quinolizine-3-carboxylic acid

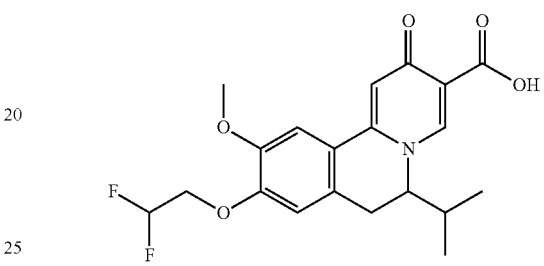

To a solution of crude ethyl 9-(2,2-difluoroethoxy)-6-isopropyl-10-methoxy-2-oxo-6,7-dihydrobenzo[a]quinolizine-3-carboxylate (Step 1) in a mixture solvent of methanol and water (3:1, 80 mL) was added LiOH.H$_2$O (2.52 g, 60.0 mmol). The mixture was stirred for two hours at room temperature and concentrated under reduced pressure. The residue was dissolved in water (100 mL) and acidified with 6 M hydrochloric acid. The mixture was filtered and the filter cake was dried under vacuum to give 9-(2, 2-difluoroethoxy)-6-isopropyl-10-methoxy-2-oxo-6, 7-dihydrobenzo[a]quinolizine-3-carboxylic acid.

Step 3: Preparation of (+)-9-(2, 2-difluoroethoxy)-6-isopropyl-10-methoxy-2-oxo-6,7-dihydrobenzo[a]quinolizine-3-carboxylic acid and (−)-9-(2, 2-difluoroethoxy)-6-isopropyl-10-methoxy-2-oxo-6,7-dihydrobenzo[a]quinolizine-3-carboxylic acid

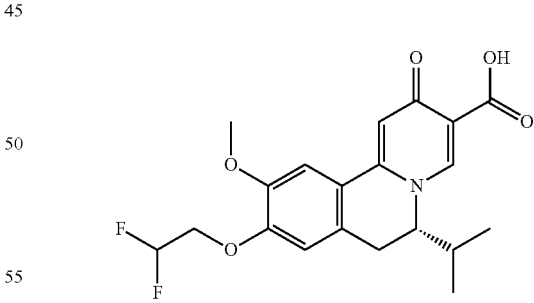

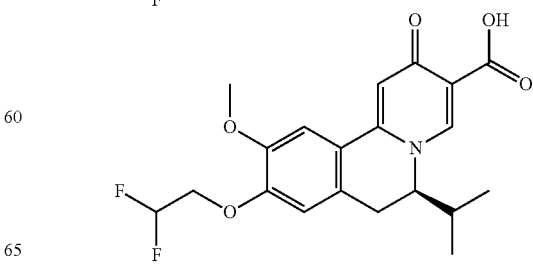

Separation of 9-(2, 2-difluoroethoxy)-6-isopropyl-10-methoxy-2-oxo-6,7-dihydrobenzo[a]quinolizine-3-carboxylic acid by chiral HPLC provided (+)-9-(2, 2-difluoroethoxy)-6-isopropyl-10-methoxy-2-oxo-6,7-dihydrobenzo[a]quinolizine-3-carboxylic acid (755.0 mg) and (−)-9-(2, 2-difluoroethoxy)-6-isopropyl-10-methoxy-2-oxo-6,7-dihydrobenzo[a]quinolizine-3-carboxylic acid (750.0 mg).

Example 142

$^1$H NMR (400 MHz, DMSO) δ 8.80 (s, 1H), 7.58 (s, 1H), 7.50 (s, 1H), 7.18 (s, 1H), 6.26-6.64 (m, 1H), 4.28-4.53 (m, 3H), 3.90 (s, 3H), 3.27-3.32 (m, 1H), 3.08-3.19 (m, 1H), 1.62 (td, 9.66 Hz, 1H), 0.88 (d, 3H), 0.71 (d, 3H). MS obsd. (ESI$^+$) [(M+H)$^+$]: 394. [α]$_D^{20}$=+100.0° (0.070%, CH$_3$CN).

Example 143

$^1$H NMR (400 MHz, DMSO) δ 8.80 (s, 1H), 7.58 (s, 1H), 7.50 (s, 1H), 7.18 (s, 1H), 6.26-6.64 (m, 1H), 4.28-4.53 (m, 3H), 3.90 (s, 3H), 3.27-3.32 (m, 1H), 3.08-3.19 (m, 1H), 1.62 (td, 9.66 Hz, 1H), 0.88 (d, 3H), 0.71 (d, 3H). MS obsd. (ESI$^+$) [(M+H)$^+$]: 394.

Example 144: 9-(3-hydroxy-2, 2-dimethyl-propoxy)-6-isopropyl-10-methoxy-2-oxo-6, 7-dihydrobenzo[a]quinolizine-3-carboxylic acid

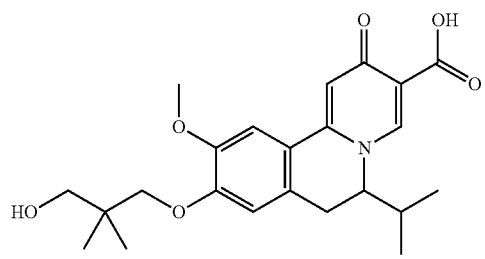 [SMILES: COc1cc2c(cc1OCC(C)(C)CO)CC(C(C)C)n1cc(C(=O)O)c(=O)cc1-2]

Step 1: Preparation of ethyl 9-(3-hydroxy-2, 2-dimethyl-propoxy)-6-isopropyl-10-methoxy-2-oxo-6,7-dihydrobenzo[a]quinolizine-3-carboxylate

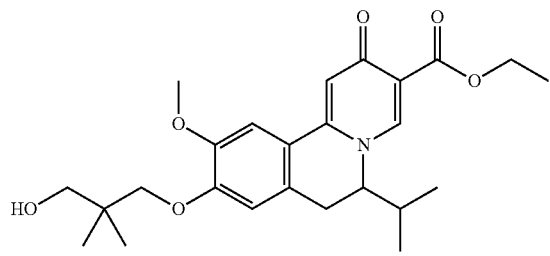 [SMILES: CCOC(=O)c1cn2c(cc1=O)-c1cc(OC)c(OCC(C)(C)CO)cc1CC2C(C)C]

To a solution of ethyl 9-hydroxy-6-isopropyl-10-methoxy-2-oxo-6,7-dihydrobenzo[a]quinolizine-3-carboxylate (300 mg, 0.84 mmol) in DMF (5 mL) was added 3-bromo-2,2-dimethyl-propan-1-ol (420.8 mg, 2.52 mmol) and K$_2$CO$_3$ (231.8 mg, 1.68 mmol). The reaction was heated at 120° C. for 36 hours. After being cooled to rt, the mixture was filtered and the filtrate was concentrated. The residue was directly used in the next step without further purification.

Step 2: Preparation of 9-(3-hydroxy-2, 2-dimethyl-propoxy)-6-isopropyl-10-methoxy-2-oxo-6,7-dihydrobenzo[a]quinolizine-3-carboxylic acid

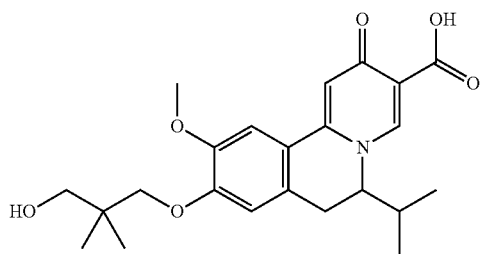 [SMILES: COc1cc2c(cc1OCC(C)(C)CO)CC(C(C)C)n1cc(C(=O)O)c(=O)cc1-2]

To a solution of crude ethyl 9-(3-hydroxy-2, 2-dimethyl-propoxy)-6-isopropyl-10-methoxy-2-oxo-6,7-dihydrobenzo[a]quinolizine-3-carboxylate (Step 1) in a mixture solvent of methanol and water (3:1, 12 mL) was added LiOH.H$_2$O (317.5 mg, 7.56 mmol). The mixture was stirred for two hours at room temperature, and then concentrated under reduced pressure. The residue was dissolved in water (20 mL) and the aqueous mixture was acidified with 6 M hydrochloric acid and extracted with DCM. The organic layer was dried over anhydrous Na$_2$SO$_4$ and concentrated. The residue was purified by preparative HPLC to give 9-(3-hydroxy-2,2-dimethyl-propoxy)-6-isopropyl-10-methoxy-2-oxo-6,7-dihydrobenzo[a]quinolizine-3-carboxylic acid (42 mg). $^1$H NMR (400 MHz, MeOD): δ 8.80 (s, 1H), 7.47 (s, 1H), 7.41 (s, 1H), 7.04 (s, 1H), 4.25-4.44 (m, 1H), 3.74-4.01 (m, 5H), 3.46-3.56 (m, 2H), 3.36-3.43 (m, 1H), 3.19-3.29 (m, 1H), 1.78-1.86 (m, 1H), 1.06 (s, 6H), 1.00 (d, 3H), 0.82 (d, 3H). MS obsd. (ESI$^+$) [(M+H)$^+$]: 416.

Example 145 and 146

(+)-9-(3-hydroxy-2,2-dimethyl-propoxy)-6-isopropyl-10-methoxy-2-oxo-6,7-dihydrobenzo[a]quinolizine-3-carboxylic acid and (−)-9-(3-hydroxy-2,2-dimethyl-propoxy)-6-isopropyl-10-methoxy-2-oxo-6,7-dihydrobenzo[a]quinolizine-3-carboxylic acid

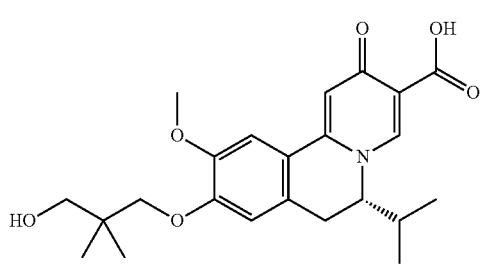

-continued

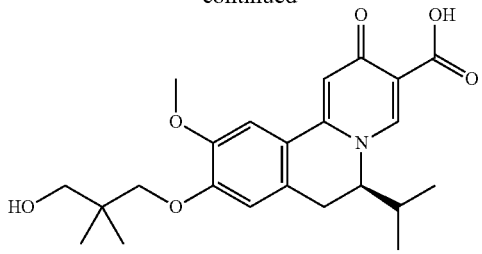

Separation of 9-(3-hydroxy-2,2-dimethyl-propoxy)-6-isopropyl-10-methoxy-2-oxo-6,7-dihydrobenzo[a]quinolizine-3-carboxylic acid by chiral HPLC provided (+)-9-(3-hydroxy-2,2-dimethyl-propoxy)-6-isopropyl-10-methoxy-2-oxo-6,7-dihydrobenzo[a]quinolizine-3-carboxylic acid (7.5 mg) and (−)-9-(3-hydroxy-2,2-dimethyl-propoxy)-6-isopropyl-10-methoxy-2-oxo-6,7-dihydrobenzo[a]quinolizine-3-carboxylic acid (12.8 mg).

Example 145

$^1$H NMR (400 MHz, MeOD) δ 8.80 (s, 1H), 7.47 (s, 1H), 7.41 (s, 1H), 7.04 (s, 1H), 4.25-4.44 (m, 1H), 3.74-4.01 (m, 5H), 3.46-3.56 (m, 2H), 3.36-3.43 (m, 1H), 3.19-3.29 (m, 1H), 1.78-1.86 (m, 1H), 1.06 (s, 6H), 1.00 (d, 3H), 0.82 (d, 3H). MS obsd. (ESI$^+$) [(M+H)$^+$]: 416. [α]$_D^{20}$=+47.3° (0.055%, CH$_3$CN).

Example 146

$^1$H NMR (400 MHz, MeOD) δ 8.80 (s, 1H), 7.47 (s, 1H), 7.41 (s, 1H), 7.04 (s, 1H), 4.25-4.44 (m, 1H), 3.74-4.01 (m, 5H), 3.46-3.56 (m, 2H), 3.36-3.43 (m, 1H), 3.19-3.29 (m, 1H), 1.78-1.86 (m, 1H), 1.06 (s, 6H), 1.00 (d, 3H), 0.82 (d, 3H). MS obsd. (ESI$^+$) [(M+H)$^+$]: 416.

Example 147: 9-(3-hydroxypropoxy)-6-isopropyl-10-methoxy-2-oxo-6,7-dihydrobenzo[a]quinolizine-3-carboxylic acid

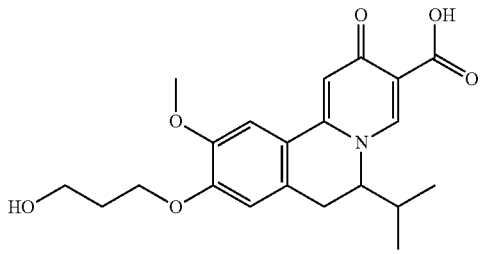 [SMILES: COc1cc2c(cc1OCCCO)CC(C(C)C)n1cc(C(=O)O)c(=O)cc1-2]

Step 1: Preparation of ethyl 9-(3-hydroxypropoxy)-6-isopropyl-10-methoxy-2-oxo-6,7-dihydrobenzo[a]quinolizine-3-carboxylate

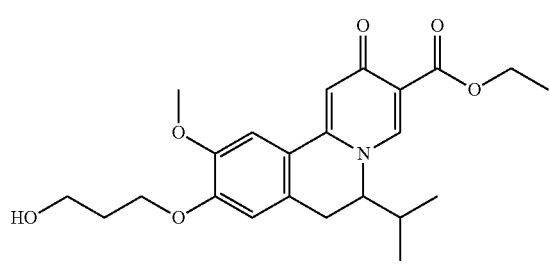 [SMILES: CCOC(=O)c1cn2c(cc1=O)-c1cc(OC)c(OCCCO)cc1CC2C(C)C]

To a solution of ethyl 9-hydroxy-6-isopropyl-10-methoxy-2-oxo-6,7-dihydrobenzo[a]quinolizine-3-carboxylate (300 mg, 0.84 mmol) in DMF was added 3-bromopropan-1-ol (350 mg, 2.52 mmol) and K$_2$CO$_3$ (231.8 mg, 1.68 mmol). The mixture was heated at 80° C. for 12 hours and filtered. The filtrate was concentrated under reduced pressure, and the residue was purified by column chromatography to give ethyl 9-(3-hydroxypropoxy)-6-isopropyl-10-methoxy-2-oxo-6,7-dihydrobenzo[a]quinolizine-3-carboxylate (50 mg).

Step 2: Preparation of 9-(3-hydroxypropoxy)-6-isopropyl-10-methoxy-2-oxo-6,7-dihydrobenzo[a]quinolizine-3-carboxylic acid

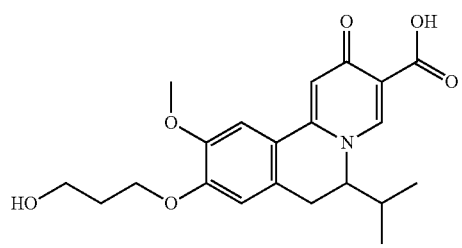 [SMILES: COc1cc2c(cc1OCCCO)CC(C(C)C)n1cc(C(=O)O)c(=O)cc1-2]

To a solution of ethyl 9-(3-hydroxypropoxy)-6-isopropyl-10-methoxy-2-oxo-6,7-dihydrobenzo[a]quinolizine-3-carboxylate (50 mg, 0.12 mmol) in a mixture solvent of methanol and water (3:1, 4 mL) was added LiOH.H$_2$O (15.2 mg, 0.36 mmol). The mixture was stirred for 2 h at room temperature, and concentrated under reduced pressure. The residue was dissolved in water (5 mL) and the aqueous mixture was acidified by 6 M hydrochloric acid and extracted with DCM. The organic layer was dried over anhydrous Na$_2$SO$_4$ and concentrated. The residue was purified by preparative HPLC to give 9-(3-hydroxypropoxy)-6-isopropyl-10-methoxy-2-oxo-6, 7-dihydrobenzo[a]quinolizine-3-carboxylic acid. $^1$H NMR (400 MHz, MeOD): δ 8.72 (s, 1H), 7.46 (s, 1H), 7.30 (s, 1H), 7.05 (s, 1H), 4.16-4.35 (m, 3H), 3.95 (s, 3H), 3.75-3.84 (m, 2H), 3.34-3.43 (m, 1H), 3.19-3.28 (m, 1H), 2.03-2.11 (m, 2H), 1.74-1.87 (m, 1H), 0.99 (d, 3H), 0.82 (d, 3H). MS obsd. (ESI$^+$) [(M+H)$^+$]: 388.

Example 148: 6-isopropyl-10-methoxy-9-(4-methoxybutoxy)-2-oxo-6,7-dihydrobenzo[a]quinolizine-3-carboxylic acid

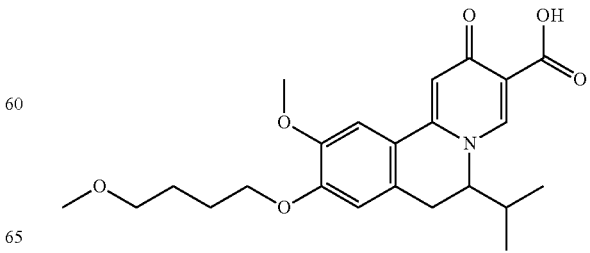

Step 1: Preparation of ethyl 6-isopropyl-10-methoxy-9-(4-methoxybutoxy)-2-oxo-6,7-dihydrobenzo[a]quinolizine-3-carboxylate

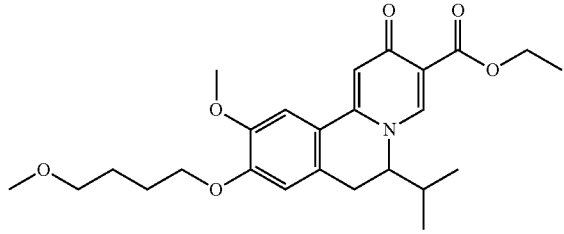 [SMILES: CCOC(=O)c1cn2c(cc1=O)-c1cc(OC)c(OCCCCOC)cc1CC2C(C)C]

To a solution of ethyl 9-hydroxy-6-isopropyl-10-methoxy-2-oxo-6,7-dihydrobenzo[a]quinolizine-3-carboxylate (100 mg, 0.28 mmol) in DMF (5 mL) was added 1-bromo-4-methoxy-butane (140.4 mg, 0.84 mmol) and K$_2$CO$_3$ (77.3 mg, 0.56 mmol). The mixture was heated at 100° C. for 3 hours and then filtered. The filtrate was concentrated. The residue was used in the next step without further purification.

Step 2: Preparation of 6-isopropyl-10-methoxy-9-(4-methoxybutoxy)-2-oxo-6,7-dihydrobenzo[a]quinolizine-3-carboxylic acid

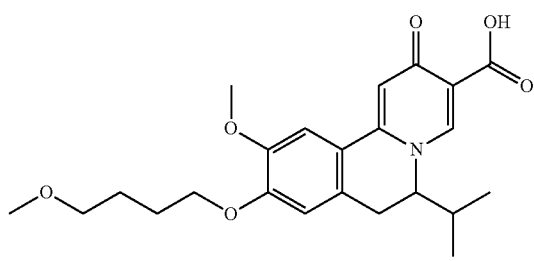 [SMILES: COCCCCOc1cc2c(cc1OC)-c1cc(=O)c(C(=O)O)cn1C(C(C)C)C2]

To a solution of crude ethyl 6-isopropyl-10-methoxy-9-(4-methoxybutoxy)-2-oxo-6,7-dihydrobenzo[a]quinolizine-3-carboxylate in a mixture solvent of methanol and water (3:1, 4 mL) was added LiOH.H$_2$O (35.3 mg, 0.84 mmol). The mixture was stirred for 2 hours at room temperature and concentrated under reduced pressure. The residue was dissolved in water (5 mL).

The aqueous solution was acidified with 6 M hydrochloric acid and filtered. The filter cake was dried in vacuo to give 6-isopropyl-10-methoxy-9-(4-methoxybutoxy)-2-oxo-6,7-dihydrobenzo[a]quinolizine-3-carboxylic acid (38.5 mg). $^1$H NMR (400 MHz, CDCl$_3$): δ 8.48 (s, 1H), 7.19 (s, 1H), 7.08 (s, 1H), 6.76 (s, 1H), 4.10-4.18 (m, 2H), 3.94 (s, 3H), 3.89-3.92 (m, 1H), 3.46-3.52 (m, 2H), 3.38 (s, 3H), 3.32-3.36 (m, 1H), 3.05-3.12 (m, 1H), 1.94-2.03 (m, 2H), 1.76-1.86 (m, 3H), 1.67-1.72 (m, 1H), 0.97 (d, 3H), 0.85 (d, 3H). MS obsd. (ESI$^+$) [(M+H)$^+$]: 416.

Example 149: 6-tert-butyl-9-(3-hydroxy-2,2-dimethyl-propoxy)-10-methoxy-2-oxo-6,7-dihydrobenzo[a]quinolizine-3-carboxylic acid

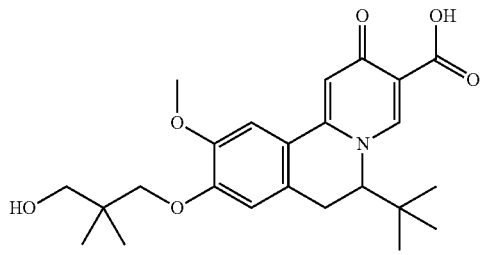 [SMILES: COc1cc2c(cc1OCC(C)(C)CO)CC(C(C)(C)C)n1cc(C(=O)O)c(=O)cc1-2]

Step 1: Preparation of ethyl 6-tert-butyl-9-(3-hydroxy-2, 2-dimethyl-propoxy)-10-methoxy-2-oxo-6, 7-dihydrobenzo[a]quinolizine-3-carboxylate

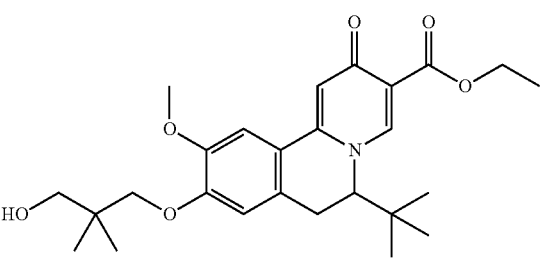 [SMILES: CCOC(=O)c1cn2c(cc1=O)-c1cc(OC)c(OCC(C)(C)CO)cc1CC2C(C)(C)C]

To a solution of ethyl 6-tert-butyl-9-hydroxy-10-methoxy-2-oxo-6,7-dihydrobenzo[a]quinolizine-3-carboxylate (1.0 g, 2.7 mmol) in DMF (20 mL) was added 3-bromo-2,2-dimethyl-propan-1-ol (1.4 g, 8.1 mmol) and K$_2$CO$_3$ (0.75 g, 5.4 mmol). The reaction was heated at 120° C. for 24 hours. After being cooled to rt, the mixture was filtered and the filtrate was concentrated. The residue was directly used for the next step without further purification.

Step 2: Preparation of 6-tert-butyl-9-(3-hydroxy-2, 2-dimethyl-propoxy)-10-methoxy-2-oxo-6,7-dihydrobenzo[a]quinolizine-3-carboxylic acid

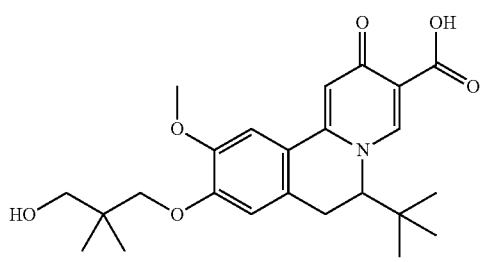 [SMILES: COc1cc2c(cc1OCC(C)(C)CO)CC(C(C)(C)C)n1cc(C(=O)O)c(=O)cc1-2]

To a solution of crude ethyl 6-tert-butyl-9-(3-hydroxy-2, 2-dimethyl-propoxy)-10-methoxy-2-oxo-6,7-dihydrobenzo [a]quinolizine-3-carboxylate in a mixture solvent of methanol and water (3:1, 12 mL) was added LiOH.H$_2$O (340.2 mg, 8.1 mmol). The mixture was stirred for 2 hours at room temperature, and then concentrated under reduced pressure.

The residue was dissolved in water (20 mL), and the aqueous solution was acidified with 6 M hydrochloric acid and extracted with DCM. The organic layer was dried over anhydrous Na$_2$SO$_4$ and concentrated.

The residue was purified by preparative HPLC to give 6-tert-butyl-9-(3-hydroxy-2,2-dimethyl-propoxy)-10-methoxy-2-oxo-6,7-dihydrobenzo[a]quinolizine-3-carboxylic acid (480 mg). $^1$H NMR (400 MHz, CDCl$_3$) δ 8.51 (s, 1H), 7.15 (s, 1H), 7.10 (s, 1H), 6.75 (s, 1H), 4.04-4.09 (m, 1H), 3.86-3.96 (m, 5H), 3.59-3.63 (m, 2H), 3.40-3.50 (m, 1H), 3.16-3.24 (m, 1H), 1.06-1.17 (m, 6H), 0.85 (s, 9H). MS obsd. (ESI$^+$) [(M+H)$^+$]: 430.

Example 150 and 151

(+)-6-tert-butyl-9-(3-hydroxy-2,2-dimethyl-propoxy)-10-methoxy-2-oxo-6,7-dihydrobenzo[a]quinolizine-3-carboxylic acid and (−)-6-tert-butyl-9-(3-hydroxy-2,2-dimethyl-propoxy)-10-methoxy-2-oxo-6,7-dihydrobenzo[a]quinolizine-3-carboxylic acid

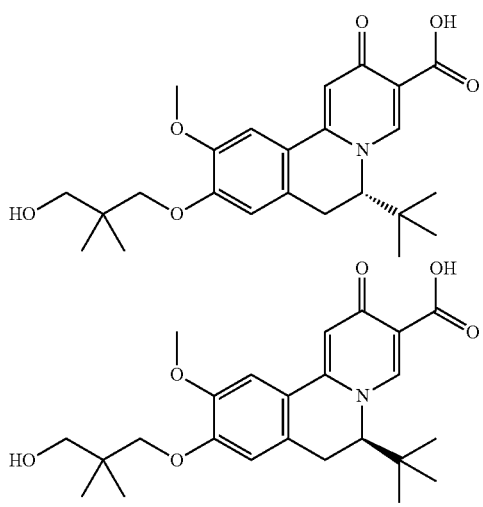

Separation of 6-tert-butyl-9-(3-hydroxy-2,2-dimethyl-propoxy)-10-methoxy-2-oxo-6,7-dihydrobenzo[a]quinolizine-3-carboxylic acid by chiral HPLC provided (+)-6-tert-butyl-9-(3-hydroxy-2,2-dimethyl-propoxy)-10-methoxy-2-oxo-6,7-dihydrobenzo[a]quinolizine-3-carboxylic acid (116 mg) and (−)-6-tert-butyl-9-(3-hydroxy-2,2-dimethyl-propoxy)-10-methoxy-2-oxo-6,7-dihydrobenzo[a]quinolizine-3-carboxylic acid (120 mg).

Example 150

$^1$H NMR (400 MHz, CDCl$_3$) δ 8.51 (s, 1H), 7.15 (s, 1H), 7.10 (s, 1H), 6.75 (s, 1H), 4.04-4.09 (m, 1H), 3.86-3.96 (m, 5H), 3.59-3.63 (m, 2H), 3.40-3.50 (m, 1H), 3.16-3.24 (m, 1H), 1.06-1.17 (m, 6H), 0.85 (s, 9H). MS obsd. (ESI$^+$) [(M+H)$^+$]: 430. [α]$_D^{20}$ +55.0° (0.080%, CH$_3$CN).

Example 151

$^1$H NMR (400 MHz, CDCl$_3$) δ 8.51 (s, 1H), 7.15 (s, 1H), 7.10 (s, 1H), 6.75 (s, 1H), 4.04-4.09 (m, 1H), 3.86-3.96 (m, 5H), 3.59-3.63 (m, 2H), 3.40-3.50 (m, 1H), 3.16-3.24 (m, 1H), 1.06-1.17 (m, 6H), 0.85 (s, 9H). MS obsd. (ESI$^+$) [(M+H)$^+$]: 430.

Example 152: 6-tert-butyl-9-(5-hydroxypentoxy)-10-methoxy-2-oxo-6,7-dihydrobenzo[a]quinolizine-3-carboxylic acid

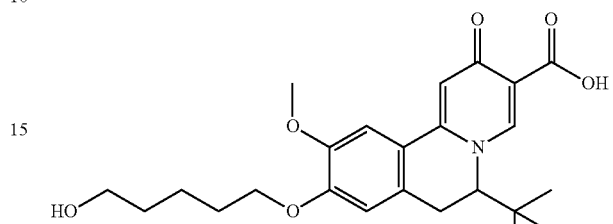

Step 1: Preparation of ethyl 6-tert-butyl-9-(5-hydroxypentoxy)-10-methoxy-2-oxo-6,7-dihydrobenzo[a]quinolizine-3-carboxylate

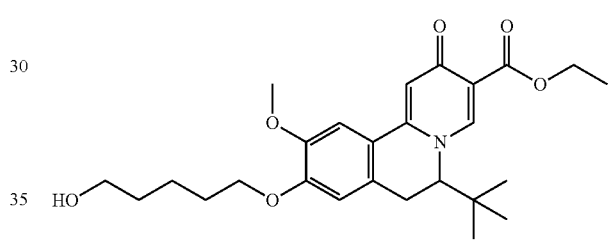

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 5-bromopentan-1-ol (135.4 mg, 0.81 mmol) and K$_2$CO$_3$ (74.5 mg, 0.54 mmol). The reaction was heated at 120° C. for 3 hours. After being cooled to rt, the mixture was filtered and the filtrate was concentrated. The residue was used in the next step without further purification.

Step 2: Preparation of 6-tert-butyl-9-(5-hydroxypentoxy)-10-methoxy-2-oxo-6,7-dihydrobenzo[a]quinolizine-3-carboxylic acid

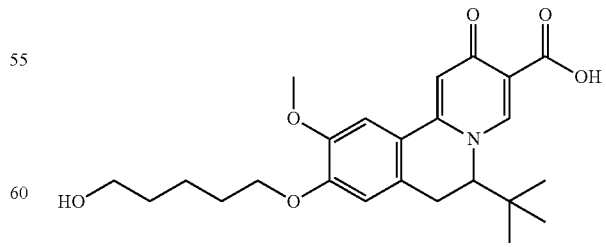

To a solution of crude ethyl 6-tert-butyl-9-(5-hydroxypentoxy)-10-methoxy-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The mixture was stirred for 2 hours at room temperature and then concentrated under reduced pressure. The residue was dissolved in water (5 mL), and then the aqueous solution was acidified with 6 M hydrochloric acid and extracted with DCM. The organic layer was dried over anhydrous $Na_2SO_4$ and concentrated. The residue was purified by preparative HPLC to give 6-tert-butyl-9-(5-hydroxypentoxy)-10-methoxy-2-oxo-6,7-dihydrobenzo[a]quinolizine-3-carboxylic acid (73.5 mg). $^1$H NMR (400 MHz, $CDCl_3$): δ 8.50 (s, 1H), 7.16 (s, 1H), 7.09 (s, 1H), 6.73 (s, 1H), 4.00-4.18 (m, 3H), 3.94 (s, 3H), 3.69-3.76 (m, 2H), 3.40-3.51 (m, 1H), 3.15-3.23 (m, 1H), 1.92-2.00 (m, 2H), 1.58-1.73 (m, 4H), 0.84 (s, 9H). MS obsd. $(ESI^+)$ $[(M+H)^+]$: 430.

Example 153 and 154

(+)-6-tert-butyl-9-(5-hydroxypentoxy)-10-methoxy-2-oxo-6,7-dihydrobenzo[a]quinolizine-3-carboxylic acid and (−)-6-tert-butyl-9-(5-hydroxypentoxy)-10-methoxy-2-oxo-6,7-dihydrobenzo[a]quinolizine-3-carboxylic acid

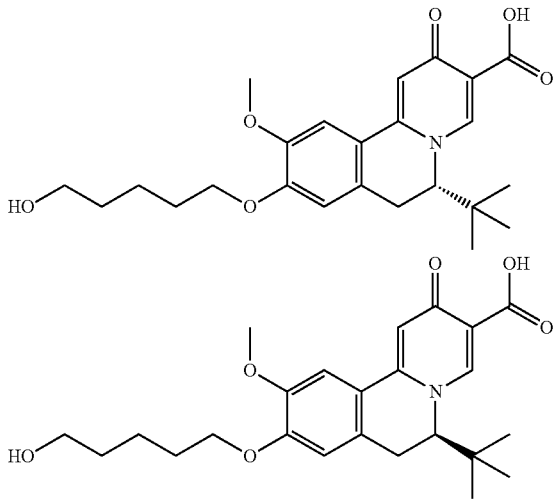

Separation of 6-tert-butyl-9-(5-hydroxypentoxy)-10-methoxy-2-oxo-6,7-dihydrobenzo[a]quinolizine-3-carboxylic acid by chiral HPLC provided (+)-6-tert-butyl-9-(5-hydroxypentoxy)-10-methoxy-2-oxo-6,7-dihydrobenzo[a]quinolizine-3-carboxylic acid (26 mg) and (−)-6-tert-butyl-9-(5-hydroxypentoxy)-10-methoxy-2-oxo-6,7-dihydrobenzo[a]quinolizine-3-carboxylic acid (26 mg).

Example 153

$^1$H NMR (400 MHz, $CDCl_3$) δ 8.50 (s, 1H), 7.16 (s, 1H), 7.09 (s, 1H), 6.73 (s, 1H), 4.00-4.18 (m, 3H), 3.94 (s, 3H), 3.69-3.76 (m, 2H), 3.40-3.51 (m, 1H), 3.15-3.23 (m, 1H), 1.92-2.00 (m, 2H), 1.58-1.73 (m, 4H), 0.84 (s, 9H). MS obsd. $(ESI^+)$ $[(M+H)^+]$: 430.

Example 154

$^1$H NMR (400 MHz, $CDCl_3$) δ 8.50 (s, 1H), 7.16 (s, 1H), 7.09 (s, 1H), 6.73 (s, 1H), 4.00-4.18 (m, 3H), 3.94 (s, 3H), 3.69-3.76 (m, 2H), 3.40-3.51 (m, 1H), 3.15-3.23 (m, 1H), 1.92-2.00 (m, 2H), 1.58-1.73 (m, 4H), 0.84 (s, 9H). MS obsd. $(ESI^{30})$ $[(M+H)^+]$: 430. $[α]_D^2=−80.000°$ (0.070%, $CH_3CN$).

Example 155: 6-tert-butyl-9-(6-hydroxyhexoxy)-10-methoxy-2-oxo-6,7-dihydrobenzo[a]quinolizine-3-carboxylic acid

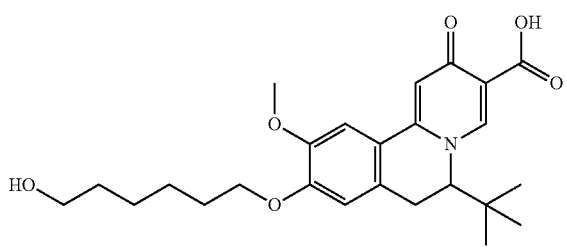 [SMILES: COc1cc2c(cc1OCCCCCCO)CC(C(C)(C)C)n1cc(C(=O)O)c(=O)cc1-2]

Step 1: Preparation of ethyl 6-tert-butyl-9-(6-hydroxyhexoxy)-10-methoxy-2-oxo-6,7-dihydrobenzo[a]quinolizine-3-carboxylate

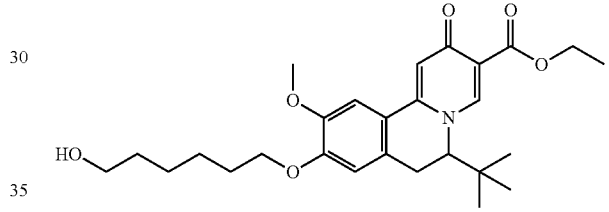

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 5-bromopentan-1-ol (146.7 mg, 0.81 mmol) and $K_2CO_3$ (74.5 mg, 0.54 mmol). The mixture was heated at 120° C. for 3 hours. After being cooled to rt, the mixture was filtered and the filtrate was concentrated to give crude ethyl 6-tert-butyl-9-(6-hydroxyhexoxy)-10-methoxy-2-oxo-6,7-dihydrobenzo[a]quinolizine-3-carboxylate which was used in the next step without further purification.

Step 2: Preparation of 6-tert-butyl-9-(6-hydroxyhexoxy)-10-methoxy-2-oxo-6,7-dihydrobenzo[a]quinolizine-3-carboxylic acid

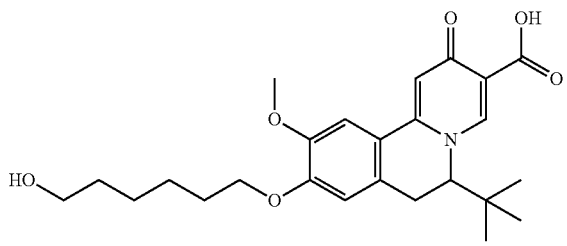 [SMILES: COc1cc2c(cc1OCCCCCCO)CC(C(C)(C)C)n1cc(C(=O)O)c(=O)cc1-2]

To a solution of crude ethyl 6-tert-butyl-9-(6-hydroxyhexoxy)-10-methoxy-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The reaction was stirred at room temperature for 2 hours, and then concentrated under reduced pressure. The residue was dissolved in water (5 mL) and the aqueous mixture was acidified by 6 M hydrochloric acid, and extracted with DCM. The organic layer was dried over anhydrous Na$_2$SO$_4$, and concentrated in vacuo. The residue was purified by prep-HPLC to give 6-tert-butyl-9-(6-hydroxyhexoxy)-10-methoxy-2-oxo-6,7-dihydrobenzo[a]quinolizine-3-carboxylic acid (73 mg). $^1$H NMR (400 MHz, CDCl$_3$) δ 8.51 (s, 1H), 7.16 (s, 1H), 7.10 (s, 1H), 6.73 (s, 1H), 4.02-4.18 (m, 3H), 3.94 (s, 3H), 3.66-3.73 (m, 2H), 3.38-3.53 (m, 1H), 3.12-3.27 (m, 1H), 1.90-1.98 (m, 2H), 1.61-1.69 (m, 2H), 1.46-1.59 (m, 4H), 0.84 (s, 9H). MS obsd. (ESI$^+$) [(M+H)$^+$]: 444.

Example 156 and 157

(+)-6-tert-butyl-9-(6-hydroxyhexoxy)-10-methoxy-2-oxo-6,7-dihydrobenzo[a]quinolizine-3-carboxylic acid and (−)-6-tert-butyl-9-(6-hydroxyhexoxy)-10-methoxy-2-oxo-6,7-dihydrobenzo[a]quinolizine-3-carboxylic acid

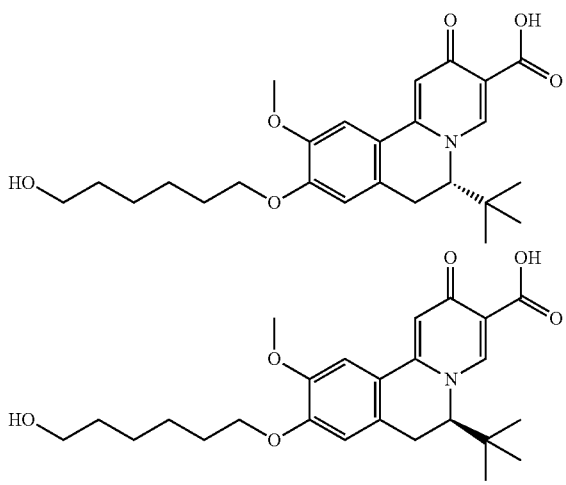

Separation of 6-tert-butyl-9-(6-hydroxyhexoxy)-10-methoxy-2-oxo-6,7-dihydrobenzo[a]quinolizine-3-carboxylic acid by chiral HPLC provided (+)-6-tert-butyl-9-(6-hydroxyhexoxy)-10-methoxy-2-oxo-6,7-dihydrobenzo[a]quinolizine-3-carboxylic acid (29 mg) and (−)-6-tert-butyl-9-(6-hydroxyhexoxy)-10-methoxy-2-oxo-6,7-dihydrobenzo[a]quinolizine-3-carboxylic acid (26 mg).

Example 156

$^1$H NMR (400 MHz, CDCl$_3$) δ 8.51 (s, 1H), 7.16 (s, 1H), 7.10 (s, 1H), 6.73 (s, 1H), 4.02-4.18 (m, 3H), 3.94 (s, 3H), 3.66-3.73 (m, 2H), 3.38-3.53 (m, 1H), 3.12-3.27 (m, 1H), 1.90-1.98 (m, 2H), 1.61-1.69 (m, 2H), 1.46-1.59 (m, 4H), 0.84 (s, 9H). MS obsd. (ESI$^+$) [(M+H)$^+$]: 444. [α]$_D^{20}$=+52.381° (0.084%, CH$_3$CN).

Example 157

$^1$H NMR (400 MHz, CDCl$_3$) δ 8.51 (s, 1H), 7.16 (s, 1H), 7.10 (s, 1H), 6.73 (s, 1H), 4.02-4.18 (m, 3H), 3.94 (s, 3H), 3.66-3.73 (m, 2H), 3.38-3.53 (m, 1H), 3.12-3.27 (m, 1H), 1.90-1.98 (m, 2H), 1.61-1.69 (m, 2H), 1.46-1.59 (m, 4H), 0.84 (s, 9H). MS obsd. (ESI$^+$) [(M+H)$^+$]: 444.

Example 158: 6-tert-butyl-9-(4-hydroxybutoxy)-10-methoxy-2-oxo-6,7-dihydrobenzo[a]quinolizine-3-carboxylic acid

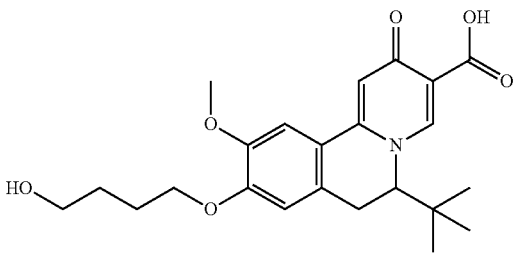 [SMILES: COc1cc2c(cc1OCCCCO)CC(C(C)(C)C)n1cc(C(=O)O)c(=O)cc1-2]

Step 1: Preparation of ethyl 9-(4-benzoyloxybutoxy)-6-tert-butyl-10-methoxy-2-oxo-6,7-dihydrobenzo[a]quinolizine-3-carboxylate

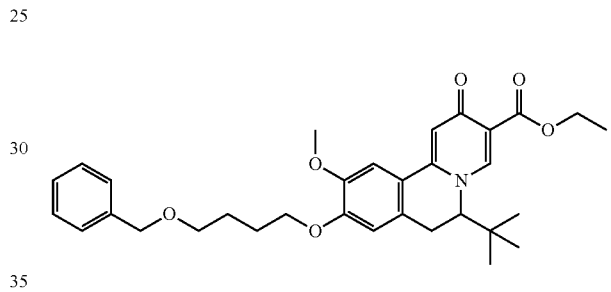

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 4-bromobutoxymethylbenzene (92.8 mg, 0.41 mmol) and K$_2$CO$_3$ (74.5 mg, 0.54 mmol). The mixture was heated at 120° C. for 4 hours. After being cooled to rt, the mixture was filtered and the filtrate was concentrated to give crude ethyl 9-(4-benzoyloxybutoxy)-6-tert-butyl-10-methoxy-2-oxo-6,7-dihydrobenzo[a]quinolizine-3-carboxylate which was directly used for the next step without further purification.

Step 2: Preparation of 9-(4-benzyloxybutoxy)-6-tert-butyl-10-methoxy-2-oxo-6,7-dihydrobenzo[a]quinolizine-3-carboxylic acid

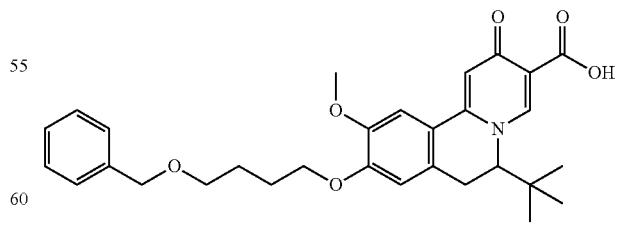

To a solution of crude ethyl 9-(4-benzyloxybutoxy)-6-tert-butyl-10-methoxy-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The mixture was stirred at rt for 2 hours and then acidified by 6 M hydrochloric acid, and extracted with DCM. The organic layer was dried over anhydrous Na₂SO₄ and concentrated under reduced pressure to give crude 9-(4-benzyloxybutoxy)-6-tert-butyl-10-methoxy-2-oxo-6,7-dihydrobenzo[a]quinolizine-3-carboxylic acid.

Step 3: Preparation of 6-tert-butyl-9-(4-hydroxybutoxy)-10-methoxy-2-oxo-6,7-dihydrobenzo[a]quinolizine-3-carboxylic acid

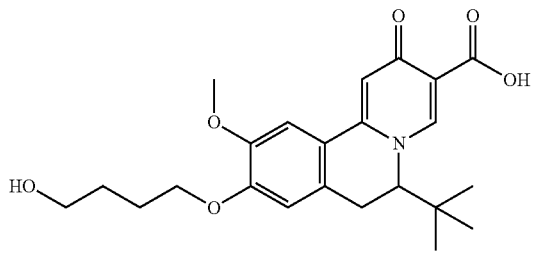 [SMILES: COc1cc2c(cc1OCCCCO)CC(C(C)(C)C)n1cc(C(=O)O)c(=O)cc1-2]

To a solution of crude 9-(4-benzyloxybutoxy)-6-tert-butyl-10-methoxy-2-oxo-6,7-dihydrobenzo[a]quinolizine-3-carboxylic acid (Step 2) in methanol was added Pd/C (20 mg). The mixture was stirred at rt for 48 hours under atmosphere of hydrogen. Then the mixture was filtered and the filtrate was concentrated under reduced pressure. The residue was purified by prep-HPLC to give 6-tert-butyl-9-(4-hydroxybutoxy)-10-methoxy-2-oxo-6,7-dihydrobenzo[a]quinolizine-3-carboxylic acid (7 mg). ¹H NMR (400 MHz, CDCl₃) δ 8.48 (s, 1H), 7.15 (s, 1H), 7.08 (s, 1H), 6.74 (s, 1H), 4.11-4.20 (m, 2H), 4.01-4.06 (m, 1H), 3.94 (s, 3H), 3.73-3.83 (m, 2H), 3.39-3.51 (m, 1H), 3.15-3.25 (m, 1H), 1.93-2.14 (m, 2H), 1.77-1.87 (m, 2H), 0.84 (s, 9H). MS obsd. (ESI⁺) [(M+H)⁺]: 416.

Example 159: 6-tert-butyl-9-(4-hydroxybut-2-ynoxy)-10-methoxy-2-oxo-6,7-dihydrobenzo[a]quinolizine-3-carboxylic acid

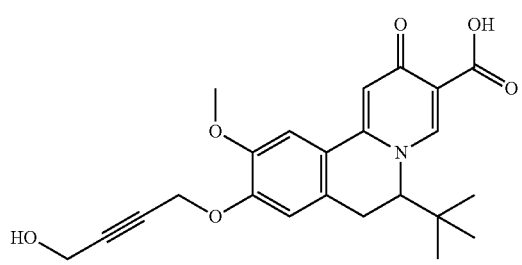 [SMILES: COc1cc2c(cc1OCC#CCO)CC(C(C)(C)C)n1cc(C(=O)O)c(=O)cc1-2]

Step 1: Preparation of ethyl 6-tert-butyl-9-(4-hydroxybut-2-ynoxy)-10-methoxy-2-oxo-6,7-dihydrobenzo[a]quinolizine-3-carboxylate

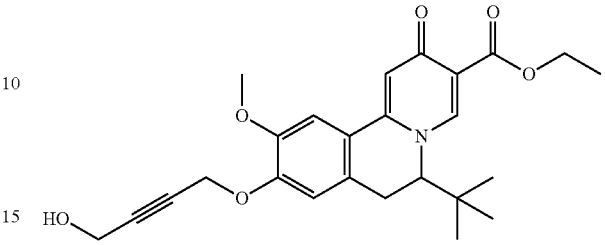

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 4-chlorobut-2-yn-1-ol (56.4 mg, 0.54 mmol) and K₂CO₃ (74.5 mg, 0.54 mmol). The mixture was stirred at 120° C. for 16 hours. After being cooled to rt, the mixture was filtered and the filtrate was concentrated to give crude ethyl 6-tert-butyl-9-(4-hydroxybut-2-ynoxy)-10-methoxy-2-oxo-6,7-dihydrobenzo[a]quinolizine-3-carboxylate which was used in next step without purification.

Step 2: Preparation of 6-tert-butyl-9-(4-hydroxybut-2-ynoxy)-10-methoxy-2-oxo-6,7-dihydrobenzo[a]quinolizine-3-carboxylic acid

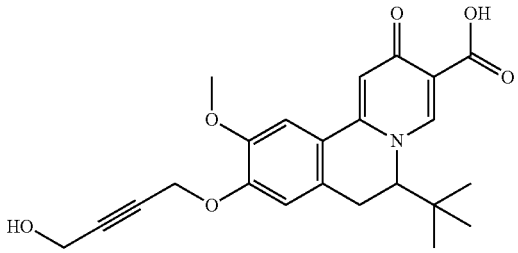 [SMILES: COc1cc2c(cc1OCC#CCO)CC(C(C)(C)C)n1cc(C(=O)O)c(=O)cc1-2]

To a solution of crude ethyl 6-tert-butyl-9-(4-hydroxybut-2-ynoxy)-10-methoxy-2-oxo-6, 7-dihydrobenzo[a]quinolizine-3-carboxylate in the mixture solvent of methanol and water (3:1, 4 mL) was added LiOH.H₂O (34.0 mg, 0.81 mmol). The mixture was stirred at rt for 2 hours, and then acidified by 6 M hydrochloric acid, and extracted with DCM. The organic layer was dried over anhydrous Na₂SO₄ and concentrated under reduced pressure. The residue was purified by preparative HPLC to give 6-tert-butyl-9-(4-hydroxybut-2-ynoxy)-10-methoxy-2-oxo-6,7-dihydrobenzo[a]quinolizine-3-carboxylic acid (9 mg). ¹H NMR (400 MHz, CDCl₃) δ 8.49 (s, 1H), 7.19 (s, 1H), 7.10 (s, 1H), 6.88 (s, 1H), 4.87-4.96 (m, 2H), 4.22-4.39 (m, 2H), 4.05 (d, 1H), 3.96 (s, 3H), 3.46 (dd, 1H), 3.23 (d, 1H), 0.85 (s, 9H). MS obsd. (ESI⁺) [(M+H)⁺]: 412.

Example 160: 9-(6-aminohexoxy)-6-tert-butyl-10-methoxy-2-oxo-6,7-dihydrobenzo[a]quinolizine-3-carboxylic acid

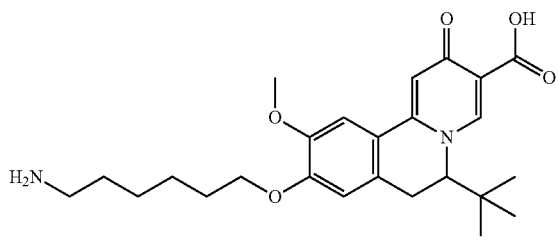 [SMILES: COc1cc2c(cc1OCCCCCCN)CC(C(C)(C)C)n1cc(C(=O)O)c(=O)cc1-2]

Step 1: Preparation of 6-(tert-butoxycarbonylamino) hexyl 4-methylbenzenesulfonate

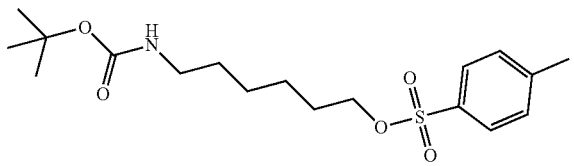 [SMILES: Cc1ccc(S(=O)(=O)OCCCCCCNC(=O)OC(C)(C)C)cc1]

To a solution of tert-butyl N-(6-hydroxyhexyl)carbamate (2.0 g, 9.2 mmol) in DCM (30 mL) was added Et$_3$N (2.6 mL, 18.4 mmol) and catalytic amount of DMAP. The mixture was stirred for 20 minutes, then to the mixture 4-methylbenzenesulfonyl chloride (1.75 g, 9.2 mmol) was added portionwise at 0° C. The resulting mixture was allowed to warm to room temperature and stirred for 16 hours. The mixture was washed with 1 M hydrochloric acid, followed by saturated aqueous NaHCO$_3$ solution. The organic layer was dried over anhydrous Na$_2$SO$_4$ and concentrated to give 6-(tert-butoxycarbonylamino) hexyl 4-methylbenzenesulfonate.

Step 2: Preparation of ethyl 9-[6-(tert-butoxycarbonylamino)hexoxy]-6-tert-butyl-10-methoxy-2-oxo-6,7-dihydrobenzo[a]quinolizine-3-carboxylate To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 6-(tert-butoxycarbonylamino) hexyl 4-methylbenzenesulfonate (130.4 mg, 0.35 mmol) and K$_2$CO$_3$ (74.5 mg, 0.54 mmol). The mixture was stirred at 120° C. for 5 hours. After being cooled to rt, the mixture was filtered and the filtrate was concentrated in vacuo to give crude ethyl 9-[6-(tert-butoxycarbonylamino)hexoxy]-6-tert-butyl-10-methoxy-2-oxo-6,7-dihydrobenzo[a]quinolizine-3-carboxylate which was directly used in the next step without purification.

Step 3: Preparation of 9-(6-aminohexoxy)-6-tert-butyl-10-methoxy-2-oxo-6,7-dihydrobenzo[a]quinolizine-3-carboxylic acid

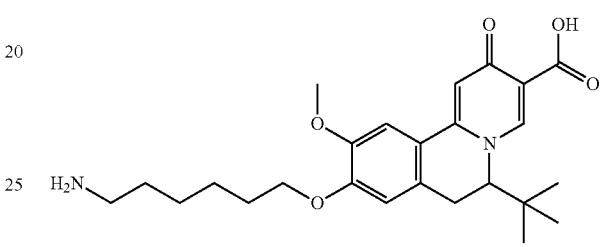

To a solution of crude ethyl 9-[6-(tert-butoxycarbonylamino) hexoxy]-6-tert-butyl-10-methoxy-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The reaction was stirred for 2 hours at room temperature, and then acidified by 6 M hydrochloric acid. Then the mixture was neutralized with aqueous NaHCO$_3$ solution to pH=7-8 and then extracted with DCM. The organic layer was dried over anhydrous Na$_2$SO$_4$ and concentrated under reduced pressure. The residue was purified by preparative HPLC to give 9-(6-aminohexoxy)-6-tert-butyl-10-methoxy-2-oxo-6,7-dihydrobenzo[a]quinolizine-3-carboxylic acid (13 mg). $^1$H NMR (400 MHz, MeOD) δ 8.37 (s, 1H), 7.31 (s, 1H), 7.02 (s, 1H), 6.89 (s, 1H), 4.22-4.29 (m, 1H), 3.99-4.14 (m, 2H), 3.90 (s, 3H), 3.20-3.29 (m, 1H), 3.06-3.17 (m, 1H), 2.82-2.93 (m, 2H), 1.79-1.88 (m, 2H), 1.61-1.71 (m, 2H), 1.42-1.60 (m, 4H), 0.82 (s, 9H). MS obsd. (ESI$^+$) [(M+H)$^+$]: 443.

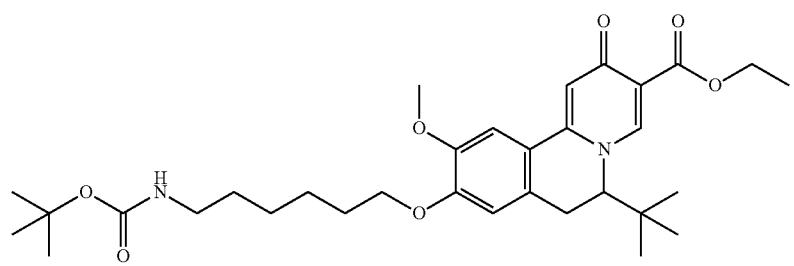 [SMILES: CCOC(=O)c1cn2c(cc1=O)-c1cc(OC)c(OCCCCCCNC(=O)OC(C)(C)C)cc1CC2C(C)(C)C]

Example 161: 9-[6-(tert-butoxycarbonylamino) hexoxy]-6-tert-butyl-10-methoxy-2-oxo-6,7-dihydrobenzo[a]quinolizine-3-carboxylic acid

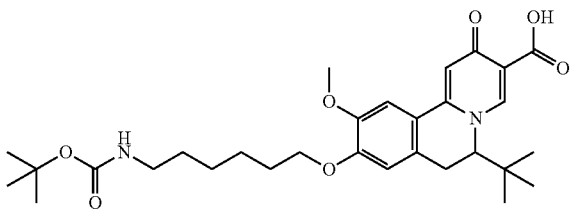 [SMILES: COc1cc2c(cc1OCCCCCCNC(=O)OC(C)(C)C)CC(C(C)(C)C)n1cc(C(=O)O)c(=O)cc1-2]

Step 1: Preparation of ethyl 9-[6-(tert-butoxycarbonylamino)hexoxy]-6-tert-butyl-10-methoxy-2-oxo-6,7-dihydrobenzo[a]quinolizine-3-carboxylate

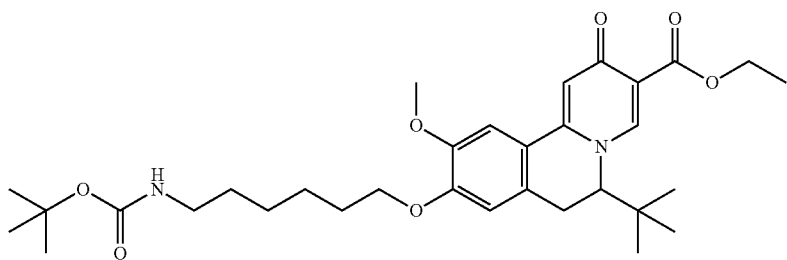 [SMILES: CCOC(=O)c1cn2c(cc1=O)-c1cc(OC)c(OCCCCCCNC(=O)OC(C)(C)C)cc1CC2C(C)(C)C]

To a solution of ethyl 6-tert-butyl-9-hydroxy-10-methoxy-2-oxo-6,7-dihydrobenzo[a]quinolizine-3-carboxylate (300 mg, 0.81 mmol) in DMF (10 mL) was added 6-(tert-butoxycarbonylamino) hexyl 4-methylbenzenesulfonate (408 mg, 1.1 mmol) and $K_2CO_3$ (223.6 mg, 1.62 mmol). The mixture was stirred at 120° C. for 5 hours. After being cooled to rt, the mixture was filtered and the filtrate was concentrated to give crude ethyl 9-[6-(tert-butoxycarbonylamino)hexoxy]-6-tert-butyl-10-methoxy-2-oxo-6,7-dihydrobenzo[a]quinolizine-3-carboxylate.

Step 2: Preparation of 9-[6-(tert-butoxycarbonylamino) hexoxy]-6-tert-butyl-10-methoxy-2-oxo-6,7-dihydrobenzo[a]quinolizine-3-carboxylic acid To a solution of crude ethyl 9-[6-(tert-butoxycarbonylamino) hexoxy]-6-tert-butyl-10-methoxy-2-oxo-6,7-dihydrobenzo[a]quinolizine-3-carboxylate from step 1 in a mixture solvent of methanol and water (3:1, 16 mL) was added $LiOH \cdot H_2O$ (102.1 mg, 2.43 mmol). The mixture was stirred for 2 hours at room temperature, and then acidified with acetic acid and extracted with DCM. The organic layer was dried over anhydrous $Na_2SO_4$ and concentrated under reduced pressure. The residue was purified by column chromatography to give 9-[6-(tert-butoxycarbonylamino) hexoxy]-6-tert-butyl-10-methoxy-2-oxo-6,7-dihydrobenzo[a]quinolizine-3-carboxylic acid (180 mg). $^1$H NMR (400 MHz, $CDCl_3$) δ 8.50 (s, 1H), 7.15 (s, 1H), 7.09 (s, 1H), 6.72 (s, 1H), 4.44-4.66 (m, 1H), 4.01-4.15 (m, 3H), 3.94 (s, 3H), 3.40-3.50 (m, 1H), 3.09-3.23 (m, 3H), 1.86-1.96 (m, 2H), 1.43-1.57 (m, 15H), 0.84 (s, 9H). MS obsd. ($ESI^{30}$) [(M+H)$^+$]: 543.

Example 162 and 163

(+)-9-[6-(tert-butoxycarbonylamino)hexoxy]-6-tert-butyl-10-methoxy-2-oxo-6,7-dihydrobenzo[a]quinolizine-3-carboxylic acid and (−)-9-[6-(tert-butoxycarbonylamino)hexoxy]-6-tert-butyl-10-methoxy-2-oxo-6,7-dihydrobenzo[a]quinolizine-3-carboxylic acid

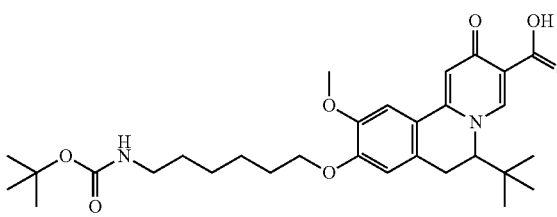

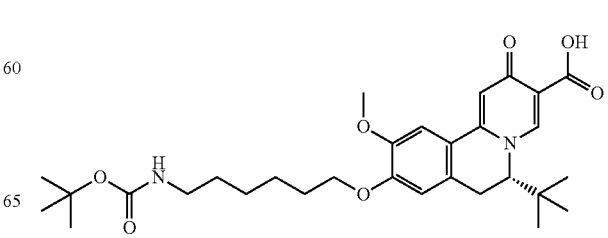

-continued

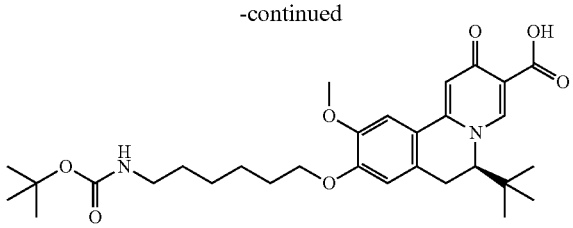

Separation of 9-[6-(tert-butoxycarbonylamino) hexoxy]-6-tert-butyl-10-methoxy-2-oxo-6,7-dihydrobenzo[a]quinolizine-3-carboxylic acid by chiral HPLC provided (+)-9-[6-(tert-butoxycarbonylamino)hexoxy]-6-tert-butyl-10-methoxy-2-oxo-6,7-dihydrobenzo[a]quinolizine-3-carboxylic acid (63 mg) and (−)-9-[6-(tert-butoxycarbonylamino)hexoxy]-6-tert-butyl-10-methoxy-2-oxo-6,7-dihydrobenzo[a]quinolizine-3-carboxylic acid (66 mg).

Example 162

$^1$H NMR (400 MHz, CDCl$_3$) δ 8.50 (s, 1H), 7.15 (s, 1H), 7.09 (s, 1H), 6.72 (s, 1H), 4.44-4.66 (m, 1H), 4.01-4.15 (m, 3H), 3.94 (s, 3H), 3.40-3.50 (m, 1H), 3.09-3.23 (m, 3H), 1.86-1.96 (m, 2H), 1.43-1.57 (m, 15H), 0.84 (s, 9H). MS obsd. (ESI$^+$) [(M+H)$^+$]: 543.

Example 163

$^1$H NMR (400 MHz, CDCl$_3$) δ 8.50 (s, 1H), 7.15 (s, 1H), 7.09 (s, 1H), 6.72 (s, 1H), 4.44-4.66 (m, 1H), 4.01-4.15 (m, 3H), 3.94 (s, 3H), 3.40-3.50 (m, 1H), 3.09-3.23 (m, 3H), 1.86-1.96 (m, 2H), 1.43-1.57 (m, 15H), 0.84 (s, 9H). MS obsd. (ESI$^+$) [(M+H)$^+$]: 543. [α]$_D^{20}$=−53.630° (0.135%, CH$_3$CN).

Example 164 and 165

(+)-9-(6-aminohexoxy)-6-tert-butyl-10-methoxy-2-oxo-6,7-dihydrobenzo[a]quinolizine-3-carboxylic acid hydrochloride and (−)-9-(6-aminohexoxy)-6-tert-butyl-10-methoxy-2-oxo-6,7-dihydrobenzo[a]quinolizine-3-carboxylic acid hydrochloride

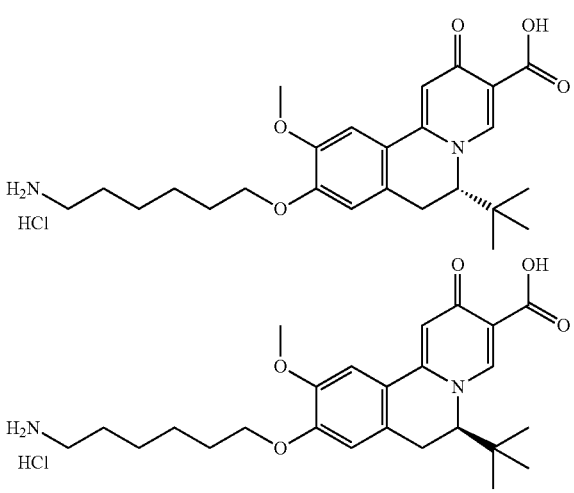

To a solution of (+)-9-[6-(tert-butoxycarbonylamino) hexoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature and then lyophilized to give (+)-9-(6-aminohexoxy)-6-tert-butyl-10-methoxy-2-oxo-6,7-dihydrobenzo[a]quinolizine-3-carboxylic acid hydrochloride (Example 164, 53 mg). $^1$H NMR (400 MHz, DMSO) δ 8.73 (s, 1H), 7.85-8.02 (m, 3H), 7.47 (s, 1H), 7.46 (s, 1H), 7.07 (s, 1H), 4.54-4.61 (m, 1H), 3.99-4.12 (m, 2H), 3.87 (s, 3H), 3.32-3.42 (m, 1H), 3.21-3.29 (m, 1H), 2.73-2.84 (m, 2H), 1.72-1.79 (m, 2H), 1.55-1.62 (m, 2H), 1.36-1.47 (m, 4H), 0.73 (s, 9H). MS obsd. (ESI$^+$) [(M+H)$^+$]: 443. [α]$_D^{20}$+56.842° (0.095%, MeOH).

To a solution of (−)-9-[6-(tert-butoxycarbonylamino) hexoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature and then lyophilized to give (−)-9-(6-aminohexoxy)-6-tert-butyl-10-methoxy-2-oxo-6,7-dihydrobenzo[a]quinolizine-3-carboxylic acid hydrochloride (Example 165, 50 mg). $^1$H NMR (400 MHz, DMSO) δ 8.73 (s, 1H), 7.85-8.02 (m, 3H), 7.47 (s, 1H), 7.46 (s, 1H), 7.07 (s, 1H), 4.54-4.61 (m, 1H), 3.99-4.12 (m, 2H), 3.87 (s, 3H), 3.32-3.42 (m, 1H), 3.21-3.29 (m, 1H), 2.73-2.84 (m, 2H), 1.72-1.79 (m, 2H), 1.55-1.62 (m, 2H), 1.36-1.47 (m, 4H), 0.73 (s, 9H). MS obsd. (ESI$^+$) [(M+H)$^+$]: 443.

Example 166: 9-(8-aminooctoxy)-6-tert-butyl-10-methoxy-2-oxo-6,7-dihydrobenzo[a]quinolizine-3-carboxylic acid

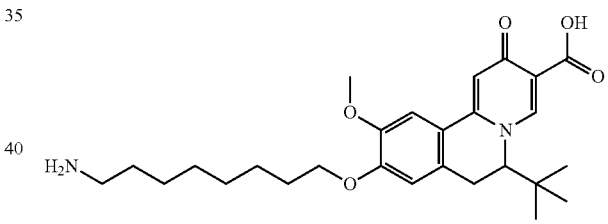

Step 1: Preparation of 8-(tert-butoxycarbonylamino)octyl 4-methylbenzenesulfonate

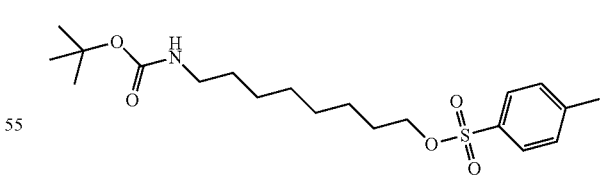

To a solution of tert-butyl N-(8-hydroxyoctyl)carbamate (3.0 g, 12.2 mmol) in DCM (50 mL) was added Et$_3$N (3.5 mL, 24.4 mmol) and catalytic amount of DMAP. The mixture was stirred for 20 minutes, and then to the mixture, 4-methylbenzenesulfonyl chloride (2.56 g, 13.4 mmol) was added at 0° C. portionwise. The mixture was allowed to warm to room temperature and stirred for 16 hours, then washed with 1 M hydrochloric acid, followed by saturated aqueous NaHCO$_3$. The organic layer was dried over anhydrous Na₂SO₄ and concentrated to give 8-(tert-butoxycarbonylamino)octyl 4-methylbenzenesulfonate which was used in the next step without further purification.

Step 2: Preparation of ethyl 9-[8-(tert-butoxycarbonylamino)octoxy]-6-tert-butyl-10-methoxy-2-oxo-6,7-dihydrobenzo[a]quinolizine-3-carboxylate

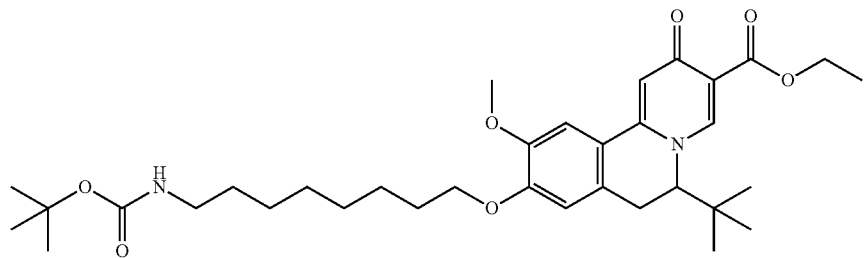 [SMILES: CCOC(=O)c1cn2c(cc1=O)-c1cc(OC)c(OCCCCCCCCNC(=O)OC(C)(C)C)cc1CC2C(C)(C)C]

To a solution of ethyl 6-tert-butyl-9-hydroxy-10-methoxy-2-oxo-6,7-dihydrobenzo[a]quinolizine-3-carboxylate (300 mg, 0.81 mmol) in DMF (10 mL) was added 8-(tert-butoxycarbonylamino)octyl 4-methylbenzenesulfonate (388.2 mg, 0.97 mmol) and K₂CO₃ (223.6 mg, 1.62 mmol). The mixture was stirred for 3 hours at 120° C. After being cooled to rt, the mixture was filtered and the filtrate was concentrated to give crude ethyl 9-[8-(tert-butoxycarbonylamino) octoxy]-6-tert-butyl-10-methoxy-2-oxo-6,7-dihydrobenzo[a]quinolizine-3-carboxylate.

Step 3: Preparation of 9-(8-aminooctoxy)-6-tert-butyl-10-methoxy-2-oxo-6,7-dihydrobenzo[a]quinolizine-3-carboxylic acid

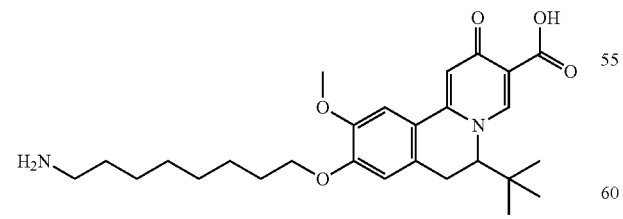

To a solution of crude ethyl 9-[8-(tert-butoxycarbonylamino)octoxy]-6-tert-butyl-10-methoxy-2-oxo-6,7-dihydrobenzo[a]quinolizine-3-carboxylate in a mixture solvent of methanol and water (3:1, 4 mL) was added LiOH.H₂O (34.0 mg, 0.81 mmol). The reaction was stirred for 2 hours at room temperature, and then acidified by 6 M hydrochloric acid. The mixture was then neutralized by NaHCO₃ to pH=7-8 and extracted with DCM. The organic layer was dried over anhydrous Na₂SO₄ and concentrated under reduced pressure. The residue was purified by preparative HPLC to give 9-(8-aminooctoxy)-6-tert-butyl-10-methoxy-2-oxo-6,7-dihydrobenzo[a]quinolizine-3-carboxylic acid (16 mg). ¹H NMR (400 MHz, CDCl₃) δ 8.49 (s, 1H), 7.17 (s, 1H), 7.10 (s, 1H), 6.73 (s, 1H), 4.04-4.12 (m, 3H), 3.94 (s, 3H), 3.41-3.50 (m, 1H), 3.15-3.23 (m, 1H), 2.84-2.97 (m, 2H), 1.84-1.93 (m, 2H), 1.65-1.74 (m, 2H), 1.47-1.53 (m, 2H), 1.33-1.39 (m, 6H), 0.84 (s, 9H). MS obsd. (ESI⁺) [(M+H)⁺]: 471.

Example 167: 9-[8-(tert-butoxycarbonylamino)octoxy]-6-tert-butyl-10-methoxy-2-oxo-6,7-dihydrobenzo[a]quinolizine-3-carboxylic acid

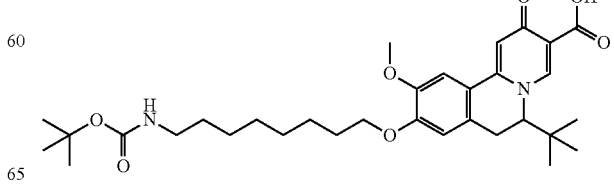

Step 1: Preparation of ethyl 9-[8-(tert-butoxycarbonylamino)octoxy]-6-tert-butyl-10-methoxy-2-oxo-6,7-dihydrobenzo[a]quinolizine-3-carboxylate

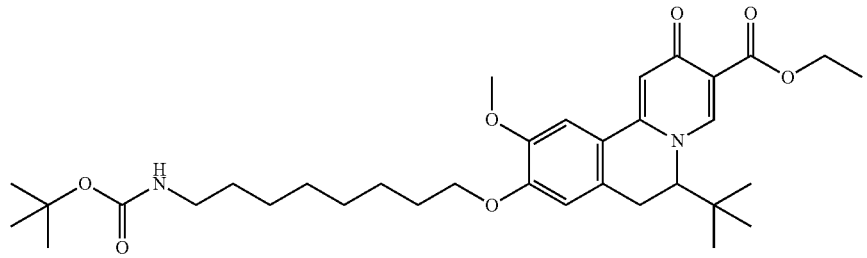 [SMILES: CCOC(=O)c1cn2c(cc1=O)-c1cc(OC)c(OCCCCCCCCNC(=O)OC(C)(C)C)cc1CC2C(C)(C)C]

To a solution of ethyl 6-tert-butyl-9-hydroxy-10-methoxy-2-oxo-6,7-dihydrobenzo[a]quinolizine-3-carboxylate (300 mg, 0.81 mmol) in DMF (10 mL) was added 8-(tert-butoxycarbonylamino)octyl 4-methylbenzenesulfonate (388.2 mg, 0.97 mmol) and $K_2CO_3$ (223.6 mg, 1.62 mmol). The mixture was stirred at 120° C. for 3 hours. After being cooled to rt, the mixture was filtered and the filtrate was concentrated to give crude ethyl 9-[8-(tert-butoxycarbonylamino) octoxy]-6-tert-butyl-10-methoxy-2-oxo-6,7-dihydrobenzo[a]quinolizine-3-carboxylate.

Step 2: Preparation of 9-[8-(tert-butoxycarbonylamino)octoxy]-6-tert-butyl-10-methoxy-2-oxo-6,7-dihydrobenzo[a]quinolizine-3-carboxylic acid

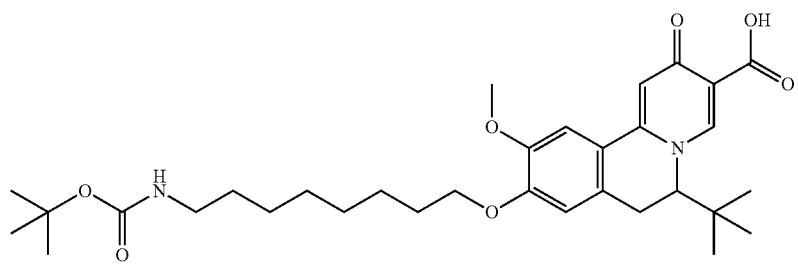 [SMILES: COc1cc2c(cc1OCCCCCCCCNC(=O)OC(C)(C)C)CC(C(C)(C)C)n1cc(C(=O)O)c(=O)cc1-2]

To a solution of crude ethyl 9-[8-(tert-butoxycarbonylamino)octoxy]-6-tert-butyl-10-methoxy-2-oxo-6,7-dihydrobenzo[a]quinolizine-3-carboxylate in a mixture solvent of methanol and water (3:1, 16 mL) was added $LiOH \cdot H_2O$ (102.1 mg, 2.43 mmol). The mixture was stirred for one hour at room temperature, and acidified with acetic acid. The resulting mixture was extracted in DCM. The organic layer was dried over anhydrous $Na_2SO_4$ and concentrated under reduced pressure. The residue was purified by column chromatography to give 9-[8-(tert-butoxycarbonylamino) octoxy]-6-tert-butyl-10-methoxy-2-oxo-6,7-dihydrobenzo[a]quinolizine-3-carboxylic acid (161.0 mg). $^1H$ NMR (400 MHz, $CDCl_3$) δ 8.48 (s, 1H), 7.15 (s, 1H), 7.08 (s, 1H), 6.72 (s, 1H), 4.44-4.59 (m, 1H), 3.99-4.18 (m, 3H), 3.91-3.95 (m, 3H), 3.40-3.48 (m, 1H), 3.08-3.22 (m, 3H), 1.86-1.95 (m, 2H), 1.28-1.56 (m, 19H), 0.84 (s, 9H). MS obsd. $(ESI^+)$ $[(M+H)^+]$: 571.

Example 168 and 169

(+)-9-[8-(tert-butoxycarbonylamino)octoxy]-6-tert-butyl-10-methoxy-2-oxo-6,7-dihydrobenzo[a]quinolizine-3-carboxylic acid and (−)-9-[8-(tert-butoxycarbonylamino)octoxy]-6-tert-butyl-10-methoxy-2-oxo-6,7-dihydrobenzo[a]quinolizine-3-carboxylic acid

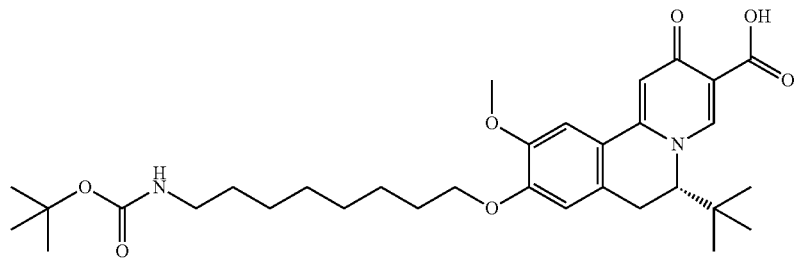

Separation of 9-[8-(tert-butoxycarbonylamino)octoxy]-6-tert-butyl-10-methoxy-2-oxo-6,7-dihydrobenzo[a]quinolizine-3-carboxylic acid by chiral HPLC provided (+)-9-[8-(tert-butoxycarbonylamino)octoxy]-6-tert-butyl-10-methoxy-2-oxo-6,7-dihydrobenzo[a]quinolizine-3-carboxylic acid (70 mg) and (−)-9-[8-(tert-butoxycarbonylamino)octoxy]-6-tert-butyl-10-methoxy-2-oxo-6,7-dihydrobenzo[a]quinolizine-3-carboxylic acid (71 mg).

Example 168

$^1$H NMR (400 MHz, CDCl$_3$) δ 8.48 (s, 1H), 7.15 (s, 1H), 7.08 (s, 1H), 6.72 (s, 1H), 4.44-4.59 (m, 1H), 3.99-4.18 (m, 3H), 3.91-3.95 (m, 3H), 3.40-3.48 (m, 1H), 3.08-3.22 (m, 3H), 1.86-1.95 (m, 2H), 1.28-1.56 (m, 19H), 0.84 (s, 9H). MS obsd. (ESI$^+$) [(M+H)$^+$]: 571. [α]$_D^{20}$=+46.667° (0.060%, CH$_3$CN).

Example 169

$^1$H NMR (400 MHz, CDCl$_3$) δ 8.48 (s, 1H), 7.15 (s, 1H), 7.08 (s, 1H), 6.72 (s, 1H), 4.44-4.59 (m, 1H), 3.99-4.18 (m, 3H), 3.91-3.95 (m, 3H), 3.40-3.48 (m, 1H), 3.08-3.22 (m, 3H), 1.86-1.95 (m, 2H), 1.28-1.56 (m, 19H), 0.84 (s, 9H). MS obsd. (ESI$^+$) [(M+H)$^+$]: 571.

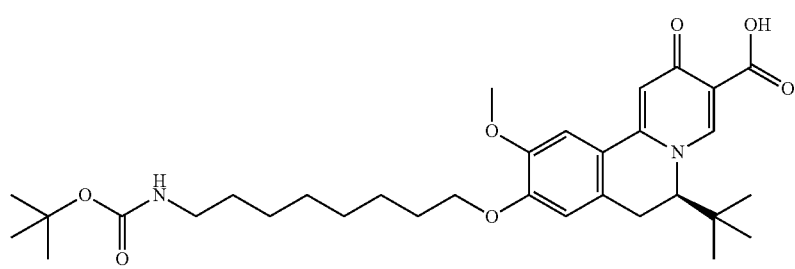

Example 170 and 171

(+)-9-(8-aminooctoxy)-6-tert-butyl-10-methoxy-2-oxo-6,7-dihydrobenzo[a]quinolizine-3-carboxylic acid hydrochloride and (−)-9-(8-aminooctoxy)-6-tert-butyl-10-methoxy-2-oxo-6,7-dihydrobenzo[a]quinolizine-3-carboxylic acid hydrochloride

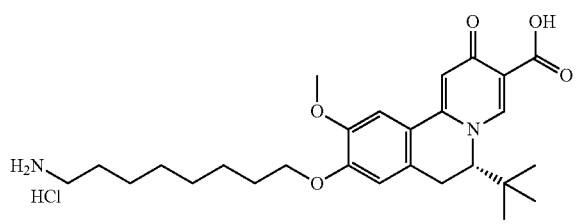

-continued

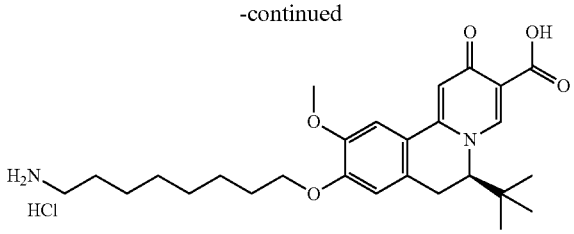

To a solution of (+)-9-[8-(tert-butoxycarbonylamino)octoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature, and then lyophilized to give (+)-9-(8-aminooctoxy)-6-tert-butyl-10-methoxy-2-oxo-6,7-dihydrobenzo[a]quinolizine-3-carboxylic acid hydrochloride (Example 170, 61 mg). $^1$H NMR (400 MHz, DMSO) δ 8.72 (s, 1H), 7.75-7.95 (m, 3H), 7.47 (s, 1H), 7.45 (s, 1H), 7.06 (s, 1H), 4.57-4.56 (m, 1H), 4.05-4.03 (m, 2H), 3.86 (s, 3H), 3.31-3.38 (m, 1H), 3.20-3.30 (m, 1H), 2.75-2.77 (m, 2H), 1.73-1.77 (m, 2H), 1.53-1.55 (m, 2H), 1.31-1.42 (m, 2H), 1.23-1.30 (m, 6H), 0.73 (s, 9H). MS obsd. (ESI$^+$) [(M+H)$^+$]: 471. $[\alpha]_D^{20}$=+38.000° (0.1000%, MeOH).

To a solution of (−)-9-[8-(tert-butoxycarbonylamino)octoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature, and then lyophilized to give (−)-9-(8-aminooctoxy)-6-tert-butyl-10-methoxy-2-oxo-6,7-dihydrobenzo[a]quinolizine-3-carboxylic acid hydrochloride (Example 171, 38 mg). $^1$H NMR (400 MHz, DMSO) δ 8.72 (s, 1H), 7.75-7.95 (m, 3H), 7.47 (s, 1H), 7.45 (s, 1H), 7.06 (s, 1H), 4.57-4.56 (m, 1H), 4.05-4.03 (m, 2H), 3.86 (s, 3H), 3.31-3.38 (m, 1H), 3.20-3.30 (m, 1H), 2.75-2.77 (m, 2H), 1.73-1.77 (m, 2H), 1.53-1.55 (m, 2H), 1.31-1.42 (m, 2H), 1.23-1.30 (m, 6H), 0.73 (s, 9H). MS obsd. (ESI$^+$) [(M+H)$^+$]: 471.

Example 172: 9-[5-(tert-butoxycarbonylamino)pentoxy]-6-tert-butyl-10-methoxy-2-oxo-6,7-dihydrobenzo[a]quinolizine-3-carboxylic acid

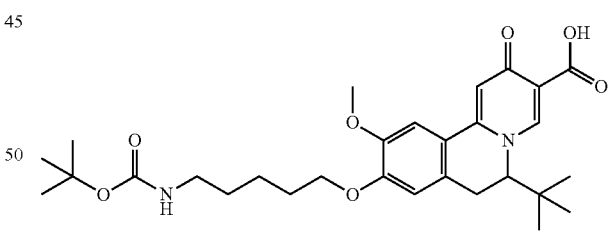

Step 1: Preparation of 5-(tert-butoxycarbonylamino)pentyl 4-methylbenzenesulfonate

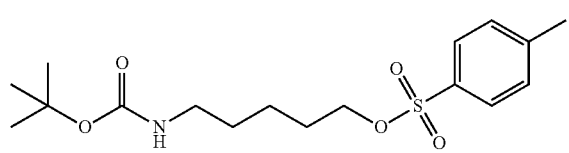 [SMILES: Cc1ccc(S(=O)(=O)OCCCCCNC(=O)OC(C)(C)C)cc1]

To a solution of tert-butyl N-(5-hydroxypentyl)carbamate (2.0 g, 9.84 mmol) in DCM (50 mL) was added Et$_3$N (2.76 mL, 19.68 mmol) and catalytic amount of DMAP. The mixture was stirred for 20 minutes, and then to the mixture 4-methylbenzenesulfonyl chloride (1.88 g, 9.84 mmol) was added portionwise at 0° C. The mixture was warmed to room temperature and stirred for 16 hours. The mixture was washed with 1 M hydrochloric acid, followed by saturated aqueous NaHCO$_3$ solution. The organic layer was dried over anhydrous Na$_2$SO$_4$ and concentrated to give 5-(tert-butoxycarbonylamino)pentyl 4-methylbenzenesulfonate which was directly used for the next step without further purification.

Step 2: Preparation of ethyl 9-[5-(tert-butoxycarbonylamino) pentoxy]-6-tert-butyl-10-methoxy-2-oxo-6,7-dihydrobenzo[a]quinolizine-3-carboxylate

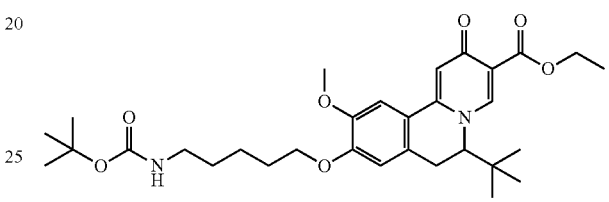

To a solution of ethyl 6-tert-butyl-9-hydroxy-10-methoxy-2-oxo-6,7-dihydrobenzo[a]quinolizine-3-carboxylate (200 mg, 0.54 mmol) in DMF (10 mL) was added 5-(tert-butoxycarbonylamino)pentyl 4-methylbenzenesulfonate (250 mg, 0.70 mmol) and K$_2$CO$_3$ (149 mg, 1.08 mmol). The mixture was stirred at 120° C. for 3 hours. After being cooled to rt, the mixture was filtered and the filtrate was concentrated to give crude ethyl 9-[5-(tert-butoxycarbonylamino)pentoxy]-6-tert-butyl-10-methoxy-2-oxo-6,7-dihydrobenzo[a]quinolizine-3-carboxylate.

Step 3: Preparation of 9-[5-(tert-butoxycarbonylamino)pentoxy]-6-tert-butyl-10-methoxy-2-oxo-6,7-dihydrobenzo[a]quinolizine-3-carboxylic acid To a solution of crude ethyl 9-[5-(tert-butoxycarbonylamino)pentoxy]-6-tert-butyl-10-methoxy-2-oxo-6,7-dihydrobenzo[a]quinolizine-3-carboxylate in a mixture solvent of methanol and water (3:1, 16 mL) was added LiOH.H$_2$O (68 mg, 1.62 mmol). The mixture was stirred for 2 hours at room temperature, and then acidified with acetic acid. The resulting mixture was extracted with DCM. The organic layer was dried over anhydrous Na$_2$SO$_4$ and concentrated under reduced pressure. The residue was purified by column chromatography to give 9-[5-(tert-butoxycarbonylamino)pentoxy]-6-tert-butyl-10-methoxy-2-oxo-6,7-dihydrobenzo[a]quinolizine-3-carboxylic acid (72 mg). $^1$H NMR (400 MHz, CDCl$_3$) δ 8.50 (s, 1H), 7.15 (s, 1H), 7.09

(s, 1H), 6.73 (s, 1H), 4.46-4.70 (m, 1H), 4.02-4.15 (m, 3H), 3.94 (s, 3H), 3.40-3.49 (m, 1H), 3.13-3.24 (m, 3H), 1.88-1.98 (m, 2H), 1.53-1.64 (m, 4H), 1.47 (s, 9H), 0.85 (s, 9H). MS obsd. (ESI$^{+}$) [(M+H)$^+$]: 529.

Example 173 and 174

(+)-9-(5-aminopentoxy)-6-tert-butyl-10-methoxy-2-oxo-6,7-dihydrobenzo[a]quinolizine-3-carboxylic acid hydrochloride and (−)-9-(5-aminopentoxy)-6-tert-butyl-10-methoxy-2-oxo-6,7-dihydrobenzo[a]quinolizine-3-carboxylic acid hydrochloride

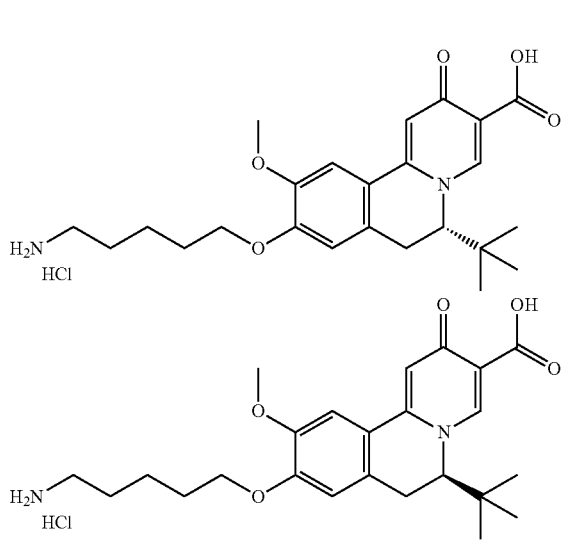

Step 1: Preparation of (+)-9-[5-(tert-butoxycarbonylamino)pentoxy]-6-tert-butyl-10-methoxy-2-oxo-6,7-dihydrobenzo[a]quinolizine-3-carboxylic acid and (−)-9-[5-(tert-butoxycarbonylamino)pentoxy]-6-tert-butyl-10-methoxy-2-oxo-6,7-dihydrobenzo[a]quinolizine-3-carboxylic acid

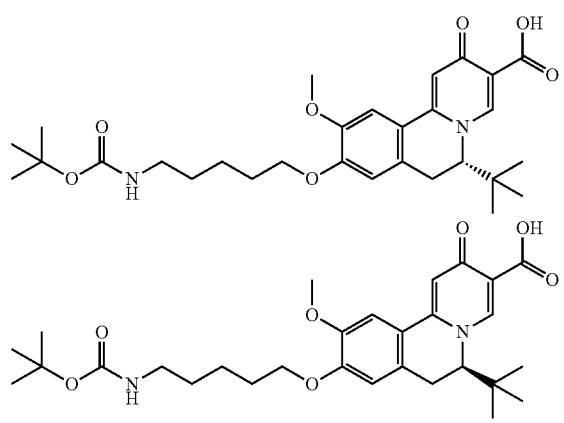

Separation of 9-[5-(tert-butoxycarbonylamino)pentoxy]-6-tert-butyl-10-methoxy-2-oxo-6,7-dihydrobenzo[a]quinolizine-3-carboxylic acid by chiral HPLC provided (+)-9-[5-(tert-butoxycarbonylamino)pentoxy]-6-tert-butyl-10-methoxy-2-oxo-6,7-dihydrobenzo[a]quinolizine-3-carboxylic acid and (−)-9-[5-(tert-butoxycarbonylamino)pentoxy]-6-tert-butyl-10-methoxy-2-oxo-6,7-dihydrobenzo[a]quinolizine-3-carboxylic acid.

Step 2: Preparation of (+)-9-(5-aminopentoxy)-6-tert-butyl-10-methoxy-2-oxo-6,7-dihydrobenzo[a]quinolizine-3-carboxylic acid hydrochloride and (−)-9-(5-aminopentoxy)-6-tert-butyl-10-methoxy-2-oxo-6,7-dihydrobenzo[a]quinolizine-3-carboxylic acid hydrochloride

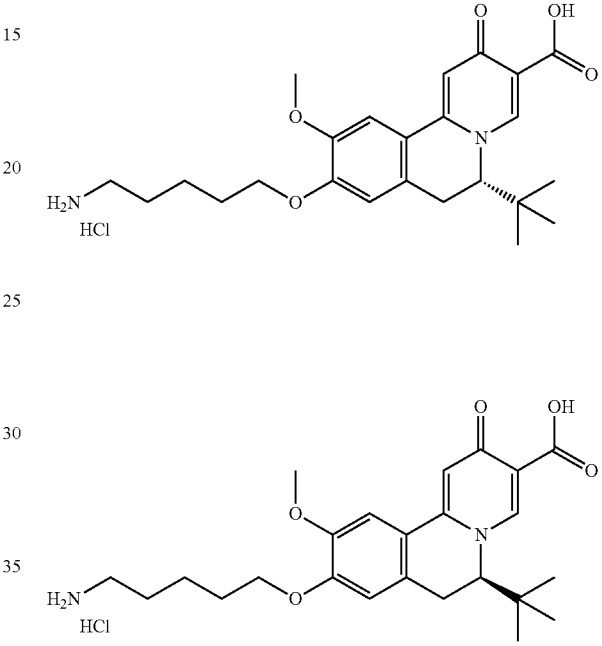

To a solution of (+)-9-[5-(tert-butoxycarbonylamino)pentoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature, and then lyophilized to give (+)-9-(5-aminopentoxy)-6-tert-butyl-10-methoxy-2-oxo-6,7-dihydrobenzo[a]quinolizine-3-carboxylic acid hydrochloride (18 mg). $^1$H NMR (400 MHz, DMSO) δ 8.73 (s, 1H), 7.89-8.08 (m, 3H), 7.47 (s, 1H), 7.46 (s, 1H), 7.07 (s, 1H), 4.54-4.61 (m, 1H), 4.00-4.12 (m, 2H), 3.87 (s, 3H), 3.33-3.43 (m, 1H), 3.22-3.31 (m, 1H), 2.74-2.86 (m, 2H), 1.71-1.81 (m, 2H), 1.58-1.70 (m, 2H), 1.41-1.53 (m, 2H), 0.73 (s, 9H). MS obsd. (ESI$^{30}$) [(M+H)$^+$]: 429. [α]$_D^{20}$=+38.333° (0.120%, MeOH).

To a solution of (−)-9-[5-(tert-butoxycarbonylamino)pentoxy]-6-tert-butyl-10-methoxy-2-oxo-6,7-dihydrobenzo[a]quinolizine-3-carboxylic acid in MeCN was added 6 M hydrochloric acid. The mixture was stirred for 20 minutes at room temperature, and then lyophilized to give (−)-9-(5-aminopentoxy)-6-tert-butyl-10-methoxy-2-oxo-6,7-dihydrobenzo[a]quinolizine-3-carboxylic acid hydrochloride (11 mg). $^1$H NMR (400 MHz, DMSO) δ 8.73 (s, 1H), 7.89-8.08 (m, 3H), 7.47 (s, 1H), 7.46 (s, 1H), 7.07 (s, 1H), 4.54-4.61 (m, 1H), 4.00-4.12 (m, 2H), 3.87 (s, 3H), 3.33-3.43 (m, 1H), 3.22-3.31 (m, 1H), 2.74-2.86 (m, 2H), 1.71-1.81 (m, 2H), 1.58-1.70 (m, 2H), 1.41-1.53 (m, 2H), 0.73 (s, 9H). MS obsd. (ESI$^+$) [(M+H)$^+$]: 429.

Example 175: 9-(5-acetamidopentoxy)-6-tert-butyl-10-methoxy-2-oxo-6,7-dihydrobenzo[a]quinolizine-3-carboxylic acid

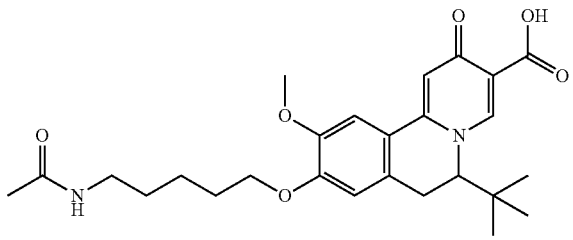 [SMILES: COc1cc2c(cc1OCCCCCNC(C)=O)CC(C(C)(C)C)n1cc(C(=O)O)c(=O)cc1-2]

Step 1: Preparation of ethyl 9-(5-aminopentoxy)-6-tert-butyl-10-methoxy-2-oxo-6,7-dihydrobenzo[a]quinolizine-3-carboxylate

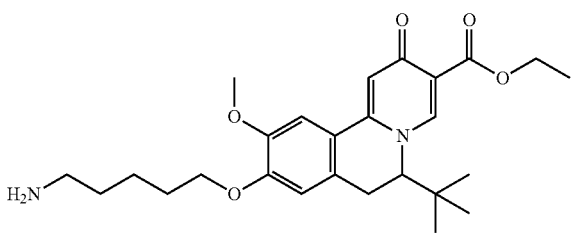 [SMILES: CCOC(=O)c1cn2c(cc1=O)-c1cc(OC)c(OCCCCCN)cc1CC2C(C)(C)C]

To a solution of crude ethyl 9-[5-(tert-butoxycarbonylamino) pentoxy]-6-tert-butyl-10-methoxy-2-oxo-6,7-dihydrobenzo[a]quinolizine-3-carboxylate (0.5 g) in EtOH (20 mL) was added 6 M hydrochloric acid. The mixture was stirred for one hour at room temperature, then neutralized by with aqueous NaHCO₃ to pH=7-8 and extracted with DCM. The organic layer was dried over anhydrous Na₂SO₄ and concentrated under reduced pressure. The residue was purified by column chromatography to give ethyl 9-(5-aminopentoxy)-6-tert-butyl-10-methoxy-2-oxo-6,7-dihydrobenzo[a]quinolizine-3-carboxylate (0.2 g).

Step 2: Preparation of ethyl 9-(5-acetamidopentoxy)-6-tert-butyl-10-methoxy-2-oxo-6,7-dihydrobenzo[a]quinolizine-3-carboxylate

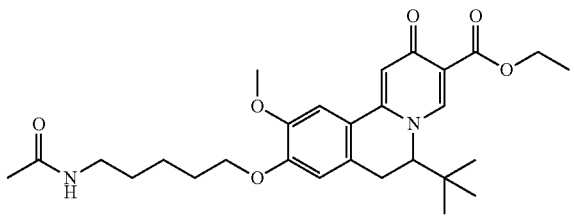 [SMILES: CCOC(=O)c1cn2c(cc1=O)-c1cc(OC)c(OCCCCCNC(C)=O)cc1CC2C(C)(C)C]

To a solution of ethyl 9-(5-aminopentoxy)-6-tert-butyl-10-methoxy-2-oxo-6,7-dihydrobenzo[a]quinolizine-3-carboxylate (60 mg, 0.13 mmol) in DCM (2 mL) was added acetic anhydride (15 μL, 0.16 mmol) and Et₃N (36.5 μL, 0.26 mmol). The mixture was stirred for 2 hours at room temperature and then concentrated under reduced pressure to give crude ethyl 9-(5-acetamidopentoxy)-6-tert-butyl-10-methoxy-2-oxo-6,7-dihydrobenzo[a]quinolizine-3-carboxylate.

Step 3: Preparation of 9-(5-acetamidopentoxy)-6-tert-butyl-10-methoxy-2-oxo-6,7-dihydrobenzo[a]quinolizine-3-carboxylic acid

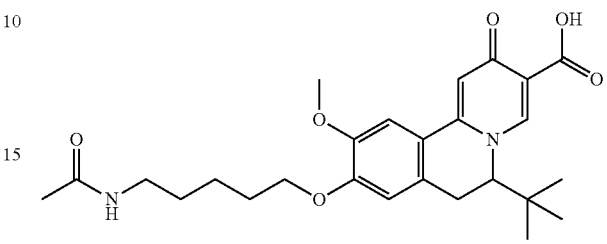

To a solution of crude ethyl 9-(5-acetamidopentoxy)-6-tert-butyl-10-methoxy-2-oxo-6,7-dihydrobenzo[a]quinolizine-3-carboxylate in a mixture solvent of methanol and water (3:1, 4 mL) was added LiOH.H₂O (16.4 mg, 0.39 mmol). The mixture was stirred for 2 hours at room temperature, then acidified with 6 M hydrochloric acid and extracted with DCM. The organic layer was dried over anhydrous Na₂SO₄ and concentrated under reduced pressure. The residue was purified by preparative HPLC to give 9-(5-acetamidopentoxy)-6-tert-butyl-10-methoxy-2-oxo-6,7-dihydrobenzo[a]quinolizine-3-carboxylic acid (22 mg). $^1$H NMR (400 MHz, DMSO) δ 8.72 (s, 1H), 7.78-7.88 (m, 1H), 7.47 (s, 1H), 7.45 (s, 1H), 7.06 (s, 1H), 4.51-4.60 (m, 1H), 3.97-4.11 (m, 2H), 3.86 (s, 3H), 3.38-3.46 (m, 1H), 3.22-3.28 (m, 1H), 3.00-3.09 (m, 2H), 1.79 (s, 3H), 1.72-1.78 (m, 2H), 1.37-1.48 (m, 4H), 0.73 (s, 9H). MS obsd. (ESI⁺) [(M+H)⁺]: 471.

Example 176: 6-tert-butyl-9-[5-(methanesulfonamido)pentoxy]-10-methoxy-2-oxo-6,7-dihydrobenzo[a]quinolizine-3-carboxylic acid

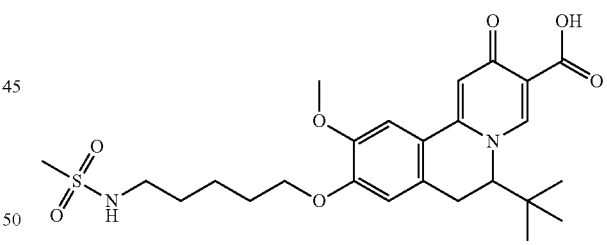

Step 1: Preparation of ethyl 6-tert-butyl-9-[5-(methanesulfonamido)pentoxy]-10-methoxy-2-oxo-6,7-dihydrobenzo[a]quinolizine-3-carboxylate

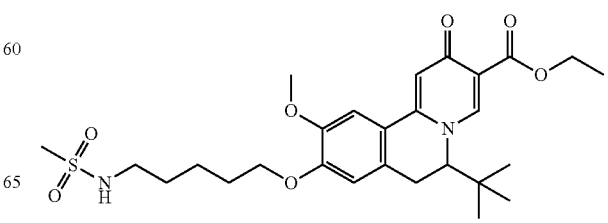

To a solution of ethyl 9-(5-aminopentoxy)-6-tert-butyl-10-methoxy-2-oxo-6,7-dihydrobenzo[a]quinolizine-3-carboxylate (60 mg, 0.13 mmol) in DCM (2 mL) was added methanesulfonic anhydride (27.9 mg, 0.16 mmol) and Et₃N (36.5 μL, 0.26 mmol). The mixture was stirred at room temperature for 2 hours and then concentrated under reduced pressure to give crude ethyl 6-tert-butyl-9-[5-(methanesulfonamido)pentoxy]-10-methoxy-2-oxo-6,7-dihydrobenzo[a]quinolizine-3-carboxylate.

Step 2: Preparation of 6-tert-butyl-9-[5-(methanesulfonamido) pentoxy]-10-methoxy-2-oxo-6,7-dihydrobenzo[a]quinolizine-3-carboxylic acid

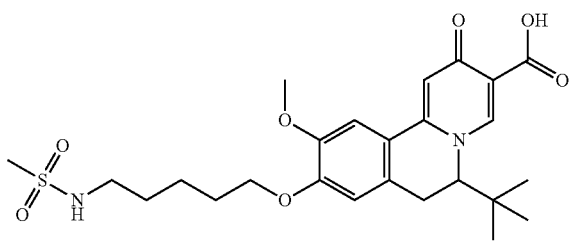 [SMILES: COc1cc2c(cc1OCCCCCNS(C)(=O)=O)CC(C(C)(C)C)n1cc(C(=O)O)c(=O)cc1-2]

To a solution of crude ethyl 6-tert-butyl-9-[5-(methanesulfonamido)pentoxy]-10-methoxy-2-oxo-6,7-dihydrobenzo[a]quinolizine-3-carboxylate in a mixture solvent of methanol and water (3:1, 4 mL) was added LiOH.H₂O (16.4 mg, 0.39 mmol). The mixture was stirred for 2 hours at room temperature, acidified with 6 M hydrochloric acid and extracted in DCM. The organic layer was dried over anhydrous Na₂SO₄ and concentrated under reduced pressure. The residue was purified by preparative HPLC to give 6-tert-butyl-9-[5-(methanesulfonamido)pentoxy]-10-methoxy-2-oxo-6,7-dihydrobenzo[a]quinolizine-3-carboxylic acid (7 mg). $^1$H NMR (400 MHz, DMSO) δ 8.72 (s, 1H), 7.47 (s, 1H), 7.45 (s, 1H), 7.06 (s, 1H), 6.95-7.00 (m, 1H), 4.53-4.59 (m, 1H), 3.99-4.10 (m, 2H), 3.87 (s, 3H), 3.36-3.44 (m, 1H), 3.22-3.29 (m, 1H), 2.92-3.0 (m, 2H), 2.89 (s, 3H), 1.72-1.81 (m, 2H), 1.42-1.56 (m, 4H), 0.73 (s, 9H). MS obsd. (ESI⁺) [(M+H)⁺]: 507.

Example 177: 9-(2-aminoethoxy)-6-tert-butyl-10-methoxy-2-oxo-6,7-dihydrobenzo[a]quinolizine-3-carboxylic acid Step 1: Preparation of ethyl 6-tert-butyl-9-[2-(1,3-dioxoisoindolin-2-yl)ethoxy]-10-methoxy-2-oxo-6,7-dihydrobenzo[a]quinolizine-3-carboxylate

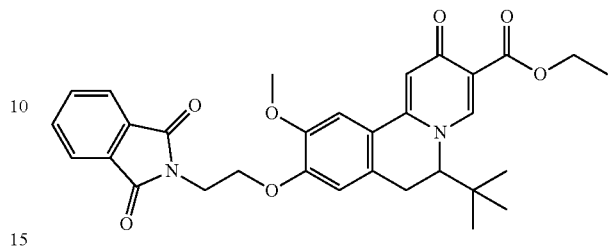

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 2-(2-bromoethyl)isoindoline-1,3-dione (103 mg, 0.41 mmol) and K₂CO₃ (74.5 mg, 0.54 mmol). The mixture was stirred at 80° C. for 12 hours. After being cooled to rt, the mixture was filtered and the filtrate was concentrated. The residue was purified by column chromatography to give ethyl 6-tert-butyl-9-[2-(1, 3-dioxoisoindolin-2-yl) ethoxy]-10-methoxy-2-oxo-6,7-dihydrobenzo[a]quinolizine-3-carboxylate (78 mg).

Step 2: Preparation of ethyl 9-(2-aminoethoxy)-6-tert-butyl-10-methoxy-2-oxo-6,7-dihydrobenzo[a]quinolizine-3-carboxylate

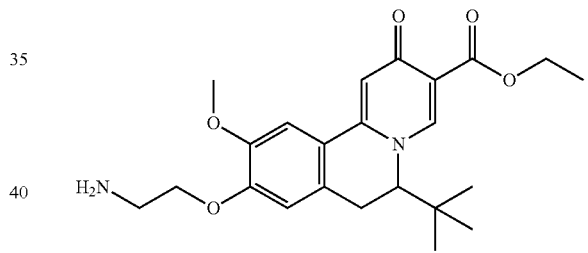

To a solution of ethyl 6-tert-butyl-9-[2-(1, 3-dioxoisoindolin-2-yl)ethoxy]-10-methoxy-2-oxo-6,7-dihydrobenzo[a]quinolizine-3-carboxylate (78 mg, 0.14 mmol) in EtOH (2 mL) was added hydrazinehydrate (85%, 16.5 mg, 0.28 mmol). The mixture was stirred at 60° C. for 3 hours. After being cooled to rt, the mixture was concentrated to give crude ethyl 9-(2-aminoethoxy)-6-tert-butyl-10-methoxy-2-oxo-6,7-dihydrobenzo[a]quinolizine-3-carboxylate.

Step 3: Preparation of 9-(2-aminoethoxy)-6-tert-butyl-10-methoxy-2-oxo-6,7-dihydrobenzo[a]quinolizine-3-carboxylic acid

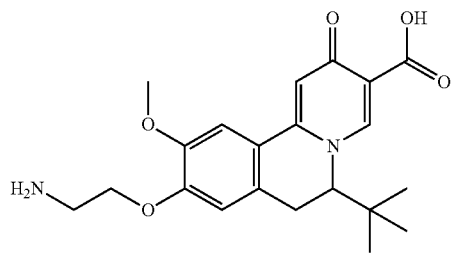 [SMILES: COc1cc2c(cc1OCCN)CC(C(C)(C)C)n1cc(C(=O)O)c(=O)cc1-2]

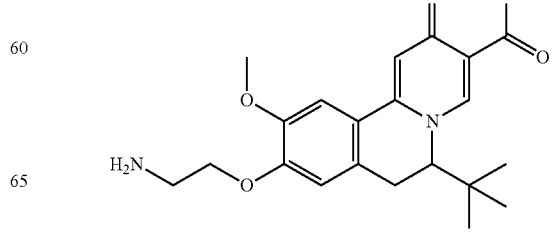

To a solution of crude ethyl 9-(2-aminoethoxy)-6-tert-butyl-10-methoxy-2-oxo-6,7-dihydrobenzo[a]quinolizine-3-carboxylate in a mixture solvent of methanol and water (3:1, 4 mL) was added LiOH.H$_2$O (17.6 mg, 0.42 mmol). The mixture was stirred for one hour at room temperature and then acidified with acetic acid. The mixture was diluted with water and extracted with DCM. The organic layer was dried over anhydrous Na$_2$SO$_4$ and concentrated under reduced pressure. The residue was purified by preparative HPLC to give 9-(2-aminoethoxy)-6-tert-butyl-10-methoxy-2-oxo-6,7-dihydrobenzo[a]quinolizine-3-carboxylic acid (22 mg). $^1$H NMR (400 MHz, MeOD): δ 8.70 (s, 1H), 7.48 (s, 1H), 7.32 (s, 1H), 7.08 (s, 1H), 4.44-4.49 (m, 1H), 4.34-4.41 (m, 2H), 4.00 (s, 3H), 3.41-3.51 (m, 3H), 3.36-3.40 (m, 1H), 0.83 (s, 9H). MS obsd. (ESI$^+$) [(M+H)$^+$]: 387.

Example 178 and 179

9-[3-(2-aminoethoxy)propoxy]-6-tert-butyl-10-methoxy-2-oxo-6,7-dihydrobenzo[a]quinolizine-3-carboxylic acid and 6-tert-butyl-9-[3-[2-(ethylamino)ethoxy]propoxy]-10-methoxy-2-oxo-6,7-dihydrobenzo[a]quinolizine-3-carboxylic acid

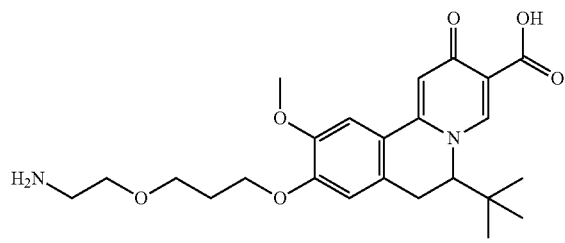

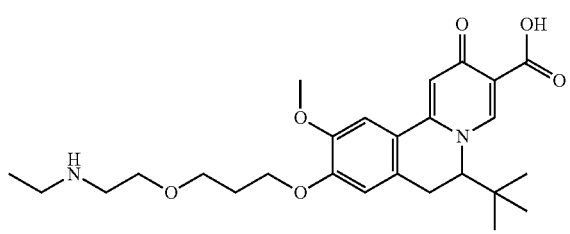

Step 1: Preparation of 2-(dibenzylamino) ethanol

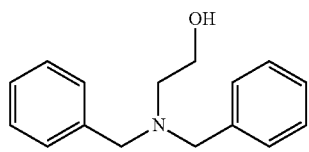 [SMILES: OCCN(Cc1ccccc1)Cc1ccccc1]

To a solution of 2-aminoethanol (10 g, 0.16 mol) in MeCN (150 mL) was added bromomethylbenzene (57.5 g, 0.34 mol) and K$_2$CO$_3$ (45.3 g, 0.33 mol). The mixture was stirred at 60° C. for 6 hours, then cooled to room temperature and filtered. The filtrate was concentrated to give crude 2-(dibenzylamino) ethanol.

Step 2: Preparation of N, N-dibenzyl-2-[3-[tert-butyl (dimethyl)silyl]oxypropoxy]ethanamine

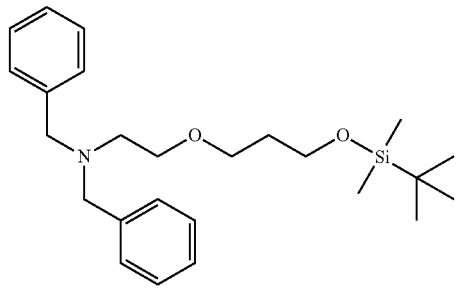 [SMILES: CC(C)(C)[Si](C)(C)OCCCOCCN(Cc1ccccc1)Cc1ccccc1]

To a solution of crude 2-(dibenzylamino) ethanol (2.0 g) in DMF (30 mL) was added NaH (purity: 95%, 0.42 g, 16.6 mmol) portionwise at 0° C. The mixture was stirred for 30 minutes, then to the mixture was added 3-bromopropoxy-tert-butyl-dimethyl-silane (3.2 g, 12.5 mmol). The mixture was warmed to 60° C. and stirred at this temperature for 12 hours. After the reaction mixture was cooled to room temperature, the reaction was quenched with saturated aqueous ammonium chloride solution. The resulting mixture was extracted with DCM. The organic layer was dried over anhydrous Na$_2$SO$_4$ and concentrated. The residue was purified by column chromatography to give N, N-dibenzyl-2-[3-[tert-butyl (dimethyl) silyl]oxypropoxy]ethanamine (1.0 g).

Step 3: Preparation of 3-[2-(dibenzylamino) ethoxy]propan-1-ol

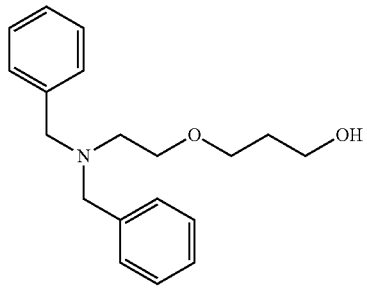 [SMILES: OCCCOCCN(Cc1ccccc1)Cc1ccccc1]

To a solution of N, N-dibenzyl-2-[3-[tert-butyl(dimethyl) silyl]oxypropoxy]ethanamine (2.0 g, 4.8 mmol) in THF (20 mL) was added tetrabutylammonium fluoride (1.5 g, 5.8 mmol) at 0° C. The mixture was stirred at rt for 16 hours, and then partitioned between brine and DCM. The organic layer was dried over anhydrous Na$_2$SO$_4$ and concentrated. The residue was purified by column chromatography to give 3-[2-(dibenzylamino) ethoxy]propan-1-ol (1.3 g).

Step 4: Preparation of 3-[2-(dibenzylamino)ethoxy]propyl 4-methylbenzenesulfonate

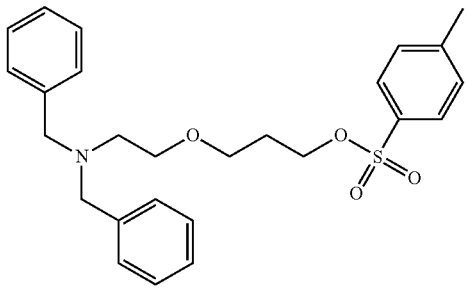 [SMILES: Cc1ccc(S(=O)(=O)OCCCOCCN(Cc2ccccc2)Cc2ccccc2)cc1]

To a solution of 3-[2-(dibenzylamino)ethoxy]propan-1-ol (1.3 g, 4.3 mmol) in DCM (20 mL) was added Et$_3$N (1.2 mL, 8.6 mmol) and catalytic amount of DMAP. The mixture was stirred for 20 minutes, then to the mixture was added 4-methylbenzenesulfonyl chloride (0.99 g, 5.2 mmol) portionwise at 0° C. The mixture was warmed to room temperature and stirred for 18 hours, then washed with 1 M hydrochloric acid, followed by saturated aqueous NaHCO$_3$ solution. The organic layer was dried over anhydrous Na$_2$SO$_4$ and concentrated. The residue was purified by column chromatography to give 3-[2-(dibenzylamino)ethoxy]propyl 4-methylbenzenesulfonate (0.5 g).

Step 5: Preparation of ethyl 6-tert-butyl-9-[3-[2-(dibenzylamino)ethoxy]propoxy]-10-methoxy-2-oxo-6,7-dihydrobenzo[a]quinolizine-3-carboxylate

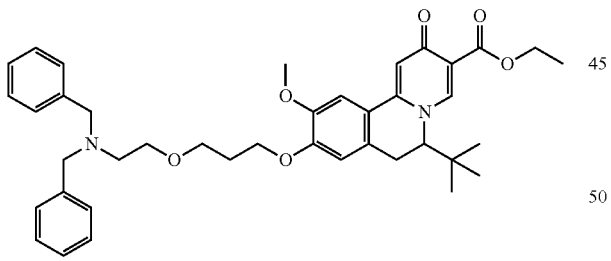

To a solution of ethyl 6-tert-butyl-9-hydroxy-10-methoxy-2-oxo-6,7-dihydrobenzo[a]quinolizine-3-carboxylate (300 mg, 0.81 mmol) in DMF (10 mL) was added 3-[2-(dibenzylamino)ethoxy]propyl 4-methylbenzenesulfonate (476.3 mg, 1.05 mmol) and K$_2$CO$_3$ (223.6 mg, 1.62 mmol). The mixture was stirred at 120° C. for 4 hours. After being cooled to rt, the mixture was filtered and the filtrate was concentrated. The residue was purified by column chromatography to give ethyl 6-tert-butyl-9-[3-[2-(dibenzylamino)ethoxy]propoxy]-10-methoxy-2-oxo-6,7-dihydrobenzo[a]quinolizine-3-carboxylate (0.42 g).

Step 6: Preparation of ethyl 9-[3-(2-aminoethoxy)propoxy]-6-tert-butyl-10-methoxy-2-oxo-6,7-dihydrobenzo[a]quinolizine-3-carboxylate and ethyl 6-tert-butyl-9-[3-[2-(ethylamino)ethoxy]propoxy]-10-methoxy-2-oxo-6,7-dihydrobenzo[a]quinolizine-3-carboxylate

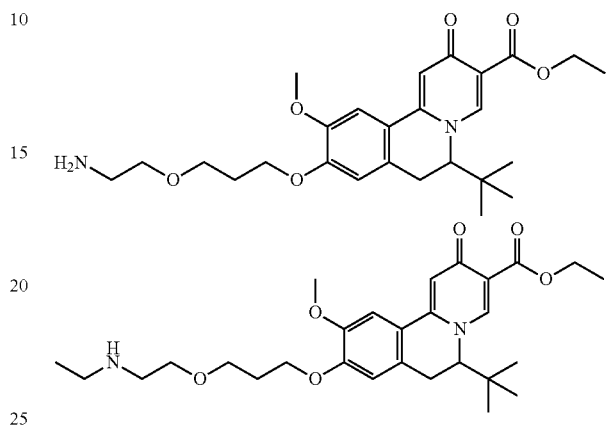

To a solution of ethyl 6-tert-butyl-9-[3-[2-(dibenzylamino)ethoxy]propoxy]-10-methoxy-2-oxo-6,7-dihydrobenzo[a]quinolizine-3-carboxylate (0.42 g) in EtOH (10 mL) was added Pd/C (42 mg). The mixture was stirred for 48 hours at room temperature under atmosphere of hydrogen. The mixture was filtered and the filtrate was concentrated to give a crude mixture of ethyl 9-[3-(2-aminoethoxy)propoxy]-6-tert-butyl-10-methoxy-2-oxo-6,7-dihydrobenzo[a]quinolizine-3-carboxylate and ethyl 6-tert-butyl-9-[3-[2-(ethylamino)ethoxy]propoxy]-10-methoxy-2-oxo-6,7-dihydrobenzo[a]quinolizine-3-carboxylate.

Step 7: Preparation of 9-[3-(2-aminoethoxy)propoxy]-6-tert-butyl-10-methoxy-2-oxo-6,7-dihydrobenzo[a]quinolizine-3-carboxylic acid and 6-tert-butyl-9-[3-[2-(ethylamino)ethoxy]propoxy]-10-methoxy-2-oxo-6,7-dihydrobenzo[a]quinolizine-3-carboxylic acid

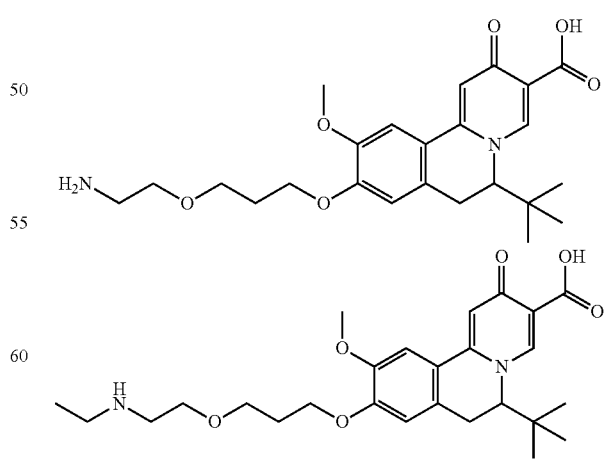

To a solution of the mixture of ethyl 9-[3-(2-aminoethoxy)propoxy]-6-tert-butyl-10-methoxy-2-oxo-6,7-dihydrobenzo[a]quinolizine-3-carboxylate and ethyl 6-tert-butyl-9-[3-[2-(ethylamino)ethoxy]propoxy]-10-methoxy-2-oxo-6,7-dihydrobenzo[a]quinolizine-3-carboxylate (100 mg) in a mixture solvent of methanol and water (3:1, 12 mL) was added LiOH.H$_2$O (26.5 mg, 0.63 mmol). The mixture was stirred for 3 hours at room temperature and then acidified with acetic acid. The resulting mixture was diluted with water and extracted with DCM. The organic layer was dried over anhydrous Na$_2$SO$_4$ and concentrated under reduced pressure. The residue was purified by preparative HPLC to give 9-[3-(2-aminoethoxy)propoxy]-6-tert-butyl-10-methoxy-2-oxo-6,7-dihydrobenzo[a]quinolizine-3-carboxylic acid (Example 178, 7 mg) and 6-tert-butyl-9-[3-[2-(ethylamino)ethoxy]propoxy]-10-methoxy-2-oxo-6,7-dihydrobenzo[a]quinolizine-3-carboxylic acid (Example 179, 20 mg).

Example 178

$^1$H NMR (400 MHz, DMSO) δ 8.72 (s, 1H), 7.47 (s, 1H), 7.45 (s, 1H), 7.08 (s, 1H), 4.53-4.60 (m, 1H), 4.04-4.18 (m, 2H), 3.87 (s, 3H), 3.54 (t, 2H), 3.37-3.43 (m, 3H), 3.23-3.29 (m, 1H), 2.66 (t, 2H), 1.99 (t, 2H), 0.73 (s, 9H). MS obsd. (ESI$^+$) [(M+H)$^+$]: 445.

Example 179

$^1$H NMR (400 MHz, DMSO) δ 8.72 (s, 1H), 7.48 (s, 1H), 7.45 (s, 1H), 7.07 (s, 1H), 4.53-4.60 (m, 1H), 4.04-4.18 (m, 2H), 3.87 (s, 3H), 3.54 (t, 2H), 3.44 (t, 2H), 3.38-3.41 (m, 1H), 3.23-3.29 (m, 1H), 2.64 (t, 2H), 2.52-2.55 (m, 2H), 1.94-2.03 (m, 2H), 0.97 (t, 3H), 0.73 (s, 9H). MS obsd. (ESI$^+$) [(M+H)$^+$]:473.

Example 180 and 181

6-tert-butyl-9-(3, 3-difluoropropoxy)-10-methoxy-2-oxo-6,7-dihydrobenzo[a]quinolizine-3-carboxylic acid and 6-tert-butyl-9-(1,1-difluoropropoxy)-10-methoxy-2-oxo-6,7-dihydrobenzo[a]quinolizine-3-carboxylic acid

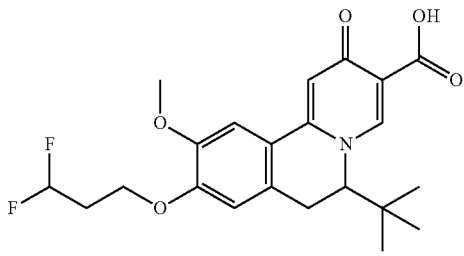

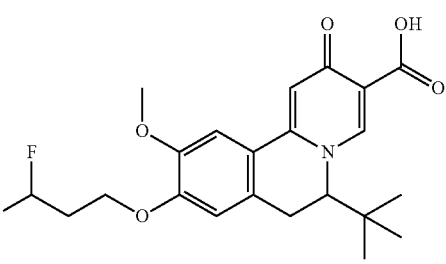

Step 1: Preparation of ethyl 6-tert-butyl-9-(3,3-difluoroallyloxy)-10-methoxy-2-oxo-6,7-dihydrobenzo[a]quinolizine-3-carboxylate and ethyl 6-tert-butyl-9-(1,1-difluoroallyloxy)-10-methoxy-2-oxo-6,7-dihydrobenzo[a]quinolizine-3-carboxylate

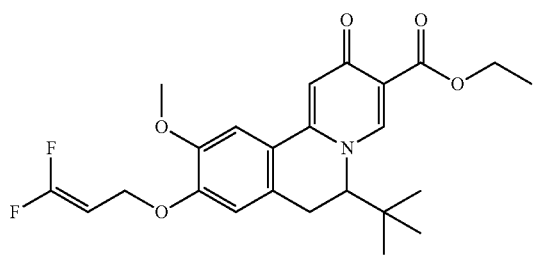

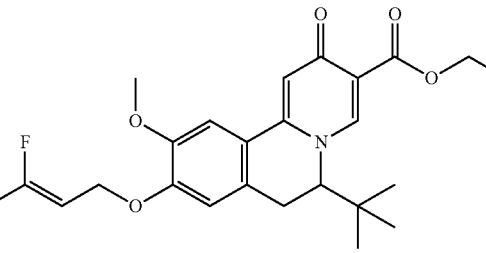

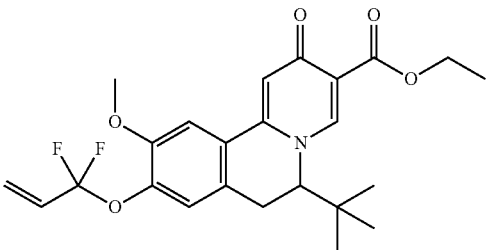

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 3-bromo-3,3-difluoro-prop-1-ene (84.8 mg, 0.54 mmol) and K$_2$CO$_3$ (74.5 mg, 0.54 mmol). The mixture was stirred at 40° C. for 20 hours. After being cooled to rt, the mixture was filtered and the filtrate was concentrated to give a crude mixture of ethyl 6-tert-butyl-9-(3,3-difluoroallyloxy)-10-methoxy-2-oxo-6,7-dihydrobenzo[a]quinolizine-3-carboxylate and ethyl 6-tert-butyl-9-(1,1-difluoroallyloxy)-10-methoxy-2-oxo-6,7-dihydrobenzo[a]quinolizine-3-carboxylate.

Step 2: Preparation of ethyl 6-tert-butyl-9-(3,3-difluoropropoxy)-10-methoxy-2-oxo-6,7-dihydrobenzo[a]quinolizine-3-carboxylate and ethyl 6-tert-butyl-9-(1,1-difluoropropoxy)-10-methoxy-2-oxo-6,7-dihydrobenzo[a]quinolizine-3-carboxylate

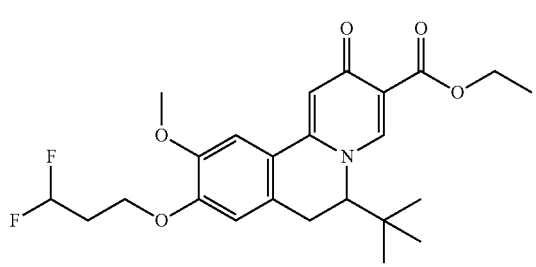

-continued

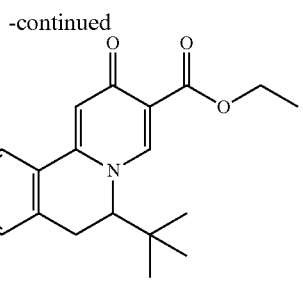

To a solution of the mixture of crude ethyl 6-tert-butyl-9-(3,3-difluoroallyloxy)-10-methoxy-2-oxo-6,7-dihydrobenzo[a]quinolizine-3-carboxylate and ethyl 6-tert-butyl-9-(1,1-difluoroallyloxy)-10-methoxy-2-oxo-6,7-dihydrobenzo[a]quinolizine-3-carboxylate (120 mg) in EtOH (10 mL) was added Pd/C (12 mg). The mixture was stirred for 18 hours at room temperature under atmosphere of hydrogen, and then filtered. The filtrate was concentrated to give a crude mixture of ethyl 6-tert-butyl-9-(3,3-difluoropropoxy)-10-methoxy-2-oxo-6,7-dihydrobenzo[a]quinolizine-3-carboxylate and ethyl 6-tert-butyl-9-(1,1-difluoropropoxy)-10-methoxy-2-oxo-6,7-dihydrobenzo[a]quinolizine-3-carboxylate.

Step 3: Preparation of 6-tert-butyl-9-(3, 3-difluoropropoxy)-10-methoxy-2-oxo-6,7-dihydrobenzo[a]quinolizine-3-carboxylic acid and 6-tert-butyl-9-(1,1-difluoropropoxy)-10-methoxy-2-oxo-6,7-dihydrobenzo[a]quinolizine-3-carboxylic acid

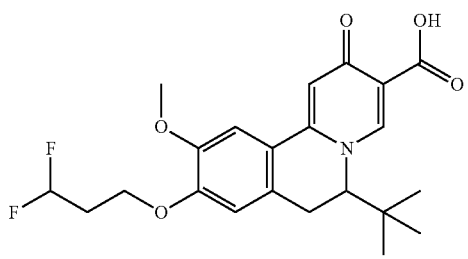

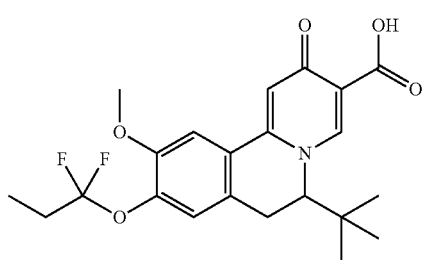 [SMILES: C=CC(F)(F)Oc1cc2c(cc1OC)-c1cc(=O)c(C(=O)O)cn1C(C(C)(C)C)C2]

To a solution of the mixture of crude ethyl 6-tert-butyl-9-(3,3-difluoropropoxy)-10-methoxy-2-oxo-6,7-dihydrobenzo[a]quinolizine-3-carboxylate and ethyl 6-tert-butyl-9-(1,1-difluoropropoxy)-10-methoxy-2-oxo-6,7-dihydrobenzo[a]quinolizine-3-carboxylate in the mixture solvent of methanol and water (3:1, 12 mL) was added LiOH.H$_2$O (68 mg, 1.62 mmol). The mixture was stirred at room temperature for 2 hours, and then acidified with 6 M hydrochloric acid and extracted with DCM. The organic layer was dried over anhydrous Na$_2$SO$_4$ and concentrated under reduced pressure. The residue was purified by preparative HPLC to give 6-tert-butyl-9-(3, 3-difluoropropoxy)-10-methoxy-2-oxo-6,7-dihydrobenzo[a]quinolizine-3-carboxylic acid (Example 180, 15 mg) and 6-tert-butyl-9-(1,1-difluoropropoxy)-10-methoxy-2-oxo-6,7-dihydrobenzo[a]quinolizine-3-carboxylic acid (Example 181, 11 mg).

Example 180

$^1$H NMR (400 MHz, CDCl$_3$) δ 8.51 (s, 1H), 7.18 (s, 1H), 7.10 (s, 1H), 6.75 (s, 1H), 5.99-6.33 (m, 1H), 4.19-4.33 (m, 2H), 4.07-4.09 (m, 1H), 3.94 (s, 3H), 3.40-3.51 (m, 1H), 3.13-3.25 (m, 1H), 2.36-2.53 (m, 2H), 0.84 (s, 9H). MS obsd. (ESI$^+$) [(M+H)$^+$]: 422.

Example 181

$^1$H NMR (400 MHz, CDCl$_3$) δ 8.55 (s, 1H), 7.27 (s, 1H), 7.22 (s, 1H), 7.17 (s, 1H), 4.08-4.17 (m, 1H), 3.94 (s, 3H), 3.39-3.50 (m, 1H), 3.17-3.27 (m, 1H), 2.18-2.33 (m, 2H), 1.21 (t, 3H), 0.83 (s, 9H). MS obsd. (ESI$^+$) [(M+H)$^+$]: 422.

Example 182: 6-tert-butyl-9-(1, 1-difluoroallyloxy)-10-methoxy-2-oxo-6,7-dihydrobenzo[a]quinolizine-3-carboxylic acid

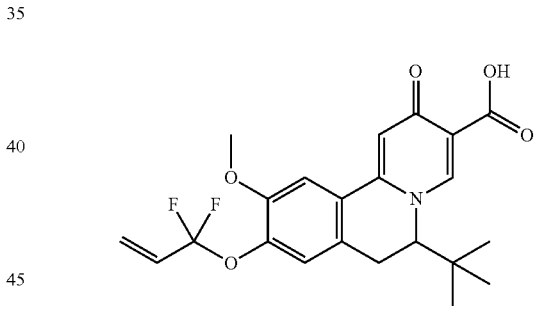

To a solution of crude ethyl 6-tert-butyl-9-(3,3-difluoroallyloxy)-10-methoxy-2-oxo-6,7-dihydrobenzo[a]quinolizine-3-carboxylate and ethyl 6-tert-butyl-9-(1,1-difluoroallyloxy)-10-methoxy-2-oxo-6,7-dihydrobenzo[a]quinolizine-3-carboxylate (from step 1 of the procedure to prepare Example 180 and 181, 120 mg) in a mixture solvent of methanol and water (3:1, 12 mL) was added LiOH.H$_2$O (34 mg, 0.81 mmol). The mixture was stirred at room temperature for 2 hours, then acidified with 6 M hydrochloric acid and extracted with DCM. The organic layer was dried over anhydrous Na$_2$SO$_4$ and concentrated under reduced pressure. The residue was purified by preparative HPLC to give 6-tert-butyl-9-(1, 1-difluoroallyloxy)-10-methoxy-2-oxo-6,7-dihydrobenzo[a]quinolizine-3-carboxylic acid (6.5 mg). $^1$H NMR (400 MHz, CDCl$_3$) δ 8.52 (s, 1H), 7.27 (s, 1H), 7.24 (s, 1H), 7.16 (s, 1H), 5.96-6.18 (m, 2H), 5.65-5.69 (m, 1H), 4.05-4.09 (m, 1H), 3.95 (s, 3H), 3.39-3.48 (m, 1H), 3.19-3.28 (m, 1H), 0.84 (s, 9H). MS obsd. (ESI$^+$) [(M+H)$^+$]: 420.

Example 183: 6-tert-butyl-10-methoxy-9-(3-methylsulfanylpropoxy)-2-oxo-6,7-dihydrobenzo[a]quinolizine-3-carboxylic acid

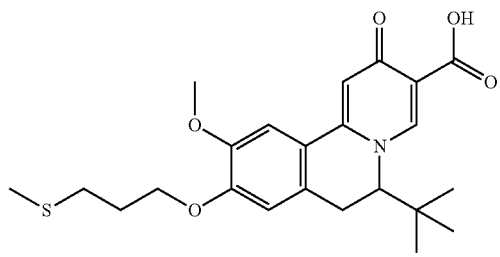 [SMILES: COc1cc2c(cc1OCCCSC)CC(C(C)(C)C)n1cc(C(=O)O)c(=O)cc1-2]

Step 1: Preparation of 3-methylsulfanylpropyl 4-methylbenzenesulfonate

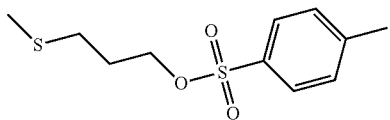

To a solution of 3-methylsulfanylpropan-1-ol (3.0 g, 28.2 mmol) in DCM (50 mL) was added Et₃N (7.9 mL, 56.4 mmol) and catalytic amount of DMAP. The mixture was stirred for 20 minutes, then to the mixture was added 4-methylbenzenesulfonyl chloride (5.4 g, 28.2 mmol) portionwise at 0° C. The mixture was warmed to room temperature and stirred at rt for 16 hours. The resulting mixture was washed with 4 M hydrochloric acid, followed by saturated aqueous NaHCO₃ solution. The organic layer was dried over anhydrous Na₂SO₄ and concentrated to give crude 3-methylsulfanylpropyl 4-methylbenzenesulfonate.

Step 2: Preparation of ethyl 6-tert-butyl-10-methoxy-9-(3-methylsulfanylpropoxy)-2-oxo-6,7-dihydrobenzo[a]quinolizine-3-carboxylate

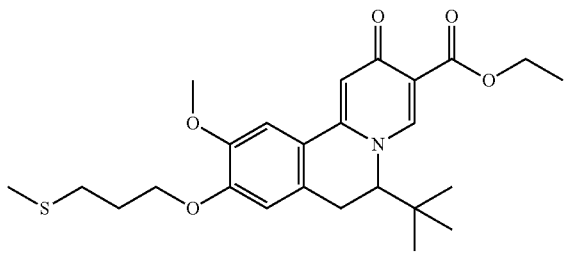 [SMILES: CCOC(=O)c1cn2c(cc1=O)-c1cc(OC)c(OCCCSC)cc1CC2C(C)(C)C]

To a solution of ethyl 6-tert-butyl-9-hydroxy-10-methoxy-2-oxo-6,7-dihydrobenzo[a]quinolizine-3-carboxylate (200 mg, 0.54 mmol) in DMF (10 mL) was added 3-methylsulfanylpropyl 4-methylbenzenesulfonate (182.7 mg, 0.70 mmol) and K₂CO₃ (149 mg, 1.08 mmol). The mixture was stirred at 120° C. for 3 hours. After being cooled to rt, the mixture was filtered and the filtrate was concentrated to give crude ethyl 6-tert-butyl-10-methoxy-9-(3-methylsulfanylpropoxy)-2-oxo-6,7-dihydrobenzo[a]quinolizine-3-carboxylate which was used in the next step without purification.

Step 3: Preparation of 6-tert-butyl-10-methoxy-9-(3-methylsulfanylpropoxy)-2-oxo-6,7-dihydrobenzo[a]quinolizine-3-carboxylic acid

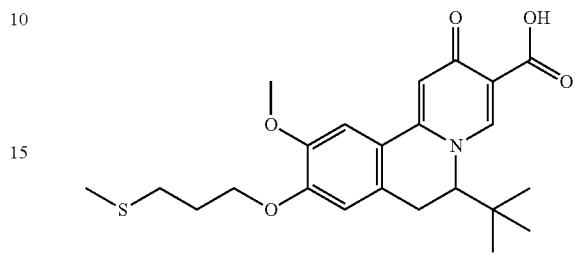

To a solution of crude ethyl 6-tert-butyl-10-methoxy-9-(3-methylsulfanylpropoxy)-2-oxo-6,7-dihydrobenzo[a]quinolizine-3-carboxylate in a mixture solvent of methanol and water (3:1, 12 mL) was added LiOH.H₂O (68 mg, 1.62 mmol). The mixture was stirred at room temperature for 2 hours, then acidified with 6 M hydrochloric acid and extracted with DCM. The organic layer was dried over anhydrous Na₂SO₄ and concentrated under reduced pressure. The residue was purified by column chromatography to give 6-tert-butyl-10-methoxy-9-(3-methylsulfanylpropoxy)-2-oxo-6,7-dihydrobenzo[a]quinolizine-3-carboxylic acid (37 mg). $^1$H NMR (400 MHz, DMSO) δ 8.72 (s, 1H), 7.48 (s, 1H), 7.45 (s, 1H), 7.08 (s, 1H), 4.52-4.61 (m, 1H), 4.06-4.21 (m, 2H), 3.87 (s, 3H), 3.34-3.42 (m, 1H), 3.22-3.29 (m, 1H), 2.59-2.66 (m, 2H), 2.08 (s, 3H), 1.98-2.05 (m, 2H), 0.73 (s, 9H). MS obsd. (ESI⁺) [(M+H)⁺]: 432.

Example 184 and 185

(+)-6-tert-butyl-10-methoxy-9-(3-methylsulfanylpropoxy)-2-oxo-6,7-dihydrobenzo[a]quinolizine-3-carboxylic acid and (−)-6-tert-butyl-10-methoxy-9-(3-methylsulfanylpropoxy)-2-oxo-6,7-dihydrobenzo[a]quinolizine-3-carboxylic acid

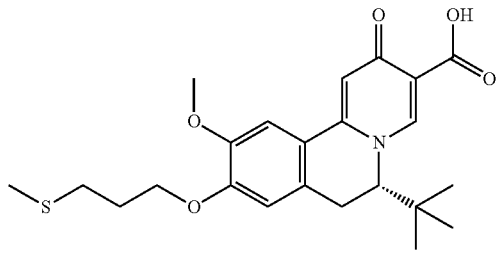 [SMILES: COc1cc2c(cc1OCCCSC)CC(C(C)(C)C)n1cc(C(=O)O)c(=O)cc1-2]

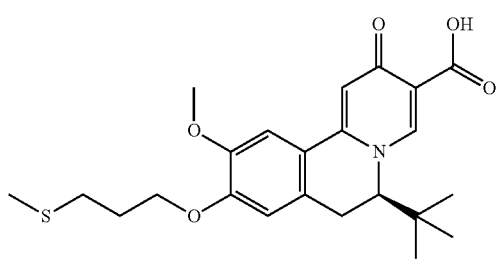

Separation of 6-tert-butyl-10-methoxy-9-(3-methylsulfanylpropoxy)-2-oxo-6,7-dihydrobenzo[a]quinolizine-3-carboxylic acid by chiral HPLC provided (+)-6-tert-butyl-10-methoxy-9-(3-methylsulfanylpropoxy)-2-oxo-6,7-dihydrobenzo[a]quinolizine-3-carboxylic acid (11 mg) and (−)-6-tert-butyl-10-methoxy-9-(3-methylsulfanylpropoxy)-2-oxo-6,7-dihydrobenzo[a]quinolizine-3-carboxylic acid (10 mg).

Example 184

$^1$H NMR (400 MHz, DMSO) δ 8.72 (s, 1H), 7.48 (s, 1H), 7.45 (s, 1H), 7.08 (s, 1H), 4.52-4.61 (m, 1H), 4.06-4.21 (m, 2H), 3.87 (s, 3H), 3.34-3.42 (m, 1H), 3.22-3.29 (m, 1H), 2.59-2.66 (m, 2H), 2.08 (s, 3H), 1.98-2.05 (m, 2H), 0.73 (s, 9H). MS obsd. (ESI$^+$) [(M+H)$^+$]: 432.

Example 185

$^1$H NMR (400 MHz, DMSO) δ 8.72 (s, 1H), 7.48 (s, 1H), 7.45 (s, 1H), 7.08 (s, 1H), 4.52-4.61 (m, 1H), 4.06-4.21 (m, 2H), 3.87 (s, 3H), 3.34-3.42 (m, 1H), 3.22-3.29 (m, 1H), 2.59-2.66 (m, 2H), 2.08 (s, 3H), 1.98-2.05 (m, 2H), 0.73 (s, 9H). MS obsd. (ESI$^{3O}$) [(M+H)$^+$]: 432. [α]$_D^{20}$=−74.133° (0.075%, CH$_3$CN).

Example 186: 6-tert-butyl-10-methoxy-9-(3-methylsulfonylpropoxy)-2-oxo-6,7-dihydrobenzo[a]quinolizine-3-carboxylic acid

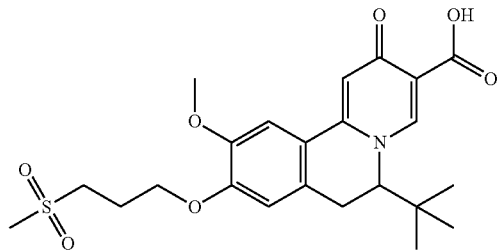

To a solution of 6-tert-butyl-10-methoxy-9-(3-methylsulfanylpropoxy)-2-oxo-6,7-dihydrobenzo[a]quinolizine-3-carboxylic acid (150 mg, 0.35 mmol) in DCM (10 mL) was added 3-chloroperoxybenzoic acid (purity: 70%, 172.6 mg, 0.70 mmol). The mixture was stirred at room temperature for 2 hours and then filtered. The filtrate was concentrated under reduced pressure. The residue was purified by column chromatography to give 6-tert-butyl-10-methoxy-9-(3-methylsulfonylpropoxy)-2-oxo-6,7-dihydrobenzo[a]quinolizine-3-carboxylic acid (32.0 mg). $^1$H NMR (400 MHz, DMSO) δ 8.73 (s, 1H), 7.50 (s, 1H), 7.47 (s, 1H), 7.08 (s, 1H), 4.54-4.61 (m, 1H), 4.13-4.25 (m, 2H), 3.88 (s, 3H), 3.36-3.42 (m, 1H), 3.23-3.30 (m, 3H), 3.04 (s, 3H), 2.14-2.25 (m, 2H), 0.73 (s, 9H). MS obsd. (ESI$^+$) [(M+H)$^+$]: 464.

Example 187 and 188

(+)-6-tert-butyl-10-methoxy-9-(3-methylsulfonylpropoxy)-2-oxo-6,7-dihydrobenzo[a]quinolizine-3-carboxylic acid and (−)-6-tert-butyl-10-methoxy-9-(3-methylsulfonylpropoxy)-2-oxo-6,7-dihydrobenzo[a]quinolizine-3-carboxylic acid

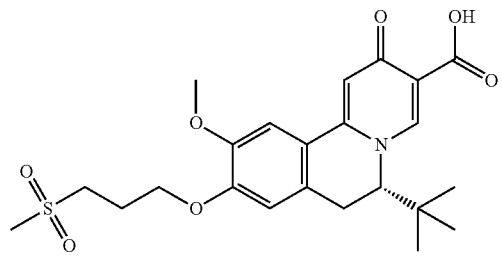 [SMILES: COc1cc2c(cc1OCCCS(C)(=O)=O)CC(C(C)(C)C)n1cc(C(=O)O)c(=O)cc1-2]

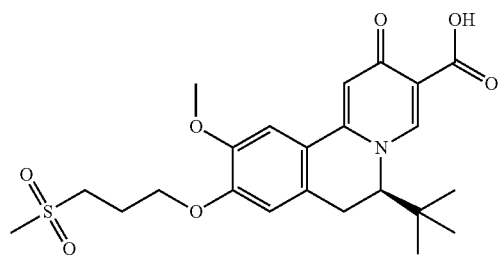

Separation of 6-tert-butyl-10-methoxy-9-(3-methylsulfonylpropoxy)-2-oxo-6,7-dihydrobenzo[a]quinolizine-3-carboxylic acid by chiral HPLC provided (+)-6-tert-butyl-10-methoxy-9-(3-methylsulfonylpropoxy)-2-oxo-6,7-dihydrobenzo[a]quinolizine-3-carboxylic acid (9.0 mg) and (−)-6-tert-butyl-10-methoxy-9-(3-methylsulfonylpropoxy)-2-oxo-6,7-dihydrobenzo[a]quinolizine-3-carboxylic acid (8.0 mg).

Example 187

$^1$H NMR (400 MHz, DMSO) δ 8.73 (s, 1H), 7.50 (s, 1H), 7.47 (s, 1H), 7.08 (s, 1H), 4.54-4.61 (m, 1H), 4.13-4.25 (m, 2H), 3.88 (s, 3H), 3.36-3.42 (m, 1H), 3.23-3.30 (m, 3H), 3.04 (s, 3H), 2.14-2.25 (m, 2H), 0.73 (s, 9H). MS obsd. (ESI$^+$) [(M+H)$^+$]: 464

Example 188

$^1$H NMR (400 MHz, DMSO) δ 8.73 (s, 1H), 7.50 (s, 1H), 7.47 (s, 1H), 7.08 (s, 1H), 4.54-4.61 (m, 1H), 4.13-4.25 (m, 2H), 3.88 (s, 3H), 3.36-3.42 (m, 1H), 3.23-3.30 (m, 3H), 3.04 (s, 3H), 2.14-2.25 (m, 2H), 0.73 (s, 9H). MS obsd. (ESI$^+$) [(M+H)$^+$]: 464. [α]$_D^{20}$=−94.400° (0.050%, CH$_3$CN).

Example 189: 6-tert-butyl-10-methoxy-9-(2-morpholinoethoxy)-2-oxo-6,7-dihydrobenzo[a]quinolizine-3-carboxylic acid hydrochloride

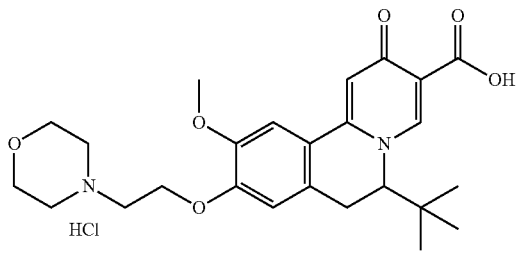 [SMILES: COc1cc2c(cc1OCCN1CCOCC1)CC(C(C)(C)C)n1cc(C(=O)O)c(=O)cc1-2 ; Cl]

Step 1: Preparation of ethyl 6-tert-butyl-10-methoxy-9-(2-morpholinoethoxy)-2-oxo-6, 7-dihydrobenzo[a]quinolizine-3-carboxylate

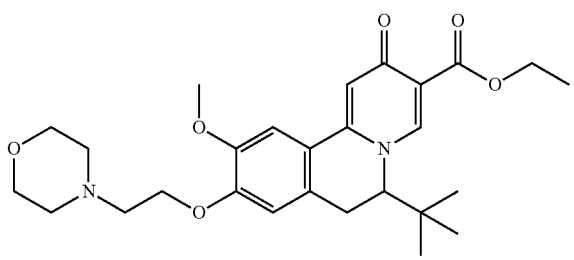 [SMILES: CCOC(=O)c1cn2c(cc1=O)-c1cc(OC)c(OCCN3CCOCC3)cc1CC2C(C)(C)C]

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 4-(2-bromoethyl) morpholine, hydrobromide (96.3 mg, 0.35 mmol) and K$_2$CO$_3$ (74.5 mg, 0.54 mmol). The mixture was heated at 120° C. for 3 hours. After being cooled to rt, the mixture was filtered and the filtrate was concentrated to give ethyl 6-tert-butyl-10-methoxy-9-(2-morpholinoethoxy)-2-oxo-6,7-dihydrobenzo[a]quinolizine-3-carboxylate.

Step 2: Preparation of 6-tert-butyl-10-methoxy-9-(2-morpholinoethoxy)-2-oxo-6,7-dihydrobenzo[a]quinolizine-3-carboxylic acid hydrochloride

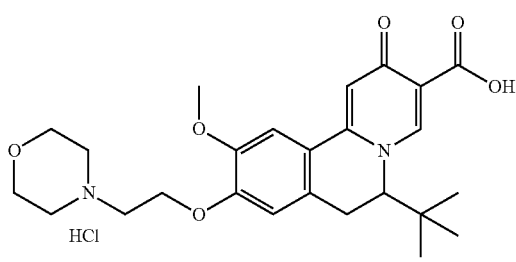 [SMILES: COc1cc2c(cc1OCCN1CCOCC1)CC(C(C)(C)C)n1cc(C(=O)O)c(=O)cc1-2 ; Cl]

To a solution of crude ethyl 6-tert-butyl-10-methoxy-9-(2-morpholinoethoxy)-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The mixture was stirred at room temperature for 2 hours, and then acidified with 6 M hydrochloric acid. The mixture was purified by preparative HPLC to give 6-tert-butyl-10-methoxy-9-(2-morpholinoethoxy)-2-oxo-6,7-dihydrobenzo[a]quinolizine-3-carboxylic acid hydrochloride (65 mg). $^1$H NMR (400 MHz, DMSO) δ 10.05-10.53 (m, 1H), 8.74 (s, 1H), 7.54 (s, 1H), 7.50 (s, 1H), 7.15 (s, 1H), 4.56-4.64 (m, 1H), 4.41-4.48 (m, 2H), 3.94-4.10 (m, 2H), 3.89 (s, 3H), 3.59-3.66 (m, 6H), 3.22-3.45 (m, 4H), 0.74 (s, 9H). MS obsd. (ESI$^+$) [(M+H)$^+$]: 457.

Example 190 and 191

(+)-6-tert-butyl-10-methoxy-9-(2-morpholinoethoxy)-2-oxo-6,7-dihydrobenzo[a]quinolizine-3-carboxylic acid and (−)-6-tert-butyl-10-methoxy-9-(2-morpholinoethoxy)-2-oxo-6,7-dihydrobenzo[a]quinolizine-3-carboxylic acid

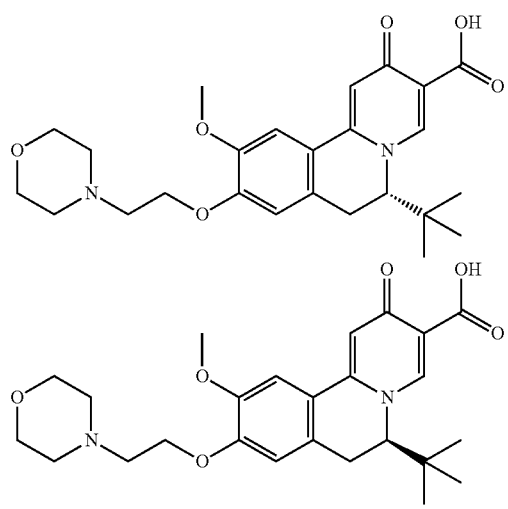

Separation of 6-tert-butyl-10-methoxy-9-(2-morpholinoethoxy)-2-oxo-6,7-dihydrobenzo[a]quinolizine-3-carboxylic acid by chiral HPLC provided (+)-6-tert-butyl-10-methoxy-9-(2-morpholinoethoxy)-2-oxo-6,7-dihydrobenzo[a]quinolizine-3-carboxylic acid (17 mg) and (−)-6-tert-butyl-10-methoxy-9-(2-morpholinoethoxy)-2-oxo-6,7-dihydrobenzo[a]quinolizine-3-carboxylic acid (15 mg).

Example 190

$^1$H NMR (400 MHz, DMSO) δ 8.72 (s, 1H), 7.48 (s, 1H), 7.45 (s, 1H), 7.10 (s, 1H), 4.54-4.60 (m, 1H), 4.11-4.24 (m, 2H), 3.86 (s, 3H), 3.55-3.63 (m, 4H), 3.34-3.42 (m, 1H), 3.20-3.27 (m, 1H), 2.70-2.76 (m, 2H), 2.43-2.50 (m, 4H), 0.73 (s, 9H). MS obsd. (ESI$^+$) [(M+H)$^+$]: 457. $[α]_D^{20}$=+78.095° (0.105° %, CH$_3$CN).

Example 191

$^1$H NMR (400 MHz, DMSO) δ 8.72 (s, 1H), 7.48 (s, 1H), 7.45 (s, 1H), 7.10 (s, 1H), 4.54-4.60 (m, 1H), 4.11-4.24 (m, 2H), 3.86 (s, 3H), 3.55-3.63 (m, 4H), 3.34-3.42 (m, 1H), 3.20-3.27 (m, 1H), 2.70-2.76 (m, 2H), 2.43-2.50 (m, 4H), 0.73 (s, 9H). MS obsd. (ESI$^+$) [(M+H)$^+$]: 457.

Example 192: 6-tert-butyl-10-methoxy-9-(3-morpholinopropoxy)-2-oxo-6,7-dihydrobenzo[a]quinolizine-3-carboxylic acid hydrochloride

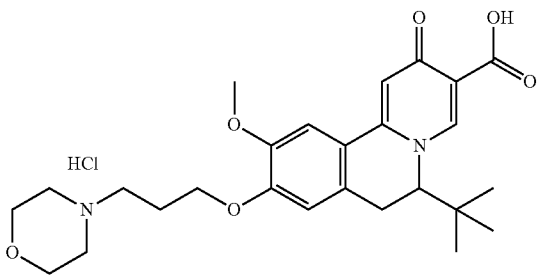 [SMILES: COc1cc2c(cc1OCCCN1CCOCC1)CC(C(C)(C)C)n1cc(C(=O)O)c(=O)cc1-2 ; Cl]

Step 1: Preparation of ethyl 6-tert-butyl-10-methoxy-9-(3-morpholinopropoxy)-2-oxo-6,7-dihydrobenzo[a]quinolizine-3-carboxylate

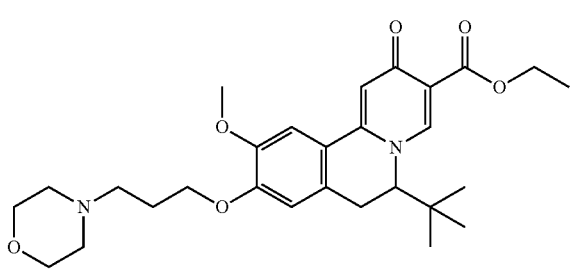 [SMILES: CCOC(=O)c1cn2c(cc1=O)-c1cc(OC)c(OCCCN3CCOCC3)cc1CC2C(C)(C)C]

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 4-(3-chloropropyl)morpholine (57.3 mg, 0.35 mmol) and K$_2$CO$_3$ (74.5 mg, 0.54 mmol). The mixture was stirred at 120° C. for 3 hours. After being cooled to rt, the mixture was filtered and the filtrate was concentrated to give crude ethyl 6-tert-butyl-10-methoxy-9-(3-morpholinopropoxy)-2-oxo-6, 7-dihydrobenzo[a]quinolizine-3-carboxylate which was used in the next step without purification.

Step 2: Preparation of 6-tert-butyl-10-methoxy-9-(3-morpholinopropoxy)-2-oxo-6,7-dihydrobenzo[a]quinolizine-3-carboxylic acid hydrochloride

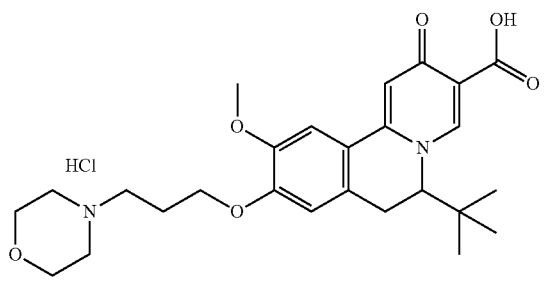 [SMILES: COc1cc2c(cc1OCCCN1CCOCC1)CC(C(C)(C)C)n1cc(C(=O)O)c(=O)cc1-2 ; Cl]

To a solution of crude ethyl 6-tert-butyl-10-methoxy-9-(3-morpholinopropoxy)-2-oxo-6,7-dihydrobenzo[a]quinolizine-3-carboxylate in a mixture solvent of methanol and water (3:1, 4 mL) was added LiOH.H$_2$O (34.0 mg, 0.81 mmol). The mixture was stirred for 2 hours at room temperature, and then acidified with 6 M hydrochloric acid. The mixture was purified by preparative HPLC to give 6-tert-butyl-10-methoxy-9-(3-morpholinopropoxy)-2-oxo-6,7-dihydrobenzo[a]quinolizine-3-carboxylic acid hydrochloride (61.0 mg). $^1$H NMR (400 MHz, DMSO) δ 9.82-10.08 (m, 1H), 8.73 (s, 1H), 7.51 (s, 1H), 7.48 (s, 1H), 7.07 (s, 1H), 4.49-4.63 (m, 1H), 4.10-4.20 (m, 2H), 3.97-4.07 (m, 2H), 3.88 (s, 3H), 3.47-3.59 (m, 4H), 3.36-3.44 (m, 1H), 3.27-3.34 (m, 2H), 3.21-3.26 (m, 1H), 3.06-3.19 (m, 2H), 2.13-2.25 (m, 2H), 0.73 (s, 9H). MS obsd. (ESI$^+$) [(M+H)$^+$]: 471.

Example 193 and 194

(+)-6-tert-butyl-10-methoxy-9-(3-morpholinopropoxy)-2-oxo-6,7-dihydrobenzo[a]quinolizine-3-carboxylic acid and (−)-6-tert-butyl-10-methoxy-9-(3-morpholinopropoxy)-2-oxo-6,7-dihydrobenzo[a]quinolizine-3-carboxylic acid

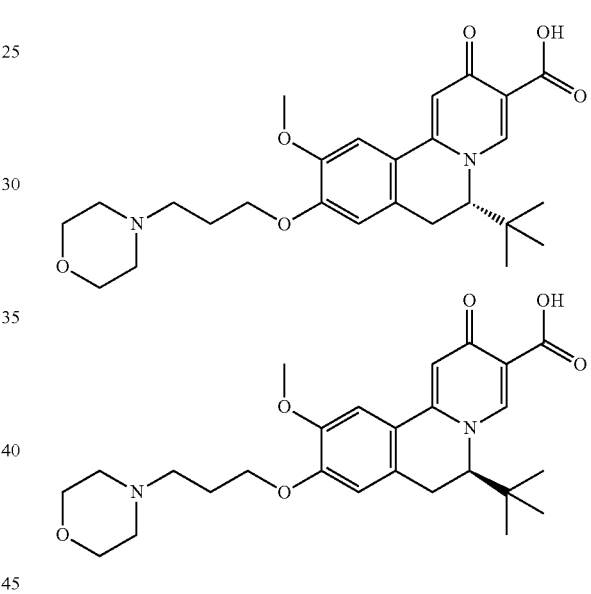

Separation of 6-tert-butyl-10-methoxy-9-(3-morpholinopropoxy)-2-oxo-6,7-dihydrobenzo[a]quinolizine-3-carboxylic acid by chiral HPLC provided (+)-6-tert-butyl-10-methoxy-9-(3-morpholinopropoxy)-2-oxo-6,7-dihydrobenzo[a]quinolizine-3-carboxylic acid (16.0 mg) and (−)-6-tert-butyl-10-methoxy-9-(3-morpholinopropoxy)-2-oxo-6,7-dihydrobenzo[a]quinolizine-3-carboxylic acid (15.0 mg).

Example 193

$^1$H NMR (400 MHz, DMSO) δ 8.72 (s, 1H), 7.47 (s, 1H), 7.45 (s, 1H), 7.06 (s, 1H), 4.54-4.59 (m, 1H), 4.05-4.14 (m, 2H), 3.86 (s, 3H), 3.55-3.60 (m, 4H), 3.34-3.41 (m, 1H), 3.23-3.29 (m, 1H), 2.40-2.46 (m, 2H), 2.31-2.39 (m, 4H), 1.88-1.97 (m, 2H), 0.73 (s, 9H). MS obsd. (ESI$^+$) [(M+H)$^+$]: 471. [α]$_D^{20}$=+76.16° (0.223%, CH$_3$CN).

Example 194

$^1$H NMR (400 MHz, DMSO) δ 8.72 (s, 1H), 7.47 (s, 1H), 7.45 (s, 1H), 7.06 (s, 1H), 4.54-4.59 (m, 1H), 4.05-4.14 (m,

2H), 3.86 (s, 3H), 3.55-3.60 (m, 4H), 3.34-3.41 (m, 1H), 3.23-3.29 (m, 1H), 2.40-2.46 (m, 2H), 2.31-2.39 (m, 4H), 1.88-1.97 (m, 2H), 0.73 (s, 9H). MS obsd. (ESI$^+$) [(M+H)$^+$]: 471.

Example 195: 6-tert-butyl-10-methoxy-2-oxo-9-[3-(2-oxopyrrolidin-1-yl) propoxy]-6,7-dihydrobenzo[a]quinolizine-3-carboxylic acid

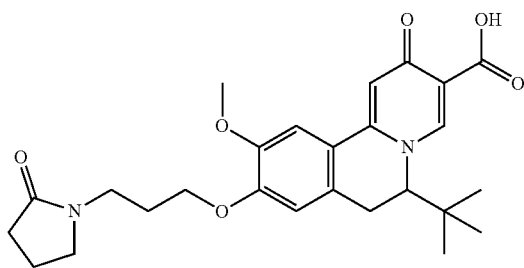 [SMILES: COc1cc2c(cc1OCCCN1CCCC1=O)CC(C(C)(C)C)n1cc(C(=O)O)c(=O)cc1-2]

Step 1: Preparation of 3-(2-oxopyrrolidin-1-yl) propyl 4-methylbenzenesulfonate

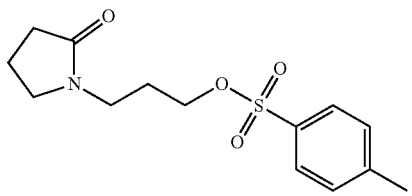 [SMILES: Cc1ccc(S(=O)(=O)OCCCN2CCCC2=O)cc1]

To a solution of 1-(3-hydroxypropyl)pyrrolidin-2-one (2.0 g, 14.0 mmol) in DCM (30 mL) was added Et$_3$N (3.9 mL, 28.0 mmol) and catalytic amount of DMAP. The mixture was stirred for 20 minutes, then to the mixture was added 4-methylbenzenesulfonyl chloride (2.7 g, 14.0 mmol) portionwise at 0° C. The mixture was allowed to warm to room temperature and stirred at rt for 16 hours. The mixture was washed with 4 M hydrochloric acid, followed by saturated aqueous NaHCO$_3$ solution. The organic layer was dried over anhydrous Na$_2$SO$_4$ and concentrated to give 3-(2-oxopyrrolidin-1-yl) propyl 4-methylbenzenesulfonate which was used in the next step without further purification.

Step 2: Preparation of ethyl 6-tert-butyl-10-methoxy-2-oxo-9-[3-(2-oxopyrrolidin-1-yl) propoxy]-6,7-dihydrobenzo[a]quinolizine-3-carboxylate

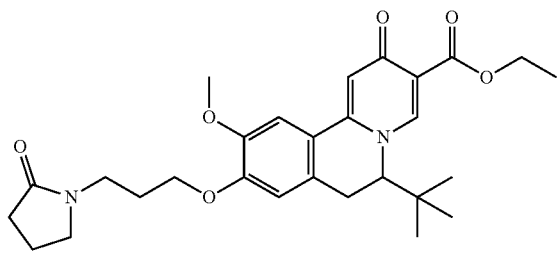 [SMILES: CCOC(=O)c1cn2c(cc1=O)-c1cc(OC)c(OCCCN3CCCC3=O)cc1CC2C(C)(C)C]

To a solution of ethyl 6-tert-butyl-9-hydroxy-10-methoxy-2-oxo-6,7-dihydrobenzo[a]quinolizine-3-carboxylate (100 mg, 0.27 mmol) in DMF (3 mL) was added 3-(2-oxopyrrolidin-1-yl)propyl 4-methylbenzenesulfonate (104.1 mg, 0.35 mmol) and K$_2$CO$_3$ (74.5 mg, 0.54 mmol). The mixture was stirred at 120° C. for 3 hours. After being cooled to rt, the mixture was filtered and the filtrate was concentrated to give crude ethyl 6-tert-butyl-10-methoxy-2-oxo-9-[3-(2-oxopyrrolidin-1-yl) propoxy]-6,7-dihydrobenzo[a]quinolizine-3-carboxylate which was used in the next step without further purification.

Step 3: Preparation of 6-tert-butyl-10-methoxy-2-oxo-9-[3-(2-oxopyrrolidin-1-yl)propoxy]-6,7-dihydrobenzo[a]quinolizine-3-carboxylic acid

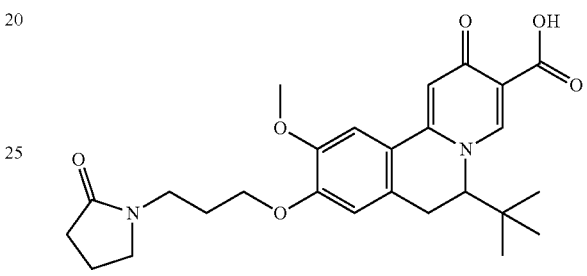

To a solution of crude ethyl 6-tert-butyl-10-methoxy-2-oxo-9-[3-(2-oxopyrrolidin-1-yl) propoxy]-6,7-dihydrobenzo[a]quinolizine-3-carboxylate in a mixture solvent of methanol and water (3:1, 4 mL) was added LiOH.H$_2$O (34.0 mg, 0.81 mmol). The mixture was stirred at room temperature for 2 hours, then acidified with 6 M hydrochloric acid and extracted with DCM. The organic layer was dried over anhydrous Na$_2$SO$_4$ and concentrated under reduced pressure. The residue was purified by preparative HPLC to give 6-tert-butyl-10-methoxy-2-oxo-9-[3-(2-oxopyrrolidin-1-yl) propoxy]-6,7-dihydrobenzo[a]quinolizine-3-carboxylic acid (31.5 mg). $^1$H NMR (400 MHz, CDCl$_3$) δ 8.50 (s, 1H), 7.15 (s, 1H), 7.10 (s, 1H), 6.74 (s, 1H), 4.05-4.15 (m, 3H), 3.93 (s, 3H), 3.48-3.56 (m, 4H), 3.39-3.47 (m, 1H), 3.15-3.25 (m, 1H), 2.37-2.45 (m, 2H), 2.12-2.20 (m, 2H), 2.03-2.10 (m, 2H), 0.84 (s, 9H). MS obsd. (ESI$^+$) [(M+H)$^+$]: 469.

Example 196: 6-tert-butyl-10-methoxy-2-oxo-9-(3-pyrrolidin-1-ylpropoxy)-6,7-dihydrobenzo[a]quinolizine-3-carboxylic acid

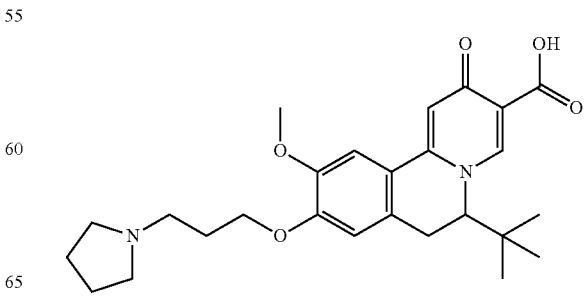

307

Step 1: Preparation of ethyl 6-tert-butyl-10-methoxy-2-oxo-9-(3-pyrrolidin-1-ylpropoxy)-6,7-dihydrobenzo[a]quinolizine-3-carboxylate

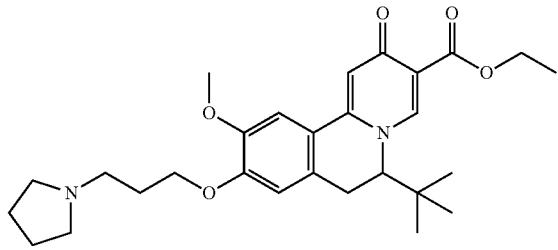 [SMILES: CCOC(=O)c1cn2c(cc1=O)-c1cc(OC)c(OCCCN3CCCC3)cc1CC2C(C)(C)C]

To a solution of ethyl 6-tert-butyl-9-hydroxy-10-methoxy-2-oxo-6,7-dihydrobenzo[a]quinolizine-3-carboxylate (60 mg, 0.16 mmol) in DMF (3 mL) was added 1-(3-chloropropyl)pyrrolidine hydrochloride (35.0 mg, 0.19 mmol) and $K_2CO_3$ (44.2 mg, 0.32 mmol). The mixture was stirred at 120° C. for 2 hours. After being cooled to rt, the mixture was filtered and the filtrate was concentrated to give ethyl 6-tert-butyl-10-methoxy-2-oxo-9-(3-pyrrolidin-1-ylpropoxy)-6,7-dihydrobenzo[a]quinolizine-3-carboxylate which was used in the next step without purification.

Step 2: Preparation of 6-tert-butyl-10-methoxy-2-oxo-9-(3-pyrrolidin-1-ylpropoxy)-6,7-dihydrobenzo[a]quinolizine-3-carboxylic acid

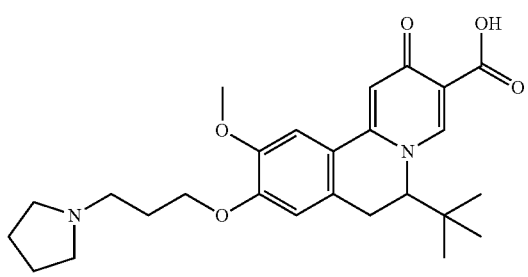 [SMILES: COc1cc2c(cc1OCCCN1CCCC1)CC(C(C)(C)C)n1cc(C(=O)O)c(=O)cc1-2]

To a solution of crude ethyl 6-tert-butyl-10-methoxy-2-oxo-9-(3-pyrrolidin-1-ylpropoxy)-6,7-dihydrobenzo[a]quinolizine-3-carboxylate in a mixture solvent of methanol and water (3:1, 4 mL) was added $LiOH.H_2O$ (20.2 mg, 0.48 mmol). The mixture was stirred at room temperature for 2 hours, and then acidified with 6 M hydrochloric acid. The mixture was then basified with saturated aqueous $NaHCO_3$ solution. The resulting mixture was extracted with DCM. The organic layer was dried over anhydrous $Na_2SO_4$ and concentrated under reduced pressure. The residue was purified by preparative HPLC to give 6-tert-butyl-10-methoxy-2-oxo-9-(3-pyrrolidin-1-ylpropoxy)-6,7-dihydrobenzo[a]quinolizine-3-carboxylic acid (7.0 mg). $^1$H NMR (400 MHz, DMSO) δ 8.72 (s, 1H), 7.47 (s, 1H), 7.45 (s, 1H), 7.07 (s, 1H), 4.53-4.59 (m, 1H), 4.04-4.16 (m, 2H), 3.87 (s, 3H), 3.35-3.41 (m, 1H), 3.24-3.30 (m, 1H), 2.52-2.56 (m, 2H), 2.36-2.46 (m, 4H), 1.88-1.97 (m, 2H), 1.63-1.71 (m, 4H), 0.73 (s, 9H). MS obsd. (ESI$^+$) [(M+H)$^+$]: 455.

308

Example 197: 6-cyclobutyl-10-methoxy-9-(3-methoxypropoxy)-2-oxo-6,7-dihydrobenzo[a]quinolizine-3-carboxylic acid

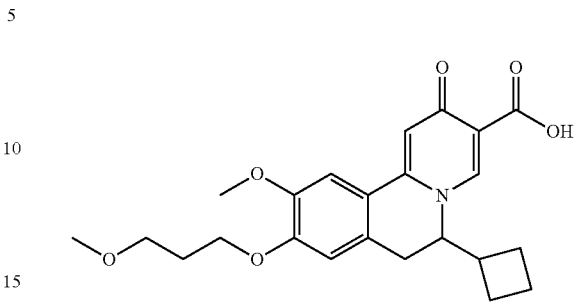

Step 1: Preparation of 1-cyclobutyl-2-[4-methoxy-3-(3-methoxypropoxy)phenyl]ethanone

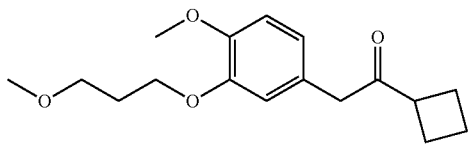 [SMILES: COCCCOc1cc(CC(=O)C2CCC2)ccc1OC]

To a mixture of 4-bromo-1-methoxy-2-(3-methoxypropoxy)benzene (2.74 g, 10 mmol), tris(dibenzylideneacetone)dipalladium(0) (92 mg, 0.1 mmol), 9,9-dimethyl-4,5-bis(diphenylphosphino)xanthene (116 mg, 0.2 mmol) and t-BuONa (2.02 g, 22 mmol) in THF (20 mL) was added 3-methylbutan-2-one (1.96 g, 20 mmol). The resulting mixture was heated at 50° C. for 7 h under argon. After being cooled to room temperature, the mixture was partitioned between water and EtOAc. The separated aqueous layer was extracted with EtOAc (50 mL×2), and then the combined organic extracts were filtered. The filtrate was washed with brine, dried over anhydrous $Na_2SO_4$, and concentrated under reduced pressure to give crude 1-cyclobutyl-2-[4-methoxy-3-(3-methoxypropoxy)phenyl]ethanone (3.47 g) as a yellow oil which was directly used in the next step.

Step 2: Preparation of 1-cyclobutyl-2-[4-methoxy-3-(3-methoxypropoxy)phenyl]ethanamine

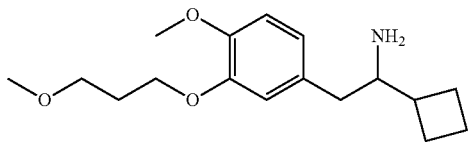 [SMILES: COCCCOc1cc(CC(N)C2CCC2)ccc1OC]

To a mixture of crude 1-cyclobutyl-2-[4-methoxy-3-(3-methoxypropoxy)phenyl]ethanone (3.47 g, 10 mmol) and ammonium acetate (11.55 g, 150 mmol) in methanol (20 mL) was added $NaBH_3CN$ (605 mg, 9.6 mmol). The resulting mixture was stirred at room temperature for 40 h. The mixture was basified with 2 M NaOH aqueous solution to pH=12-14, and then extracted with $CH_2Cl_2$ (30 mL×3). The combined organic layers were concentrated under reduced pressure. The residue was dissolved in $CH_2Cl_2$ (20 mL), and then the solution was washed with 1 M hydrochloric acid (30 mL×3). The separated aqueous layers were combined, basified with 2 M NaOH aqueous solution to pH=12-14, and then extracted with CH₂Cl₂ (40 mL×3). The combined organic layers were washed with brine, dried over anhydrous Na₂SO₄, and concentrated to give crude 1-cyclobutyl-2-[4-methoxy-3-(3-methoxypropoxy)phenyl]ethanamine (1.13 g) as a yellow oil.

Step 3: Preparation of N-[1-cyclobutyl-2-[4-methoxy-3-(3-methoxypropoxy)phenyl]ethyl]formamide

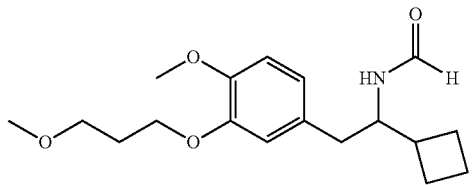 [SMILES: COCCCOc1cc(CC(NC=O)C2CCC2)ccc1OC]

A solution of 1-cyclobutyl-2-[4-methoxy-3-(3-methoxypropoxy)phenyl]ethanamine (1.13 g, 3.86 mmol) and formic acid (0.2 mL) in ethyl formate (20 mL) was heated at 90° C. overnight. The solvent was removed under reduced pressure to get crude N-[1-cyclobutyl-2-[4-methoxy-3-(3-methoxypropoxy)phenyl]ethyl]formamide (1.24 g) as a yellow oil which was directly used in the next step.

Step 4: Preparation of 3-cyclobutyl-7-methoxy-6-(3-methoxypropoxy)-3,4-dihydroisoquinoline

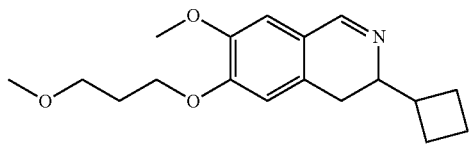 [SMILES: COCCCOc1cc2c(cc1OC)C=NC(C1CCC1)C2]

To a solution of N-[1-cyclobutyl-2-[4-methoxy-3-(3-methoxypropoxy)phenyl]ethyl]formamide (1.24 g, 3.86 mmol) in CH₃CN (10 mL) was added POCl₃ (708 mg, 4.63 mmol). The mixture was heated at 60° C. for 2 h and then concentrated under reduced pressure. The residue was dissolved in CH₃CN (10 mL), and then the mixture was basified with ammonium hydroxide to pH=10 at 0° C. The resulting mixture was extracted with CH₂Cl₂. The combined organic layers were washed with brine, dried over anhydrous Na₂SO₄, and concentrated to give crude 3-cyclobutyl-7-methoxy-6-(3-methoxypropoxy)-3,4-dihydroisoquinoline (920 mg) as a yellow oil.

Step 5: Preparation of ethyl 6-cyclobutyl-10-methoxy-9-(3-methoxypropoxy)-2-oxo-1,6,7,11b-tetrahydrobenzo[a]quinolizine-3-carboxylate

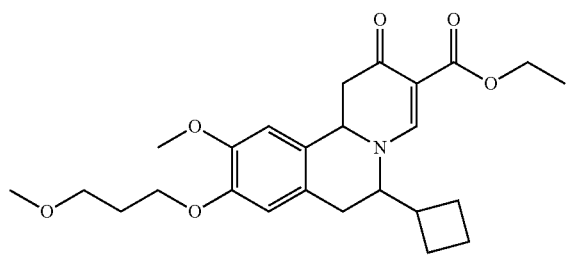 [SMILES: CCOC(=O)C1=CN2C(CC1=O)c1cc(OC)c(OCCCOC)cc1CC2C1CCC1]

A mixture of crude 3-cyclobutyl-7-methoxy-6-(3-methoxypropoxy)-3,4-dihydroisoquinoline (920 mg, 3 mmol) and ethyl 2-(ethoxymethylene)-3-oxo-butanoate (1.67 g, 9 mmol) in ethanol (10 mL) was heated at 100° C. for 16 h. The mixture was concentrated under reduced pressure to give crude ethyl 6-cyclobutyl-10-methoxy-9-(3-methoxypropoxy)-2-oxo-1,6,7,11b-tetrahydrobenzo[a]quinolizine-3-carboxylate (2.43 g) as a brown oil which was used in the next step without purification.

Step 6: Preparation of ethyl 6-cyclobutyl-10-methoxy-9-(3-methoxypropoxy)-2-oxo-6,7-dihydrobenzo[a]quinolizine-3-carboxylate

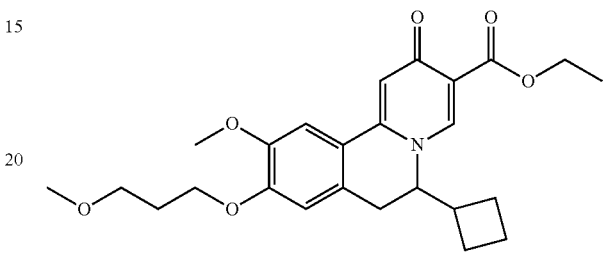

A mixture of crude ethyl 6-cyclobutyl-10-methoxy-9-(3-methoxypropoxy)-2-oxo-1,6,7,11b-tetrahydrobenzo[a]quinolizine-3-carboxylate (2.43 g, 3 mmol) and p-chloranil (738 mg, 3 mmol) in DME (10 mL) was heated at 70° C. for 3 h under argon. After being cooled to room temperature, the mixture was diluted with CH₂Cl₂ and H₂O. The separated organic layer was washed with saturated NaHCO₃ aqueous solution and brine, dried over anhydrous Na₂SO₄, and concentrated to give crude ethyl 6-cyclobutyl-10-methoxy-9-(3-methoxypropoxy)-2-oxo-6,7-dihydrobenzo[a]quinolizine-3-carboxylate (2.62 g) as a brown oil.

Step 7: Preparation of 6-cyclobutyl-10-methoxy-9-(3-methoxypropoxy)-2-oxo-6,7-dihydrobenzo[a]quinolizine-3-carboxylic acid

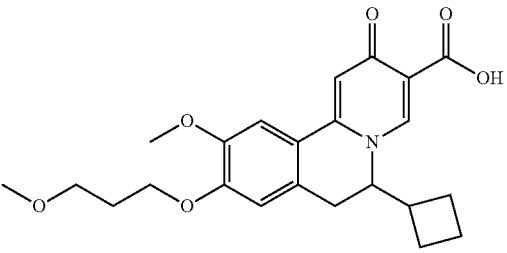 [SMILES: COCCCOc1cc2c(cc1OC)-c1cc(=O)c(C(=O)O)cn1C(C1CCC1)C2]

To a mixture of crude ethyl 6-cyclobutyl-10-methoxy-9-(3-methoxypropoxy)-2-oxo-6,7-dihydrobenzo[a]quinolizine-3-carboxylate (2.62 g, 3 mmol) in methanol (12 mL) and H₂O (3 mL) was added LiOH.H₂O (492 mg, 12 mmol). The resulting mixture was stirred at room temperature for 16 h. The reaction mixture was acidified by 1 M hydrochloric acid to pH=2-3, and then extracted with CH₂Cl₂ (50 mL×3). The combined organic layers were washed with brine, dried over anhydrous Na₂SO₄, and concentrated. The residue was precipitated from diethyl ether/ethanol to afford 6-cyclobutyl-10-methoxy-9-(3-methoxypropoxy)-2-oxo-6,7-dihydrobenzo[a]quinolizine-3-carboxylic acid (500 mg) as a pale solid. $^1$H NMR (400 MHz, DMSO-d6): δ 8.83 (s, 1H), 7.52 (s, 1H), 7.47 (s, 1H), 7.01 (s, 1H), 4.74 (dd, 1H), 4.16-4.02 (m, 2H), 3.88 (s, 3H), 3.48 (t, 2H), 3.29 (d, 1H), 3.26 (s, 3H), 2.89 (d, 1H), 2.40-2.26 (m, 1H), 1.99 (quin, 2H), 1.93-1.81 (m, 2H), 1.78-1.65 (m, 3H), 1.61-1.51 (m, 1H). MS obsd. (ESI⁺) [(M+H)⁺]: 414.

Example 198: 9,10-dimethoxy-2-oxo-6-(2,2,2-trifluoroethyl)-6,7-dihydrobenzo[a]quinolizine-3-carboxylic acid

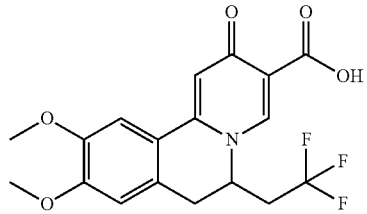 [SMILES: COc1cc2c(cc1OC)-c1cc(=O)c(C(=O)O)cn1C(CC(F)(F)F)C2]

Step 1: Preparation of 1-(3,4-dimethoxyphenyl)-4,4,4-trifluoro-butane-1,3-dione

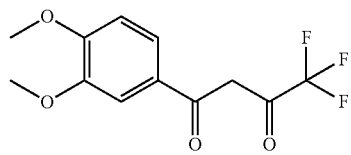 [SMILES: COc1ccc(C(=O)CC(=O)C(F)(F)F)cc1OC]

To a solution of 1-(3,4-dimethoxyphenyl)ethanone (5.4 g, 30 mmol) in DMF (30 mL) was added 60% NaH in mineral oil (1.56 g, 39 mmol) in portions at a temperature between −5° C. and 0° C. After the mixture was stirred at this temperature for 30 minutes, to the resulting mixture was added methyl 2,2,2-trifluoroacetate (5.0 g, 39 mmol). The mixture was allowed to warm to rt and stirred overnight, and then poured into ice-water. The resulting mixture was acidified with 2 M hydrochloric acid to pH=3, and extracted with EtOAc. The combined organic layers were washed with water and brine, dried over anhydrous $Na_2SO_4$ and concentrated to give crude 1-(3,4-dimethoxyphenyl)-4,4,4-trifluoro-butane-1,3-dione (9.48 g) as an orange solid which was used in the next step without purification.

Step 2: Preparation of 3-(3,4-dimethoxyphenyl)-5-(trifluoromethyl)-4H-isoxazol-5-ol

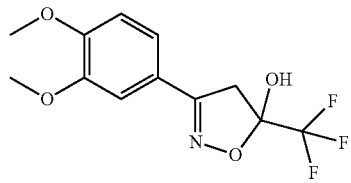 [SMILES: COc1ccc(C2=NOC(O)(C(F)(F)F)C2)cc1OC]

A mixture of hydroxylamine hydrochloride (1.38 g, 20 mmol) and sodium acetate (1.64 g, 20 mmol) in ethanol (100 mL) was heated at 90° C. for 15 minutes. Then to the mixture was added 1-(3,4-dimethoxyphenyl)-4,4,4-trifluoro-butane-1,3-dione (6.32 g, 20 mmol) and the mixture was stirred at 90° C. for 4 h. The resulting mixture was concentrated and the residue was extracted with $CHCl_3$. The combined organic extracts were washed with brine, dried over anhydrous $Na_2SO_4$, and concentrated to give 3-(3,4-dimethoxyphenyl)-5-(trifluoromethyl)-4H-isoxazol-5-ol (5.95 g) as a yellow solid which was directly used in the next step without purification.

Step 3: Preparation of 3-(3,4-dimethoxyphenyl)-5-(trifluoromethyl)isoxazole

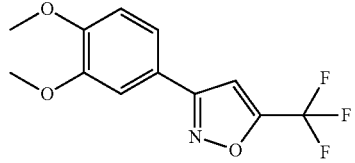 [SMILES: COc1ccc(-c2cc(C(F)(F)F)on2)cc1OC]

A mixture of 3-(3,4-dimethoxyphenyl)-5-(trifluoromethyl)-4H-isoxazol-5-ol (5.95 g, 20 mmol) and concentrated $H_2SO_4$ (0.4 mL) in acetic acid (60 mL) was heated at 115° C. overnight. After the solvent was removed by concentration under reduced pressure, the residue was poured into water. The resulting suspension was stirred at room temperature for 15 minutes, and then filtered. The filter cake was dissolved in $CH_2Cl_2$. The organic solution was washed with brine, dried over anhydrous $Na_2SO_4$, and concentrated. The residue was purified by flash column to afford 3-(3,4-dimethoxyphenyl)-5-(trifluoromethyl)isoxazole (4.43 g) as a yellow oil which was used in the next step without purification.

Step 4: Preparation of 2-(3,4-dimethoxyphenyl)-3-(2,2,2-trifluoroethyl)aziridine

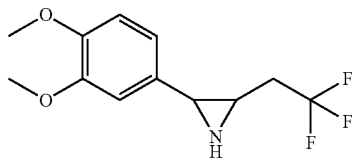 [SMILES: COc1ccc(C2NC2CC(F)(F)F)cc1OC]

To a solution of $LiAlH_4$ in THF (60 mL, 120 mmol) was added 3-(3,4-dimethoxyphenyl)-5-(trifluoromethyl)isoxazole (5.42 g, 20 mmol) in THF (40 mL). The resulting mixture was stirred at 65° C. for 2 h. Then to the mixture was added additional $LiAlH_4$ in THF (20 mL, 40 mmol). The resulting mixture was stirred at 75° C. for 4 h, and then cooled to room temperature.

The reaction was quenched with $H_2O$ at 0° C. Then to the resulting mixture was added potassium sodium tartrate tetrahydrate aqueous solution. The resulting mixture was stirred at room temperature for 2 h, and then extracted with EtOAc (100 mL×5). The combined organic layers were washed with brine, dried over anhydrous $Na_2SO_4$, and concentrated. The residue was purified by flash chromatography to afford 2-(3,4-dimethoxyphenyl)-3-(2,2,2-trifluoroethyl)aziridine (1.90 g) as a yellow oil which was used in the next step without further purification.

Step 5: Preparation of 1-(3,4-dimethoxyphenyl)-4,4,4-trifluoro-butan-2-amine

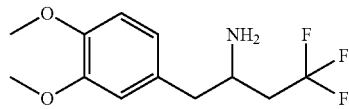 [SMILES: COc1ccc(CC(N)CC(F)(F)F)cc1OC]

A mixture of 2-(3,4-dimethoxyphenyl)-3-(2,2,2-trifluoroethyl)aziridine (783 mg, 3 mmol) and 10% palladium on carbon (78 mg) in methanol (8 mL) was stirred under hydrogen atmosphere at room temperature for 16 h, and then filtered. The filtrate was concentrated and the residue was dissolved in $CH_2Cl_2$ (30 mL). The solution was washed by 1 M hydrochloric acid. The separated aqueous layer was basified by saturated $NaHCO_3$ aqueous solution to pH=8-9, and then extracted with $CH_2Cl_2$ (30 mL×3). The combined organic layers were washed with brine, dried over anhydrous $Na_2SO_4$, and concentrated to afford 1-(3,4-dimethoxyphenyl)-4,4,4-trifluoro-butan-2-amine (573 mg) as a red oil which was used in the next step without further purification.

Step 6: Preparation of N-[1-[(3,4-dimethoxyphenyl)methyl]-3,3,3-trifluoro-propyl]formamide

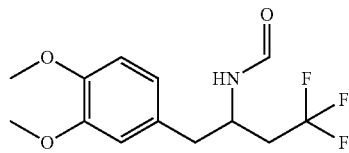 [SMILES: COc1ccc(CC(CC(F)(F)F)NC=O)cc1OC]

A solution of 1-(3,4-dimethoxyphenyl)-4,4,4-trifluoro-butan-2-amine (563 mg, 2.14 mmol) in ethyl formate (10 mL) and formic acid (0.1 mL) was heated at 90° C. overnight. The mixture was concentrated under reduced pressure to afford N-[1-[(3,4-dimethoxyphenyl)methyl]-3,3,3-trifluoro-propyl]formamide (663 mg) as a green oil which was used in the next step without purification.

Step 7: Preparation of 6,7-dimethoxy-3-(2,2,2-trifluoroethyl)-3,4-dihydroisoquinoline

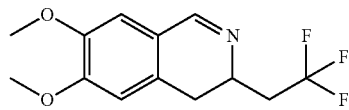 [SMILES: COc1cc2c(cc1OC)CC(CC(F)(F)F)N=C2]

To a solution of crude N-[1-[(3,4-dimethoxyphenyl)methyl]-3,3,3-trifluoro-propyl]formamide (663 mg, 2.14 mmol) in acetonitrile (6 mL) was added $POCl_3$ (393 mg, 2.57 mmol). The reaction mixture was heated at 60° C. for 2 h and concentrated. The residue was dissolved in $CH_2Cl_2$ (20 mL) and then basified by ammonium hydroxide to pH=9-10 at 0° C. The resulting mixture was stirred at room temperature for 1 h, and extracted with $CH_2Cl_2$ (30 mL×3).

The combined organic layers were washed with brine, dried over anhydrous $Na_2SO_4$, and concentrated under reduced pressure to afford crude 6,7-dimethoxy-3-(2,2,2-trifluoroethyl)-3,4-dihydroisoquinoline (577 mg) as a yellow oil.

Step 8: Preparation of ethyl 9,10-dimethoxy-2-oxo-6-(2,2,2-trifluoroethyl)-1,6,7,11b-tetrahydrobenzo[a]quinolizine-3-carboxylate

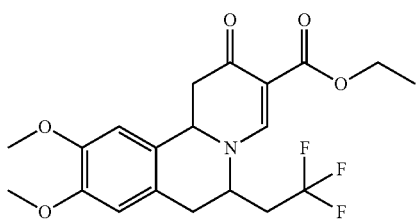 [SMILES: CCOC(=O)C1=CN2C(CC(F)(F)F)Cc3cc(OC)c(OC)cc3C2CC1=O]

A mixture of crude 6,7-dimethoxy-3-(2,2,2-trifluoroethyl)-3,4-dihydroisoquinoline (577 mg, 2.14 mmol) and ethyl 2-(dimethylaminomethylene)-3-oxo-butanoate (1.19 g, 6.42 mmol) in ethanol (6 mL) was heated at 100° C. for 16 h. The mixture was concentrated, and the residue was purified by recrystallization from diethyl ether/petroleum ether to afford ethyl 9,10-dimethoxy-2-oxo-6-(2,2,2-trifluoroethyl)-1,6,7,11b-tetrahydrobenzo[a]quinolizine-3-carboxylate (568 mg) as a yellow solid which was used in the next step without further purification.

Step 9: Preparation of ethyl 9,10-dimethoxy-2-oxo-6-(2,2,2-trifluoroethyl)-6,7-dihydrobenzo[a]quinolizine-3-carboxylate

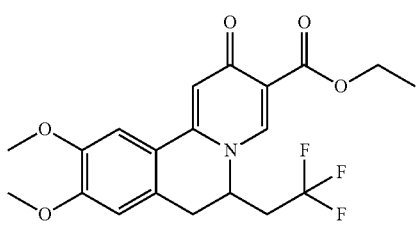 [SMILES: CCOC(=O)c1cn2c(cc1=O)-c1cc(OC)c(OC)cc1CC2CC(F)(F)F]

A mixture of ethyl 9,10-dimethoxy-2-oxo-6-(2,2,2-trifluoroethyl)-1,6,7,11b-tetrahydrobenzo[a]quinolizine-3-carboxylate (568 mg, 1.4 mmol) and p-chloranil (344 mg, 1.4 mmol) in DME (5 mL) was heated at 70° C. for 3 h under argon. After being cooled to room temperature, the resulting suspension was filtered. The filter cake was washed with DME, then dried to give ethyl 9,10-dimethoxy-2-oxo-6-(2,2,2-trifluoroethyl)-6,7-dihydrobenzo[a]quinolizine-3-carboxylate (375 mg) as a light-yellow solid.

Step 10: Preparation of 9,10-dimethoxy-2-oxo-6-(2,2,2-trifluoroethyl)-6,7-dihydrobenzo[a]quinolizine-3-carboxylic acid

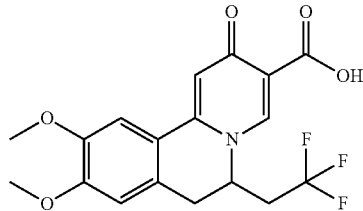 [SMILES: COc1cc2c(cc1OC)-c1cc(=O)c(C(=O)O)cn1C(CC(F)(F)F)C2]

To a solution of ethyl 9,10-dimethoxy-2-oxo-6-(2,2,2-trifluoroethyl)-6,7-dihydrobenzo[a]quinolizine-3-carboxylate (375 mg, 0.81 mmol) in methanol (4 mL) and H$_2$O (1 mL) was added LiOH.H$_2$O (153 mg, 3.64 mmol). The resulting mixture was stirred at room temperature for 2 h, and then acidified with 1 M hydrochloric acid to pH=2-3. The resulting precipitate was filtered. The filter cake was dried to afford 9,10-dimethoxy-2-oxo-6-(2,2,2-trifluoroethyl)-6,7-dihydrobenzo[a]quinolizine-3-carboxylic acid (285 mg) as a yellow solid. $^1$H NMR (400 MHz, DMSO-d6): δ 8.76 (s, 1H), 7.56 (s, 1H), 7.50 (s, 1H), 7.03 (s, 1H), 5.29 (m, 1H), 3.89 (s, 3H), 3.85 (s, 3H), 3.44 (d, 1H), 3.02 (d, 1H), 2.62 (d, 2H). MS obsd. (ESI$^+$) [(M+H)$^+$]: 384.

Example 199: 10-methoxy-9-(3-methoxypropoxy)-2-oxo-6-(2,2,2-trifluoroethyl)-6,7-dihydrobenzo[a]quinolizine-3-carboxylic acid

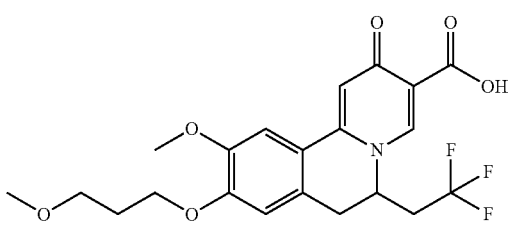 [SMILES: COCCCOc1cc2c(cc1OC)-c1cc(=O)c(C(=O)O)cn1C(CC(F)(F)F)C2]

Step 1: Preparation of 1-[4-methoxy-3-(3-methoxypropoxy)phenyl]ethanone

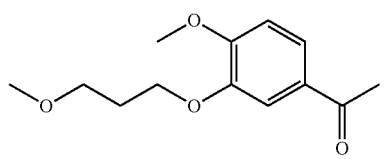 [SMILES: COCCCOc1cc(C(C)=O)ccc1OC]

To a mixture of 1-(3-hydroxy-4-methoxy-phenyl)ethanone (5.0 g, 30 mmol) and K$_2$CO$_3$ (8.28 g, 60 mmol) in acetone (60 mL) was added 1-bromo-3-methoxy-propane (13.78 g, 90 mmol), the resulting mixture was stirred at 60° C. for 16 h. After being cooled to room temperature, the reaction mixture was filtered. The filtrate was concentrated under reduced pressure to afford 1-[4-methoxy-3-(3-methoxypropoxy)phenyl]ethanone (7.20 g) as a yellow oil which was directly used in the next step without purification.

Step 2: Preparation of 4,4,4-trifluoro-1-[4-methoxy-3-(3-methoxypropoxy)phenyl]butane-1,3-dione

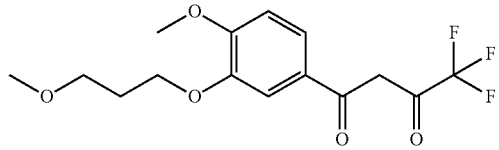 [SMILES: COCCCOc1cc(C(=O)CC(=O)C(F)(F)F)ccc1OC]

To a solution of 1-[4-methoxy-3-(3-methoxypropoxy)phenyl]ethanone (7.20 g, 30 mmol) in DMF (30 mL) was added 60% NaH in mineral oil (1.56 g, 39 mmol) in portions at a temperature between −5° C. and 0° C. The resulting mixture was stirred at this temperature for 30 minutes, then to the mixture was added methyl 2,2,2-trifluoroacetate (5.0 g, 39 mmol). The mixture was allowed to warm to room temperature, stirred overnight, and then poured into ice-water. The resulting mixture was acidified with 2 M hydrochloric acid to pH=3, and then extracted with EtOAc. The combined organic layers were washed with water and brine, dried over anhydrous Na$_2$SO$_4$ and concentrated to give crude 4,4,4-trifluoro-1-[4-methoxy-3-(3-methoxypropoxy)phenyl]butane-1,3-dione (12.1 g) as a red oil which was directly used in the next step without purification.

Step 3: Preparation of 3-[4-methoxy-3-(3-methoxypropoxy)phenyl]-5-(trifluoromethyl)-4H-isoxazol-5-ol

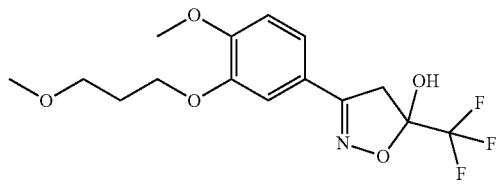 [SMILES: COCCCOc1cc(C2=NOC(O)(C(F)(F)F)C2)ccc1OC]

A mixture of hydroxylamine hydrochloride (2.07 g, 30 mmol) and sodium acetate (2.46 g, 30 mmol) in ethanol (150 mL) was heated at 90° C. for 15 minutes. Then to the resulting mixture was added 4,4,4-trifluoro-1-[4-methoxy-3-(3-methoxypropoxy)phenyl]butane-1,3-dione (12.1 g, 30 mmol). The mixture was stirred at 90° C. for 4 h and then concentrated. The residue was extracted with CHCl$_3$. The combined organic solution was washed with brine, dried over anhydrous Na$_2$SO$_4$, and concentrated. The residue was purified by flash chromatography to afford 3-[4-methoxy-3-(3-methoxypropoxy)phenyl]-5-(trifluoromethyl)-4H-isoxazol-5-ol (9.36 g) as a yellow solid which was directly used in the next step without purification.

Step 4: Preparation of 3-[4-methoxy-3-(3-methoxypropoxy)phenyl]-5-(trifluoromethyl)isoxazole

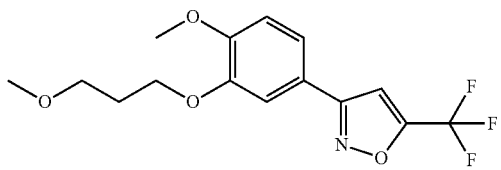 [SMILES: COCCCOc1cc(-c2cc(C(F)(F)F)on2)ccc1OC]

A mixture of 3-[4-methoxy-3-(3-methoxypropoxy)phenyl]-5-(trifluoromethyl)-4H-isoxazol-5-ol (2.45 g, 7 mmol) and concentrated H₂SO₄ (0.1 mL) in acetic acid (20 mL) was heated at 115° C. for 16 h. The mixture was concentrated, and the residue was poured into water. The resulting mixture was extracted with CH₂Cl₂ (50 mL×3). The combined organic layers were washed with brine, dried over anhydrous Na₂SO₄, and concentrated. The residue was purified by flash chromatography to afford 3-[4-methoxy-3-(3-methoxypropoxy)phenyl]-5-(trifluoromethyl)isoxazole (1.63 g) as a white solid which was used in the next step without purification.

Step 5: Preparation of 2-[4-methoxy-3-(3-methoxypropoxy)phenyl]-3-(2,2,2-trifluoroethyl)aziridine

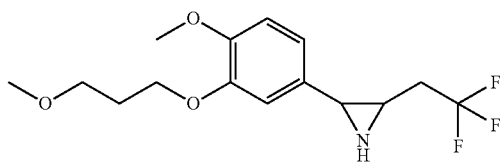 [SMILES: COCCCOc1cc(C2NC2CC(F)(F)F)ccc1OC]

To a solution of LiAlH₄ in THF (14.7 mL, 29.4 mmol) was added 3-[4-methoxy-3-(3-methoxypropoxy)phenyl]-5-(trifluoromethyl)isoxazole (1.63 g, 4.9 mmol) in THF (10 mL). The resulting mixture was stirred at 75° C. for 3 h under argon. After the mixture was cooled to room temperature, the reaction was quenched by addition of potassium sodium tartrate tetrahydrate aqueous solution (80 mL) at 0° C. The mixture was extracted with EtOAc (40 mL×3). The combined organic layers were washed with brine, dried over anhydrous Na₂SO₄, and concentrated to give crude 2-[4-methoxy-3-(3-methoxypropoxy)phenyl]-3-(2,2,2-trifluoroethyl)aziridine (1.38 g) as a yellow oil which was directly used in the next step without purification.

Step 6: Preparation of 4,4,4-trifluoro-1-[4-methoxy-3-(3-methoxypropoxy)phenyl]butan-2-amine

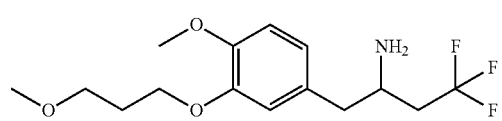 [SMILES: COCCCOc1cc(CC(N)CC(F)(F)F)ccc1OC]

A mixture of 2-[4-methoxy-3-(3-methoxypropoxy)phenyl]-3-(2,2,2-trifluoroethyl)aziridine (1.38 g, 4.3 mmol) and 10% palladium on carbon (276 mg) in methanol (10 mL) was stirred under hydrogen atmosphere at room temperature for 48 h, and then filtered. The filtrate was concentrated, and the residue was dissolved in CH₂Cl₂ (30 mL). The organic solution was washed with 1 M hydrochloric acid. The separated aqueous layer was basified by saturated NaHCO₃ aqueous solution to pH=8-9, and then extracted with CH₂Cl₂ (30 mL×3). The combined organic layers were washed with brine, dried over anhydrous Na₂SO₄ and concentrated to afford 4,4,4-trifluoro-1-[4-methoxy-3-(3-methoxypropoxy)phenyl]butan-2-amine (854 mg) as a yellow oil.

Step 7: Preparation of N-[3,3,3-trifluoro-1-[[4-methoxy-3-(3-methoxypropoxy)phenyl]methyl]propyl]formamide

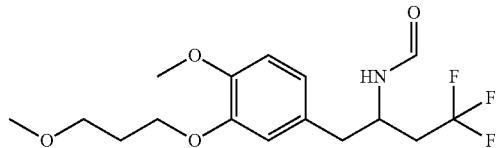 [SMILES: COCCCOc1cc(CC(CC(F)(F)F)NC=O)ccc1OC]

A solution of 4,4,4-trifluoro-1-[4-methoxy-3-(3-methoxypropoxy)phenyl]butan-2-amine (854 mg, 2.7 mmol) in ethyl formate (10 mL) and formic acid (0.1 mL) was heated at 90° C. overnight. The mixture was concentrated to give crude N-[3,3,3-trifluoro-1-[[4-methoxy-3-(3-methoxypropoxy)phenyl]methyl]propyl]formamide (930 mg) as a yellow oil which was directly used in the next step without purification.

Step 8: Preparation of 7-methoxy-6-(3-methoxypropoxy)-3-(2,2,2-trifluoroethyl)-3,4-dihydroisoquinoline

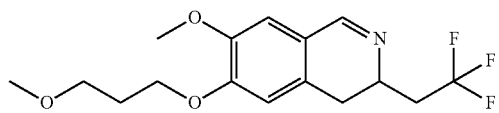 [SMILES: COCCCOc1cc2c(cc1OC)C=NC(CC(F)(F)F)C2]

To a solution of crude N-[3,3,3-trifluoro-1-[[4-methoxy-3-(3-methoxypropoxy)phenyl]methyl]propyl]formamide (930 mg, 2.67 mmol) in acetonitrile (10 mL) was added POCl₃ (490 mg, 3.20 mmol). The reaction mixture was heated at 60° C. for 2 h, and then concentrated under reduced pressure. The residue was dissolved in CH₂Cl₂ and then basified with ammonium hydroxide at 0° C. The resulting mixture was stirred at room temperature for 1 h. The separated aqueous layer was extracted with CH₂Cl₂. The combined organic layers were washed with brine, dried over anhydrous Na₂SO₄, and concentrated under reduced pressure to afford crude 7-methoxy-6-(3-methoxypropoxy)-3-(2,2,2-trifluoroethyl)-3,4-dihydroisoquinoline (900 mg) as a yellow oil which was directly used in the next step without purification.

Step 9: Preparation of ethyl 10-methoxy-9-(3-methoxypropoxy)-2-oxo-6-(2,2,2-trifluoroethyl)-1,6,7,11b-tetrahydrobenzo[a]quinolizine-3-carboxylate

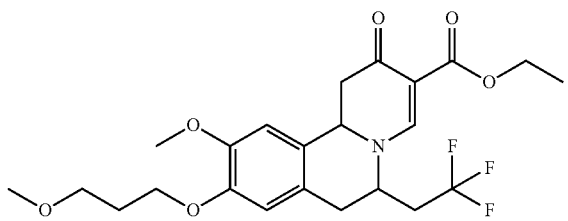 [SMILES: CCOC(=O)C1=CN2C(CC(F)(F)F)Cc3cc(OCCCOC)c(OC)cc3C2CC1=O]

A mixture of crude 7-methoxy-6-(3-methoxypropoxy)-3-(2,2,2-trifluoroethyl)-3,4-dihydroisoquinoline (900 mg, 2.67 mmol) and ethyl 2-(dimethylaminomethylene)-3-oxo-butanoate (1.49 g, 8.01 mmol) in ethanol (10 mL) was refluxed overnight. The mixture was concentrated under reduced pressure to give crude ethyl 10-methoxy-9-(3-methoxypropoxy)-2-oxo-6-(2,2,2-trifluoroethyl)-1,6,7,11b-tetrahydrobenzo[a]quinolizine-3-carboxylate (2.21 g) as a yellow oil which was directly used in the next step without purification.

Step 10: Preparation of ethyl 10-methoxy-9-(3-methoxypropoxy)-2-oxo-6-(2,2,2-trifluoroethyl)-6,7-dihydrobenzo[a]quinolizine-3-carboxylate

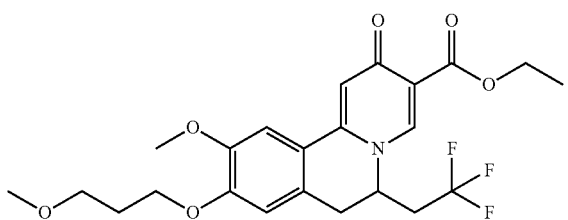 [SMILES: CCOC(=O)c1cn2c(cc1=O)-c1cc(OC)c(OCCCOC)cc1CC2CC(F)(F)F]

A mixture of crude ethyl 10-methoxy-9-(3-methoxypropoxy)-2-oxo-6-(2,2,2-trifluoroethyl)-1,6,7,11b-tetrahydrobenzo[a]quinolizine-3-carboxylate (2.22 g, 2.67 mmol) and p-chloranil (657 mg, 2.67 mmol) in DME (10 mL) was heated at 70° C. for 3 h under argon. After being cooled to room temperature, the mixture was diluted with CH$_2$Cl$_2$ (60 mL) and water (10 mL). The separated organic layer was washed with saturated NaHCO$_3$ aqueous solution (20 mL×5) and brine, dried over anhydrous Na$_2$SO$_4$ and concentrated under reduced pressure. The residue was precipitated from diethyl ether to afford ethyl 10-methoxy-9-(3-methoxypropoxy)-2-oxo-6-(2,2,2-trifluoroethyl)-6,7-dihydrobenzo[a]quinolizine-3-carboxylate (820 mg) as a yellow solid.

Step 11: Preparation of 10-methoxy-9-(3-methoxypropoxy)-2-oxo-6-(2,2,2-trifluoroethyl)-6,7-dihydrobenzo[a]quinolizine-3-carboxylic acid

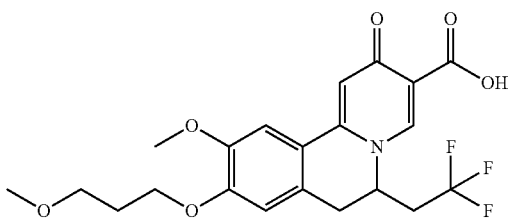 [SMILES: COCCCOc1cc2c(cc1OC)-c1cc(=O)c(C(=O)O)cn1C(CC(F)(F)F)C2]

To a suspension of ethyl 10-methoxy-9-(3-methoxypropoxy)-2-oxo-6-(2,2,2-trifluoroethyl)-6,7-dihydrobenzo[a]quinolizine-3-carboxylate (820 mg, 1.75 mmol) in methanol (8 mL) and H$_2$O (2 mL) was added LiOH.H$_2$O (296 mg, 7.0 mmol). The resulting reaction mixture was stirred at room temperature for 2 h and then acidified with 1 M hydrochloric acid to pH=2-3. The resulting precipitate was filtered, and the filter cake was washed with water. Then the filter cake was dissolved in CH$_2$Cl$_2$ (100 mL). The organic solution was washed with brine, dried over anhydrous Na$_2$SO$_4$ and concentrated. The residue was precipitated from diethyl ether/ethanol to afford 10-methoxy-9-(3-methoxypropoxy)-2-oxo-6-(2,2,2-trifluoroethyl)-6,7-dihydrobenzo[a]quinolizine-3-carboxylic acid (315 mg) as a yellow solid. $^1$H NMR (400 MHz, DMSO-d6): δ 8.75 (s, 1H), 7.56 (s, 1H), 7.49 (s, 1H), 7.04 (s, 1H), 5.28 (m, 1H), 4.10 (t, 2H), 3.90 (s, 3H), 3.48 (t, 2H), 3.42 (dd, 1H), 3.26 (s, 3H), 3.01 (d, 1H), 2.69-2.56 (m, 2H), 1.99 (quin, 2H). MS obsd. (ESI$^+$) [(M+H)$^+$]: 442.

Example 200 and 201

(+)-10-methoxy-9-(3-methoxypropoxy)-2-oxo-6-(2,2,2-trifluoroethyl)-6,7-dihydrobenzo[a]quinolizine-3-carboxylic acid and (−)-10-methoxy-9-(3-methoxypropoxy)-2-oxo-6-(2,2,2-trifluoroethyl)-6,7-dihydrobenzo[a]quinolizine-3-carboxylic acid

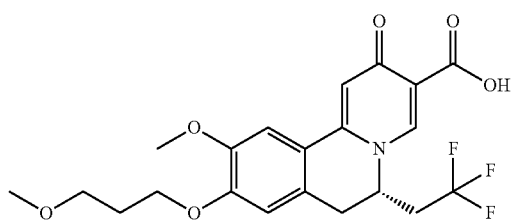

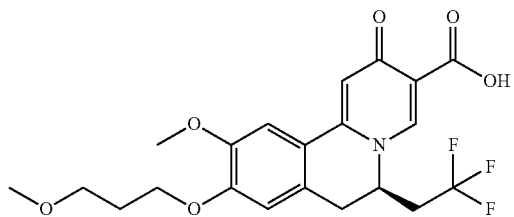

Separation of 10-methoxy-9-(3-methoxypropoxy)-2-oxo-6-(2,2,2-trifluoroethyl)-6,7-dihydrobenzo[a]quinolizine-3-carboxylic acid by chiral HPLC provided (+)-10-methoxy-9-(3-methoxypropoxy)-2-oxo-6-(2,2,2-trifluoroethyl)-6,7-dihydrobenzo[a]quinolizine-3-carboxylic acid and (−)-10-methoxy-9-(3-methoxypropoxy)-2-oxo-6-(2,2,2-trifluoroethyl)-6,7-dihydrobenzo[a]quinolizine-3-carboxylic acid.

Example 200

$^1$H NMR (400 MHz, DMSO) δ: 8.75 (s, 1H), 7.56 (s, 1H), 7.49 (s, 1H), 7.04 (s, 1H), 5.28 (m, 1H), 4.10 (t, 2H), 3.90 (s, 3H), 3.48 (t, 2H), 3.42 (dd, 1H), 3.26 (s, 3H), 3.01 (d, 1H), 2.69-2.56 (m, 2H), 1.99 (quin, 2H). MS obsd. (ESI$^+$) [(M+H)$^+$]: 442. $[α]_D^{20}$=+72.0° (0.100%, CH$_3$CN).

Example 201

$^1$H NMR (400 MHz, DMSO) δ: 8.75 (s, 1H), 7.56 (s, 1H), 7.49 (s, 1H), 7.04 (s, 1H), 5.28 (m, 1H), 4.10 (t, 2H), 3.90 (s, 3H), 3.48 (t, 2H), 3.42 (dd, 1H), 3.26 (s, 3H), 3.01 (d, 1H), 2.69-2.56 (m, 2H), 1.99 (quin, 2H). MS obsd. (ESI$^+$) [(M+H)$^+$]: 442.

Example 202: 6-tert-butyl-10-chloro-9-(3-methoxy-propoxy)-2-oxo-6,7-dihydrobenzo[a]quinolizine-3-carboxylic acid

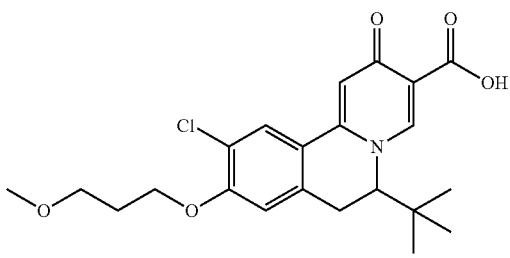 [SMILES: COCCCOc1cc2c(cc1Cl)-c1cc(=O)c(C(=O)O)cn1C(C(C)(C)C)C2]

Step 1: Preparation of 1-[4-chloro-3-(3-methoxy-propoxy)phenyl]-3,3-dimethyl-butan-2-one

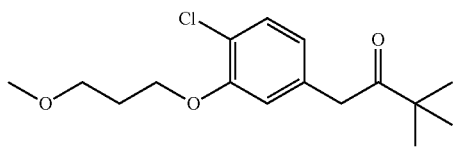 [SMILES: COCCCOc1cc(CC(=O)C(C)(C)C)ccc1Cl]

To a mixture of crude 4-bromo-1-chloro-2-(3-methoxypropoxy)benzene (3.08 g, 10 mmol), tris(dibenzylideneacetone)dipalladium(0) (92 mg, 0.1 mmol), 9,9-dimethyl-4,5-bis(diphenylphosphino)xanthene (116 mg, 0.2 mmol) and t-BuONa (3.17 g, 33 mmol) in THF (20 mL) was added 3,3-dimethylbutan-2-one (3.0 g, 30 mmol). The resulting mixture was heated at 50° C. for 3 h under argon. After being cooled to room temperature, the mixture was filtered. The filtrate was concentrated under reduced pressure to give crude 1-[4-chloro-3-(3-methoxypropoxy)phenyl]-3,3-dimethyl-butan-2-one (3.35 g) as a brown oil which was directly used in the next step without purification.

Step 2: Preparation of 1-[4-chloro-3-(3-methoxy-propoxy)phenyl]-3,3-dimethyl-butan-2-amine

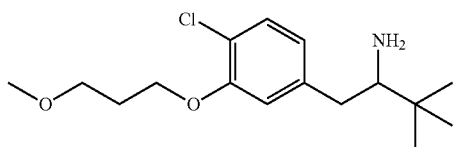 [SMILES: COCCCOc1cc(CC(N)C(C)(C)C)ccc1Cl]

To a mixture of crude 1-[4-chloro-3-(3-methoxypropoxy)phenyl]-3,3-dimethyl-butan-2-one (3.25 g, 10 mmol) and ammonium acetate (11.55 g, 150 mmol) in methanol (50 mL) was added NaBH₃CN (1.26 g, 20 mmol). The resulting mixture was stirred at room temperature overnight. Then to the mixture, additional ammonium acetate (11.55 g, 150 mmol) and NaBH₃CN (1.26 g, 20 mmol) were added, and the mixture was stirred at room temperature for 24 h. The reaction mixture was basified with 2 M NaOH aqueous solution to pH=12-14. Then the resulting mixture was extracted with CH₂Cl₂ (50 mL×3). The combined organic layers were washed with brine, dried over anhydrous Na₂SO₄ and concentrated to give crude 1-[4-chloro-3-(3-methoxypropoxy)phenyl]-3,3-dimethyl-butan-2-amine (2.33 g) as a yellow oil which was directly used in the next step without purification.

Step 3: Preparation of N-[1-[[4-chloro-3-(3-methoxypropoxy)phenyl]methyl]-2,2-dimethyl-propyl]formamide

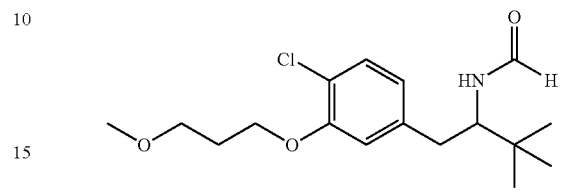

A solution of crude 1-[4-chloro-3-(3-methoxypropoxy)phenyl]-3,3-dimethyl-butan-2-amine (2.33 g, 7.8 mmol) and formic acid (0.2 mL) in ethyl formate (20 mL) was heated at 90° C. overnight. The mixture was concentrated and the residue was purified by flash chromatography to give N-[1-[[4-chloro-3-(3-methoxypropoxy)phenyl]methyl]-2,2-dimethyl-propyl]formamide (900 mg) as a yellow oil which was directly used in the next step without further purification.

Step 4: Preparation of 3-tert-butyl-7-chloro-6-(3-methoxypropoxy)-3,4-dihydroisoquinoline

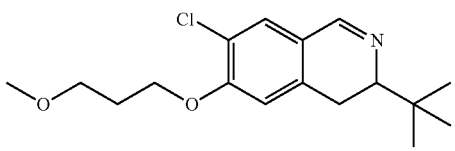 [SMILES: COCCCOc1cc2c(cc1Cl)C=NC(C(C)(C)C)C2]

To a solution of N-[1-[[4-chloro-3-(3-methoxypropoxy)phenyl]methyl]-2,2-dimethyl-propyl]formamide (900 mg, 2.75 mmol) in CH₃CN (10 mL) was added POCl₃ (505 mg, 3.30 mmol). The reaction mixture was heated at 60° C. for 2 h and then concentrated. The residue was dissolved in CH₃CN (10 mL) and then basified with ammonium hydroxide at 0° C. The resulting mixture was extracted with CH₂Cl₂. The organic layer was washed with brine, dried over anhydrous Na₂SO₄ and concentrated under reduced pressure to give crude 3-tert-butyl-7-chloro-6-(3-methoxypropoxy)-3,4-dihydroisoquinoline (871 mg) as a yellow oil which was directly used in the next step without purification.

Step 5: Preparation of ethyl 6-tert-butyl-10-chloro-9-(3-methoxypropoxy)-2-oxo-1,6,7,11b-tetrahydrobenzo[a]quinolizine-3-carboxylate

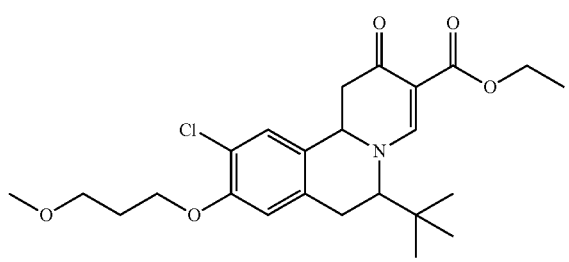 [SMILES: CCOC(=O)C1=CN2C(CC1=O)c1cc(Cl)c(OCCCOC)cc1CC2C(C)(C)C]

A mixture of crude 3-tert-butyl-7-chloro-6-(3-methoxypropoxy)-3,4-dihydroisoquinoline (871 mg, 2.82 mmol) and ethyl 2-(ethoxymethylene)-3-oxo-butanoate (1.57 g, 8.46 mmol) in ethanol (10 mL) was heated at 100° C. for 16 h. The mixture was concentrated under reduced pressure to give crude ethyl 6-tert-butyl-10-chloro-9-(3-methoxypropoxy)-2-oxo-1,6,7,11b-tetrahydrobenzo[a]quinolizine-3-carboxylate (2.44 g) as a brown oil which was directly used in the next step without purification.

Step 6: Preparation of ethyl 6-tert-butyl-10-chloro-9-(3-methoxypropoxy)-2-oxo-6,7-dihydrobenzo[a]quinolizine-3-carboxylate

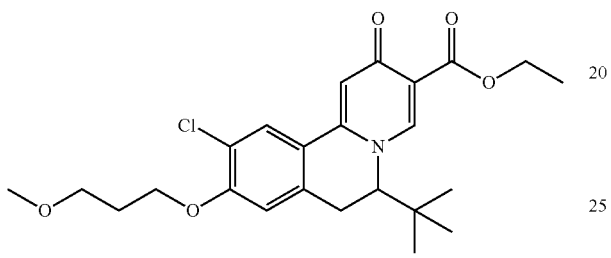

A mixture of crude ethyl 6-tert-butyl-10-chloro-9-(3-methoxypropoxy)-2-oxo-1,6,7,11b-tetrahydrobenzo[a]quinolizine-3-carboxylate (2.44 g, 2.82 mmol) and p-chloranil (694 mg, 2.82 mmol) in DME (10 mL) was heated at 70° C. for 3 h under argon. After being cooled to room temperature, the mixture was diluted with CH₂Cl₂ and H₂O. The separated organic layer was washed with saturated NaHCO₃ aqueous solution and brine, dried over anhydrous Na₂SO₄ and concentrated to give crude ethyl 6-tert-butyl-10-chloro-9-(3-methoxypropoxy)-2-oxo-6,7-dihydrobenzo[a]quinolizine-3-carboxylate (2.18 g) as a brown oil which was directly used in the next step without purification.

Step 7: Preparation of 6-tert-butyl-10-chloro-9-(3-methoxypropoxy)-2-oxo-6,7-dihydrobenzo[a]quinolizine-3-carboxylic acid

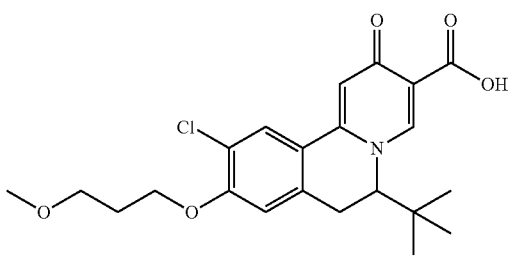

To a mixture of crude ethyl 6-tert-butyl-10-chloro-9-(3-methoxypropoxy)-2-oxo-6,7-dihydrobenzo[a]quinolizine-3-carboxylate (2.18 g, 2.82 mmol) in methanol (8 mL) and H₂O (2 mL) was added LiOH.H₂O (474 mg, 11.28 mmol). The resulting mixture was stirred at room temperature overnight and then acidified with 1 M hydrochloric acid to pH=2-3. The mixture was filtered, and the filter cake was dried to give 6-tert-butyl-10-chloro-9-(3-methoxypropoxy)-2-oxo-6,7-dihydrobenzo[a]quinolizine-3-carboxylic acid (450 mg) as a white solid. ¹H NMR (400 MHz, DMSO-d6): δ 8.74 s, 1H), 8.17 (s, 1H), 7.41 (s, 1H), 7.30 (s, 1H), 4.61 (m, 1H), 4.30-4.11 (m, 2H), 3.52 (m, 2H), 3.44-3.37 (m, 2H), 3.27 (s, 3H), 2.08-1.96 (m, 2H), 0.74 (br. s., 9H). MS obsd. (ESI⁺) [(M+H)⁺]: 420.

Example 203 and 204

(+)-6-tert-butyl-10-chloro-9-(3-methoxypropoxy)-2-oxo-6,7-dihydrobenzo[a]quinolizine-3-carboxylic acid and (−)-6-tert-butyl-10-chloro-9-(3-methoxypropoxy)-2-oxo-6,7-dihydrobenzo[a]quinolizine-3-carboxylic acid

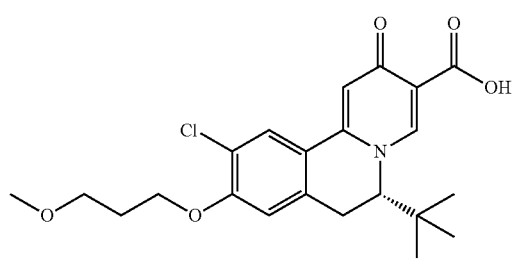 [SMILES: COCCCOc1cc2c(cc1Cl)-c1cc(=O)c(C(=O)O)cn1C(C(C)(C)C)C2]

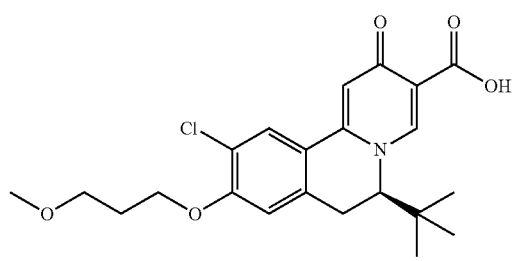

Separation of 6-tert-butyl-10-chloro-9-(3-methoxypropoxy)-2-oxo-6,7-dihydrobenzo[a]quinolizine-3-carboxylic acid by chiral HPLC provided (+)-6-tert-butyl-10-chloro-9-(3-methoxypropoxy)-2-oxo-6,7-dihydrobenzo[a]quinolizine-3-carboxylic acid and (−)-6-tert-butyl-10-chloro-9-(3-methoxypropoxy)-2-oxo-6,7-dihydrobenzo[a]quinolizine-3-carboxylic acid.

Example 203

¹H NMR (400 MHz, DMSO) δ: 8.74 (s, 1H), 8.17 (s, 1H), 7.41 (s, 1H), 7.30 (s, 1H), 4.61 (m, 1H), 4.27-4.14 (m, 2H), 3.51 (t, 2H), 3.48-3.37 (m, 2H), 3.26 (s, 3H), 2.02 (quin, 2H), 0.73 (s, 9H). MS obsd. (ESI⁺) [(M+H)⁺]: 420. [α]_D20=+76.0° (0.100%, CH₃CN).

Example 204

¹H NMR (400 MHz, DMSO) δ: 8.74 (s, 1H), 8.17 (s, 1H), 7.41 (s, 1H), 7.30 (s, 1H), 4.61 (m, 1H), 4.27-4.14 (m, 2H), 3.51 (t, 2H), 3.48-3.37 (m, 2H), 3.26 (s, 3H), 2.02 (quin, 2H), 0.73 (s, 9H). MS obsd. (ESI⁺) [(M+H)⁺]: 420.

Example 205: 10-chloro-9-(3-methoxypropoxy)-6-(1-methylcyclopropyl)-2-oxo-6,7-dihydrobenzo[a]quinolizine-3-carboxylic acid

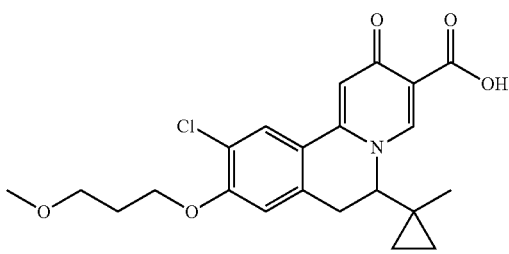

Step 1: Preparation of 2-[4-chloro-3-(3-methoxypropoxy)phenyl]-1-(1-methylcyclopropyl)ethanone

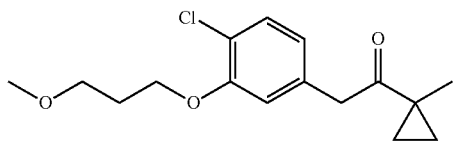

To a mixture of crude 4-bromo-1-chloro-2-(3-methoxypropoxy)benzene (3.08 g, 10 mmol), tris(dibenzylideneacetone)dipalladium(0) (92 mg, 0.1 mmol), 9,9-dimethyl-4,5-bis(diphenylphosphino)xanthene (116 mg, 0.2 mmol) and t-BuONa (3.17 g, 33 mmol) in THF (20 mL) was added 1-(1-methylcyclopropyl)ethanone (2.94 g, 30 mmol). The resulting mixture was heated at 50° C. for 3 h under argon. After being cooled to room temperature, the mixture was partitioned between EtOAc and H₂O. The separated aqueous layer was extracted with EtOAc. The combined organic layers were washed with brine, dried over anhydrous Na₂SO₄ and concentrated. The residue was purified by flash chromatography to afford 2-[4-chloro-3-(3-methoxypropoxy)phenyl]-1-(1-methylcyclopropyl)ethanone (2.17 g) as a yellow oil which was directly used in the next step without further purification.

Step 2: Preparation of 2-[4-chloro-3-(3-methoxypropoxy)phenyl]-1-(1-methylcyclopropyl)ethanamine

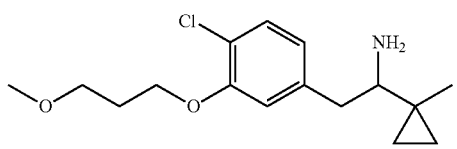

To a mixture of crude 2-[4-chloro-3-(3-methoxypropoxy)phenyl]-1-(1-methylcyclopropyl)ethanone (2.17 g, 7.33 mmol) and ammonium acetate (8.47 g, 110 mmol) in methanol (40 mL) was added NaBH₃CN (924 mg, 14.66 mmol). The resulting mixture was stirred at room temperature overnight, then diluted with water (50 mL) and extracted with CH₂Cl₂ (50 mL×3). The combined organic layers were washed with brine, dried over anhydrous Na₂SO₄ and concentrated to give crude 2-[4-chloro-3-(3-methoxypropoxy)phenyl]-1-(1-methylcyclopropyl)ethanamine (1.72 g) as a yellow oil which was directly used in the next step without purification.

Step 3: Preparation of N-[2-[4-chloro-3-(3-methoxypropoxy)phenyl]-1-(1-methylcyclopropyl)ethyl]formamide

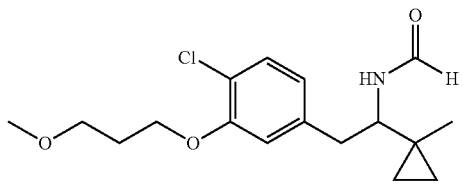 [SMILES: COCCCOc1cc(CC(NC=O)C2(C)CC2)ccc1Cl]

A solution of crude 2-[4-chloro-3-(3-methoxypropoxy)phenyl]-1-(1-methylcyclopropyl)ethanamine (1.72 g, 5.8 mmol) and formic acid (0.2 mL) in ethyl formate (20 mL) was heated at 90° C. overnight. The resulting mixture was concentrated under reduced pressure to give crude N-[2-[4-chloro-3-(3-methoxypropoxy)phenyl]-1-(1-methylcyclopropyl)ethyl]formamide (1.91 g) as a yellow oil which was directly used in the next step without purification.

Step 4: Preparation of 7-chloro-6-(3-methoxypropoxy)-3-(1-methylcyclopropyl)-3,4-dihydroisoquinoline

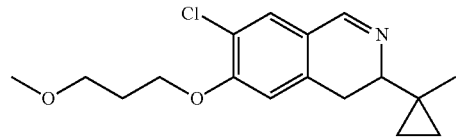

To a solution of crude N-[2-[4-chloro-3-(3-methoxypropoxy)phenyl]-1-(1-methylcyclopropyl)ethyl]formamide (1.91 g, 5.9 mmol) in CH₃CN (20 mL) was added POCl₃ (903 mg, 5.9 mmol). The reaction mixture was heated at 60° C. for 3 h and then concentrated under reduced pressure. The residue was dissolved in CH₃CN (10 mL) and then basified with ammonium hydroxide at 0° C. The resulting mixture was extracted with CH₂Cl₂, and the organic layer was washed with brine, dried over anhydrous Na₂SO₄ and concentrated to give crude 7-chloro-6-(3-methoxypropoxy)-3-(1-methylcyclopropyl)-3,4-dihydroisoquinoline (1.42 g) as a yellow oil which was directly used in the next step without purification.

Step 5: Preparation of ethyl 10-chloro-9-(3-methoxypropoxy)-6-(1-methylcyclopropyl)-2-oxo-1,6,7,11b-tetrahydrobenzo[a]quinolizine-3-carboxylate

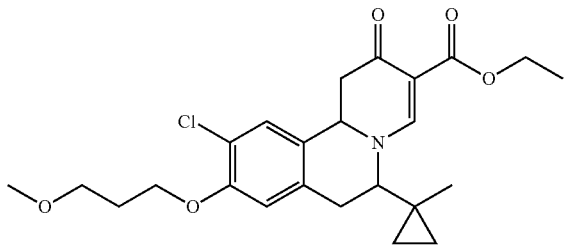 [SMILES: CCOC(=O)C1=CN2C(CC1=O)c1cc(Cl)c(OCCCOC)cc1CC2C1(C)CC1]

A mixture of crude 7-chloro-6-(3-methoxypropoxy)-3-(1-methylcyclopropyl)-3,4-dihydroisoquinoline (1.42 g, 4.6 mmol) and ethyl 2-(ethoxymethylene)-3-oxo-butanoate (2.57 g, 13.8 mmol) in ethanol (15 mL) was heated at 100° C. for 16 h. The mixture was concentrated under reduced pressure to give crude ethyl 10-chloro-9-(3-methoxypropoxy)-6-(1-methylcyclopropyl)-2-oxo-1,6,7,11b-tetrahydrobenzo[a]quinolizine-3-carboxylate (3.90 g) as a brown oil which was directly used in the next step without purification.

Step 6: Preparation of ethyl 10-chloro-9-(3-methoxypropoxy)-6-(1-methylcyclopropyl)-2-oxo-6,7-dihydrobenzo[a]quinolizine-3-carboxylate

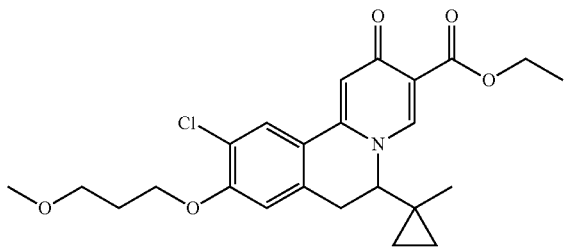 [SMILES: CCOC(=O)c1cn2c(cc1=O)-c1cc(Cl)c(OCCCOC)cc1CC2C1(C)CC1]

A mixture of crude ethyl 10-chloro-9-(3-methoxypropoxy)-6-(1-methylcyclopropyl)-2-oxo-1,6,7,11b-tetrahydrobenzo[a]quinolizine-3-carboxylate (3.90 g, 4.6 mmol) and p-chloranil (1.13 g, 4.6 mmol) in DME (20 mL) was heated at 70° C. for 3 h under argon. After being cooled to room temperature, the mixture was diluted with CH$_2$Cl$_2$ and H$_2$O. The separated organic layer was washed with saturated NaHCO$_3$ aqueous solution and brine, dried over anhydrous Na$_2$SO$_4$ and concentrated to give crude ethyl 10-chloro-9-(3-methoxypropoxy)-6-(1-methylcyclopropyl)-2-oxo-6,7-dihydrobenzo[a]quinolizine-3-carboxylate (3.65 g) as a brown oil which was directly used in the next step without purification.

Step 7: Preparation of 10-chloro-9-(3-methoxypropoxy)-6-(1-methylcyclopropyl)-2-oxo-6,7-dihydrobenzo[a]quinolizine-3-carboxylic acid

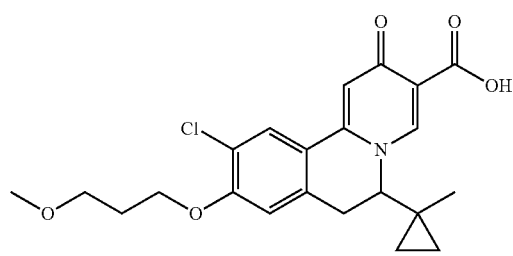

To a mixture of crude ethyl 10-chloro-9-(3-methoxypropoxy)-6-(1-methylcyclopropyl)-2-oxo-6,7-dihydrobenzo[a]quinolizine-3-carboxylate (3.65 g, 4.6 mmol) in methanol (12 mL) and H$_2$O (3 mL) was added LiOH.H$_2$O (773 mg, 18.4 mmol). The resulting mixture was stirred at room temperature overnight, then acidified with 1 M hydrochloric acid to pH=2-3 and extracted with CH$_2$Cl$_2$ (40 mL×3). The combined organic layers were washed with brine, dried over anhydrous Na$_2$SO$_4$ and concentrated. The residue was precipitated from diethyl ether/ethanol to afford 10-chloro-9-(3-methoxypropoxy)-6-(1-methylcyclopropyl)-2-oxo-6,7-dihydrobenzo[a]quinolizine-3-carboxylic acid (556 mg) as a yellow solid. $^1$H NMR (400 MHz, DMSO-d6): δ 8.82 (s, 1H), 8.21 (s, 1H), 7.45 (s, 1H), 7.30 (s, 1H), 4.28-4.18 (m, 2H), 4.14 (m, 1H), 3.51 (t, 2H), 3.48-3.41 (m, 1H), 3.26 (s, 3H), 3.25-3.20 (m, 1H), 2.02 (t, 2H), 0.83 (d, 1H), 0.63 (s, 3H), 0.53 (d, 1H), 0.48-0.33 (m, 2H). MS obsd. (ESI$^+$) [(M+H)$^+$]: 418.

Example 206 and 207

(+)-10-chloro-9-(3-methoxypropoxy)-6-(1-methylcyclopropyl)-2-oxo-6,7-dihydrobenzo[a]quinolizine-3-carboxylic acid and (−)-10-chloro-9-(3-methoxypropoxy)-6-(1-methylcyclopropyl)-2-oxo-6,7-dihydrobenzo[a]quinolizine-3-carboxylic acid

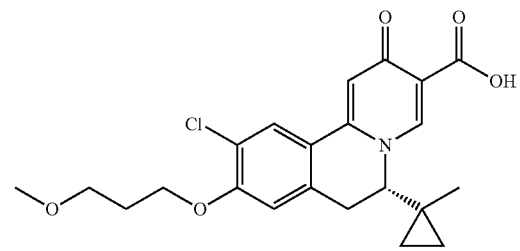 [SMILES: COCCCOc1cc2c(cc1Cl)-c1cc(=O)c(C(=O)O)cn1C(C1(C)CC1)C2]

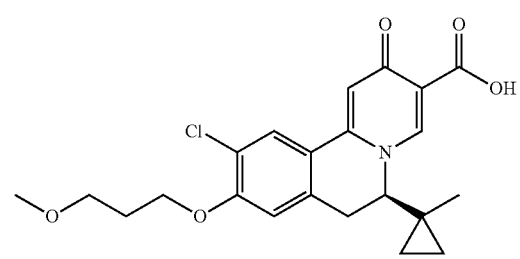

Separation of 10-chloro-9-(3-methoxypropoxy)-6-(1-methylcyclopropyl)-2-oxo-6,7-dihydrobenzo[a]quinolizine-3-carboxylic acid by chiral HPLC provided (+)-10-chloro-9-(3-methoxypropoxy)-6-(1-methylcyclopropyl)-2-oxo-6,7-dihydrobenzo[a]quinolizine-3-carboxylic acid and (−)-10-chloro-9-(3-methoxypropoxy)-6-(1-methylcyclopropyl)-2-oxo-6,7-dihydrobenzo[a]quinolizine-3-carboxylic acid.

Example 206

$^1$H NMR (400 MHz, DMSO-d6): δ 8.81 (s, 1H), 8.21 (s, 1H), 7.45 (s, 1H), 7.30 (s, 1H), 4.28-4.18 (m, 2H), 4.14 (dd, 1H), 3.52 (t, 2H), 3.45 (dd, 1H), 3.27 (s, 3H), 3.29-3.22 (m, 1H), 2.02 (quin, 2H), 0.88-0.79 (m, 1H), 0.64 (s, 3H), 0.53 (td, 1H), 0.46-0.34 (m, 2H). MS obsd. (ESI$^+$) [(M+H)$^+$]: 418. [α]$_D^{20}$=+50.0° (0.100%, CH$_3$CN).

Example 207

$^1$H NMR (400 MHz, DMSO-d6): δ 8.81 (s, 1H), 8.21 (s, 1H), 7.45 (s, 1H), 7.30 (s, 1H), 4.28-4.18 (m, 2H), 4.14 (dd, 1H), 3.52 (t, 2H), 3.45 (dd, 1H), 3.27 (s, 3H), 3.29-3.22 (m, 1H), 2.02 (quin, 2H), 0.88-0.79 (m, 1H), 0.64 (s, 3H), 0.53 (td, 1H), 0.46-0.34 (m, 2H). MS obsd. (ESI$^+$) [(M+H)$^+$]: 418.

Example 208: 10-methoxy-9-(3-methoxypropoxy)-6-(1-methylcyclopropyl)-2-oxo-6,7-dihydrobenzo[a]quinolizine-3-carboxylic acid

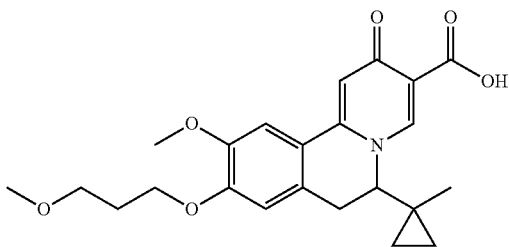 [SMILES: COCCCOc1cc2c(cc1OC)-c1cc(=O)c(C(=O)O)cn1C(C1(C)CC1)C2]

Step 1: Preparation of 2-[4-methoxy-3-(3-methoxypropoxy)phenyl]-1-(1-methylcyclopropyl)ethanone

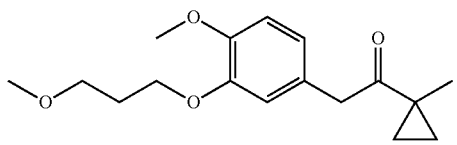

To a mixture of crude 4-bromo-1-methoxy-2-(3-methoxypropoxy)benzene (2.74 g, 10 mmol), tris(dibenzylideneacetone)dipalladium(0) (92 mg, 0.1 mmol), 9,9-dimethyl-4,5-bis(diphenylphosphino)xanthene (116 mg, 0.2 mmol) and t-BuONa (1.25 g, 13 mmol) in THF (20 mL) was added 1-(1-methylcyclopropyl)ethanone (1.18 g, 12 mmol). The resulting mixture was heated at 70° C. overnight under argon. After being cooled to room temperature, the mixture was partitioned between EtOAc and H$_2$O. The separated aqueous layer was extracted with EtOAc. The combined organic layers were washed with brine, dried over anhydrous Na$_2$SO$_4$ and concentrated. The residue was purified by flash chromatography to afford 2-[4-methoxy-3-(3-methoxypropoxy)phenyl]-1-(1-methylcyclopropyl)ethanone (1.27 g) as a yellow oil which was used in the next step without further purification.

Step 2: Preparation of 2-[4-methoxy-3-(3-methoxypropoxy)phenyl]-1-(1-methylcyclopropyl)ethanamine

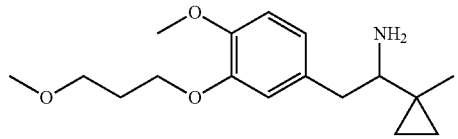

To a mixture of crude 2-[4-methoxy-3-(3-methoxypropoxy)phenyl]-1-(1-methylcyclopropyl)ethanone (1.27 g, 4.3 mmol) and ammonium acetate (4.97 g, 64.5 mmol) in methanol (15 mL) was added NaBH$_3$CN (542 mg, 8.6 mmol). The resulting mixture was stirred at room temperature overnight. The mixture was basified with 2 M NaOH aqueous solution to pH=12-14, then extracted with CH$_2$Cl$_2$ (40 mL×3). The combined organic layers were acidified with 1 M hydrochloric acid to pH=1-2. The separated aqueous layer was basified with 2 M NaOH aqueous solution to pH=12-14, then extracted with CH$_2$Cl$_2$ (40 mL×3). The combined organic layers were washed with brine, dried over anhydrous Na$_2$SO$_4$ and concentrated to give crude 2-[4-methoxy-3-(3-methoxypropoxy)phenyl]-1-(1-methylcyclopropyl)ethanamine (820 mg) as a colorless oil which was directly used in the next step without purification.

Step 3: Preparation of N-[2-[4-methoxy-3-(3-methoxypropoxy)phenyl]-1-(1-methylcyclopropyl)ethyl]formamide

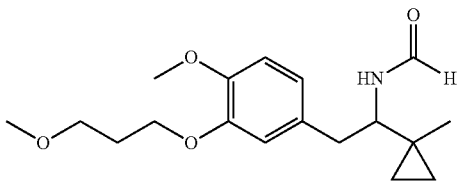 [SMILES: COCCCOc1cc(CC(NC=O)C2(C)CC2)ccc1OC]

A solution of crude 2-[4-methoxy-3-(3-methoxypropoxy)phenyl]-1-(1-methylcyclopropyl)ethanamine (820 mg, 2.8 mmol) and formic acid (0.15 mL) in ethyl formate (15 mL) was heated at 90° C. overnight. The resulting mixture was concentrated under reduced pressure to give crude N-[2-[4-methoxy-3-(3-methoxypropoxy)phenyl]-1-(1-methylcyclopropyl)ethyl]formamide (990 mg) as a colorless oil which was directly used in the next step without purification.

Step 4: Preparation of 7-methoxy-6-(3-methoxypropoxy)-3-(1-methylcyclopropyl)-3,4-dihydroisoquinoline

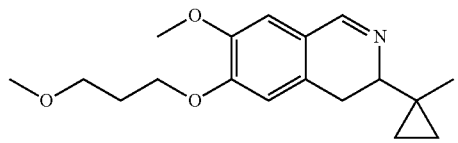

To a solution of crude N-[2-[4-methoxy-3-(3-methoxypropoxy)phenyl]-1-(1-methylcyclopropyl)ethyl]formamide (990 mg, 2.8 mmol) in CH₃CN (10 mL) was added POCl₃ (520 mg, 3.4 mmol). The reaction mixture was heated at 60° C. for 2 h and then concentrated under reduced pressure. The residue was dissolved in CH₃CN (10 mL) and basified with ammonium hydroxide at 0° C. The resulting mixture was extracted with CH₂Cl₂, and the organic layer was washed with brine, dried over anhydrous Na₂SO₄ and concentrated to give crude 7-methoxy-6-(3-methoxypropoxy)-3-(1-methylcyclopropyl)-3,4-dihydroisoquinoline (827 mg) as a yellow oil which was directly used in the next step without purification.

Step 5: Preparation of ethyl 10-methoxy-9-(3-methoxypropoxy)-6-(1-methylcyclopropyl)-2-oxo-1,6,7,11b-tetrahydrobenzo[a]quinolizine-3-carboxylate

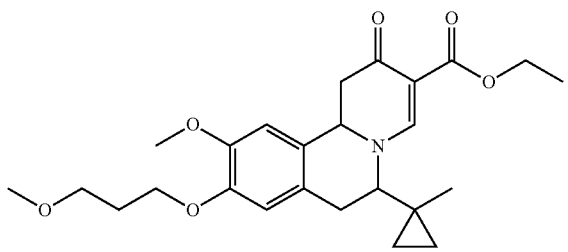 [SMILES: CCOC(=O)C1=CN2C(CC1=O)c1cc(OC)c(OCCCOC)cc1CC2C1(C)CC1]

A mixture of crude 7-methoxy-6-(3-methoxypropoxy)-3-(1-methylcyclopropyl)-3,4-dihydroisoquinoline (827 mg, 2.7 mmol) and ethyl 2-(ethoxymethylene)-3-oxo-butanoate (1.51 g, 8.1 mmol) in ethanol (10 mL) was heated at 100° C. for 16 h. The mixture was concentrated under reduced pressure to give crude ethyl 10-methoxy-9-(3-methoxypropoxy)-6-(1-methylcyclopropyl)-2-oxo-1,6,7,11b-tetrahydrobenzo[a]quinolizine-3-carboxylate (2.25 g) as a brown oil which was directly used in the next step without purification.

Step 6: Preparation of ethyl 10-methoxy-9-(3-methoxypropoxy)-6-(1-methylcyclopropyl)-2-oxo-6,7-dihydrobenzo[a]quinolizine-3-carboxylate

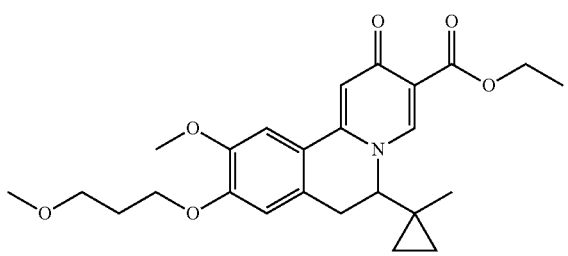

A mixture of crude ethyl 10-methoxy-9-(3-methoxypropoxy)-6-(1-methylcyclopropyl)-2-oxo-1,6,7,11b-tetrahydrobenzo[a]quinolizine-3-carboxylate (2.25 g, 2.7 mmol) and p-chloranil (664 mg, 2.7 mmol) in DME (10 mL) was heated at 70° C. for 3 h under argon. After being cooled to room temperature, the mixture was partitioned between CH₂Cl₂ and H₂O. The separated organic layer was washed with saturated NaHCO₃ aqueous solution and brine, dried over anhydrous Na₂SO₄ and concentrated to give crude ethyl 10-methoxy-9-(3-methoxypropoxy)-6-(1-methylcyclopropyl)-2-oxo-6,7-dihydrobenzo[a]quinolizine-3-carboxylate (2.19 g) as a brown oil which was directly used in the next step without purification.

Step 7: Preparation of 10-methoxy-9-(3-methoxypropoxy)-6-(1-methylcyclopropyl)-2-oxo-6,7-dihydrobenzo[a]quinolizine-3-carboxylic acid

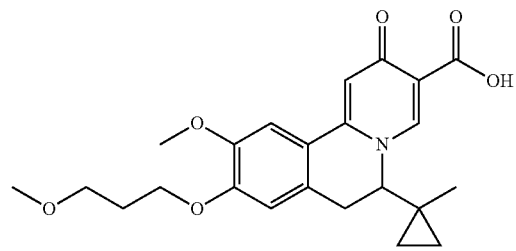 [SMILES: COCCCOc1cc2c(cc1OC)-c1cc(=O)c(C(=O)O)cn1C(C1(C)CC1)C2]

To a mixture of crude ethyl 10-methoxy-9-(3-methoxypropoxy)-6-(1-methylcyclopropyl)-2-oxo-6,7-dihydrobenzo[a]quinolizine-3-carboxylate (2.19 g, 2.7 mmol) in methanol (8 mL) and H₂O (2 mL) was added LiOH.H₂O (454 mg, 10.8 mmol). The resulting mixture was stirred at room temperature overnight, and then acidified with 1 M hydrochloric acid to pH=2-3, extracted with CH₂Cl₂ (40 mL×3). The combined organic layers were washed with brine, dried over anhydrous Na₂SO₄ and concentrated. The residue was precipitated from diethyl ether/ethanol to afford 10-methoxy-9-(3-methoxypropoxy)-6-(1-methylcyclopropyl)-2-oxo-6,7-dihydrobenzo[a]quinolizine-3-carboxylic acid (370 mg) as a yellow solid. $^1$H NMR (400 MHz, DMSO-d6): δ 8.80 (s, 1H), 7.51 (s, 1H), 7.49 (s, 1H), 7.07 (s, 1H), 4.17-4.04 (m, 3H), 3.88 (s, 3H), 3.48 (t, 2H), 3.42-3.35 (m, 1H), 3.26 (s, 3H), 3.16 (dd, 1H), 1.99 (quin, 2H), 0.91-0.77 (m, 1H), 0.63 (s, 3H), 0.52 (td, 1H), 0.45-0.33 (m, 2H). MS obsd. (ESI⁺) [(M+H)⁺]: 414.

Example 209 and 210

(+)-10-methoxy-9-(3-methoxypropoxy)-6-(1-methylcyclopropyl)-2-oxo-6,7-dihydrobenzo[a]quinolizine-3-carboxylic acid and (−)-10-methoxy-9-(3-methoxypropoxy)-6-(1-methylcyclopropyl)-2-oxo-6,7-dihydrobenzo[a]quinolizine-3-carboxylic acid

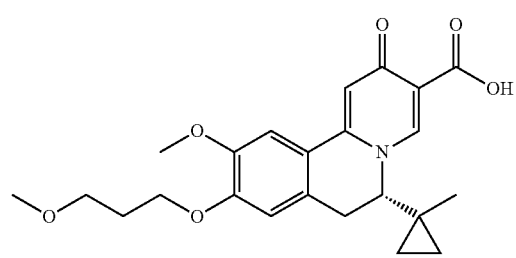

-continued

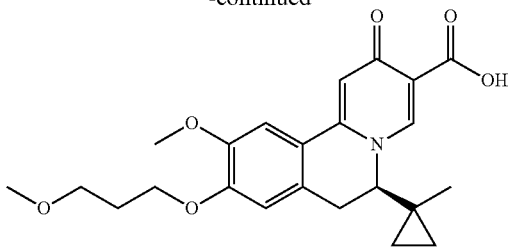

Separation of 10-methoxy-9-(3-methoxypropoxy)-6-(1-methylcyclopropyl)-2-oxo-6,7-dihydrobenzo[a]quinolizine-3-carboxylic acid by chiral HPLC provided (+)-10-methoxy-9-(3-methoxypropoxy)-6-(1-methylcyclopropyl)-2-oxo-6,7-dihydrobenzo[a]quinolizine-3-carboxylic acid and (−)-10-methoxy-9-(3-methoxypropoxy)-6-(1-methylcyclopropyl)-2-oxo-6,7-dihydrobenzo[a]quinolizine-3-carboxylic acid.

Example 209

$^1$H NMR (400 MHz, DMSO-d6): δ 8.80 (s, 1H), 7.51 (s, 1H), 7.49 (s, 1H), 7.07 (s, 1H), 4.16-4.05 (m, 3H), 3.88 (s, 3H), 3.48 (t, 2H), 3.42-3.36 (m, 1H), 3.26 (s, 3H), 3.16 (dd, 16.6 Hz, 1H), 1.99 (quin, 2H), 0.89-0.77 (m, 1H), 0.63 (s, 3H), 0.55-0.48 (m, 1H), 0.46-0.32 (m, 2H). MS obsd. (ESI$^+$) [(M+H)$^+$]: 414. [α]$_D^{20}$=+42.0° (0.100%, CH$_3$CN).

Example 210

$^1$H NMR (400 MHz, DMSO-d6): δ 8.80 (s, 1H), 7.51 (s, 1H), 7.49 (s, 1H), 7.07 (s, 1H), 4.16-4.05 (m, 3H), 3.88 (s, 3H), 3.48 (t, 2H), 3.42-3.36 (m, 1H), 3.26 (s, 3H), 3.16 (dd, 16.6 Hz, 1H), 1.99 (quin, 2H), 0.89-0.77 (m, 1H), 0.63 (s, 3H), 0.55-0.48 (m, 1H), 0.46-0.32 (m, 2H). MS obsd. (ESI$^+$) [(M+H)$^+$]: 414.

Example 211: 6-benzyl-9,10-dimethoxy-2-oxo-6,7-dihydrobenzo[a]quinolizine-3-carboxylic acid

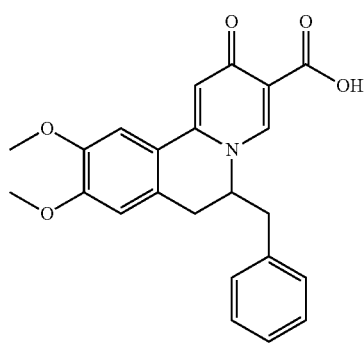 [SMILES: COc1cc2c(cc1OC)-c1cc(=O)c(C(=O)O)cn1C(Cc1ccccc1)C2]

Step 1: Preparation of 2-(3,4-dimethoxyphenyl)-N-methoxy-N-methyl-acetamide

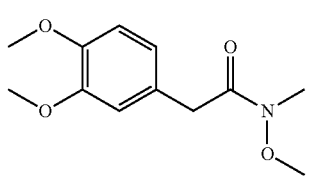

To a solution of 2-(3,4-dimethoxyphenyl)acetic acid (25.2 g, 129 mmol) in CH$_2$Cl$_2$ (300 mL) was added di(imidazol-1-yl)methanone (25.1 g, 155 mmol) in portions at 0° C. The resulting mixture was stirred at 0° C. to room temperature for 2 h. To the reaction mixture, N, O-Dimethylhydroxylamine hydrochloride (37.9 g, 387 mmol) was added at 0° C., and then Et$_3$N (52.1 g, 516 mmol) was added dropwise. The resulting mixture was stirred at 0° C. to room temperature overnight. The reaction mixture was diluted with 2 M hydrochloric acid (100 mL) and extracted with EtOAc. The separated organic layer was washed with 2 M hydrochloric acid (50 mL×5) and brine, dried over anhydrous Na$_2$SO$_4$ and concentrated to give 2-(3,4-dimethoxyphenyl)-N-methoxy-N-methyl-acetamide (31.2 g) as an orange oil.

Step 2: Preparation of 1-(3,4-dimethoxyphenyl)-3-phenyl-propan-2-one

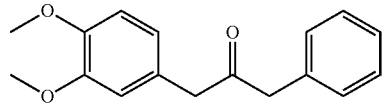 [SMILES: COc1ccc(CC(=O)Cc2ccccc2)cc1OC]

To a solution of 2-(3,4-dimethoxyphenyl)-N-methoxy-N-methyl-acetamide (1.43 g, 6 mmol) in THF (15 mL) was added benzylmagnesium chloride (6 mL, 12 mmol) dropwise at 0° C. The resulting mixture was allowed to warm to rt and stirred at this temperature overnight. The reaction was quenched by saturated NH$_4$Cl aqueous solution, and then the resulting mixture was diluted with EtOAc and H$_2$O. The separated aqueous layer was extracted with EtOAc, and the combined extracts were washed with brine, dried over anhydrous Na$_2$SO$_4$ and concentrated. The residue was purified by flash chromatography to afford 1-(3,4-dimethoxyphenyl)-3-phenyl-propan-2-one (612 mg) which was directly used in the next step without further purification.

Step 3: Preparation of 1-(3,4-dimethoxyphenyl)-3-phenyl-propan-2-amine

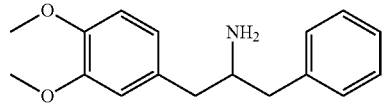 [SMILES: COc1ccc(CC(N)Cc2ccccc2)cc1OC]

To a mixture of 1-(3,4-dimethoxyphenyl)-3-phenyl-propan-2-one (612 mg, 2.3 mmol) and ammonium acetate (2.66 g, 34.5 mmol) in methanol (10 mL) was added NaBH$_3$CN (290 mg, 4.6 mmol). The resulting mixture was stirred at room temperature overnight and basified with 2 M NaOH aqueous solution to pH=12-14. The mixture was extracted with CH$_2$Cl$_2$ (50 mL×3), and the combined organic layers were washed with brine, dried over anhydrous Na$_2$SO$_4$ and concentrated to give crude 1-(3,4-dimethoxyphenyl)-3-phenyl-propan-2-amine (615 mg) as a yellow oil which was directly used in the next step without purification.

Step 4: Preparation of N-[1-benzyl-2-(3,4-dimethoxyphenyl)ethyl]formamide

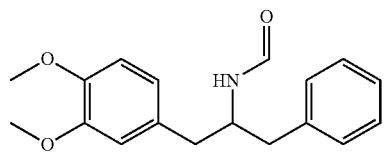 [SMILES: COc1ccc(CC(Cc2ccccc2)NC=O)cc1OC]

A solution of 1-(3,4-dimethoxyphenyl)-3-phenyl-propan-2-amine (615 mg, 2.3 mmol) and formic acid (0.15 mL) in ethyl formate (15 mL) was heated at 90° C. for 3 h. The resulting mixture was concentrated under reduced pressure to give crude N-[1-benzyl-2-(3,4-dimethoxyphenyl)ethyl]formamide (676 mg) as a yellow oil which was directly used in the next step without purification.

Step 5: Preparation of 3-benzyl-6,7-dimethoxy-3,4-dihydroisoquinoline

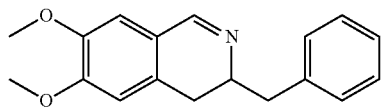 [SMILES: COc1cc2c(cc1OC)CC(Cc1ccccc1)N=C2]

To a solution of N-[1-benzyl-2-(3,4-dimethoxyphenyl)ethyl]formamide (676 mg, 2.3 mmol) in acetonitrile (10 mL) was added diphenylphosphinyl chloride (545 mg, 2.3 mmol). The resulting mixture was stirred at room temperature overnight. Then to the mixture additional diphenylphosphinyl chloride (545 mg, 2.3 mmol) was added and the resulting mixture was heated at 80° C. for 6 h. After being cooled to room temperature, the mixture was basified with ammonium hydroxide, then diluted with H$_2$O and extracted with CH$_2$Cl$_2$. The combined extracts were washed with brine, dried over anhydrous Na$_2$SO$_4$ and concentrated to give crude 3-benzyl-6,7-dimethoxy-3,4-dihydroisoquinoline (910 mg) as a yellow oil which was directly used in the next step without purification.

Step 6: Preparation of ethyl 6-benzyl-9,10-dimethoxy-2-oxo-1,6,7,11b-tetrahydrobenzo[a]quinolizine-3-carboxylate

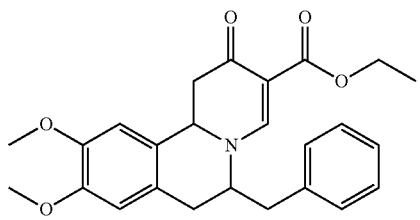 [SMILES: CCOC(=O)C1=CN2C(Cc3ccccc3)Cc3cc(OC)c(OC)cc3C2CC1=O]

A mixture of crude 3-benzyl-6,7-dimethoxy-3,4-dihydroisoquinoline (910 mg, 2.3 mmol) and ethyl 2-(ethoxymethylene)-3-oxo-butanoate (1.28 g, 6.9 mmol) in ethanol (10 mL) was refluxed for 16 h. The mixture was concentrated under reduced pressure to give crude ethyl 6-benzyl-9,10-dimethoxy-2-oxo-1,6,7,11b-tetrahydrobenzo[a]quinolizine-3-carboxylate (2.31 g) as a brown oil which was directly used in the next step without purification.

Step 7: Preparation of ethyl 6-benzyl-9,10-dimethoxy-2-oxo-6,7-dihydrobenzo[a]quinolizine-3-carboxylate

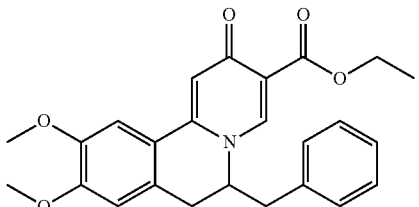

A mixture of crude ethyl 6-benzyl-9,10-dimethoxy-2-oxo-1,6,7,11b-tetrahydrobenzo[a]quinolizine-3-carboxylate (2.31 g, 2.3 mmol) and p-chloranil (566 mg, 2.3 mmol) in DME (15 mL) was heated at 70° C. for 3 h under argon. After being cooled to room temperature, the mixture was partitioned between CH$_2$Cl$_2$ and H$_2$O. The separated organic layer was washed with saturated NaHCO$_3$ aqueous solution and brine, dried over anhydrous Na$_2$SO$_4$ and concentrated to give crude ethyl 6-benzyl-9,10-dimethoxy-2-oxo-6,7-dihydrobenzo[a]quinolizine-3-carboxylate (1.87 g) as a dark brown oil which was directly used in the next step without purification.

Step 8: Preparation of 6-benzyl-9,10-dimethoxy-2-oxo-6,7-dihydrobenzo[a]quinolizine-3-carboxylic acid

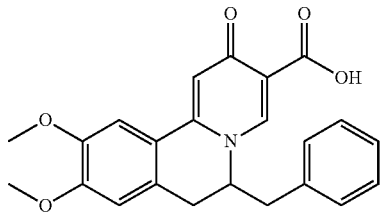 [SMILES: COc1cc2c(cc1OC)-c1cc(=O)c(C(=O)O)cn1C(Cc1ccccc1)C2]

To a solution of ethyl 6-benzyl-9,10-dimethoxy-2-oxo-6,7-dihydrobenzo[a]quinolizine-3-carboxylate (1.87 g, 2.3 mmol) in methanol (8 mL) and H$_2$O (2 mL) was added LiOH.H$_2$O (386 mg, 9.2 mmol). The resulting reaction mixture was stirred at room temperature overnight. Additional LiOH.H$_2$O (386 mg, 9.2 mmol) was added and the mixture was stirred at room temperature for 2 h. The mixture was acidified by 1 M hydrochloric acid to pH=2-3, then extracted with CH$_2$Cl$_2$. The combined extracts were washed with brine, dried over anhydrous Na$_2$SO$_4$ and concentrated. The residue was purified by flash chromatography, followed by precipitation from methyl tert-butyl ether to give 6-benzyl-9,10-dimethoxy-2-oxo-6,7-dihydrobenzo[a]quinolizine-3-carboxylic acid (56 mg) as an off-white solid. $^1$H NMR (400 MHz, DMSO-d6): δ 8.36 (s, 1H), 7.60 (s, 1H), 7.50 (s, 1H), 7.30-7.19 (m, 3H), 7.05 (d, 2H), 7.01 (s, 1H), 5.07-4.96 (m, 1H), 3.92 (s, 3H), 3.87 (s, 3H), 3.41-3.34 (m, 1H), 2.89 (d, 1H), 2.78 (d, 2H). MS obsd. (ESI$^+$) [(M+H)$^+$]: 392.

Example 212: 10-chloro-6-ethyl-9-(2-methoxy-ethoxy)-7-methyl-2-oxo-6,7-dihydrobenzo[a]quinolizine-3-carboxylic acid

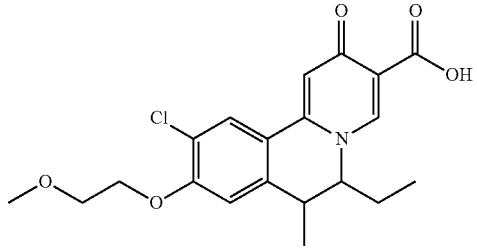 [SMILES: CCC1C(C)c2cc(OCCOC)c(Cl)cc2-c2cc(=O)c(C(=O)O)cn21]

Step 1: Preparation of 2-[4-chloro-3-(2-methoxy-ethoxy)phenyl]pentan-3-one

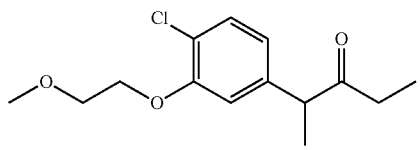 [SMILES: CCC(=O)C(C)c1ccc(Cl)c(OCCOC)c1]

To a mixture of crude 4-bromo-1-chloro-2-(3-methoxy-propoxy)benzene (5.06 g, 19.2 mmol), palladium acetate (43.2 mg, 0.192 mmol), 2-(dicyclohexylphosphino)-2'-methylbiphenyl (139.4 mg, 0.384 mmol) and t-BuONa (3.68 g, 38.3 mmol) in THF (19.2 mL) was added pentan-3-one (3.30 g, 38.3 mmol). The resulting mixture was heated at 70° C. overnight under argon. After being cooled to room temperature, the mixture was diluted with water and extracted with $CH_2Cl_2$. The combined extracts were washed with brine, dried over anhydrous $Na_2SO_4$ and concentrated. The residue was purified by flash chromatography to afford 2-[4-chloro-3-(2-methoxyethoxy)phenyl]pentan-3-one (3.29 g) which was directly used in the next step without further purification.

Step 2: Preparation of 2-[4-chloro-3-(2-methoxy-ethoxy)phenyl]pentan-3-amine

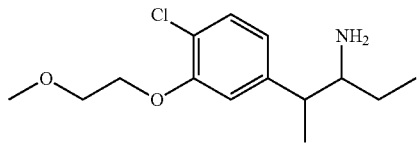

To a mixture of 2-[4-chloro-3-(2-methoxyethoxy)phenyl]pentan-3-one (3.29 g, 12.2 mmol) and ammonium acetate (14.1 g, 183 mmol) in methanol (34 mL) was added $NaBH_3CN$ (1.54 g, 24.4 mmol). The resulting mixture was stirred at room temperature overnight, then basified with 2 M NaOH aqueous solution to pH=12-14, and extracted with $CH_2Cl_2$. The combined organic layers were washed with 2 M hydrochloric acid, and the separated aqueous layer was basified with 2 M NaOH aqueous solution to pH=12-14, extracted with $CH_2Cl_2$. The combined extracts were washed with brine, dried over anhydrous $Na_2SO_4$ and concentrated to give 2-[4-chloro-3-(2-methoxyethoxy)phenyl]pentan-3-amine (1.40 g) which was directly used in the next step without purification.

Step 3: Preparation of N-[2-[4-chloro-3-(2-methoxyethoxy)phenyl]-1-ethyl-propyl]formamide

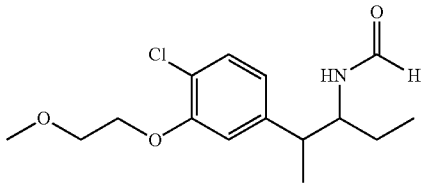 [SMILES: CCC(NC=O)C(C)c1ccc(Cl)c(OCCOC)c1]

A solution of crude 2-[4-chloro-3-(2-methoxyethoxy)phenyl]pentan-3-amine (1.56 g, 5.8 mmol) and formic acid (0.2 mL) in ethyl formate (20 mL) was heated at 90° C. for 19 h. The solvent was removed under reduced pressure to give crude N-[2-[4-chloro-3-(2-methoxyethoxy)phenyl]-1-ethyl-propyl]formamide (1.76 g) which was directly used in the next step without purification.

Step 4: Preparation of 7-chloro-3-ethyl-6-(2-methoxyethoxy)-4-methyl-3,4-dihydroisoquinoline

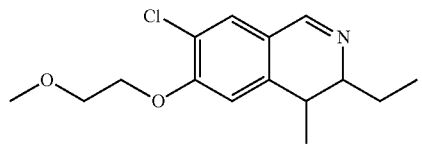 [SMILES: CCC1N=Cc2cc(Cl)c(OCCOC)cc2C1C]

To a solution of crude N-[2-[4-chloro-3-(2-methoxyethoxy)phenyl]-1-ethyl-propyl]formamide (1.76 g, 5.9 mmol) in $CH_3CN$ (12 mL) was added $POCl_3$ (1.07 g, 7.0 mmol). The reaction mixture was heated at 80° C. for 2 h and then concentrated under reduced pressure. The residue was dissolved in $CH_3CN$ (10 mL) and then basified with ammonium hydroxide at 0° C. The resulting mixture was extracted with $CH_2Cl_2$. The combined organic layers were washed with brine, dried over anhydrous $Na_2SO_4$ and concentrated under reduced pressure to afford crude 7-chloro-3-ethyl-6-(2-methoxyethoxy)-4-methyl-3,4-dihydroisoquinoline (1.43 g) which was directly used in the next step without purification.

Step 5: Preparation of ethyl 10-chloro-6-ethyl-9-(2-methoxyethoxy)-7-methyl-2-oxo-1,6,7,11b-tetrahydrobenzo[a]quinolizine-3-carboxylate

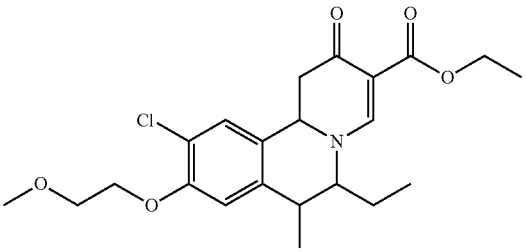 [SMILES: CCOC(=O)C1=CN2C(CC1=O)c1cc(Cl)c(OCCOC)cc1C(C)C2CC]

To a solution of crude 7-chloro-3-ethyl-6-(2-methoxyethoxy)-4-methyl-3,4-dihydroisoquinoline (1.43 g, 5 mmol) and ethyl 2-(dimethylaminomethylene)-3-oxo-butanoate (1.39 g, 7.5 mmol) in DMSO (8 mL) was added 4 M HCl in dioxane (0.25 mL, 1 mmol). The resulting mixture was heated at 130° C. for 5 h under microwave. After being cooled to room temperature, the reaction mixture was partitioned between EtOAc and water. The separated aqueous layer was extracted with EtOAc. The combined extracts were washed with water, dried over anhydrous Na₂SO₄ and concentrated to give ethyl 10-chloro-6-ethyl-9-(2-methoxyethoxy)-7-methyl-2-oxo-1,6,7,11b-tetrahydrobenzo[a]quinolizine-3-carboxylate (2.61 g) which was directly used in the next step without purification.

Step 6: Preparation of ethyl 10-chloro-6-ethyl-9-(2-methoxyethoxy)-7-methyl-2-oxo-6,7-dihydrobenzo[a]quinolizine-3-carboxylate

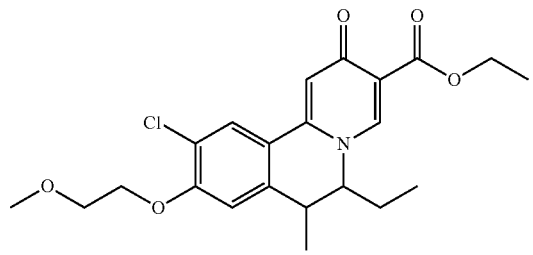 [SMILES: CCOC(=O)c1cn2c(cc1=O)-c1cc(Cl)c(OCCOC)cc1C(C)C2CC]

A mixture of crude ethyl 10-chloro-6-ethyl-9-(2-methoxyethoxy)-7-methyl-2-oxo-1,6,7,11b-tetrahydrobenzo[a]quinolizine-3-carboxylate (2.61 g, 5 mmol) and p-chloranil (984 mg, 4 mmol) in DME (15 mL) was heated at 70° C. for 1 h under argon. After being cooled to room temperature, the mixture was partitioned between CH₂Cl₂ and water. The separated organic layer was washed with saturated NaHCO₃ aqueous solution and brine, dried over anhydrous Na₂SO₄, and concentrated to give crude ethyl 10-chloro-6-ethyl-9-(2-methoxyethoxy)-7-methyl-2-oxo-6,7-dihydrobenzo[a]quinolizine-3-carboxylate (2.70 g) as a dark oil which was directly used in the next step without purification.

Step 7: Preparation of 10-chloro-6-ethyl-9-(2-methoxyethoxy)-7-methyl-2-oxo-6,7-dihydrobenzo[a]quinolizine-3-carboxylic acid

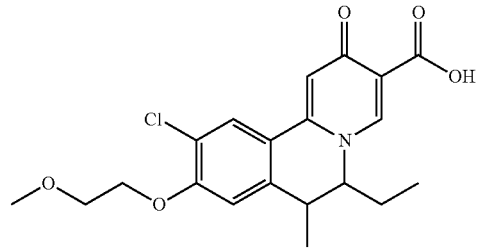 [SMILES: CCC1C(C)c2cc(OCCOC)c(Cl)cc2-c2cc(=O)c(C(=O)O)cn21]

To a mixture of crude ethyl 10-chloro-6-ethyl-9-(2-methoxyethoxy)-7-methyl-2-oxo-6,7-dihydrobenzo[a]quinolizine-3-carboxylate (2.70 g, 5 mmol) in methanol (16 mL) and H₂O (4 mL) was added LiOH.H₂O (840 mg, 20 mmol). The resulting mixture was stirred at room temperature for 2 h, then acidified with 1 M hydrochloric acid to pH=2-3, and extracted with CH₂Cl₂. The organic layer was washed with brine, dried over anhydrous Na₂SO₄ and concentrated to afford 10-chloro-6-ethyl-9-(2-methoxyethoxy)-7-methyl-2-oxo-6,7-dihydrobenzo[a]quinolizine-3-carboxylic acid (Example 212).

Step 8: Preparation of (6R*,7S*)-10-chloro-6-ethyl-9-(2-methoxyethoxy)-7-methyl-2-oxo-6,7-dihydrobenzo[a]quinolizine-3-carboxylic acid (Example 212A) and (6R*,7R*)-10-chloro-6-ethyl-9-(2-methoxyethoxy)-7-methyl-2-oxo-6,7-dihydrobenzo[a]quinolizine-3-carboxylic acid (Example 212B)

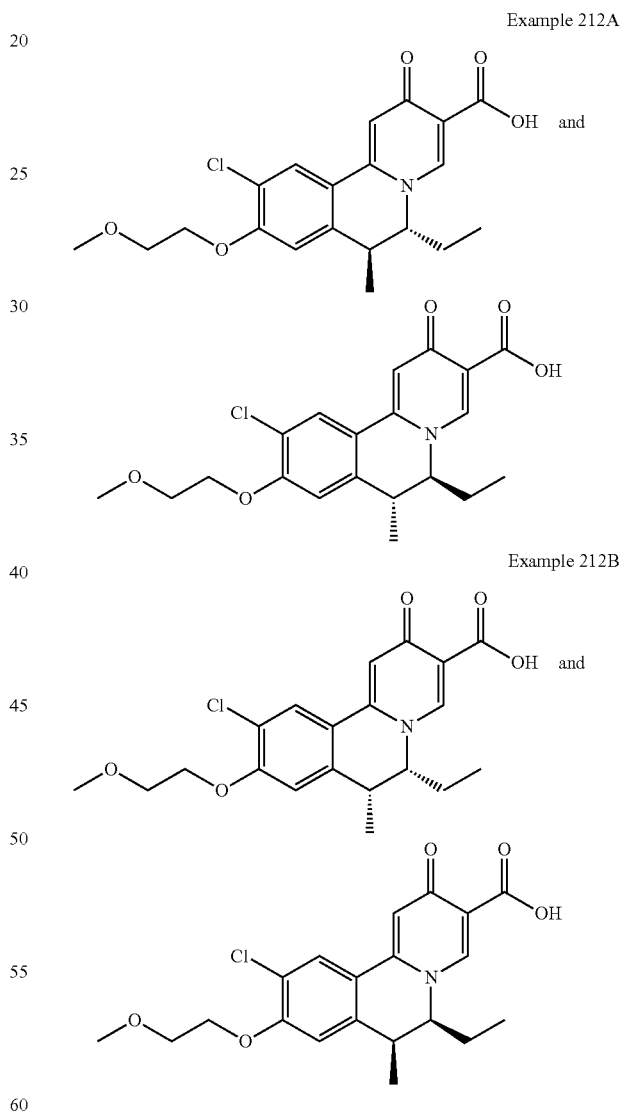

Purification and separation of 10-chloro-6-ethyl-9-(2-methoxyethoxy)-7-methyl-2-oxo-6,7-dihydrobenzo[a]quinolizine-3-carboxylic acid (Example 212) by preparative HPLC afforded (6R*,7S*)-10-chloro-6-ethyl-9-(2-methoxyethoxy)-7-methyl-2-oxo-6,7-dihydrobenzo[a]quinolizine-3-carboxylic acid (Example 212A) and (6R*,7R*)-10-chloro- 6-ethyl-9-(2-methoxyethoxy)-7-methyl-2-oxo-6,7-dihydrobenzo[a]quinolizine-3-carboxylic acid (Example 212B) as white solid.

Example 212A $^1$H NMR (400 MHz, DMSO) δ: 8.84 (s, 1H), 8.22 (s, 1H), 7.46 (s, 1H), 7.30 (s, 1H), 4.57 (t, 1H), 4.31 (m, 2H), 3.73 (m, 2H), 3.46-3.28 (m, 4H), 1.51-1.37 (m, 2H), 1.11 (d, 3H), 0.80 (t, 3H). MS obsd. (ESI$^+$) [(M+H)$^+$]: 392.

Example 212B $^1$H NMR (400 MHz, DMSO) δ: 8.72 (s, 1H), 8.18 (s, 1H), 7.41 (s, 1H), 7.10 (s, 1H), 4.59 (m, 1H), 4.35 (m, 2H), 3.74 (m, 2H), 3.59 (m, 1H), 3.31 (s, 3H), 1.57 (m, 1H), 1.41 (m, 3H), 1.12 (m, 1H), 0.71 (m, 3H). MS obsd. (ESI$^+$) [(M+H)$^+$]: 392.

Example 213: 10,11-difluoro-6-isopropyl-9-(3-methoxypropoxy)-2-oxo-6,7-dihydrobenzo[a]quinolizine-3-carboxylic acid Step 1: Preparation of 5-bromo-1,2-difluoro-3-(3-methoxypropoxy)benzene

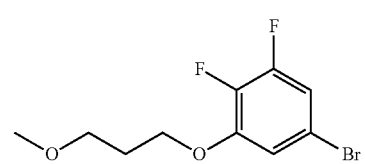

A mixture of 5-bromo-2,3-difluoro-phenol (15 g, 71.77 mmol), 1-bromo-3-methoxy-propane (12.1 g, 78.95 mmol) and potassium carbonate (19.8 g, 143.55 mmol) in DMF (100 mL) was heated at 85° C. for 4 h. The resulting mixture was concentrated and the residue was dissolved in ethyl acetate. The organic mixture was washed with water twice, dried over anhydrous Na$_2$SO$_4$ and concentrated. The residue was purified by column chromatography to give crude 5-bromo-1,2-difluoro-3-(3-methoxypropoxy)benzene as an oil (18.75 g).

Step 2: Preparation of 1-[3,4-difluoro-5-(3-methoxypropoxy)phenyl]-3-methyl-butan-2-one

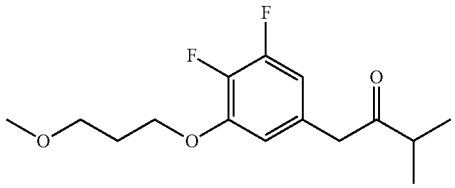 [SMILES: COCCCOc1cc(CC(=O)C(C)C)cc(F)c1F]

A mixture of 5-bromo-1,2-difluoro-3-(3-methoxypropoxy)benzene (18 g, 0.064 mol), 3-methylbutan-2-one (16.61 g, 0.193 mol), tris(dibenzylideneacetone)dipalladium (0.589 g, 0.00064 mol), Xantphos (0.744 g, 0.00128 mol) and sodium tert-butoxide (20.36 g, 0.212 mol) in anhydrous THF was heated at 60° C. overnight. After being cooled to room temperature, the mixture was filtered and the filtrate was concentrated. The residue was purified by column chromatography to give crude 1-[3,4-difluoro-5-(3-methoxypropoxy)phenyl]-3-methyl-butan-2-one as an oil (11.1 g).

Step 3: Preparation of 1-[3,4-difluoro-5-(3-methoxypropoxy)phenyl]-3-methyl-butan-2-amine

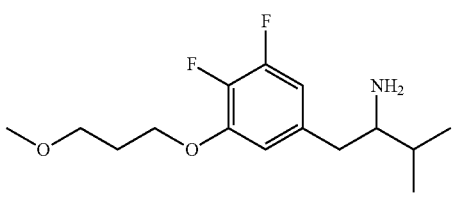 [SMILES: COCCCOc1cc(CC(N)C(C)C)cc(F)c1F]

To a solution of 1-[3,4-difluoro-5-(3-methoxypropoxy)phenyl]-3-methyl-butan-2-one (11.1 g, 0.0388 mol) and ammonium acetate (44.87 g, 0.582 mol) in methanol (200 mL) was added sodium cyanoborohydride (4.88 g, 0.0776 mol). The resultant mixture was stirred overnight at room temperature and then concentrated. The residue was dissolved in ethyl acetate. To the resulting solution was added 2.0 M NaOH aqueous solution, and the resulting mixture was stirred for 0.5 h. The separated aqueous layer was extracted with ethyl acetate (200 mL). The combined organic layers were washed with water (100 mL×2) and brine, dried over anhydrous Na$_2$SO$_4$ and concentrated to give crude 1-[3,4-difluoro-5-(3-methoxypropoxy)phenyl]-3-methyl-butan-2-amine (11 g) which was used in the next step without further purification.

Step 4: Preparation of N-[1-[[3,4-difluoro-5-(3-methoxypropoxy)phenyl]methyl]-2-methyl-propyl]formamide

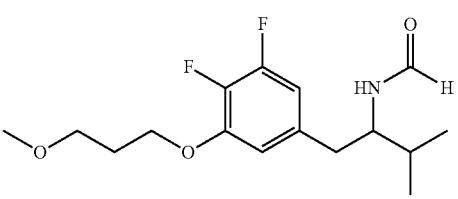 [SMILES: COCCCOc1cc(CC(NC=O)C(C)C)cc(F)c1F]

A mixture of 1-[3,4-difluoro-5-(3-methoxypropoxy)phenyl]-3-methyl-butan-2-amine (11 g, 38.33 mmol) and formic acid (50 mL) in 1,4-dioxane (300 mL) was refluxed overnight and then concentrated under reduced pressure. The residue was dissolved in ethyl acetate. The organic solution was washed with NaHCO$_3$ aqueous solution, water, dried over anhydrous Na$_2$SO$_4$ and concentrated to give crude N-[1-[[3,4-difluoro-5-(3-methoxypropoxy)phenyl]methyl]-2-methyl-propyl]formamide (12 g) as a yellow solid which was used in the next step without purification.

Step 5: Preparation of 7,8-difluoro-3-isopropyl-6-(3-methoxypropoxy)-3,4-dihydroisoquinoline

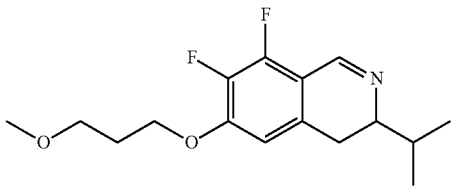 [SMILES: COCCCOc1cc2c(c(F)c1F)C=NC(C(C)C)C2]

A mixture of N-[1-[[3,4-difluoro-5-(3-methoxypropoxy)phenyl]methyl]-2-methyl-propyl]formamide (11.7 g, 37 mmol), POCl$_3$ (6.83 g, 44.6 mmol) in CH$_3$CN (400 mL) was heated at 90° C. for 3 h. Then the mixture was concentrated, and the residue was dissolved in CH$_3$CN (50 mL). The solution was basified with ammonia water at 0° C. Then the resulting mixture was extracted with CH$_2$Cl$_2$ (100 mL×3). The combined organic layers were washed with water, dried over anhydrous Na$_2$SO$_4$ and concentrated to give crude 7,8-difluoro-3-isopropyl-6-(3-methoxypropoxy)-3,4-dihydroisoquinoline as a deep brown oil (11 g) which was used in the next step without purification.

Step 6: Preparation of ethyl 10,11-difluoro-6-isopropyl-9-(3-methoxypropoxy)-2-oxo-1,6,7,11b-tetrahydrobenzo[a]quinolizine-3-carboxylate

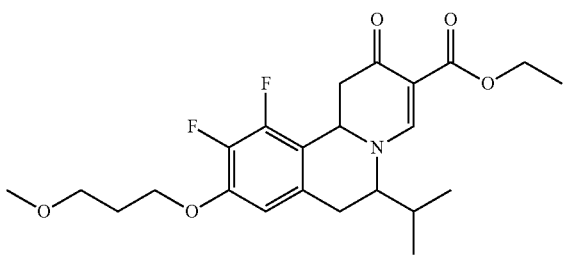 [SMILES: CCOC(=O)C1=CN2C(CC1=O)c1c(cc(OCCCOC)c(F)c1F)CC2C(C)C]

A mixture of 7,8-difluoro-3-isopropyl-6-(3-methoxypropoxy)-3,4-dihydroisoquinoline (11.5 g, 38.7 mmol) and ethyl 2-(ethoxymethylene)-3-oxo-butanoate (21.6 g, 116 mmol) in ethanol (300 mL) was refluxed overnight. The mixture was concentrated and the residue was dissolved in ethyl acetate. The organic solution was washed with water, dried over anhydrous Na$_2$SO$_4$ and concentrated. Half of the residue was purified by column chromatography to give ethyl 10,11-difluoro-6-isopropyl-9-(3-methoxypropoxy)-2-oxo-1,6,7,11b-tetrahydrobenzo[a]quinolizine-3-carboxylate (3.6 g) as a dark oil.

Step 7: Preparation of ethyl 10,11-difluoro-6-isopropyl-9-(3-methoxypropoxy)-2-oxo-6,7-dihydrobenzo[a]quinolizine-3-carboxylate

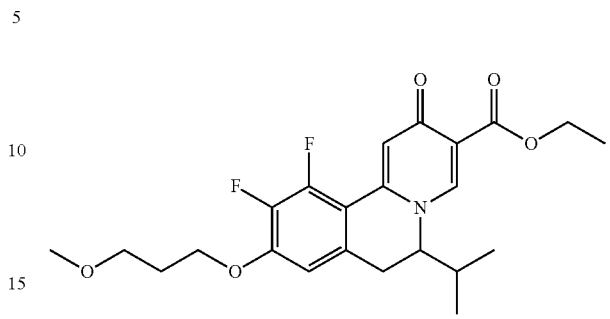

A mixture of ethyl 10,11-difluoro-6-isopropyl-9-(3-methoxypropoxy)-2-oxo-1,6,7,11b-tetrahydrobenzo[a]quinolizine-3-carboxylate (3.6 g, 8.24 mmol) and p-chloranil (2.03 g, 8.24 mmol) in DME (30 mL) was refluxed for 4 h. The resulting mixture was diluted with CH$_2$Cl$_2$, washed with NaHCO$_3$ aqueous solution (50 mL×6), dried over anhydrous Na$_2$SO$_4$ and concentrated to give crude ethyl 10,11-difluoro-6-isopropyl-9-(3-methoxypropoxy)-2-oxo-6,7-dihydrobenzo[a]quinolizine-3-carboxylate (3 g).

Step 8: Preparation of 10,11-difluoro-6-isopropyl-9-(3-methoxypropoxy)-2-oxo-6,7-dihydrobenzo[a]quinolizine-3-carboxylic acid

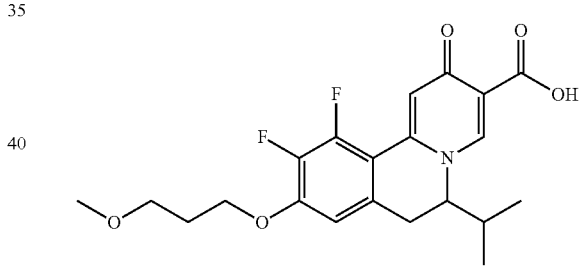

To a solution of ethyl 10,11-difluoro-6-isopropyl-9-(3-methoxypropoxy)-2-oxo-6,7-dihydrobenzo[a]quinolizine-3-carboxylate (1.5 g, 3.45 mmol) in THF (15 mL), methanol (25 mL) and H$_2$O (5 mL) was added LiOH.H$_2$O (0.434 g, 10.35 mmol) at rt. The mixture was stirred for 4 h, then acidified to pH=1-2 with 2 M hydrochloric acid, and extracted with DCM (50 mL×2). The combined organic layers were washed with brine, dried over anhydrous Na$_2$SO$_4$ and concentrated. The residue was purified by prep-HPLC to give 10,11-difluoro-6-isopropyl-9-(3-methoxypropoxy)-2-oxo-6,7-dihydrobenzo[a]quinolizine-3-carboxylic acid (103 mg). $^1$H NMR (400 MHz, CDCl$_3$): δ 15.76-16.08 (br. s., 1H), 8.42-8.61 (s, 1H), 7.40 (s, 1H), 6.69-6.80 (s, 1H), 4.17-4.31 (m, 2H), 3.74-4.01 (m, 1H), 3.60 (br. s., 2H), 3.28-3.46 (m, 4H), 3.08-3.20 (m, 1H), 2.08-2.21 (m, 2H), 1.75-1.85 (m, 1H), 0.80-1.03 (m, 6H). MS obsd. (ESI$^+$) [(M+H)$^+$]: 408.

Example 214 and 215

(+)-10,11-difluoro-6-isopropyl-9-(3-methoxy-propoxy)-2-oxo-6,7-dihydrobenzo[a]quinolizine-3-carboxylic acid and (−)-10,11-difluoro-6-isopropyl-9-(3-methoxypropoxy)-2-oxo-6,7-dihydrobenzo[a]quinolizine-3-carboxylic acid

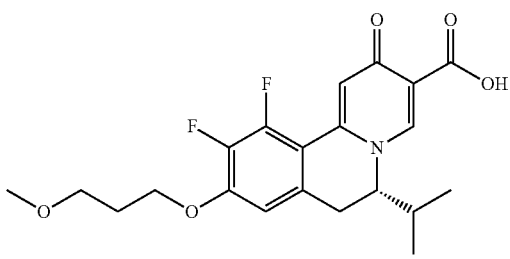 [SMILES: COCCCOc1cc2c(c(F)c1F)-c1cc(=O)c(C(=O)O)cn1C(C(C)C)C2]

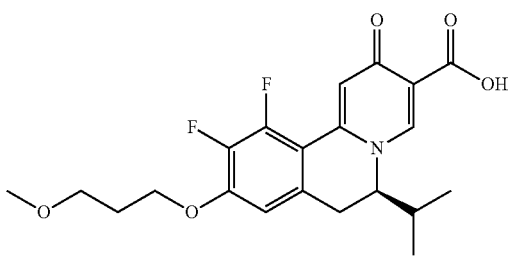

Separation of 10,11-difluoro-6-isopropyl-9-(3-methoxypropoxy)-2-oxo-6,7-dihydrobenzo[a]quinolizine-3-carboxylic acid by chiral HPLC afforded (+)-10,11-difluoro-6-isopropyl-9-(3-methoxypropoxy)-2-oxo-6,7-dihydrobenzo[a]quinolizine-3-carboxylic acid (Example 214) and (−)-10,11-difluoro-6-isopropyl-9-(3-methoxypropoxy)-2-oxo-6,7-dihydrobenzo[a]quinolizine-3-carboxylic acid (Example 215).

Example 214

$^1$H NMR (400 MHz, CDCl$_3$) δ 15.93-15.97 (br. s., 1H), 8.51-8.57 (s, 1H), 7.38 (s, 1H), 6.70-6.78 (s, 1H), 4.18-4.32 (m, 2H), 3.91-4.01 (m, 1H), 3.54-3.66 (m, 2H), 3.38 (s, 4H), 3.07-3.22 (m, 1H), 2.08-2.20 (m, 2H), 1.69-1.83 (m, 1H), 0.82-1.04 (m, 6H). MS obsd. (ESI$^+$) [(M+H)$^+$]: 408. [α]$_D^{20}$=+70.0° (0.100%, CH$_3$OH).

Example 215

$^1$H NMR (400 MHz, CDCl$_3$) δ 15.80-16.01 (br. S., 1H), 8.39-8.66 (s, 1H), 7.40 (s, 1H), 6.63-6.86 (s, 1H), 4.16-4.33 (m, 2H), 3.84-4.00 (m, 1H), 3.51-3.67 (m, 2H), 3.39 (s, 4H), 3.05-3.24 (m, 1H), 2.07-2.24 (m, 2H), 1.69-1.87 (m, 1H), 0.76-1.04 (m, 6H). MS obsd. (ESI$^+$) [(M+H)$^+$]: 408.

Example 216: 6-tert-butyl-10-methoxy-2-oxo-9-(3-pyrazol-1-ylpropoxy)-6,7-dihydrobenzo[a]quinolizine-3-carboxylic acid

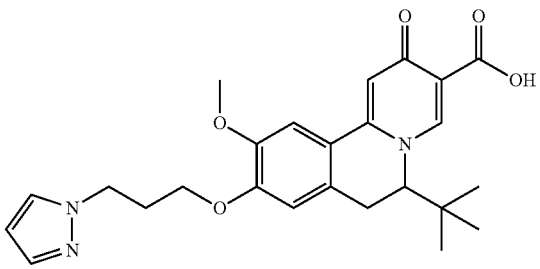 [SMILES: COc1cc2c(cc1OCCCn1cccn1)CC(C(C)(C)C)n1cc(C(=O)O)c(=O)cc1-2]

Step 1: Preparation of 1-(3-bromopropyl)pyrazole

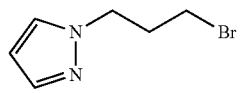

To a mixture of 1H-pyrazole (12 g, 29.4 mmol) in acetone (30 mL) was added K$_2$CO$_3$ (4.26 g, 30.9 mmol) followed by 1,3-dibromopropane (29.7 g, 147 mmol). The mixture was stirred at 30° C. for 16 h. The mixture was filtered. The filtrate was concentrated. The residue was purified by column chromatography to give 1-(3-bromopropyl)pyrazole (350 mg) as a yellow oil.

Step 2: Preparation of ethyl 6-tert-butyl-10-methoxy-2-oxo-9-(3-pyrazol-1-ylpropoxy)-6,7-dihydrobenzo[a]quinolizine-3-carboxylate

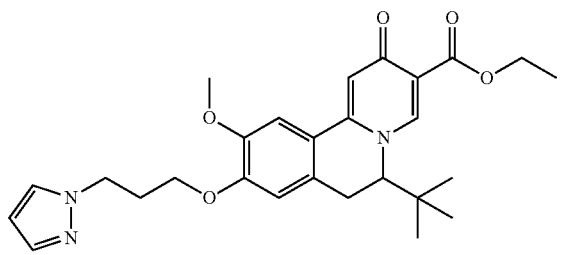 [SMILES: CCOC(=O)c1cn2c(cc1=O)-c1cc(OC)c(OCCCn3cccn3)cc1CC2C(C)(C)C]

A mixture of ethyl 6-tert-butyl-9-hydroxy-10-methoxy-2-oxo-6,7-dihydrobenzo[a]quinolizine-3-carboxylate (150 mg, 0.40 mmol), K$_2$CO$_3$ (167 mg, 1.21 mmol) and 1-(3-bromopropyl)pyrazole (115 mg, 0.61 mmol) in DMF (3 mL) was stirred at room temperature for 16 h. The reaction mixture was diluted with EtOAc and washed with brine. The organic layer was dried over anhydrous Na$_2$SO$_4$ and concentrated. The residue was purified by column chromatography to give ethyl 6-tert-butyl-10-methoxy-2-oxo-9-(3-pyrazol-1-ylpropoxy)-6,7-dihydrobenzo[a]quinolizine-3-carboxylate (120 mg) as a yellow oil.

Step 3: Preparation of 6-tert-butyl-10-methoxy-2-oxo-9-(3-pyrazol-1-ylpropoxy)-6,7-dihydrobenzo[a]quinolizine-3-carboxylic acid

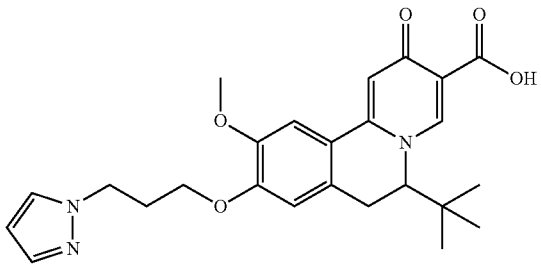 [SMILES: COc1cc2c(cc1OCCCn1cccn1)CC(C(C)(C)C)n1cc(C(=O)O)c(=O)cc1-2]

A mixture of ethyl 6-tert-butyl-10-methoxy-2-oxo-9-(3-pyrazol-1-ylpropoxy)-6,7-dihydrobenzo[a]quinolizine-3-carboxylate (120 mg, 0.25 mmol) and 2 M NaOH aqueous solution (0.25 mL, 0.50 mmol) in EtOH (1 mL) was stirred at room temperature for 16 h. The reaction mixture was diluted with H$_2$O. The resulting mixture was acidified with 1 M hydrochloric acid to pH=3-4. The formed solid was collected by filtration, dried to give 6-tert-butyl-10-methoxy-2-oxo-9-(3-pyrazol-1-ylpropoxy)-6,7-dihydrobenzo[a]quinolizine-3-carboxylic acid (70 mg) as a yellow solid. $^1$H NMR (400 MHz, DMSO) δ 0.72 (s, 9H), 2.26 (m, 2H), 3.25-3.21 (m, 2H), 3.89 (s, 3H), 4.04-4.00 (m, 2H), 4.29 (m, 2H), 4.54 (m, 1H), 6.24 (s, 1H), 6.70 (s, 1H), 7.46 (m, 3H), 7.74 (s, 1H), 8.704 (s, 1H). MS obsd. (ESI$^+$) [(M+H)$^+$]: 452.

Example 217: 6-tert-butyl-10-methoxy-2-oxo-9-[3-(1,2,4-triazol-1-yl)propoxy]-6,7-dihydrobenzo[a]quinolizine-3-carboxylic acid

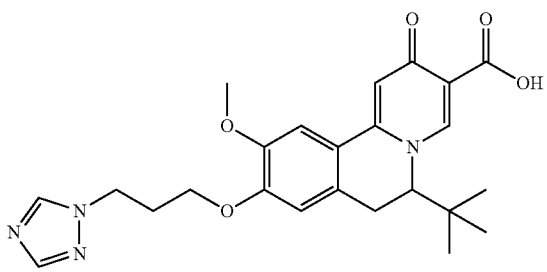 [SMILES: COc1cc2c(cc1OCCCn1cncn1)CC(C(C)(C)C)n1cc(C(=O)O)c(=O)cc1-2]

Step 1: Preparation of 1-(3-bromopropyl)-1,2,4-triazole

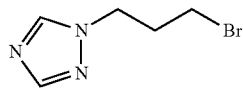

To a solution of 1,3-dibromopropane (14.6 g, 72.5 mmol) in DMF (20 mL) was added 1H-1,2,4-triazole (1.32 g, 14.5 mmol). The mixture was stirred at 30° C. for 16 h. The mixture was diluted with EtOAc. The resulting mixture was washed with water, brine, dried over anhydrous Na$_2$SO$_4$ and concentrated. The residue was purified by column chromatography to give 1-(3-bromopropyl)-1,2,4-triazole (300 mg) as a colorless oil.

Step 2: Preparation of ethyl 6-tert-butyl-O-methoxy-2-oxo-9-[3-(1,2,4-triazol-1-yl)propoxy]-6,7-dihydrobenzo[a]quinolizine-3-carboxylate

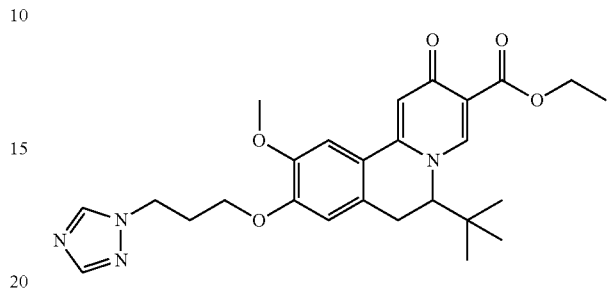

A mixture of ethyl 6-tert-butyl-9-hydroxy-10-methoxy-2-oxo-6,7-dihydrobenzo[a]quinolizine-3-carboxylate (150 mg, 0.40 mmol), K$_2$CO$_3$ (167 mg, 1.21 mmol) and 1-(3-bromopropyl)-1,2,4-triazole (115 mg, 0.60 mmol) in DMF (3 mL) was stirred at room temperature for 16 h. The reaction mixture was partitioned between EtOAc and brine. The separated organic layer was dried over anhydrous Na$_2$SO$_4$ and concentrated. The residue was purified by column chromatography to give ethyl 6-tert-butyl-10-methoxy-2-oxo-9-[3-(1,2,4-triazol-1-yl)propoxy]-6,7-dihydrobenzo[a]quinolizine-3-carboxylate (60 mg) as a yellow solid.

Step 3: Preparation of 6-tert-butyl-10-methoxy-2-oxo-9-[3-(1,2,4-triazol-1-yl)propoxy]-6,7-dihydrobenzo[a]quinolizine-3-carboxylic acid

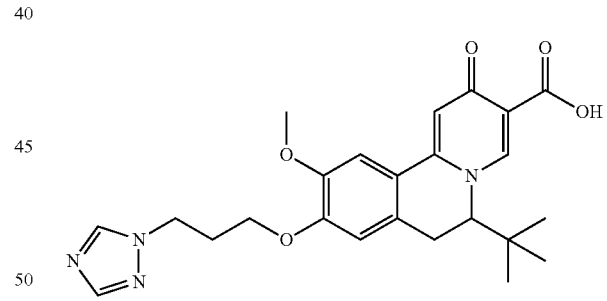

A mixture of ethyl 6-tert-butyl-10-methoxy-2-oxo-9-[3-(1,2,4-triazol-1-yl)propoxy]-6,7-dihydrobenzo[a]quinolizine-3-carboxylate (160 mg, 0.33 mmol) and 2.2 M NaOH aqueous solution (0.3 mL, 0.66 mmol) in EtOH (2 mL) was stirred at room temperature for 16 h. The reaction mixture was diluted with H$_2$O. The resulting mixture was acidified with 1 M hydrochloric acid to pH=3-4. The formed solid was collected by filtration and dried to give 6-tert-butyl-10-methoxy-2-oxo-9-[3-(1,2,4-triazol-1-yl)propoxy]-6,7-dihydrobenzo[a]quinolizine-3-carboxylic acid (51 mg) as a yellow solid. $^1$H NMR (400 MHz, DMSO) δ 0.72 (s, 9H), 2.21-2.35 (m, 2H), 3.19-3.27 (m, 1H), 3.32-3.35 (m, 1H), 3.88 (s, 3H), 3.97-4.14 (m, 2H), 4.36 (t, 2H), 4.56 (d, 1H), 7.00-7.06 (m, 1H), 7.47 (d, 2H), 7.99 (s, 1H), 8.55 (s, 1H), 8.72 (s, 1H). MS obsd. (ESI$^+$) [(M+H)$^+$]: 453.

Example 218: 6-tert-butyl-9-(3-carboxypropoxy)-10-methoxy-2-oxo-6,7-dihydrobenzo[a]quinolizine-3-carboxylic acid

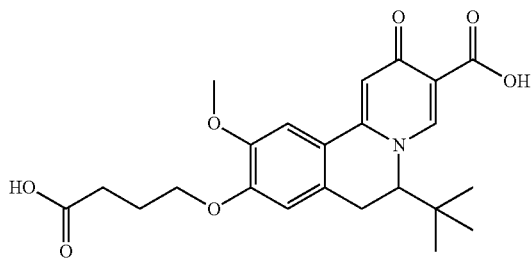 [SMILES: COc1cc2c(cc1OCCCC(=O)O)CC(C(C)(C)C)n1cc(C(=O)O)c(=O)cc1-2]

Step 1: Preparation of ethyl 6-tert-butyl-9-(4-ethoxy-4-oxo-butoxy)-10-methoxy-2-oxo-6,7-dihydrobenzo[a]quinolizine-3-carboxylate

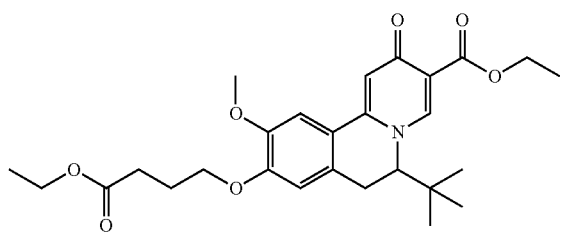 [SMILES: CCOC(=O)CCCOc1cc2c(cc1OC)-c1cc(=O)c(C(=O)OCC)cn1C(C(C)(C)C)C2]

A mixture of ethyl 6-tert-butyl-9-hydroxy-10-methoxy-2-oxo-6,7-dihydrobenzo[a]quinolizine-3-carboxylate (100 mg, 0.27 mmol), $K_2CO_3$ (112 mg, 0.81 mmol) and ethyl 4-bromobutanoate (79 mg, 0.40 mmol) in DMF (2 mL) was stirred at room temperature for 16 h. The reaction mixture was partitioned between EtOAc and brine. The separated organic layer was dried over anhydrous $Na_2SO_4$ and concentrated. The residue was purified by column chromatography to give ethyl 6-tert-butyl-9-(4-ethoxy-4-oxo-butoxy)-10-methoxy-2-oxo-6,7-dihydrobenzo[a]quinolizine-3-carboxylate (92 mg) as a yellow oil.

Step 2: Preparation of 6-tert-butyl-9-(3-carboxypropoxy)-10-methoxy-2-oxo-6,7-dihydrobenzo[a]quinolizine-3-carboxylic acid

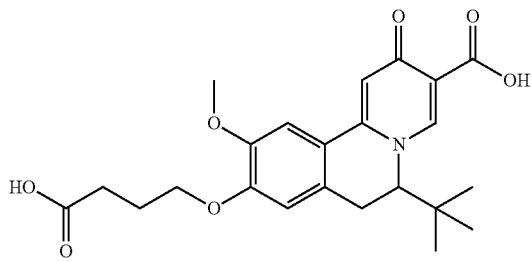 [SMILES: COc1cc2c(cc1OCCCC(=O)O)CC(C(C)(C)C)n1cc(C(=O)O)c(=O)cc1-2]

A mixture of ethyl 6-tert-butyl-9-(4-ethoxy-4-oxo-butoxy)-10-methoxy-2-oxo-6,7-dihydrobenzo[a]quinolizine-3-carboxylate (138 mg, 0.28 mmol) and 1.9 M NaOH aqueous solution (0.6 mL, 1.14 mmol) in THF (2 mL) was stirred at room temperature for 16 h. The reaction mixture was diluted with $H_2O$. The resulting mixture was acidified with 1 M hydrochloric acid to pH=3-4. The formed solid was collected by filtration and dried to give 6-tert-butyl-9-(3-carboxypropoxy)-10-methoxy-2-oxo-6,7-dihydrobenzo[a]quinolizine-3-carboxylic acid (54 mg) as a yellow solid. $^1$H NMR (400 MHz, DMSO) δ 0.72 (s, 9H), 1.96 (m, 2H), 2.38 (t, 2H), 3.14-3.29 (m, 1H), 3.31-3.41 (m, 1H), 3.82-3.91 (m, 3H), 4.00-4.12 (m, 2H), 4.56 (d, 1H), 7.06 (s, 1H), 7.46 (d, 2H), 8.71 (s, 1H). MS obsd. (ESI$^{30}$) [(M+H)$^+$]: 430.

BIOLOGICAL EXAMPLES

Example 219: Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their capacity to inhibit HBsAg as described herein. The Examples were tested in the above assay and found to have $IC_{50}$ of about 0.0003 μM to about 30.0 μM. Particular compounds of formula I were found to have $IC_{50}$ of about 0.0003 μM to about 0.1 μM. More Particular compounds of formula I were found to have $IC_{50}$ of about 0.0003 μM to about 0.010 μM. Results of HBsAg assay are given in Table 1.

TABLE 1

Activity data of particular compounds

| Example No. | IC$_{50}$ (µM) | Example No. | IC$_{50}$ (µM) | Example No. | IC$_{50}$ (µM) | Example No. | IC$_{50}$ (µM) |
|---|---|---|---|---|---|---|---|
| 1 | 0.013 | 2 | 7.2 | 3 | 4.6 | 4 | 0.098 |
| 5 | 0.018 | 6 | 0.006 | 7 | 1.9 | 8 | 0.15 |
| 9 | 0.015 | 10 | 1.24 | 11 | 0.017 | 12 | 5.2 |
| 13 | 0.09 | 14 | 0.014 | 15 | 0.016 | 16 | 0.015 |
| 17 | 0.19 | 18 | 9.47 | 19 | 0.25 | 20 | 0.22 |
| 21 | 0.45 | 22 | 0.039 | 23 | 0.012 | 24 | 1.35 |
| 25 | 0.155 | 26 | 1.65 | 27 | 0.056 | 28 | 0.029 |
| 29 | 1.95 | 30 | 0.024 | 31 | 0.009 | 32 | 0.075 |
| 33 | 0.008 | 34 | 0.004 | 35 | 1.39 | 36 | 0.053 |
| 37 | 0.008 | 38 | 1.81 | 39 | 0.016 | 40 | 0.013 |
| 41 | 5.77 | 42 | 0.057 | 43 | 0.046 | 44 | 5.46 |
| 45 | 0.104 | 46 | 0.044 | 47 | 3.40 | 48 | 0.024 |
| 49 | 0.015 | 50 | 0.40 | 51 | 3.9 | 52 | 0.17 |
| 53 | 1.54 | 54 | 0.13 | 55 | 0.72 | 56 | 3.3 |
| 57 | 0.17 | 58 | 3.86 | 59 | 4.75 | 60 | 1.24 |
| 61 | 6.02 | 62 | 0.99 | 63 | 7.18 | 64 | 24.9 |
| 65 | 0.32 | 66 | 0.43 | 67 | 0.38 | 68 | 5.67 |
| 69 | 1.30 | 70 | 0.07 | 71 | 0.037 | 72 | 11.98 |
| 73 | 0.14 | 74 | 0.14 | 75 | 1.11 | 76 | 0.35 |
| 77 | 0.83 | 78 | 0.021 | 79 | 0.004 | 80 | 0.19 |
| 81 | 0.33 | 82 | 5.27 | 83 | 5.60 | 84 | 7.67 |
| 85 | 29.0 | 86 | 1.20 | 87 | 1.55 | 88 | 0.02 |
| 89 | 0.008 | 90 | 0.01 | 91 | 0.50 | 92 | 0.23 |
| 93 | 0.19 | 94 | 0.41 | 95 | 7.83 | 96 | 0.049 |
| 97 | 0.07 | 98 | 0.016 | 99 | 0.016 | 100 | 5.4 |
| 101 | 0.045 | 102 | 0.042 | 103 | 3.42 | 104 | 0.018 |
| 105 | 0.016 | 106 | 7.31 | 107 | 0.012 | 108 | 0.003 |
| 109 | 0.061 | 110 | 0.052 | 111 | 0.04 | 112 | 0.14 |
| 113 | 0.64 | 114 | 0.15 | 115 | 0.029 | 116 | 0.033 |
| 117 | 0.91 | 118 | 0.004 | 119 | 0.33 | 120 | 0.002 |
| 121 | 0.002 | 122 | 0.69 | 123 | 0.009 | 124 | 0.002 |
| 125 | 3.15 | 126 | 0.008 | 127 | 0.008 | 128 | 0.67 |
| 129 | 0.012 | 130 | 1.54 | 131 | 0.001 | 132 | 0.001 |
| 133 | 0.33 | 134 | 0.007 | 135 | 0.004 | 136 | 0.40 |
| 137 | 0.015 | 138 | 0.009 | 139 | 0.129 | 140 | 0.031 |
| 141 | 0.007 | 142 | 0.004 | 143 | 0.19 | 144 | 0.026 |
| 145 | 0.006 | 146 | 0.52 | 147 | 0.030 | 148 | 0.005 |
| 149 | 0.002 | 150 | 0.002 | 151 | 0.16 | 152 | 0.002 |
| 153 | 0.001 | 154 | 0.12 | 155 | 0.002 | 156 | 0.001 |
| 157 | 0.17 | 158 | 0.003 | 159 | 0.066 | 160 | 0.018 |
| 161 | 0.009 | 162 | 0.002 | 163 | 0.35 | 164 | 0.003 |
| 165 | 1.55 | 166 | 0.006 | 167 | 0.011 | 168 | 0.006 |
| 169 | 0.19 | 170 | 0.008 | 171 | 0.42 | 172 | 0.002 |
| 173 | 0.021 | 174 | 2.42 | 175 | 0.033 | 176 | 0.003 |
| 177 | 1.38 | 178 | 0.063 | 179 | 0.038 | 180 | 0.004 |
| 181 | 0.012 | 182 | 0.016 | 183 | 0.002 | 184 | 0.001 |
| 185 | 0.055 | 186 | 0.02 | 187 | 0.013 | 188 | 0.22 |
| 189 | 0.018 | 190 | 0.006 | 191 | 0.19 | 192 | 0.01 |
| 193 | 0.003 | 194 | 0.27 | 195 | 0.057 | 196 | 0.12 |
| 197 | 0.003 | 198 | 0.23 | 199 | 0.033 | 200 | 0.024 |
| 201 | 14.2 | 202 | 0.002 | 203 | 0.0003 | 204 | 0.14 |
| 205 | 0.001 | 206 | 0.001 | 207 | 0.040 | 208 | 0.002 |
| 209 | 0.001 | 210 | 0.092 | 211 | 8.25 | 212A | 0.33 |
| 212B | 0.029 | 213 | 0.024 | 214 | 0.015 | 215 | 1.14 |
| 216 | 0.006 | 217 | 0.034 | 218 | 0.145 | | |

HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. Antiviral activity was calculated from the reduction in HBV DNA levels (IC$_{50}$).

The compounds of the present invention were tested for their capacity to inhibit HBV DNA as described herein. The Examples were tested in the above assay and found to have IC$_{50}$ below 0.13 µM. Particular compounds of formula I were found to have IC$_{50}$ below 0.010 µM.

Results of HBV DNA assay are given in Table 2.

TABLE 2

Anti HBV DNA production activity in HepG2.2.15 cells

| Example No. | IC$_{50}$ (µM) |
|---|---|
| 5 | 0.009 |
| 6 | 0.006 |
| 76 | 0.13 |
| 78 | 0.004 |
| 11 | 0.004 |
| 30 | 0.002 |
| 33 | 0.003 |
| 79 | 0.002 |
| 99 | 0.003 |
| 108 | 0.002 |
| 119 | 0.002 |
| 121 | <0.0001 |
| 124 | <0.0001 |
| 190 | 0.002 |
| 206 | 0.0001 |
| 209 | 0.0003 |

The invention claimed is:

1. A method of inhibiting HBsAg production or secretion in a patient, comprising administering, to a patient in need thereof, a compound of formula IA,

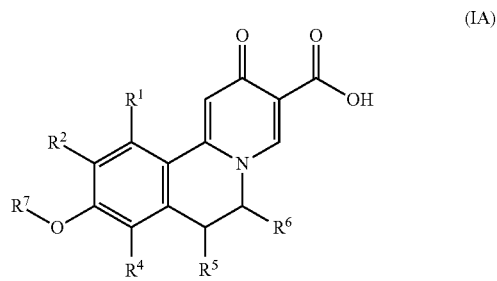

(IA)

wherein
R$^1$ is hydrogen, halogen or C$_{1-6}$alkoxy;
R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;
R$^4$ is hydrogen or halogen;
R$^5$ is hydrogen or C$_{1-6}$alkyl;
R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;
R$^7$ is hydrogen; C$_{1-6}$alkyl, which is unsubstituted or substituted with one to three substituents independently selected from fluoro, hydroxy and ethenyl; C$_{1-6}$alkoxyC$_{1-6}$alkyl; C$_{1-6}$alkoxyC$_{1-6}$alkoxyC$_{1-6}$alkyl; aminoC$_{1-8}$alkyl; C$_{1-6}$alkylcarbonylaminoC$_{1-8}$alkyl; C$_{1-6}$alkylsulfonylaminoC$_{1-8}$alkyl; C$_{1-6}$alkylsulfanylC$_{1-6}$alkyl; C$_{1-6}$alkylsulfonylC$_{1-6}$alkyl; cyanoC$_{1-6}$alkyl; C$_{3-7}$cycloalkylC$_{1-6}$alkyl; cyanoC$_{3-7}$cycloalkylC$_{1-6}$alkyl; phenylC$_{1-6}$alkyl; pyrrolidinylcarbonylC$_{1-6}$alkyl; C$_{2-6}$alkynyl; hydroxyC$_{1-6}$alkylC$_{2-6}$alkynyl; aminoC$_{1-6}$alkoxyC$_{1-6}$alkyl; C$_{1-6}$alkylaminoC$_{1-6}$alkoxyC$_{1-6}$alkyl; carboxyC$_{1-6}$alkyl; C$_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl; and x is 1-6;

or a pharmaceutically acceptable salt, or enantiomer thereof.

2. A method of inhibiting HBV DNA production in a patient, comprising administering, to a patient in need thereof, a compound of formula IA, (IA)

wherein

R$^1$ is hydrogen, halogen or C$_{1-6}$alkoxy;

R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;

R$^4$ is hydrogen or halogen;

R$^5$ is hydrogen or C$_{1-6}$alkyl;

R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;

R$^7$ is hydrogen; C$_{1-6}$alkyl, which is unsubstituted or substituted with one to three substituents independently selected from fluoro, hydroxy and ethenyl; C$_{1-6}$alkoxyC$_{1-6}$alkyl; C$_{1-6}$alkoxyC$_{1-6}$alkoxyC$_{1-6}$alkyl; aminoC$_{1-8}$alkyl; C$_{1-6}$alkylcarbonylaminoC$_{1-8}$alkyl; C$_{1-6}$alkylsulfonylaminoC$_{1-8}$alkyl; C$_{1-6}$alkylsulfanylC$_{1-6}$alkyl; C$_{1-6}$alkylsulfonylC$_{1-6}$alkyl; cyanoC$_{1-6}$alkyl; C$_{3-7}$cycloalkylC$_{1-6}$alkyl; cyanoC$_{3-7}$cycloalkylC$_{1-6}$alkyl; phenylC$_{1-6}$alkyl; pyrrolidinylcarbonylC$_{1-6}$alkyl; C$_{2-6}$alkynyl; hydroxyC$_{1-6}$alkylC$_{2-6}$alkynyl; aminoC$_{1-6}$alkoxyC$_{1-6}$alkyl; C$_{1-6}$alkylaminoC$_{1-6}$alkoxyC$_{1-6}$alkyl; carboxyC$_{1-6}$alkyl; C$_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl; and x is 1-6;

or a pharmaceutically acceptable salt, or enantiomer thereof.

3. A method for the treatment or prophylaxis of HBV infection in a patient, comprising administering, to a patient in need thereof, a compound of formula IA, (IA)

wherein

R$^1$ is hydrogen, halogen or C$_{1-6}$alkoxy;

R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;

R$^4$ is hydrogen or halogen;

R$^5$ is hydrogen or C$_{1-6}$alkyl;

R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;

R$^7$ is hydrogen; C$_{1-6}$alkyl, which is unsubstituted or substituted with one to three substituents independently selected from fluoro, hydroxy and ethenyl; C$_{1-6}$alkoxyC$_{1-6}$alkyl; C$_{1-6}$alkoxyC$_{1-6}$alkoxyC$_{1-6}$alkyl; aminoC$_{1-8}$alkyl; C$_{1-6}$alkylcarbonylaminoC$_{1-8}$alkyl; C$_{1-6}$alkylsulfonylaminoC$_{1-8}$alkyl; C$_{1-6}$alkylsulfanylC$_{1-6}$alkyl; C$_{1-6}$alkylsulfonylC$_{1-6}$alkyl; cyanoC$_{1-6}$alkyl; C$_{3-7}$cycloalkylC$_{1-6}$alkyl; cyanoC$_{3-7}$cycloalkylC$_{1-6}$alkyl; phenylC$_{1-6}$alkyl; pyrrolidinylcarbonylC$_{1-6}$alkyl; C$_{2-6}$alkynyl; hydroxyC$_{1-6}$alkylC$_{2-6}$alkynyl; aminoC$_{1-6}$alkoxyC$_{1-6}$alkyl; C$_{1-6}$alkylaminoC$_{1-6}$alkoxyC$_{1-6}$alkyl; carboxyC$_{1-6}$alkyl; C$_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl; and x is 1-6;

or a pharmaceutically acceptable salt, or enantiomer thereof.

4. The method according to any one of claims 1-3, wherein

R$^1$ is hydrogen, fluoro, chloro or methoxy;

R$^2$ is hydrogen, fluoro, chloro, methyl, ethyl, methoxy, ethoxy, propoxy, cyclopropyl, hydroxy or phenylmethyl-O—;

R$^4$ is hydrogen or chloro;

R$^5$ is hydrogen or methyl;

R$^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl; and R$^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminopentyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylamino-ethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl.

5. The method according to any one of claims 1-3, wherein
   $R^1$ is hydrogen or halogen;
   $R^2$ is $C_{1-6}$alkyl, halogen or $C_{3-7}$cycloalkyl;
   $R^4$ is hydrogen;
   $R^5$ is hydrogen or $C_{1-6}$alkyl;
   $R^6$ is $C_{1-6}$alkyl or $C_{1-6}$alkyl$C_{3-7}$cycloalkyl; and
   $R^7$ is $C_{1-6}$alkyl, $C_{1-6}$alkoxy$C_{1-6}$alkyl; or phenyl$C_{1-6}$alkyl.

6. The method according to any one of claims 1-3, wherein
   $R^1$ is hydrogen, fluoro or chloro;
   $R^2$ is methyl, ethyl, fluoro, chloro or cyclopropyl;
   $R^4$ is hydrogen;
   $R^5$ is hydrogen or methyl;
   $R^6$ is methyl, ethyl, isopropyl, isobutyl, tert-butyl or methylcyclopropyl; and
   $R^7$ is methyl, ethyl, methoxyethyl, methoxypropyl or phenylmethyl.

7. The method according to any one of claims 1-3, wherein
   $R^1$ is hydrogen;
   $R^2$ is $C_{1-6}$alkoxy;
   $R^4$ is hydrogen or halogen;
   $R^5$ is hydrogen or $C_{1-6}$alkyl;
   $R^6$ is hydrogen; $C_{1-6}$alkyl, which is unsubstituted or once, twice or three times substituted by fluoro; $C_{3-7}$cycloalkyl; $C_{1-6}$alkyl$C_{3-7}$cycloalkyl; or phenyl-$C_xH_{2x}$—;
   $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$ alkyl; $C_{1-6}$alkylsulfonyl$C_{1-6}$alkyl; cyano$C_{1-6}$alkyl; cyano$C_{3-7}$cycloalkyl$C_{1-6}$alkyl; $C_{3-7}$cycloalkyl$C_{1-6}$ alkyl; phenyl$C_{1-6}$alkyl; pyrrolidinylcarbonyl$C_{1-6}$ alkyl; $C_{2-6}$alkynyl; hydroxy$C_{1-6}$alkyl$C_{2-6}$alkynyl; amino$C_{1-6}$alkoxy$C_{1-6}$ alkyl; $C_{1-6}$alkylamino$C_{1-6}$ alkoxy$C_{1-6}$alkyl; carboxy$C_{1-6}$alkyl; $C_{1-6}$alkoxycarbonylamino$C_{1-8}$alkyl; imidazolyl$C_{1-6}$alkyl; pyrazolyl$C_{1-6}$ alkyl; triazolyl$C_{1-6}$ alkyl; morpholinyl$C_{1-6}$alkyl; (2-oxo-pyrrolidinyl)$C_{1-6}$ alkyl; pyrrolidinyl$C_{1-6}$alkyl; or tetrahydropyranyl$C_{1-6}$ alkyl; and
   x is 1-6.

8. The method according to any one of claims 1-3, wherein
   $R^1$ is hydrogen;
   $R^2$ is methoxy, ethoxy or propoxy;
   $R^4$ is hydrogen or chloro;
   $R^5$ is hydrogen or methyl;
   $R^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl; and
   $R^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminopentyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylamino-ethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl.

9. The method according to any one of claims 1-3, wherein
   $R^1$ is hydrogen or halogen;
   $R^2$ is halogen, $C_{1-6}$alkyl, $C_{1-6}$alkoxy or $C_{3-7}$cycloalkyl;
   $R^4$ is hydrogen;
   $R^5$ is hydrogen or $C_{1-6}$alkyl;
   $R^6$ is $C_{1-6}$alkyl, which is unsubstituted or once, twice or three times substituted by fluoro; $C_{3-7}$cycloalkyl or $C_{1-6}$alkyl$C_{3-7}$cycloalkyl; and
   $R^7$ is $C_{1-6}$alkyl, which is unsubstituted or substituted with one to three substituents independently selected from fluoro and hydroxy; $C_{1-6}$alkoxy$C_{1-6}$alkyl; amino$C_{1-}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; $C_{3-7}$cycloalkyl$C_{1-6}$alkyl; phenyl$C_{1-6}$alkyl; $C_{1-6}$alkylamino$C_{1-6}$alkoxy$C_{1-6}$alkyl; $C_{1-6}$alkoxycarbonylamino$C_{1-8}$alkyl; morpholinyl$C_{1-6}$ alkyl or tetrahydropyranyl$C_{1-6}$alkyl.

10. The method according to any one of claims 1-3, wherein
    $R^1$ is hydrogen, fluoro, or chloro;
    $R^2$ is fluoro, chloro, methyl, ethyl, methoxy, ethoxy or cyclopropyl;
    $R^4$ is hydrogen;
    $R^5$ is hydrogen or methyl;
    $R^6$ is methyl, ethyl, isopropyl, isobutyl, tert-butyl, trifluoromethylmethyl, cyclobutyl or methylcyclopropyl; and
    $R^7$ is methyl, ethyl, propyl, butyl, isobutyl, cyclopropylmethyl, difluoromethylmethyl, difluoroethylmethyl, difluoromethylethyl, trifluoromethylmethyl, ethyldifluoromethyl, methoxyethyl, methoxypropyl, ethoxyethyl, aminohexyl, aminooctyl, tert-butoxycarbonylaminopentyl, tert-butoxycarbonylaminooctyl, methylcarbonylaminopentyl, methylsulfonylaminopentyl, methylsulfonylpropyl, methylsulfanylpropyl, hydroxypropyl, hydroxy-dimethylpropyl, hydroxy-difluoropropyl, hydroxybutyl, hydroxypentyl, hydroxyhexyl, ethylamino-ethyl-O-propyl-, morpholinylethyl, morpholinylpropyl, phenylmethyl or tetrahydropyranylmethyl.

11. The method according to any one of claims 1-3, wherein, $R^7$ is methoxyethyl, methoxypropyl, hydroxydimethylpropyl, hydroxybutyl, hydroxypentyl, hydroxyhexyl, aminobutyl, aminopentyl or aminohexyl.

12. The method according to any one of claims 1-3, wherein, the compound of formula IA is selected from:

9-Benzyloxy-10-methoxy-6-methyl-2-oxo-6,7-dihydrobenzo[a]quinolizine-3-carboxylic acid;
9-Hydroxy-10-methoxy-6-methyl-2-oxo-6,7-dihydrobenzo[a]quinolizine-3-carboxylic acid;
9,11-Dimethoxy-6-methyl-2-oxo-6,7-dihydrobenzo[a]quinolizine-3-carboxylic acid;
9-Ethoxy-10-methoxy-6-methyl-2-oxo-6,7-dihydrobenzo[a]quinolizine-3-carboxylic acid;
9,10-Diethoxy-6-ethyl-2-oxo-6,7-dihydrobenzo[a]quinolizine-3-carboxylic acid;
(+)-9,10-Diethoxy-6-ethyl-2-oxo-6,7-dihydrobenzo[a]quinolizine-3-carboxylic acid;
(−)-9,10-Diethoxy-6-ethyl-2-oxo-6,7-dihydrobenzo[a]quinolizine-3-carboxylic acid;
9-Benzyloxy-6-ethyl-10-methoxy-2-oxo-6,7-dihydrobenzo[a]quinolizine-3-carboxylic acid;
(+)-9-Benzyloxy-6-ethyl-10-methoxy-2-oxo-6,7-dihydrobenzo[a]quinolizine-3-carboxylic acid;
(−)-9-Benzyloxy-6-ethyl-10-methoxy-2-oxo-6,7-dihydrobenzo[a]quinolizine-3-carboxylic acid;
(+)-6-Ethyl-10-methoxy-2-oxo-9-(2,2,2-trifluoroethoxy)-6,7-dihydrobenzo[a]quinolizine-3-carboxylic acid;
(−)-6-Ethyl-10-methoxy-2-oxo-9-(2,2,2-trifluoroethoxy)-6,7-dihydrobenzo[a]quinolizine-3-carboxylic acid;
6-Ethyl-9-isopropoxy-10-methoxy-2-oxo-6,7-dihydrobenzo[a]quinolizine-3-carboxylic acid;
6-Ethyl-10-methoxy-2-oxo-9-(2-phenylethoxy)-6,7-dihydrobenzo[a]quinolizine-3-carboxylic acid;
9-Butoxy-6-ethyl-10-methoxy-2-oxo-6,7-dihydrobenzo[a]quinolizine-3-carboxylic acid;
9-(2-Cyclohexylethoxy)-6-ethyl-10-methoxy-2-oxo-6,7-dihydrobenzo[a]quinolizine-3-carboxylic acid;
6-Ethyl-10-methoxy-2-oxo-9-prop-2-ynoxy-6,7-dihydrobenzo[a]quinolizine-3-carboxylic acid;
6-Ethyl-10-methoxy-2-oxo-9-(2-oxo-2-pyrrolidin-1-yl-ethoxy)-6,7-dihydrobenzo[a]quinolizine-3-carboxylic acid;
6-Ethyl-10-methoxy-9-[2-(2-methoxyethoxy)ethoxy]-2-oxo-6,7-dihydrobenzo[a]quinolizine-3-carboxylic acid;
6-Ethyl-10-methoxy-9-(2-morpholinoethoxy)-2-oxo-6,7-dihydrobenzo[a]quinolizine-3-carboxylic acid;
6-Ethyl-9-(2-hydroxyethoxy)-10-methoxy-2-oxo-6,7-dihydrobenzo[a]quinolizine-3-carboxylic acid;
6-Ethyl-9-(3-hydroxy-2,2-dimethyl-propoxy)-10-methoxy-2-oxo-6,7-dihydrobenzo[a]quinolizine-3-carboxylic acid;
(+)-6-Ethyl-9-(3-hydroxy-2,2-dimethyl-propoxy)-10-methoxy-2-oxo-6,7-dihydrobenzo[a]quinolizine-3-carboxylic acid;
(−)-6-Ethyl-9-(3-hydroxy-2,2-dimethyl-propoxy)-10-methoxy-2-oxo-6,7-dihydrobenzo[a]quinolizine-3-carboxylic acid;
6-Ethyl-9-(3-hydroxypropoxy)-10-methoxy-2-oxo-6,7-dihydrobenzo[a]quinolizine-3-carboxylic acid;
6-Ethyl-9-(2-imidazol-1-ylethoxy)-10-methoxy-2-oxo-6,7-dihydrobenzo[a]quinolizine-3-carboxylic acid;
6-Ethyl-10-methoxy-9-(2-methoxyethoxy)-2-oxo-6,7-dihydrobenzo[a]quinolizine-3-carboxylic acid;
(+)-6-Ethyl-10-methoxy-9-(2-methoxyethoxy)-2-oxo-6,7-dihydrobenzo[a]quinolizine-3-carboxylic acid;
(−)-6-Ethyl-10-methoxy-9-(2-methoxyethoxy)-2-oxo-6,7-dihydrobenzo[a]quinolizine-3-carboxylic acid;
9-(Cyclopropylmethoxy)-6-ethyl-10-methoxy-2-oxo-6,7-dihydrobenzo[a]quinolizine-3-carboxylic acid;
(+)-9-(Cyclopropylmethoxy)-6-ethyl-10-methoxy-2-oxo-6,7-dihydrobenzo[a]quinolizine-3-carboxylic acid;
(−)-9-(Cyclopropylmethoxy)-6-ethyl-10-methoxy-2-oxo-6,7-dihydrobenzo[a]quinolizine-3-carboxylic acid;
6-Ethyl-9-isobutoxy-10-methoxy-2-oxo-6,7-dihydrobenzo[a]quinolizine-3-carboxylic acid;
(+)-6-Ethyl-9-isobutoxy-10-methoxy-2-oxo-6,7-dihydrobenzo[a]quinolizine-3-carboxylic acid;
(−)-6-Ethyl-9-isobutoxy-10-methoxy-2-oxo-6,7-dihydrobenzo[a]quinolizine-3-carboxylic acid;
9-Ethoxy-6-ethyl-10-methoxy-2-oxo-6,7-dihydrobenzo[a]quinolizine-3-carboxylic acid;
(+)-9-Ethoxy-6-ethyl-10-methoxy-2-oxo-6,7-dihydrobenzo[a]quinolizine-3-carboxylic acid;
(−)-9-Ethoxy-6-ethyl-10-methoxy-2-oxo-6,7-dihydrobenzo[a]quinolizine-3-carboxylic acid;
6-Ethyl-10-methoxy-9-(3-methoxypropoxy)-2-oxo-6,7-dihydrobenzo[a]quinolizine-3-carboxylic acid;
(+)-6-Ethyl-10-methoxy-9-(3-methoxypropoxy)-2-oxo-6,7-dihydrobenzo[a]quinolizine-3-carboxylic acid;
(−)-6-Ethyl-10-methoxy-9-(3-methoxypropoxy)-2-oxo-6,7-dihydrobenzo[a]quinolizine-3-carboxylic acid;
9-(2-Ethoxyethoxy)-6-ethyl-10-methoxy-2-oxo-6,7-dihydrobenzo[a]quinolizine-3-carboxylic acid;
(+)-9-(2-Ethoxyethoxy)-6-ethyl-10-methoxy-2-oxo-6,7-dihydrobenzo[a]quinolizine-3-carboxylic acid;
(−)-9-(2-Ethoxyethoxy)-6-ethyl-10-methoxy-2-oxo-6,7-dihydrobenzo[a]quinolizine-3-carboxylic acid;
9-(2,2-Difluoroethoxy)-6-ethyl-10-methoxy-2-oxo-6,7-dihydrobenzo[a]quinolizine-3-carboxylic acid;
(+)-9-(2,2-Difluoroethoxy)-6-ethyl-10-methoxy-2-oxo-6,7-dihydrobenzo[a]quinolizine-3-carboxylic acid;
(−)-9-(2,2-Difluoroethoxy)-6-ethyl-10-methoxy-2-oxo-6,7-dihydrobenzo[a]quinolizine-3-carboxylic acid;
6-Ethyl-10-methoxy-2-oxo-9-(tetrahydropyran-4-yl-methoxy)-6,7-dihydrobenzo[a]quinolizine-3-carboxylic acid;
(+)-6-Ethyl-10-methoxy-2-oxo-9-(tetrahydropyran-4-yl-methoxy)-6,7-dihydrobenzo[a]quinolizine-3-carboxylic acid;
(−)-6-Ethyl-10-methoxy-2-oxo-9-(tetrahydropyran-4-yl-methoxy)-6,7-dihydrobenzo[a]quinolizine-3-carboxylic acid;
6-Ethyl-10-methoxy-2-oxo-9-(2-pyrrolidin-1-ylethoxy)-6,7-dihydrobenzo[a]quinolizine-3-carboxylic acid;
9-(3-Cyanopropoxy)-6-ethyl-10-methoxy-2-oxo-6,7-dihydrobenzo[a]quinolizine-3-carboxylic acid;
6-Ethyl-10-methoxy-9-(2-methylsulfonylethoxy)-2-oxo-6,7-dihydrobenzo[a]quinolizine-3-carboxylic acid;
6-Ethyl-10-methoxy-2-oxo-9-[2-(2-oxopyrrolidin-1-yl)ethoxy]-6,7-dihydrobenzo[a]quinolizine-3-carboxylic acid;
(+)-6-Ethyl-10-methoxy-2-oxo-9-[2-(2-oxopyrrolidin-1-yl)ethoxy]-6,7-dihydrobenzo[a]quinolizine-3-carboxylic acid;
6-Ethyl-9-[2-(methanesulfonamido)ethoxy]-10-methoxy-2-oxo-6,7-dihydrobenzo[a]quinolizine-3-carboxylic acid;
9-[(1-Cyanocyclopropyl)methoxy]-6-ethyl-10-methoxy-2-oxo-6,7-dihydrobenzo[a]quinolizine-3-carboxylic acid;
9-(2-Acetamidoethoxy)-6-ethyl-10-methoxy-2-oxo-6,7-dihydrobenzo[a]quinolizine-3-carboxylic acid;
10-Chloro-9-methoxy-6-methyl-2-oxo-6,7-dihydrobenzo[a]quinolizine-3-carboxylic acid;
9,10-Dimethoxy-6-methyl-2-oxo-6,7-dihydrobenzo[a]quinolizine-3-carboxylic acid;
(+)-9,10-Dimethoxy-6-methyl-2-oxo-6,7-dihydrobenzo[a]quinolizine-3-carboxylic acid;

(−)-9,10-Dimethoxy-6-methyl-2-oxo-6,7-dihydrobenzo[a]quinolizine-3-carboxylic acid;
9,10-Dimethoxy-7-methyl-2-oxo-6,7-dihydrobenzo[a]quinolizine-3-carboxylic acid;
6-Ethyl-9,10-dimethoxy-2-oxo-6,7-dihydrobenzo[a]quinolizine-3-carboxylic acid;
(6R)-(+)-6-Ethyl-9,10-dimethoxy-2-oxo-6,7-dihydrobenzo[a]quinolizine-3-carboxylic acid;
(6S)-(−)-6-Ethyl-9,10-dimethoxy-2-oxo-6,7-dihydrobenzo[a]quinolizine-3-carboxylic acid;
9-Methoxy-6,10-dimethyl-2-oxo-6,7-dihydrobenzo[a]quinolizine-3-carboxylic acid;
9,10-Diethoxy-6-methyl-2-oxo-6,7-dihydrobenzo[a]quinolizine-3-carboxylic acid;
9-Ethoxy-6-methyl-10-hydroxy-2-oxo-6,7-dihydrobenzo[a]quinolizine-3-carboxylic acid;
9,10-Diethoxy-2-oxo-6,7-dihydrobenzo[a]quinolizine-3-carboxylic acid;
2-Oxo-9,10-dipropoxy-6,7-dihydrobenzo[a]quinolizine-3-carboxylic acid;
6-Ethyl-10-methoxy-2-oxo-9-propoxy-6,7-dihydrobenzo[a]quinolizine-3-carboxylic acid;
(+)-6-Ethyl-10-methoxy-2-oxo-9-propoxyl-6,7-dihydrobenzo[a]quinolizine-3-carboxylic acid;
(−)-6-Ethyl-10-methoxy-2-oxo-9-propoxyl-6,7-dihydrobenzo[a]quinolizine-3-carboxylic acid;
8-Chloro-9-methoxy-6-methyl-2-oxo-6,7-dihydrobenzo[a]quinolizine-3-carboxylic acid;
8-Chloro-9,1-dimethoxy-6-methyl-2-oxo-6,7-dihydrobenzo[a]quinolizine-3-carboxylic acid;
10-Benzyloxy-9-methoxy-6-methyl-2-oxo-6,7-dihydrobenzo[a]quinolizine-3-carboxylic acid;
10-Ethoxy-9-methoxy-6-methyl-2-oxo-6,7-dihydrobenzo[a]quinolizine-3-carboxylic acid;
9-Methoxy-6-methyl-2-oxo-1-propoxy-6,7-dihydrobenzo[a]quinolizine-3-carboxylic acid;
6,10-Diethyl-9-methoxy-2-oxo-6,7-dihydrobenzo[a]quinolizine-3-carboxylic acid;
10-Cyclopropyl-6-ethyl-9-methoxy-2-oxo-6,7-dihydrobenzo[a]quinolizine-3-carboxylic acid;
(+)-10-Cyclopropyl-6-ethyl-9-methoxy-2-oxo-6,7-dihydrobenzo[a]quinolizine-3-carboxylic acid;
(−)-10-Cyclopropyl-6-ethyl-9-methoxy-2-oxo-6,7-dihydrobenzo[a]quinolizine-3-carboxylic acid;
9,10-Dimethoxy-2-oxo-6-propyl-6,7-dihydrobenzo[a]quinolizine-3-carboxylic acid;
6-Cyclopropyl-9,1-dimethoxy-2-oxo-6,7-dihydrobenzo[a]quinolizine-3-carboxylic acid;
6-Isopropyl-9,1-dimethoxy-2-oxo-6,7-dihydrobenzo[a]quinolizine-3-carboxylic acid;
(+)-6-Isopropyl-9,1-dimethoxy-2-oxo-6,7-dihydrobenzo[a]quinolizine-3-carboxylic acid;
(−)-6-Isopropyl-9,1-dimethoxy-2-oxo-6,7-dihydrobenzo[a]quinolizine-3-carboxylic acid;
6-Isobutyl-9,1-dimethoxy-2-oxo-6,7-dihydrobenzo[a]quinolizine-3-carboxylic acid;
(+)-6-Isobutyl-9,1-dimethoxy-2-oxo-6,7-dihydrobenzo[a]quinolizine-3-carboxylic acid;
(−)-6-Isobutyl-9,1-dimethoxy-2-oxo-6,7-dihydrobenzo[a]quinolizine-3-carboxylic acid;
10-Chloro-6-isobutyl-9-(2-methoxyethoxy)-2-oxo-6,7-dihydrobenzo[a]quinolizine-3-carboxylic acid;
(+)-10-Chloro-6-isobutyl-9-(2-methoxyethoxy)-2-oxo-6,7-dihydrobenzo[a]quinolizine-3-carboxylic acid;
(−)-10-Chloro-6-isobutyl-9-(2-methoxyethoxy)-2-oxo-6,7-dihydrobenzo[a]quinolizine-3-carboxylic acid;
10-Chloro-6-isopropyl-9-(2-methoxyethoxy)-2-oxo-6,7-dihydrobenzo[a]quinolizine-3-carboxylic acid;
(+)-10-Chloro-6-isopropyl-9-(2-methoxyethoxy)-2-oxo-6,7-dihydrobenzo[a]quinolizine-3-carboxylic acid;
(−)-10-Chloro-6-isopropyl-9-(2-methoxyethoxy)-2-oxo-6,7-dihydrobenzo[a]quinolizine-3-carboxylic acid;
10-Fluoro-6-isopropyl-9-(2-methoxyethoxy)-2-oxo-6,7-dihydrobenzo[a]quinolizine-3-carboxylic acid;
11-Chloro-6-isopropyl-9-(2-methoxyethoxy)-2-oxo-6,7-dihydrobenzo[a]quinolizine-3-carboxylic acid;
9,10-Dimethoxy-2-oxo-6-(trifluoromethyl)-6,7-dihydrobenzo[a]quinolizine-3-carboxylic acid;
9-Benzyloxy-6-ethyl-10-methyl-2-oxo-6,7-dihydrobenzo[a]quinolizine-3-carboxylic acid;
(+)-9-Benzyloxy-6-ethyl-10-methyl-2-oxo-6,7-dihydrobenzo[a]quinolizine-3-carboxylic acid;
(−)-9-Benzyloxy-6-ethyl-10-methyl-2-oxo-6,7-dihydrobenzo[a]quinolizine-3-carboxylic acid;
(+)-10-Chloro-9-ethoxy-6-ethyl-2-oxo-6,7-dihydrobenzo[a]quinolizine-3-carboxylic acid;
(−)-10-Chloro-9-ethoxy-6-ethyl-2-oxo-6,7-dihydrobenzo[a]quinolizine-3-carboxylic acid;
10-Chloro-6-isopropyl-9-(3-methoxypropoxy)-2-oxo-6,7-dihydrobenzo[a]quinolizine-3-carboxylic acid;
(+)-10-Chloro-6-isopropyl-9-(3-methoxypropoxy)-2-oxo-6,7-dihydrobenzo[a]quinolizine-3-carboxylic acid;
(−)-10-Chloro-6-isopropyl-9-(3-methoxypropoxy)-2-oxo-6,7-dihydrobenzo[a]quinolizine-3-carboxylic acid;
10-Methoxy-6-isopropyl-9-(3-methoxypropoxy)-2-oxo-6,7-dihydrobenzo[a]quinolizine-3-carboxylic acid;
(+)-10-Methoxy-6-isopropyl-9-(3-methoxypropoxy)-2-oxo-6,7-dihydrobenzo[a]quinolizine-3-carboxylic acid;
(−)-10-Methoxy-6-isopropyl-9-(3-methoxypropoxy)-2-oxo-6,7-dihydrobenzo[a]quinolizine-3-carboxylic acid;
6-Isopropyl-10-methoxy-2-oxo-9-(2,2,2-trifluoroethoxy)-6,7-dihydrobenzo[a]quinolizine-3-carboxylic acid;
(+)-6-Isopropyl-10-methoxy-2-oxo-9-(2,2,2-trifluoroethoxy)-6,7-dihydrobenzo[a]quinolizine-3-carboxylic acid;
(−)-6-Isopropyl-10-methoxy-2-oxo-9-(2,2,2-trifluoroethoxy)-6,7-dihydrobenzo[a]quinolizine-3-carboxylic acid;
(+)-6-Isopropyl-10-methoxy-9-(2-methoxyethoxy)-2-oxo-6,7-dihydrobenzo[a]quinolizine-3-carboxylic acid;
(−)-6-Isopropyl-10-methoxy-9-(2-methoxyethoxy)-2-oxo-6,7-dihydrobenzo[a]quinolizine-3-carboxylic acid;
6-tert-Butyl-10-methoxy-9-(3-methoxypropoxy)-2-oxo-6,7-dihydrobenzo[a]quinolizine-3-carboxylic acid;
(+)-6-tert-Butyl-10-methoxy-9-(3-methoxypropoxy)-2-oxo-6,7-dihydrobenzo[a]quinolizine-3-carboxylic acid;
(−)-6-tert-Butyl-10-methoxy-9-(3-methoxypropoxy)-2-oxo-6,7-dihydrobenzo[a]quinolizine-3-carboxylic acid;
10-Methoxy-9-(2-methoxyethoxy)-6-(1-methylcyclopropyl)-2-oxo-6,7-dihydrobenzo[a]quinolizine-3-carboxylic acid;
(+)-10-Methoxy-9-(2-methoxyethoxy)-6-(1-methylcyclopropyl)-2-oxo-6,7-dihydrobenzo[a]quinolizine-3-carboxylic acid;

(−)-10-Methoxy-9-(2-methoxyethoxy)-6-(1-methylcyclopropyl)-2-oxo-6,7-dihydrobenzo[a]quinolizine-3-carboxylic acid;
11-Chloro-10-fluoro-6-isopropyl-9-(3-methoxypropoxy)-2-oxo-6,7-dihydrobenzo[a]quinolizine-3-carboxylic acid;
(+)-11-Chloro-10-fluoro-6-isopropyl-9-(3-methoxypropoxy)-2-oxo-6,7-dihydrobenzo[a]quinolizine-3-carboxylic acid;
(−)-11-Chloro-10-fluoro-6-isopropyl-9-(3-methoxypropoxy)-2-oxo-6,7-dihydrobenzo[a]quinolizine-3-carboxylic acid;
10-Fluoro-6-isopropyl-9-(3-methoxypropoxy)-2-oxo-6,7-dihydrobenzo[a]quinolizine-3-carboxylic acid;
6-tert-Butyl-9-(2,2-difluoro-3-hydroxy-propoxy)-10-methoxy-2-oxo-6,7-dihydrobenzo[a]quinolizine-3-carboxylic acid;
(+)-9-(2,2-Difluoroethoxy)-6-isopropyl-10-methoxy-2-oxo-6,7-dihydrobenzo[a]quinolizine-3-carboxylic acid;
(−)-9-(2,2-Difluoroethoxy)-6-isopropyl-10-methoxy-2-oxo-6,7-dihydrobenzo[a]quinolizine-3-carboxylic acid;
9-(3-Hydroxy-2,2-dimethyl-propoxy)-6-isopropyl-10-methoxy-2-oxo-6,7-dihydrobenzo[a]quinolizine-3-carboxylic acid;
(+)-9-(3-Hydroxy-2,2-dimethyl-propoxy)-6-isopropyl-10-methoxy-2-oxo-6,7-dihydrobenzo[a]quinolizine-3-carboxylic acid;
(−)-9-(3-Hydroxy-2,2-dimethyl-propoxy)-6-isopropyl-10-methoxy-2-oxo-6,7-dihydrobenzo[a]quinolizine-3-carboxylic acid;
9-(3-Hydroxypropoxy)-6-isopropyl-10-methoxy-2-oxo-6,7-dihydrobenzo[a]quinolizine-3-carboxylic acid;
6-Isopropyl-10-methoxy-9-(4-methoxybutoxy)-2-oxo-6,7-dihydrobenzo[a]quinolizine-3-carboxylic acid;
6-tert-Butyl-9-(3-hydroxy-2,2-dimethyl-propoxy)-10-methoxy-2-oxo-6,7-dihydrobenzo[a]quinolizine-3-carboxylic acid;
(+)-6-tert-Butyl-9-(3-hydroxy-2,2-dimethyl-propoxy)-10-methoxy-2-oxo-6,7-dihydrobenzo[a]quinolizine-3-carboxylic acid;
(−)-6-tert-Butyl-9-(3-hydroxy-2,2-dimethyl-propoxy)-10-methoxy-2-oxo-6,7-dihydrobenzo[a]quinolizine-3-carboxylic acid;
6-tert-Butyl-9-(5-hydroxypentoxy)-10-methoxy-2-oxo-6,7-dihydrobenzo[a]quinolizine-3-carboxylic acid;
(+)-6-tert-Butyl-9-(5-hydroxypentoxy)-10-methoxy-2-oxo-6,7-dihydrobenzo[a]quinolizine-3-carboxylic acid;
(−)-6-tert-Butyl-9-(5-hydroxypentoxy)-10-methoxy-2-oxo-6,7-dihydrobenzo[a]quinolizine-3-carboxylic acid;
6-tert-Butyl-9-(6-hydroxyhexoxy)-10-methoxy-2-oxo-6,7-dihydrobenzo[a]quinolizine-3-carboxylic acid;
(+)-6-tert-Butyl-9-(6-hydroxyhexoxy)-10-methoxy-2-oxo-6,7-dihydrobenzo[a]quinolizine-3-carboxylic acid;
(−)-6-tert-Butyl-9-(6-hydroxyhexoxy)-10-methoxy-2-oxo-6,7-dihydrobenzo[a]quinolizine-3-carboxylic acid;
6-tert-Butyl-9-(4-hydroxybutoxy)-10-methoxy-2-oxo-6,7-dihydrobenzo[a]quinolizine-3-carboxylic acid;
6-tert-Butyl-9-(4-hydroxybut-2-ynoxy)-10-methoxy-2-oxo-6,7-dihydrobenzo[a]quinolizine-3-carboxylic acid;
9-(6-Aminohexoxy)-6-tert-butyl-10-methoxy-2-oxo-6,7-dihydrobenzo[a]quinolizine-3-carboxylic acid;
9-[6-(tert-Butoxycarbonylamino)hexoxy]-6-tert-butyl-10-methoxy-2-oxo-6,7-dihydrobenzo[a]quinolizine-3-carboxylic acid;
(+)-9-[6-(tert-Butoxycarbonylamino)hexoxy]-6-tert-butyl-10-methoxy-2-oxo-6,7-dihydrobenzo[a]quinolizine-3-carboxylic acid;
(−)-9-[6-(tert-Butoxycarbonylamino)hexoxy]-6-tert-butyl-10-methoxy-2-oxo-6,7-dihydrobenzo[a]quinolizine-3-carboxylic acid;
(+)-9-(6-Aminohexoxy)-6-tert-butyl-10-methoxy-2-oxo-6,7-dihydrobenzo[a]quinolizine-3-carboxylic acid hydrochloride;
(−)-9-(6-Aminohexoxy)-6-tert-butyl-10-methoxy-2-oxo-6,7-dihydrobenzo[a]quinolizine-3-carboxylic acid hydrochloride;
9-(8-Aminooctoxy)-6-tert-butyl-10-methoxy-2-oxo-6,7-dihydrobenzo[a]quinolizine-3-carboxylic acid;
9-[8-(tert-Butoxycarbonylamino)octoxy]-6-tert-butyl-10-methoxy-2-oxo-6,7-dihydrobenzo[a]quinolizine-3-carboxylic acid;
(+)-9-[8-(tert-Butoxycarbonylamino)octoxy]-6-tert-butyl-10-methoxy-2-oxo-6,7-dihydrobenzo[a]quinolizine-3-carboxylic acid;
(−)-9-[8-(tert-Butoxycarbonylamino)octoxy]-6-tert-butyl-10-methoxy-2-oxo-6,7-dihydrobenzo[a]quinolizine-3-carboxylic acid;
(+)-9-(8-Aminooctoxy)-6-tert-butyl-10-methoxy-2-oxo-6,7-dihydrobenzo[a]quinolizine-3-carboxylic acid hydrochloride;
(−)-9-(8-Aminooctoxy)-6-tert-butyl-10-methoxy-2-oxo-6,7-dihydrobenzo[a]quinolizine-3-carboxylic acid hydrochloride;
9-[5-(tert-Butoxycarbonylamino)pentoxy]-6-tert-butyl-10-methoxy-2-oxo-6,7-dihydrobenzo[a]quinolizine-3-carboxylic acid;
(+)-9-(5-Aminopentoxy)-6-tert-butyl-10-methoxy-2-oxo-6,7-dihydrobenzo[a]quinolizine-3-carboxylic acid hydrochloride;
(−)-9-(5-Aminopentoxy)-6-tert-butyl-10-methoxy-2-oxo-6,7-dihydrobenzo[a]quinolizine-3-carboxylic acid hydrochloride;
9-(5-Acetamidopentoxy)-6-tert-butyl-10-methoxy-2-oxo-6,7-dihydrobenzo[a]quinolizine-3-carboxylic acid;
6-tert-Butyl-9-[5-(methanesulfonamido)pentoxy]-10-methoxy-2-oxo-6,7-dihydrobenzo[a]quinolizine-3-carboxylic acid;
9-(2-Aminoethoxy)-6-tert-butyl-10-methoxy-2-oxo-6,7-dihydrobenzo[a]quinolizine-3-carboxylic acid;
9-[3-(2-Aminoethoxy)propoxy]-6-tert-butyl-10-methoxy-2-oxo-6,7-dihydrobenzo[a]quinolizine-3-carboxylic acid;
6-tert-Butyl-9-[3-[2-(ethylamino)ethoxy]propoxy]-10-methoxy-2-oxo-6,7-dihydrobenzo[a]quinolizine-3-carboxylic acid;
6-tert-Butyl-9-(3,3-difluoropropoxy)-10-methoxy-2-oxo-6,7-dihydrobenzo[a]quinolizine-3-carboxylic acid;
6-tert-Butyl-9-(1,1-difluoropropoxy)-10-methoxy-2-oxo-6,7-dihydrobenzo[a]quinolizine-3-carboxylic acid;
6-tert-Butyl-9-(1,1-difluoroallyloxy)-10-methoxy-2-oxo-6,7-dihydrobenzo[a]quinolizine-3-carboxylic acid;
6-tert-Butyl-10-methoxy-9-(3-methylsulfanylpropoxy)-2-oxo-6,7-dihydrobenzo[a]quinolizine-3-carboxylic acid;

(+)-6-tert-Butyl-10-methoxy-9-(3-methylsulfanyl-propoxy)-2-oxo-6,7-dihydrobenzo[a]quinolizine-3-carboxylic acid;
(−)-6-tert-Butyl-10-methoxy-9-(3-methylsulfanyl-propoxy)-2-oxo-6,7-dihydrobenzo[a]quinolizine-3-carboxylic acid;
6-tert-Butyl-10-methoxy-9-(3-methylsulfonylpropoxy)-2-oxo-6,7-dihydrobenzo[a]quinolizine-3-carboxylic acid;
(+)-6-tert-Butyl-10-methoxy-9-(3-methylsulfonyl-propoxy)-2-oxo-6,7-dihydrobenzo[a]quinolizine-3-carboxylic acid;
(−)-6-tert-Butyl-10-methoxy-9-(3-methylsulfonyl-propoxy)-2-oxo-6,7-dihydrobenzo[a]quinolizine-3-carboxylic acid;
6-tert-Butyl-10-methoxy-9-(2-morpholinoethoxy)-2-oxo-6,7-dihydrobenzo[a]quinolizine-3-carboxylic acid hydrochloride;
(+)-tert-Butyl-10-methoxy-9-(2-morpholinoethoxy)-2-oxo-6,7-dihydrobenzo[a]quinolizine-3-carboxylic acid;
(−)-6-tert-Butyl-10-methoxy-9-(2-morpholinoethoxy)-2-oxo-6,7-dihydrobenzo[a]quinolizine-3-carboxylic acid;
6-tert-Butyl-10-methoxy-9-(3-morpholinopropoxy)-2-oxo-6,7-dihydrobenzo[a]quinolizine-3-carboxylic acid hydrochloride;
(+)-6-tert-Butyl-10-methoxy-9-(3-morpholinopropoxy)-2-oxo-6,7-dihydrobenzo[a]quinolizine-3-carboxylic acid;
(−)-6-tert-Butyl-10-methoxy-9-(3-morpholinopropoxy)-2-oxo-6,7-dihydrobenzo[a]quinolizine-3-carboxylic acid;
6-tert-Butyl-10-methoxy-2-oxo-9-[3-(2-oxopyrrolidin-1-yl) propoxy]-6,7-dihydrobenzo[a]quinolizine-3-carboxylic acid;
6-tert-Butyl-10-methoxy-2-oxo-9-(3-pyrrolidin-1-yl-propoxy)-6,7-dihydrobenzo[a]quinolizine-3-carboxylic acid;
6-Cyclobutyl-10-methoxy-9-(3-methoxypropoxy)-2-oxo-6,7-dihydrobenzo[a]quinolizine-3-carboxylic acid;
9,10-Dimethoxy-2-oxo-6-(2,2,2-trifluoroethyl)-6,7-dihydrobenzo[a]quinolizine-3-carboxylic acid;
10-Methoxy-9-(3-methoxypropoxy)-2-oxo-6-(2,2,2-trifluoroethyl)-6,7-dihydrobenzo[a]quinolizine-3-carboxylic acid;
(+)-10-Methoxy-9-(3-methoxypropoxy)-2-oxo-6-(2,2,2-trifluoroethyl)-6,7-dihydrobenzo[a]quinolizine-3-carboxylic acid;
(−)-10-Methoxy-9-(3-methoxypropoxy)-2-oxo-6-(2,2,2-trifluoroethyl)-6,7-dihydrobenzo[a]quinolizine-3-carboxylic acid;
6-tert-Butyl-10-chloro-9-(3-methoxypropoxy)-2-oxo-6,7-dihydrobenzo[a]quinolizine-3-carboxylic acid;
(+)-6-tert-Butyl-10-chloro-9-(3-methoxypropoxy)-2-oxo-6,7-dihydrobenzo[a]quinolizine-3-carboxylic acid;
(−)-6-tert-Butyl-10-chloro-9-(3-methoxypropoxy)-2-oxo-6,7-dihydrobenzo[a]quinolizine-3-carboxylic acid;
10-Chloro-9-(3-methoxypropoxy)-6-(1-methylcyclopropyl)-2-oxo-6,7-dihydrobenzo[a]quinolizine-3-carboxylic acid;
(+)-10-Chloro-9-(3-methoxypropoxy)-6-(1-methylcyclopropyl)-2-oxo-6,7-dihydrobenzo[a]quinolizine-3-carboxylic acid;
(−)-10-Chloro-9-(3-methoxypropoxy)-6-(1-methylcyclopropyl)-2-oxo-6,7-dihydrobenzo[a]quinolizine-3-carboxylic acid;
10-Methoxy-9-(3-methoxypropoxy)-6-(1-methylcyclopropyl)-2-oxo-6,7-dihydrobenzo[a]quinolizine-3-carboxylic acid;
(+)-10-Methoxy-9-(3-methoxypropoxy)-6-(1-methylcyclopropyl)-2-oxo-6,7-dihydrobenzo[a]quinolizine-3-carboxylic acid;
(−)-10-Methoxy-9-(3-methoxypropoxy)-6-(1-methylcyclopropyl)-2-oxo-6,7-dihydrobenzo[a]quinolizine-3-carboxylic acid;
6-Benzyl-9,10-dimethoxy-2-oxo-6,7-dihydrobenzo[a]quinolizine-3-carboxylic acid;
10-Chloro-6-ethyl-9-(2-methoxyethoxy)-7-methyl-2-oxo-6,7-dihydrobenzo[a]quinolizine-3-carboxylic acid;
(6R,7S*)-10-Chloro-6-ethyl-9-(2-methoxyethoxy)-7-methyl-2-oxo-6,7-dihydrobenzo[a]quinolizine-3-carboxylic acid;
(6R*,7R*)-10-Chloro-6-ethyl-9-(2-methoxyethoxy)-7-methyl-2-oxo-6,7-dihydrobenzo[a]quinolizine-3-carboxylic acid;
10,11-Difluoro-6-isopropyl-9-(3-methoxypropoxy)-2-oxo-6,7-dihydrobenzo[a]quinolizine-3-carboxylic acid;
(+)-10,11-Difluoro-6-isopropyl-9-(3-methoxypropoxy)-2-oxo-6,7-dihydrobenzo[a]quinolizine-3-carboxylic acid;
(−)-10,11-Difluoro-6-isopropyl-9-(3-methoxypropoxy)-2-oxo-6,7-dihydrobenzo[a]quinolizine-3-carboxylic acid;
6-tert-Butyl-10-methoxy-2-oxo-9-(3-pyrazol-1-yl-propoxy)-6,7-dihydrobenzo[a]quinolizine-3-carboxylic acid;
6-tert-Butyl-10-methoxy-2-oxo-9-[3-(1,2,4-triazol-1-yl)propoxy]-6,7-dihydrobenzo[a]quinolizine-3-carboxylic acid; and
6-tert-Butyl-9-(3-carboxypropoxy)-10-methoxy-2-oxo-6,7-dihydrobenzo[a]quinolizine-3-carboxylic acid;
and pharmaceutically acceptable salts, enantiomers and diastereomers thereof.

13. The method according to any one of claims 1-3, wherein, the compound of formula IA is selected from:
9-Benzyloxy-10-methoxy-6-methyl-2-oxo-6,7-dihydrobenzo[a]quinolizine-3-carboxylic acid;
9,10-Diethoxy-6-ethyl-2-oxo-6,7-dihydrobenzo[a]quinolizine-3-carboxylic acid;
(+)-6-Ethyl-10-methoxy-2-oxo-9-(2,2,2-trifluoroethoxy)-6,7-dihydrobenzo[a]quinolizine-3-carboxylic acid;
9-Butoxy-6-ethyl-10-methoxy-2-oxo-6,7-dihydrobenzo[a]quinolizine-3-carboxylic acid;
6-Ethyl-9-(3-hydroxy-2,2-dimethyl-propoxy)-10-methoxy-2-oxo-6,7-dihydrobenzo[a]quinolizine-3-carboxylic acid;
6-Ethyl-10-methoxy-9-(2-methoxyethoxy)-2-oxo-6,7-dihydrobenzo[a]quinolizine-3-carboxylic acid;
9-(Cyclopropylmethoxy)-6-ethyl-10-methoxy-2-oxo-6,7-dihydrobenzo[a]quinolizine-3-carboxylic acid;
6-Ethyl-9-isobutoxy-10-methoxy-2-oxo-6,7-dihydrobenzo[a]quinolizine-3-carboxylic acid;
9-Ethoxy-6-ethyl-10-methoxy-2-oxo-6,7-dihydrobenzo[a]quinolizine-3-carboxylic acid;
6-Ethyl-10-methoxy-9-(3-methoxypropoxy)-2-oxo-6,7-dihydrobenzo[a]quinolizine-3-carboxylic acid;
9-(2-Ethoxyethoxy)-6-ethyl-10-methoxy-2-oxo-6,7-dihydrobenzo[a]quinolizine-3-carboxylic acid;
6-Ethyl-10-methoxy-2-oxo-9-(tetrahydropyran-4-yl-methoxy)-6,7-dihydrobenzo[a]quinolizine-3-carboxylic acid;

6-Ethyl-9,10-dimethoxy-2-oxo-6,7-dihydrobenzo[a]quinolizine-3-carboxylic acid;
(6R)-(+)-6-Ethyl-9,10-dimethoxy-2-oxo-6,7-dihydrobenzo[a]quinolizine-3-carboxylic acid;
6-Ethyl-10-methoxy-2-oxo-9-propoxy-6,7-dihydrobenzo[a]quinolizine-3-carboxylic acid;
6,10-Diethyl-9-methoxy-2-oxo-6,7-dihydrobenzo[a]quinolizine-3-carboxylic acid;
10-Cyclopropyl-6-ethyl-9-methoxy-2-oxo-6,7-dihydrobenzo[a]quinolizine-3-carboxylic acid;
6-Isopropyl-9,10-dimethoxy-2-oxo-6,7-dihydrobenzo[a]quinolizine-3-carboxylic acid;
6-Isobutyl-9,10-dimethoxy-2-oxo-6,7-dihydrobenzo[a]quinolizine-3-carboxylic acid;
10-Chloro-6-isobutyl-9-(2-methoxyethoxy)-2-oxo-6,7-dihydrobenzo[a]quinolizine-3-carboxylic acid;
10-Chloro-6-isopropyl-9-(2-methoxyethoxy)-2-oxo-6,7-dihydrobenzo[a]quinolizine-3-carboxylic acid;
10-Fluoro-6-isopropyl-9-(2-methoxyethoxy)-2-oxo-6,7-dihydrobenzo[a]quinolizine-3-carboxylic acid;
9-Benzyloxy-6-ethyl-10-methyl-2-oxo-6,7-dihydrobenzo[a]quinolizine-3-carboxylic acid;
10-Chloro-6-isopropyl-9-(3-methoxypropoxy)-2-oxo-6,7-dihydrobenzo[a]quinolizine-3-carboxylic acid;
10-Methoxy-6-isopropyl-9-(3-methoxypropoxy)-2-oxo-6,7-dihydrobenzo[a]quinolizine-3-carboxylic acid;
(+)-10-Methoxy-6-isopropyl-9-(3-methoxypropoxy)-2-oxo-6,7-dihydrobenzo[a]quinolizine-3-carboxylic acid;
6-Isopropyl-10-methoxy-2-oxo-9-(2,2,2-trifluoroethoxy)-6,7-dihydrobenzo[a]quinolizine-3-carboxylic acid;
(+)-6-Isopropyl-10-methoxy-9-(2-methoxyethoxy)-2-oxo-6,7-dihydrobenzo[a]quinolizine-3-carboxylic acid;
6-tert-Butyl-10-methoxy-9-(3-methoxypropoxy)-2-oxo-6,7-dihydrobenzo[a]quinolizine-3-carboxylic acid;
(+)-6-tert-Butyl-10-methoxy-9-(3-methoxypropoxy)-2-oxo-6,7-dihydrobenzo[a]quinolizine-3-carboxylic acid;
10-Methoxy-9-(2-methoxyethoxy)-6-(1-methylcyclopropyl)-2-oxo-6,7-dihydrobenzo[a]quinolizine-3-carboxylic acid;
(+)-10-Methoxy-9-(2-methoxyethoxy)-6-(1-methylcyclopropyl)-2-oxo-6,7-dihydrobenzo[a]quinolizine-3-carboxylic acid;
11-Chloro-10-fluoro-6-isopropyl-9-(3-methoxypropoxy)-2-oxo-6,7-dihydrobenzo[a]quinolizine-3-carboxylic acid;
10-Fluoro-6-isopropyl-9-(3-methoxypropoxy)-2-oxo-6,7-dihydrobenzo[a]quinolizine-3-carboxylic acid;
6-tert-Butyl-9-(2,2-difluoro-3-hydroxy-propoxy)-10-methoxy-2-oxo-6,7-dihydrobenzo[a]quinolizine-3-carboxylic acid;
(+)-9-(2,2-Difluoroethoxy)-6-isopropyl-10-methoxy-2-oxo-6,7-dihydrobenzo[a]quinolizine-3-carboxylic acid;
9-(3-Hydroxy-2,2-dimethyl-propoxy)-6-isopropyl-10-methoxy-2-oxo-6,7-dihydrobenzo[a]quinolizine-3-carboxylic acid;
9-(3-Hydroxypropoxy)-6-isopropyl-10-methoxy-2-oxo-6,7-dihydrobenzo[a]quinolizine-3-carboxylic acid;
6-Isopropyl-10-methoxy-9-(4-methoxybutoxy)-2-oxo-6,7-dihydrobenzo[a]quinolizine-3-carboxylic acid;
6-tert-Butyl-9-(3-hydroxy-2,2-dimethyl-propoxy)-10-methoxy-2-oxo-6,7-dihydrobenzo[a]quinolizine-3-carboxylic acid;
6-tert-Butyl-9-(5-hydroxypentoxy)-10-methoxy-2-oxo-6,7-dihydrobenzo[a]quinolizine-3-carboxylic acid;
6-tert-Butyl-9-(6-hydroxyhexoxy)-10-methoxy-2-oxo-6,7-dihydrobenzo[a]quinolizine-3-carboxylic acid;
6-tert-Butyl-9-(4-hydroxybutoxy)-10-methoxy-2-oxo-6,7-dihydrobenzo[a]quinolizine-3-carboxylic acid;
9-(6-Aminohexoxy)-6-tert-butyl-10-methoxy-2-oxo-6,7-dihydrobenzo[a]quinolizine-3-carboxylic acid;
9-[8-(tert-Butoxycarbonylamino)octoxy]-6-tert-butyl-10-methoxy-2-oxo-6,7-dihydrobenzo[a]quinolizine-3-carboxylic acid;
9-[5-(tert-Butoxycarbonylamino)pentoxy]-6-tert-butyl-10-methoxy-2-oxo-6,7-dihydrobenzo[a]quinolizine-3-carboxylic acid;
9-(5-Acetamidopentoxy)-6-tert-butyl-10-methoxy-2-oxo-6,7-dihydrobenzo[a]quinolizine-3-carboxylic acid;
6-tert-Butyl-9-[5-(methanesulfonamido)pentoxy]-10-methoxy-2-oxo-6,7-dihydrobenzo[a]quinolizine-3-carboxylic acid;
6-tert-Butyl-9-[3-[2-(ethylamino)ethoxy]propoxy]-10-methoxy-2-oxo-6,7-dihydrobenzo[a]quinolizine-3-carboxylic acid;
6-tert-Butyl-9-(3,3-difluoropropoxy)-10-methoxy-2-oxo-6,7-dihydrobenzo[a]quinolizine-3-carboxylic acid;
6-tert-Butyl-9-(1,1-difluoropropoxy)-10-methoxy-2-oxo-6,7-dihydrobenzo[a]quinolizine-3-carboxylic acid;
6-tert-Butyl-10-methoxy-9-(3-methylsulfanylpropoxy)-2-oxo-6,7-dihydrobenzo[a]quinolizine-3-carboxylic acid;
6-tert-Butyl-10-methoxy-9-(3-methylsulfonylpropoxy)-2-oxo-6,7-dihydrobenzo[a]quinolizine-3-carboxylic acid;
6-tert-Butyl-10-methoxy-9-(2-morpholinoethoxy)-2-oxo-6,7-dihydrobenzo[a]quinolizine-3-carboxylic acid hydrochloride;
6-tert-Butyl-10-methoxy-9-(3-morpholinopropoxy)-2-oxo-6,7-dihydrobenzo[a]quinolizine-3-carboxylic acid hydrochloride;
6-Cyclobutyl-10-methoxy-9-(3-methoxypropoxy)-2-oxo-6,7-dihydrobenzo[a]quinolizine-3-carboxylic acid;
10-Methoxy-9-(3-methoxypropoxy)-2-oxo-6-(2,2,2-trifluoroethyl)-6,7-dihydrobenzo[a]quinolizine-3-carboxylic acid;
6-tert-Butyl-10-chloro-9-(3-methoxypropoxy)-2-oxo-6,7-dihydrobenzo[a]quinolizine-3-carboxylic acid;
10-Chloro-9-(3-methoxypropoxy)-6-(1-methylcyclopropyl)-2-oxo-6,7-dihydrobenzo[a]quinolizine-3-carboxylic acid;
10-Methoxy-9-(3-methoxypropoxy)-6-(1-methylcyclopropyl)-2-oxo-6,7-dihydrobenzo[a]quinolizine-3-carboxylic acid;
(6R*,7S*)-10-Chloro-6-ethyl-9-(2-methoxyethoxy)-7-methyl-2-oxo-6,7-dihydrobenzo[a]quinolizine-3-carboxylic acid; and
10,11-Difluoro-6-isopropyl-9-(3-methoxypropoxy)-2-oxo-6,7-dihydrobenzo[a]quinolizine-3-carboxylic acid;
and pharmaceutically acceptable salts, enantiomers and diastereomers thereof.

14. The method according to any one of claims 1-3, wherein, the compound of formula IA is selected from:
9,10-diethoxy-6-ethyl-2-oxo-6,7-dihydrobenzo[a]quinolizine-3-carboxylic acid;
9-benzyloxy-6-ethyl-10-methoxy-2-oxo-6,7-dihydrobenzo[a]quinolizine-3-carboxylic acid;
(+)-6-ethyl-10-methoxy-2-oxo-9-(2,2,2-trifluoroethoxy)-6,7-dihydrobenzo[a]quinolizine-3-carboxylic acid;

(+)-9-(cyclopropylmethoxy)-6-ethyl-10-methoxy-2-oxo-6,7-dihydrobenzo[a]quinolizine-3-carboxylic acid;
(+)-6-ethyl-9-isobutoxy-10-methoxy-2-oxo-6,7-dihydrobenzo[a]quinolizine-3-carboxylic acid;
(+)-6-ethyl-10-methoxy-9-(3-methoxypropoxy)-2-oxo-6,7-dihydrobenzo[a]quinolizine-3-carboxylic acid;
(+)-10-cyclopropyl-6-ethyl-9-methoxy-2-oxo-6,7-dihydrobenzo[a]quinolizine-3-carboxylic acid;
(+)-6-isopropyl-9,10-dimethoxy-2-oxo-6,7-dihydrobenzo[a]quinolizine-3-carboxylic acid;
(+)-6-isobutyl-9,10-dimethoxy-2-oxo-6,7-dihydrobenzo[a]quinolizine-3-carboxylic acid;
(+)-10-chloro-6-isopropyl-9-(2-methoxyethoxy)-2-oxo-6,7-dihydrobenzo[a]quinolizine-3-carboxylic acid;
(+)-10-chloro-6-isopropyl-9-(3-methoxypropoxy)-2-oxo-6,7-dihydrobenzo[a]quinolizine-3-carboxylic acid;
10-methoxy-6-isopropyl-9-(3-methoxypropoxy)-2-oxo-6,7-dihydrobenzo[a]quinolizine-3-carboxylic acid;
(+)-10-methoxy-6-isopropyl-9-(3-methoxypropoxy)-2-oxo-6,7-dihydrobenzo[a]quinolizine-3-carboxylic acid;
(−)-10-methoxy-6-isopropyl-9-(3-methoxypropoxy)-2-oxo-6,7-dihydrobenzo[a]quinolizine-3-carboxylic acid;
(+)-6-isopropyl-10-methoxy-2-oxo-9-(2,2,2-trifluoroethoxy)-6,7-dihydrobenzo[a]quinolizine-3-carboxylic acid;
(+)-6-tert-butyl-10-methoxy-9-(3-methoxypropoxy)-2-oxo-6,7-dihydrobenzo[a]quinolizine-3-carboxylic acid;
(−)-6-tert-butyl-10-methoxy-9-(3-methoxypropoxy)-2-oxo-6,7-dihydrobenzo[a]quinolizine-3-carboxylic acid;
(+)-10-methoxy-9-(2-methoxyethoxy)-6-(1-methylcyclopropyl)-2-oxo-6,7-dihydrobenzo[a]quinolizine-3-carboxylic acid;
(+)-9-(2,2-difluoroethoxy)-6-isopropyl-10-methoxy-2-oxo-6,7-dihydrobenzo[a]quinolizine-3-carboxylic acid;
(+)-6-tert-butyl-9-(5-hydroxypentoxy)-10-methoxy-2-oxo-6,7-dihydrobenzo[a]quinolizine-3-carboxylic acid;
(+)-9-(6-aminohexoxy)-6-tert-butyl-10-methoxy-2-oxo-6,7-dihydrobenzo[a]quinolizine-3-carboxylic acid hydrochloride;
(+)-6-tert-butyl-10-methoxy-9-(3-methylsulfonylpropoxy)-2-oxo-6,7-dihydrobenzo[a]quinolizine-3-carboxylic acid;
(+)-10-methoxy-9-(3-methoxypropoxy)-2-oxo-6-(2,2,2-trifluoroethyl)-6,7-dihydrobenzo[a]quinolizine-3-carboxylic acid;
(+)-6-tert-butyl-10-chloro-9-(3-methoxypropoxy)-2-oxo-6,7-dihydrobenzo[a]quinolizine-3-carboxylic acid; and
(+)-10-methoxy-9-(3-methoxypropoxy)-6-(1-methylcyclopropyl)-2-oxo-6,7-dihydrobenzo[a]quinolizine-3-carboxylic acid;
and pharmaceutically acceptable salts thereof.

15. The method according to any one of claims 1-3, wherein, the compound of formula IA is defined as 9,10-diethoxy-6-ethyl-2-oxo-6,7-dihydrobenzo[a]quinolizine-3-carboxylic acid, or a pharmaceutically acceptable salt thereof.

16. The method according to any one of claims 1-3 wherein, the compound of formula IA is defined as (+)-9-(cyclopropylmethoxy)-6-ethyl-10-methoxy-2-oxo-6,7-dihydrobenzo[a]quinolizine-3-carboxylic acid, or a pharmaceutically acceptable salt thereof.

17. The method according to any one of claims 1-3, wherein, the compound of formula IA is defined as (+)-10-cyclopropyl-6-ethyl-9-methoxy-2-oxo-6,7-dihydrobenzo[a]quinolizine-3-carboxylic acid, or a pharmaceutically acceptable salt thereof.

18. The method according to any one of claims 1-3, wherein, the compound of formula IA is defined as (+)-10-chloro-6-isopropyl-9-(2-methoxyethoxy)-2-oxo-6,7-dihydrobenzo[a]quinolizine-3-carboxylic acid, or a pharmaceutically acceptable salt thereof.

19. The method according to any one of claims 1-3, wherein, the compound of formula IA is defined as (+)-10-methoxy-6-isopropyl-9-(3-methoxypropoxy)-2-oxo-6,7-dihydrobenzo[a]quinolizine-3-carboxylic acid, or a pharmaceutically acceptable salt thereof.

20. The method according to any one of claims 1-3, wherein, the compound of formula IA is defined as (+)-6-tert-butyl-10-methoxy-9-(3-methoxypropoxy)-2-oxo-6,7-dihydrobenzo[a]quinolizine-3-carboxylic acid, or a pharmaceutically acceptable salt thereof, or a pharmaceutically acceptable salt thereof.

21. The method according to any one of claims 1-3, wherein, the compound of formula IA is defined as (+)-9-(2,2-difluoroethoxy)-6-isopropyl-10-methoxy-2-oxo-6,7-dihydrobenzo[a]quinolizine-3-carboxylic acid, or a pharmaceutically acceptable salt thereof.

* * * * *